United States Patent
Blume-Jensen et al.

(10) Patent No.: US 11,433,136 B2
(45) Date of Patent: Sep. 6, 2022

(54) POLYACETAL POLYMERS, CONJUGATES, PARTICLES AND USES THEREOF

(71) Applicants: THE GENERAL HOSPITAL CORPORATION, Boston, MA (US); MASSACHUSETTS INSTITUTE OF TECHNOLOGY, Cambridge, MA (US); XTUIT PHARMACEUTICALS, INC., Waltham, MA (US)

(72) Inventors: Peter Blume-Jensen, Newton, MA (US); Donald E. Chickering, III, Framingham, MA (US); Paul W. Kopesky, Lexington, MA (US); Lawrence A. Reiter, Mystic, CT (US); Alan Crane, Newton, MA (US); Robert S. Langer, Newton, MA (US); Rong Tong, Cambridge, MA (US); Rakesh K. Jain, Wellesley, MA (US); Vikash Pal Singh Chauhan, Boston, MA (US); Joao Incio, Boston, MA (US); Dai Fukumura, Newton, MA (US)

(73) Assignees: The General Hospital Corporation, Boston, MA (US); Massachusetts Institute of Technology, Cambridge, MA (US); XTUIT Pharmaceuticals, Inc., Waltham, MA (US)

( * ) Notice: Subject to any disclaimer, the term of this patent is extended or adjusted under 35 U.S.C. 154(b) by 297 days.

(21) Appl. No.: 16/063,353

(22) PCT Filed: Dec. 16, 2016

(86) PCT No.: PCT/US2016/067149
§ 371 (c)(1),
(2) Date: Jun. 18, 2018

(87) PCT Pub. No.: WO2017/106630
PCT Pub. Date: Jun. 22, 2017

(65) Prior Publication Data
US 2018/0360978 A1  Dec. 20, 2018

Related U.S. Application Data

(60) Provisional application No. 62/269,438, filed on Dec. 18, 2015.

(51) Int. Cl.
| | |
|---|---|
| A61K 47/60 | (2017.01) |
| A61K 9/14 | (2006.01) |
| A61K 31/41 | (2006.01) |
| A61K 31/4184 | (2006.01) |
| A61K 31/4545 | (2006.01) |
| A61P 35/00 | (2006.01) |
| C08G 65/48 | (2006.01) |

(52) U.S. Cl.
CPC .............. *A61K 47/60* (2017.08); *A61K 9/146* (2013.01); *A61K 31/41* (2013.01); *A61K 31/4184* (2013.01); *A61K 31/4545* (2013.01); *A61P 35/00* (2018.01); *C08G 65/48* (2013.01)

(58) Field of Classification Search
CPC ................ A61K 31/41; A61K 31/4184; A61K 31/4545; A61K 47/60; A61K 9/146; A61P 35/00; C08G 65/48
See application file for complete search history.

(56) References Cited

U.S. PATENT DOCUMENTS

| | | | | |
|---|---|---|---|---|
| 7,790,150 | B2 * | 9/2010 | Papisov | ................... A61P 35/00 424/78.3 |
| 2015/0352094 | A1 * | 12/2015 | Bemis | ................... A61K 47/542 424/146.1 |

FOREIGN PATENT DOCUMENTS

WO   2004009082 A1   1/2004

OTHER PUBLICATIONS

Diop-Frimpong et al: Losartan inhibits collagen I synthesis and improves the distribution and efficacy of nanotherapeutics in tumors, Proceedings of the National Acadmey of Sciences, vol. 108, No. 7, Jan. 31, 2011, pp. 2909-2914, XP055176833, ISSN: 0027-8424, DOI: 10.18892108 abstract.

Godugu Chandraiah et al: "Inhalation delivery of Telmisartan enhances intratumoral distribution of nanoparticles in lung cancer models", Journal of Controlled Release, vol. 172, No. 1, Jul. 7, 2013 (Jul. 7, 2013), pp. 86-95, XP028772902, ISSN: 0168-3659, DOI: 10.1016/J.JCONREL.2013.06.036 abstract.

Kim J K et al: "Novel pH-sensitive polyacetal-based block copolymers for controlled drug delivery", International Journal of Pharmaceutics,, vol. 401, No. 1-2, Nov. 30, 2010 (Nov. 30, 2010), pp. 79-86, XP027450387, ISSN: 0378-5173, [retrieved on Aug. 27, 2010], DOI: 10.1016/J.IJPHARM.2010.08.029 abstract.

Miao Lei et al: "Stromal barriers and strategies for the delivery of nanomedicine to desmoplastic tumors", Journal of Controlled Release, Elsevier, Amsterdam, NL, vol. 219, Aug. 12, 2015 (Aug. 12, 2015), pp. 192-204, XP029303650, ISSN: 0168-3659, DOI: 10.1016/J. JCONREL.2015.08.017 abstract.

(Continued)

*Primary Examiner* — Jeffrey T. Palenik
(74) *Attorney, Agent, or Firm* — Nixon Peabody LLP; David S. Resnick; Ravinderjit Braich

(57) ABSTRACT

Provided herein are polymers, pH-sensitive polymers and/or linkers; conjugates comprising said polymers and/or linkers, optionally, coupled to one or more agents and/or targeting moieties; and particles (e.g., nanoparticles comprising the aforesaid polymers, linkers and/or conjugates), which can be used to enhance the delivery and/or efficacy of one or more agents in a subject.

14 Claims, 59 Drawing Sheets

(56) References Cited

OTHER PUBLICATIONS

Montserrat Moreno et al: "Reduction of advanced liver fibrosis by short-term targeted delivery of an angiotensin receptor blocker to hepatic stellate cells in rats", Hepatology, Jan. 1, 2010 (Jan. 1, 2010), pp. NA-NA, XP055356986, ISSN: 0270-9139, DOI: 10.1002/hep.23419 abstract.
Yudan Gu et al: "Acetal-Linked Paclitaxel Prodrug Micellar Nanoparticles as a Versatile and Potent Platform for Cancer Therapy", Biomacromolecules, vol. 14, No. 8, Aug. 12, 2013 (Aug. 12, 2013), pp. 2772-2780, XP055357256, ISSN: 1525-7797, DOI: 10.1021/bm400615n abstract.

* cited by examiner

FIG. 1C
$R_2 =$
 B1
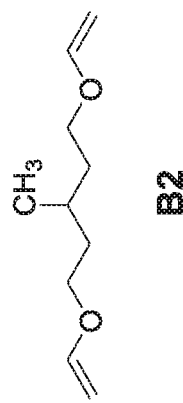 B2
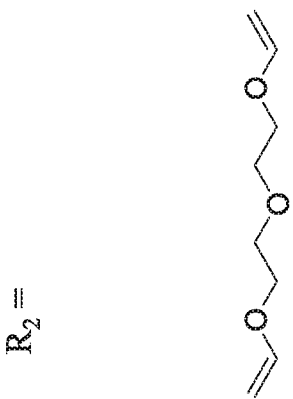 B3
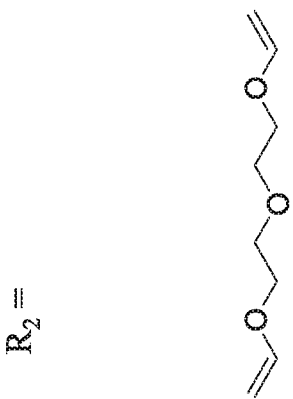 B4
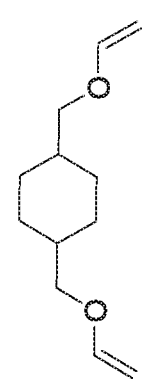 B5
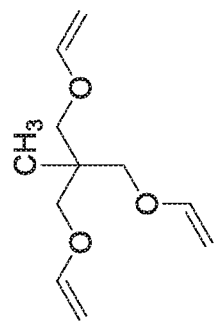 B6

R1 = polyol precursor
R2 = vinyl ether precursor
x = 200 - 5000
ARB = angiotensin II receptor blocker

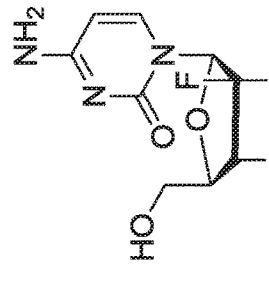
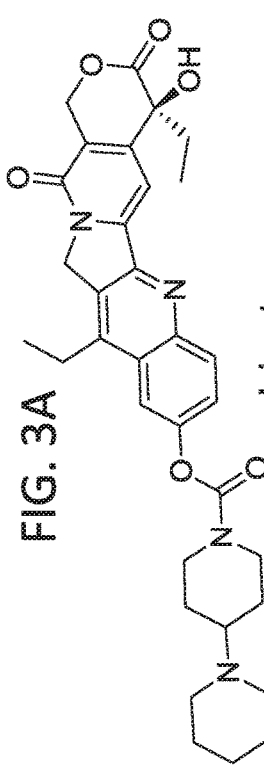
FIG. 3A
Irinotecan
pH sensitive linkers between drugs (R group) and polymer
FIG. 3B
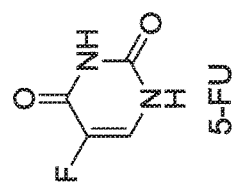
5-FU

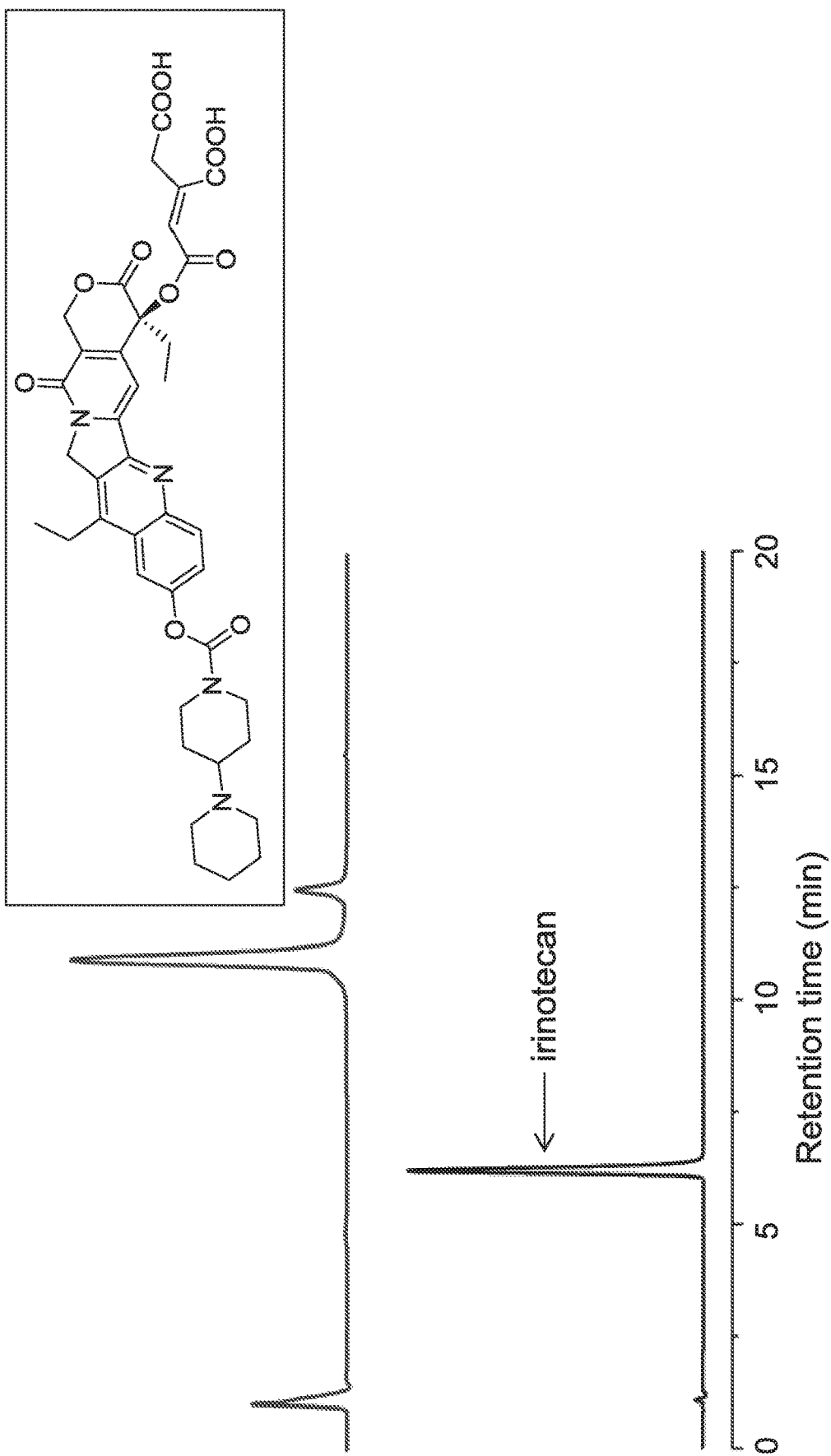

Selection of pH sensitive linker (R: irinotecan and gemcitabine)

AK4.4

PAN02

Mesenteries

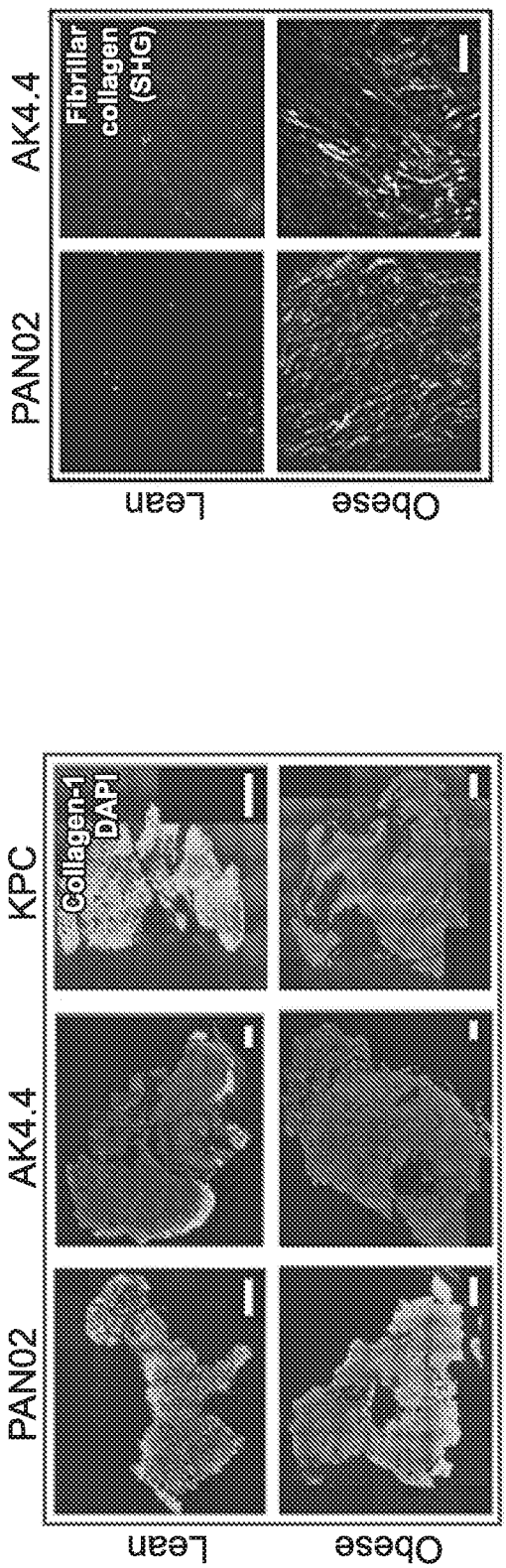
FIG. 8E
FIG. 8F
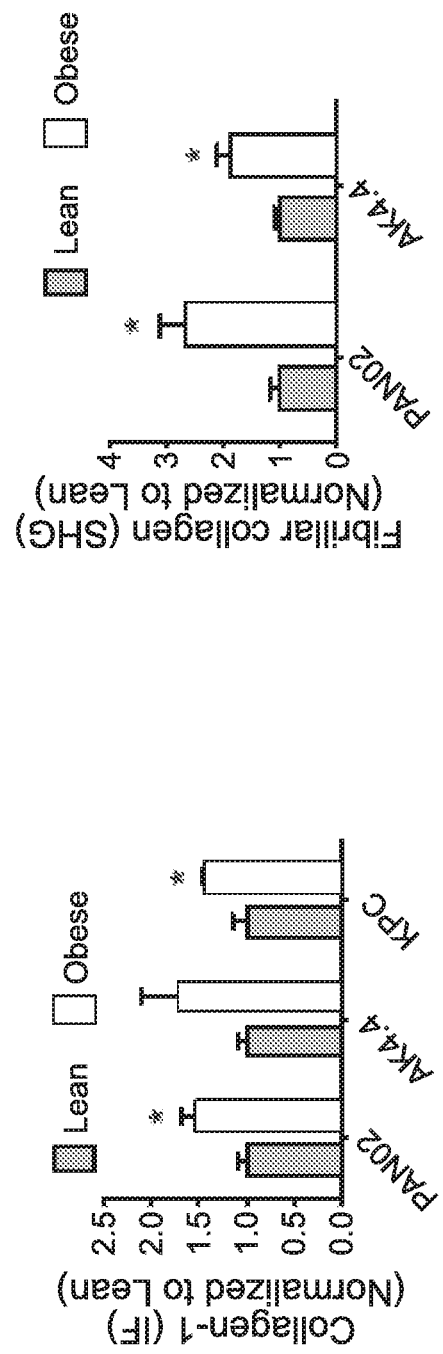
FIG. 8G
FIG. 8H

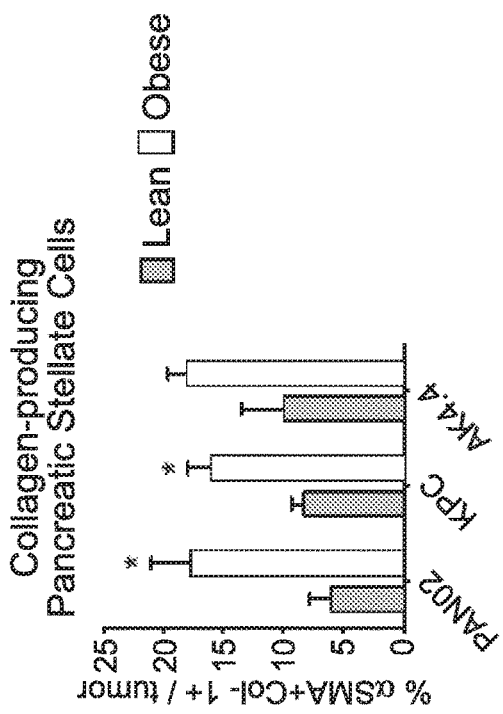
FIG. 8J Pancreatic Stellate Cells
FIG. 8K Collagen-producing Pancreatic Stellate Cells
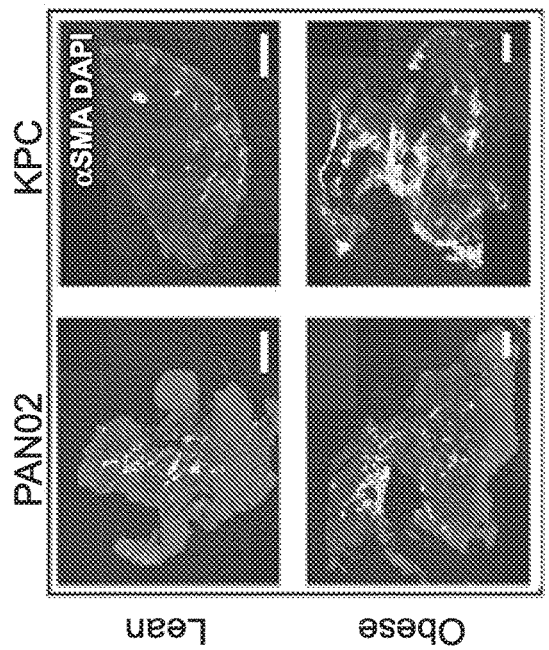
FIG. 8I

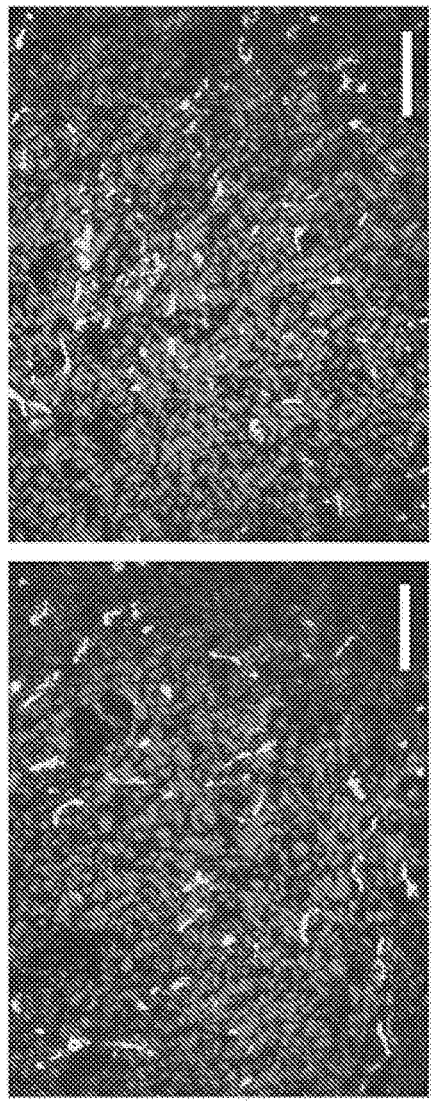
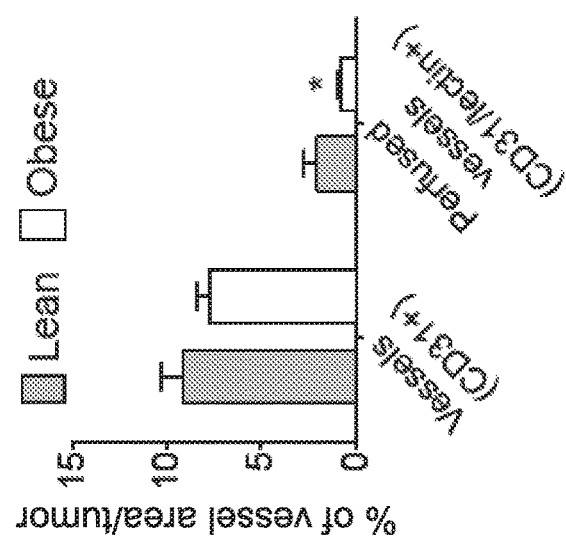
FIG. 9A
FIG. 9B

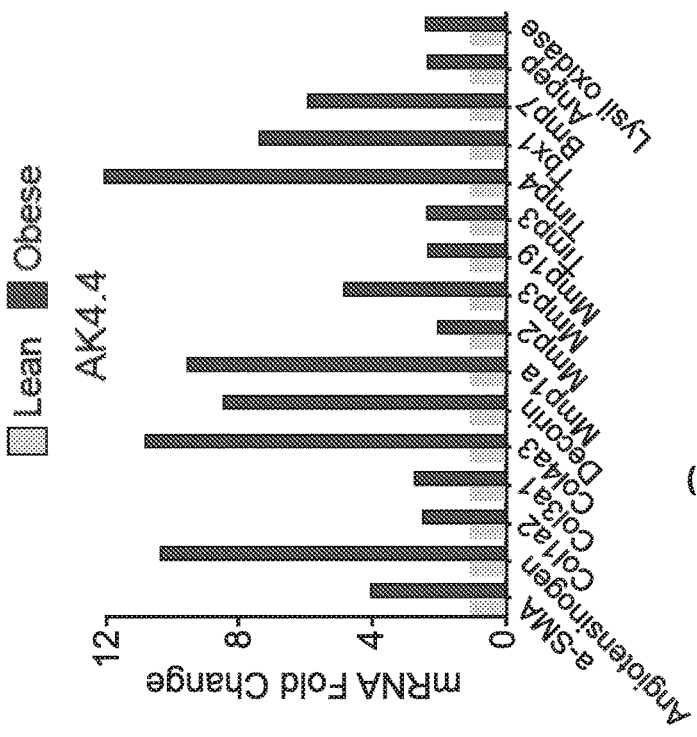
FIG. 10A
FIG. 10B
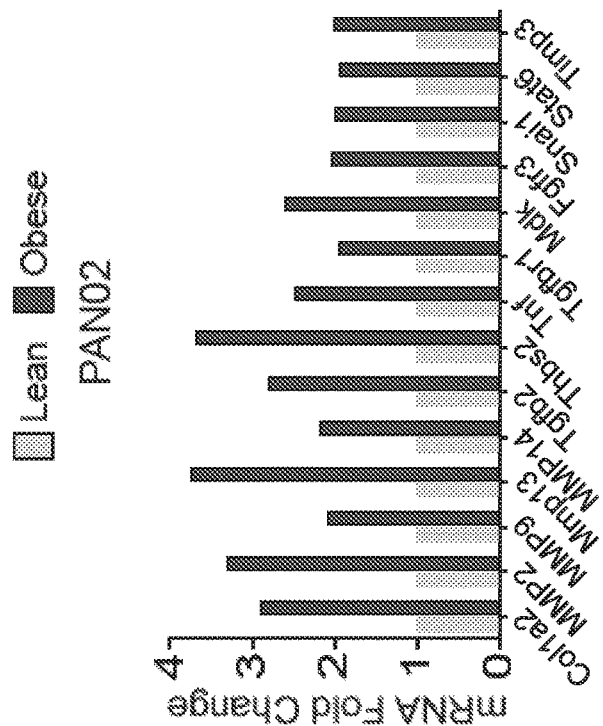
FIG. 10C
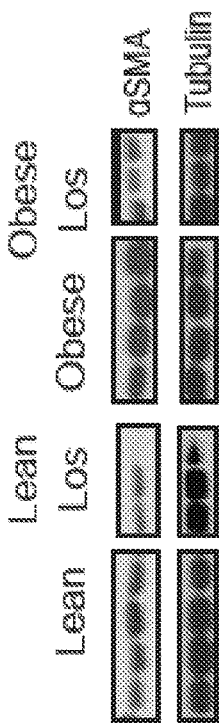
FIG. 10D

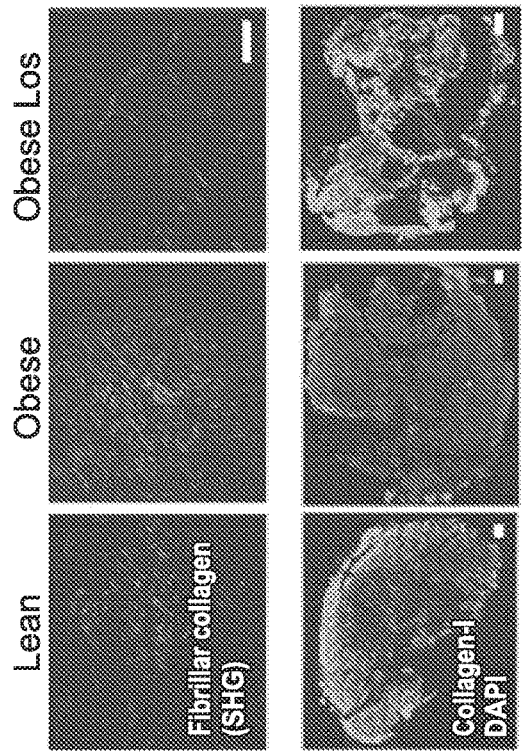
FIG. 10E
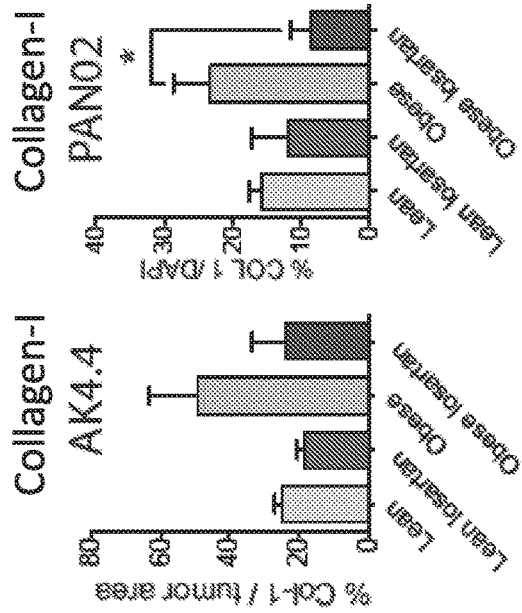
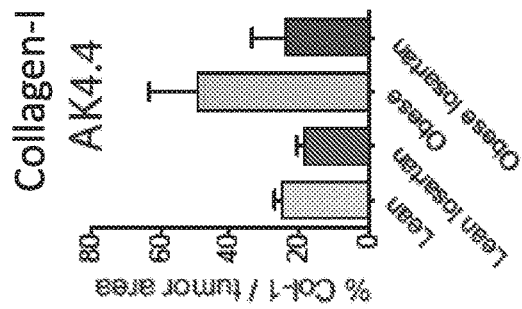
FIG. 10F SHG AK4.4
FIG. 10G Collagen-I AK4.4
FIG. 10H Collagen-I PAN02

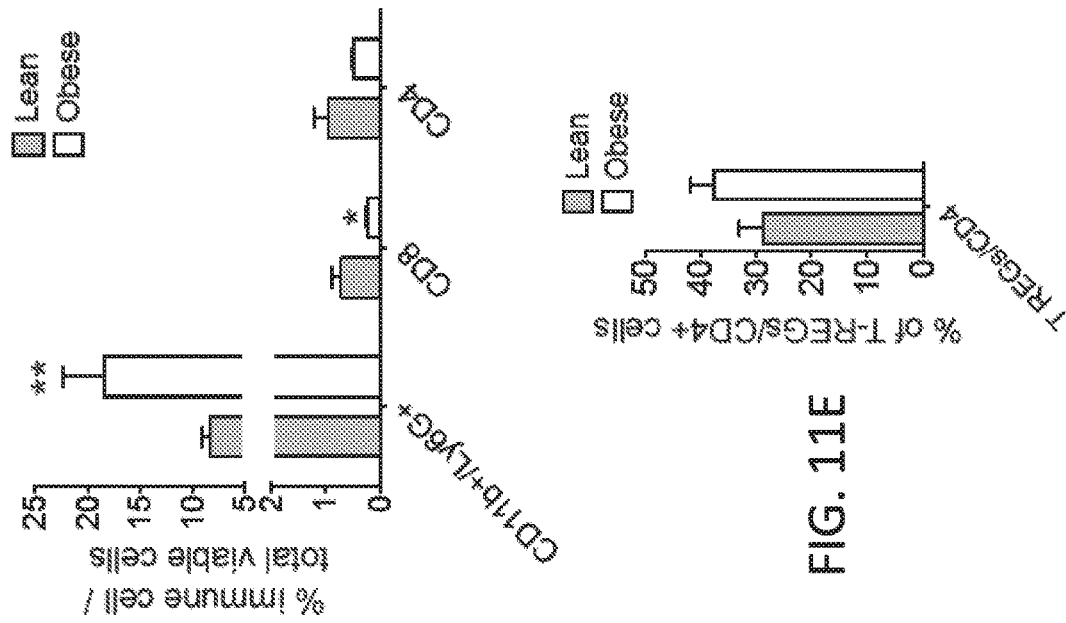
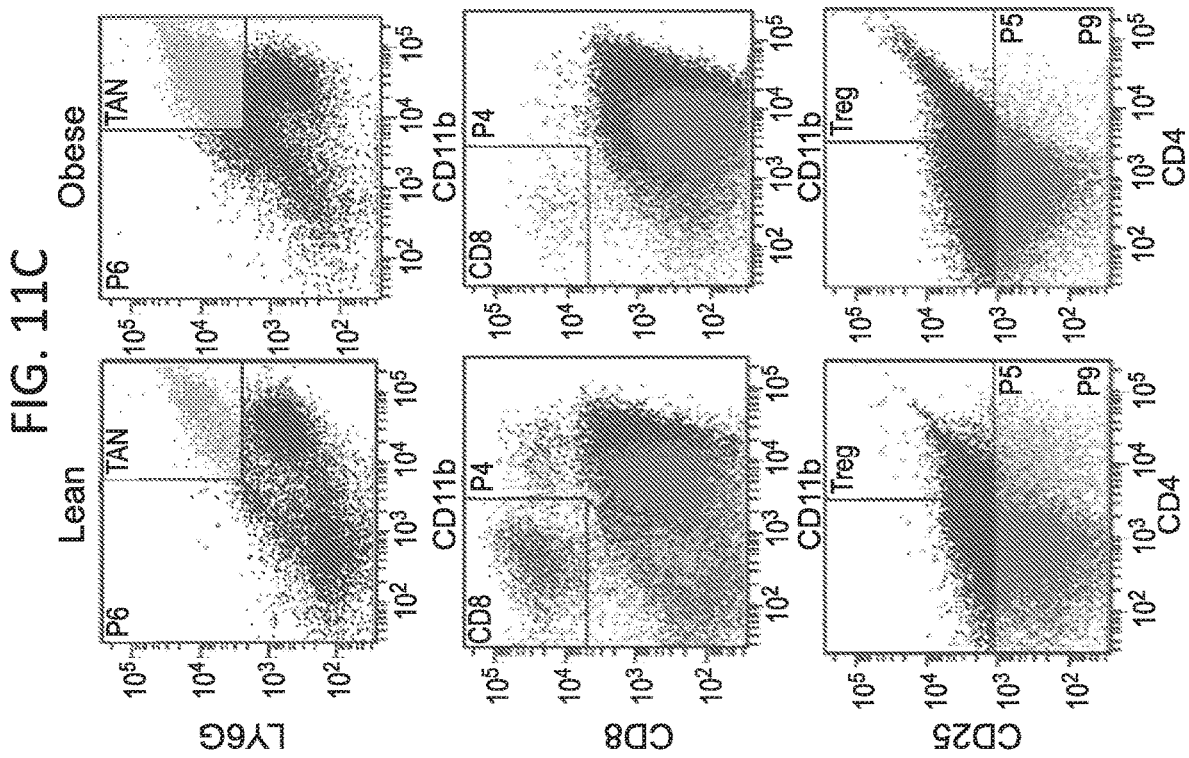

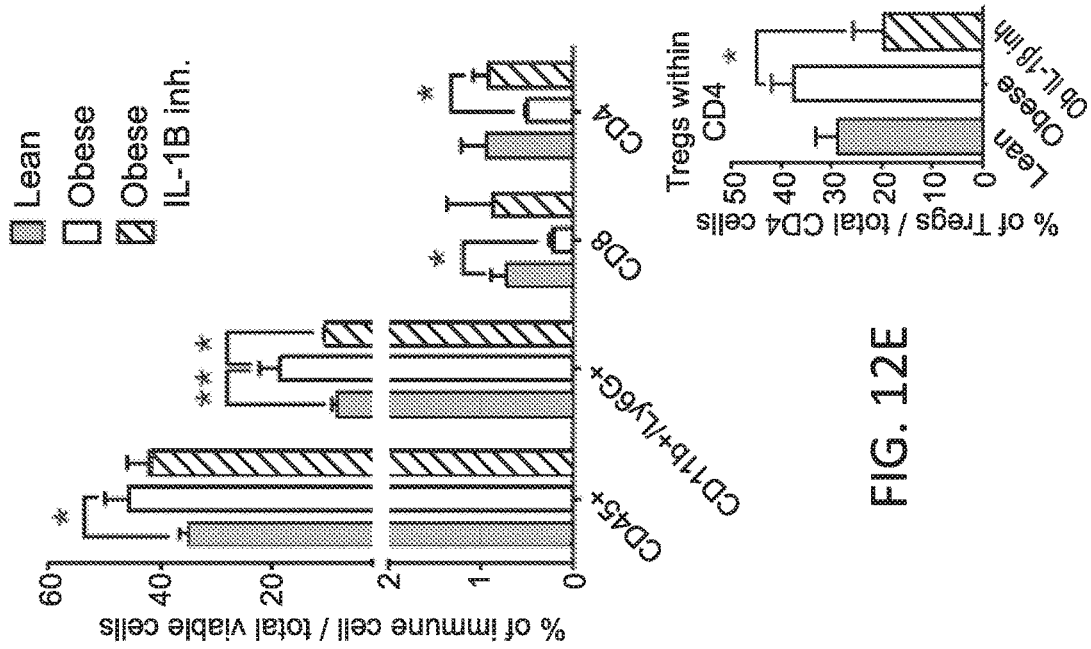
FIG. 12D
FIG. 12E
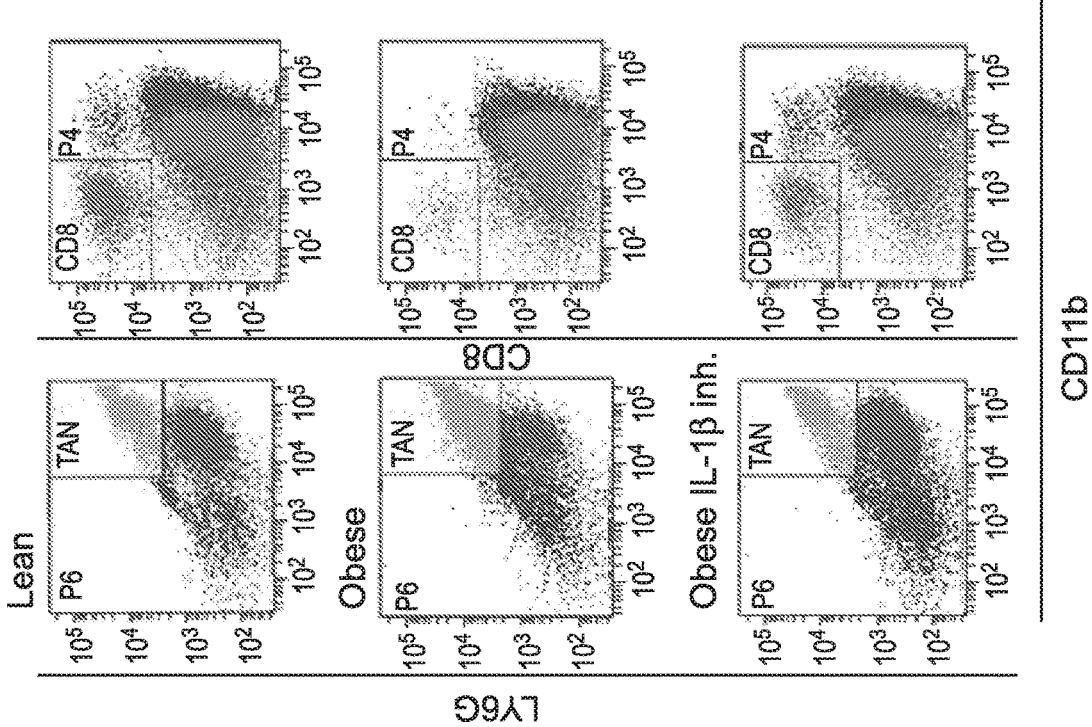
FIG. 12C

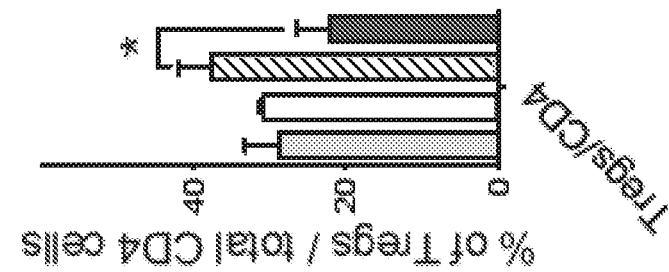
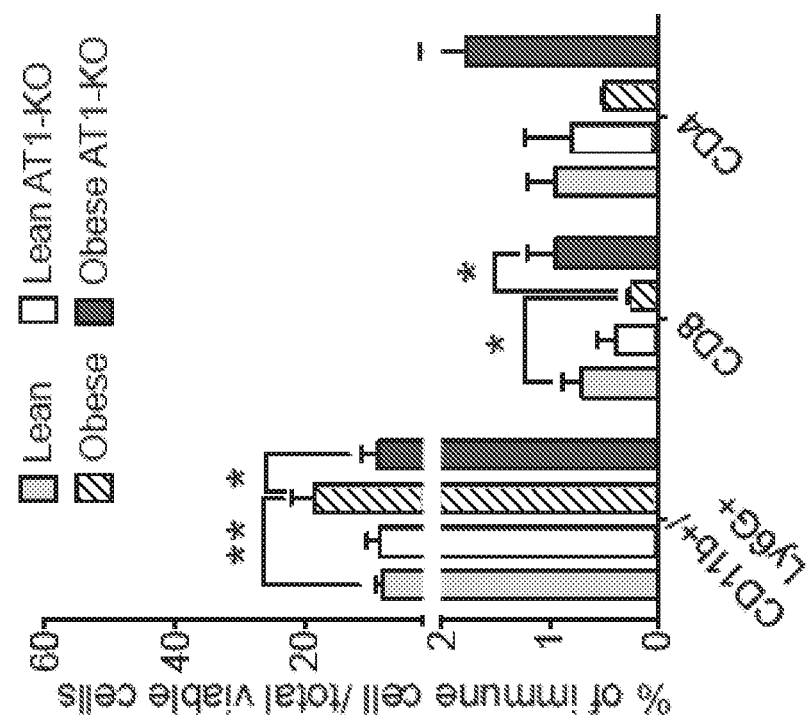

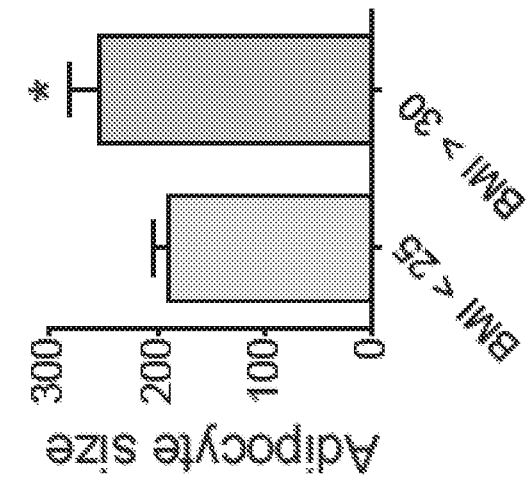
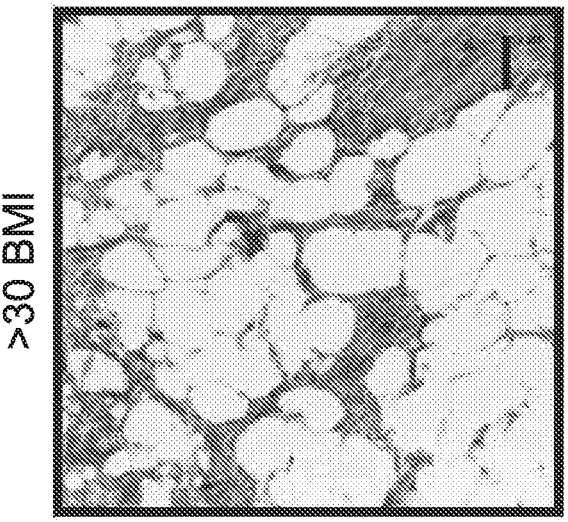
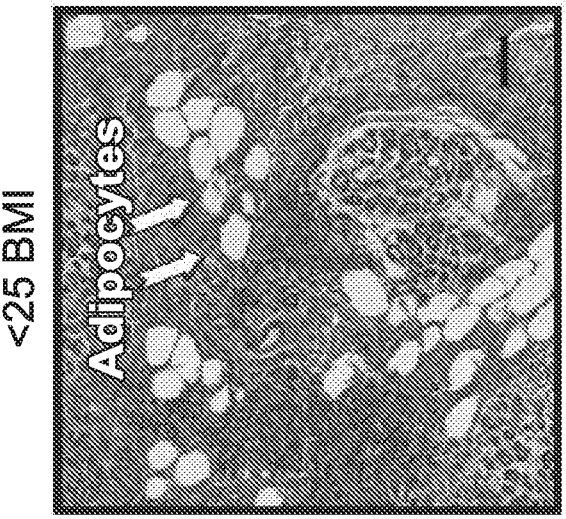
FIG. 13A
FIG. 13B

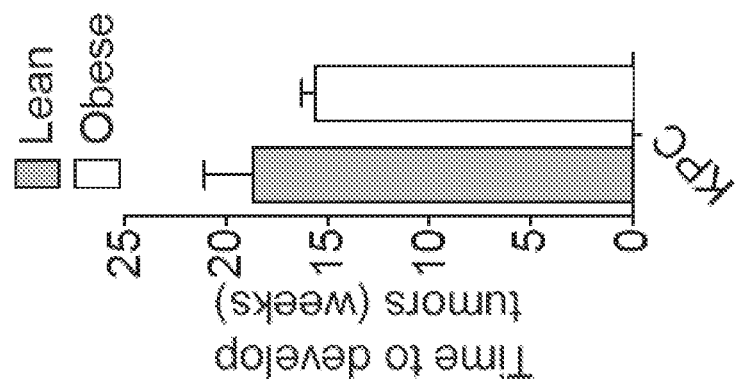

AK4.4

PAN02

AK4.4

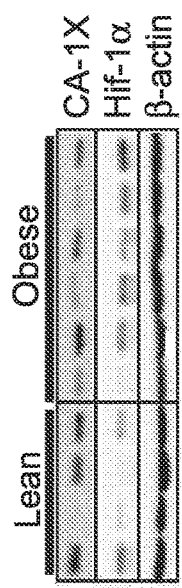
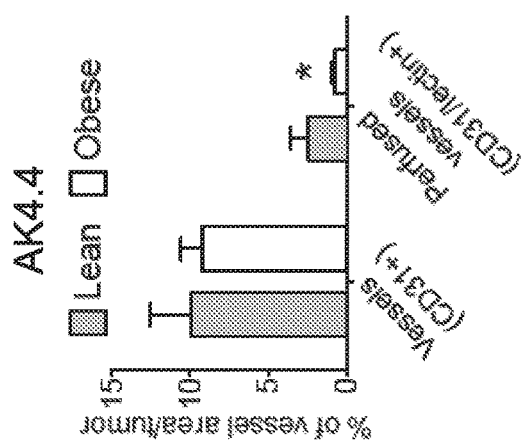
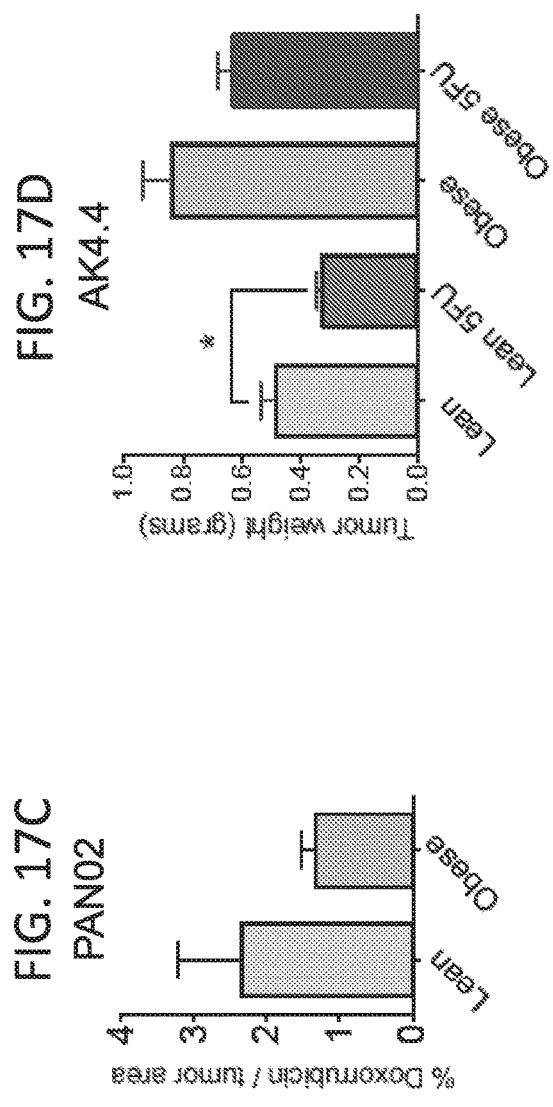
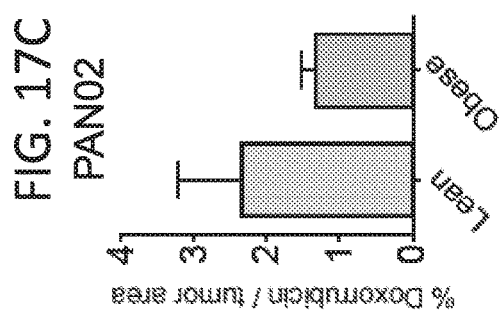

FIG. 24

| Identification number | Name | Structure |
|---|---|---|
| [1] | 1α,25(OH)$_2$D$_3$ | 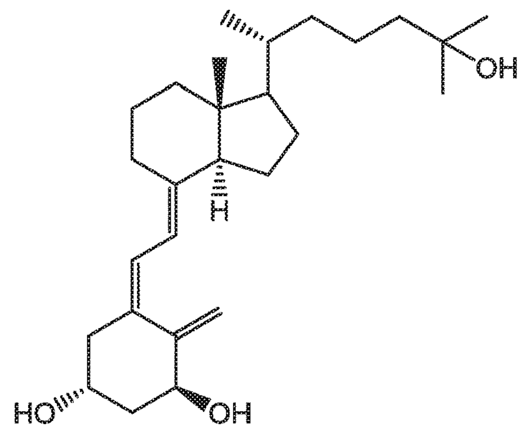 |
| [2] | Paricalcitol (19-nor-1α,25(OH)$_2$D$_2$) | 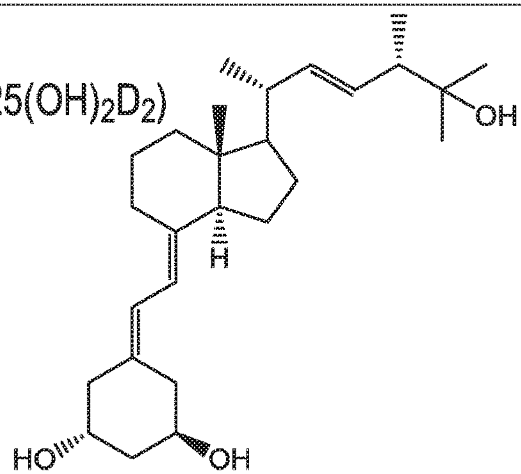 |
| [3] | Doxercalciferol (1α(OH)D$_2$) | 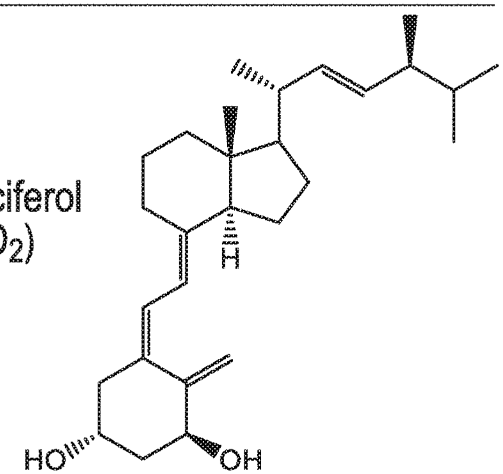 |
| [4] | Falecalcitriol (26,27 F6-1α,25(OH)$_2$D$_3$) | 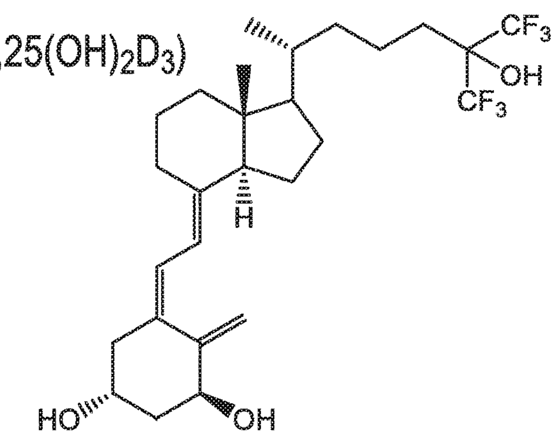 |

FIG. 24 Continued
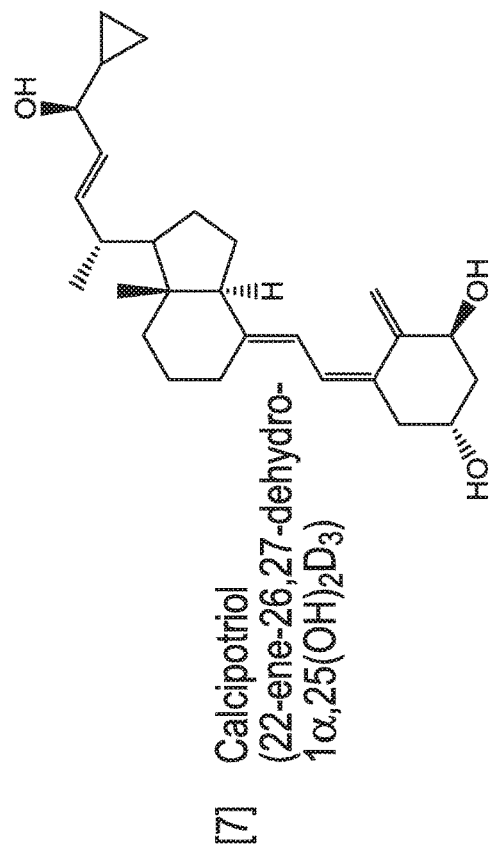
[7] Calcipotriol
(22-ene-26,27-dehydro-1α,25(OH)₂D₃)
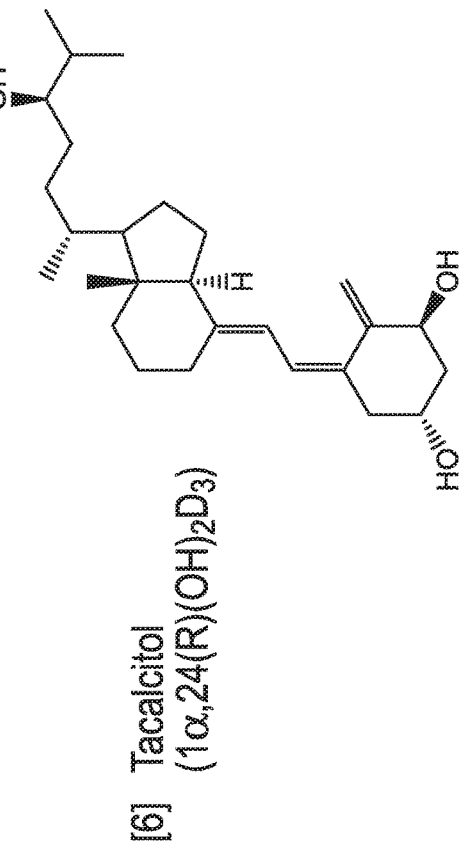
[8] Alfacalcidol
(1α(OH)D₃)
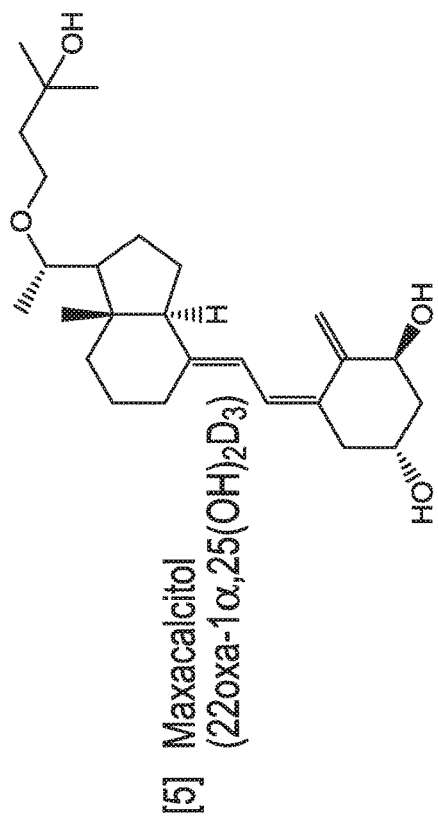
[5] Maxacalcitol
(22oxa-1α,25(OH)₂D₃)
[6] Tacalcitol
(1α,24(R)(OH)₂D₃)

[11] 20-epi-1α,25(OH)$_2$D$_3$

[12] Lexicalcitol (20-epi-22-oxa-24,26,27-trishomo-1α,25(OH)$_2$D$_3$)

[9] Eldecalcidol (2β-(3-hydroxypropoxy)-1α,25(OH)$_2$D$_3$)

[10] Seocalcitol (22,24-diene-24,26,27-trishomo-1α,25(OH)$_2$D$_3$)

FIG. 24 Continued
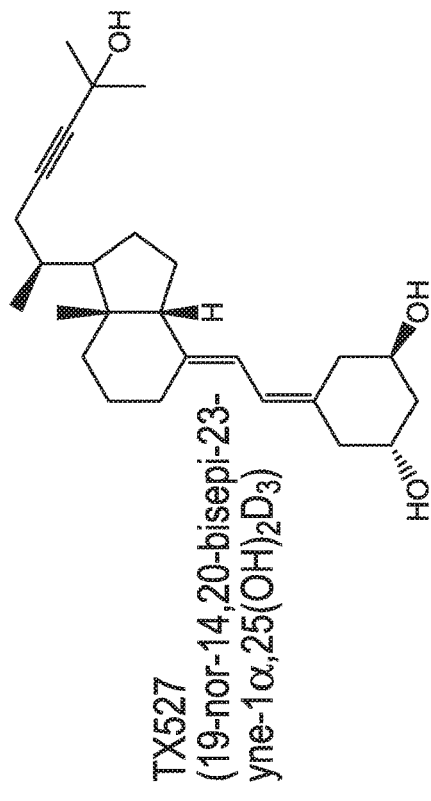
[13] CD578
(17-methyl-19-nor-21-nor-23-yne-26,27-F6-1α,25(OH)₂D₃)
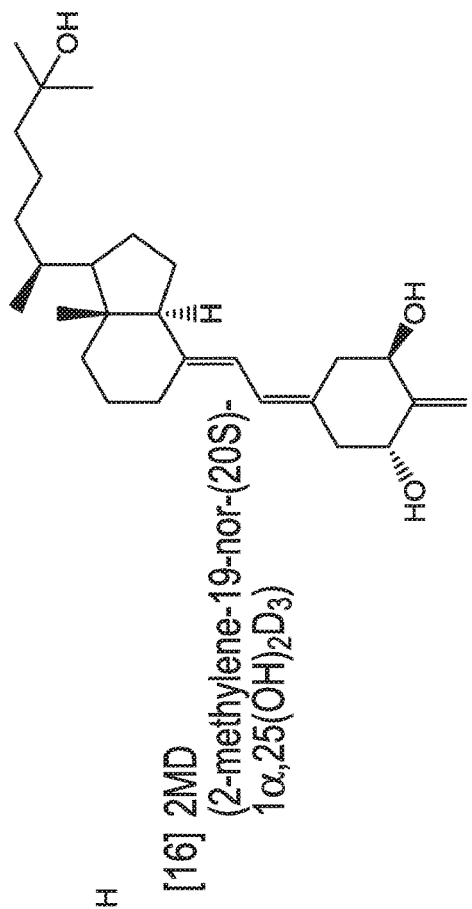
[15] TX527
(19-nor-14,20-bisepi-23-yne-1α,25(OH)₂D₃)
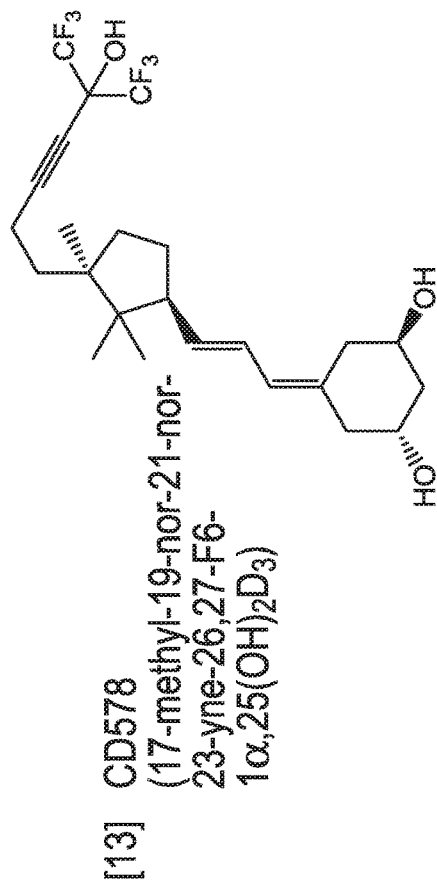
[14] Inecalcitol
(19-nor-14-epi-23-yne-1α,25(OH)₂D₃)
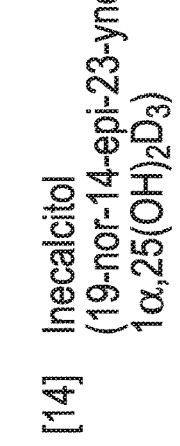
[16] 2MD
(2-methylene-19-nor-(20S)-1α,25(OH)₂D₃)

FIG. 24 Continued
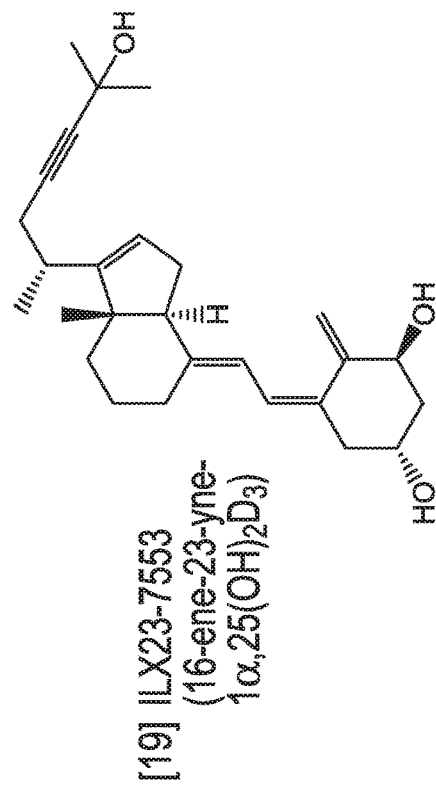
[17] WY1112
(Seco-C-9,11-bisnor-17-methyl-20-epi-26,27-F6-1α,25(OH)₂D₃)
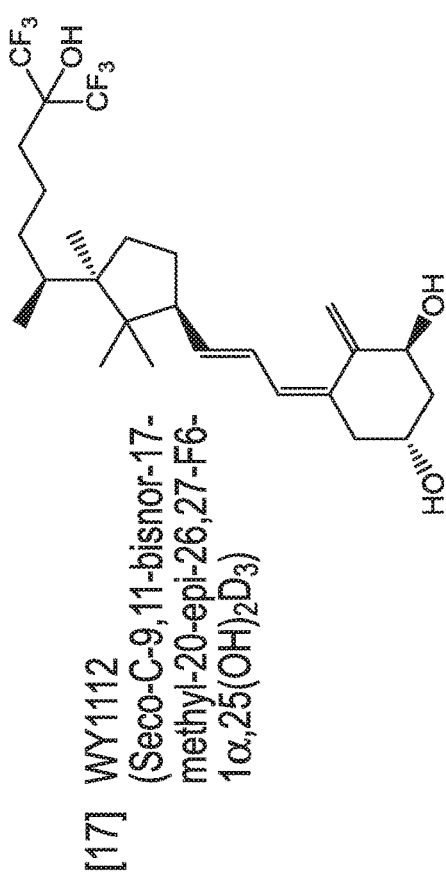
[18] PRI-2205
((5E,7E)-22-ene-26,27-dehydro-1α,25(OH)₂D₃)
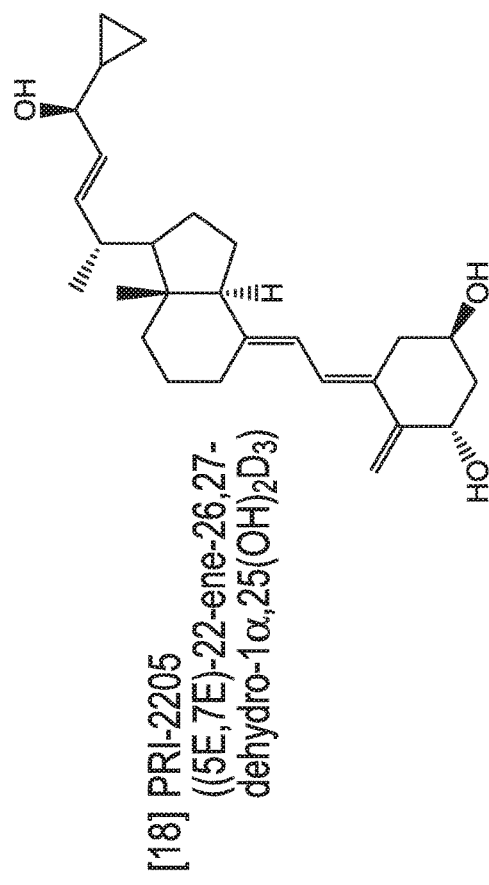
[19] ILX23-7553
(16-ene-23-yne-1α,25(OH)₂D₃)

POLYACETAL POLYMERS, CONJUGATES, PARTICLES AND USES THEREOF

CROSS REFERENCE TO RELATED APPLICATIONS

This application is a 371 National Phase Entry of International Patent Application No. PCT/US2016/067149 filed on Dec. 16, 2016, which designates the U.S., and which claims benefit under 35 U.S.C. § 119(e) of U.S. Provisional Application No. 62/269,438 filed Dec. 18, 2015, the contents of which are incorporated herein by reference in their entirety.

GOVERNMENT SUPPORT

This invention was made with Government support under Grant No. CA80124-15 awarded by the National Institutes of Health. The Government has certain rights in the invention.

TECHNICAL FIELD

The present invention generally relates to particles, such as nanoparticles, the polymers of which the particles are comprised, as well as to compositions thereof. The present invention also generally relates to methods of using the compositions provided for delivery of agents, such as one or more pharmaceutical agents (e.g., one or more drugs).

BACKGROUND

Advances in biomedical research have led to the introduction of several novel systemically administered molecular and nanotherapeutic agents in both preclinical and clinical settings (Jones. D. (2007) *Nat Rev Drug Discov* 6, 174-175; Moghimi, S. M. et al. (2005) *Faseb J.* 19, 311-330). While these new agents act on unique targets that afford greater specificity to target cells, e.g., tumor cells, or improved pharmacodynamic properties, their effectiveness suffers from limitations in their delivery owing to the properties of the target microenvironment (Jain, R. K. (1998) *Nat Med* 4, 655-657; Sanhai, W. R. et al. (2008) *Nat Nanotechnol* 3, 242-244; Chauhan, V et al. (2011) *Annu Rev Chem Biomol Eng.* 2(1):281-98). Limited approaches are currently available to overcome the delivery barriers for drugs.

Thus, the need exists for identifying new agents and formulations that enhance the delivery, distribution, and/or efficacy of therapeutic agents, including nanotherapeutics (e.g., lipid- or polymeric nanoparticles and viruses), protein and nucleic acid drugs, targeted therapies, immune therapies (e.g., immune checkpoint blockers, vaccines and/or immune cells), and small molecule chemotherapeutic agents.

SUMMARY

The present invention discloses, at least in part, pH-sensitive and/or polyacetal polymers and/or linkers; conjugates comprising said polymers and/or linkers, optionally, coupled to one or more agents and/or targeting moieties; and particles (e.g., nanoparticles comprising the aforesaid polymers, linkers and/or conjugates), collectively referred to herein as "compositions," which can be used to enhance the delivery and/or efficacy of one or more agents in a subject.

Without wishing to be bound by theory, the compositions disclosed herein may improve the efficiency of an agent, e.g., a therapeutic and/or diagnostic agent. In one embodiment, the compositions can result in one or more of: (i) increasing the localization and/or delivery of the agent to a target cell or tissue (e.g., a cancer or a fibrotic cell or tissue; or a liver cell or tissue); (ii) selectively penetrating into a fibrotic tissue (e.g., a desmoplastic tumor or a fibrotic tissue chosen from liver, kidney, lung or bone marrow (e.g., myelofibrotic bone marrow)); (iii) selectively penetrating into a diseased blood vessel (e.g., a leaky tumor vessel); (iv) exhibiting increased pH-sensitivity and/or enhanced agent release in a hypoxic microenvironment, e.g., in a tumor or a fibrotic tissue (e.g., fibrotic or cirrhotic liver, or a tissue having renal fibrosis, pulmonary fibrosis or myelofibrosis); (v) increasing the selective delivery and/or release of the agent to the tumor or fibrotic tissue; or (vi) increasing the half-life of the agent. In some embodiments, by selectively targeting an agent to a cell or tissue in need (e.g., a cancer or a fibrotic tissue), the composition described herein can comprise an agent at a concentration that would otherwise produce an adverse effect when administered systemically as a free form (e.g., not coupled to pH-sensitive and/or polyacetal polymer or particle as described herein).

Certain embodiments disclosed herein provide compositions and methods for treating or preventing a disorder. In some embodiments, the disorder is a fibrotic disorder. In some embodiments, the disorder is a cancer disorder (e.g., a desmoplastic tumor or metastatic lesion). In some embodiments, the disorder is a liver disease or disorder. These embodiments comprise administering to a subject a particle, e.g., a pH-sensitive and/or polyacetal particle described herein, as a single agent or as a combination with one or more therapeutic agents. The compositions disclosed herein can result in a higher amount of released agent at a target site (e.g., in a hypoxic tumor), while having minimal or no effect at other non-target sites (e.g., in intact and/or healthy blood vessels and/or normal or healthy tissues). In one embodiment, the agent delivered or released is a therapeutic and/or diagnostic agent (e.g., an Anti-hypertensive and/or Collagen Modifying Agent (AHCM) (e.g., an angiotensin receptor blocker (ARB) as described herein). Alternatively, or in combination, the agent delivered or released is an anti-cancer therapeutic agent and/or a liver therapeutic agent. Thus, provided herein are compositions and methods for improving the delivery and/or efficacy of a therapy (e.g., a cancer, anti-fibrotic, or a liver therapy), ranging in size from a cell (e.g., an immune cell) or a large nanotherapeutic (e.g., lipid- or polymeric nanoparticles and viruses), protein and nucleic acid drugs, to low molecular weight chemotherapeutics and/or oxygen radicals.

Polymers

In one aspect, the invention features a pH-sensitive polymer, e.g., a polymer comprising a polyacetal polymer (e.g., a polyacetal polymer of Formula (I), Formula (I-a), or Formula (IV) described herein).

In some embodiments, the average molecular weight of the polymer (e.g., a polyacetal polymer as described herein) used in a particle (e.g., a micelle or a nanoparticle as described herein) is from about 2 kDa to about 200 kDa, (e.g., from about 2.5 kDa to about 175 kDa, from about 5 kDa about 150 kDa, from about 10 kDa to about 125 kDa, from about 12.5 kDa to about 100 kDa, from about 15 kDa to about 90 kDa, from about 17.5 kDa to about 80 kDa, from about 20 kDa to about 70 kDa, from about 22.5 kDa to about 60 kDa, or from about 25 kDa to about 50 kDa). In some embodiments, the average molecular weight of the polymer used in a particle (e.g., a micelle or a nanoparticle as described herein) is from about 5 kDa to about 100 kDa (e.g., from about 6 kDa to about 90 kDa, from about 7 kDa to about 95 kDa, from about 8 kDa to about 85 kDa, from about 9 kDa to about 80 kDa, from about 10 kDa to about 75 kDa, from about 11 kDa to about 70 kDa, from about 12 kDa to about 65 kDa, from about 13 kDa to about 60 kDa, from about 14 kDa to about 55 kDa, or from about 15 kDa to about 50 kDa). In some embodiments, the average molecular weight of the polymer used in a particle (e.g., a micelle or a nanoparticle as described herein) is from about 7 kDa to about 100 kDa, (e.g., from about 7 kDa to about 95 kDa, about 7 kDa to about 90 kDa, about 7 kDa to about 80 kDa, about 7 kDa to 75 kDa, about 7 kDa to about 70 kDa, about 7 kDa to about 65 kDa, about 7 kDa to about 60 kDa, about 7 kDa to about 55 kDa, about 7 kDa to about 50 kDa, about 7 kDa to about 45 kDa, about 7 kDa to about 40 kDa, about 7 kDa to about 35 kDa, about 7 kDa to about 30 kDa, about 7 kDa to about 25 kDa, about 7 kDa to about 20 kDa, about 7 kDa to about 15 kDa, or from about 7 kDa to about 75 kDa, about 7.5 kDa to about 75 kDa, about 10 kDa to about 75 kDa, about 12.5 kDa to about 75 kDa, about 15 kDa to about 75 kDa, about 17.5 kDa to about 75 kDa, about 20 kDa to about 75 kDa, about 22.5 kDa to about 75 kDa, about 25 kDa to about 75 kDa, about 27.5 kDa to about 75 kDa, about 30 kDa to about 75 kDa, about 32.5 kDa to about 75 kDa, about 35 kDa to about 75 kDa, about 40 kDa to about 75 kDa, about 42.5 kDa to about 75 kDa, about 45 kDa to about 75 kDa, about 47.5 kDa to about 75 kDa, or about 50 kDa to about 75 kDa). In one embodiment, the average molecular weight of the polymer used in a particle (e.g., a micelle or a nanoparticle as described herein) is from about 5 kDa to about 50 kDa. In another embodiment, the average molecular weight of the polymer used in a particle (e.g., a micelle or a nanoparticle as described herein) is from about 10 kDa to about 50 kDa. In another embodiment, the average molecular weight of the polymer used in a particle (e.g., a micelle or a nanoparticle as described herein) is from about 15 kDa to about 40 kDa. In another embodiment, the average molecular weight of the polymer used in a particle (e.g., a micelle or a nanoparticle as described herein) is from about 15 kDa to about 25 kDa. In another embodiment, the average molecular weight of the polymer used in a particle (e.g., a micelle or a nanoparticle as described herein) is from about 20 kDa to about 40 kDa. In another embodiment, the average molecular weight of the polymer used in a particle (e.g., a micelle or a nanoparticle as described herein) is from about 10 kDa to about 100 kDa. In another embodiment, the average molecular weight of the polymer used in a particle (e.g., a micelle or a nanoparticle as described herein) is from about 10 kDa to about 50 kDa. In some embodiments, the average molecular weight of the polymer used in a particle (e.g., a micelle or a nanoparticle as described herein) is not less than about 10 KDa, about 9 kDa, about 8 kDa, about 7 kDa, about 6 kDa, or about 5 kDa.

In one embodiment, the polymer is sensitive to a pH between about 5.0 and about 7.4, between 5.0 and 7.0, between 5.0 and 6.5, between 5.0 and 5.5, or between 5.9 and 6.2. In one embodiment, the polymer is sensitive to a pH between about 6.0 and about 7.0, between about 6.2 and about 6.9, between about 6.5 and about 6.8, or between about 6.5 and about 6.7. In one embodiment, the polymer is sensitive to a pH between about 5.5 and about 6.5, e.g., between 5.9 and 6.2. In one embodiment, the polymer is sensitive to a hypoxic pH, e.g., a pH about 6.7 to 6.9, e.g., compared to a physiological pH of about 7.4.

In some embodiments, the polymer is sensitive to a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the polymer is preferentially cleaved or degraded upon exposure to a first pH relative to a second pH. In one embodiment, the polymer is cleaved or degraded at least 2, 5, 10, 20, 30, 40, 50, 60, 70, 80, or 100 times faster upon exposure to a first pH relative to a second pH. In other embodiments, the polymer shows a greater release or degradation rate at a first acidic pH (e.g., pH=6.7) relative to a second more basic pH (e.g., pH=7.4). In one embodiment, ratio of release or degradation rate of the polymer (e.g., when present in a linker, a conjugate (e.g., an agent-polymer conjugate) or a particle (e.g., a nanoparticle)) at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the polymer at pH=6.7 relative to pH=7.4 is greater than 2. In one embodiment, the polymer shows increased pH-sensitivity in a hypoxic microenvironment, e.g., in a tumor, or fibrotic tissue.

In some embodiments, the polymer (e.g., the polyacetal polymer) is soluble in water (e.g., hydrophilic). In some embodiments, the polymer (e.g., the polyacetal polymer) is soluble in water, and between about 0.1 to about 5 parts water are required to dissolve 1 part polymer, or between about 1 part to about 5 parts water are required to dissolve 1 part polymer. In some embodiments, the polymer (e.g., the polyacetal polymer) is partially soluble in water. In some embodiments, the polymer (e.g., the polyacetal polymer) is partially soluble in water, and between about 5 to about 50 parts water are required to dissolve 1 part polymer. In some embodiments, the polymer (e.g., the polyacetal polymer) is sparingly soluble in water. In some embodiments, the polymer (e.g., the polyacetal polymer) is sparingly soluble in water, and between about 25 to about 100 parts water is required to dissolve 1 part polymer. In some embodiments, the polymer (e.g., the polyacetal polymer) is slightly soluble in water. In some embodiments, the polymer (e.g., the polyacetal polymer) is slightly soluble in water, and between 100 to about 1,000 parts water are required to dissolve 1 part polymer. In some embodiments, the polymer (e.g., the polyacetal polymer) is very slightly soluble in water. In some embodiments, the polymer (e.g., the polyacetal polymer) is very slightly soluble in water, and between 1,000 to about 10,000 parts water are required to dissolve 1 part polymer. In some embodiments, the polymer (e.g., the polyacetal polymer) is substantially insoluble in water (e.g., hydrophobic). In some embodiments, the polymer (e.g., the polyacetal polymer) is substantially insoluble in water and greater than about 10,000 parts water are required to dissolve 1 part polymer.

In one embodiment, the polymer (e.g., a polyacetal polymer) is amphiphilic. In one embodiment, the polymer (e.g., a polyacetal polymer) comprises a segment that is hydrophobic and a segment that is hydrophilic.

In some embodiments, the polymer (e.g., a polyacetal polymer) is a liquid (e.g., a fluid liquid) at room temperature (e.g., at 25° C.). In some embodiments, the polymer (e.g., a polyacetal polymer) is viscous (e.g., a viscous liquid) at room temperature (e.g., at 25° C.). In some embodiments, the polymer (e.g., a polyacetal polymer) is a gel at room temperature (e.g., at 25° C.). In some embodiments, the polymer (e.g., a polyacetal polymer) is solid (e.g., a crystalline, semi-crystalline, amorphous, glassy, or rubbery solid) at room temperature (e.g., at 25° C.). In some embodiments, the melting temperature ($T_m$) of the polymer (e.g., a polyacetal polymer) is greater than about 25° C. In some embodiments, the melting temperature ($T_m$) of the polymer (e.g., a polyacetal polymer) is greater than about 30° C., about 32° C., about 34° C., about 36° C., about 38° C., about 40° C., about 42° C., about 44° C., about 46° C., about 48° C., about 50° C., or higher. In some embodiments, the melting temperature ($T_m$) of the polymer (e.g., a polyacetal polymer) is between about 30° C. and about 50° C. In some embodiments, the melting temperature ($T_m$) of the polymer (e.g., a polyacetal polymer) is between about 35° C. and about 45° C.

In some embodiments, the polymer (e.g., the polyacetal polymer) comprises a linear structure. In some embodiments, the polymer (e.g., the polyacetal polymer) comprises a branched structure. In some embodiments, the polymer (e.g., the polyacetal polymer) comprises a branched structure, and each repeating unit in the polymer comprises at least 1, at least 2, at least 3, at least 4, at least 5, at least 6, at least 7, or at least 8 branch points.

In some embodiments, the polymer (e.g., the polyacetal polymer) comprises a structure according to Formula (I):

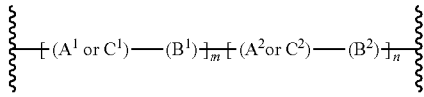

Formula (I)

wherein:
each of $A^1$ and $A^2$ is independently heteroalkylene, heteroalkenylene, heteroalkynylene, heterocyclyl, aryloxy, heteroaryloxy, wherein each heteroalkylene, heteroalkenylene, heteroalkynylene, heterocyclyl, aryloxy, or heteroaryloxy is optionally substituted with 1-5 $R^1$;
each of $B^1$ and $B^2$ is independently heteroalkyl, or heterocyclyl, each of which is optionally substituted with 1-6 $R^2$;
each of $C^1$ and $C^2$ is independently heteroalkyl, cyclyl, or heterocyclyl, each of which is optionally substituted with 1-6 $R^3$, e.g., each of $C^1$ and $C^2$ is independently PEG400, PEG1000, or PEG2050;
each of $R^1$, $R^2$, and $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, a protecting group, or a branching point; and
each of m or n is independently an integer from 1 to 500.

In some embodiments of a polymer of Formula (I), each of $A^1$ and $A^2$ is independently heteroalkyl or aryloxy, each of which may be optionally substituted with 1-5 $R^1$. In some embodiments, each of $A^1$ and $A^2$ is independently heteroalkyl, each of which may be optionally substituted with 1-5 $R^1$. In some embodiments, each of $A^1$ and $A^2$ is independently $C_1$-$C_{20}$ heteroalkyl, each of which may be optionally substituted with 1-5 $R^1$. In some embodiments, each of $A^1$ and $A^2$ is the same $C_1$-$C_{20}$ heteroalkyl, each of which may be optionally substituted with 1-5 $R^1$. In some embodiments, each of $A^1$ and $A^2$ is a different $C_1$-$C_{20}$ heteroalkyl, each of which may be optionally substituted with 1-5 $R^1$.

In some embodiments, each of $A^1$ and $A^2$ is independently represented by a moiety of Formula (II):

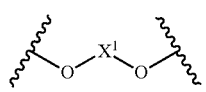

Formula (II)

wherein:
$X^1$ is $C_1$-$C_{12}$ alkylene, $C_2$-$C_{12}$ alkenylene, $C_2$-$C_{12}$ alkynylene, $C_1$-$C_{12}$ heteroalkylene, $C_3$-$C_8$ cyclyl, or $C_3$-$C_8$ heterocyclyl, wherein each alkylene, alkenylene, alkynylene, heteroalkylene, cyclyl, or heterocyclyl is optionally substituted with 1-6 $R^4$;
each $R^4$ is independently $C_1$-$C_6$ alkyl, $C_2$-$C_6$ alkenyl, $C_2$-$C_6$ alkynyl, $C_1$-$C_6$ heteroalkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, ($C_1$-$C_6$ alkylene)-OC(O)O—($C_1$-$C_6$ alkylene)-$OR^5$, ($C_1$-$C_6$ alkylene)-$NR^6$—($C_1$-$C_6$ alkylene)-$OR^5$, ($C_1$-$C_6$ alkylene)-C(O)$NR^6$—($C_1$-$C_6$ alkylene)-$OR^5$, or ($C_1$-$C_6$ alkylene)-$NR^6$C(O)—($C_1$-$C_6$ alkylene)-$OR^5$, wherein each alkyl, alkenyl, alkynyl, heteroalkyl, or alkylene is optionally substituted with 1-6 $R^7$;
each $R^5$ is independently hydrogen, $C_1$-$C_6$ alkyl, cyclyl, heterocyclyl, aryl, heteroaryl, arylalkyl, heteroarylalkyl, a linker, an agent, a targeting moiety, a protecting group, or a branching point, wherein each alkyl, cyclyl, heterocyclyl, aryl, heteroaryl, arylalkyl, heteroarylalkyl is optionally substituted with 1-6 $R^8$;
$R^6$ is hydrogen or $C_1$-$C_6$ alkyl;
each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, ($C_1$-$C_6$ alkylene)-$OR^5$, ($C_1$-$C_6$ alkylene)-O—($C_1$-$C_6$ alkylene)-$OR^5$, cyano, cyclyl, heterocyclyl, aryl, or heteroaryl; and
each $R^8$ is independently $C_1$-$C_6$ alkyl, $C_2$-$C_6$ alkynyl, $C_1$-$C_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 $R^9$; and
each $R^9$ is independently $C_1$-$C_6$ alkyl, $C_1$-$C_6$ heteroalkyl, halo, cyano, cyclyl, or heterocyclyl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl, wherein each alkylene, heteroalkylene, cyclyl, or heterocyclyl is optionally substituted with 1-6 $R^4$. In some embodiments, $X^1$ is $C_1$-$C_{12}$ alkylene or $C_1$-$C_{12}$ heteroalkylene, optionally substituted with 1-6 $R^4$. In some embodiments, $X^1$ is $C_1$-$C_6$ alkylene, optionally substituted with 1-6 $R^4$. In some embodiments, $X^1$ is $C_1$-$C_{12}$ heteroalkylene, optionally substituted with 1-6 $R^4$.

In some embodiments, $X^1$ is $C_3$-$C_8$ cyclyl or $C_3$-$C_8$ heterocyclyl, wherein each cyclyl or heterocyclyl is optionally substituted with 1-6 $R^4$. In some embodiments, $X^1$ is $C_3$-$C_6$ cyclyl or $C_3$-$C_6$ heterocyclyl, wherein each cyclyl or heterocyclyl is optionally substituted with 1-6 $R^4$. In some embodiments, $X^1$ is $C_3$-$C_6$ cyclyl, optionally substituted with 1-6 $R^4$. In some embodiments, $X^1$ is cyclopropyl, cyclobutyl, cyclopentyl, or cyclohexyl, each of which is optionally substituted with 1-6 $R^4$. In some embodiments, $X^1$ is cyclopentyl or cyclohexyl, each of which is optionally substituted with 1-6 $R^4$. In some embodiments, $X^1$ is cyclopentyl or cyclohexyl, each of which is optionally substituted with 1-4 $R^4$. In some embodiments, $X^1$ is cyclopentyl or cyclohexyl, each of which is optionally substituted with 1-2 $R^4$, and each $R^4$ is independently $C_1$-$C_6$ alkyl or $OR^5$. In some embodiments, $X^1$ is cyclohexyl substituted with 1 $R^4$. In some embodiments, $X^1$ is cyclohexyl substituted with $OR^5$.

In some embodiments, $R^5$ is hydrogen, $C_1$-$C_6$ alkyl, cyclyl, heterocyclyl, aryl, heteroaryl, arylalkyl, or heteroarylalkyl. In some embodiments, $R^5$ is hydrogen. In some embodiments, $R^5$ is arylalkyl or heteroarylalkyl. In some embodiments, $R^5$ is a linker. In some embodiments, $R^5$ is an agent (e.g., an ARB). In some embodiments, $R^5$ is a targeting moiety. In some embodiments, $R^5$ is a protecting group. In some embodiments, $R^5$ is a branching point.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol)ethane and the polymer of Formula (I) is greater than about 10 kDa in size.

In some embodiments, each of $A^1$ and $A^2$ independently includes, or is independently derived from, tri(methylol)ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments of a polymer of Formula (I), each of $A^1$ and $A^2$ is independently hydrophobic. In some embodiments, each of $A^1$ and $A^2$ has a partition coefficient (c Log P) value greater than about −2.0. In some embodiments, each of $A^1$ and $A^2$ has a c Log P value greater than about −1.5, e.g., about −1.4, about −1.3, about −1.2, about −1.1, about −1.0, about −0.9, about −0.8, about −0.7, about −0.6, about −0.5, about −0.4, about −0.3, about −0.2, about −0.1, about 0, or higher. In some embodiments, each of $A^1$ and $A^2$ has a c Log P value between about −2.0 and 2.5. In some embodiments, each of $A^1$ and $A^2$ has a c Log P value greater than about −0.5, e.g., about −0.4, about −0.3, about −0.2, about −0.1, about 0, about 0.1, about 0.2, about 0.3, about 0.4, about 0.5, or higher. In some embodiments, each of $A^1$ and $A^2$ has a c Log P value greater than about 0, e.g., about 0.1, about 0.2, about 0.3, about 0.4, about 0.5, about 0.6, about 0.7, about 0.8, about 0.9, about 1.0, or higher. In some embodiments, each of $A^1$ and $A^2$ has a c Log P value between about −2.0 and 4.0.

In some embodiments, each of $A^1$ and $A^2$ has a linear structure. In some embodiments, each of $A^1$ and $A^2$ has a branched structure. In some embodiments, each of $A^1$ and $A^2$ comprises a protected reactive group, e.g., a protected hydroxyl, a protected carboxylic acid, or a protected amine. In some embodiments, each of $A^1$ and $A^2$ comprises 1, 2, 3, 4, 5, 6, 7, 8, or more protected reactive groups, e.g., a protected hydroxyl, a protected carboxylic acid, or a protected amine.

In some embodiments, each of $A^1$ and $A^2$ is represented by a compound of Formula (II-a):

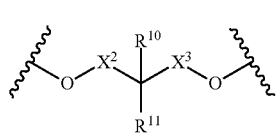

Formula (II-a)

wherein:
each of $X^2$ and $X^3$ is independently $C_1$-$C_6$ alkylene, $C_2$-$C_6$ alkenylene, $C_2$-$C_{12}$ alkynylene, $C_1$-$C_{12}$ heteroalkylene, $C_3$-$C_8$ cyclyl, $C_3$-$C_8$ heterocyclyl, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), ($C_1$-$C_6$ alkylene)-NR$^{13}$—($C_1$-$C_6$ alkylene), ($C_1$-$C_6$ alkylene)-C(O)NR$^{13}$—($C_1$-$C_6$ alkylene), or ($C_1$-$C_6$ alkylene)-NR$^{13}$C(O)—($C_1$-$C_6$ alkylene), wherein each alkylene, alkenylene, alkynylene, heteroalkylene, cyclyl, or heterocyclyl is optionally substituted with 1-6 $R^{12}$;

$R^{10}$ is $C_1$-$C_6$ alkyl, $C_2$-$C_6$ alkenyl, $C_2$-$C_6$ alkynyl, $C_1$-$C_6$ heteroalkyl, OR$^{14}$, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-C(O)—($C_1$-$C_6$ alkylene)-OR$^{14}$, ($C_1$-$C_6$ alkylene)-OC(O)—($C_1$-$C_6$ alkylene)-OR$^{14}$, ($C_1$-$C_6$ alkylene)-C(O)O—($C_1$-$C_6$ alkylene)-OR$^{14}$, ($C_1$-$C_6$ alkylene)-OC(O)O—($C_1$-$C_6$ alkylene)-OR$^{14}$, ($C_1$-$C_6$ alkylene)-NR$^{13}$—($C_1$-$C_6$ alkylene)-OR$^{14}$, ($C_1$-$C_6$ alkylene)-C(O)NR$^{13}$—($C_1$-$C_6$ alkylene)-OR$^{14}$, or ($C_1$-$C_6$ alkylene)-NR$^{13}$C(O)—($C_1$-$C_6$ alkylene)-OR$^{14}$, wherein each alkyl, alkenyl, alkynyl, heteroalkyl, or alkylene is optionally substituted with 1-6 $R^{15}$;

$R^{11}$ is hydrogen, $C_1$-$C_6$ alkyl, $C_2$-$C_6$ alkenyl, $C_2$-$C_6$ alkynyl, $C_1$-$C_6$ heteroalkyl, OR$^{14}$, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-C(O)—($C_1$-$C_6$ alkylene)-OR$^{14}$, ($C_1$-$C_6$ alkylene)-OC(O)—($C_1$-$C_6$ alkylene)-OR$^{14}$, ($C_1$-$C_6$ alkylene)-C(O)O—($C_1$-$C_6$ alkylene)-OR$^{14}$, ($C_1$-$C_6$ alkylene)-OC(O)O—($C_1$-$C_6$ alkylene)-OR$^{14}$, ($C_1$-$C_6$ alkylene)-NR$^{13}$—($C_1$-$C_6$ alkylene)-OR$^{14}$, ($C_1$-$C_6$ alkylene)-C(O)NR$^{13}$—($C_1$-$C_6$ alkylene)-OR$^{14}$, or ($C_1$-$C_6$ alkylene)-NR$^{13}$C(O)—($C_1$-$C_6$ alkylene)-OR$^{14}$, wherein each alkyl, alkenyl, alkynyl, heteroalkyl, or alkylene is optionally substituted with 1-6 $R^{15}$;

each $R^{12}$ and $R^{15}$ is independently $C_1$-$C_6$ alkyl, $C_2$-$C_6$ alkenyl, $C_2$-$C_6$ alkynyl, $C_1$-$C_6$ heteroalkyl, halo, OR$^{14}$, ($C_1$-$C_6$ alkylene)-OR$^{14}$, ($C_1$-$C_6$ alkylene)-O—($C_1$-$C_6$ alkylene)-OR$^{14}$, cyano, cyclyl, heterocyclyl, aryl, or heteroaryl;

$R^{13}$ is hydrogen or $C_1$-$C_6$ alkyl;

$R^{14}$ is hydrogen, $C_1$-$C_6$ alkyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^{16}$, and each $R^{16}$ is independently $C_1$-$C_6$ alkyl, $C_1$-$C_6$ heteroalkyl, halo, cyano, cyclyl, or heterocyclyl.

In some embodiments, each of $X^2$ and $X^3$ is independently $C_1$-$C_6$ alkylene, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), wherein each alkyl or alkylene is optionally substituted with 1-6 $R^8$. In some embodiments, each of $X^1$ and $X^2$ is independently $C_1$-$C_4$ alkyl, ($C_1$-$C_4$ alkylene)-O—($C_1$-$C_4$ alkylene), ($C_1$-$C_4$ alkylene)-C(O)—($C_1$-$C_4$ alkylene), ($C_1$-$C_4$ alkylene)-OC(O)—($C_1$-$C_4$ alkylene), ($C_1$-$C_4$ alkylene)-C(O)O—($C_1$-$C_4$ alkylene), ($C_1$-$C_4$ alkylene)-OC(O)O—($C_1$-$C_4$ alkylene), wherein each alkyl or alkylene is optionally substituted with 1-6 $R^{12}$.

In some embodiments, each of $X^2$ and $X^3$ is independently $C_1$-$C_2$ alkylene, e.g., $CH_2$, $CH_2CH_2$. In some embodiments, each of $X^2$ and $X^3$ is independently ($C_1$-$C_4$ alkylene)-O—($C_1$-$C_4$ alkylene), e.g., $CH_2$—O—$CH_2CH_2$, $CH_2CH_2$—O—$CH_2CH_2$. In some embodiments, each of $X^1$ and $X^2$ is independently ($C_1$-$C_4$ alkylene)-OC(O)—($C_1$-$C_4$ alkylene), e.g., $CH_2$—OC(O)—$CH_2$, $CH_2$—OC(O)—$CH_2CH_2$, $CH_2$—OC(O)—$CH(CH_3)$, $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—$CH(CH_3)$. In some embodiments, each of $X^2$ and $X^3$ is independently ($C_1$-$C_4$ alkylene)-OC(O)O—($C_1$-$C_4$ alkylene), e.g., $CH_2$—OC(O)O—$CH_2CH_2$). In some embodiments, each of $X^2$ and $X^3$ is the same.

In some embodiments, $R^{10}$ is $C_1$-$C_6$ alkyl, ($C_1$-$C_6$ alkylene)-$OR^{14}$, ($C_1$-$C_6$ alkylene)-O—($C_1$-$C_6$ alkylene)-$OR^{14}$, ($C_1$-$C_6$ alkylene)-OC(O)—($C_1$-$C_6$ alkylene)-$OR^{14}$, ($C_1$-$C_6$ alkylene)-OC(O)O—($C_1$-$C_6$ alkylene)-$OR^{14}$, wherein each alkyl or alkylene is optionally substituted with 1-6 $R^{15}$. In some embodiments, $R^{10}$ is $C_1$-$C_6$ alkyl, e.g., $CH_3$, $CH_2CH_3$. In some embodiments, $R^{10}$ is ($C_1$-$C_6$ alkylene)-$OR^{14}$, e.g., $CH_2OR^{14}$, $CH_2CH_2OR^{14}$. In some embodiments, $R^{10}$ is ($C_1$-$C_6$ alkylene)-O—($C_1$-$C_6$ alkylene)-$OR^{14}$, In some embodiments, $R^{10}$ is ($C_1$-$C_6$ alkylene)-OC(O)—($C_1$-$C_6$ alkylene)-$OR^{14}$, e.g., $CH_2$—OC(O)—$CH_2$, $CH_2$—OC(O)—$CH_2CH_2$, $CH_2$—OC(O)—CH($CH_3$), $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—CH($CH_3$). In some embodiments, $R^{10}$ is ($C_1$-$C_4$ alkylene)-OC(O)O—($C_1$-$C_4$ alkylene), e.g., $CH_2$—OC(O)O—$CH_2CH_2$).

In some embodiments, $R^{11}$ is hydrogen or $C_1$-$C_6$ alkyl. In some embodiments, $R^{11}$ is hydrogen. In some embodiments, $R^{11}$ is $C_1$-$C_6$ alkyl. In some embodiments, $R^{11}$ is $C_1$-$C_4$ alkyl, e.g., $CH_3$, $CH_2CH_3$. In some embodiments. $R^{11}$ is ($C_1$-$C_6$ alkylene)-$OR^{14}$, e.g., $CH_2OR^{14}$, $CH_2CH_2OR^{14}$.

In some embodiments, $R^{14}$ is hydrogen, $C_1$-$C_6$ alkyl, cyclyl, heterocyclyl, aryl, heteroaryl, arylalkyl, or heteroarylalkyl. In some embodiments, $R^{14}$ is hydrogen. In some embodiments, $R^{14}$ is arylalkyl or heteroarylalkyl. In some embodiments, $R^{14}$ is a linker. In some embodiments, $R^{14}$ is an agent (e.g., an ARB). In some embodiments, $R^{14}$ is a targeting moiety. In some embodiments, $R^{14}$ is a protecting group. In some embodiments, $R^{14}$ is a branching point.

In some embodiments, each of $A^1$ and $A^2$ does not independently include, or is not independently derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol) ethane and the polymer of Formula (I) is greater than about 10 kDa in size.

In some embodiments, each of $A^1$ and $A^2$ independently includes, or is independently derived from, tri(methylol) ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments, the agent is a therapeutic or a diagnostic agent as described herein. In some embodiments, the agent is an AHCM as described herein. In some embodiments, the agent is an ARB as described herein, e.g., losartan, valsartan, telmisartan, candesartan, eprosartan, irbesartan, azilsartan, EXP-3174, olmesartan, or a prodrug or active metabolite thereof, e.g., a compound shown in FIG. 23.

In some embodiments, the agent is a vitamin D analog or derivative as described herein. In some embodiments, the agent is a vitamin D analog or derivative as described herein, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, ercalcitriol, EB1089 (seocalcitol), BXL-628 (elocalcitol), MC1288, CB966, BCB 1093, GS1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and analogs and derivatives thereof, e.g., as shown in FIG. 24.

In some embodiments, the agent is a bromodomain and extra-terminal protein inhibitor (i-BET) as described herein. In some embodiments, the agent is a bromodomain and extra-terminal protein inhibitor (i-BET) as described herein, e.g MS436, PFI-1, I-BET 151, OTX-015, JQ1, CPI-203, bromosporine, RVX-208, I-BET 762, I-BET 151, OFXBD02, OFXBD03, XD14, AZD5153, and analogs and derivatives thereof, e.g., as shown in FIGS. 25A and 25B.

In some embodiments, the agent is an IDO inhibitor (i.e., indoleamine 2,3-dioxygenase (IDO) pathway inhibitor) as described herein. In some embodiments, the agent is an IDO inhibitor as described herein, e.g., GDC-0919, indoximod, 1-methyltryptophan (e.g., 1-methyl-L-tryptophan, 1-methyl-D-tryptophan), NLG8189, INCB024360, NLG919, methyl-thiohydantoin tryptophan, brassinin, annulin B, exiguamine A, INCB023843, or an analog or derivative thereof.

In some embodiments, each of $A^1$ and $A^2$ is represented by a compound of Formula (II-b):

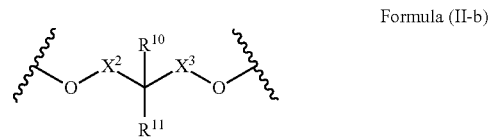

Formula (II-b)

wherein:
each of $X^2$ and $X^3$ is independently $C_1$-$C_6$ alkylene, ($C_1$-$C_6$ alkylene)-O—($C_1$-$C_6$ alkylene), ($C_1$-$C_6$ alkylene)-OC(O)—($C_1$-$C_6$ alkylene), or ($C_1$-$C_6$ alkylene)-OC(O)O—($C_1$-$C_6$ alkylene);

$R^{10}$ is $C_1$-$C_6$ alkyl, ($C_1$-$C_6$ alkylene)-$OR^{14}$, ($C_1$-$C_6$ alkylene)-O—($C_1$-$C_6$ alkylene)-$OR^{14}$, ($C_1$-$C_6$ alkylene)-OC(O)—($C_1$-$C_6$ alkylene)-$OR^{14}$, or ($C_1$-$C_6$ alkylene)-OC(O)O—($C_1$-$C_6$ alkylene)-$OR^{14}$, wherein each alkylene is optionally substituted with 1-4 ($C_1$-$C_6$ alkylene)-$OR^{14}$;

$R^{11}$ is hydrogen, $C_1$-$C_6$ alkyl, or ($C_1$-$C_6$ alkylene)-$OR^{14}$; and $R^{14}$ is hydrogen, $C_1$-$C_6$ alkyl, cyclyl, heterocyclyl, aryl, heteroaryl, arylalkyl, heteroarylalkyl, a linker, an agent, a targeting moiety, a protecting group, or a branching point.

In some embodiments, each of $X^2$ and $X^3$ is independently $C_1$-$C_2$ alkylene, e.g., $CH_2$, $CH_2CH_2$. In some embodiments, each of $X^2$ and $X^3$ is independently ($C_1$-$C_4$ alkylene)-O—($C_1$-$C_4$ alkylene), e.g., $CH_2$—O—$CH_2CH_2$, $CH_2CH_2$—O—$CH_2CH_2$. In some embodiments, each of $X^1$ and $X^2$ is independently ($C_1$-$C_4$ alkylene)-OC(O)—($C_1$-$C_4$ alkylene), e.g., $CH_2$—OC(O)—$CH_2$, $CH_2$—OC(O)—$CH_2CH_2$, $CH_2$—OC(O)—CH($CH_3$), $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—CH($CH_3$). In some embodiments, each of $X^2$ and $X^3$ is independently ($C_1$-$C_4$ alkylene)-OC(O)O—($C_1$-$C_4$ alkylene), e.g., $CH_2$—OC(O)O—$CH_2CH_2$). In some embodiments, each of $X^2$ and $X^3$ is the same.

In some embodiments, $R^{10}$ is $C_1$-$C_6$ alkyl, e.g., $CH_3$, $CH_2CH_3$. In some embodiments, $R^{10}$ is ($C_1$-$C_6$ alkylene)-$OR^{14}$, e.g., $CH_2OR^{14}$, $CH_2CH_2OR^{14}$. In some embodiments, $R^{10}$ is ($C_1$-$C_6$ alkylene)-O—($C_1$-$C_6$ alkylene)-$OR^{14}$, In some embodiments, $R^{10}$ is ($C_1$-$C_6$ alkylene)-OC(O)—($C_1$-$C_6$ alkylene)-$OR^{14}$, e.g., $CH_2$—OC(O)—$CH_2$, $CH_2$—OC(O)—$CH_2CH_2$, $CH_2$—OC(O)—CH($CH_3$), $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—CH($CH_3$). In some embodiments, $R^{10}$ is $(C_1-C_4$ alkylene)-OC(O)O—$(C_1-C_4$ alkylene), e.g., $CH_2$—OC(O)O—$CH_2CH_2$).

In some embodiments, $R^{11}$ is hydrogen or $C_1-C_6$ alkyl. In some embodiments, $R^{11}$ is hydrogen. In some embodiments, $R^{11}$ is $C_1-C_6$ alkyl. In some embodiments, $R^{11}$ is $C_1-C_4$ alkyl, e.g., $CH_3$, $CH_2CH_3$. In some embodiments, $R^{11}$ is $(C_1-C_6$ alkylene)-$OR^{14}$, e.g., $CH_2OR^{14}$, $CH_2CH_2OR^{14}$.

In some embodiments, $R^{14}$ is hydrogen, $C_1-C_6$ alkyl, cyclyl, heterocyclyl, aryl, heteroaryl, arylalkyl, or heteroarylalkyl. In some embodiments, $R^{14}$ is hydrogen. In some embodiments, $R^{14}$ is arylalkyl or heteroarylalkyl. In some embodiments, $R^{14}$ is a linker. In some embodiments, $R^{14}$ is an agent (e.g., an ARB). In some embodiments, $R^{14}$ is a targeting moiety. In some embodiments, $R^{14}$ is a protecting group. In some embodiments, $R^{14}$ is a branching point.

In some embodiments, each of $A^1$ and $A^2$ is the same. In some embodiments, each of $A^1$ and $A^2$ is the same, e.g., the same compound of Formula (II), Formula (II-a), or Formula (II-b). In some embodiments, each of $A^1$ and $A^2$ is different. In some embodiments, each of $A^1$ and $A^2$ is the different, e.g., a different compound of Formula (II), Formula (II-a), or Formula (II-b).

In some embodiments, the precursor of each of $A^1$ and $A^2$ is independently selected from the following polyols:

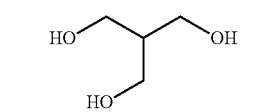
A1

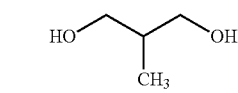
A2

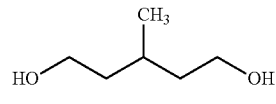
A3

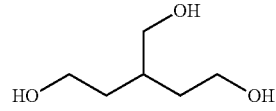
A4

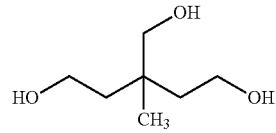
A5

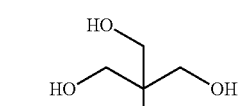
A6

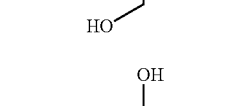
A7

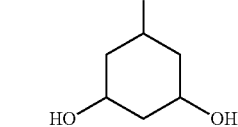
A8

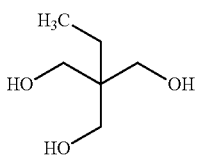
A8

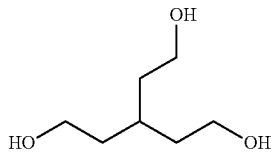
A9

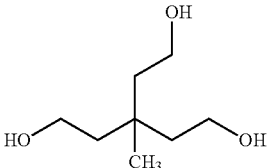
A10

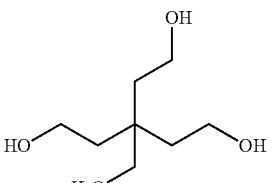
A11

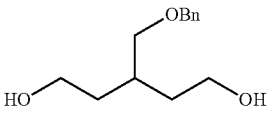
A12

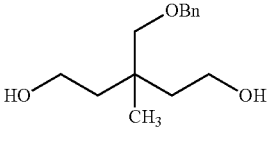
A13

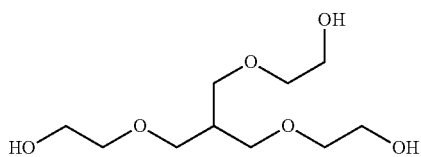
A14

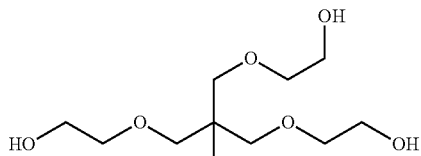
A15

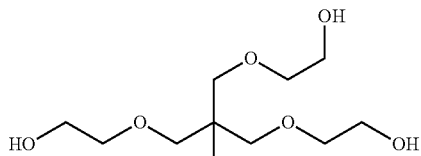
A16

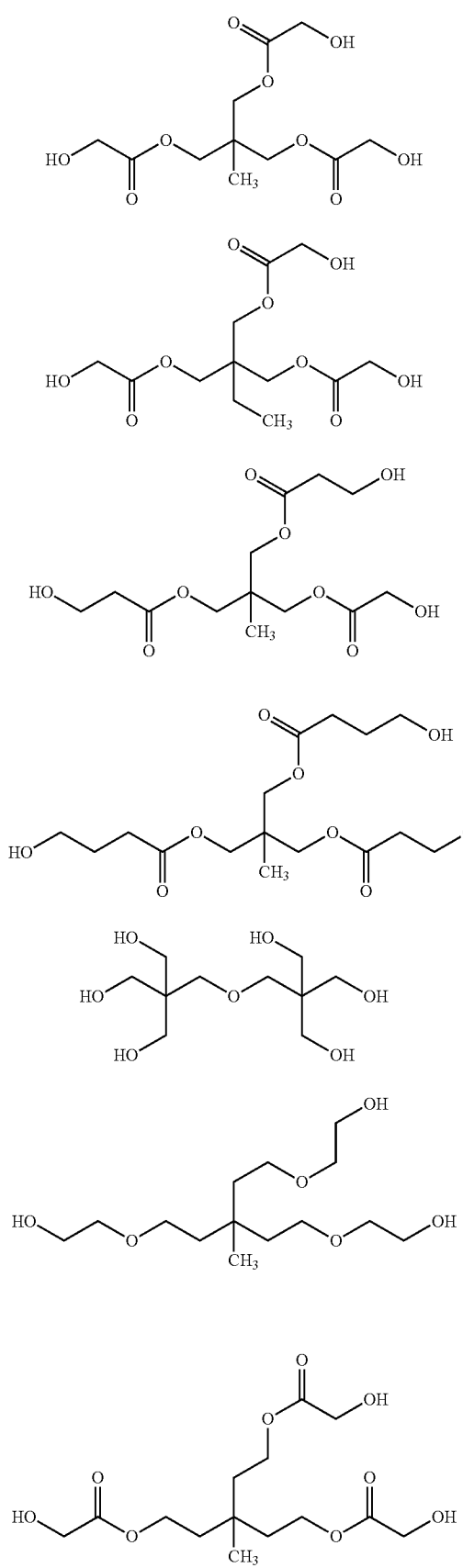
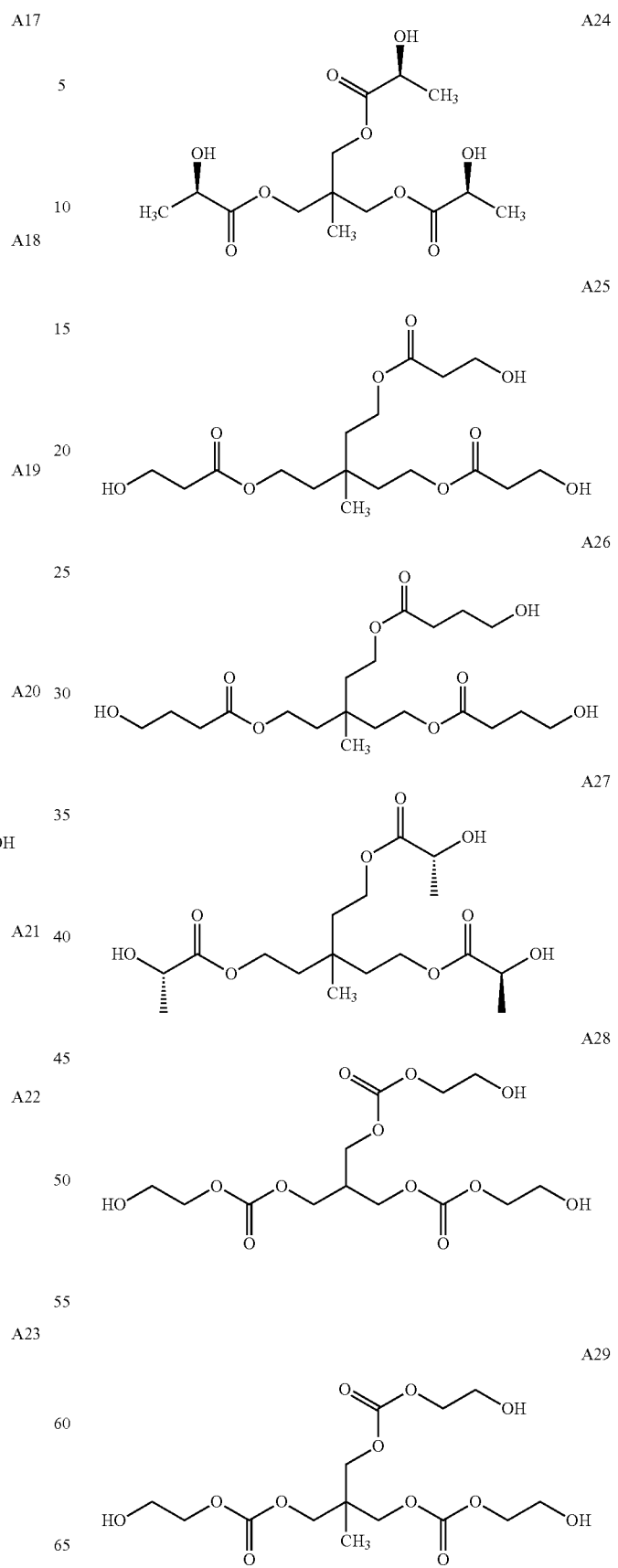

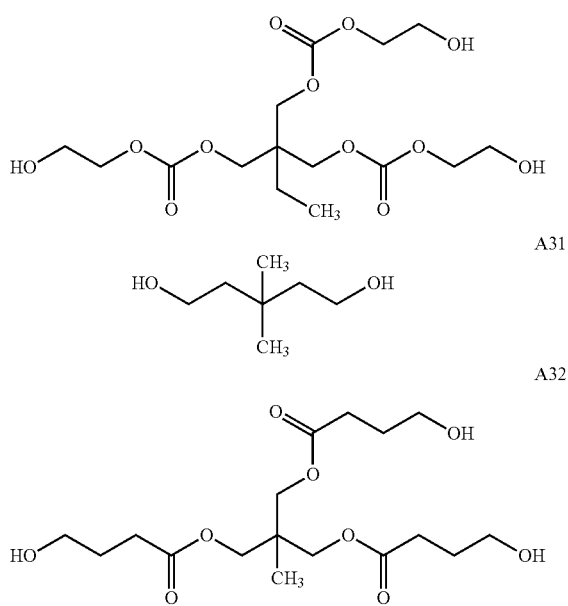

A30

A31

A32

In some embodiments, the precursor to each of $A^1$ and $A^2$ is independently selected from one of A1, A2, A3, A4, A5, A6, A7, A8, A9, A10, A11, A12, A13, A4, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, $X^1$ includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, each of $A^1$ and $A^2$ is represented by a compound of Formula (II-c):

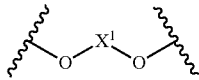

Formula (II-c)

wherein:

$X^1$ includes or is derived from any of the polyols shown in FIG. 1B, e.g., a polyol selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, $X^1$ includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, $X^1$ includes or is derived from A1. In some embodiments, $X^1$ includes or is derived from A2. In some embodiments, $X^1$ includes or is derived from A3. In some embodiments, $X^1$ includes or is derived from A4. In some embodiments, $X^1$ includes or is derived from A5. In some embodiments, $X^1$ includes or is derived from A6. In some embodiments, $X^1$ includes or is derived from A7. In some embodiments, $X^1$ includes or is derived from A8. In some embodiments, $X^1$ includes or is derived from A9. In some embodiments, $X^1$ includes or is derived from A10. In some embodiments, $X^1$ includes or is derived from A11. In some embodiments, $X^1$ includes or is derived from A12. In some embodiments, $X^1$ includes or is derived from A13. In some embodiments, $X^1$ includes or is derived from A14. In some embodiments, $X^1$ includes or is derived from A15. In some embodiments, $X^1$ includes or is derived from A16. In some embodiments, $X^1$ includes or is derived from A17. In some embodiments, $X^1$ includes or is derived from A18. In some embodiments, $X^1$ includes or is derived from A19. In some embodiments, $X^1$ includes or is derived from A20. In some embodiments, $X^1$ includes or is derived from A21. In some embodiments, $X^1$ includes or is derived from A22. In some embodiments, $X^1$ includes or is derived from A23. In some embodiments, $X^1$ includes or is derived from A24. In some embodiments, $X^1$ includes or is derived from A25. In some embodiments, $X^1$ includes or is derived from A26. In some embodiments, $X^1$ includes or is derived from A27. In some embodiments, $X^1$ includes or is derived from A28. In some embodiments, $X^1$ includes or is derived from A29. In some embodiments, $X^1$ includes or is derived from A30. In some embodiments, $X^1$ includes or is derived from A31. In some embodiments, $X^1$ includes or is derived from A32.

In some embodiments, each of $A^1$ and $A^2$ includes or is derived from the same polyol, e.g., a polyol selected from one of A1-A32. In some embodiments, each of $A^1$ and $A^2$ includes or is derived from a different polyol, e.g., a polyol selected from one of A1-A32.

In some embodiments, one or both of $A^1$ and $A^2$ is represented by a compound of Formula (II-d):

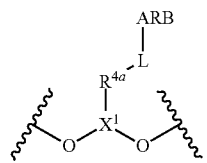

Formula (II-d)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl or ($C_1$-$C_6$ alkylene)-O-L-ARB;

L is a bond or a linker, e.g., a linker as described herein;

ARB is an angiotensin II receptor blocker, e.g., losartan, valsartan, telmisartan, candesartan, eprosartan, irbesartan, azilsartan, EXP-3174, olmesartan, or a prodrug or active metabolite thereof;

$R^6$ is hydrogen or $C_1$-$C_6$ alkyl; and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-ARB, ($C_1$-$C_6$ alkylene)-O-L-ARB, ($C_1$-$C_6$ alkylene)-O—($C_1$-$C_6$ alkylene)-O-L-ARB, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-ARB, e.g., ($CH_2$—O-L-ARB).

In some embodiments, L is a bond. In some embodiments, L is a linker. In some embodiments, L is a linker as described herein, e.g., a polyacetal polymer.

In some embodiments, ARB is losartan, valsartan, telmisartan, candesartan, eprosartan, irbesartan, azilsartan, EXP-3174, olmesartan, or a prodrug or active metabolite thereof. In some embodiments, ARB is losartan. In some embodiments, ARB is valsartan. In some embodiments, ARB is telmisartan. In some embodiments, ARB is candesartan. In some embodiments, ARB is eprosartan. In some embodiments, ARB is azilsartan. In some embodiments, ARB is EXP-3174. In some embodiments, ARB is olmesartan. In some embodiments, ARB is azilsartan medoxomil. In some embodiments, ARB is candesartan cilexetil. In some embodiments, ARB is olmesartan medoxomil. In some embodiments, ARB is a compound shown in FIG. 23.

In some embodiments, one or both of $A^1$ and $A^2$ is represented by a compound of Formula (II-e), Formula (II-f), Formula (II-g), Formula (II-h), or Formula (II-i):

Formula (II-e)

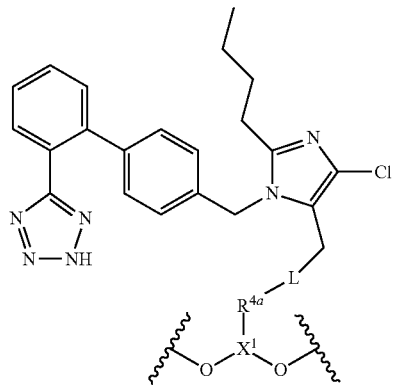

Formula (II-f)

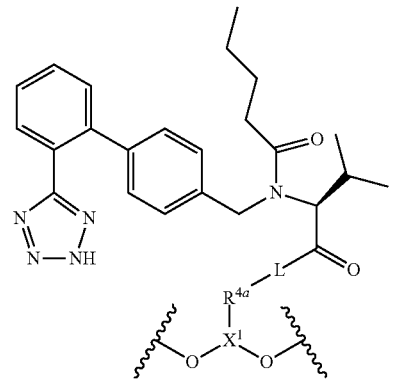

Formula (II-g)

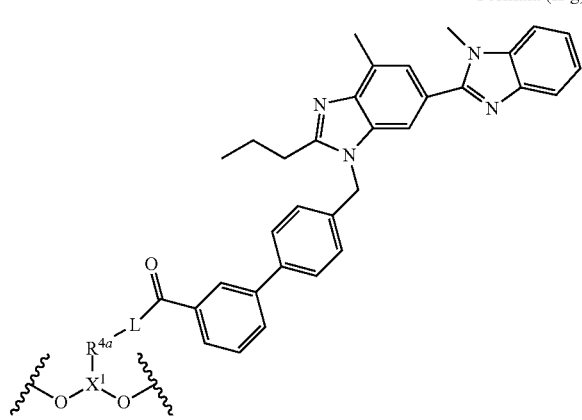

-continued

Formula (II-h)

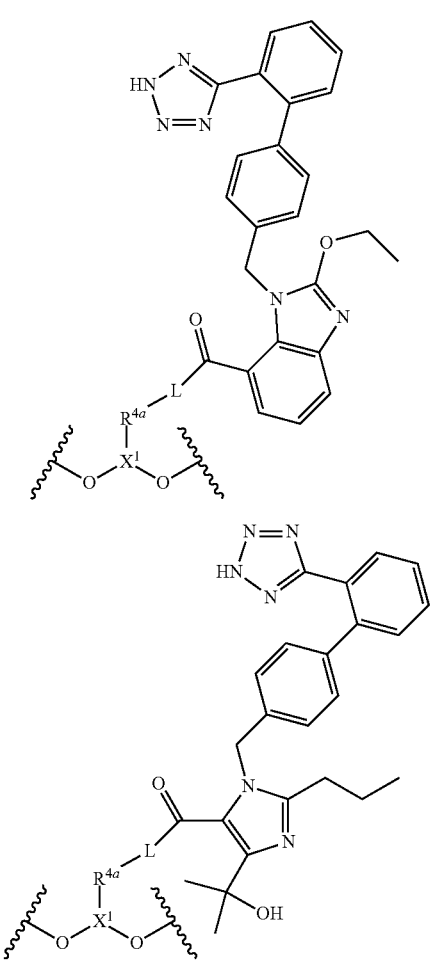

Formula (II-i)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl, ($C_1$-$C_6$ alkylene)-O-L-losartan, ($C_1$-$C_6$ alkylene)-O-L-valsartan, ($C_1$-$C_6$ alkylene)-O-L-telmisartan, ($C_1$-$C_6$ alkylene)-O-L-candesartan, or ($C_1$-$C_6$ alkylene)-O-L-olmesartan;

L is a linker, e.g., a linker as described herein;

$R^6$ is hydrogen or $C_1$-$C_6$ alkyl; and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-losartan, O-L-valsartan, O-L-telmisartan, O-L-candesartan, O-L-olmesartan, ($C_1$-$C_6$ alkylene)-O-L-losartan, ($C_1$-$C_6$ alkylene)-O-L-valsartan, ($C_1$-$C_6$ alkylene)-O-L-telmisartan, ($C_1$-$C_6$ alkylene)-O-L-candesartan, ($C_1$-$C_6$ alkylene)-O-L-olmesartan, ($C_1$-$C_6$ alkylene)-O—($C_1$-$C_6$ alkylene)-O-L-losartan, ($C_1$-$C_6$ alkylene)-O—($C_1$-$C_6$ alkylene)-O-L-valsartan, ($C_1$-$C_6$ alkylene)-O—($C_1$-$C_6$ alkylene)-O-L-telmisartan, ($C_1$-$C_6$ alkylene)-O—($C_1$-$C_6$ alkylene)-O-L-candesartan, ($C_1$-$C_6$ alkylene)-O—($C_1$-$C_6$ alkylene)-O-L-olmesartan, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-losartan, e.g., ($CH_2$—O-L-losartan). In some embodiments, $R^{4b}$ is ($C_1$-$C_6$ alkylene)-O-L-valsartan, e.g., ($CH_2$—O-L-valsartan). In some embodiments, $R^{4b}$ is ($C_1$-$C_6$ alkylene)-O-L-telmisartan, e.g., ($CH_2$—O-L-telmisartan). In some embodiments, $R^{4b}$ is ($C_1$-$C_6$ alkylene)-O-L-candesartan, e.g., ($CH_2$—O-L-candesartan). In some embodiments, $R^{4b}$ is ($C_1$-$C_6$ alkylene)-O-L-olmesartan, e.g., ($CH_2$—O-L-olmesartan).

In some embodiments, L is a bond. In some embodiments, L is a linker. In some embodiments, L is a linker as described herein, e.g., a polyacetal polymer.

In some embodiments, one or both of $A^1$ and $A^2$ is represented by a compound of Formula (II-j):

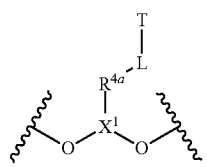

Formula (II-j)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl, ($C_1$-$C_6$ alkylene)-O-L-T, or ($C_1$-$C_6$ alkylene)-O-L-ARB;

L is a bond or a linker, e.g., a linker as described herein;

T is a targeting moiety, e.g., mannose-6-phosphate;

ARB is an angiotensin II receptor blocker, e.g., losartan, valsartan, telmisartan, candesartan, eprosartan, irbesartan, azilsartan, EXP-3174, olmesartan, or an analog or a derivative thereof (e.g., a prodrug or active metabolite thereof);

$R^6$ is hydrogen or $C_1$-$C_6$ alkyl, and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-T, ($C_1$-$C_6$ alkylene)-O-L-T, ($C_1$-$C_6$ alkylene)-O—($C_1$-$C_6$ alkylene)-O-L-T, O-L-ARB, ($C_1$-$C_6$ alkylene)-O-L-ARB, ($C_1$-$C_6$ alkylene)-O—($C_1$-$C_6$ alkylene)-O-L-ARB, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-T, e.g., ($CH_2$—O-L-T). In some embodiments, $R^{4b}$ is ($C_1$-$C_6$ alkylene)-O-L-ARB, e.g., ($CH_2$—O-L-ARB).

In some embodiments, L is a bond. In some embodiments, L is a linker. In some embodiments, L is a linker as described herein, e.g., a polyacetal polymer.

In some embodiments, T is a targeting moiety described herein. In some embodiments, T is mannose-6-phosphate.

In some embodiments, ARB is losartan, valsartan, telmisartan, candesartan, eprosartan, irbesartan, azilsartan, EXP- 3174, olmesartan, or an analog or a derivative thereof (e.g., a prodrug or active metabolite thereof). In some embodiments, ARB is losartan. In some embodiments, ARB is valsartan. In some embodiments, ARB is telmisartan. In some embodiments, ARB is candesartan. In some embodiments, ARB is eprosartan. In some embodiments, ARB is azilsartan. In some embodiments, ARB is EXP-3174. In some embodiments, ARB is olmesartan. In some embodiments, ARB is azilsartan medoxomil. In some embodiments, ARB is candesartan cilexetil. In some embodiments, ARB is olmesartan medoxomil. In some embodiments, ARB is a compound shown in FIG. 23.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol) ethane and the polymer of Formula (I) is greater than about 10 kDa in size.

In some embodiments, each of $A^1$ and $A^2$ independently includes, or is independently derived from, tri(methylol) ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments of a polymer of Formula (I), each of $B^1$ and $B^2$ is independently heteroalkyl or aryloxy, each of which may be optionally substituted with 1-5 $R^1$. In some embodiments, each of $B^1$ and $B^2$ is independently heteroalkyl, each of which may be optionally substituted with 1-5 $R^1$. In some embodiments, each of $B^1$ and $B^2$ is independently $C_1$-$C_{20}$ heteroalkyl, each of which may be optionally substituted with 1-5 $R^1$. In some embodiments, each of $B^1$ and $B^2$ is the same. In some embodiments, each of $B^1$ and $B^2$ is the different.

In some embodiments, each of $B^1$ and $B^2$ is independently represented by a moiety of Formula (III):

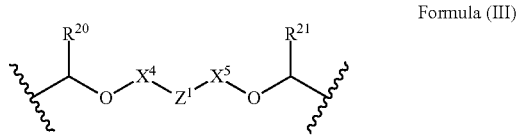

Formula (III)

wherein:

$Z^1$ is O, $C_3$-$C_8$ cyclyl, $C_3$-$C_8$ heterocyclyl, or $C(R^{22})(R^{23})$, wherein each of cyclyl and heterocyclyl is optionally substituted with 1-4 $R^{25}$;

each of $X^4$ and $X^5$ is independently $C_1$-$C_6$ alkylene, $C_2$-$C_6$ alkenylene, $C_2$-$C_6$ alkynylene, $C_1$-$C_6$ heteroalkylene. ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), ($C_1$-$C_6$ alkylene)-NR$^{24}$—($C_1$-$C_6$ alkylene), ($C_1$-$C_6$ alkylene)-C(O)NR$^{24}$—($C_1$-$C_6$ alkylene), or ($C_1$-$C_6$ alkylene)-NR$^{24}$C(O)—($C_1$-$C_6$ alkylene), wherein each alkylene, alkenylene, alkynylene, or heteroalkylene is optionally substituted with 1-6 $R^{25}$;

each of $R^{20}$ and $R^{21}$ is independently $C_1$-$C_6$ alkyl, $OR^{26}$, cyclyl, heterocyclyl;

each of $R^{22}$ and $R^{23}$ is independently hydrogen, $C_1$-$C_6$ alkyl, $OR^{26}$, ($C_1$-$C_6$ alkylene)-$OR^{26}$, halo, cyclyl, heterocyclyl, aryl, heteroaryl, wherein each alkyl, alkylene, cyclyl, heterocyclyl, aryl, or heteroaryl is optionally substituted with 1-6 $R^{27}$;

each $R^{25}$ and $R^{27}$ is $C_1$-$C_6$ alkyl, $C_1$-$C_6$ heteroalkyl, halo, cyano, cyclyl, or heterocyclyl, and $R^{26}$ is hydrogen, $C_1$-$C_6$ alkyl, $C_1$-$C_6$ alkenyl, $C_1$-$C_6$ alkynyl, cyclyl, heterocyclyl, aryl, heteroaryl, arylalkyl, heteroarylalkyl, a linker, an agent, a targeting moiety, a protecting group, or a branching point, wherein each alkyl, cyclyl, heterocyclyl, aryl, heteroaryl, arylalkyl, heteroarylalkyl is optionally substituted with 1-6 $R^{28}$; and each $R^{28}$ is independently $C_1$-$C_6$ alkyl, $C_1$-$C_6$ heteroalkyl, halo, cyano, cyclyl, or heterocyclyl.

In some embodiments, $Z^1$ is O.

In some embodiments, $Z^1$ is $C_3$-$C_8$ cyclyl or $C_3$-$C_8$ heterocyclyl, each of which is optionally substituted with 1-4 $R^{25}$. In some embodiments, $Z^1$ is $C_3$-$C_6$ cyclyl or $C_3$-$C_6$ heterocyclyl, each of which is optionally substituted with 1-4 $R^{25}$. In some embodiments, $Z^1$ is $C_3$-$C_6$ cyclyl, optionally substituted with 1-4 $R^{25}$. In some embodiments, $Z^1$ is cyclopropyl, cyclobutyl, cyclopentyl, or cyclohexyl, each of which is optionally substituted with 1-4 $R^{25}$. In some embodiments, $Z^1$ is cyclopentyl, or cyclohexyl, each of which is optionally substituted with 1-4 $R^{25}$. In some embodiments, $Z^1$ is cyclohexyl, optionally substituted with 1-4 $R^{25}$. In some embodiments, $Z^1$ is cyclohexyl.

In some embodiments, $Z^1$ is $C(R^{22})(R^{23})$. In some embodiments, $Z^1$ is $C(R^{23})(R^{24})$ and each of $R^{22}$ and $R^{23}$ is independently hydrogen, $C_1$-$C_6$ alkyl, or ($C_1$-$C_6$ alkylene)-$OR^{26}$. In some embodiments, each of $R^{22}$ and $R^{23}$ is independently hydrogen. In some embodiments, each of $R^{22}$ and $R^{23}$ is independently hydrogen or $C_1$-$C_6$ alkyl, e.g., $CH_3$. In some embodiments, each of $R^{22}$ and $R^{23}$ is independently hydrogen. In some embodiments, each of $R^{22}$ and $R^{23}$ is independently $C_1$-$C_6$ alkyl, e.g., $CH_3$. In some embodiments, $R^{22}$ is hydrogen and $R^{23}$ is independently $C_1$-$C_6$ alkyl, e.g., $CH_3$. In some embodiments, each of $R^{22}$ and $R^{23}$ is independently ($C_1$-$C_6$ alkylene)-$OR^{26}$. In some embodiments, each of $R^{22}$ and $R^{23}$ is independently ($C_1$-$C_2$ alkylene)-$OR^{26}$. In some embodiments, each of $R^{22}$ and $R^{23}$ is independently ($C_1$-$C_2$ alkylene)-$OR^{26}$, and $R^{26}$ is $C_2$-$C_6$ alkenyl (e.g., $CH\!=\!CH_2$) or a branching point. In some embodiments, $R^{22}$ is hydrogen or $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH\!=\!CH_2$) or a branching point. In some embodiments, $R^{22}$ is $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH\!=\!CH_2$) or a branching point.

In some embodiments, each of $X^4$ and $X^5$ is independently $C_1$-$C_6$ alkylene, wherein alkylene is optionally substituted with 1-6 $R^{25}$. In some embodiments, each of $X^4$ and $X^5$ is independently $C_1$-$C_4$ alkylene, wherein alkylene is optionally substituted with 1-6 $R^{25}$. In some embodiments, each of $X^4$ and $X^5$ is independently $C_1$-$C_2$ alkylene, wherein alkylene is optionally substituted with 1-6 $R^{25}$. In some embodiments, each of $X^4$ and $X^5$ is independently $C_1$-$C_2$ alkylene (e.g., $CH_2$, $CH_2CH_2$).

In some embodiments, each of $R^{20}$ and $R^{21}$ is independently $C_1$-$C_6$ alkyl or $OR^{26}$. In some embodiments, each of $R^{20}$ and $R^{21}$ is independently $C_1$-$C_6$ alkyl. In some embodiments, each of $R^{20}$ and $R^{21}$ is independently $C_1$-$C_4$ alkyl. In some embodiments, each of $R^{20}$ and $R^{21}$ is independently $C_1$-$C_2$ alkyl, e.g., $CH_3$. In some embodiments, each of $R^{20}$ and $R^{21}$ is independently $OR^{26}$. In some embodiments, each of $R^{20}$ and $R^{21}$ is independently $OR^{26}$, and $R^{26}$ is $C_2$-$C_6$ alkenyl (e.g., $CH\!=\!CH_2$) or a branching point.

In some embodiments of a polymer of Formula (I), each of $B^1$ and $B^2$ is independently hydrophobic. In some embodiments, each of $B^1$ and $B^2$ has a partition coefficient (c Log P) value greater than about −2.0. In some embodiments, each of $B^1$ and $B^2$ has a c Log P value greater than about −1.5, e.g., about −1.4, about −1.3, about −1.2, about −1.1, about −1.0, about −0.9, about −0.8, about −0.7, about −0.6, about −0.5, about −0.4, about −0.3, about −0.2, about −0.1, about 0, or higher. In some embodiments, each of $B^1$ and $B^2$ has a c Log P value between about −2.0 and 4.0. In some embodiments, each of $B^1$ and $B^2$ has a c Log P value greater than about −0.5, e.g., about −0.4, about −0.3, about −0.2, about −0.1, about 0, about 0.1, about 0.2, about 0.3, about 0.4, about 0.5, or higher. In some embodiments, each of $B^1$ and $B^2$ has a c Log P value between about 0 and 4.0. In some embodiments, each of $B^1$ and $B^2$ has a c Log P value greater than about 0, e.g., about 0.1, about 0.2, about 0.3, about 0.4, about 0.5, about 0.6, about 0.7, about 0.8, about 0.9, about 1.0, or higher.

In some embodiments, each of $B^1$ and $B^2$ has a linear structure. In some embodiments, each of $B^1$ and $B^2$ has a branched structure. In some embodiments, each of $B^1$ and $B^2$ comprises a protected reactive group, e.g., a protected hydroxyl, a protected carboxylic acid, or a protected amine. In some embodiments, each of $B^1$ and $B^2$ comprises 1, 2, 3, 4, 5, 6, 7, 8, or more protected reactive groups, e.g., a protected hydroxyl, a protected carboxylic acid, or a protected amine.

In some embodiments, the agent is a therapeutic or a diagnostic agent as described herein. In some embodiments, the agent is an AHCM as described herein. In some embodiments, the agent is an ARB as described herein, e.g., losartan, valsartan, telmisartan, candesartan, eprosartan, irbesartan, azilsartan, EXP-3174, olmesartan, or an analog or a derivative thereof (e.g., a prodrug or active metabolite thereof), e.g., a compound shown in FIG. 23.

In some embodiments, the agent is a vitamin D analog or derivative as described herein. In some embodiments, the agent is a vitamin D analog or derivative as described herein, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, ercalcitriol, EB1089 (seocalcitol), BXL-628 (elocalcitol), MC1288, CB966, BCB 1093, GS 1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and analogs and derivatives thereof, e.g., as shown in FIG. 24.

In some embodiments, the agent is a bromodomain and extra-terminal protein inhibitor (i-BET) as described herein. In some embodiments, the agent is a bromodomain and extra-terminal protein inhibitor (i-BET) as described herein, e.g MS436, PFI-1, I-BET 151, OTX-015, JQ1, CPI-203, bromosporine, RVX-208, I-BET 762, I-BET 151, OFXBD02, OFXBD03, XD14, AZD5153, and analogs and derivatives thereof, e.g., as shown in FIGS. 25A and 25B.

In some embodiments, the agent is an IDO inhibitor (i.e., indoleamine 2,3-dioxygenase (IDO) pathway inhibitor) as described herein. In some embodiments, the agent is an IDO inhibitor as described herein, e.g., GDC-0919, indoximod, 1-methyltryptophan (e.g., 1-methyl-L-tryptophan, 1-methyl-D-tryptophan), NLG8189, INCB024360, NLG919, methyl-thiohydantoin tryptophan, brassinin, annulin B, exiguamine A, INCB023843, or an analog or derivative thereof.

In some embodiments, each of $B^1$ and $B^2$ is independently represented by a moiety of Formula (III-a):

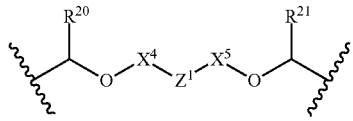

Formula (III-a)

wherein:

$Z^1$ is O, $C_3$-$C_8$ cyclyl, or $C(R^{22})(R^{23})$;

each of $X^4$ and $X^5$ is independently $C_1$-$C_6$ alkylene;

each of $R^{20}$ and $R^{21}$ is independently $C_1$-$C_6$ alkyl or $OR^{20}$;

each of $R^{22}$ and $R^{23}$ is independently hydrogen, $C_1$-$C_6$ alkyl, or ($C_1$-$C_6$ alkylene)-$OR^{26}$; and each $R^{26}$ is $C_1$-$C_6$ alkyl, $C_2$-$C_6$ alkenyl, a linker, an agent, a targeting moiety, a protecting group, or a branching point.

In some embodiments, $Z^1$ is O.

In some embodiments, $Z^1$ is $C_3$-$C_6$ cyclyl. In some embodiments, $Z^1$ is cyclopentyl, or cyclohexyl. In some embodiments, $Z^1$ is cyclohexyl.

In some embodiments, $Z^1$ is $C(R^{22})(R^{23})$. In some embodiments, $Z^1$ is $C(R^{23})(R^{24})$ and each of $R^{22}$ and $R^{23}$ is independently hydrogen. In some embodiments, each of $R^{22}$ and $R^{23}$ is independently hydrogen or $C_1$-$C_6$ alkyl, e.g., $CH_3$. In some embodiments, each of $R^{22}$ and $R^{23}$ is independently hydrogen. In some embodiments, each of $R^{22}$ and $R^{23}$ is independently $C_1$-$C_6$ alkyl, e.g., $CH_3$. In some embodiments, $R^{22}$ is hydrogen and $R^{23}$ is independently $C_1$-$C_6$ alkyl, e.g., $CH_3$. In some embodiments, each of $R^{22}$ and $R^{23}$ is independently ($C_1$-$C_6$ alkylene)-$OR^{26}$. In some embodiments, each of $R^{22}$ and $R^{23}$ is independently ($C_1$-$C_2$ alkylene)-$OR^{26}$. In some embodiments, each of $R^{22}$ and $R^{23}$ is independently ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is hydrogen or $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point.

In some embodiments, each of $X^4$ and $X^5$ is independently $C_1$-$C_4$ alkylene. In some embodiments, each of $X^4$ and $X^5$ is independently $C_1$-$C_2$ alkylene. In some embodiments, each of $X^4$ and $X^5$ is independently $C_1$-$C_2$ alkylene (e.g., $CH_2$, $CH_2CH_2$).

In some embodiments, each of $R^{20}$ and $R^{21}$ is independently $C_1$-$C_6$ alkyl. In some embodiments, each of $R^{20}$ and $R^{21}$ is independently $C_1$-$C_4$ alkyl. In some embodiments, each of $R^{20}$ and $R^{21}$ is independently $C_1$-$C_2$ alkyl, e.g., $CH_3$. In some embodiments, each of $R^{20}$ and $R^{21}$ is independently $OR^{26}$. In some embodiments, each of $R^{20}$ and $R^{21}$ is independently $OR^{26}$, and $R^{26}$ is $C_2$-$C_6$ alkenyl (e.g., $CH=CH_2$) or a branching point.

In some embodiments, the precursor of each of $B^1$ to $B^2$ is independently selected from the following vinyl ethers:

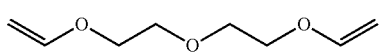

B1

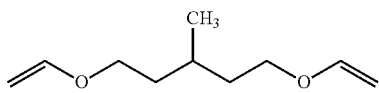

B2

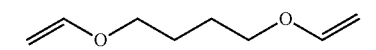

B3

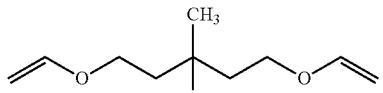

B4

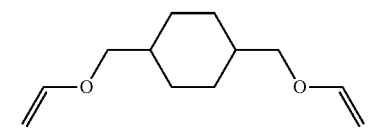

B5

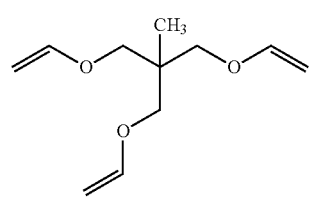

B6

In some embodiments, the precursor to each of $B^1$ and $B^2$ is independently selected from one of B1, B2, B3, B4, B5, and B6, e.g., as depicted in FIG. 1C. It is to be understood that when the precursor to $B^1$ or $B^2$ is one of the vinyl ethers in the above-noted group selected from B1-B6, $A^1$ or $A^2$ and $C^1$ or $C^2$ is connected at the (CH) group of the vinyl moiety in each of said vinyl ethers.

In some embodiments, each of $B^1$ and $B^2$ is independently represented by a moiety of Formula (III-b):

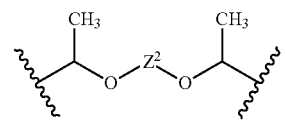

Formula (III-b)

wherein:

$Z^2$ includes or is derived from any of the vinyl ethers shown in FIG. 1C, e.g., a vinyl ether selected from one of B1, B2, B3, B4, B5, or B6, and two of the hydrogen atoms of the vinyl groups are replaced linkage indicated in Formula (III-b).

In some embodiments, $Z^2$ includes or is derived from B1. In some embodiments, $Z^2$ includes or is derived from B2. In some embodiments, $Z^2$ includes or is derived from B3. In some embodiments, $Z^2$ includes or is derived from B4. In some embodiments, $Z^2$ includes or is derived from B5. In some embodiments, $Z^2$ includes or is derived from B6.

In some embodiments, each of $B^1$ and $B^2$ includes or is derived from the same vinyl ether, e.g., a vinyl ether selected from one of B1-B6. In some embodiments, each of $B^1$ and $B^2$ includes or is derived from a different vinyl ether, e.g., a vinyl ether selected from one of B1-B6.

In some embodiments of a polymer of Formula (I), each of $C^1$ and $C^2$ is heteroalkyl, optionally substituted with 1-6 $R^3$. In some embodiments, each of $C^1$ and $C^2$ is $C_1$-$C_{20}$ heteroalkyl, optionally substituted with 1-6 $R^3$. In some embodiments, each of $C^1$ and $C^2$ is $C_1$-$C_{10}$ heteroalkyl. In some embodiments, each of $C^1$ and $C^2$ is $C_1$-$C_{10}$ heteroalkyl. In some embodiments, each of $C^1$ and $C^2$ is $C_1$-$C_{10}$ heteroalkyl, e.g., an oxygen-containing $C_1$-$C_4$ heteroalkyl and/or an amine-containing heteroalkyl. In some embodiments, each of C¹ and C² comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of C¹ and C² comprises a polyethylene glycol (PEG). In some embodiments, each of C¹ and C² comprises a polyethylene glycol (PEG) or a polyethylene oxide (PEO). In some embodiments, each of C¹ and C² comprises a polyethylene oxide (PEO) or a polypropylene glycol (PPG). In some embodiments, each of C¹ and C² comprises a polybutylene oxide (PBO).

In some embodiments, each of C¹ or C² has a linear structure, e.g., does not comprise a branching point or cyclic group. In some embodiments, each of C¹ or C² has a branched structure, e.g., comprising at least 1, at least 2, at least 3, at least 4, at least 5, or at least 6 branching points.

In some embodiments, each of C¹ or C² comprises a cyclic structure. In some embodiments, each of C¹ or C² comprises a cyclic structure, e.g., a cyclyl or heterocyclyl group. In some embodiments, each of C¹ or C² comprises a carbohydrate (e.g., a glucose derivative, galactose derivative, mannose derivative, fucose derivative, sialic acid derivative, or other carbohydrate derivative). In some embodiments, each of C¹ or C² comprises a dextran, a cyclodextran, chitosan, or other carbohydrate based moiety.

In some embodiments, each of C¹ or C² is independently about 200 Da to about 20,000 Da in size. In some embodiments, each of C¹ or C² is independently about 200 Da to about 17,500 Da, from about 200 Da to about 15,000 Da, from about 200 Da to about 12,500 Da, from about 200 Da to about 10,000 Da, from about 200 Da to about 9,000 Da, from about 200 Da to about 8,000 Da, from about 200 Da to about 7,000 Da, from about 200 Da to about 6,000 Da, from about 200 Da to about 5,000 Da, from about 200 Da to about 4,000 Da, from about 200 Da to about 3,000 Da, or from about 200 Da to about 2,000 Da in size. In some embodiments, each of C¹ or C² is independently from about 200 Da to about 5,000 Da in size. In some embodiments, each of C¹ or C² is independently from about 200 Da to about 2,000 Da in size.

In some embodiments, each of C¹ or C² is independently about 200 Da to about 2,000 Da in size. In some embodiments, each of C¹ or C² is independently about 200 Da to about 1,750 Da, from about 200 Da to about 1,500 Da, from about 200 to about 1,400 Da, from about 200 to about 1,300 Da, from about 200 to about 1,200, from about 200 to about 1,100, or from about 200 to about 1,000 in size. In some embodiments, each of C¹ or C² is independently about 200 Da to about 900 Da, from about 200 Da to about 800, from about 200 to about 700 Da, from about 200 to about 600 Da, from about 200 to about 500 Da, or from about 200 to about 400 Da. each of C¹ or C² is independently about 400 Da in size In some embodiments, each of C¹ or C² is independently about 200 Da to about 2,000 Da in size. In some embodiments, each of C¹ or C² is independently about 200 Da to about 2,000 Da in size, from about 250 Da to about 1,900 in size, from about 300 Da to about 1,800, from about 350 Da to about 1,700, or from about 400 Da to about 1,600 in size. In some embodiments, each of C¹ or C² is independently about 500 Da to about 1,500 in size, from about 600 Da to about 1,500 in size, from about 700 Da to about 1,400, from about 800 Da to about 1,300, or from about 900 Da to about 1,200 in size. In some embodiments, each of C¹ or C² is independently about 1,000 Da to about 1,200 Da in size. In some embodiments, each of C¹ or C² is independently about 1,000 Da in size.

In some embodiments, each of C¹ and C² is the same. In some embodiments, both of C¹ and C² is from about 200 Da to about 1200 Da, from about 300 Da to about 1100 Da, or from about 400 Da to about 1000 Da in size. In some embodiments, both of C¹ and C² are from about 100 Da to about 500 Da or from about 800 Da to about 1200 Da in size. In some embodiments, both of C¹ and C² are 400 Da or 1000 Da in size.

In some embodiments, each of C¹ and C² is different. In some embodiments, each of C¹ and C² is from about 200 Da to about 1200 Da, from about 300 Da to about 1100 Da, or from about 400 Da to about 1000 Da in size. In some embodiments, one of C¹ and C² is from about 100 Da to about 500 Da and the other of C¹ and C² is from bout 800 Da to about 1200 Da in size. In some embodiments, one of C¹ and C² is about 400 Da in size and the other of C¹ and C² is about 1000 Da in size.

In some embodiments of the polymer of Formula (I), the precursor to each of C¹ and C¹ is PEG (e.g., polyethylene glycol). In some embodiments, the PEG comprises PEG 100, PEG 200, PEG 300, PEG 400, PEG 500, PEG 600, PEG 800, PEG 1000, PEG 1500, PEG 2000, PEG 2050, PEG 4000, or PEG 6000, also referred to herein as P100, P200, P300, P400, P500, P600, P800, P1000, P1500, P2000, P2050, P4000, and P6000, or any combination thereof. In some embodiments, the PEG comprises P400, P1000, or a combination of P400 and P1000. In some embodiments, the PEG comprises PEG2050.

In some embodiments of a polymer (e.g., a polymer described herein, e.g., a polymer of Formula (I)), each of m and n independently an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50.

In an embodiment, m and n taken together are between 10 and 100, 20 and 80, 20 and 60, or 30 and 60.

In some embodiments, the polymer (e.g., the polyacetal polymer) comprises a structure according to Formula (I-a):

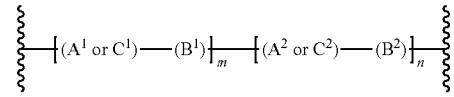

Formula (I-a)

wherein:

each of A¹ and A² is independently represented by a structure of Formula (II);

each of $B^1$ and $B^2$ is independently represented by a structure of Formula (III);

each of $C^1$ and $C^2$ is independently heteroalkyl, cyclyl, or heterocyclyl, each of which is optionally substituted with 1-6 $R^3$, e.g., each of $C^1$ and $C^2$ is independently PEG;

each of $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, or a branching point; and each of m or n is independently an integer from 1 to 200;

wherein the structure of Formula (II) is represented by:

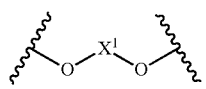

Formula (II)

$X^1$ is $C_1$-$C_{12}$ alkylene, $C_2$-$C_{12}$ alkenylene, $C_2$-$C_{12}$ alkynylene, $C_1$-$C_{12}$ heteroalkylene, $C_3$-$C_8$ cyclyl, or $C_3$-$C_8$ heterocyclyl, wherein each alkylene, alkenylene, alkynylene, heteroalkylene, cyclyl, or heterocyclyl is optionally substituted with 1-6 $R^4$;

each $R^4$ is independently $C_1$-$C_6$ alkyl, $C_2$-$C_6$ alkenyl, $C_2$-$C_6$ alkynyl, $C_1$-$C_6$ heteroalkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, ($C_1$-$C_6$ alkylene)-OC(O)O—($C_1$-$C_6$ alkylene)-$OR^5$, ($C_1$-$C_6$ alkylene)-$NR^6$—($C_1$-$C_6$ alkylene)-$OR^5$, ($C_1$-$C_6$ alkylene)-C(O)$NR^6$—($C_1$-$C_6$ alkylene)-$OR^5$, or ($C_1$-$C_6$ alkylene)-$NR^6$C(O)—($C_1$-$C_6$ alkylene)-$OR^5$, wherein each alkyl, alkenyl, alkynyl, heteroalkyl, or alkylene is optionally substituted with 1-6 $R^7$;

each $R^5$ is independently hydrogen, $C_1$-$C_6$ alkyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^8$;

$R^6$ is hydrogen or $C_1$-$C_6$ alkyl;

each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, ($C_1$-$C_6$ alkylene)-$OR^5$, ($C_1$-$C_6$ alkylene)-O—($C_1$-$C_6$ alkylene)-$OR^5$, cyano, cyclyl, heterocyclyl, aryl, or heteroaryl; and each $R^8$ is independently $C_1$-$C_6$ alkyl, $C_2$-$C_6$ alkenyl, $C_2$-$C_6$ alkynyl, $C_1$-$C_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 $R^9$; and each $R^9$ is independently $C_1$-$C_6$ alkyl, $C_1$-$C_6$ heteroalkyl, halo, cyano, cyclyl, or heterocyclyl;

and the structure of Formula (III) is represented by:

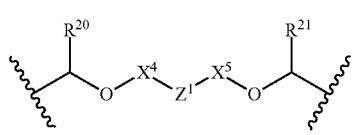

Formula (III)

wherein:

$Z^1$ is O, $C_3$-$C_8$ cyclyl, $C_3$-$C_8$ heterocyclyl, or C($R^{22}$)($R^{23}$), wherein each of cyclyl and heterocyclyl is optionally substituted with 1-4 $R^{25}$;

each of $X^4$ and $X^5$ is independently $C_1$-$C_6$ alkylene, $C_2$-$C_6$ alkenylene, $C_2$-$C_6$ alkynylene, $C_1$-$C_6$ heteroalkylene, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), ($C_1$-$C_6$ alkylene)-$NR^{24}$—($C_1$-$C_6$ alkylene), ($C_1$-$C_6$ alkylene)-C(O)$NR^{24}$—($C_1$-$C_6$ alkylene), or ($C_1$-$C_6$ alkylene)-$NR^{24}$C(O)—($C_1$-$C_6$ alkylene), wherein each alkylene, alkenylene, alkynylene, or heteroalkylene is optionally substituted with 1-6 $R^{25}$;

each of $R^{20}$ and $R^{21}$ is independently $C_1$-$C_6$ alkyl, $OR^{26}$, cyclyl, heterocyclyl;

each of $R^{22}$ and $R^{23}$ is independently hydrogen, $C_1$-$C_6$ alkyl, $OR^{26}$, ($C_1$-$C_6$ alkylene)-$OR^{26}$, halo, cyclyl, heterocyclyl, aryl, heteroaryl, wherein each alkyl, alkylene, cyclyl, heterocyclyl, aryl, or heteroaryl is optionally substituted with 1-6 $R^{27}$;

each $R^{25}$ and $R^{27}$ is $C_1$-$C_6$ alkyl, $C_1$-$C_6$ heteroalkyl, halo, cyano, cyclyl, or heterocyclyl;

$R^{26}$ is hydrogen, $C_1$-$C_6$ alkyl, $C_1$-$C_6$ alkenyl, $C_1$-$C_6$ alkynyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^{28}$; and each $R^{28}$ is independently $C_1$-$C_6$ alkyl, $C_1$-$C_6$ heteroalkyl, halo, cyano, cyclyl, or heterocyclyl.

In some embodiments, each of $A^1$ and $A^2$ is the same, e.g., the same structure of Formula (II). In some embodiments, each of $A^1$ and $A^2$ is different, e.g., a different structure of Formula (II).

In some embodiments, $X^1$ is $C_1$-$C_{12}$ alkylene or $C_1$-$C_{12}$ heteroalkylene, optionally substituted with 1-6 $R^4$. In some embodiments, $X^1$ is $C_1$-$C_{12}$ heteroalkylene optionally substituted with 1-6 $R^4$, e.g., ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), wherein each alkylene is optionally substituted with 1-6 $R^4$. In some embodiments, $X^1$ is $C_3$-$C_6$ cyclyl, optionally substituted with 1-6 $R^4$ (e.g., cyclohexyl substituted with $OR^5$).

In some embodiments, each $R^4$ is independently $C_1$-$C_6$ alkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, or ($C_1$-$C_6$ alkylene)-OC(O)O—($C_1$-$C_6$ alkylene)-$OR^5$.

In some embodiments, each $R^5$ is independently hydrogen, $C_1$-$C_6$ alkyl, a linker, a branching point, a protecting group, an agent, or a targeting moiety.

In some embodiments, the precursor to each of $A^1$ and $A^2$ is independently selected from the following polyols:

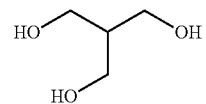

A1

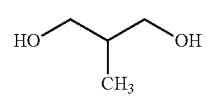

A2

-continued
A3
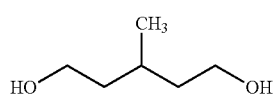
A4
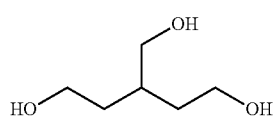
A5
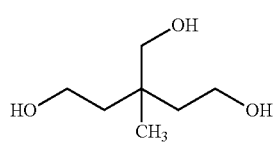
A6
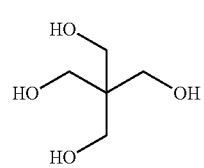
A7
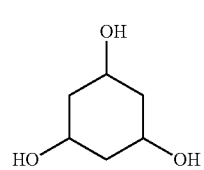
A8
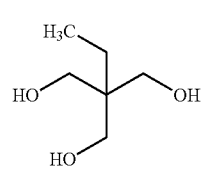
A9
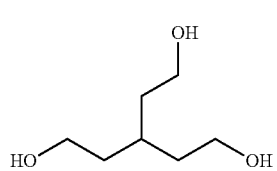
A10
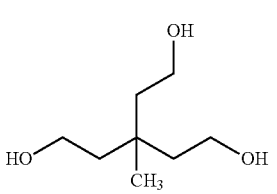
A11
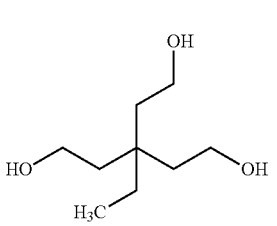
A12
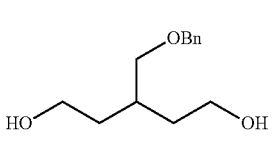
-continued
A13
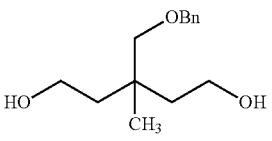
A14
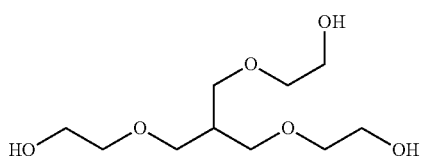
A15
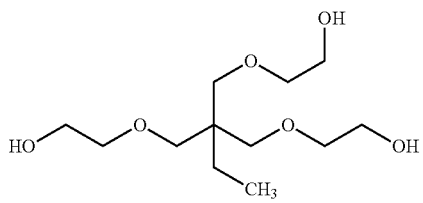
A16
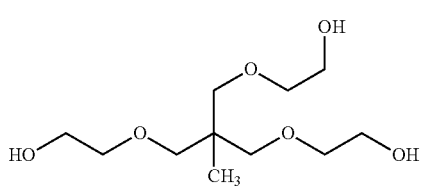
A17
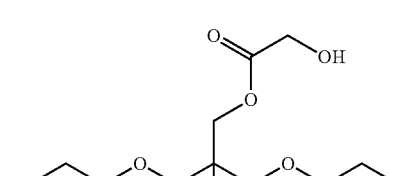
A18
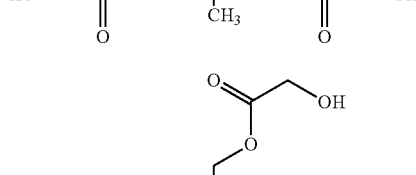
A19
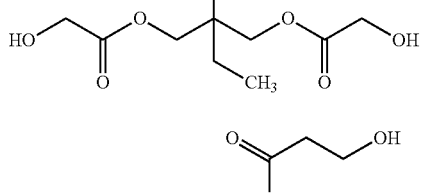
A20
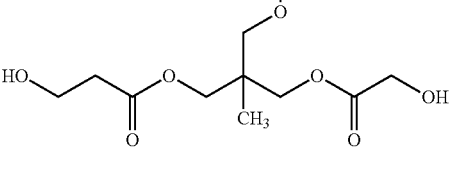
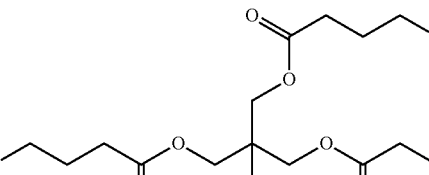

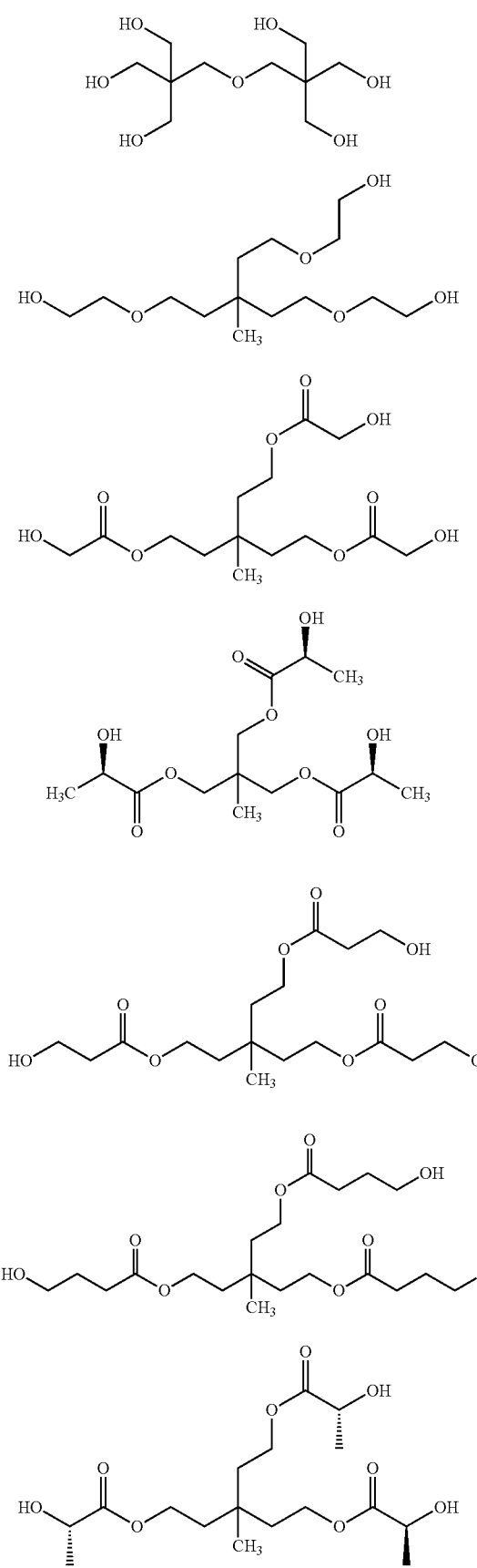

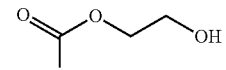

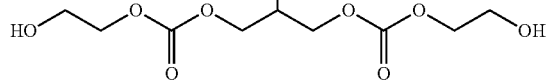

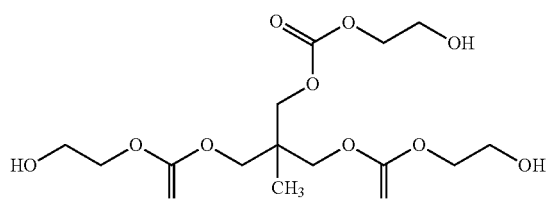

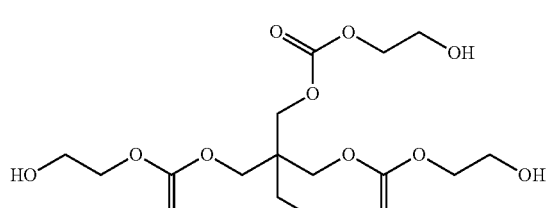

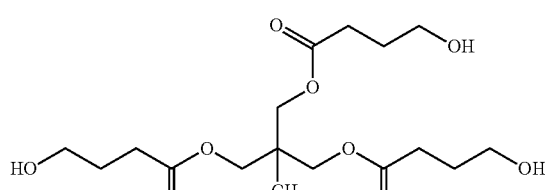

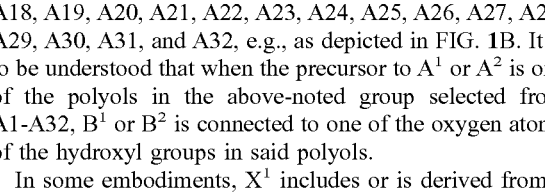

In some embodiments, the precursor to each of $A^1$ and $A^2$ is independently selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, $X^1$ includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, each of $B^1$ and $B^2$ is the same, e.g., the same structure of Formula (II). In some embodiments, each of $B^1$ and $B^2$ is different, e.g., a different structure of Formula (II).

In some embodiments, $Z^1$ is $C(R^{23})(R^{24})$ and each of $R^{22}$ and $R^{23}$ is independently hydrogen, $C_1$-$C_6$ alkyl, or $(C_1$-$C_6$ alkylene)-$OR^{26}$. In some embodiments, $R^{22}$ is hydrogen and $R^{23}$ is independently $C_1$-$C_6$ alkyl, e.g., $CH_3$. In some embodiments, $R^{22}$ is hydrogen or $C_1$-$C_6$ alkyl (e.g., $CH_3$), $R^{23}$ is $(C_1$-$C_2$ alkylene)-$OR^{26}$, and $R^{26}$ is $C_2$-$C_6$ alkenyl (e.g., $CH=CH_2$) or a branching point. In some embodiments, $Z^1$ is $C_3$-$C_6$ cyclyl, optionally substituted with 1-4 $R^{25}$ (e.g., cyclohexyl).

In some embodiments, each of $X^4$ and $X^5$ is independently $C_1$-$C_6$ alkylene (e.g., $CH_2$, $CH_2CH_2$), wherein alkylene is optionally substituted with 1-6 $R^{25}$.

In some embodiments, each of $R^{20}$ and $R^{21}$ is independently $C_1$-$C_6$ alkyl (e.g., $CH_3$) or $OR^{26}$ (e.g., $C_2$-$C_6$ alkenyl (e.g., $CH=CH_2$) or a branching point).

In some embodiments, the precursor to each of $B^1$ and $B^2$ is independently selected from the following vinyl ethers:

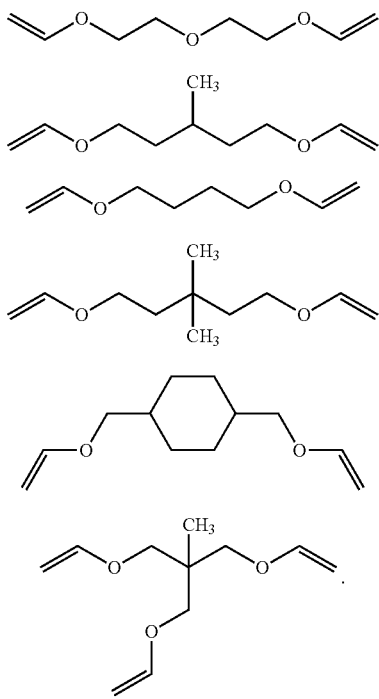

In some embodiments, each of $C^1$ and $C^2$ is the same, e.g., the same structure of Formula (II). In some embodiments, each of $C^1$ and $C^2$ is different, e.g., a different structure of Formula (II).

In some embodiments, each of $C^1$ and $C^2$ is independently heteroalkyl (e.g., an oxygen-containing $C_1$-$C_4$ heteroalkyl and/or an amine-containing heteroalkyl), optionally substituted with 1-6 $R^3$.

In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ has a linear structure, e.g., does not comprise a branching point or cyclic group. In some embodiments, each of $C^1$ and $C^2$ has a $C^1$ or $C^2$ has a branched structure, e.g., comprising at least 1, at least 2, at least 3, at least 4, at least 5, or at least 6 branching points.

In some embodiments, each of $C^1$ and $C^2$ comprises a cyclic structure, e.g., a cyclyl or heterocyclyl group, e.g., a dextran, a cyclodextran, chitosan, or other carbohydrate based moiety.

In some embodiments, each of $C^1$ and $C^2$ is independently 200 to 5000 Da in size.

In some embodiments, each of $C^1$ and $C^2$ is a polyethylene glycol (PEG). In some embodiments, each of $C^1$ and $C^2$ is independently a polyethylene glycol (PEG) and is between about 200 and 1200 Da in size. In some embodiments, each of $C^1$ and $C^2$ is independently PEG 400, PEG 1000, or PEG 2050.

In some embodiments of a polymer (e.g., a polymer described herein, e.g., a polymer of Formula (I)), each of m and n independently an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In some embodiments, each of m and n independently an integer from 2 to 200, e.g., 5 to 200 or 10 to 200. In some embodiments, each of m and n independently an integer from 5 to 100, e.g., 10 to 50.

In some embodiments, the agent is a therapeutic or a diagnostic agent as described herein. In some embodiments, the agent is an AHCM as described herein. In some embodiments, the agent is an ARB as described herein, e.g., losartan, valsartan, telmisartan, candesartan, eprosartan, irbesartan, azilsartan, EXP-3174, olmesartan, or a prodrug or active metabolite thereof, e.g., a compound shown in FIG. 23.

In some embodiments, the agent is a vitamin D analog or derivative as described herein. In some embodiments, the agent is a vitamin D analog or derivative as described herein, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY112, PRI-2205, ILX23-7553, ercalcitriol, EB1089 (seocalcitol), BXL-628 (elocalcitol), MC1288, CB966, BCB 1093, GS 1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and analogs and derivatives thereof, e.g., as shown in FIG. 24.

In some embodiments, the agent is a bromodomain and extra-terminal protein inhibitor (i-BET) as described herein. In some embodiments, the agent is a bromodomain and extra-terminal protein inhibitor (i-BET) as described herein, e.g MS436, PFI-1, I-BET 151, OTX-015, JQ1, CPI-203, bromosporine, RVX-208, I-BET 762, I-BET 151, OFXBD02, OFXBD03, XD14, AZD5153, and analogs and derivatives thereof, e.g., as shown in FIGS. 25A and 25B.

In some embodiments, the agent is an IDO inhibitor (i.e., indoleamine 2,3-dioxygenase (IDO) pathway inhibitor) as described herein. In some embodiments, the agent is an IDO inhibitor as described herein, e.g., GDC-0919, indoximod, 1-methyltryptophan (e.g., 1-methyl-L-tryptophan, 1-methyl-D-tryptophan), NLG8189, INCB024360, NLG919, methyl-thiohydantoin tryptophan, brassinin, annulin B, exiguamine A, INCB023843, or an analog or derivative thereof.

In some embodiments, the polymer (e.g., the polyacetal polymer) comprises a structure according to Formula (I-b):

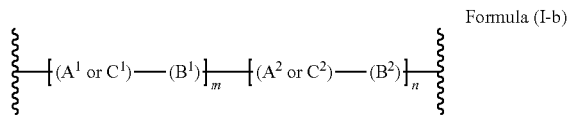

Formula (I-b)

wherein:
each of $A^1$ and $A^2$ is independently represented by a structure of Formula (II-c);
each of $B^1$ and $B^2$ is independently represented by a structure of Formula (III-b);
each of $C^1$ and $C^2$ is heteroalkyl, cyclyl, or heterocyclyl, each of which is optionally substituted with 1-6 $R^3$;
each of $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, or a branching point;
and
each of m or n is independently an integer from 1 to 200.

In some embodiments, each of $A^1$ and $A^2$ is independently represented by a structure of Formula (II-c), in which $X^1$ is includes or is derived from any of the polyols shown in FIG. 1B, e.g., a polyol selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, each of $A^1$ and $A^2$ is independently represented by a structure of Formula (II-c), in which $X^1$ is includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, each of $A^1$ and $A^2$ is includes or is derived from the same polyol, e.g., a polyol selected from one of A1-A32. In some embodiments, each of $A^1$ and $A^2$ includes or is derived from a different polyol, e.g., a polyol selected from one of A1-A32.

In some embodiments, $X^1$ includes or is derived from A1. In some embodiments, $X^1$ includes or is derived from A2. In some embodiments, $X^1$ includes or is derived from A3. In some embodiments, $X^1$ includes or is derived from A4. In some embodiments, $X^1$ $X^1$ includes or is derived from A5. In some embodiments, $X^1$ includes or is derived from A6. In some embodiments, $X^1$ includes or is derived from A7. In some embodiments, $X^1$ includes or is derived from A8. In some embodiments, $X^1$ includes or is derived from A9. In some embodiments, $X^1$ includes or is derived from A10. In some embodiments, $X^1$ includes or is derived from A11. In some embodiments, $X^1$ includes or is derived from A12. In some embodiments, $X^1$ includes or is derived from A13. In some embodiments, $X^1$ includes or is derived from A14. In some embodiments, $X^1$ includes or is derived from A15. In some embodiments, $X^1$ includes or is derived from A16. In some embodiments, $X^1$ includes or is derived from A17. In some embodiments, $X^1$ includes or is derived from A18. In some embodiments, $X^1$ includes or is derived from A19. In some embodiments, $X^1$ includes or is derived from A20. In some embodiments, $X^1$ includes or is derived from A21. In some embodiments, $X^1$ includes or is derived from A22. In some embodiments, $X^1$ includes or is derived from A23. In some embodiments, $X^1$ includes or is derived from A24. In some embodiments, $X^1$ includes or is derived from A25. In some embodiments, $X^1$ includes or is derived from A26. In some embodiments, $X^1$ includes or is derived from A27. In some embodiments, $X^1$ includes or is derived from A28. In some embodiments, $X^1$ includes or is derived from A29. In some embodiments, $X^1$ includes or is derived from A30. In some embodiments, $X^1$ includes or is derived from A31. In some embodiments, $X^1$ includes or is derived from A32.

In some embodiments, each of $B^1$ and $B^2$ is independently represented by a structure of Formula (III-b), in which $Z^2$ includes or is derived from any of the vinyl ethers shown in FIG. 1C, e.g., a vinyl ether selected from one of B1, B2, B3, B4, B5, or B6, and two of the hydrogen atoms of the vinyl groups are replaced linkage indicated in Formula (III-b).

In some embodiments, each of $B^1$ and $B^2$ includes or is derived from the same vinyl ether, e.g., a vinyl ether selected from one of B1-B6. In some embodiments, each of $B^1$ and $B^2$ includes or is derived from a different vinyl ether, e.g., a vinyl ether selected from one of B1-B6.

In some embodiments, $Z^2$ includes or is derived from B1. In some embodiments, $Z^2$ includes or is derived from B2. In some embodiments, $Z^2$ includes or is derived from B3. In some embodiments, $Z^2$ includes or is derived from B4. In some embodiments, $Z^2$ includes or is derived from B5. In some embodiments, $Z^2$ includes or is derived from B6.

In some embodiments, each of $C^1$ and $C^2$ is heteroalkyl, optionally substituted with 1-6 $R^3$. In some embodiments, each of $C^1$ and $C^2$ is $C_1$-$C_{20}$ heteroalkyl, optionally substituted with 1-6 $R^3$. In some embodiments, each of $C^1$ and $C^2$ is $C_1$-$C_{10}$ heteroalkyl. In some embodiments, each of $C^1$ and $C^2$ is $C_1$-$C_{10}$ heteroalkyl. In some embodiments, each of $C^1$ and $C^2$ is $C_1$-$C_{10}$ heteroalkyl, e.g., an oxygen-containing $C_1$-$C_4$ heteroalkyl and/or an amine-containing heteroalkyl. In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ comprises a polyethylene glycol (PEG). In some embodiments, each of $C^1$ and $C^2$ comprises a polyethylene glycol (PEG) or a polyethylene oxide (PEO). In some embodiments, each of $C^1$ and $C^2$ comprises a polyethylene oxide (PEO) or a polypropylene glycol (PPG). In some embodiments, each of $C^1$ and $C^2$ comprises a polybutylene oxide (PBO).

In some embodiments, each of $C^1$ or $C^2$ comprises a cyclic structure. In some embodiments, each of $C^1$ or $C^2$ comprises a cyclic structure, e.g., a cyclyl or heterocyclyl group. In some embodiments, each of $C^1$ or $C^2$ comprises a carbohydrate (e.g., a glucose derivative, galactose derivative, mannose derivative, fucose derivative, sialic acid derivative, or other carbohydrate derivative). In some embodiments, each of $C^1$ or $C^2$ comprises a dextran, a cyclodextran, chitosan, or other carbohydrate based moiety.

In some embodiments, each of $C^1$ or $C^2$ is independently about 200 Da to about 20,000 Da in size. In some embodiments, each of $C^1$ or $C^2$ is independently about 200 Da to about 17,500 Da, from about 200 Da to about 15,000 Da, from about 200 Da to about 12,500 Da, from about 200 Da to about 10,000 Da, from about 200 Da to about 9,000 Da, from about 200 Da to about 8,000 Da, from about 200 Da to about 7,000 Da, from about 200 Da to about 6,000 Da, from about 200 Da to about 5,000 Da, from about 200 Da to about 4,000 Da, from about 200 Da to about 3,000 Da, or from about 200 Da to about 2,000 Da in size. In some embodiments, each of $C^1$ or $C^2$ is independently from about 200 Da to about 5,000 Da in size. In some embodiments, each of $C^1$ or $C^2$ is independently from about 200 Da to about 2,000 Da in size.

In some embodiments, each of $C^1$ or $C^2$ is independently about 200 Da to about 2,000 Da in size. In some embodiments, each of $C^1$ or $C^2$ is independently about 200 Da to about 1,750 Da, from about 200 Da to about 1,500 Da, from about 200 to about 1,400 Da, from about 200 to about 1,300 Da, from about 200 to about 1,200, from about 200 to about 1,100, or from about 200 to about 1,000 in size. In some embodiments, each of $C^1$ or $C^2$ is independently about 200 Da to about 900 Da, from about 200 Da to about 800, from about 200 to about 700 Da, from about 200 to about 600 Da, from about 200 to about 500 Da, or from about 200 to about 400 Da. each of $C^1$ or $C^2$ is independently about 400 Da in size In some embodiments, each of $C^1$ or $C^2$ is independently about 200 Da to about 2,000 Da in size. In some embodiments, each of $C^1$ or $C^2$ is independently about 200 Da to about 2,000 Da in size, from about 250 Da to about 1,900 in size, from about 300 Da to about 1,800, from about 350 Da to about 1,700, or from about 400 Da to about 1,600 in size. In some embodiments, each of $C^1$ or $C^2$ is independently about 500 Da to about 1,500 in size, from about 600 Da to about 1,500 in size, from about 700 Da to about 1,400, from about 800 Da to about 1,300, or from about 900 Da to about 1,200 in size. In some embodiments, each of $C^1$ or $C^2$ is independently about 1,000 Da to about 1,200 Da in size. In some embodiments, each of $C^1$ or $C^2$ is independently about 1,000 Da in size.

In some embodiments, each of $C^1$ and $C^2$ is the same. In some embodiments, both of $C^1$ and $C^2$ is from about 200 Da to about 1200 Da, from about 300 Da to about 1100 Da, or from about 400 Da to about 1000 Da in size. In some embodiments, both of $C^1$ and $C^2$ are from about 100 Da to about 500 Da or from about 800 Da to about 1200 Da in size. In some embodiments, both of $C^1$ and $C^2$ are 400 Da or 1000 Da in size.

In some embodiments, each of $C^1$ and $C^2$ is different. In some embodiments, each of $C^1$ and $C^2$ is from about 200 Da to about 1200 Da, from about 300 Da to about 1100 Da, or from about 400 Da to about 1000 Da in size. In some embodiments, one of $C^1$ and $C^2$ is from about 100 Da to about 500 Da and the other of $C^1$ and $C^2$ is from bout 800 Da to about 1200 Da in size. In some embodiments, one of $C^1$ and $C^2$ is about 400 Da in size and the other of $C^1$ and $C^2$ is about 1000 Da in size.

In some embodiments of the polymer of Formula (I), the precursor to each of $C^1$ and $C^1$ is PEG (e.g., polyethylene glycol). In some embodiments, the PEG comprises PEG 100, PEG 200, PEG 300, PEG 400, PEG 500, PEG 600, PEG 800, PEG 1000, PEG 1500, PEG 2000, PEG 2050, PEG 4000, or PEG 6000, also referred to herein as P100, P200, P300, P400, P500, P600, P800, P1000, P1500, P2000, P2050, P4000, and P6000, or any combination thereof. In some embodiments, the PEG comprises P400, P1000, or a combination of P400 and P1000. In some embodiments, the PEG comprises PEG2050.

In some embodiments of a polymer of Formula (I-b), each of m and n independently an integer from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 5 to 100, from 5 to 95, from 5 to 85, from 5 to 80, from 5 to 75, from 5 to 70, from 5 to 65, from 5 to 60, from 5 to 55, from 5 to 50, from 5 to 45, from 5 to 40, from 5 to 35, from 5 to 30, from 5 to 25, or from 5 to 20. In some embodiments, each of m and n independently is an integer from 5 to 50. In some embodiments, each of m and n independently is an integer from 10 to 100, from 10 to 95, from 10 to 85, from 10 to 80, from 10 to 75, from 10 to 70, from 10 to 65, from 10 to 60, from 10 to 55, from 10 to 50, from 10 to 45, from 10 to 40, from 10 to 35, from 10 to 30, from 10 to 25, or from 10 to 20. In some embodiments, each of m and n independently is an integer from 10 to 50.

In some embodiments, the agent is a therapeutic or a diagnostic agent as described herein. In some embodiments, the agent is an AHCM as described herein. In some embodiments, the agent is an ARB as described herein, e.g., losartan, valsartan, telmisartan, candesartan, eprosartan, irbesartan, azilsartan, EXP-3174, olmesartan, or a prodrug or active metabolite thereof, e.g., a compound shown in FIG. 23.

In some embodiments, the agent is a vitamin D analog or derivative as described herein. In some embodiments, the agent is a vitamin D analog or derivative as described herein, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, ercalcitriol, EB1089 (seocalcitol), BXL-628 (elocalcitol), MC1288, CB966, BCB 1093, GS 1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and analogs and derivatives thereof, e.g., as shown in FIG. 24.

In some embodiments, the agent is a bromodomain and extra-terminal protein inhibitor (i-BET) as described herein. In some embodiments, the agent is a bromodomain and extra-terminal protein inhibitor (i-BET) as described herein, e.g MS436, PFI-1, I-BET 151, OTX-015, JQ1, CPI-203, bromosporine, RVX-208, I-BET 762, I-BET 151, OFXBD02, OFXBD03, XD14, AZD5153, and analogs and derivatives thereof, e.g., as shown in FIGS. 25A and 25B.

In some embodiments, the agent is an IDO inhibitor (i.e., indoleamine 2,3-dioxygenase (IDO) pathway inhibitor) as described herein. In some embodiments, the agent is an IDO inhibitor as described herein, e.g., GDC-0919, indoximod, 1-methyltryptophan (e.g., 1-methyl-L-tryptophan, 1-methyl-D-tryptophan), NLG8189, INCB024360, NLG919, methylthiohydantoin tryptophan, brassinin, annulin B, exiguamine A, INCB023843, or an analog or derivative thereof.

In some embodiments, each of $A^1$ and $A^2$ is the same. In some embodiments, each of $A^1$ and $A^2$ is different. In some embodiments, the polymer (e.g., a polyacetal polymer as described herein, e.g., a polyacetal polymer of Formula (I), Formula (I-a), or Formula (I-b)), comprises only one of $A^1$ or $A^2$. In some embodiments, the polymer (e.g., a polyacetal polymer as described herein), comprises only one of $A^1$ or $A^2$, and each of m and n is an integer between 2 and 100. In some embodiments, the polymer (e.g., a polyacetal polymer as described herein), comprises only one of $A^1$ or $A^2$, and each of m and n is an integer between 10 and 100. In some embodiments, the polymer (e.g., a polyacetal polymer as described herein), does not comprise $A^1$ or $A^2$, or both $A^1$ and $A^2$.

In some embodiments, each of $B^1$ and $B^2$ is the same. In some embodiments, each of $B^1$ and $B^2$ is different.

In some embodiments, each of $C^1$ and $C^2$ is the same. In some embodiments, each of $C^1$ and $C^2$ is different. In some embodiments, the polymer (e.g., a polyacetal polymer as described herein, e.g., a polyacetal polymer of Formula (I), Formula (I-a), or Formula (I-b)), comprises only one of $C^1$ or $C^2$. In some embodiments, the polymer (e.g., a polyacetal polymer as described herein), comprises only one of $C^1$ or $C^2$, and each of m and n is an integer between 2 and 100. In some embodiments, the polymer (e.g., a polyacetal polymer as described herein), comprises only one of $C^1$ or $C^2$, and each of m and n is an integer between 10 and 100. In some embodiments, the polymer (e.g., a polyacetal polymer as described herein), does not comprise $C^1$ or $C^2$, or both $C^1$ and $C^2$.

In any and all embodiments, ∿∿∿ -represents a linkage to another portion of the polymer (e.g., a polyacetal polymer described herein) or the terminus of the polymer (e.g., a polyacetal polymer described herein). In some embodiments, when ∿∿∿ represents a terminus of the polymer (e.g., a polyacetal polymer described herein), the terminus may be further modified with hydrogen, a linker (e.g., a linker described herein), an agent (e.g., an agent described herein, e.g., an ARB), or a targeting moiety (e.g., a linker described herein).

In some embodiments, the polymer (e.g., a polyacetal polymer of described herein) comprises a structure according to Formula (I-c):

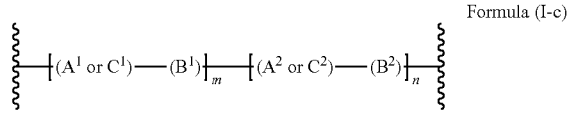

Formula (I-c)

wherein:
each of $A^1$ and $A^2$ is independently represented by a structure of Formula (II-d), Formula (II-e), Formula (II-f), Formula (II-g), Formula (II-h), Formula (II-i), or Formula (II-j);
each of $B^1$ and $B^2$ is independently represented by a structure of Formula (III-a);
each of $C^1$ and $C^2$ is heteroalkyl, cyclyl, or heterocyclyl, each of which is optionally substituted with 1-6 $R^3$;
each of $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, or a branching point;
each of m or n is independently an integer from 1 to 200; and
wherein the structures of Formula (II-d), Formula (II-e), Formula (II-f), Formula (II-g), Formula (II-h), Formula (II-i), and Formula (II-j) are as described herein; and
the structure of Formula (III-a) is as described herein.

In some embodiments, each of $A^1$ and $A^2$ is the same, e.g., the same structure of Formula (II). In some embodiments, each of $A^1$ and $A^2$ is different, e.g., a different structure of Formula (II).

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-losartan, e.g., ($CH_2$—O-L-losartan). In some embodiments, $R^{4b}$ is ($C_1$-$C_6$ alkylene)-O-L-valsartan, e.g., ($CH_2$—O-L-valsartan). In some embodiments, $R^{4b}$ is ($C_1$-$C_6$ alkylene)-O-L-telmisartan, e.g., ($CH_2$—O-L-telmisartan). In some embodiments, $R^{4b}$ is ($C_1$-$C_6$ alkylene)-O-L-candesartan, e.g., ($CH_2$—O-L-candesartan). In some embodiments, $R^{4b}$ is ($C_1$-$C_6$ alkylene)-O-L-olmesartan, e.g., ($CH_2$—O-L-olmesartan).

In some embodiments, L is a bond. In some embodiments, L is a linker. In some embodiments, L is a linker as described herein, e.g., a polyacetal polymer.

In some embodiments, ARB is losartan, valsartan, telmisartan, candesartan, or olmesartan. In some embodiments, ARB is losartan or valsartan. In some embodiments, ARB is telmisartan or candesartan. In some embodiments, ARB is losartan. In some embodiments, ARB is valsartan. In some embodiments, ARB is telmisartan. In some embodiments, ARB is candesartan. In some embodiments, ARB is olmesartan.

In some embodiments, T is a targeting moiety described herein. In some embodiments, T is mannose-6-phosphate.

In some embodiments, the precursor to each of $A^1$ and $A^2$ is independently selected from the following polyols:

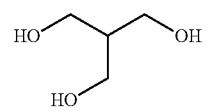

A1

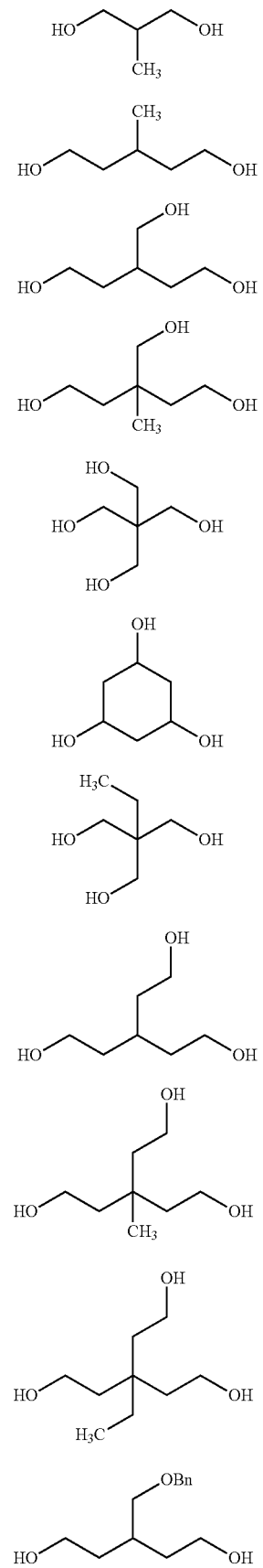
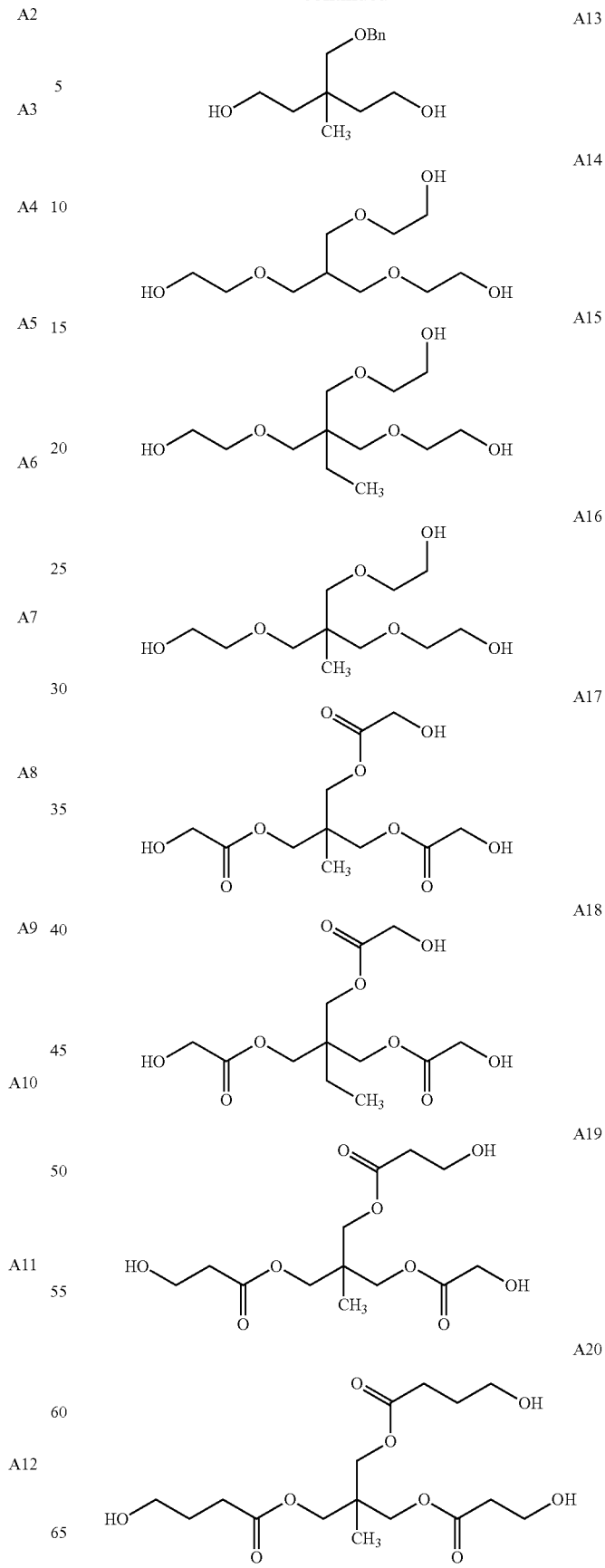

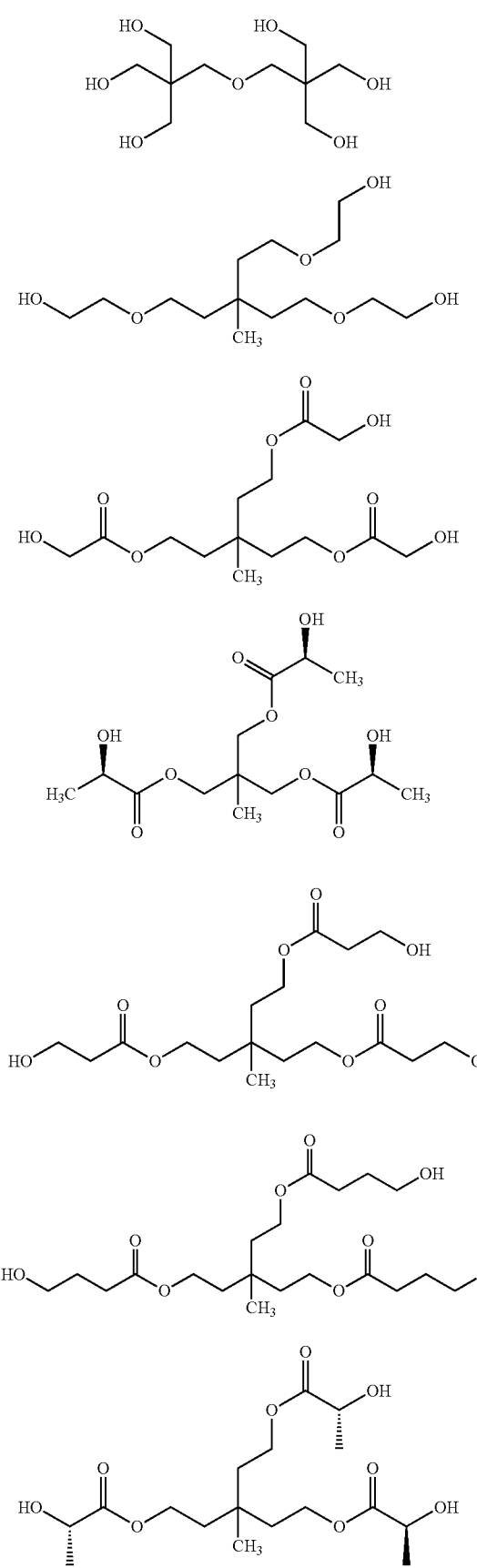

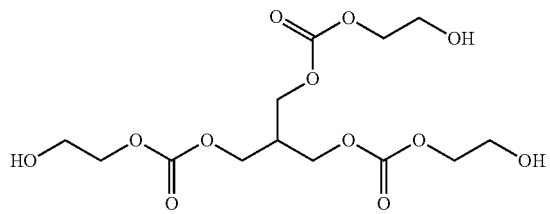

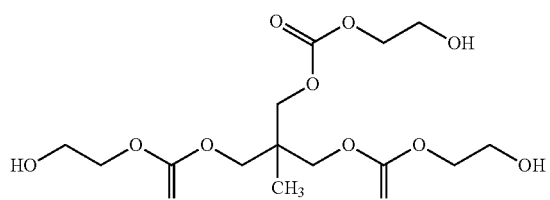

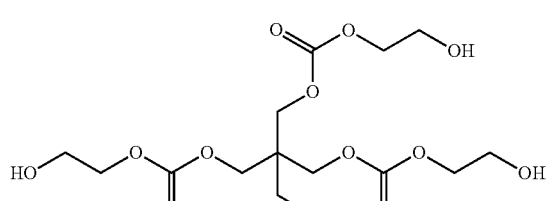

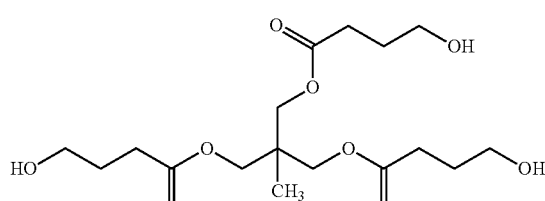

In some embodiments, the precursor to each of $A^1$ and $A^2$ is independently selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, $X^1$ includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, each of $B^1$ and $B^2$ is the same, e.g., the same structure of Formula (II). In some embodiments, each of $B^1$ and $B^2$ is different, e.g., a different structure of Formula (II).

In some embodiments, $Z^1$ is $C(R^{23})(R^{24})$ and each of $R^{22}$ and $R^{23}$ is independently hydrogen, $C_1$-$C_6$ alkyl, or $(C_1$-$C_6$ alkylene)-$OR^{26}$. In some embodiments, $R^{22}$ is hydrogen and $R^{23}$ is independently $C_1$-$C_6$ alkyl, e.g., $CH_3$. In some embodiments, $R^{22}$ is hydrogen or $C_1$-$C_6$ alkyl (e.g., $CH_3$), $R^{23}$ is $(C_1$-$C_2$ alkylene)-$OR^{26}$, and $R^{26}$ is $C_2$-$C_6$ alkenyl (e.g., $CH=CH_2$) or a branching point. In some embodiments, $Z^1$ is $C_3$-$C_6$ cyclyl, optionally substituted with 1-4 $R^{25}$ (e.g., cyclohexyl).

In some embodiments, each of $X^4$ and $X^5$ is independently $C_1$-$C_6$ alkylene (e.g., $CH_2$, $CH_2CH_2$), wherein alkylene is optionally substituted with 1-6 $R^{25}$.

In some embodiments, each of $R^{20}$ and $R^{21}$ is independently $C_1$-$C_6$ alkyl (e.g., $CH_3$) or $OR^{26}$ (e.g., $C_2$-$C_6$ alkenyl (e.g., $CH=CH_2$) or a branching point).

In some embodiments, the precursor to each of $B^1$ and $B^2$ is independently selected from the following vinyl ethers:

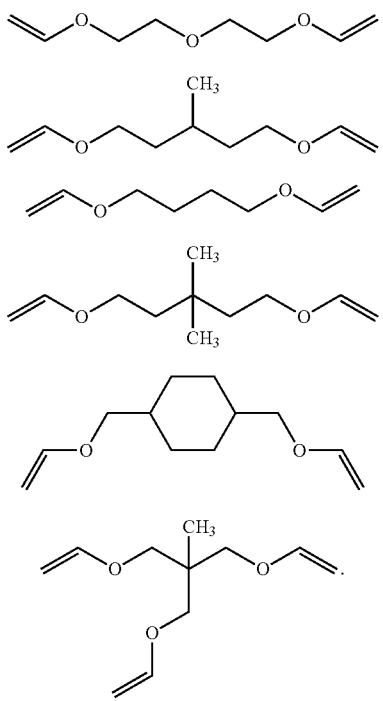

In some embodiments, each of $C^1$ and $C^2$ is the same, e.g., the same structure of Formula (II). In some embodiments, each of $C^1$ and $C^2$ is different, e.g., a different structure of Formula (II).

In some embodiments, each of $C^1$ and $C^2$ is independently heteroalkyl (e.g., an oxygen-containing $C_1$-$C_4$ heteroalkyl and/or an amine-containing heteroalkyl), optionally substituted with 1-6 $R^3$.

In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ has a linear structure, e.g., does not comprise a branching point or cyclic group. In some embodiments, each of $C^1$ and $C^2$ has a $C^1$ or $C^2$ has a branched structure, e.g., comprising at least 1, at least 2, at least 3, at least 4, at least 5, or at least 6 branching points.

In some embodiments, each of $C^1$ and $C^2$ comprises a cyclic structure, e.g., a cyclyl or heterocyclyl group, e.g., a dextran, a cyclodextran, chitosan, or other carbohydrate based moiety.

In some embodiments, each of $C^1$ and $C^2$ is independently 200 to 5000 Da in size.

In some embodiments, each of $C^1$ and $C^2$ is a polyethylene glycol (PEG). In some embodiments, each of $C^1$ and $C^2$ is independently a polyethylene glycol (PEG) and is between about 200 and 1200 Da in size. In some embodiments, each of $C^1$ and $C^2$ is independently PEG 400, PEG 1000, or PEG 2050.

In some embodiments of a polymer (e.g., a polymer described herein), each of m and n independently an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In some embodiments, each of m and n independently an integer from 2 to 200, e.g., 5 to 200 or 10 to 200. In some embodiments, each of m and n independently an integer from 5 to 100, e.g., 10 to 50.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I-c) is greater than about 5 kDa in size. In some embodiments, each of $A^1$ and $A^2$ does not independently include, or is not independently derived from, tri(methylol) ethane and the polymer of Formula (I-c) is greater than about 10 kDa in size.

In some embodiments, each of $A^1$ and $A^2$ independently includes, or is independently derived from, tri(methylol) ethane. In some embodiments, each of $A^1$ and $A^2$ independently includes, or is independently derived from, tri(methylol)ethane and the polymer of Formula (I-c) is greater than about 5 kDa in size. In some embodiments, each of $A^1$ and $A^2$ independently includes, or is independently derived from, tri(methylol)ethane and the polymer of Formula (I-c) is greater than about 10 kDa in size.

In some embodiments, the polymer (e.g., a polyacetal polymer described herein) comprises a structure according to Formula (I-d) or Formula (I-e):

Formula (I-d)

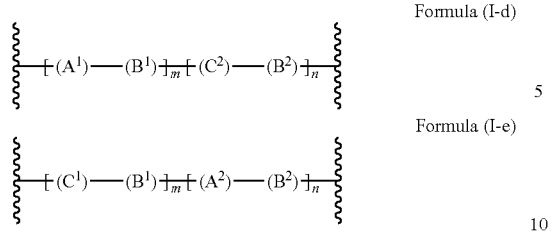

Formula (I-e)

wherein:
each of $A^1$ or $A^2$ is independently represented by a structure of Formula (II);
each of $B^1$ and $B^2$ is independently represented by a structure of Formula (III);
each of $C^1$ or $C^2$ is independently heteroalkyl, cyclyl, or heterocyclyl, each of which is optionally substituted with 1-6 $R^3$;
each of $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, or a branching point; and
each of m and n is an integer between 1 to 200.
wherein the structure of Formula (II) is as described herein;
and the structure of Formula (III) is as described herein.

In some embodiments, each of $A^1$ and $A^2$ is the same, e.g., the same structure of Formula (II). In some embodiments, each of $A^1$ and $A^2$ is different, e.g., a different structure of Formula (II).

In some embodiments, $X^1$ is $C_1$-$C_{12}$ alkylene or $C_1$-$C_{12}$ heteroalkylene, optionally substituted with 1-6 $R^4$. In some embodiments, $X^1$ is $C_1$-$C_{12}$ heteroalkylene optionally substituted with 1-6 $R^4$, e.g., ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), wherein each alkylene is optionally substituted with 1-6 $R^4$. In some embodiments, $X^1$ is $C_3$-$C_6$ cyclyl, optionally substituted with 1-6 $R^4$ (e.g., cyclohexyl substituted with $OR^5$).

In some embodiments, each $R^4$ is independently $C_1$-$C_6$ alkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, or ($C_1$-$C_6$ alkylene)-OC(O)O—($C_1$-$C_6$ alkylene)-$OR^5$.

In some embodiments, each $R^5$ is independently hydrogen, $C_1$-$C_6$ alkyl, a linker, a branching point, a protecting group, an agent, or a targeting moiety.

In some embodiments, the precursor to each of $A^1$ and $A^2$ is independently selected from the following polyols:

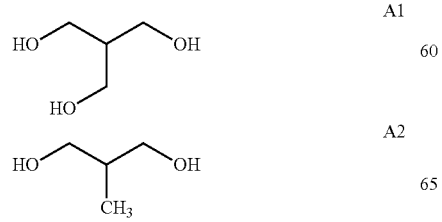

A1

A2

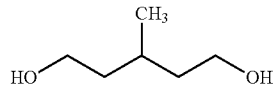

A3

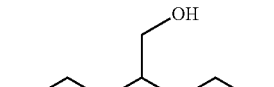

A4

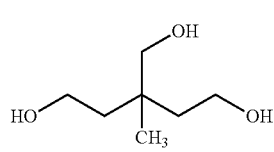

A5

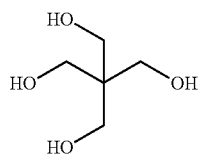

A6

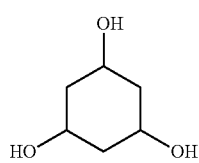

A7

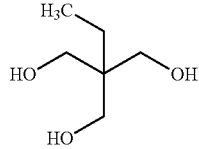

A8

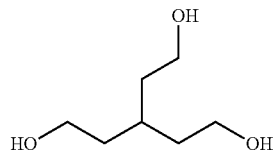

A9

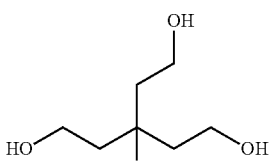

A10

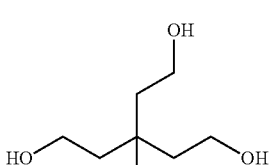

A11

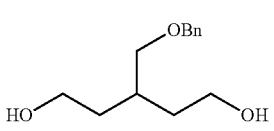

A12

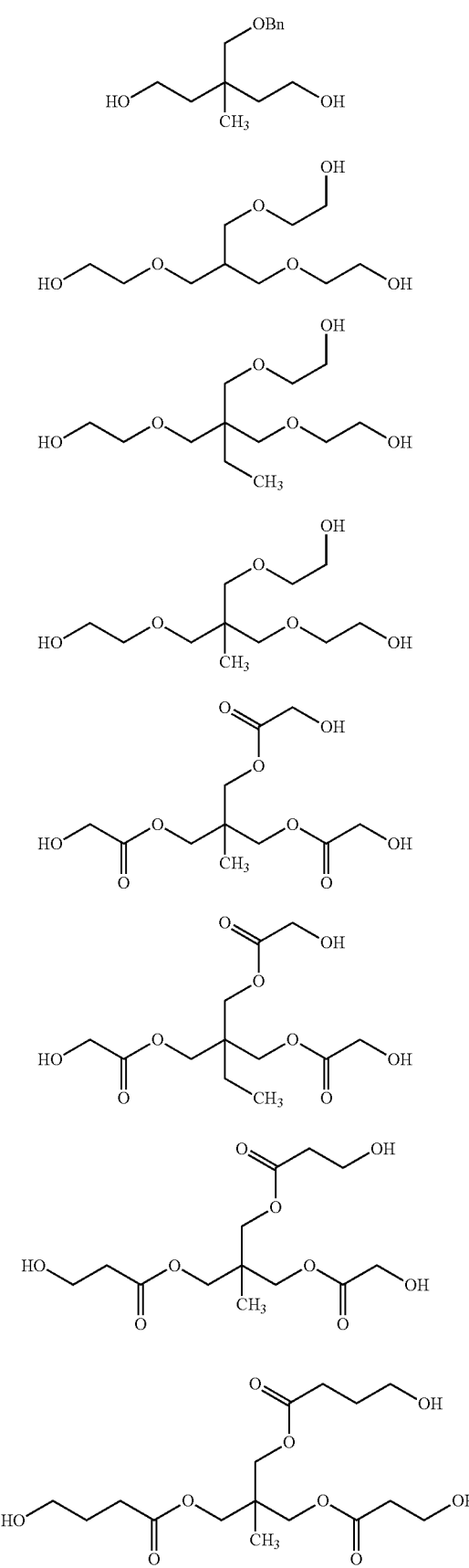

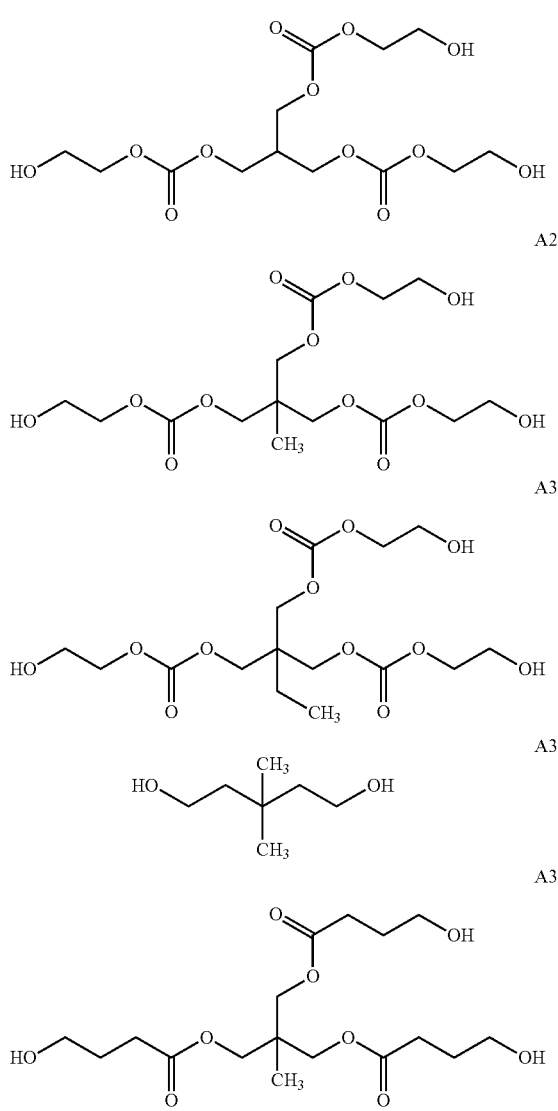

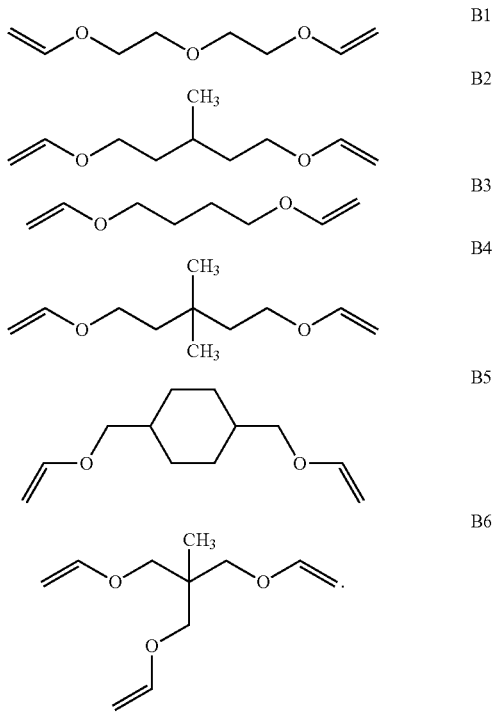

In some embodiments, the precursor to each of $A^1$ and $A^2$ is independently selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A31, and A32, $B^1$ or $B^2$ is connected to one of the oxygen atoms of the hydroxyl groups in said polyols.

In some embodiments, $X^1$ includes or is derived from a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, each of $B^1$ and $B^2$ is the same, e.g., the same structure of Formula (II). In some embodiments, each of $B^1$ and $B^2$ is different, e.g., a different structure of Formula (II).

In some embodiments, $Z^1$ is $C(R^{23})(R^{24})$ and each of $R^{22}$ and $R^{23}$ is independently hydrogen, $C_1$-$C_6$ alkyl, or ($C_1$-$C_6$ alkylene)-$OR^{26}$. In some embodiments, $R^{22}$ is hydrogen and $R^{23}$ is independently $C_1$-$C_6$ alkyl, e.g., $CH_3$. In some embodiments, $R^{22}$ is hydrogen or $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point. In some embodiments, $Z^1$ is $C_3$-$C_6$ cyclyl, optionally substituted with 1-4 $R^{25}$ (e.g., cyclohexyl).

In some embodiments, each of $X^4$ and $X^5$ is independently $C_1$-$C_6$ alkylene (e.g., $CH_2$, $CH_2CH_2$), wherein alkylene is optionally substituted with 1-6 $R^{25}$.

In some embodiments, each of $R^{20}$ and $R^{21}$ is independently $C_1$-$C_6$ alkyl (e.g., $CH_3$) or $OR^{26}$ (e.g., $C_2$-$C_6$ alkenyl (e.g., $CH=CH_2$) or a branching point).

In some embodiments, the precursor to each of $B^1$ and $B^2$ is independently selected from the following vinyl ethers:

In some embodiments, each of $C^1$ and $C^2$ is the same, e.g., the same structure of Formula (II). In some embodiments, each of $C^1$ and $C^2$ is different, e.g., a different structure of Formula (II).

In some embodiments, each of $C^1$ and $C^2$ is independently heteroalkyl (e.g., an oxygen-containing $C_1$-$C_4$ heteroalkyl and/or an amine-containing heteroalkyl), optionally substituted with 1-6 $R^3$.

In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ has a linear structure, e.g., does not comprise a branching point or cyclic group. In some embodiments, each of $C^1$ and $C^2$ has a $C^1$ or $C^2$ has a branched structure, e.g., comprising at least 1, at least 2, at least 3, at least 4, at least 5, or at least 6 branching points.

In some embodiments, each of $C^1$ and $C^2$ comprises a cyclic structure, e.g., a cyclyl or heterocyclyl group, e.g., a dextran, a cyclodextran, chitosan, or other carbohydrate based moiety.

In some embodiments, each of $C^1$ and $C^2$ is independently 200 to 5000 Da in size.

In some embodiments, each of $C^1$ and $C^2$ is a polyethylene glycol (PEG). In some embodiments, each of $C^1$ and $C^2$ is independently a polyethylene glycol (PEG) and is between about 200 and 1200 Da in size. In some embodiments, each of $C^1$ and $C^2$ is independently PEG 400, PEG 1000, or PEG 2050.

In some embodiments of a polymer (e.g., a polymer described herein, e.g., a polymer of Formula (I)), each of m and n independently an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In some embodiments, each of m and n independently an integer from 2 to 200, e.g., 5 to 200 or 10 to 200. In some embodiments, each of m and n independently an integer from 5 to 100, e.g., 10 to 50.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I-d) or Formula (I-e) is greater than about 5 kDa in size. In some embodiments, each of $A^1$ and $A^2$ does not independently include, or is not independently derived from, tri(methylol)ethane and the polymer of Formula (I-d) or Formula (I-e) is greater than about 10 kDa in size.

In some embodiments, each of $A^1$ and $A^2$ independently includes, or is independently derived from, tri(methylol)ethane. In some embodiments, each of $A^1$ and $A^2$ independently includes, or is independently derived from, tri(methylol)ethane and the polymer of Formula (I-d) or Formula (I-e) is greater than about 5 kDa in size. In some embodiments, each of $A^1$ and $A^2$ independently includes, or is independently derived from, tri(methylol)ethane and the polymer of Formula (I-d) or Formula (I-e) is greater than about 10 kDa in size.

In some embodiments, the polymer (e.g., the polyacetal polymer) comprises a structure according to Formula (IV):

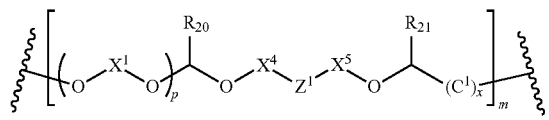

Formula (IV)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, or heterocyclyl is optionally substituted with 1-6 $R^4$;

each of $X^4$ and $X^5$ is independently $C_1$-$C_6$ alkylene, optionally substituted with 1-6 $R^4$;

$Z^1$ is O, $C_3$-$C_8$ cyclyl, or $C(R^{22})(R^{23})$;

each of $C^1$ and $C^2$ is heteroalkyl, cyclyl, or heterocyclyl, each of which is optionally substituted with 1-6 $R^3$;

each of $R^3$ is independently alkyl, hydroxyl, halo, heteroalkyl, keto, alkoxy, ester, cyclyl, heterocyclyl, arylalkyl, heteroarylalkyl, a linker, an agent, a targeting moiety, a protecting group, or a branching point;

each $R^4$ is independently $C_1$-$C_6$ alkyl, $C_1$-$C_6$ heteroalkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, or ($C_1$-$C_6$ alkylene)-OC(O)O—($C_1$-$C_6$ alkylene)-$OR^5$, wherein each alkyl, alkenyl, alkynyl, heteroalkyl, or alkylene is optionally substituted with 1-6 $R^7$;

each $R^5$ is independently hydrogen, $C_1$-$C_6$ alkyl, cyclyl, heterocyclyl, aryl, heteroaryl, arylalkyl, heteroarylalkyl, a linker, an agent, a targeting moiety, a protecting group, or a branching point, wherein each alkyl, cyclyl, heterocyclyl, aryl, heteroaryl, arylalkyl, heteroarylalkyl is optionally substituted with 1-6 $R^8$;

each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, ($C_1$-$C_6$ alkylene)-$OR^5$, ($C_1$-$C_6$ alkylene)-O—($C_1$-$C_6$ alkylene)-$OR^5$, cyano, cyclyl, heterocyclyl, aryl, or heteroaryl; and each $R^8$ is independently $C_1$-$C_6$ alkyl, $C_2$-$C_6$ alkynyl, $C_1$-$C_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 $R^9$;

each $R^9$ is independently $C_1$-$C_6$ alkyl, $C_1$-$C_6$ heteroalkyl, halo, cyano, cyclyl, or heterocyclyl;

each of $R^{20}$ and $R^{21}$ is independently $C_1$-$C_6$ alkyl or $OR^{26}$;

each of $R^{22}$ and $R^{23}$ is independently hydrogen, $C_1$-$C_6$ alkyl, or ($C_1$-$C_6$ alkylene)-$OR^{26}$; and each $R^{26}$ is $C_1$-$C_6$ alkyl, $C_2$-$C_6$ alkenyl, a linker, an agent, a targeting moiety, a protecting group, or a branching point;

each of p and x is independently 0 or 1;

and one of p or x is 1; and m or n is independently an integer from 5 to 200.

In some embodiments, $X^1$ is $C_1$-$C_{12}$ alkylene or $C_1$-$C_{12}$ heteroalkylene, optionally substituted with 1-6 $R^4$. In some embodiments, $X^1$ is $C_1$-$C_6$ alkylene, optionally substituted with 1-6 $R^4$. In some embodiments, $X^1$ is $C_1$-$C_{12}$ heteroalkylene, optionally substituted with 1-6 $R^4$.

In some embodiments, $X^1$ is $C_3$-$C_6$ cyclyl or $C_3$-$C_6$ heterocyclyl, wherein each cyclyl or heterocyclyl is optionally substituted with 1-6 $R^4$. In some embodiments, $X^1$ is $C_3$-$C_6$ cyclyl, optionally substituted with 1-6 $R^4$. In some embodiments, $X^1$ is cyclopropyl, cyclobutyl, cyclopentyl, or cyclohexyl, each of which is optionally substituted with 1-6

$R^4$. In some embodiments, $X^1$ is cyclopentyl or cyclohexyl, each of which is optionally substituted with 1-6 $R^4$. In some embodiments, $X^1$ is cyclopentyl or cyclohexyl, each of which is optionally substituted with 1-4 $R^4$. In some embodiments, $X^1$ is cyclopentyl or cyclohexyl, each of which is optionally substituted with 1-2 $R^4$, and each $R^4$ is independently $C_1$-$C_6$ alkyl or $OR^5$. In some embodiments, $X^1$ is cyclohexyl substituted with 1 $R^4$. In some embodiments, $X^1$ is cyclohexyl substituted with $OR^5$.

In some embodiments, $R^5$ is hydrogen, $C_1$-$C_6$ alkyl, cyclyl, heterocyclyl, aryl, heteroaryl, arylalkyl, or heteroarylalkyl. In some embodiments, $R^5$ is hydrogen. In some embodiments, $R^5$ is arylalkyl or heteroarylalkyl. In some embodiments, $R^5$ is a linker. In some embodiments, $R^5$ is an agent (e.g., an ARB). In some embodiments, $R^5$ is a targeting moiety. In some embodiments, $R^5$ is a protecting group. In some embodiments, $R^5$ is a branching point.

In some embodiments, $Z^1$ is O.

In some embodiments, $Z^1$ is $C_3$-$C_8$ cyclyl or $C_3$-$C_8$ heterocyclyl, each of which is optionally substituted with 1-4 $R^{25}$. In some embodiments, $Z^1$ is $C_1$-$C_6$ cyclyl or $C_1$-$C_6$ heterocyclyl, each of which is optionally substituted with 1-4 $R^{25}$. In some embodiments, $Z^1$ is $C_3$-$C_6$ cyclyl, optionally substituted with 1-4 $R^{25}$. In some embodiments, $Z^1$ is cyclopropyl, cyclobutyl, cyclopentyl, or cyclohexyl, each of which is optionally substituted with 1-4 $R^{25}$. In some embodiments, $Z^1$ is cyclopentyl, or cyclohexyl, each of which is optionally substituted with 1-4 $R^{25}$. In some embodiments, $Z^1$ is cyclohexyl, optionally substituted with 1-4 $R^{25}$. In some embodiments, $Z^1$ is cyclohexyl.

In some embodiments, $Z^1$ is $C(R^{22})(R^{23})$. In some embodiments, $Z^1$ is $C(R^{23})(R^{24})$ and each of $R^{22}$ and $R^{23}$ is independently hydrogen, $C_1$-$C_6$ alkyl, or ($C_1$-$C_6$ alkylene)-$OR^{26}$. In some embodiments, each of $R^{22}$ and $R^{23}$ is independently hydrogen. In some embodiments, each of $R^{22}$ and $R^{23}$ is independently hydrogen or $C_1$-$C_6$ alkyl, e.g., $CH_3$. In some embodiments, each of $R^{22}$ and $R^{23}$ is independently hydrogen. In some embodiments, each of $R^{22}$ and $R^{23}$ is independently $C_1$-$C_6$ alkyl, e.g., $CH_3$. In some embodiments, $R^{22}$ is hydrogen and $R^{23}$ is independently $C_1$-$C_6$ alkyl, e.g., $CH_3$. In some embodiments, each of $R^{22}$ and $R^{23}$ is independently ($C_1$-$C_6$ alkylene)-$OR^{26}$. In some embodiments, each of $R^{22}$ and $R^{23}$ is independently ($C_1$-$C_2$ alkylene)-$OR^{26}$. In some embodiments, each of $R^{22}$ and $R^{23}$ is independently ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is hydrogen or $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point.

In some embodiments, each of $X^4$ and $X^5$ is independently $C_1$-$C_6$ alkylene, wherein alkylene is optionally substituted with 1-6 $R^{25}$. In some embodiments, each of $X^4$ and $X^5$ is independently $C_1$-$C_4$ alkylene, wherein alkylene is optionally substituted with 1-6 $R^{25}$. In some embodiments, each of $X^4$ and $X^5$ is independently $C_1$-$C_2$ alkylene, wherein alkylene is optionally substituted with 1-6 $R^{25}$. In some embodiments, each of $X^4$ and $X^5$ is independently $C_1$-$C_2$ alkylene (e.g., $CH_2$, $CH_2CH_2$).

In some embodiments, each of $R^{20}$ and $R^{21}$ is independently $C_1$-$C_6$ alkyl or $OR^{20}$. In some embodiments, each of $R^{20}$ and $R^{21}$ is independently $C_1$-$C_6$ alkyl. In some embodiments, each of $R^{20}$ and $R^{21}$ is independently $C_1$-$C_4$ alkyl. In some embodiments, each of $R^{20}$ and $R^{21}$ is independently $C_1$-$C_2$ alkyl, e.g., $CH_3$. In some embodiments, each of $R^{20}$ and $R^{21}$ is independently $OR^{26}$. In some embodiments, each of $R^{20}$ and $R^{21}$ is independently $OR^{26}$, and $R^{26}$ is $C_2$-$C_6$ alkenyl (e.g., $CH=CH_2$) or a branching point.

In some embodiments, each of $C^1$ and $C^2$ is $C_1$-$C_{10}$ heteroalkyl, e.g., an oxygen-containing $C_1$-$C_4$ heteroalkyl and/or an amine-containing heteroalkyl. In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ comprises a polyethylene glycol (PEG). In some embodiments, each of $C^1$ and $C^2$ comprises a polyethylene glycol (PEG) or a polyethylene oxide (PEO). In some embodiments, each of $C^1$ and $C^2$ comprises a polyethylene oxide (PEO) or a polypropylene glycol (PPG). In some embodiments, each of $C^1$ and $C^2$ comprises a polybutylene oxide (PBO).

In some embodiments, each of $C^1$ or $C^2$ comprises a cyclic structure. In some embodiments, each of $C^1$ or $C^2$ comprises a cyclic structure, e.g., a cyclyl or heterocyclyl group. In some embodiments, each of $C^1$ or $C^2$ comprises a carbohydrate (e.g., a glucose derivative, galactose derivative, mannose derivative, fucose derivative, sialic acid derivative, or other carbohydrate derivative). In some embodiments, each of $C^1$ or $C^2$ comprises a dextran, a cyclodextran, chitosan, or other carbohydrate based moiety.

In some embodiments, the precursor to $C^1$ is PEG (e.g., polyethylene glycol). In some embodiments, the PEG comprises PEG 100, PEG 200, PEG 300, PEG 400, PEG 500, PEG 600, PEG 800, PEG 1000, PEG 1500, PEG 2000, PEG 2050, PEG 4000, or PEG 6000, also referred to herein as P100, P200, P300, P400, P500, P600, P800, P1000, P1500, P2000, P2050, P4000, and P6000, or any combination thereof. In some embodiments, the PEG comprises P400, P1000, or a combination of P400 and P1000. In some embodiments, the PEG comprises PEG 2050.

In some embodiments, m is integer from 5 to 175, from 5 to 150, from 5 to 125, from 5 to 100. In some embodiments, m is integer from 5 to 100, from 5 to 95, from 5 to 85, from 5 to 80, from 5 to 75, from 5 to 70, from 5 to 65, from 5 to 60, from 5 to 55, from 5 to 50, from 5 to 45, from 5 to 40, from 5 to 35, from 5 to 30, from 5 to 25, or from 5 to 20. In some embodiments, m is an integer from 5 to 50. In some embodiments, m is an integer from 10 to 100, from 10 to 95, from 10 to 85, from 10 to 80, from 10 to 75, from 10 to 70, from 10 to 65, from 10 to 60, from 10 to 55, from 10 to 50, from 10 to 45, from 10 to 40, from 10 to 35, from 10 to 30, from 10 to 25, or from 10 to 20. In some embodiments, m is an integer from 10 to 50.

In some embodiments, the polymer (e.g., a polyacetal polymer described herein) is derived from or comprises a compound of Formula (II) (e.g., a polyol) selected from one or more of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32; a compound of Formula (III) (e.g., a vinyl ether) selected from one or more of B1, B2, B3, B4, B5 and B6; and a compound of $C^1$ or $C^2$ (e.g., a PEG). In one embodiment, the polymer is derived from or comprises A1 and a vinyl ether chosen from one or more of B1, B2, B3, B4, B5, and B6, and may or may not comprise a PEG moiety (e.g., P400, P1000, or P2050). In one embodiment, the polymer is derived from or comprises A2 and a vinyl ether chosen from one or more of B1, B2, B3, B4, B5, and B6, and may or may not comprise a PEG moiety (e.g., P400, P1000, or P2050). In one embodiment, the polymer is derived from or comprises A3 and a vinyl ether chosen from one or more of B1, B2, B3, B4, B5, and B6, and may or may not comprise a PEG moiety (e.g., P400, P1000, or P2050). In one embodiment, the polymer is derived from or comprises A4 and a vinyl ether chosen from one or more of B1, B2, B3, B4, B5, and B6, and may or may not comprise a PEG moiety (e.g., P400, P1000, or P2050). In one embodiment, the polymer is derived from or comprises A5 and a vinyl ether chosen from one or more of B1, B2, B3, B4, B5, and B6, and may or may not comprise a PEG moiety (e.g., P400, P1000, or P2050). In one embodiment, the polymer is derived from or comprises A6 and a vinyl ether chosen from one or more of B1, B2, B3, B4, B5, and B6, and may or may not comprise a PEG moiety (e.g., P400, P1000, or P2050). In one embodiment, the polymer is derived from or comprises A7 and a vinyl ether chosen from one or more of B1, B2, B3, B4, B5, and B6, and may or may not comprise a PEG moiety (e.g., P400, P1000, or P2050). In one embodiment, the polymer is derived from or comprises A8 and a vinyl ether chosen from one or more of B1, B2, B3, B4, B5, and B6, and may or may not comprise a PEG moiety (e.g., P400, P1000, or P2050). In one embodiment, the polymer is derived from or comprises A9 and a vinyl ether chosen from one or more of B1, B2, B3, B4, B5, and B6, and may or may not comprise a PEG moiety (e.g., P400, P1000, or P2050). In one embodiment, the polymer is derived from or comprises A10 and a vinyl ether chosen from one or more of B1, B2, B3, B4, B5, and B6, and may or may not comprise a PEG moiety (e.g., P400, P1000, or P2050). In one embodiment, the polymer is derived from or comprises A11 and a vinyl ether chosen from one or more of B1, B2, B3, B4, B5, and B6, and may or may not comprise a PEG moiety (e.g., P400, P1000, or P2050). In one embodiment, the polymer is derived from or comprises A12 and a vinyl ether chosen from one or more of B1, B2, B3, B4, B5, and B6, and may or may not comprise a PEG moiety (e.g., P400, P1000, or P2050). In one embodiment, the polymer is derived from or comprises A13 and a vinyl ether chosen from one or more of B1, B2, B3, B4, B5, and B6, and may or may not comprise a PEG moiety (e.g., P400, P1000, or P2050). In one embodiment, the polymer is derived from or comprises A14 and a vinyl ether chosen from one or more of B1, B2, B3, B4, B5, and B6, and may or may not comprise a PEG moiety (e.g., P400, P1000, or P2050). In one embodiment, the polymer is derived from or comprises A15 and a vinyl ether chosen from one or more of B1, B2, B3, B4, B5, and B6, and may or may not comprise a PEG moiety (e.g., P400, P1000, or P2050). In one embodiment, the polymer is derived from or comprises A16 and a vinyl ether chosen from one or more of B1, B2, B3, B4, B5, and B6, and may or may not comprise a PEG moiety (e.g., P400, P1000, or P2050). In one embodiment, the polymer is derived from or comprises A17 and a vinyl ether chosen from one or more of B1, B2, B3, B4, B5, and B6, and may or may not comprise a PEG moiety (e.g., P400, P1000, or P2050). In one embodiment, the polymer is derived from or comprises A18 and a vinyl ether chosen from one or more of B1, B2, B3, B4, B5, and B6, and may or may not comprise a PEG moiety (e.g., P400, P1000, or P2050). In one embodiment, the polymer is derived from or comprises A19 and a vinyl ether chosen from one or more of B1, B2, B3, B4, B5, and B6, and may or may not comprise a PEG moiety (e.g., P400, P1000, or P2050). In one embodiment, the polymer is derived from or comprises A20 and a vinyl ether chosen from one or more of B1, B2, B3, B4, B5, and B6, and may or may not comprise a PEG moiety (e.g., P400, P1000, or P2050). In one embodiment, the polymer is derived from or comprises A21 and a vinyl ether chosen from one or more of B1, B2, B3, B4, B5, and B6, and may or may not comprise a PEG moiety (e.g., P400, P1000, or P2050). In one embodiment, the polymer is derived from or comprises A22 and a vinyl ether chosen from one or more of B1, B2, B3, B4, B5, and B6, and may or may not comprise a PEG moiety (e.g., P400, P1000, or P2050). In one embodiment, the polymer is derived from or comprises A23 and a vinyl ether chosen from one or more of B1, B2, B3, B4, B5, and B6, and may or may not comprise a PEG moiety (e.g., P400, P1000, or P2050). In one embodiment, the polymer is derived from or comprises A24 and a vinyl ether chosen from one or more of B1, B2, B3, B4, B5, and B6, and may or may not comprise a PEG moiety (e.g., P400, P1000, or P2050). In one embodiment, the polymer is derived from or comprises A25 and a vinyl ether chosen from one or more of B1, B2, B3, B4, B5, and B6, and may or may not comprise a PEG moiety (e.g., P400, P1000, or P2050). In one embodiment, the polymer is derived from or comprises A26 and a vinyl ether chosen from one or more of B1, B2, B3, B4, B5, and B6, and may or may not comprise a PEG moiety (e.g., P400, P1000, or P2050). In one embodiment, the polymer is derived from or comprises A27 and a vinyl ether chosen from one or more of B1, B2, B3, B4, B5, and B6, and may or may not comprise a PEG moiety (e.g., P400, P1000, or P2050). In one embodiment, the polymer is derived from or comprises A28 and a vinyl ether chosen from one or more of B1, B2, B3, B4, B5, and B6, and may or may not comprise a PEG moiety (e.g., P400, P1000, or P2050). In one embodiment, the polymer is derived from or comprises A29 and a vinyl ether chosen from one or more of B1, B2, B3, B4, B5, and B6, and may or may not comprise a PEG moiety (e.g., P400, P1000, or P2050). In one embodiment, the polymer is derived from or comprises A30 and a vinyl ether chosen from one or more of B1, B2, B3, B4, B5, and B6, and may or may not comprise a PEG moiety (e.g., P400, P1000, or P2050). In one embodiment, the polymer is derived from or comprises A31 and a vinyl ether chosen from one or more of B1, B2, B3, B4, B5, and B6, and may or may not comprise a PEG moiety (e.g., P400, P1000, or P2050). In one embodiment, the polymer is derived from or comprises A32 and a vinyl ether chosen from one or more of B1, B2, B3, B4, B5, and B6, and may or may not comprise a PEG moiety (e.g., P400, P1000, or P2050). Each of the foregoing polyol and vinyl ethers are shown in FIGS. 1B and 1C.

In one embodiment, the polymer (e.g., a polyacetal polymer described herein) is derived from or comprises a polyol and a vinyl ether depicted in FIGS. 1B and 1C. In one embodiment, the polymer (e.g., a polyacetal polymer, e.g., of Formula (I), Formula (I-a), Formula (I-b), Formula (I-c), Formula (I-d), Formula (I-e), or Formula (IV)) is derived from or comprises a polyol and a vinyl ether depicted in FIGS. 1B and 1C and has a ratio of release or degradation rate of the polymer at a first pH (e.g., a first more acidic pH such as pH=6.7) relative to a second pH (e.g., a second less acidic pH such as pH=7.4) is greater than 1, 1.2, 1.4, 1.6, 1.8, 2, 2.2, 2.4, 2.6, 2.8, 3 or higher. In one embodiment, the ratio of release or degradation rate of the polymer at pH=6.7 relative to pH=7.4 is greater than 2. In these embodiments, the polymer is pH-sensitive such that it can degrade or release an agent attached thereto selectively at a target site, which has a different pH from a non-target-site. The release or degradation rate of the polymer can be measured at a temperature of about 37° C.

In one embodiment, the polymer (e.g., a polyacetal polymer described herein) is derived from or comprises a polyol and a vinyl ether depicted in FIGS. 1B and 1C and is hydrophobic (e.g., insoluble in water). In one embodiment, the polymer (e.g., a polyacetal polymer described herein) is derived from or comprises a polyol and a vinyl ether depicted in FIGS. 1B and 1C and is sparingly soluble in water. In one embodiment, the polymer (e.g., a polyacetal polymer described herein) is derived from or comprises a polyol and a vinyl ether depicted in FIGS. 1B and 1C and is slightly soluble in water. In one embodiment, the polymer (e.g., a polyacetal polymer described herein) is derived from or comprises a polyol and a vinyl ether depicted in FIGS. 1B and 1C and is partially soluble in water.

In one embodiment, the polymer (e.g., a polyacetal polymer described herein) is derived from or comprises a polyol and a vinyl ether depicted in FIGS. 1B and 1C and is amphiphilic. In one embodiment, the polymer (e.g., a polyacetal polymer described herein) is derived from or comprises a polyol and a vinyl ether depicted in FIGS. 1B and 1C and comprises one segment that is hydrophobic and one segment that is hydrophilic.

In some embodiments, the polymer (e.g., a polymer as described herein) is present in (e.g., is part or all of) a linker, e.g., pH-sensitive linker as described herein.

In some embodiments, the polymer (e.g., a polymer as described herein) is present in a conjugate (e.g., an agent-polymer conjugate, a targeting moiety-polymer conjugate, or an agent-polymer-targeting moiety conjugate, as described herein). In one embodiment, the agent and/or targeting moiety are directly coupled (e.g., covalently coupled) to the polyacetal polymer. In another embodiment, an acetal monomer or a polyacetal polymer couples or links (e.g., covalently couples or links) the agent and/or targeting moiety to a second polymer (e.g., a polymer other than a polyacetal polymer). In one embodiment, the agent is a therapeutic or a diagnostic agent as described herein. In one embodiment, the agent is an AHCM as described herein.

In some embodiments, the polymer (e.g., a polymer as described herein) when present in a particle is associated (e.g., covalently or non-covalently) to an agent. In one embodiment, the agent is a therapeutic or a diagnostic agent as described herein. In one embodiment, the agent is an AHCM as described herein.

In some embodiments, the polymer is at least 5%, 10%, 20%, 30%, 40%, 50%, 60%, 70%, 80%, 90% or 100% made of polyacetal polymers (e.g., a polyacetal polymer according to Formula (I)). In certain embodiments, the polymer can further comprise one or more hydrophobic or hydrophilic polymers to enhance a desired property. In certain embodiments, the polymer comprises (e.g., is linked to) a water-soluble monomer or polymer (e.g., polyethylene glycol (PEG) monomer or polymer), e.g., to increase one or more of amphiphilicity, hydrophilicity, water-solubility, pH sensitivity or stability. In other embodiments, the polymer comprises one or more of a polyacetal monomer or polymer with or without PEG, and one or more of: dextran (e.g., with a molecular weight of about 50 kDa or above), polylactic acid (PLA), polyglycolic acid (PGA), poly(lactic-co-glycolic acid) (PLGA), polycaprolactone (PCL), polydioxanone (PDO), polyanhydrides, polyorthoesters, cyclodextrin, or chitosan, or a pegylated form thereof. In other embodiments, the polymer comprises one or more of a polyol monomer (e.g., a monomer according to Formula (II), Formula (II-a), Formula (II-b), or Formula (II-c), or a polyol as shown in FIG. 1B, with or without a compound of $C^1$ or $C^2$, e.g., a PEG and one or more of: a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester. In some embodiments, the polymer comprises a plurality of a PLA, dextran, or a polyacetal polymer described herein. In one embodiment, the dextran has a molecular weight of at least about 200 kDa. In one embodiment, the dextran has a molecular weight of at least about 500 kDa. Exemplary polymers that can be combined with the polyacetal polymers are described herein, e.g., in the section entitled "Polymers."

In one embodiment, the polyacetal monomer or polymer (with or without an agent, e.g., an AHCM, and/or a targeting moiety) is coupled (e.g., covalently coupled) to a second polymer, e.g., one or more of: dextran, polylactic acid (PLA), polyglycolic acid (PGA), poly(lactic-co-glycolic acid) (PLGA), polycaprolactone (PCL), polydioxanone (PDO), polyanhydrides, polyorthoesters, cyclodextrin, or chitosan, or a pegylated form thereof (e.g., poly(lactic acid)-b-poly(ethylene glycol) (PLA-PEG), poly(lactic acid)-b-poly(ethylene glycol) (PLGA-PEG), or (cyclodextrin)-co-poly(ethylene glycol) (CDP)).

Linkers

In another aspect, the invention features a linker, e.g., a pH-sensitive linker. In one embodiment, the linker couples (e.g., covalently links) a first moiety to a second moiety. In one embodiment, the linker comprises, or consists of, a polyacetal polymer as described herein.

In some embodiments, the first moiety is an agent (e.g., a therapeutic agent as described herein) and/or a targeting moiety, and the second moiety is a polymer (e.g., a polyacetal polymer). In some embodiments, the polyacetal is a polymer described herein (e.g., a polymer of Formula (I), Formula (I-a), Formula (I-b), Formula (I-c), Formula (I-d), Formula (I-e), or Formula (IV)).

In other embodiments, the first moiety is an agent (e.g., a therapeutic agent as described herein) and/or a targeting moiety, and the second moiety is a polymer other than a polyacetal monomer (e.g., a second polymer, e.g., one or more of: polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, a polyorthoester, a dextran, a cyclodextran, chitosan, or other carbohydrate based polymer as described herein).

In some embodiments, the first moiety is an agent, and the second moiety comprises a targeting moiety (optionally in combination with a polymer other than a polyacetal polymer described herein).

In some embodiments, the linker (e.g., a linker comprising a polyacetal polymer described herein, e.g., a structure of Formula (I), Formula (I-a), Formula (I-b), or Formula (IV)) is pH-sensitive. In certain embodiments, the linker is sensitive to a pH between about 5.0 and about 7.4, between 5.0 and 7.0, between 5.0 and 6.5, between 5.0 and 5.5, or between 5.9 and 6.2. In one embodiment, the linker is sensitive to a pH between about 5.5 and about 6.5, e.g., between 5.9 and 6.2.

In some embodiments, the linker is sensitive to a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the linker is sensitive to a hypoxic pH, e.g., a pH about 6.7 to 6.9, e.g., compared to a physiological pH of about 7.4.

In one embodiment, the linker is preferentially cleaved or degraded upon exposure to a first pH relative to a second pH. In one embodiment, the linker is cleaved or degraded at least 2, 5, 10, 20, 30, 40, 50, 60, 70, 80, or 100 times faster upon exposure to a first pH relative to a second pH. In other embodiments, the linker shows a greater release or degradation rate at a first acidic pH (e.g., pH=6.7) relative to a second more basic pH (e.g., pH=7.4). In one embodiment, ratio of release or degradation rate of the linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the linker at pH=6.7 relative to pH=7.4 is greater than 2. In one embodiment, the linker shows increased pH-sensitivity in a hypoxic microenvironment, e.g., in a tumor or fibrotic tissue.

In some embodiments, the average molecular weight of the linker (e.g., a polyacetal polymer as described herein) is from about 2 kDa to about 200 kDa, (e.g., from about 2.5 kDa to about 175 kDa, from about 5 kDa about 150 kDa, from about 10 kDa to about 125 kDa, from about 12.5 kDa to about 100 kDa, from about 15 kDa to about 90 kDa, from about 17.5 kDa to about 80 kDa, from about 20 kDa to about 70 kDa, from about 22.5 kDa to about 60 kDa, or from about 25 kDa to about 50 kDa). In some embodiments, the average molecular weight of the linker (e.g., a polyacetal polymer as described herein) is from about 5 kDa to about 100 kDa (e.g., from about 6 kDa to about 90 kDa, from about 7 kDa to about 95 kDa, from about 8 kDa to about 85 kDa, from about 9 kDa to about 80 kDa, from about 10 kDa to about 75 kDa, from about 11 kDa to about 70 kDa, from about 12 kDa to about 65 kDa, from about 13 kDa to about 60 kDa, from about 14 kDa to about 55 kDa, or from about 15 kDa to about 50 kDa). In some embodiments, the average molecular weight of the polymer used in a linker (e.g., a polyacetal polymer as described herein) is from about 7 kDa to about 100 kDa, (e.g., from about 7 kDa to about 95 kDa, about 7 kDa to about 90 kDa, about 7 kDa to about 80 kDa, about 7 kDa to 75 kDa, about 7 kDa to about 70 kDa, about 7 kDa to about 65 kDa, about 7 kDa to about 60 kDa, about 7 kDa to about 55 kDa, about 7 kDa to about 50 kDa, about 7 kDa to about 45 kDa, about 7 kDa to about 40 kDa, about 7 kDa to about 35 kDa, about 7 kDa to about 30 kDa, about 7 kDa to about 25 kDa, about 7 kDa to about 20 kDa, about 7 kDa to about 15 kDa, or from about 7 kDa to about 75 kDa, about 7.5 kDa to about 75 kDa, about 10 kDa to about 75 kDa, about 12.5 kDa to about 75 kDa, about 15 kDa to about 75 kDa, about 17.5 kDa to about 75 kDa, about 20 kDa to about 75 kDa, about 22.5 kDa to about 75 kDa, about 25 kDa to about 75 kDa, about 27.5 kDa to about 75 kDa, about 30 kDa to about 75 kDa, about 32.5 kDa to about 75 kDa, about 35 kDa to about 75 kDa, about 40 kDa to about 75 kDa, about 42.5 kDa to about 75 kDa, about 45 kDa to about 75 kDa, about 47.5 kDa to about 75 kDa, or about 50 kDa to about 75 kDa). In one embodiment, the average molecular weight of the linker is from about 5 kDa to about 50 kDa. In another embodiment, the average molecular weight of the linker is from about 10 kDa to about 50 kDa. In another embodiment, the average molecular weight of the linker is from about 15 kDa to about 40 kDa. In another embodiment, the average molecular weight of the linker is from about 15 kDa to about 25 kDa. In another embodiment, the average molecular weight of the linker is from about 20 kDa to about 40 kDa. In some embodiments, the average molecular weight of the linker is not less than about 10 KDa, about 9 kDa, about 8 kDa, about 7 kDa, about 6 kDa, or about 5 kDa.

In some embodiments, the linker (e.g., a polyacetal polymer described herein) is soluble in water (e.g., hydrophilic). In some embodiments, the linker (e.g., a polyacetal polymer described herein) is soluble in water, and between about 0.1 to about 5 parts water are required to dissolve 1 part linker, or between about 1 part to about 5 parts water are required to dissolve 1 part polymer. In some embodiments, the linker (e.g., a polyacetal polymer described herein) is partially soluble in water. In some embodiments, the linker (e.g., a polyacetal polymer described herein) is partially soluble in water, and between about 5 to about 50 parts water are required to dissolve 1 part linker. In some embodiments, the linker (e.g., a polyacetal polymer described herein) is sparingly soluble in water. In some embodiments the linker (e.g., a polyacetal polymer described herein) is sparingly soluble in water, and between about 25 to about 100 parts water is required to dissolve 1 part linker. In some embodiments, the linker (e.g., a polyacetal polymer described herein) is slightly soluble in water. In some embodiments, the linker (e.g., a polyacetal polymer described herein) is slightly soluble in water, and between 100 to about 1,000 parts water are required to dissolve 1 part linker. In some embodiments, the linker (e.g., a polyacetal polymer described herein) is very slightly soluble in water. In some embodiments, the linker (e.g., a polyacetal polymer described herein) is very slightly soluble in water, and between 1,000 to about 10,000 parts water are required to dissolve 1 part linker. In some embodiments, the linker (e.g., a polyacetal polymer described herein) is substantially insoluble in water (e.g., hydrophobic). In some embodiments, the linker (e.g., a polyacetal polymer described herein) is substantially insoluble in water and greater than about 10,000 parts water are required to dissolve 1 part linker.

In one embodiment, the linker (e.g., a polyacetal polymer described herein) is amphiphilic. In one embodiment, the linker (e.g., a polyacetal polymer described herein) comprises a segment that is hydrophobic and a segment that is hydrophilic.

In some embodiments, the polymer (e.g., a polyacetal polymer) is a liquid (e.g., a fluid liquid) at room temperature (e.g., at 25° C.). In some embodiments, the linker (e.g., a polyacetal polymer described herein) is viscous (e.g., a viscous liquid) at room temperature (e.g., at 25° C.). In some embodiments, the linker (e.g., a polyacetal polymer described herein) comprises a gel at room temperature (e.g., at 25° C.). In some embodiments, the linker (e.g., a polyacetal polymer described herein) is solid (e.g., a crystalline, semi-crystalline, amorphous, glassy, or rubbery solid) at room temperature (e.g., at 25° C.). In some embodiments, the melting temperature ($T_m$) of the linker (e.g., a polyacetal polymer) is greater than about 25° C. In some embodiments, the melting temperature ($T_m$) of the linker (e.g., a polyacetal polymer described herein) is greater than about 30° C., about 32° C., about 34° C., about 36° C., about 38° C., about 40° C., about 42° C., about 44° C., about 46° C., about 48° C., about 50° C., or higher. In some embodiments, the melting temperature ($T_m$) of the linker (e.g., a polyacetal polymer described herein) is between about 30° C. and about 50° C. In some embodiments, the melting temperature ($T_m$) of the linker (e.g., a polyacetal polymer described herein) is between about 35° C. and about 45° C.

In some embodiments, the linker (e.g., a polyacetal polymer described herein) comprises a linear structure. In some embodiments, the linker (e.g., a polyacetal polymer described herein) comprises a branched structure. In some embodiments, the linker (e.g., a polyacetal polymer described herein) comprises a branched structure, and each repeating unit in the linker comprises at least 1, at least 2, at least 3, at least 4, at least 5, at least 6, at least 7, or at least 8 branch points.

In one embodiment, the linker is chosen from one or more of an acetal group, a ketal group, an anhydride group, an ester group, a hydrazone group, a silyl ether group, a combination of acetal or ketal with ester group, an oligoacetal or oligo-ketal group, a combination of the oligo-ketal and silyl ether group, or a combination of the oligo-ketal and vinyl ether group. In other embodiments, the linker is chosen from a combination of acetal or ketal with cis-aconityl, hydrazine, oxime, imidazole or trityl groups. Any of the aforesaid groups or combination of groups can modified to enhance the pH sensitivity of the linker, e.g., as described herein.

In some embodiments, the linker is a cleavable moiety. In some embodiments, the linker is degraded or hydrolyzed at physiological conditions. In some embodiments, the linker is pH sensitive. In some embodiments, the linker is degraded or hydrolyzed through the action of an enzyme (e.g., a protease or esterase).

In some embodiments, the linker is a peptide. In some embodiments, the linker is a peptide, and the peptide sequence is comprised of naturally occurring amino acids. In some embodiments, the linker is a peptide, and the peptide sequence comprises at least one synthetically derived amino acids, e.g., at least 2, at least 3, at least 4, at least 5, at least 8, at least 10, at least 15, at least 20, or more synthetically derived amino acids. In some embodiments, the peptide has a linear structure. In some embodiments, the peptide has a branched structure. In some embodiments, the peptide has a branched structure with, e.g., at least 2, at least 3, at least 4, at least 5, at least 6, at least 7, or at least 8 branching points. In some embodiments, the peptide has a cyclic structure.

In some embodiments, the linker is a peptide, and the peptide sequence comprises at least 2 amino acid residues. In some embodiments, the peptide sequence comprises at least 3, at least 4, at least 5, at least 6, at least 7, at least 8, at least 9, or at least 10 amino acid residues. In some embodiments, the peptide sequence is from about 1 to about 10 amino acid residues. In some embodiments, the peptide sequence is from about 1 to about 15, about 20, about 25, about 30, about 40, about 50, about 60, about 70, about 80, about 90, or about 100 amino acid residues. In some embodiments, the peptide sequence is from about 10 to about 100 amino acid residues. In some embodiments, the peptide sequence is from about 25 to about 100 amino acid residues. In some embodiments, the peptide sequence is from about 50 to about 100 amino acid residues.

In some embodiments, the linker comprises a substrate peptide that is cleaved, e.g., activated, by a matrix metalloprotease (MMP) selected from a sequence disclosed in U.S. Patent Application No. 2015/0087810. In some embodiments, the substrate peptide comprises a protease substrate comprising an amino acid sequence selected from the group consisting of SEQ ID NOs: 353-363, 372-375, 376-378, 395-401, 411-419, 426-433, 437-449, 454-456, 459-469, 475-482, 487-495, 318-323, 325-327, 330-335, 341-347, 14-33, and 159, e.g., as described in U.S. Patent Application No. 2015/0087810. In some embodiments, the linker comprises a substrate peptide derived from a sequence disclosed in U.S. Pat. No. 8,541,203, e.g., a substrate peptide chosen from an enzyme selected from the group consisting of MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the linker comprises a sequence disclosed in U.S. Pat. No. 8,513,390. In some embodiments, the linker comprises a sequence disclosed in International Patent Publication No. WO2003/079972. In some embodiments, the linker comprises a sequence disclosed in U.S. Pat. No. 7,495,099. In some embodiments, the linker comprises a sequence disclosed in U.S. Pat. No. 8,580,244. In some embodiments, the linker comprises a sequence disclosed in one of the following articles: van Kempen, et al. *Eur Cancer* (2006) 42:728-734; Desnoyers, L. R. et al. *Sci Transl Med* (2013) 5:207ra144; Rice, J. J. et al. *Protein Sci* (2006) 15:825-836; Boulware, K. T. and Daugherty, P. S. *Proc Natl Acad Sci USA* (2006) 103:7583-7588; Deperthes, D. *Biol Chem* (2002) 383:1107-1112; Harris, J. L. *Proc Natl Acad Sci USA* (2000) 97:7754-7759; Salmaso S. and Caliceti, P. J *Drug Deliv* (2013) 2013:1-19; and Eckhard, U et al *Matrix Biol* (2015) doi: 10.1016/j.matbio.2015.09.003 (epub ahead of print). The contents of any of the publications referenced herein are hereby expressly incorporated by reference.

In some embodiments, the linker comprises a substrate peptide that is cleaved, e.g., activated, by a protease, e.g., a protease present in a tumor or fibrotic microenvironment (e.g, a matrix metalloprotease (MMP), e.g., as described by Desnoyers, L. R. et al. *Sci Transl Med* (2013) 5:207ra144; Eckhard, U et al *Matrix Biol* (2015) doi: 10.1016/j.matbio.2015.09.003 (epub ahead of print); and van Kempen, et al. *Eur Cancer* (2006) 42:728-734. In one embodiment, the linker includes the amino acid sequence of a substrate for uPA, e.g., comprises the amino acid sequence LSGRSDNH (SEQ ID NO: 1), e.g., as described in U.S. Pat. No. 8,513,390. In some embodiment, the linker sequence further includes a Gly-Ser-containing peptide linker, at either end, or both ends to the substrate peptide. Additional exemplary proteases that may be upregulated in a tumor microenvironment include, but are not limited to, urokinase-type plasminogen activator (uPA), which is upregulated in human carcinomas (S. Ulisse, et al. *Curr. Cancer Drug Targets* 9, 32-71 (2009)), membrane-type serine protease 1 (MT-SP1/matriptase) (K. Uhland *Cell. Mol. Life Sci.* 63, 2968-2978 (2006); A. M. LeBeau, et al. *Proc. Natl. Acad. Sci.* U.S.A. 110, 93-98 (2013)), and legumain, a lysosomal protease found to be released and active in the acidic extracellular tumor microenvironment (C. Liu, et al. *Cancer Res.* 63, 2957-2964 (2003)). In some embodiments, the protease is produced by an inflammatory cell, e.g., a tumor infiltrating leukocyte (e.g., a leukocyte-derived MMP), e.g., as described by van Kempen, et al. *Eur Cancer* (2006) 42:728-734. In other embodiments, the MMP is chosen from MMP1, MMP2, MMP3, MMP7, MMP8, MMP9, MMP12, MMP13 or MMP14, e.g., as described by Eckhard, U et al. supra.

In some embodiments, the substrate peptide is derived from a CLiPS library (as described in, e.g., K. T. Boulware, P. S. Daugherty, *Proc. Natl. Acad. Sci.* U.S.A. 103, 7583-7588 (2006)). In other embodiments, the substrate peptide specificity is evaluated using combinatorial fluorogenic substrate libraries, e.g., as described by Harris, J. L. *Proc Natl Acad Sci USA* (2000) 97:7754-7759. In other embodiments, the substrate peptide is derived from a phage display library (e.g., it is a phase display substrate), e.g., as described by Deperthes, D. *Biol Chem* (2002) 383:1107-1112. For example, a phage display substrate is exposed to a plurality of proteases; peptides released through specific cleavage can be amplified in an expression system. In other embodiments, the substrate peptide is derived from a bacterial display library, e.g., as described by Rice, J. J. et al. *Protein Sci* (2006) 15:825-836.

In some embodiments, the linker comprises a compound of Formula (VI):

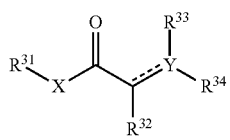

Formula (VI)

wherein:

$R^{31}$ is an agent, e.g., a therapeutic agent or diagnostic agent (e.g., an AHCM), or a targeting moiety (e.g., as described herein);

X is O or S;

$R^{32}$ is H or $C_1$-$C_6$ alkyl, $C_2$-$C_6$ alkenyl, cycloalkyl, or heterocyclyl;

Y is C, CH, N, O or S;

$R^{33}$ is C(O)$OR^a$, or $C_1$-$C_6$ alkyl, $C_2$-$C_6$ alkenyl, cycloalkyl, heterocyclyl, aryl, or heteroaryl;

$R^{34}$ is absent, H, —C(O)$OR^a$, or $C_1$-$C_6$ alkyl, cycloalkyl, heterocyclyl, aryl, or heteroaryl;

$R^a$ is H or $C_1$-$C_6$ alkyl; and wherein when Y is CH, N, O, or S, ==== represents a single bond.

In some embodiments, X is O. In some embodiments, X is S.

In some embodiments, $R^{32}$ is H. In some embodiments, $R^{32}$ is alkyl. In some embodiments, $R^{32}$ is methyl or ethyl.

In some embodiments, Y is C. In some embodiments, Y is CH. In some embodiments, Y is N, O, or S.

In some embodiments, $R^{33}$ is C(O)$OR^a$, wherein $R^a$ is H or alkyl. In some embodiments, when Y is C or CH, $R^{23}$ is —C(O)$OR^a$. In some embodiments, when Y is C or CH, $R^{33}$ is —C(O)$OR^a$, wherein $R^a$ is H or alkyl. In some embodiments, when Y is N, O, or S, $R^{33}$ is alkyl, $C_2$-$C_6$ alkenyl, cycloalkyl, heterocyclyl, aryl, or heteroaryl. In some embodiments, when Y is N, O, or S, $R^{33}$ is alkyl. In some embodiments, when Y is N, O, or S, $R^{33}$ is methyl or ethyl.

In some embodiments, when Y is CH, O, or S, $R^{34}$ is absent. In some embodiments, when Y is C or N, $R^{34}$ is alkyl. In some embodiments, when Y is C or N, $R^{34}$ is alkyl. In some embodiments, when Y is C, $R^{34}$ is alkyl.

In some embodiments, when Y is C, ==== represents a double bond. In some embodiments, when Y is CH, N, O, or S, ==== represents a single bond.

In some embodiments, the linker is a compound of Formula (VII):

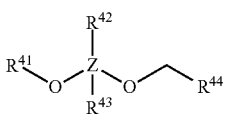

Formula (VII)

wherein:

$R^{41}$ is an agent, e.g., a therapeutic agent or diagnostic agent (e.g., an AHCM), or a targeting moiety (e.g., as described herein);

Z is C or Si;

each of $R^{42}$ or $R^{43}$ is independently alkyl, cycloalkyl, or heterocyclyl, or one of $R^{42}$ or $R^{43}$ is H; or $R^{42}$ and $R^{43}$ taken together with the Z atom they are attached to form a 4- to 8-membered cycloalkyl or heterocyclyl;

$R^{44}$ is alkyl, alkenyl, alkynyl, cycloalkyl, heterocyclyl, aryl, heteroaryl, or —C(O)$NR^cR^d$, —$NR^cC(O)R^e$—, —$NR^cC(O)OR^f$—, or $R^{44}$ taken together with the carbon atom it is attached to form a 5- to 8-membered ring with $R^{42}$ that encompasses O and Z; and each of $R^c$, $R^d$, $R^e$, or $R^f$ is independently H, or alkyl, cycloalkyl, heterocyclyl, aryl, or heteroaryl.

In some embodiments, Z is C. In some embodiments, Z is Si.

In some embodiments, each of $R^{42}$ or $R^{43}$ is independently alkyl. In some embodiments, each of $R^{42}$ or $R^{43}$ is independently methyl, ethyl, or isopropyl. In some embodiments, $R^{42}$ and $R^{43}$ are taken together with the Z atom to which they are attached to form a 4- to 8-membered cycloalkyl or heterocyclyl.

In some embodiments, $R^{44}$ is alkyl, alkenyl, alkynyl, cycloalkyl, heterocyclyl, aryl, or heteroaryl. In some embodiments, $R^{44}$ is alkyl, or cycloalkyl. In some embodiments, $R^{44}$ is alkyl, e.g., methyl or ethyl. In some embodiments, $R^{44}$ is cycloalkyl, e.g., cyclohexyl. In some embodiments, $R^{44}$ is —C(O)$NR^cR^d$, —$NR^cC(O)R^e$—, —$NR^cC(O)$$OR^f$—. In some embodiments, $R^{44}$ is —C(O)$NR^cR^d$, —$NR^cC(O)R^e$—, —$NR^cC(O)OR^f$—, wherein $R^c$, $R^d$, or $R^f$ is each independently H or alkyl and $R^e$ is alkyl. In some embodiments, $R^{44}$ is —$NR^cC(O)R^e$—, wherein $R^c$ is H or alkyl and $R^e$ is alkyl. In some embodiments, $R^{44}$ taken together with the carbon atom it is attached to forms a 5- to 8-membered ring with $R^{42}$ that encompasses O and Z (wherein e.g., Z is C).

In other embodiments, the linker is a monomer or polymer, e.g., a polyacetal polymer, as disclosed herein, optionally coupled to an agent. In one embodiment, the linker comprises the polymer of Formula (I), e.g., the polymer of Formula (I) as described herein. In other embodiments, the linker comprises the polymer of Formula (I) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (I-a), e.g., the polymer of Formula (I-a) as described herein. In other embodiments, the linker comprises the polymer of Formula (I-a) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (I-b), e.g., the polymer of Formula (I-b) as described herein. In other embodiments, the linker comprises the polymer of Formula (I-b) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (I-c), e.g., the polymer of Formula (I-c) as described herein. In other embodiments, the linker comprises the polymer of Formula (I-c) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (I-d), e.g., the polymer of Formula (I-d) as described herein. In other embodiments, the linker comprises the polymer of Formula (I-d) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (I-e), e.g., the polymer of Formula (I-e) as described herein. In other embodiments, the linker comprises the polymer of Formula (I-e) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the linker comprises the polymer of Formula (IV), e.g., the polymer of Formula (IV) as described herein. In other embodiments, the linker comprises the polymer of Formula (IV) as described herein, wherein each of m and n is independently chosen from 1, 2, 3, 4, 5, 6, 7, 8, 9, 10, 11, 12, 13, 14, 15, 16, 17, 18, 19 or 20.

In some embodiments, the linker, e.g., the pH sensitive linker, is selected from the group consisting of:

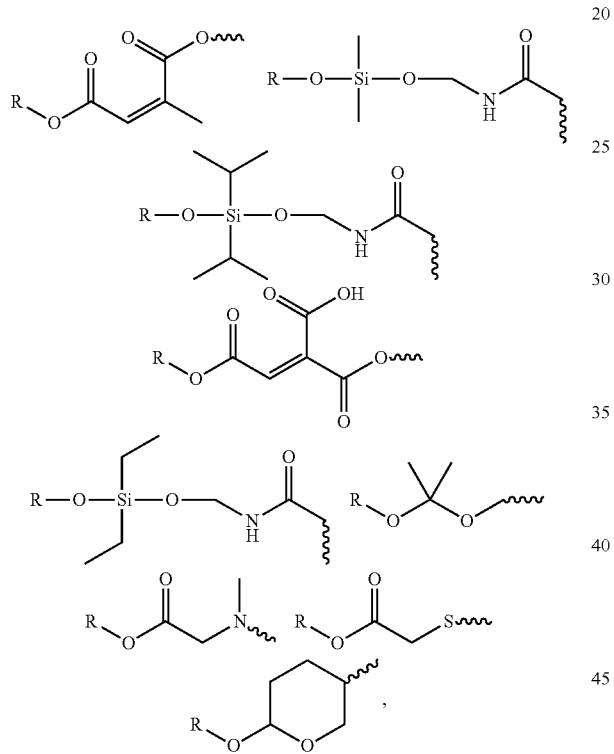

wherein R is an agent (e.g., an agent described herein) and ⌇ is linked to the polymer or R is the polymer (e.g., a polyacetal polymer described herein) and ⌇ is linked to an agent (e.g., an agent described herein). In some embodiments, R is an agent (e.g., an agent described herein) and ⌇ is linked to the polymer (e.g., a polyacetal polymer described herein).

In some embodiments, the linker, e.g., the pH sensitive linker, is derived from one or more of:

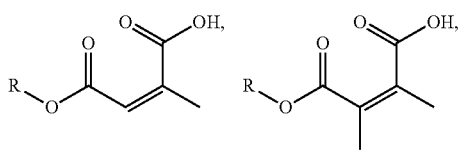

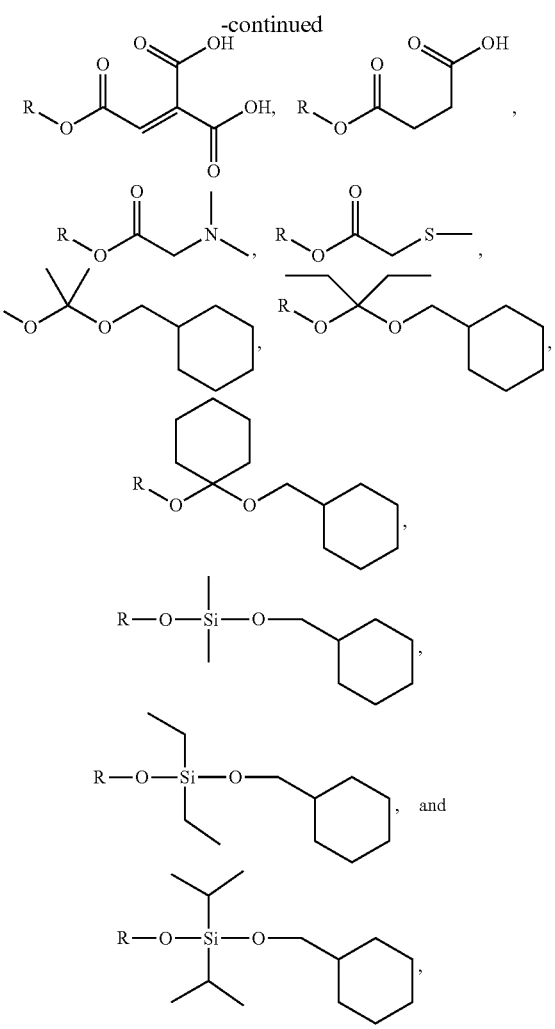

wherein R is an agent (e.g., an agent described herein) or R is the polymer (e.g., a polyacetal polymer described herein). In some embodiments, R is an agent (e.g., an agent described herein). In some embodiments, R is the polymer (e.g., a polyacetal polymer described herein).

In other embodiments, the linker, e.g., the pH sensitive linker, is chosen from L1, L2, L3, L4, L5, L6, L7, L8, L9, L10, L11, or L12, as shown in FIG. 4.

In certain embodiments, the linker, e.g., the pH sensitive linker, is coupled, e.g., covalently coupled, to an agent and/or a targeting moiety, e.g., as described herein. In one embodiment, the agent is a therapeutic agent or a diagnostic agent, e.g., a therapeutic or a diagnostic agent as described herein. In one embodiment, the agent is an AHCM as described herein.

In certain embodiments, the linker, e.g., the pH sensitive linker, is coupled, e.g., covalently coupled, to a polymer (e.g., any polymer described herein). In one embodiment, the polymer is at least 10%, 20%, 30%, 40%, 50%, 60%, 70%, 80%, 90% or 100% made of polyacetal polymers (e.g., a polymer according to Formula (I), Formula (I-a), Formula (I-b), or Formula (IV)). In certain embodiments, the linker is coupled to one or more hydrophobic or hydrophilic polymers to enhance a desired property. In certain embodiments, the linker can comprise, or be linked to a water-soluble monomer or polymer (e.g., polyethylene glycol (PEG) monomer or polymer), e.g., to increase one or more of amphiphilicity, hydrophilicity, water-solubility, pH sensitivity or stability.

In other embodiments, the linker is coupled, e.g., covalently coupled, to a plurality (e.g., one or more) of: a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, a polyorthoester, a dextran, a cyclodextran, chitosan, or other carbohydrate based polymer as described herein. In other embodiments, the linker is coupled, e.g., covalently coupled, to a plurality (e.g., one or more) of: a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, a polyorthoester, a dextran, a cyclodextran, chitosan, or other carbohydrate based polymer as described herein. In some embodiments, the polymer comprises a plurality of (e.g., 2, 3, 4, 5, or more of) a PLA-PEG, dextran, or a polyacetal polymer described herein. Exemplary polymers that can be combined with the polyacetal polymers are described herein, e.g., in the section entitled "Polymers" below.

In one embodiment, the linker (with or without an agent, e.g., an AHCM and/or a targeting moiety) is coupled (e.g., covalently coupled) to a second polymer, e.g., one or more of: a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, a polyorthoester, a dextran, a cyclodextran, chitosan, or other carbohydrate based polymer as described herein.

In one embodiment, the linker is a bond. In one embodiment, the first moiety is an agent (e.g., a therapeutic agent as described herein) and/or a targeting moiety, and the second moiety is a polymer (e.g., a polyacetal polymer), and the first moiety and the second moiety are directly connected to each other through a bond.

Conjugates and Particles

In another aspect, the invention features a conjugate comprising a polyacetal polymer, e.g., one or more polyacetal polymers as described herein. In one embodiment, the particle comprises a conjugate, e.g., one or more conjugates as described herein.

In some embodiments, the conjugate includes:
a polymer, e.g., polyacetal polymer as described herein;
an agent (e.g., one or more therapeutic and/or or diagnostic agents (e.g., an AHCM, a microenvironment modulator, an other stromal modulator, and/or an anti-cancer agent or liver therapy) as described herein), and
(optionally) a targeting moiety (e.g., a cell-targeting agent);
(optionally) wherein the polymer, the agent and/or a targeting moiety, are coupled (e.g., covalently coupled, via a linker, e.g., a pH-sensitive linker as described herein).

In another aspect, the invention features a particle (e.g., a nanoparticle, e.g., a particle having a hydrodynamic diameter of greater than about 1, 5, 10, 20, 30, 40, 50, 60, 70, 80, 90, 100, 150, or 200 nm). In embodiments, the particle includes:

a polymer, e.g., polyacetal polymer as described herein;
an agent (e.g., one or more therapeutic and/or or diagnostic agents (e.g., an AHCM, a microenvironment modulator, an other stromal modulator, and/or an anti-cancer agent or liver therapy) as described herein), and
(optionally) a targeting moiety (e.g., a cell-targeting agent);
(optionally) wherein the polymer, the agent and/or a targeting moiety, are coupled (e.g., covalently coupled, via a linker, e.g., a pH-sensitive linker as described herein).

In some embodiments, the conjugate or particle has a hydrodynamic diameter of less than about 100 nm (e.g., about 10 nm to 50 nm) and has one, two, three or all of the following properties:

(i) shows a ratio of release or degradation rate at pH=6.7 relative to pH=7.4 that is greater than 1.5 (e.g., 2);

(ii) shows increased pH-sensitivity in a hypoxic microenvironment, e.g., is sensitive to a hypoxic pH e.g., a pH about 6.7 to 6.9, e.g., compared to a physiological pH of about 7.4;

(iii) is slightly soluble (e.g., between about 100 to about 1000 parts water is required to dissolve 1 part polymer) or very slightly soluble (e.g., between about 1,000 to about 10,000 parts water are required to dissolve 1 part polymer) in water; or (iv) the polymer, e.g., the polyacetal polymer, has a melting temperature ($T_m$) of about 35° C. or greater.

In some embodiments, the conjugate or particle is essentially or close to neutrally-charged. In some embodiments, the conjugate or particle is positively-charged. In some embodiments, the conjugate or particle is negatively-charged.

In one embodiment, the conjugate or particle comprises a polymer (e.g., any polymer disclosed herein, including a polyacetal polymer (e.g., a polymer comprised of Formula (I), Formula (I-a), Formula (I-b), Formula (I-c), Formula (I-d), Formula (I-e), or Formula (IV)), a pH-sensitive linker (e.g., a pH-sensitive linker as described herein) and an agent (e.g., a therapeutic and/or diagnostic agent (e.g., an AHCM, e.g., an ARB, e.g., losartan, valsartan, telmisartan, candesartan, eprosartan, irbesartan, azilsartan, EXP-3174, olmesartan, or a prodrug or active metabolite thereof), as described herein) and/or the targeting moiety (e.g., a liver targeting moiety, e.g., M6P).

In one embodiment, the conjugate or particle comprises a pH-sensitive and/or polyacetal polymer as disclosed herein, and an agent and/or targeting moiety (e.g., an agent-polymer conjugate, a targeting moiety-polymer conjugate, or an agent-polymer-targeting moiety conjugate), any of which can be as described herein.

In another embodiment, the conjugate or particle comprises a polymer (e.g., any polymer disclosed herein, including a pH-sensitive and/or polyacetal polymer), a linker (e.g., a pH-sensitive linker as described herein) and an agent and/or targeting moiety, any of which can be as described herein. In one embodiment, the polymer, the linker, the agent and/or targeting moiety in the conjugate or particle are coupled, e.g., covalently coupled, directly or indirectly (e.g., with or without a linker). In one embodiment, the polymer (e.g., a polymer comprised of a polyol of Formula (II), a vinyl ether of Formula (III), and a PEG), the agent (e.g., an ARB, e.g., losartan, valsartan, telmisartan, candesartan, eprosartan, irbesartan, azilsartan, EXP-3174, olmesartan, or a prodrug or active metabolite thereof) and/or the targeting moiety (e.g., a liver targeting moiety, e.g., M6P) in the conjugate or particle are covalently coupled (each of the components can be covalently coupled with or without a linker).

In other embodiments, the conjugate or particle comprises a polymer (e.g., a polymer comprised of a polyol of Formula (II), a vinyl ether of Formula (III), and a PEG), and (optionally) a linker, which is noncovalently coupled, e.g., through ionic or hydrophobic interactions to one or more of the agent (e.g., an ARB, e.g., losartan, valsartan, telmisartan, candesartan, eprosartan, irbesartan, azilsartan, EXP-3174, olmesartan, or an analogue or derivative thereof (e.g., a prodrug or active metabolite thereof)) and/or the targeting moiety (e.g., a liver targeting moiety, e.g., M6P). In one embodiment, the polymer and the agent are covalently coupled (with or without a linker), and the targeting moiety is noncovalently coupled. In one embodiment, the polymer and the agent are noncovalently coupled. In one embodiment, the polymer and the agent and/or the targeting moiety are noncovalently coupled.

In other embodiments, the conjugate or particle comprises a mixture of covalently coupled components (e.g., the polymer and the agent and/or the targeting moiety) and noncovalently coupled components (e.g., the polymer and the agent and/or the targeting moiety). The mixture can have a different ratio of covalently and noncovalently coupled components. In one embodiment, the conjugate comprises: (i) the polymer covalently coupled to about 50% of the agent and/or about 50% of the targeting moiety (with or without a linker); (ii) the polymer noncovalently coupled to about 500 of the agent and/or about 500 of the targeting moiety (with or without a linker); or (iii) a mixture of (i) and (ii). In another embodiment, the conjugate comprises: (i) the polymer covalently coupled to about 75% of the agent and/or about 75% of the targeting moiety (with or without a linker); (ii) the polymer noncovalently coupled to about 25% of the agent and/or about 25% of the targeting moiety (with or without a linker); or (iii) a mixture of (i) and (ii). In another embodiment, the conjugate comprises: (i) the polymer covalently coupled to about 25% of the agent and/or about 25% of the targeting moiety (with or without a linker); (ii) the polymer noncovalently coupled to about 75% of the agent and/or about 75% of the targeting moiety (with or without a linker); or (iii) a mixture of (i) and (ii). In another embodiment, the conjugate or particle comprises: (i) the polymer covalently coupled to about 90% of the agent and/or about 90% of the targeting moiety (with or without a linker); (ii) the polymer noncovalently coupled to about 10% of the agent and/or about 10% of the targeting moiety (with or without a linker); or (iii) a mixture of (i) and (ii). In another embodiment, the conjugate or particle comprises: (i) the polymer covalently coupled to about 10% of the agent and/or about 10% of the targeting moiety (with or without a linker); (ii) the polymer noncovalently coupled to about 90% of the agent and/or about 90% of the targeting moiety (with or without a linker); or (iii) a mixture of (i) and (ii). In another embodiment, the conjugate or particle comprises: (i) the polymer covalently coupled to about 95% of the agent and/or about 95% of the targeting moiety (with or without a linker); (ii) the polymer noncovalently coupled to about 5% of the agent and/or about 5% of the targeting moiety (with or without a linker); or (iii) a mixture of (i) and (ii). In another embodiment, the conjugate or particle comprises: (i) the polymer covalently coupled to about 5% of the agent and/or about 5% of the targeting moiety (with or without a linker); (ii) the polymer noncovalently coupled to about 95% of the agent and/or about 95% of the targeting moiety (with or without a linker); or (iii) a mixture of (i) and (ii). In another embodiment, the conjugate or particle comprises: (i) the polymer covalently coupled to about 99% or higher of the agent and/or about 99% or higher of the targeting moiety (with or without a linker); (ii) the polymer noncovalently coupled to about 1% or less of the agent and/or about 1% or less of the targeting moiety (with or without a linker); or (iii) a mixture of (i) and (ii). In another embodiment, the conjugate or particle comprises: (i) the polymer covalently coupled to about 1% or less of the agent and/or about 1% or less of the targeting moiety (with or without a linker); (ii) the polymer noncovalently coupled to about 99%, or higher of the agent and/or about 99% or higher of the targeting moiety (with or without a linker); or (iii) a mixture of (i) and (ii).

In other embodiments, the polymer, the agent, and about 50% of the targeting moiety in the conjugate or particle are covalently coupled. In other embodiments, the polymer, the agent, and about 50% of the targeting moiety in the conjugate or particle are noncovalently coupled. In one embodiment, the polymer, the agent, and about 75% of the targeting moiety in the conjugate are covalently coupled. In one embodiment, the polymer, the agent, and about 75% of the targeting moiety in the conjugate or particle are noncovalently coupled. In one embodiment, the polymer, the agent, and about 90% of the targeting moiety in the conjugate or particle are covalently coupled. In one embodiment, the polymer, the agent, and about 90% of the targeting moiety in the conjugate or particle are noncovalently coupled. In one embodiment, the polymer, the agent, and about 95% or more of the targeting moiety in the conjugate or particle are covalently coupled. In one embodiment, the polymer, the agent, and about 95% or more of the targeting moiety in the conjugate or particle are noncovalently coupled. In one embodiment, the polymer, the agent, and about 99% or more of the targeting moiety in the conjugate or particle are covalently coupled. In one embodiment, the polymer, the agent, and about 99% or more of the targeting moiety in the conjugate or particle are noncovalently coupled.

In one embodiment, the conjugate or particle comprises an agent and/or a targeting moiety (e.g., as described herein), wherein one or both are directly coupled (e.g., covalently coupled) to a polyacetal polymer (e.g., a polymer comprised of a polyol of Formula (II), a vinyl ether of Formula (III), and a PEG). In one embodiment, the conjugate or particle comprises an agent and/or a targeting moiety (e.g., as described herein), wherein one or both are noncovalently coupled to a polyacetal polymer (e.g., a polymer comprised of a polyol of Formula (II), a vinyl ether of Formula (III), and a PEG).

In another embodiment, the conjugate or particle comprises an agent and/or targeting moiety (e.g., as described herein) coupled (e.g., covalently coupled), via pH-sensitive linker (e.g., as described herein; an acetal monomer or a polyacetal polymer) to a second polymer (e.g., a polymer other than a polyacetal polymer, e.g., but not limited to dextran, PEG, PLGA, PLA or combinations thereof).

In some embodiments, the agent is a therapeutic or a diagnostic agent as described herein. In some embodiments, the agent is an AHCM as described herein. In some embodiments, the agent is an ARB as described herein, e.g., losartan, valsartan, telmisartan, candesartan, eprosartan, irbesartan, azilsartan, EXP-3174, olmesartan, or an analogue or derivative thereof (e.g., a prodrug or active metabolite thereof), e.g., a compound shown in FIG. 23.

In some embodiments, the agent is a vitamin D analog or derivative as described herein. In some embodiments, the agent is a vitamin D analog or derivative as described herein, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, ercalcitriol, EB1089

(seocalcitol), BXL-628 (elocalcitol), MC1288, CB966, BCB 1093, GS 1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK161422, and analogs and derivatives thereof, e.g., as shown in FIG. 24. Additional vitamin D analogs and derivatives are described, e.g. in Leyssens, C. et al, *Front Physiol* (2014) dx.doi.org/10.3389/fphys.2014.00122, which is incorporated herein by reference in its entirety.

In some embodiments, the agent is a bromodomain and extra-terminal protein inhibitor (i-BET) as described herein. In some embodiments, the agent is a bromodomain and extra-terminal protein inhibitor (i-BET) as described herein, e.g MS436, PFI-1, I-BET 151, OTX-015, JQ1. CPI-203, bromosporine, RVX-208, I-BET 762, I-BET 151, OFXBD02, OFXBD03, XD14, AZD5153, and analogs and derivatives thereof, e.g., as shown in FIGS. 25A and 25B. Additional bromodomain and extra-terminal protein inhibitors (i-BET) are described e.g., in Haas, M. J. et al *SciBX* (2014) 7(15); *ACS Chem Biol* (2015) 10:22-39; *Expert Opin Ther Pat* (2014) 24:185-199; *Clin Cancer Res* (2015) 21:1628-1638; *Oncotarget* (2015) 6:17698-17712; *Bioorg Med Chem Lett* (2015) 25:1842-1848; *Cancer Res* (2013) 73:3336-3346; *Am. J Cardiovasc Drugs* (2015) September 18 [epub ahead of print]; and *J Med Chem* (2013) 56:9251-9264, each of which is incorporated by reference herein in its entirety.

In some embodiments, the agent is a bromodomain and extra-terminal protein inhibitor (i-BET) as described herein, e.g., in FIGS. 25A and 25B, and may be covalently coupled to the polymer, e.g., a polymer described herein, via a hydroxyl group, a sulfonamide, a carboxylic acid, a carboxamide, an amine, or a benzimidazolone. In some embodiments, the agent is OTX-2015 (5), RVX-208 (7), OXFBD02 (9), OXFBD03 (10), XD14 (18), or dinaciclib (19), e.g., as shown in FIGS. 25A and/or 25B, and may be covalently coupled to the polymer, e.g., a polymer described herein, via a hydroxyl group. In some embodiments, the agent is (12), PFI-1 (14), (15), MS436 (16), TG101348 (22), TG101209 (23), or bromosporine, e.g., as shown in FIGS. 25A and/or 25B, and may be covalently coupled to the polymer, e.g., a polymer described herein, via a sulfonamide. In some embodiments, the agent is I-BET726 (12), CPI-203 (6), or B12536 (21), e.g., as shown in FIGS. 25A and/or 25B, and may be covalently coupled to the polymer, e.g., a polymer described herein, via a carboxylic acid or a carboxamide. In some embodiments, the agent is I-BET151 (11) or B12536 (21), e.g., as shown in FIGS. 25A and/or 25B, and may be covalently coupled to the polymer, e.g., a polymer described herein, via a benzimidazolone or pyrimidine amine.

In some embodiments, the agent is an IDO inhibitor (i.e., indoleamine 2,3-dioxygenase (IDO) pathway inhibitor) as described herein, and may be covalently coupled to the polymer, e.g., a polymer described herein, via a hydroxyl group, a sulfonamide, a carboxylic acid, a carboxamide, an amine, or a benzimidazolone. Exemplary IDO inhibitors include, but are not limited to, GDC-0919, indoximod, 1-methyltryptophan (e.g., 1-methyl-L-tryptophan, 1-methyl-D-tryptophan), NLG8189, INCB024360, NLG919, methylthiohydantoin tryptophan, brassinin, annulin B, exiguamine A, INCB023843, or an analog or derivative thereof. Additional IDO inhibitors are described e.g., in Lob, S. et al *Nat Rev Cancer* (2009) 9:445-452; Rohrig, U. F. et al *J Med Chem* (2015) 58:9421-9437; and U.S. patent application Ser. No. 14/919,184, each of which is incorporated by reference herein in its entirety.

In one embodiment, the conjugate or particle (e.g., a conjugate or particle comprising a polymer comprised of a polyol of Formula (II), a vinyl ether of Formula (III), and a PEG, and/or a pH sensitive linker) is sensitive to a pH between about 5.0 and about 7.4, between 5.0 and 7.0, between 5.0 and 6.5, between 5.0 and 5.5, between 5.9 and 6.2. In one embodiment, the conjugate is sensitive to a pH between about 5.5 and about 6.5, e.g., between 5.9 and 6.2. In one embodiment, the conjugate or particle is preferentially cleaved or degraded upon exposure to a first pH relative to a second pH). In one embodiment, the conjugate or particle is sensitive to a hypoxic pH, e.g., a pH about 6.7 to 6.9, e.g., compared to a physiological pH of about 7.4.

In one embodiment, the conjugate or particle is cleaved or degraded at least 2, 5, 10, 20, 30, 40, 50, 60, 70, 80, or 100 times faster upon exposure to a first pH relative to a second pH. In other embodiments, the conjugate or particle shows a greater release or degradation rate of the pH-sensitive polymer and/or linker at a first acidic pH (e.g., pH=6.7) relative to a second more basic pH (e.g., pH=7.4). In one embodiment, ratio of release or degradation rate of the pH-sensitive polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, the ratio of release or degradation rate of the conjugate (e.g., via degradation of pH-sensitive polymer and/or linker) at pH=6.7 relative to pH=7.4 is greater than 2. In one embodiment, the conjugate or particle shows increased pH-sensitivity in a hypoxic microenvironment, e.g., in a tumor, or fibrotic tissue.

In some embodiments, the conjugate or particle comprises a polymer, e.g., a polyacetal polymer, as disclosed herein. In one embodiment, the conjugate or particle comprises the polymer of Formula (I), e.g., the polymer of Formula (I) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In one embodiment, the conjugate or particle comprises the polymer of Formula (I-a), e.g., the polymer of Formula (I-a) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In one embodiment, the conjugate or particle comprises the polymer of Formula (I-b), e.g., the polymer of Formula (I-b) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In one embodiment, the conjugate or particle comprises the polymer of Formula (I-c), e.g., the polymer of Formula (I-c) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In some embodiments, the conjugate or particle comprises a polymer, e.g., a polyacetal polymer, as disclosed herein. In one embodiment, the conjugate or particle comprises the polymer of Formula (I-d), e.g., the polymer of Formula (I-d) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In one embodiment, the conjugate or particle comprises the polymer of Formula (I-e), e.g., the polymer of Formula (I-e) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In one embodiment, the conjugate or particle comprises the polymer of Formula (IV), e.g., the polymer of Formula (IV) as described herein, wherein each of m and n is an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50. In an embodiment, m and n taken together are between 10 and 100, 20 and 80, 20 and 60, or 30 and 60.

In certain embodiments, the conjugate or particle comprises a polymer that is at least 10%, 20%, 30%, 40%, 50%, 60%, 70%, 80%, 90% or 100% made of polyacetal polymers (e.g., a polymer acceding to Formula (I), Formula (I-a), Formula (I-b), Formula (I-c), Formula (I-d), Formula (I-e), or Formula (IV)). Alternatively, or in combination, the conjugate or particle can comprise one or more hydrophobic or hydrophilic polymers to enhance a desired property. In certain embodiments, the conjugate or particle can comprise, or be linked to a water-soluble monomer or polymer (e.g., a PEG monomer or polymer), e.g., to increase one or more of amphiphilicity, hydrophilicity, water-solubility, pH sensitivity or stability.

In other embodiments, the conjugate or particle can comprise a polymer other than a polyacetal polymer, e.g., a polymer comprising one or more of: dextran, polylactic acid (PLA), polyglycolic acid (PGA), poly(lactic-co-glycolic acid) (PLGA), polycaprolactone (PCL), polydioxanone (PDO), polyanhydrides, polyorthoesters, cyclodextrin, or chitosan, or a pegylated form thereof. In other embodiments, the conjugate comprises (e.g., is coupled, e.g., covalently coupled), to one or more of: poly(lactic acid)-b-poly(ethylene glycol) (PLA-PEG), poly(lactic acid)-b-poly(ethylene glycol) (PLGA-PEG), or (cyclodextrin)-co-poly(ethylene glycol) (CDP). In some embodiments, the polymer comprises a PLA-PEG, dextran, or a polyacetal polymer described herein, or any combination thereof. Exemplary polymers that can be combined with the polyacetal polymers are described herein, e.g., in the section entitled "Polymers".

In one embodiment, the conjugate or particle comprises a linker (with or without an agent, e.g., an AHCM) coupled (e.g., covalently coupled) to a second polymer, e.g., one or more of: dextran, polylactic acid (PLA), polyglycolic acid (PGA), poly(lactic-co-glycolic acid) (PLGA), polycaprolactone (PCL), polydioxanone (PDO), polyanhydrides, polyorthoesters, cyclodextrin, or chitosan, or a pegylated form thereof (e.g., poly(lactic acid)-b-poly(ethylene glycol) (PLA-PEG), poly(lactic acid)-b-poly(ethylene glycol) (PLGA-PEG), or (cyclodextrin)-co-poly(ethylene glycol) (CDP)).

In one embodiment, the conjugate or particle comprises a linker chosen from one or more of an acetal group, a ketal group, an anhydride group, a silyl ether group, a combination of acetal or ketal with ester group, an oligo-acetal or oligo-ketal group, a combination of the oligo-ketal and silyl ether group, or a combination of the oligo-ketal and vinyl ether group. In other embodiments, the conjugate is chosen from a combination of acetal or ketal with cis-aconityl, hydrazine, oxime, imidazole or trityl groups. Any of the aforesaid groups or combination of groups can be modified to enhance the pH sensitivity of the conjugate, e.g., as described herein.

In one embodiment, the conjugate or particle comprises a linker having the polymer of Formula (I) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (I-a) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (I-b) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (I-c) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (I-d) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (I-e) as described herein, wherein each of m and n is independently chosen from 0, 1, 2, 3, 4, 5, 6, 7, 8, 9, 10, 11, 12, 13, 14, 15, 16, 17, 18, 19 or 20, wherein the sum of m and n is greater than 0. In one embodiment, the conjugate or particle comprises a linker having the polymer of Formula (IV) as described herein, wherein m is independently chosen from 2, 3, 4, 5, 6, 7, 8, 9, 10, 11, 12, 13, 14, 15, 16, 17, 18, 19 or 20.

In some embodiments, the conjugate or particle comprises a linker, e.g., the pH sensitive linker, chosen from a compound of Formula (VI) or Formula (VII). In some embodiments, $R^{31}$ or $R^{41}$ of Formula (VI) or Formula (VII) includes the agent and/or targeting moiety described herein.

In some embodiments, the conjugate or particle, e.g., the pH sensitive conjugate or particle, comprises a linker selected from the group consisting of:

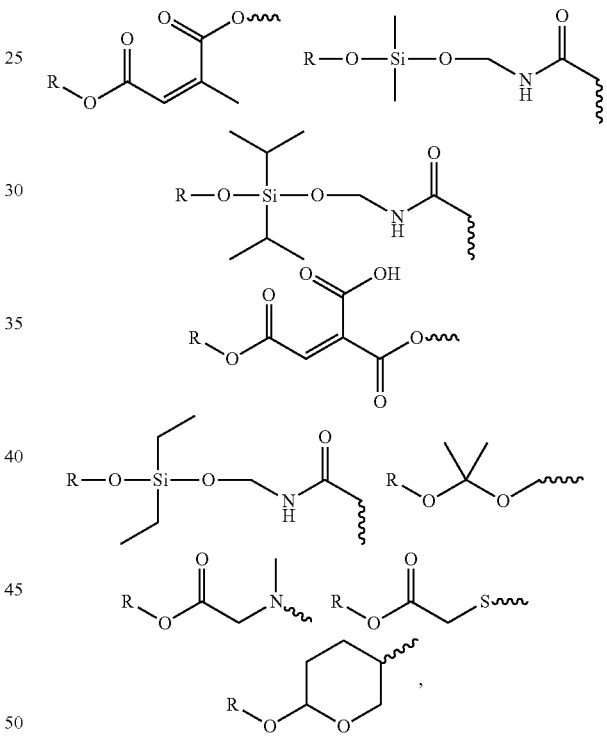

wherein R can be the agent (e.g., an agent described herein) and ~~~ is linked to the polymer or R can be the polymer and ~~~ is linked to the agent (e.g., an agent described herein). In some embodiments, R is the agent and ~~~ is linked to the polymer.

In some embodiments, the conjugate or particle comprises a linker selected from the group consisting of:

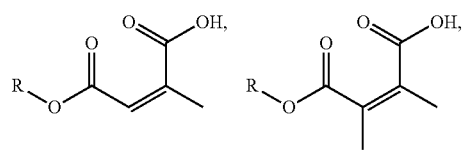

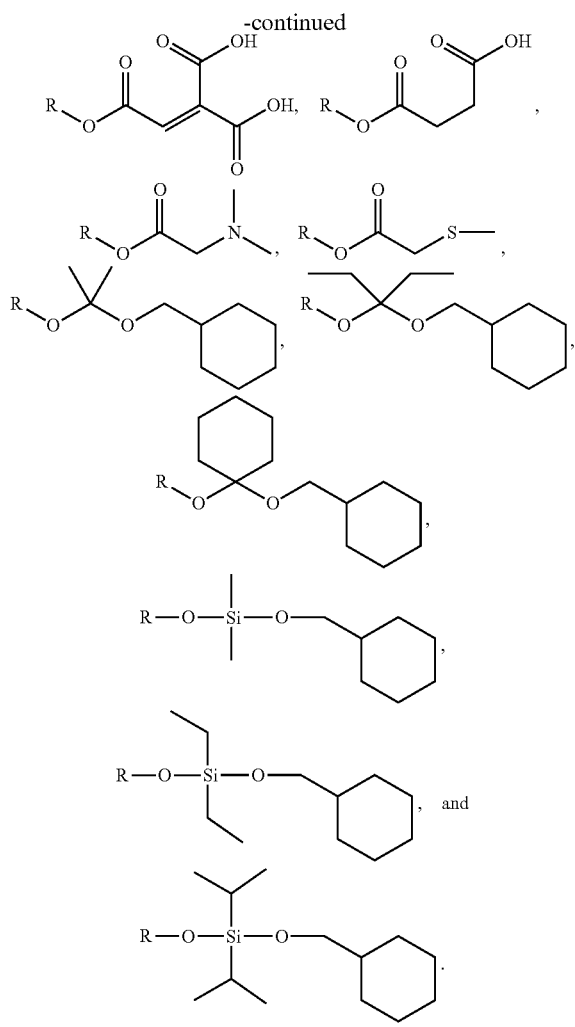

In other embodiments, the conjugate or particle comprises a linker, e.g., a pH sensitive linker, chosen from L1, L2, L3, L4, L5, L6, L7, L8, L9, L10, L11, or L12, e.g., as shown in FIG. 4.

In some embodiments, the conjugate or particle comprises a single agent (e.g., one or more of the same agent) and/or targeting moiety (e.g., one or more of the same agent and/or targeting moiety as described herein). In some embodiments, the conjugate or particle comprises multiple agents and/or targeting moieties (e.g., 2, 3, 4, 5, 6 or more different agents and/or targeting moieties). In some embodiments, the agents are attached directly to a polymer (e.g., any polymer described herein) or a linker as described herein. In other embodiments, the agent(s) and/or targeting moiety(ies) are attached to the polymer (e.g., any polymer described herein) via a linker (e.g., any linker including a pH-sensitive linker as described herein). In some embodiments, the agents are the same agent. In some embodiments, the agents are different agents.

In one embodiment, conjugate or particle comprises an agent and/or targeting moiety attached at one end of the polymer, e.g., surface exposed end of the polymer. In other embodiments, the conjugate or particle comprises an agent and/or targeting moiety in the middle of the polymer. In one embodiment, the conjugate or particle comprises an agent and/or targeting moiety attached to at least two polymers such that the agent and/or targeting moiety is present between the two polymers.

In some embodiments, the agent and/or targeting moiety contains a reactive functional group for conjugation to the linker or polymer (e.g., the pH sensitive linker or polymer as described herein). In some embodiments, the functional group is chosen from a hydroxyl group, amino group (e.g., a primary or secondary amino group), thiol group, carboxylic acid group, aldehyde group, ketone group, hydrazino group, azido group, vinyl ether group, alkenyl group, isothiocyanate group, or acrylate group. In other embodiments, the agent and/or targeting moiety can be activated for conjugation to the linker or polymer (e.g., the pH sensitive linker or polymer as described herein) through the use of an activating agent. In some embodiments, the activating agent is, e.g., succinic anhydride, thiophosgene, 4-nitrophenyl chloroformate, or ethylenediamine. In other embodiments, the agent and/or targeting moiety can be activated for conjugation to a polymer (e.g., a polyacetal polymer described herein) or another moiety or polymer (e.g., PEG, PLA, PLGA, PDO, cyclodextrin) through the use of an activating agent, e.g., succinic anhydride, thiophosgene, 4-nitrophenyl chloroformate, ethylenediamine, or cis-acotinic anhydride. In other embodiments, the agent and/or targeting moiety is coupled to a polymer (e.g., the polyacetal polymer) and then activated for conjugation to another moiety or polymer (e.g., PEG, PLA, PLGA, PDO, cyclodextrin) through the use of an activating agent, e.g., succinic anhydride, thiophosgene, 4-nitrophenyl chloroformate, ethylenediamine, or cis-acotinic anhydride. In still other embodiments, the agent and/or targeting moiety is coupled to a moiety (e.g., PEG, PLA, PLGA, PDO, cyclodextrin) and then activated for conjugation to a polymer (e.g., the polyacetal polymer) through the use of an activation agent, e.g., succinic anhydride, thiophosgene, 4-nitrophenyl chloroformate, ethylenediamine, or cis-acotinic anhydride.

In some embodiments, the conjugate or particle is amphiphilic.

In some embodiments, the particle can be formed from the conjugates described herein, e.g., by precipitation and/or self-assembly.

In some embodiments, the conjugate is not precipitated from solution and/or self-assembled.

In another embodiment, the particle comprises a polyacetal polymer, e.g., a pH sensitive polyacetal polymer as described herein, a linker (e.g., a pH-sensitive linker as described herein) and an agent (e.g., a therapeutic and/or diagnostic agent (e.g., an AHCM), as described herein) and/or the targeting moiety. In one embodiment, the polymer, the linker, the agent and/or the targeting moiety in the particle are coupled, e.g., covalently coupled, directly or indirectly. In one embodiment, the polymer, the linker, the agent and/or the targeting moiety in the particle are coupled, e.g., noncovalently coupled, e.g., through ionic or hydrophobic interactions.

In another embodiment, the particle is modified in the surface or portion thereof to prevent, e.g., reduce, opsonin interactions and/or phagocyte clearance, e.g., as described in Salmaso S. and Caliceti, P. J *Drug Deliv* (2013) 2013:1-19. In some embodiments, the particle comprises a polymer that increases the flexibility and/or hydrophilicity of the particle surface. Exemplary polymers that can be used include, but are not limited to, natural and semisynthetic polysaccharides or synthetic polymers. For example, dextran (Dex), polysialicacid (PSA), hyaluronic acid (HA), chitosan (CH), and heparin are frequently used natural polysaccharides. Synthetic polymers include polyvinyl pyrrolidone (PVP), polyvinyl alcohol (PVA), polyacrylamide (Pam), poly(ethylene glycol) (PEG), and PEG-based copolymers such as poloxamers, poloxamines, and polysorbates, e.g., as described in Salmaso S. and Caliceti, supra.

In other embodiments, the particle comprises a water-soluble derivative of camptothecins, e.g., as described in U.S. Pat. No. 7,495,099. In some embodiments, the particle comprises a water-soluble high-molecular weight derivative of camptothecins, which is obtained by ester-bonding a carboxylic acid group of a polyethylene glycol-polycarboxylic acid polymer to a phenolic hydroxyl group of phenolic camptothecins.

In other embodiments, the particle comprises a cyclodextrin-based polymer, e.g., as described in U.S. Pat. No. 8,580,244.

In one embodiment, the particle comprises an agent and/or a targeting moiety (e.g., as described herein), wherein one or both are directly coupled (e.g., covalently coupled) to the polyacetal polymer (e.g., a polymer that comprises the compound of Formula (I), Formula (I-a), Formula (I-b), Formula (I-c), Formula (I-d), Formula (I-e), or Formula (IV)). In another embodiment, the particle comprises an agent and/or targeting moiety (e.g., as described herein) coupled (e.g., covalently coupled), via pH-sensitive linker (e.g., as described herein; an acetal monomer or a polyacetal polymer) to a second polymer (e.g., a polymer other than a polyacetal polymer).

In one embodiment, the particle is not selectively delivered or targeted to a target site, e.g., the particle does not include a targeting moiety (e.g., a cell- or liver-targeting agent as described herein).

In another embodiment, the particle is selectively delivered or targeted to a target site. In some embodiments, selective delivery can occur without targeting. In one embodiment, the particle is delivered to a target site via a targeting moiety (e.g., a cell- or liver-targeting agent). In one embodiment, the targeting moiety is chosen from one or more of a ligand, e.g., a cell surface receptor, a glycoprotein, a vitamin, cholesterol, an antibody or fragment thereof, a peptide, a protein, a lectin, an aptamer, a nucleic acid, a lipoprotein, a hormone, a charged molecule, a mono-, olio-, and polysaccharide, or low molecular weight ligands such as sugars, folic acids, and peptides. Exemplary targeting moieties are further described in detail herein, e.g., in the sections entitled "Targeting Moieties."

Any of the particles disclosed herein, including any of the particles described in the section entitled "Particles" in the Detailed Description, including liposomal, polymeric and other particles. Such particles can include the agents disclosed herein, or in combination with the agents disclosed herein (e.g., in free or particle form).

Size of the Particles

In one embodiment, the particle, e.g., a particle as described herein, including a pH-sensitive and/or polyacetal polymer has a size to include any of the agents described herein, e.g., the AHCM, the microenvironment modulator, the other stromal modulator, the small molecule therapeutic or protein, e.g., an antibody.

In one embodiment, the particle includes one or more agents (e.g., therapeutic and/or diagnostic agent described herein). In one embodiment, the particle includes the same agent. In one embodiment, the particle includes different agents. The agent(s) can be coupled to the particle (e.g., as a conjugate as described herein) and/or contained non-covalently inside the particle.

In one embodiment, the particle is substantially or completely size-excluded from reaching arteriole smooth muscle, which is protected by non-leaky vessels. In other embodiments, the particle selectively penetrates a leaky vessel, e.g., a leaky vessel of a tumor or liver.

In some embodiments, the particle, e.g., a particle as described herein, has hydrodynamic diameter of greater than about 1, 5, 10, 15, 20, 25, 30, 35, 45, 50, 75, 100, 150, 200 nm, but less than 300 nm, e.g., as a nanoparticle. In one embodiment, the particle, e.g., a particle as described herein, has a hydrodynamic diameter of less than 100 nm, less than 90 nm, less than 80 nm, less than 70 nm, less than 60 nm, less than 50 nm, less than 40 nm, less than 30 nm, less than 20 nm, less than 15 nm, less than 14 nm, less than 13 nm, less than 12 nm, less than 11 nm, less than 10 nm, less than 5 nm, or less than 1 nm. In other embodiments, the particle, e.g., a particle described herein, has a hydrodynamic diameter between about 5 to 50 nm, 10 to 40 nm, 10 to 30 nm, or 10 to 20 nm.

In an embodiment, the AHCM, the microenvironment modulator and/or the other stromal modulator: is a small molecule therapeutic; is a protein, e.g., an antibody or an antibody fragment thereof or conjugate thereof (e.g., an antibody drug conjugate); or is provided in a particle. In one embodiment, the AHCM is chosen from one or more of: an angiotensin II receptor blocker ($AT_1$ blocker or ARB), an antagonist of RAAS antagonist, an ACE inhibitor, a TSP-1 inhibitor, a TGF-β1 inhibitor, a CTGF inhibitor, an SDF-1a inhibitor; an ERA; an $AT_2$ agonist; a VDR agonist; or a combination of two, three or more of the above.

In an embodiment, the anti-cancer agent, the anti-fibrotic therapeutic agent, the liver therapeutic agent, or second therapeutic agent: is a small molecule therapeutic with a hydrodynamic diameter of 1 nm or less; is a protein, e.g., an antibody or an antibody fragment thereof or conjugate thereof (e.g., an antibody drug conjugate); or is provided in a particle.

In an embodiment, the therapy is a cancer therapeutic (also referred to herein as "an anti-cancer agent"), anti-fibrotic agent, a liver therapeutic agent, or second therapeutic agent (e.g., but not limited to an immunomodulator or an anti-angiogenic agent) is administered as an entity having a hydrodynamic diameter of greater than about 1, 5, 10, 20, 30, 40, 50, 60, 70, 80, 90, 100, 150, 200, or 500 nm. For example, the second therapeutic agent (e.g., the anti-cancer agent or liver therapeutic agent) can be a protein, e.g., an antibody or an antibody fragment or conjugate thereof (e.g., an antibody drug conjugate). The second therapeutic agent (e.g., the anti-cancer agent or liver therapeutic agent) can also be administered as a particle, e.g., a polymeric nanoparticle (e.g., a pH-sensitive particle as described herein) or a liposome, that includes the agent as a small molecule therapeutic (i.e., a molecule having a hydrodynamic diameter of about 1 nm or less) or a protein, e.g., an antibody.

In an embodiment, an AHCM, microenvironment modulator and/or other stromal modulator is administered as an entity having a hydrodynamic diameter of greater than about 1 nm (e.g., greater than about 1, 5, 10, 15, 20, 25. 30, 50, 75, 90, 100, 150, 200, or 500) and a second therapeutic agent (e.g., an anti-cancer agent and/or liver therapeutic agent) is administered as an entity having a hydrodynamic diameter of about 1 nm or less. In one embodiment, the AHCM is present in the entity without a second therapeutic agent (e.g., a chemotherapeutic agent). The AHCM can be formulated for extended release, e.g., in an extended release formulation for substantially continuous release for hours, days, weeks, months or years, for example, using pH-sensitive polymer and/or linker of different degradation rates.

In an embodiment, an AHCM, microenvironment modulator and/or other stromal modulator is administered as an entity having a hydrodynamic diameter of about 1 nm, or less, and a second therapeutic agent (e.g., an anti-cancer agent and/or liver therapeutic agent) is administered as an entity having a hydrodynamic diameter of about 1 nm or greater (e.g., greater than about 1, 5, 10, 20, 50, 75, 100, 150, 200, 500, or 1,000 nm).

In an embodiment, an AHCM, microenvironment modulator and/or other stromal modulator is administered as an entity having a hydrodynamic diameter of less than, or equal to, about 1 nm and a second therapeutic agent (e.g., an anti-cancer agent) is administered as an entity having a hydrodynamic diameter of less than about 1 nm.

In an embodiment, an AHCM, microenvironment modulator and/or other stromal modulator is administered as an entity having a hydrodynamic diameter of greater than about 1 nm (e.g., greater than about 1, 5, 10, 20, 50, 75, 100, 150, 200, 500, or 1,000 nm), and a second therapeutic agent (e.g., an anti-cancer agent) is administered as an entity having a hydrodynamic diameter of greater than about 1 nm (e.g., greater than about 1, 5, 10, 20, 50, 75, 100, 150, 200, 500, or 1,000 nm).

The AHCM, microenvironment modulator and/or other stromal modulator and the second therapeutic agent (e.g., the anti-cancer agent or liver therapeutic) can be in separate or the same entity. For example, if provided as separate entities the AHCM can be provided as a first particle (e.g., a pH sensitive and/or polyacetal particle as disclosed herein; a particle (e.g., pH-sensitive and/or polyacetal particle comprising AHCM, microenvironment modulator and/or other stromal modulator)) and the second therapeutic agent (e.g., the anti-cancer agent and/or anti-fibrotic or liver therapeutic agent) provided as a second particle (e.g., where the second particle has a structural property (e.g., size or composition) or a functional property (e.g., release kinetics or a pharmacodynamic property) that differs from the first particle). Alternatively, an AHCM, microenvironment modulator and/or other stromal modulator and a second therapeutic agent (e.g., an anti-cancer agent and/or liver therapeutic agent) can be provided on the same entity, e.g., in the same nanoparticle.

In an embodiment, the AHCM, microenvironment modulator and/or other stromal modulator is selected from a therapeutic entity having a hydrodynamic diameter: equal to or less than 1 or 2 nm; between 2-20, 10-25, 20-40, 40, 50-150 nm; between 10, 15, 20, 25, 35, 40, 45, 50-100 nm; between 10, 15, 20, 25, 35, 40, 45, 50-200 nm; between 10, 15, 20, 25, 35, 40, 45, 50, 75, 100, 150, 200, 300-500 nm; and between 10, 15, 20, 25, 35, 40, 45, 50, 75, 100, 150, 200, 300, 1000 nm; or 10, 15, 20, 25, 35, 45, 50, 75, 100, 150 or 200 nm.

In an embodiment, the anti-cancer agent, liver therapeutic agent, or second therapeutic agent is selected from a therapeutic entity having a hydrodynamic diameter: equal to or less than 1 or 2 nm; between 2-20, 10-25, 20-40, 40, 50-150 nm; between 10, 15, 20, 25, 35, 40, 45, 50-100 nm; between 10, 15, 20, 25, 35, 40, 45, 50-200 nm; between 10, 15, 20, 25, 35, 40, 45, 50, 75, 100, 150, 200, 300-500 nm; and between 10, 15, 20, 25, 35, 40, 45, 50, 75, 100, 150, 200, 300-1000 nm; or 10, 15, 20, 25, 35, 45, 50, 75, 100, 150 or 200 nm.

In an embodiment, the AHCM, microenvironment modulator and/or other stromal modulator, anti-cancer agent, liver therapeutic agent, or the second therapeutic agent (e.g., but not limited to an immunomodulator or an anti-angiogenic agent), each independently, can be provided as an entity having the following size ranges (in nm): a hydrodynamic diameter of less than or equal to 1, or between 0.1 and 1.0 nm, e.g., that of a typical small molecule; a hydrodynamic diameter of between 5 and 20, or 5 and 15 nm, e.g., that of a protein, e.g., an antibody; or a hydrodynamic diameter of 10-5,000, 20-1,000, 10-500, 10-200, 10-150, or 10-100, 10-25, 20-40, 40, 50-150 nm; between 10, 15, 20, 25, 35, 40, 45, 50-100 nm; between 10, 15, 20, 25, 35, 40, 45, 50-200 nm; between 10, 15, 20, 25, 35, 40, 45, 50, 75, 100, 150, 200, 300-500 nm; and between 10, 15, 20, 25, 35, 40, 45, 50, 75, 100, 150, 200, 300-1000 nm; or 10, 15, 20, 25, 35, 45, 50, 75, 100, 150 or 200 nm, e.g., a range of typical nanoparticles.

Particle Dosage and Drug Loading

In some embodiments, the percentage of the polymer monomers that are conjugated to an agent (e.g., a therapeutic or diagnostic agent) is between 1-100% (e.g., as many as 1, 2, 3, 4, 5, 10, 15, 20, 30, 40, 50, 60, 70, 80, 90, or 100%). In some embodiments, the percentage of polymer monomers that are conjugated to an agent is less than 10%, e.g., less than 9%, less than 8%, less than 7%, less than 6%, less than 5%, less than 4%, or less than 3%. In some embodiments, the percentage of polymer monomers that are conjugated to an agent is between, or inclusive of 2% to 10%, 3% to 9%, or 4% to 60%. In some embodiments, the percentage of polymer monomers that are conjugated to an agent is between 10-90%. In some embodiments, the percentage of polymer monomers that are conjugated to an agent is between 15-75%. In the some embodiments, the percentage of polymer monomers that are conjugated to an agent is between 20-60%. In the some embodiments, the percentage of polymer monomers that are conjugated to an agent is between 35-50%.

Without being bound by theory, the particles disclosed herein may improve the efficiency of an agent (e.g., a therapeutic and/or diagnostic agent) by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate or particle described herein).

In other embodiments, the agent-containing particle (e.g., a particle containing an AHCM) has a dose or amount of the agent that is less than the dose or amount of said agent in free form to have a desired effect (e.g., a desired therapeutic effect). In one embodiment, the agent-containing particle has a dose or amount of the agent that is less than the standard of care dose of the agent for a desired therapy (e.g., a dose that is less than 0.01, 0.02, 0.03, 0.04, 0.05, 0.06, 0.07, 0.08, 0.09, 0.1, 0.2, 0.3, 0.4, 0.5, 0.6, 0.7, that of the standard of care dose of the agent). In one embodiment, where the agent is an AHCM, the dose is less than the anti-hypertensive or anti-heart failure dose for $AT_1$ inhibitors or ARBs such as losartan, candesartan, eprosartan, irbesartan, olmesartan, telmisartin, and valsartan.

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). Since the particle described herein releases the agent at a target site based on pH microenvironment, other non-target sites (e.g., blood vessels) with different pH would be less likely to be exposed to the agent.

Exemplary Conjugates

In one embodiment, the conjugate comprises a polyacetal polymer (e.g., as described herein) and an agent (e.g., an agent as described herein, e.g., an ARB).

In another embodiment, the conjugate comprises a polyacetal-losartan conjugate. In another embodiments, the conjugate comprises a losartan-linked polyol derivative, e.g., as described in Formula (II-e). In one embodiment, the polyacetal-losartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In one embodiment, the conjugate comprises a valsartan-linked polyol derivative, e.g., as shown in FIG. 2B. In one embodiment, the conjugate comprises a valsartan-linked polyol derivative, e.g., as described in Formula (II-f). In one embodiment, the polyacetal-valsartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the conjugate comprises a polyacetal-telmisartan conjugate. In another embodiments, the conjugate comprises a telmisartan-linked polyol derivative, e.g., as described in Formula (II-g). In one embodiment, the polyacetal-telmisartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the conjugate comprises a polyacetal-candesartan conjugate.

In another embodiments, the conjugate comprises a candesartan-linked polyol derivative, e.g., as described in Formula (II-h). In one embodiment, the polyacetal-candesartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the conjugate comprises a polyacetal-olmesartan conjugate. In another embodiments, the conjugate comprises an olmesartan-linked polyol derivative, e.g., as described in Formula (II-i). In one embodiment, the polyacetal-olmesartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the conjugate comprises an agent (e.g., an agent as described herein), a linker (e.g., a linker as described herein), and a polyacetal polymer (e.g., as described herein). In another embodiment, the conjugate comprises an agent (e.g., an agent as described herein), a linker (e.g., a linker as described herein, e.g, in FIG. 3 or FIG. 4), and a polyacetal polymer (e.g., as described herein). In another embodiment, the conjugate described herein is a polyacetal polymer comprising one or more of gemcitabine, 5-fluorouracil or irinotecan. In one embodiment, the conjugate comprises a linker as shown in FIG. 3 or FIG. 4.

In another embodiment, the conjugate comprises an agent (e.g., an agent as described herein, e.g., an ARB), a linker (e.g., a linker as described herein, e.g., as shown in FIGS. 5A-5D), and a polyacetal polymer (e.g., as described herein). In another embodiment, the conjugate comprises a linker selected from succinic acid or ethylene diamine, e.g., as shown in FIGS. 5A-5D.

In other embodiments, the conjugate comprises an agent (e.g., an agent as described herein, e.g., an ARB), a linker (e.g., a linker as described herein, e.g., as shown in FIGS. 5A-5D), a polyacetal polymer (e.g., as described herein), and a targeting moiety (e.g., a targeting moiety as described herein). In one embodiment, the targeting moiety is a mannose-6-phosphate (M6P). Exemplary conjugates of losartan, a polymer (with or without a linker), and M6P as a targeting moiety are depicted in FIGS. 5A-5D. In one embodiment, the conjugate has the structure depicted in FIG. 5A. In one embodiment, the conjugate has the structure depicted in FIG. 5B. In one embodiment, the conjugate has the structure depicted in FIG. 5C. In one embodiment, the conjugate has the structure depicted in FIG. 5D.

In one embodiment, the conjugates described herein are present in a particle, e.g., a nanoparticle, from about 10 to 100 nm, about 20 to 90 nm, about 30 to 60 nm, about 30 to 45 nm, in size.

In one embodiment, the particle has a polymer polydispersity index of less than about 1 (e.g., less than about 0.5, less than about 0.25, less than or equal to about 0.15, or less than or equal to about 0.1).

In some embodiments, the conjugate is soluble in water (e.g., hydrophilic). In some embodiments, the conjugate is soluble in water, and between about 0.1 to about 5 parts water are required to dissolve 1 part conjugate, or between about 1 part to about 5 parts water are required to dissolve 1 part conjugate. In some embodiments, the conjugate is partially soluble in water. In some embodiments, the conjugate is partially soluble in water, and between about 5 to about 50 parts water are required to dissolve 1 part conjugate. In some embodiments, the conjugate is sparingly soluble in water. In some embodiments, the conjugate is sparingly soluble in water, and between about 25 to about 100 parts water is required to dissolve 1 part conjugate. In some embodiments, the conjugate is slightly soluble in water. In some embodiments, the conjugate is slightly soluble in water, and between 100 to about 1,000 parts water are required to dissolve 1 part conjugate. In some embodiments, the conjugate is very slightly soluble in water. In some embodiments, the conjugate is very slightly soluble in water, and between 1,000 to about 10,000 parts water are required to dissolve 1 part conjugate. In some embodiments, the conjugate is substantially insoluble in water (e.g., hydrophobic). In some embodiments, the conjugate is substantially insoluble in water and greater than about 10,000 parts water are required to dissolve 1 part conjugate.

Exemplary Particles

In one embodiment, the particle comprises a polyacetal polymer (e.g., as described herein) and an agent (e.g., an agent as described herein, e.g., an ARB).

In another embodiment, the particle comprises a polyacetal-losartan conjugate. In another embodiments, the particle comprises a losartan-linked polyol derivative, e.g., as described in Formula (II-e). In one embodiment, the polyacetal-losartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In one embodiment, the particle comprises a polyacetal-valsartan conjugate, e.g., a polyacetal-valsartan conjugate as shown in FIG. 2B. In one embodiment, the particle comprises a valsartan-linked polyol derivative, e.g., as described in Formula (II-f). In one embodiment, the polyacetal-valsartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the particle comprises a polyacetal-telmisartan conjugate. In another embodiments, the particle comprises a telmisartan-linked polyol derivative, e.g., as described in Formula (II-g). In one embodiment, the polyacetal-telmisartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the particle comprises a polyacetal-candesartan conjugate. In another embodiments, the particle comprises a candesartan-linked polyol derivative, e.g., as described in Formula (II-h). In one embodiment, the polyacetal-candesartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the particle comprises a polyacetal-olmesartan conjugate. In another embodiments, the particle comprises an olmesartan-linked polyol derivative, e.g., as described in Formula (II-i). In one embodiment, the polyacetal-olmesartan conjugate has a ratio of release or degradation rate of the polyacetal polymer and/or linker at pH=6.7 relative to pH=7.4 is greater than 1, 1.2, 1.4, 1.6, 1.8, 2, 2.2, 2.4, 2.6, 2.8, 3, 3.5, 4 or higher. In one embodiment, ratio of release or degradation rate of the polyacetal polymer and/or linker at pH=6.7 relative to pH=7.4 is greater than 2.

In another embodiment, the particle comprises an agent (e.g., an agent as described herein), a linker (e.g., a linker as described herein), and a polyacetal polymer (e.g., as described herein). In another embodiment, the particle comprises an agent (e.g., an agent as described herein), a linker (e.g., a linker as described herein, e.g, in FIG. 3 or FIG. 4), and a polyacetal polymer (e.g., as described herein). In another embodiment, the particle described herein comprises a polyacetal polymer comprising one or more of gemcitabine, 5-fluorouracil or irinotecan. In one embodiment, the particle comprises a linker as shown in FIG. 3 or FIG. 4.

In another embodiment, the particle comprises an agent (e.g., an agent as described herein, e.g., an ARB), a linker (e.g., a linker as described herein, e.g., as shown in FIGS. 5A-5D), and a polyacetal polymer (e.g., as described herein). In another embodiment, the particle comprises a linker selected from succinic acid or ethylene diamine, e.g., as shown in FIGS. 5A-5D.

In other embodiments, the particle comprises an agent (e.g., an agent as described herein, e.g., an ARB), a linker (e.g., a linker as described herein, e.g., as shown in FIGS. 5A-5D), a polyacetal polymer (e.g., as described herein), and a targeting moiety (e.g., a targeting moiety as described herein). In one embodiment, the targeting moiety is a mannose-6-phosphate (M6P). Exemplary particle comprising conjugates of losartan, a polymer (with or without a linker), and M6P as a targeting moiety are depicted in FIGS. 5A-5D. In one embodiment, the particle comprises a conjugate with the structure depicted in FIG. 5A. In one embodiment, the particle comprises a conjugate with the structure depicted in FIG. 5B. In one embodiment, the particle comprises a conjugate with the structure depicted in FIG. 5C. In one embodiment, the particle comprises a conjugate with the structure depicted in FIG. 5D.

In one embodiment, the particle has a polymer polydispersity index of less than about 1 (e.g., less than about 0.5, less than about 0.25, less than or equal to about 0.15, or less than or equal to about 0.1).

Method of Making the Compositions
Methods of Making Polymers

In some embodiments, the polymer described herein (e.g., polyacetal polymer, e.g., of Formula (I), Formula (I-a), Formula (I-b), Formula (I-c), Formula (I-d), Formula (I-e), or Formula (V)) are synthesized through self- or cross-polyaddition of vinyl ethers with polyols in a stepwise manner. In one embodiment, the polymerization reaction includes the polyaddition of polyols with vinyl ethers catalyzed by a Bronsted (e.g., protic) or Lewis acid catalyst (e.g., p-toluene sulfonic acid (pTSA), camphor sulfonic acid, benzene sulfonic acid, or boron trifluoride). Examples of solvents that can be used for such polyaddition reaction to synthesize polymers include, but are not limited to, toluene, chloroform, tetrahydrofuran (THF), dioxane, 2-methyltetrahydrofuran, dichloromethane (DCM), dimethylformamide (DMF), dimethylsulfoxide (DMSO), or any combinations thereof. In some embodiments, the polymerization reaction is carried out in a mixture of THF and toluene. In some embodiments, the solvent is freshly distilled prior to the reaction. In some embodiments, the solvent is anhydrous. In some embodiments, the polymerization reaction is carried out in the presence of a base (e.g., trimethylamine (TEA), or 4-dimethylaminopyridine (DMAP)).

In some embodiments, the polymerization is carried out in a dry container (e.g., glassware) in a nitrogen or argon atmosphere. In some embodiments, the reaction temperature is 0° C., room temperature, or 40-60° C. In some embodiments, the reaction temperature is 50° C. In some embodiments, the reaction temperature is 60-80° C.

In some embodiments, the individual monomer units in the polymerization reaction are of high purity. In some embodiments, the individual monomer units in the polymerization reaction are at least 90%, at least 92%, at least 95%, at least 97%, at least 98%, at least 99%, or at least 99.9% pure. In some embodiments, the individual monomer units in the polymerization reaction are vacuum dried prior to use in the reaction. In some embodiments, the individual monomer units in the polymerization reaction are freshly distilled (e.g., with $CaH_2$ or $K_2CO_3$), purified, recrystallized, or dried prior to use in the reaction. In some embodiments, the individual monomer units in the polymerization reaction are synthesized prior to use. In some embodiments, the individual monomer units in the polymerization reaction are commercially available.

In some embodiments, the individual monomer units in the polymerization reaction comprise a polyol (e.g., a compound represented by Formula (II), Formula (II-a), Formula (II-b), Formula (II-c), Formula (II-d), Formula (II-e), Formula (II-f), Formula (II-g), Formula (II-h), Formula (II-i), Formula (II-j), or as depicted in FIG. 1B), and a vinyl ether (e.g., a compound represented by Formula (III), Formula (III-a), Formula (III-b), or depicted in FIG. 1C). In some embodiments, the ratio of the polyol to the vinyl ether is from about 10:1 to about 1:10. In some embodiments, the ratio of the polyol to the vinyl ether is from about 5:1 to about 1:5. In some embodiments, the ratio of the polyol to the vinyl ether is from about 3:1 to about 1:3. In some embodiments, the ratio of the polyol to the vinyl ether is from about 2.5:1 to about 1:2.5, from about 2.25:1 to about 1:2.25, from about 2:1 to about 1:2, from about 1.9:1 to about 1:1.9, from about 1.8:1 to about 1:1.8, from about 1.7:1 to about 1:1.7, from about 1.6:1 to about 1:1.6, or from about 1.5:1 to about 1:1.5. In some embodiments, the ratio of the polyol to the vinyl ether is about 1.5:1 to about 1:1. In some embodiments, the ratio of the polyol to the vinyl ether is from about 1.4:1 to about 1:1, from about 1.3:1 to about 1:1, from about 1.2:1 to about 1:1, or from about 1.1:1 to about 1:1. In some embodiments, the ratio of the polyol to the vinyl ether is about 1:1.

In some embodiments, the ratio of the polyol to the vinyl ether is from about 1.2:1.0 to about 1.0:1.2. In some embodiments, the ratio of the polyol to the vinyl ether is from about 1.1:1 to about 1:1.1. In some embodiments, the ratio of the polyol to the vinyl ether is about 1.01:1, about 1.02:1, about 1.03:1, about 1.04:1, about 1.05:1, about 1.06:1, about 1.07:1, about 1.08:1, or about 1.09:1. In some embodiments, the ratio of the polyol to the vinyl ether is about 1:1.01, about 1:1.02, about 1:1.03, about 1:1.04, about 1:1.05, about 1:1.06, about 1:1.07, about 1:1.08, or about 1:1.09. In some embodiments, the ratio of the polyol to the vinyl ether is from about 1.05:1 to about 1:1.05.

In some embodiments, the individual monomer units in the polymerization reaction comprise a vinyl ether (e.g., a compound represented by Formula (III), Formula (III-a), Formula (III-b), or depicted in FIG. 1C), and a PEG (e.g., as described by $C^1$ or $C^2$ in Formula (I), Formula (I-a), Formula (I-b), Formula (I-c), Formula (I-d), Formula (I-e), or Formula (IV)). In some embodiments, only one PEG is used in the polymerization reaction. In some embodiments, one of PEG 400 and PEG 1000 is used in the polymerization reaction. In some embodiments, more than one PEG is used in the polymerization reaction. In some embodiments, each of PEG 400 and PEG 1000 is used in the polymerization reaction. In some embodiments, the ratio of PEG 400 to PEG 1000 used in the polymerization reaction is between about 0.25:1 to about 1:0.25, from about 0.3:1 to about 1:0.3, from about 0.5:1 to about 1:0.5, from about 0.6:1 to about 1:0.6, or from about 0.75:1 to about 1:0.75. In some embodiments, the ratio of PEG 400 to PEG 1000 is 1:1. In some embodiments, PEG 2050 is used in the polymerization reaction.

In some embodiments, the individual monomer units in the polymerization reaction comprise a polyol (e.g., a compound represented by Formula (II), Formula (II-a), Formula (II-b), Formula (II-c), Formula (II-d), Formula (II-e), Formula (II-f), Formula (II-g), Formula (II-h), Formula (II-i), Formula (II-j), or as depicted in FIG. 1B), a vinyl ether (e.g., a compound represented by Formula (III), Formula (III-a), Formula (III-b), or depicted in FIG. 1C), and a PEG (e.g., as described by $C^1$ or $C^2$ in Formula (I), Formula (I-a), Formula (I-b), Formula (I-c), Formula (I-d), Formula (I-e), or Formula (IV)).

In some embodiments, the reaction time ranges from about 1 hour to about 48 hours. In some embodiments, the reaction time ranges from about 1 hour to about 36 hours, to about 24 hours, to about 18 hours, to about 16 hours, to about 14 hours, to about 12 hours, to about 10 hours, to about 8 hours, to about 6 hours, to about 4 hours, to about 2 hours. In some embodiments, the reaction time ranges from about 1 hour to about 24 hours. In some embodiments, the reaction time ranges from about 1 hour to about 16 hours, or from about 1 hour to about 8 hours, or from about 1 hour to about 4 hours.

In some embodiments, an excess of a polyol (e.g., a compound represented by Formula (II), Formula (II-a), Formula (II-b), Formula (II-c), Formula (II-d), Formula (II-e), Formula (II-f), Formula (II-g), Formula (II-h), Formula (II-i), Formula (II-j), or as depicted in FIG. 1B) is added to the polymerization reaction in order to quench or substantially stop the polymerization process. In some embodiments, an excess of about 1.5, about 2.0, about 5.0, about 10, about 15, about 20, about 25, about 50, about 75, about 100, about 250, about 500, about 1000, or more of a polyol (e.g., a polyol described herein) is added to the polymerization reaction relative to the starting amount of said polyol in order to quench or substantially stop the polymerization process.

In some embodiments, the reaction is quenched through the addition of base (e.g., including, but not limited to, triethylamine or ammoniacal methanol). In some embodiments, the polymer mixture is purified by extraction, vacuum drying, trituration, or chromatography (e.g., silica gel chromatography, HPLC).

Methods of Making Conjugates

In some embodiments, the conjugation of an agent (e.g., an agent described herein, e.g., an ARB), a targeting moiety (e.g., M6P), or a linker (e.g., a linker described herein) to the polymers described herein can occur via a reactive group, e.g., a free hydroxyl group, on the polymers. In some embodiments, it is more desirable that the agents (e.g., an ARB) have at least one or more carboxylic acids and/or hydroxyl groups. By way of example only, in one embodiment, the agent valsartan with a carboxylic acid group or the agent losartan with a hydroxyl group can be conjugated to the polymer described herein via ester bond formation. Exemplary coupling agents used for conjugation include, but are not limited to, EDC, DIC, DCC, HOAt, HOBt, and PyBOP. In some embodiments, the conjugation reaction further comprises a base (e.g., TEA, pyridine). In some embodiments, the conjugation reaction further comprises a catalyst (e.g., DMAP). In some embodiments, conjugation of an agent to a polymer occurs through a linker (e.g., a linker described herein, in the section entitled "Linkers"). In some embodiments, conjugation of a linker to the polyacetal polymer occurs prior to conjugation of an agent or a targeting moiety to the polyacetal polymer.

In some embodiments, a free hydroxyl group on a polymer (e.g., a polyacetal polymer described herein) must be exposed through removal of a hydroxyl protecting group (e.g., a benzyl ether, a t-butyl ether, a benzoic acid ester, an acetic acid ester, or an allyl ether). In some embodiments, the polymer (e.g., a polymer described herein) comprises at least 1, at least 2, at least 3, at least 4, at least 5, at least 10, at least 15, at least 20, at least 25, at least 50, at least 75, at least 100, at least 125, at least 150, at least 200, or more protected hydroxyl groups (e.g., one or more of a benzyl ether, a t-butyl ether, a benzoic acid ester, an acetic acid ester, or an allyl ether). Methods for removal of said hydroxyl protecting groups are known in the art. In some embodiments, removal of a hydroxyl protecting group is carried out prior to conjugation of an agent to a polymer (e.g., a polyacetal polymer described herein).

In some embodiments, the number of equivalents of an agent (e.g., an agent described herein, e.g., an ARB), a targeting moiety (e.g., M6P), or a linker (e.g., a linker described herein) in the conjugation reaction is greater than the number of equivalents of the polyacetal polymer (e.g., a polyacetal polymer described herein). In some embodiments, the conjugation reaction comprises an excess of an amount of an agent (e.g., an agent described herein, e.g., an ARB), a targeting moiety (e.g., M6P), or a linker (e.g., a linker described herein) compared with the polyacetal polymer (e.g., a polyacetal polymer described herein). In some embodiments, the conjugation reaction comprises a sub-stoichiometric amount of an agent (e.g., an agent described herein, e.g., an ARB), a targeting moiety (e.g., M6P), or a linker (e.g., a linker described herein) compared with the polyacetal polymer (e.g., a polyacetal polymer described herein). In some embodiments, the ratio of an agent (e.g., an agent described herein, e.g., an ARB), a targeting moiety (e.g., M6P), or a linker (e.g., a linker described herein) to the polyacetal polymer (e.g., a polyacetal polymer described herein) is about 1000:1, about 750:1, about 500:1, about 250:1, 100:1, about 75:1, about 50:1, about 25:1, about 15:1, about 10:1, about 8:1, about 5:1, about 3:1, or about 2:1. In some embodiments, the ratio of an agent (e.g., an agent described herein, e.g., an ARB), a targeting moiety (e.g., M6P), or a linker (e.g., a linker described herein) to the polyacetal polymer (e.g., a polyacetal polymer described herein) is 1:1. In some embodiments, the ratio of the polyacetal polymer (e.g., a polyacetal polymer described herein) to an agent (e.g., an agent described herein, e.g., an ARB), a targeting moiety (e.g., M6P), or a linker (e.g., a linker described herein) is about 1:0.9, about 1:0.8, about 1:0.7, about 1:0.6, about 1:0.5, about 1:0.4, about 1:0.3, about 1:0.2, about 1:0.1, about 1:0.05, about 1:0.01, about 1:0.05, about 1:0.01, or less.

In some embodiments, the agents (e.g., drugs) lack one or more carboxylic acids and/or hydroxyl groups. In one exemplary embodiment, losartan does not have a free carboxylic acid group for conjugation to the polymer. In this exemplary embodiment, it may be desirable to convert a hydroxyl group on the polymer side chain into a carboxylic acid through the use of a modification agent. Exemplary modification agents include, e.g., succinic anhydride (e.g., as shown in FIG. 5A). An esterification reaction may then be carried out between the modified polymer and an agent (e.g., losartan) to conjugate the agent (e.g., losartan) to the polymer (e.g., as shown in FIG. 5B). In some embodiments, a sub-stoichiometric amount of the agent can be used in the esterification reaction in order to prevent full saturation of the modified polymer (e.g., the polymer modified with carboxylic acid groups). In some embodiments, a sub-stoichiometric amount of the agent can be used to provide about 50%, about 60%, about 70%, about 80, about 90%, about 95%, or about 99% or more saturation of the modified polymer (e.g., the polymer modified with carboxylic acid groups). In some embodiments, the modified polymer contains free, unreacted modifications (e.g., carboxylic acid groups) after conjugation of the agent (e.g., losartan). In some embodiments, the modified polymer contains about 50%, about 40%, about 30%, about 20%, about 10%, about 5%, or about 1% or less free, unreacted modifications (e.g., carboxylic acid groups). In some embodiments, the free, unreacted modifications on the polymer may be reacted with a second modification agent (e.g, an amine, e.g., ethylenediamine, as shown in FIG. 5C)).

In some embodiments, the conjugation of a targeting moiety to a polymer described herein (e.g., a polyacetal polymer) can involve the formation of a covalent linkage. In some embodiments, the conjugation of a targeting moiety (e.g., M6P) can involve reaction of the targeting moiety (e.g., M6P) with the modified polymer (e.g., the polymer modified with amine groups, or the losartan-polymer modified with amine groups). In some embodiments, the targeting moiety (e.g., M6P) must first be activated for conjugation to the modified polymer (e.g., the polymer modified with amine groups, or the losartan-polymer modified with amine groups). By way of example, in an embodiment, the targeting moiety M6P (e.g., α-4-nitrophenyl M6P) may be activated to yield an M6P-isothiocyanate. In some embodiments, the activation of the targeting moiety requires at least two steps (e.g., synthesis of α-4-nitrophenyl M6P followed by formation of M6P-isothiocyanate). In some embodiments, the activated targeting moiety (e.g., M6P-isothiocyanate) can be conjugated to the modified polymer (e.g., the polymer modified with amine groups, or the losartan-polymer modified with amine groups).

In some embodiments, the conjugation of a targeting moiety to a polymer described herein (e.g., a polyacetal polymer) can involve the formation of a noncovalent linkage, e.g., an ionic interaction or hydrophobic interaction. In some embodiments, the conjugation of a targeting moiety (e.g., M6P) can involve reaction of the targeting moiety (e.g., M6P) with the modified polymer (e.g., the polymer modified with amine groups, or the losartan-polymer modified with amine groups). In some embodiments, the targeting moiety (e.g., M6P) is not activated prior to conjugation to or association with the modified polymer (e.g., the polymer modified with amine groups, or the losartan-polymer modified with amine groups). By way of example, in an embodiment, the targeting moiety M6P (e.g., α-4-nitrophenyl M6P) is incubated with the modified polymer (e.g., the polymer modified with amine groups, or the losartan-polymer modified with amine groups) to yield an M6P-nanoARB (e.g., a polymer modified with both M6P and an ARB, e.g, losartan, e.g., as shown in FIG. 5D).

In some embodiments, the reaction time ranges from about 1 hour to about 48 hours. In some embodiments, the reaction time ranges from about 1 hour to about 36 hours, to about 24 hours, to about 18 hours, to about 16 hours, to about 14 hours, to about 12 hours, to about 10 hours, to about 8 hours, to about 6 hours, to about 4 hours, to about 2 hours. In some embodiments, the reaction time ranges from about 1 hour to about 24 hours. In some embodiments, the reaction time ranges from about 1 hour to about 16 hours, or from about 1 hour to about 8 hours, or from about 1 hour to about 4 hours.

In some embodiments, the reaction is quenched through the addition of base (e.g., including, but not limited to, triethylamine or ammoniacal methanol). In some embodiments, the polymer mixture is purified by extraction, vacuum drying, trituration, or chromatography (e.g., silica gel chromatography, HPLC).

Methods of Making Particles

In some embodiments, particles are prepared from the conjugates and/or polymers described herein. In some embodiments, preparation of particles is carried out through precipitation, emulsion (e.g., single emulsion or double emulsion), and/or salting out of the conjugates from an aqueous solution. In some embodiments, emulsions are formed in which an emulsion (water/oil or oil/water) is dispersed in a continuous phase (water or oil, respectively) to produce water/oil/water or oil/water/oil. In some embodiments, preparation of particles is carried out through precipitation of the conjugates from an organic solvent. In some embodiments, preparation of particles is carried out by dissolving the conjugates and/or polymers described herein in an organic solvent, e.g., THF, acetonitrile, or DMF. In some embodiments, the organic solvent comprising the conjugates and/or polymers is added drop-wise to a volume of water to form the particles. In some embodiments, the organic solvent comprising the conjugates and/or polymers is added drop-wise to a volume of water at a steady rate (e.g., 0.1 mL/min, 0.5 mL/min, 1 mL/min, 1.5 mL/min, 2 mL/min, 5 mL/min, 7.5 mL/min, 10 mL/min, 15 mL/min, 20 mL/min) to form the particles. In some embodiments, the organic solvent (e.g., THF, acetonitrile, or DMF) is removed by evaporation to provide a dried film. In some embodiments, an aqueous solution (e.g., water or a buffer, e.g., PBS) solution is used to wash the dried film, e.g., once, twice, three times, or more. In some embodiments, the mixture is then sonicated or mixed in a cold water bath (e.g., at a temperature less than 25° C., less than 20° C., less than 15° C., less than 10° C., less than 5° C., less than 0° C.) to form the precipitated particles. In some embodiments, the resulting particles are then filtered and characterized to determine the average diameter, polydispersity, and molecular weight.

Formulations and Pharmaceutical Compositions

Any of the compositions (e.g., polymer, linker, conjugate or particles) disclosed herein can be formulated in an acceptable carrier, e.g., for therapeutic or diagnostic use, or for storage.

In one embodiment, combinations of one or more particles as described herein can be administered to a subject as a single composition or two or more compositions. The compositions can be administered via the same or different route.

In one embodiment, the particle, e.g., a nanoparticle, is stored in solid form under suitable condition for storage. In one embodiment, the formulation comprises a protectant agent, for example, for freeze drying and/or reconstitution. The protectant agent can be chosen from one or more of dextran, sucrose, α or β or γ-cyclodextrin or serum albumin (e.g., bovine serum albumin). In one embodiment, the protectant agent is bovine serum albumin.

The particle(s) can be sterilized by γ-irradiation of the lyophilized formulation, or sterile filtration of liquid formulation. Other sterilization technique including ultraviolet irradiation or ethanol sterilization can also be used. See, e.g., J Pharm Sci. 2011 February; 100(2):646-54 for additional sterilization method that can be used to sterilize the particle described herein.

Uses

In another aspect, the invention features a method of treating or preventing a disorder or condition, in a subject, or of improving the delivery and/or efficacy of a therapy (e.g., a cancer therapy, or an anti-fibrotic or anti-inflammatory therapy) in a subject. The method includes:

administering a conjugate or a particle (e.g., one or more pH sensitive and/or polyacetal conjugates or particles as described herein), as a single agent or in combination with a therapy (e.g., against cancer, a fibrotic disorder, or an inflammatory disorder), to the subject;

optionally, administering the therapy (e.g., a cancer therapy, or an anti-fibrotic or anti-inflammatory therapy), under conditions sufficient to treat or prevent the disorder or condition in the subject, or to improve the delivery and/or efficacy of the therapy provided to the subject. In one embodiment, the disorder or condition is a hyperproliferative and/or fibrotic disorder (e.g., a cancer or a fibrotic or inflammatory disorder as described herein). In some embodiments, the therapy comprises a low-dose anti-angiogenic agent. In some embodiments, the therapy comprises an immunomodulator and/or a chemotherapeutic agent.

In another aspect, the invention features a combination or composition for use in treating a disorder, e.g., a cancer, or a fibrotic or inflammatory disorder, or improving the delivery and/or efficacy of a therapy (e.g., a cancer therapy, or an anti-fibrotic or anti-inflammatory therapy). In embodiments, the composition for use includes (e.g., one or more conjugate or a particle (e.g., one or more pH sensitive and/or polyacetal conjugates or particles as described herein). In one embodiment, the composition includes one, two or more of:

(i) an AHCM (e.g., an ARB);

(ii) a microenvironment modulator (e.g., an anti-angiogenic inhibitor, e.g., a low-dose anti-angiogenic inhibitor) and/or other stromal modulators;

(iii) an immunomodulator (e.g., anti-inflammatory agent (e.g., a cytokine inhibitor) or an inhibitor of an immune checkpoint molecule, and optionally, a therapy (e.g., a cancer therapy, or an anti-fibrotic or anti-inflammatory therapy).

In another aspect, the invention features a method for treating or preventing a liver disorder or condition in a subject. The method includes administering to the subject one or both of a metformin agent or an AHCM, and a vascular/stromal normalizing dose (e.g., a sub-anti-angiogenic dose) of a second agent chosen from one or more of: anti-angiogenic agent, sorafenib or an inhibitor of the angiopoietin-Tie-2 pathway (e.g., an Ang-1 or an Ang-2 inhibitor), thereby treating or preventing the liver disorder or condition.

In one embodiment, the particle administered (e.g., one or more particles as described herein), comprises:

a polymer, e.g., a pH-sensitive polymer as described herein;

an agent (e.g., one or more therapeutic and/or or diagnostic agents (e.g., an AHCM, microenvironment modulator, other stromal modulator, and/or a cancer, anti-fibrotic, or anti-inflammatory therapy));

(optionally) a targeting moiety (e.g., a cell- or a liver-targeting agent); and (optionally) one or more pegylated moieties or polymers, (optionally) wherein the polymer, the agent and/or a targeting moiety, are coupled (e.g., covalently or noncovalently coupled via a linker, e.g., a pH-sensitive linker as described herein).

In some embodiments, the particle(s) or polymer-AHCM conjugate(s) can be used or disposed in implants or devices for local or systemic drug delivery. In some embodiments, the particle(s) or polymer-AHCM conjugate(s) can be embedded in hydrogels, e.g., for local or systemic drug delivery.

In any of the methods and uses described herein, the method or use further includes identifying the subject as being in need of improved delivery and/or efficacy of the therapy (e.g., the cancer therapy, or the anti-fibrotic or anti-inflammatory therapy). In some embodiments, the method includes identifying the subject as having a desmoplastic disorder (e.g., a cancer, or a fibrotic or inflammatory disorder). In some embodiments, the method includes identifying the subject as being overweight or obese, e.g., as having a BMI greater than 25. In yet other embodiments, the method further includes identifying the subject as having a metabolic disorder, e.g., a systemic metabolic disorder. In embodiments, responsive to said identification, administering one, two, or more of: (i) an AHCM (e.g., an ARB); (ii) a microenvironment modulator (e.g., an anti-angiogenic inhibitor) and/or other stromal modulators; or (iii) an immunomodulator. In one embodiment, the subject is a patient with a metastatic cancer, e.g., a metastatic form of a cancer disclosed herein (one or more of pancreatic (e.g., pancreatic adenocarcinoma), breast, colorectal, lung (e.g., small or non-small cell lung cancer), skin, ovarian, or liver cancer.

In one embodiment, the subject is a patient having treatment-resistant cancer or hyperproliferative disorder.

In one embodiment, the subject is, or is identified as being, overweight or obese. Assessment of overweight and obesity can be determined by the classification of body mass index (BMI) as defined by "Clinical Guidelines on the Identification, Evaluation, and Treatment of Overweight and Obesity in Adults" from the National Institutes of Health. Body mass index is obtained by dividing a subject's weight, e.g., in kilograms (kg) by the square of the subject's height, e.g., in meters (m). Subjects with a BMI 18.5 to 24.9 are typically classified as normal weight, while subjects with a BMI 25.0 to 29.9 are classified as overweight. Subjects with a BMI 30.0 or greater are classified as obese, and can be subdivided into three classes: Class I (BMI=30.0 to 34.9; Class II (BMI=35.0 to 39.9); and Class III (BMI is greater or equal to 40).

In one embodiment, the subject is overweight, e.g., the subject has a BMI of greater than or equal to 25.0 but less than or equal to 29.9.

In another embodiment, the subject is, or is identified as being, obese, e.g., the subject has a BMI of greater than or equal to 30, e.g., greater than 30, greater than 35, greater than 40, greater than 45, or greater than 50.

Obesity can also be associated with one or more of: desmoplasia, e.g., in adipose tissues and the pancreas; dysfunctional adipocytes, e.g., hypertrophied adipocytes; increased hypoxia; fibrosis; accumulation of fat, e.g., steatosis; increased angiotensin II (AngII) type-1 receptor (AT1) signaling; and/or increased expression, production, and/or secretion of pro-inflammatory cytokines, e.g., interleukin-1beta (IL-1 beta).

In an embodiment, the subject is, or is identified as being, overweight or obese, and has a fibrotic or a hyperproliferative cancerous condition described herein. In an embodiment, the subject is, or is identified as being, overweight or obese and has a fibrotic disorder described herein. In an embodiment, the subject is, or is identified as being, overweight or obese and has a liver disorder or condition described herein.

In some embodiments, responsive to a determination of a weight/metabolic-related parameter indicative of normal or underweight (e.g., BMI value less than 25), performing one, two, three or more of:

(i) identifying the subject as being less likely to respond to the therapy, e.g., AHCM, microenvironment modulator, or other stromal therapy;

(ii) stratifying the subject, or a patient populations (e.g., stratifying the subject) as being less likely to respond (e.g., responders vs. non-responders) to the therapy, e.g., the metformin therapy and/or the AHCM therapy;

(iii) more effectively monitor the therapy, e.g., the metformin therapy and/or the AHCM therapy; or (iv) discontinuing or not administering the metformin agent, alone or in combination with, one, two, three or more of: (i) an AHCM (e.g., an ARB); (ii) a microenvironment modulator (e.g., an anti-angiogenic inhibitor, e.g., a low-dose anti-angiogenic inhibitor) and/or other stromal modulators; (iii) an anti-inflammatory agent (e.g., a cytokine inhibitor); or (iv) an inhibitor of an immune checkpoint molecule.

Exemplary Particle Polymers and Linkers for Use in the Methods

In one embodiment, the particle administered comprises a polymer (e.g., any polymer disclosed herein, including a pH-sensitive polymer), a pH-sensitive linker (e.g., a pH-sensitive linker as described herein) and an agent (e.g., a therapeutic and/or diagnostic agent (e.g., an AHCM)) and/or the targeting moiety, e.g., each as described herein. In one embodiment, the polymer, the linker, the agent and/or the targeting moiety in the particle are coupled, e.g., covalently coupled, directly or indirectly.

In another embodiment, the particle administered comprises a pH-sensitive polymer, e.g., a pH sensitive polyacetal polymer as described herein, a linker (e.g., a pH-sensitive linker as described herein) and an agent (e.g., a therapeutic and/or diagnostic agent (e.g., an AHCM)) and/or the targeting moiety, as described herein. In one embodiment, the polymer, the linker, the agent and/or the targeting moiety in the particle are coupled, e.g., covalently coupled, directly or indirectly.

In one embodiment, the particle administered comprises an agent and/or a targeting moiety (e.g., as described herein), wherein one or both are directly coupled (e.g., covalently coupled) to the polyacetal polymer (e.g., a polymer that comprises the compound of Formula (I), Formula (I-a), Formula (I-b), Formula (I-c), Formula (I-d), Formula (I-e), or Formula (IV)). In another embodiment, the particle administered comprises an agent and/or a targeting moiety (e.g., as described herein), wherein one or both are noncovalently coupled (e.g., through an ionic or hydrophobic interaction) to the polyacetal polymer (e.g., a polymer that comprises the compound of Formula (I), Formula (I-a), Formula (I-b), Formula (I-c), Formula (I-d), Formula (I-e), or Formula (IV)). In yet another embodiment, the particle comprises an agent and/or targeting moiety (e.g., as described herein) coupled (e.g., covalently coupled or non-covalently coupled), via pH-sensitive linker (e.g., as described herein; an acetal monomer or a polyacetal polymer) to a second polymer (e.g., a polymer other than a polyacetal polymer).

In one embodiment, the particle administered does not include a targeting moiety (e.g., a cell- or a liver-targeting agent).

In another embodiment, the particle administered is selectively targeted or delivered to a target site. In one embodiment, the particle is delivered to a target site, e.g., via a targeting moiety (e.g., a cell- or liver-targeting agent). In one embodiment, the targeting moiety is chosen from one or more of a ligand, e.g., a cell surface receptor, a glycoprotein, a vitamin, cholesterol, an antibody or fragment thereof, a peptide, a protein, a lectin, an aptamer, a lipoprotein, a hormone, a charged molecule, a mono-, olio-, and polysaccharide, or low molecular weight ligands such as sugars, folic acids, and peptides. Exemplary targeting moieties are further described in detail herein, e.g., in the sections entitled "Targeting Moieties" and "Liver Targeting Moieties."

In one embodiment, the method includes administering one, two, or all of AHCM, the microenvironment modulator, or the therapy (e.g., the cancer, fibrotic, immunomodulatory, or liver therapy), or any combination thereof, as a particle (e.g., any of the particles disclosed herein) having a hydrodynamic diameter of greater than about 1, 5, 10, 15, 20, 25, 30, 35, 45, 50, 75, 100, 150, 200 nm, but less than 300 nm, e.g., as a nanoparticle.

Additional features and embodiments of the compositions (e.g., conjugates and particles described herein) and methods disclosed herein include one or more of the following:

Agents

In certain embodiments, the compositions (e.g., conjugate or particles) and methods disclosed herein comprises at least one (including, e.g., at least two, at least three) agent(s), e.g., a therapeutic agent and/or a diagnostic agent, e.g., as described herein. The agent(s) can be coupled to the particle (e.g., as a conjugate as described herein). In other embodiments, the agent(s) can be contained non-covalently inside the particle. In some embodiments, a first agent can be coupled to the particle (e.g., as a conjugate as described herein), and a second agent can be contained non-covalently inside the particle.

In one embodiment, the agent is protein (e.g., an antibody molecule or fusion protein), a peptide, a nucleic acid molecule (e.g., an antisense or inhibitory double stranded RNA molecule), a small molecule, a chemotherapeutic agent or drug, among others. Any of the agents disclosed herein, including those listed in the section entitled "Agents" can be used in the conjugates, particles and other compositions and methods disclosed herein.

Exemplary embodiments of the agents that can be used in the conjugates, particles, other compositions and methods disclosed herein include one or more of the following:

Exemplary AHCMs for the Compositions and Methods Disclosed

In certain embodiments, the agent used in the compositions (e.g., conjugates and particles described herein) of the invention is an AHCM. The AHCM can be used a therapeutic or diagnostic agent. In some embodiments, the agent, e.g., the therapeutic and/or diagnostic agent, administered as a particle, conjugate, or as a free agent is an AHCM, e.g., an AHCM as described herein.

In one embodiment, the AHCM is chosen from one or more of:

an angiotensin II receptor type 1 blocker ($AT_1$ blocker or ARB), an renin antagonist;

an antagonist of renin angiotensin aldosterone system ("RAAS antagonist"), an angiotensin converting enzyme (ACE) inhibitor, a thrombospondin 1 (TSP-1) inhibitor, e.g., a TSP-1 pathway inhibitor, a transforming growth factor beta 1 (TGF-β1) inhibitor, e.g., a TGF-β1 pathway inhibitor, a connective tissue growth factor (CTGF) inhibitor, e.g., a CTGF pathway inhibitor, a stromal cell-derived growth factor 1 alpha (SDF-1a) inhibitor, e.g., an SDF-1a pathway inhibitor, an endothelin receptor antagonist (ERA);

an agonist of angiotensin II receptor type 2 ($AT_2$);

a vitamin D receptor (VDR) agonist; or a combination of two or more of the above.

Unless the context describes otherwise, the term "AHCM" may refer to one or more agents as described herein.

The compositions and methods disclosed herein can include one, two, three or more AHCMs, alone or in combination with one or more therapies, e.g., cancer therapies or liver therapies disclosed herein.

In another embodiment, the AHCM is an $AT_1$ inhibitor. In an embodiment, the $AT_1$ blocker is chosen from one or more of: losartan (COZAAR®), candesartan (ATACAND®), eprosartan mesylate (TEVETEN®), EXP 3174, irbesartan (AVAPRO®), L158,809, olmesartan (BENICAR®), saralasin, telmisartin (MICARDIS®), valsartan (DIOVAN®), or an analogue or derivative thereof (e.g., a prodrug or a metabolite thereof), e.g., as shown in FIG. 23.

In another embodiment, the AHCM is a vitamin D receptor (VDR) agonist.

Exemplary VDR agonists include, but are not limited to, paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, ercalcitriol, EB1089 (seocalcitol), BXL-628 (elocalcitol), MC1288, CB966, BCB 1093, GS 1558, SM-10193, EB1072, EB1129, EB1133, EB1155, EB1270, MC1288, EB1213, CB1093, VD2656, VD2668, VD2708, VD2716, VD2728, VD2736, GS1500, GS1558, KH1060, ZK61422, and analogs and derivatives thereof, e.g., as shown in FIG. 24, or molecules as described by Scolletta et al. (2013) *Mediators of Inflammation* 2013, Article ID 876319; and Adorini (2005) *Cellular Immunology* 233: 115-124.

The exemplary AHCMs are described herein are not limiting, e.g, derivatives of AHCMs described herein can be used in the methods described herein.

In an embodiment, an AHCM can modulate the microenvironment. Exemplary AHCMs that can modulate the microenvironment, e.g., by modulating collagen levels and/or changing the differentiation state of fibroblasts or stellate cells, include, but are not limited to, ARBs, VDR agonists, ERAs, and combinations thereof. In one embodiment, the AHCM (alone or in combination) enhances the efficacy, delivery and/or diffusion of a therapy.

Any of the AHCMs described herein can be prepared and used as a single agent (e.g., in free form, as a conjugate, or as a particle as described herein), or in combination, e.g., in combination with any of the agents described herein (e.g., a microenvironment modulator, other stromal modulator and/or any of therapies disclosed herein, each of which may be in free form, as a conjugate, or as a particle as described herein).

Additional description of the AHCMs is provided throughout, including the sections below entitled "Agents" and "AHCMs." Any of the AHCMs disclosed herein, including those listed in the section entitled "Agents" and "AHCMs" can be used in the conjugates, particles, other compositions and methods disclosed herein.

Exemplary Microenvironment Modulators for the Compositions and Methods Disclosed In other embodiments, the agent used in the compositions (e.g., conjugates and particles described herein) and methods of the invention is a microenvironment modulator. In another embodiment, the agent administered as a particle, conjugate, or as a free agent is a microenvironment modulator.

In an embodiment, a microenvironment modulator can alter the microenvironment by one or more of: modifying the level and/or production collagen, procollagen or extracellular matrix components; by modulating the crosslinking of matrix molecules; by altering the differentiation of fibroblast or stellate cells; and/or by having an anti-fibrotic effect. In one embodiment, the microenvironment modulator (alone or in combination) enhances the efficacy, delivery and/or diffusion of a therapy.

In one embodiment, the microenvironment modulator is chosen from one or more of an anti-angiogenic therapy, an agent that decreases the level or production of hyaluronic acid, an inhibitor of the hedgehog pathway, an agent that improves drug penetration in tumors (e.g., a disulfide-based cyclic RGD peptide (iRGD) or an analogue thereof), a taxane therapy, an agent that modulates (e.g, inhibits) a hypoxia inducible factor (HIF) (e.g., HIF-1α and HIF-2α), an agent that decreases the level or production of collagen or procollagen, an agent that modulates the crosslinking of matrix molecules, an agent that depletes or changes the differentiation state of fibroblasts or stellate cells, an anti-fibrotic agent (e.g., a pirfenidone (PFD, 5-methyl-1-phenyl-2-(1H)-pyridone); or a combination of two or more of the above.

In one embodiment, the microenvironment modulator is an anti-angiogenic agent. In one embodiment, the anti-angiogenic agent is chosen from a VEGF-inhibitor, an inhibitor of the angiopoietin-Tie-2 pathway (e.g., an Ang-1 or an Ang-2 inhibitor), or sorafenib. Examples of anti-angiopoietin/Tie-2 pathway agents (or inhibitors of the angiopoietin-Tie-2 pathway) include, but are not limited to, AMG 386, CVX-060, CVX-241, MEDI-3617, REGN910, AMG-780, CEP-1198, ARRY-614, MGCD265, Regorafenib, and combinations thereof. In one embodiment, the anti-angiogenic agent can be an inhibitor of tyrosine or Serine/Threonin kinases such as VEGFR, PDGFR, c-kit receptors, b-Raf, or combinations thereof. Additional examples of anti-angiogenic agents include, but are not limited to, agents that inhibit oncogene activation (e.g., anti-EGFR such as gefitinib; anti-HER2 such as Trastuzumab; anti-PI3K-AKT-mTOR such as NVPBEZ235, PI-103, Palomid-529, Nelfinavir; anti-Ras such as FTIs); agents that target androgens (e.g., Castration or endocrine therapy); agents that inhibits inflammatory cytokine-induced VEGF activation; anti-PlGF agents; anti-integrin agents (e.g., Cilengitide); agents that targets PHD2/HIF pathway; anti-Rgs5 agents; Ang-1 agonistic agents; SEMA3A/NRP-1 agonistic agents; PDGF-B agonistic agents; eNOS agonistic agents; PDGF-C agonistic agents; PDGF-D agonistic agents, IFN-β agonistic agents; TSP-1 agonistic agents; anti-TNFα/TNFR agents; anti-TGFβ/TGFR agents; anti-VE-PTP agents; anti-MMP agents (e.g., anti-MMP-2; anti-MMP-9; anti-MMP-14); WNT agonistic agents; extracellular matrix-inducing agents (e.g., fibronectin; laminin; netrin-1; thrombospondin 1, etc.); Notch1 agonistic agents; Frizzled agonistic agents; and a combination of two or more thereof.

Any of the microenvironment modulators described herein can be used as a single agent (e.g., in free form, as a conjugate, or as a particle as described herein), or in combination, e.g., in combination with any of the agents described herein (e.g., an AHCM, other stromal modulator and/or any of the therapies disclosed herein, each of which may be in free form, as a conjugate, or as a particle as described herein).

Additional description of the microenvironment modulators is provided throughout, including the section below entitled "Microenvironment Modulators." Any of the microenvironment modulators disclosed herein, including those listed in the section entitled "Microenvironment Modulators" can be used in the conjugates, particles, other compositions and methods disclosed herein.

Exemplary Other Stromal Modulators for the Compositions and Methods Disclosed

In other embodiments, the agent used in the compositions (e.g., conjugates and particles described herein) and methods of the invention is a stromal modulator (other than a microenvironment modulator as described herein, referred to herein as "other stromal modulator"). In one embodiment, the other stromal modulator modulates healing and/or the matrix/stromal cell microenvironment. In some embodiments, the agent, e.g., the therapeutic and/or diagnostic agent, administered as a particle, conjugate, or as a free agent is the other stromal modulator.

In one embodiment, the other stromal modulator is chosen from an inhibitor of a receptor for a VEGF ligand (e.g., a Flt-1, -2, and/or -3 receptor), an inhibitor of an FGF receptor, a c-Met/HGF receptor inhibitor, a TNFR inhibitor, a cytokine/cytokine receptor inhibitor, a JAK/STAT3 inhibitor, an Osteopontin (SPP1) modulator, a Bone morphogenic protein (BMPs) inhibitor, an inhibitor of FAK, a CSF-1R inhibitor, a c-Kit inhibitor, DDR1 inhibitor, a metabolic inhibitor, and/or a mitochondrial inhibitor.

Any of the other stromal modulators disclosed herein, including those listed in the section entitled "Other Stromal Modulator," can be used in the conjugates, particles, other compositions and methods disclosed herein. Any of the other stromal modulators described herein can be used as a single agent (e.g., in free form, as a conjugate, or as a particle as described herein), or in combination, e.g., in combination with any of the agents described herein (e.g., an AHCM, a microenvironment modulator, and/or any of the therapies disclosed herein, each of which may be in free form, as a conjugate, or as a particle as described herein).

Anti-Cancer Agents

In other embodiments, the agent used in the compositions (e.g., conjugates and particles described herein) and methods of the invention is a small molecule (e.g., a kinase inhibitor). In some embodiments, the agent, e.g., therapeutic agent, administered as a particle, conjugate, or as a free agent is an anti-cancer agent.

In some embodiments, the agent, e.g., the therapeutic agent, in the conjugate is an anti-cancer agent. In some embodiments, the anti-cancer agent is a small molecule, a kinase inhibitor, an alkylating agent, a vascular disrupting agent, a microtubule targeting agent, a mitotic inhibitor, a topoisomerase inhibitor, an anti-angiogenic agent, or an anti-metabolite. In one embodiment, the agent, e.g., the therapeutic agent, is a taxane (e.g., paclitaxel, docetaxel, larotaxel or cabazitaxel). In some embodiments, the anti-cancer agent is an anthracycline (e.g., doxorubicin). In some embodiments, the anti-cancer agent is a platinum-based agent (e.g., cisplatin or oxaliplatin). In some embodiments, the anti-cancer agent is a pyrimidine analog (e.g., gemcitabine). In some embodiments, the anti-cancer agent is chosen from camptothecin, irinotecan, rapamycin, FK506, 5-FU, leucovorin, or a combination thereof. In other embodiments, the anti-cancer agent is a protein biologic (e.g., an antibody molecule), or a nucleic acid therapy (e.g., an antisense or inhibitory double stranded RNA molecule).

Additional examples of anti-cancer agents are disclosed herein, see e.g., the section entitled "Agents." Any of the anti-cancer agents disclosed herein, including those listed in the section entitled "Agents" can be used in the conjugates, particles and other compositions disclosed herein.

Immunomodulators

In some embodiments, the agent, e.g., therapeutic agent, administered as a particle or as a free agent is an immune modulator (e.g., one or more of: an activator of a costimulatory molecule, an inhibitor of an immune checkpoint molecule, or an anti-inflammatory agent).

In certain embodiments, the immunomodulator is an inhibitor of an immune checkpoint molecule (e.g., an inhibitor of PD-1, PD-L1, LAG-3, TIM-3 or CTLA4, or any combination thereof).

In some embodiments, the immunomodulator is a cancer vaccine.

In some embodiments, the immunomodulator is an anti-inflammatory agent, e.g., an anti-inflammatory agent as described herein.

In certain embodiments, the immunomodulator administered as a particle, conjugate, or as a free agent is an activator of a costimulatory molecule. In one embodiment, the agonist of the costimulatory molecule is chosen from an agonist (e.g., an agonistic antibody or antigen-binding fragment thereof, or a soluble fusion) of OX40, OX40L, CD2, CD27, CDS, ICAM-1, LFA-1 (CD11a/CD18), ICOS (CD278), 4-1BB (CD137), GITR, GITRL, CD30, CD40, BAFFR, HVEM, CD7, LIGHT, NKG2C, SLAMF7, NKp80, CD73, CD160, B7-H3 or CD83 ligand.

In certain embodiments, the immunomodulator administered as a particle or as a free agent is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD73, CD160, 2B4 and/or TGFR beta. In one embodiment, the inhibitor of an immune checkpoint molecule inhibits PD-1, PD-L1, LAG-3, TIM-3 or CTLA4, or any combination thereof. Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof that binds to PD-1, PD-L1, PD-L2, CTLA4, TIM3, LAG3, VISTA, BTLA, TIGIT, LAIR1, CD73, CD160, 2B4 and/or TGFR beta, or a combination thereof.

In certain embodiments, the immunomodulator administered as a particle or as a free agent is an anti-inflammatory agent.

In one embodiment, the anti-inflammatory agent is an agent that blocks, inhibits, or reduces inflammation or signaling from an inflammatory signaling pathway. In one embodiment, the anti-inflammatory agent inhibits or reduces the activity of one or more of any of the following: IL-1, IL-2, IL-3, IL-4, IL-5, IL-6, IL-7, IL-8, IL-9, IL-10, IL-12, IL-13, IL-15, IL-18, IL-23, interferons (IFNs), e.g., IFNα, IFNβ, IFNγ, IFN-γ inducing factor (IGIF), transforming growth factor-β (TGF-β), transforming growth factor-α (TGF-α), tumor necrosis factors TNF-α, TNF-β, TNF-RI, TNF-RII, CD23, CD30, CD40L, EGF, G-CSF, GDNF, PDGF-BB, RANTES/CCL5, IKK, NF-kB, TLR2, TLR3, TLR4, TL5, TLR6, TLR7, TLR8, TLR8, TLR9, and/or any cognate receptors thereof.

In one embodiment, the anti-inflammatory agent is an IL-1 or IL-1 receptor antagonist, such as anakinra (KINERET®), rilonacept, or canakinumab.

In one embodiment, the anti-inflammatory agent is an IL-6 or 1-6 receptor antagonist, e.g., an anti-IL-6 antibody or an anti-IL-6 receptor antibody, such as tocilizumab (ACTEMRA®), olokizumab, clazakizumab, sarilumab, sirukumab, siltuximab, or ALX-0061.

In one embodiment, the anti-inflammatory agent is a TNF-α antagonist, e.g., an anti-TNFα antibody, such as infliximab (REMICADE®), golimumab (SIMPONI®), adalimumab (HUMIRA®), certolizumab pegol (CIMZIA®) or etanercept.

In one embodiment, the anti-inflammatory agent is a corticosteroid, e.g., as described herein.

In some embodiments, the immunomodulator can be covalently conjugated to the AHCM, and/or polymer-AHCM conjugate(s). In some embodiments, the immunomodulator can be covalently conjugated to the surface of a particle described herein comprising AHCM. In some embodiments, the immunomodulator can be linked to AHCM, polymer-AHCM conjugate(s) or AHCM particle(s) via one or more physical or chemical bondage(s), such as covalent bond, hydrogen bond, van der Waals interaction, hydrophobic interaction, electron donor-electron recipient interaction, host-guest interaction (e.g., but not limited to, biotin to avidin, or interaction between nucleobases).

Targeting Moieties for the Compositions and Methods Disclosed

In certain embodiments, any of the particles and conjugates disclosed herein, including pH-sensitive and/or polyacetal particles and conjugates, comprise a targeting moiety, e.g., a targeting moiety that is specific to a cell type. To target a specific cell, a targeting moiety or ligand can be coupled, e.g., covalently or non-covalently, to a component of a particle or a conjugate, e.g., a particle or conjugate as described herein. The targeting moiety or ligand specifically can bind to a receptor or surface molecule at the surface membrane of the targeted cell, and thus deliver the particle or conjugated to the targeted cell. In some embodiments, the targeting moiety or ligand can impart therapeutic activity by transferring said polymer, conjugate, or particle (e.g., a polymer, conjugate, or particle as described herein) across cellular membranes, altering the pharmacokinetics, and/or modulating the localization of the polymer, conjugate, or particle (e.g., a polymer, conjugate, or particle as described herein).

In one embodiment, the targeting moiety is a hydrophilic polymer, e.g., PEG.

In other embodiments, the targeting moiety is chosen from one or more of a ligand, e.g., a cell surface receptor, a glycoprotein, a vitamin, cholesterol, an antibody or fragment thereof, a peptide, a protein, a lectin, an aptamer, a lipoprotein, a hormone, a nucleic acid, a charged molecule, a mono-, olio-, and polysaccharide, or low molecular weight ligands such as sugars, folic acids, and peptides. In some embodiments, the targeting moiety is a sugar, e.g., mannose, mannosamine, mannuronic acid, galactose, galactosamine, galactosuronic acid, glucose, glucosamine, glucuronic acid, fucose, fucosamine, or sialic acid. In some embodiments, the targeting moiety is a polymer comprising several sugars, e.g., a disaccharide, trisaccharide, oligosaccharide, or polysaccharide. In some embodiments, the sugar or polymer of sugars comprises a derivatized or modified sugar, e.g., a phosphorylated sugar, e.g., mannose-6-phosphate or glucosamine 1-phosphate. Exemplary targeting moieties are further described in detail herein, e.g., in the sections entitled "Targeting Moieties" and "Liver Targeting Moieties."

Exemplary Disorders and Conditions

In certain embodiments, the disorder treated with the compositions and methods disclosed herein is chosen from one or more of a hyperproliferative disorder, a cancer (e.g., a solid or fibrotic cancer), a fibrotic disorder or condition, an inflammatory disorder or condition, or an autoimmune disorder.

In one embodiment, the disorder, e.g., a cancer, treated is an epithelial, a mesenchymal or a hematologic malignancy. In an embodiment, the cancer treated is a solid tumor (e.g., carcinoid, carcinoma or sarcoma), a soft tissue tumor (e.g., a heme malignancy), and a metastatic lesion, e.g., a metastatic lesion of any of the cancers disclosed herein.

In one embodiment, the cancer treated is a fibrotic or desmoplastic solid tumor, e.g., a tumor having one or more of: limited tumor perfusion, compressed blood vessels, high interstitial fluid pressure (IFPs), or fibrotic tumor interstitium.

In one embodiment, the solid tumor is chosen from one or more of pancreatic (e.g., pancreatic adenocarcinoma (e.g., pancreatic ductal adenocarcinoma (PDA or PDAC)), breast, gastric, colorectal, lung (e.g., small or non-small cell lung cancer), skin, ovarian, prostate, or liver cancer. Additional examples of cancers treated are described herein below.

In certain embodiments, the cancer treated contains (e.g., has elevated levels of) extracellular matrix components, such as fibers (e.g., collagen, procollagen) and/or polysaccharides (e.g., glycosaminoglycans such as hyaluronan or hyaluronic acid). The levels of the extracellular matrix components in the cancer can vary depending on the particular cancer type, the stage of malignancy, and/or in response to cancer therapy. For example, certain cancer may show elevated levels of extracellular matrix components in response to chemotherapy and/or radiation. In such cancers, the AHCM alone, or in combination with the microenvironment modulator, can be administered (as a particle or free agent) at any time before, during or after the cancer therapy.

In one embodiment, the cancer or tumor treated is a solid, fibrotic tumor chosen from one or more of pancreatic (e.g., pancreatic adenocarcinoma or pancreatic ductal adenocarcinoma), breast, colorectal, colon, lung (e.g., small or non-small cell lung cancer), skin, ovarian, prostate, cervix, gastrointestinal (e.g., carcinoid or stromal), stomach, head and neck, kidney, brain cancer or liver cancer (e.g. HCC), or a metastatic lesion thereof. Additional examples of cancers treated are described herein below.

In one embodiment, the disorder is fibrotic or desmoplastic solid tumor, e.g., a tumor having one or more of: limited tumor perfusion, compressed blood vessels, high interstitial fluid pressure (IFPs), or fibrotic tumor interstitium. In certain embodiments, the subject has a tumor having (e.g., elevated levels of) extracellular matrix components, such as fibers (e.g., collagen, procollagen) and/or polysaccharides (e.g., glycosaminoglycans such as hyaluronan or hyaluronic acid). The levels of the extracellular matrix components in the tumor can vary depending on the particular cancer type, the stage of malignancy, and/or in response to cancer therapy. For example, certain tumors may show elevated levels of extracellular matrix components in response to chemotherapy and/or radiation. In such cancers, the AHCM alone or in combination with the microenvironment modulator can be administered at any time before, during or after the cancer therapy.

In certain embodiments, the disorder is chosen from one or more of a hyperproliferative disorder, a cancer, a fibrotic disorder or condition, an inflammatory disorder or condition, or an autoimmune disorder.

In one embodiment, the disorder is a hyperproliferative disorder, e.g., a hyperproliferative connective tissue disorder (e.g., a hyperproliferative fibrotic disease). In one embodiment, the fibrotic (e.g., hyperproliferative fibrotic) disease is multisystemic or organ-specific. Exemplary fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the lung, liver, heart, kidney, pancreas, skin and other organs). In other embodiments, the fibrotic disease is chosen from liver fibrosis (e.g., liver cirrhosis. NASH, and other conditions described herein), pulmonary fibrosis, renal fibrosis, fibrosis of the bone marrow (e.g., myelofibrosis), and the like.

In other embodiments, the disorder is a fibrotic condition or disorder as described herein in the sections entitled "Treatment of Fibrotic Conditions or Disorder" in the Summary and Detailed Description below.

In other embodiment, the disorder is a hyperproliferative genetic disorder, e.g., a hyperproliferative genetic disorder chosen from Marfan's syndrome or Loeys-Dietz syndrome.

In other embodiments, the hyperproliferative disorder (e.g., the hyperproliferative fibrotic disorder) is chosen from one or more of chronic obstructive pulmonary disease, asthma, aortic aneurysm, radiation-induced fibrosis, skeletal-muscle myopathy, diabetic nephropathy, and/or arthritis.

In other embodiments, the disorder is a liver condition or disorder as described in the sections entitled "Treatment of Liver Conditions or Disorder" in the Summary and Detailed Description below.

In one embodiment, disorder is an inflammatory condition or disorder, e.g., as described herein. In one embodiment, the inflammatory disorder is osteomyelitis, e.g., chronic osteomyelitis.

Additional examples of disorders, therapies and combination therapies that can be used in the compositions and methods of the invention are provided throughout, including the sections entitled "Therapeutic Methods," "Disorders," "Combination Therapies," "Cancer Therapies," Treatment of Liver Disorders" and "Combination Therapies for Treatment of Liver Disorders" in the Summary and Detailed Description provided herein below.

Treatment of Fibrotic or Liver Conditions or Disorders

In other embodiments, the disorder or condition treated using the methods and compositions disclosed herein is a fibrotic or liver disorder or condition. In one embodiment, the fibrotic disorder is a liver disorder. In one embodiment, two or more of an AHCM, the microenvironment modulator, other stromal modulator, and/or a fibrotic or liver disorder therapy (e.g., as described herein) are administered to a subject.

In one embodiment, at least one, two, three or all of the AHCM, the microenvironment modulator, other stromal modulator or a therapy is administered as a particle (e.g., a pH-sensitive particle disclosed herein). In one embodiment, one, two, three or more of the AHCM, microenvironment modulator, other stromal modulator or therapy is provided in a non-targeted particle or a liver-targeted particle. Any particle disclosed herein can be used in these methods including a polymeric particle or a lipid particle.

In one embodiment, the polymeric particle administered comprises a polymer chosen from one or more of: (i) polysaccharides, polypeptides, polyacetals, polyketals, polyanhydrides, polyhydroxybutyric acid, polyorthoesters, polysiloxanes, polycaprolactone, poly(lactic-co-glycolic acid), poly(lactic acid), poly(glycolic acid), and copolymers or block polymers prepared from the monomers of these polymers; or (ii) a pH-sensitive polymer or monomer as described herein; or (iii) any combinations of (i) and (ii).

In one embodiment, the polymeric particle administered comprises a polymer chosen from one or more of: poly(lactic acid)-b-poly(ethylene glycol) (PLA-PEG), poly(lactic acid)-b-poly(ethylene glycol) (PLGA-PEG), dextran, (cyclodextrin)-co-poly(ethylene glycol) (CDP), or a pH-sensitive polymer or monomer as described herein; or any combination thereof.

In one embodiment, the AHCM is provided in a particle, e.g., a targeted (e.g., liver) targeted or a particle without a specific targeting moiety, or a non-targeted particle (e.g., any particle disclosed herein). In one embodiment, the particle is a pH-sensitive and/or polyacetal particle, e.g., comprises a pH-sensitive and/or polyacetal polymer and/or a linker as described herein. In other embodiments, the particle comprises a poly-acetal-agent and a targeting moiety (e.g., a targeting moiety as described herein).

In one embodiment, the targeting moiety is a mannose-6-phosphate (M6P). Exemplary conjugates include losartan, a polymer (with or without a linker) and M6P as a targeting moiety (e.g., as depicted in FIGS. 5A-5D). In one embodiment, the conjugate has the structure depicted in FIG. 5B. In other embodiments, the conjugate has the structure depicted in FIG. 5C and/or FIG. 5D. In such embodiments, the microenvironment modulator and/or a liver disorder therapy can be administered as a free agent.

In one embodiment, the microenvironment modulator, other stromal modulator and/or a fibrotic or liver disorder therapy is provided in a particle, e.g., a liver targeted or non-targeted particle (e.g., any particle disclosed herein). In one embodiment, the particle is a pH-sensitive and/or polyacetal particle, e.g., comprises a pH-sensitive and/or polyacetal polymer and/or linker as described herein. In such embodiments, the AHCM is provided as a free agent.

In certain embodiments, the combination of two or all of the AHCM, microenvironment modulator, or a liver disorder therapy is administered in an amount to cause one or more of: increase hepatic perfusion; increase vascular or sinusoidal diameter; increase hepatic vasculature; decrease the level or production of extracellular matrix proteins (e.g., area or deposition of ECM components); decrease the level or production of collagen; decrease hypoxia in the liver; decrease portal pressure; decrease hepatic inflammation (e.g., decrease ALT production or level); increase hepatic synthesis (e.g., albumin production or level), thereby enhancing the penetration and/or distribution of the liver disorder therapy.

Vascular/Stromal Normalizing Doses

In another aspect the invention features a method for treating or preventing a fibrotic or a liver disorder or condition in a subject. The method includes administering to the subject an AHCM (e.g., an AHCM as disclosed herein) and a vascular/stromal normalizing dose (e.g., a sub-anti-angiogenic dose) of a second agent, e.g., a second agent chosen from one or more of: a microenvironment modulator, an other stromal modulator, an anti-angiogenic agent, sorafenib, a sorafenib similarly-targeted pathway modulator, or an inhibitor of the angiopoietin-Tie-2 pathway (e.g., an Ang-1 or an Ang-2 inhibitor), thereby treating or preventing the liver disorder or condition.

In one embodiment, one, two, or more of the AHCM, or the second agent is provided in a particle, e.g., a liver targeted or non-targeted particle (e.g., any particle disclosed herein).

In one embodiment, the AHCM is provided in a particle, e.g., a liver targeted or non-targeted particle (e.g., any particle disclosed herein), and the second agent is administered as a free agent (e.g., non-conjugated soluble agent). In one embodiment, the particle is a pH-sensitive particle, e.g., comprises a pH-sensitive and/or polyacetal polymer and/or a linker as described herein.

In one embodiment, the second agent is chosen from one or more of: anti-angiogenic agent, sorafenib, an inhibitor of the angiopoietin-Tie-2 pathway (e.g., an Ang-1 or an Ang-2 inhibitor), a microenvironment modulator, or an other stromal modulator, or a combination thereof. In one embodiment, the second agent is provided in free form, as a conjugate, or as a particle as described herein (e.g., a liver targeted or non-targeted particle (e.g., any particle disclosed herein)). In one embodiment, the particle is a pH-sensitive and/or polyacetal particle, e.g., comprises a pH-sensitive and/or polyacetal polymer and/or linker as described herein. In one embodiment, said second agent is administered at a dose or dosage formulation that is less than 0.01, 0.05, 0.1, 0.2, 0.3, 0.4, 0.5, 0.6, 0.7, 0.8, 0.9, that of the standard of care dose.

In one embodiment, the second agent is chosen from an inhibitor of tyrosine or Ser/Thr kinase chosen from VEGFR, PDGFR, c-kit receptors, or b-Raf In one embodiment, the second agent is provided in free form, as a conjugate, or as a particle as described herein (e.g., a liver targeted or non-targeted particle (e.g., any particle disclosed herein)). In one embodiment, the particle is a pH-sensitive and/or polyacetal particle, e.g., comprises a pH-sensitive and/or polyacetal polymer and/or linker as described herein. In one embodiment, said second agent is administered at a dose or dosage formulation that is less than 0.01, 0.05, 0.1, 0.2, 0.3, 0.4, 0.5, 0.6, 0.7, 0.8, 0.9, that of the standard of care dose.

In one embodiment, the administration of the AHCM and the second agent is provided in an amount sufficient to result in one, two, three, four, five, six, seven, eight, nine, ten, eleven or more of: (i) inhibition of the hepatic renin angiotensin system; (ii) reduction in fibrosis and/or collagen deposition; (iii) increase in hepatic vascular function; (iv) repair of hepatic blood vessels; (v) increase in vascular normalization; (vi) reduction in pore size; (vii) reduction in hypoxic tissue; (viii) increase in perfusion of the diseased liver tissue; (ix) increase in agent delivery; (x) improvement of stromal signaling; (xi) improvement of or normalization of angiocrine signaling; or (xii) reduction of hepatic inflammation (e.g., as detected by plasma ALT levels), in the diseased (e.g., cirrhotic) liver.

In one embodiment, the second agent is administered at a vascular/stromal normalizing dose. A vascular/stromal normalizing dose can have an angiogenic effect. In one embodiment, the vascular/stromal normalizing dose of the second agent results in one or more of: (i) increase in hepatic vascular function; (ii) repair of hepatic blood vessels; (iii) increase in vascular normalization; (iv) reduction in pore size; (v) reduction in hypoxic tissue; (vi) increase in perfusion of the diseased liver tissue; (vii) restoration of agent delivery; (viii) improved stromal signaling; or (ix) improved or normalized angiocrine signaling. In one embodiment, the effect of the "vascular/stromal normalizing" is detected by one or more of: angiography imaging, immunostaining of level of hypoxia (e.g., using pimonidazol-FITC), increased sinusoidal perfusion, or increased stromal/angiocrine signaling, e.g., as shown in the appended Examples.

In an embodiment, the liver disorder is a fibrotic disorder or connective tissue disorder affecting the function or physiology of the liver. In one embodiment, the fibrotic disorder or connective tissue disorder can be systemic (affecting the whole body), multi-organ, or organ-specific (e.g., liver-specific). Examples of fibrotic liver disorders include, but are not limited to, liver fibrosis (hepatic fibrosis), liver cirrhosis, and any disorder associated with accumulation of extracellular matrix proteins, e.g., collagen, in the liver, liver scarring, and/or abnormal hepatic vasculature. In one embodiment, the liver disorder is liver cirrhosis. Liver cirrhosis is considered to be an end stage of liver fibrosis, involving regenerative nodules (as a result of repair processes), and is typically accompanied with the distortion of the hepatic vasculature.

In other embodiments, the liver disorder is a liver cancer. Examples of liver cancers include, but are not limited to, hepatocellular carcinoma (HCC), primary liver cell carcinoma, hepatoma, fibrolamellar carcinoma, focal nodular hyperplasia, cholangiosarcoma, intrahepatic bile duct cancer, angiosarcoma or hemangiosarcoma, hepatic adenoma, hepatic hemangiomas, hepatic hamartoma, hepatoblastoma, infantile hemangioendothelialoma, mixed tumors of the liver, tumors of mesenchymal tissue, and sarcoma of the liver. Liver cancers can also be associated with metastasis of non-liver cancers, such as breast cancer, colorectal cancer, esophageal cancer, kidney or renal cancer, lung cancer, ovarian cancer, pancreatic cancer, rectal cancer, skin cancer (e.g., melanoma), gastric or stomach cancer (including gastrointestinal cancer), and uterine cancer. In one embodiment, the liver disorder is HCC.

In certain embodiments, the liver disorder or condition is caused by one or more insults including, but not limited to, liver inflammation or damage; viral (e.g., chronic viral) infection (e.g., hepatitis B, hepatitis C virus, hepatitis A virus, hepatitis D virus (hepatitis delta virus), hepatitis E virus, Epstein-Barr adenovirus, or cytomegalovirus; or parasitic infection, such as schistosomiasis); alcoholism; fatty liver disease; metabolic disorders (e.g., hemachromatosis, diabetes, obesity, hypertension, dyslipidemia, galactosemia, or glycogen storage disease); autoimmune disorders (e.g., autoimmune hepatitis (AIH), autoimmune liver disease, lupoid hepatitis, systemic lupus erythematosus, primary biliary cirrhosis (PBC), scleroderma, or systemic scerlosis); inflammatory liver disorders (e.g., steatohepatitis, primary sclerosing cholangitis (PSC), ulcerative colitis, Crohn's disease, inflammatory bowel disease); inherited or congenital liver disease (e.g., Wilson's disease, Gilbert's disease, Byler syndrome, Greenland-Eskimo familial cholestasis, Zellweger's syndrome, Alagilles syndrome (ALGS), progressive familial intrahepatic cholestasis (PFIC), alpha 1-antitrypsin deficiency, cystic fibrosis, Indian childhood cirrhosis, or hereditary hemochromatosis); and liver injury (e.g., drug toxicity, alcoholism, ischemia, malnutrition, or physical trauma).

In one embodiment, the liver disorder is fatty liver (or FLD), alcoholic liver disease, non-alcoholic fatty liver disease (NAFLD), non-alcoholic steatohepatitis (NASH), alcoholic steatohepatitis, simple steatosis, Reye's syndrome, and any disorder associated with abnormal retention of lipids in liver cells.

Additional examples of liver disorders that can be treated by the methods and compositions of the invention are provided throughout, including the section entitled "Treatment of Liver Conditions or Disorders."

Treatment of Fibrotic Conditions or Disorders

In another aspect, the invention features a method of treating or preventing a fibrotic condition or disorder in a subject. The method includes administering a composition described herein (e.g., one or more of: a particle or conjugate as described; an AHCM and/or microenvironment modulator in free form or as a conjugate or particle), as a single agent or in combination with another agent or therapeutic modality, to a subject in need thereof, in an amount sufficient to decrease or inhibit the fibrotic condition in the subject.

In certain embodiments, reducing fibrosis, or treatment of a fibrotic condition, includes reducing or inhibiting one or more of: formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In certain embodiments, the fibrotic condition is a fibrotic condition of the lung, a fibrotic condition of the liver (e.g., as described herein), a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, an inflammatory fibrotic condition, or a combination thereof.

Additional examples of fibrotic disorders or conditions that can be treated with the compositions and methods described herein are provided herein in the section entitled "Treatment of Fibrotic Conditions or Disorders."

Subjects

The compositions and methods described herein can be used to treat subjects having characteristics or needs defined herein. In some embodiments a subject, or a treatment for a subject, is selected on the basis of a characteristic described herein. In one embodiment, the methods described herein allow optimized selection of patients and therapies. In some embodiments, subjects can be selected or identified prior to subjecting them to any aspects of the methods described herein.

In one embodiment, the subject is selected, or is identified, as being in need of receiving the AHCM and/or the microenvironment modulator on the basis of optimizing a therapy, e.g., the need for improved delivery and/or efficacy of the therapy (e.g., the cancer or liver therapy).

In one embodiment, the subject does not have hypertension, or is not being treated for hypertension, at the time of initiation of the AHCM treatment, or at the time of selection of the patient for AHCM administration.

In an embodiment, the subject, e.g., patient, has not been administered a dose of an AHCM, e.g., an AHCM named herein, or any AHCM, within 5, 10, 30, 60 or 100 days of, the diagnosis of the disorder, e.g., the cancer or liver disorder, or the initiation of the AHCM dosing.

In an embodiment, the subject, e.g., a subject with normal or low blood pressure, is selected or is identified on the basis of being in need of an AHCM and/or the microenvironment modulator, e.g., is selected or is identified as being in need of receiving the AHCM and/or the microenvironment modulator on the basis of optimizing a therapy, e.g., the need for improved delivery and/or efficacy of the therapy (e.g., the cancer therapy).

In some embodiments, subjects who are in need of receiving the AHCM and/or the microenvironment modulator on the basis of the need for improved delivery or efficacy of the cancer therapy, or optimizing the therapy, are the subjects who partially respond or do not respond to the cancer therapy alone.

In an embodiment, an AHCM and/or the microenvironment modulator is selected for treating a subject, on the basis of its ability to optimize a treatment, e.g., a cancer treatment, e.g., improving delivery and/or efficacy of the therapy, e.g., the cancer therapy.

In one embodiment, the subject is in need of cancer or liver therapy. In another embodiment, the subject is in need of, or being considered for, anti-cancer or liver therapy (e.g., treatment with any of the anti-cancer or liver therapeutics described herein). In certain embodiments, the method includes the step of determining if the subject has a cancer or a liver disorder, and, responsive to said determination, administering the AHCM and/or the microenvironment modulator, and the agent (e.g., an anti-fibrotic therapy).

In other embodiments, the subject is at risk of developing, or having a recurrence of, a cancer, e.g., a subject with pre-neoplasia or a genetic pre-disposition for cancer (e.g., a subject having a BRCA1 mutation; or a breast cancer patient treated with in an adjuvant setting (e.g., with tamoxifen).

In other embodiments, the subject has early-cancer, or more progressive (e.g., moderate), or metastatic cancer.

In one embodiment, the subject has a solid, fibrotic tumor chosen from one or more of pancreatic (e.g., pancreatic adenocarcinoma or pancreatic ductal adenocarcinoma), breast, colorectal, colon, lung (e.g., small or non-small cell lung cancer), skin, ovarian, prostate, cervix, gastrointestinal (e.g., carcinoid or stromal), stomach, head and neck, kidney, or liver cancer, or a metastatic lesion thereof. Additional examples of cancers treated are described herein below.

In one embodiment, the subject has a fibrotic or desmoplastic solid tumor, e.g., a tumor having one or more of: limited tumor perfusion, compressed blood vessels, high interstitial fluid pressure (IFPs), increased hypoxia, or fibrotic tumor interstitium. In certain embodiments, the subject has a tumor having (e.g., elevated levels of) extracellular matrix components, such as fibers (e.g., collagen, procollagen) and/or polysaccharides (e.g., glycosaminoglycans such as hyaluronan or hyaluronic acid). The levels of the extracellular matrix components in the tumor can vary depending on the particular cancer type, the stage of malignancy, and/or in response to cancer therapy. For example, certain tumors may show elevated levels of extracellular matrix components in response to chemotherapy and/or radiation. In such cancers, the AHCM alone or in combination with the microenvironment modulator can be administered at any time before, during or after the cancer therapy. In an embodiment, the fibrotic or desmoplastic solid tumor is PDAC.

In other embodiments, the subject has a hyperproliferative cancerous condition (e.g., a benign, pre-malignant or malignant condition). The subject can be one at risk of having the disorder, e.g., a subject having a relative afflicted with the disorder, or a subject having a genetic trait associated with risk for the disorder. In one embodiment, the subject can be symptomatic or asymptomatic. In an embodiment, the subject harbors an alteration in an oncogenic gene or gene product. In an embodiment, the subject is a patient who is undergoing cancer therapy (e.g., the same or other anti-cancer agents, surgery and/or radiation). In an embodiment, the subject is a patient who has undergone cancer therapy (e.g., other anti-cancer agents, surgery and/or radiation). In one embodiment, the subject has not been treated with the cancer therapy.

In one embodiment, the subject is a patient with a metastatic cancer, e.g., a metastatic form of a cancer disclosed herein (one or more of pancreatic (e.g., pancreatic adenocarcinoma), breast, colorectal, lung (e.g., small or non-small cell lung cancer), skin, ovarian, or liver cancer.

In one embodiment, the subject is a patient having treatment-resistant cancer or hyperproliferative disorder.

In one embodiment, the subject is, or is identified as being, overweight or obese.

In one embodiment, the subject is normal weight, e.g., the subject has a BMI of greater than or equal to 18.5 but less than or equal to 24.9.

In one embodiment, the subject is overweight, e.g., the subject has a BMI of greater than or equal to 25.0 but less than or equal to 29.9.

In another embodiment, the subject is, or is identified as being, obese, e.g., the subject has a BMI of greater than or equal to 30, e.g., greater than 30, greater than 35, greater than 40, greater than 45, or greater than 50. Obesity can also be associated with one or more of: desmoplasia, e.g., in adipose tissues and the pancreas; dysfunctional adipocytes, e.g., hypertrophied adipocytes; increased hypoxia; fibrosis; accumulation of fat, e.g., steatosis; increased angiotensin II (AngII) type-1 receptor (AT1) signaling; and/or increased expression, production, and/or secretion of pro-inflammatory cytokines, e.g., interleukin-1β (IL-1β).

In an embodiment, the subject is, or is identified as being, overweight or obese, and has a fibrotic or a hyperproliferative cancerous condition described herein. In an embodiment, the subject is, or is identified as being, overweight or obese and has a fibrotic disorder described herein. In an embodiment, the subject is, or is identified as being, overweight or obese and has a liver disorder or condition described herein.

In one embodiment, the subject is, or is identified as being, overweight or obese, and has a fibrotic or desmoplastic tumor, e.g., a tumor having one or more of: limited tumor perfusion, compressed blood vessels, high interstitial fluid pressure (IFPs), increased hypoxia, or fibrotic tumor interstitium. In certain embodiments, the subject is overweight or obese, and has a tumor having (e.g., elevated levels of) extracellular matrix components, such as fibers (e.g., collagen, procollagen), fibroblasts (e.g., elevated levels of cancer associated fibroblasts (CAFs) or increased activity of CAFs) and/or polysaccharides (e.g., glycosaminoglycans such as hyaluronan or hyaluronic acid).

In one embodiment, the subject is overweight or obese, and has pancreatic ductal adenocarcinoma (PDAC).

In other embodiments, the subject is, or is identified as being, overweight or obese, has a fibrotic or a hyperproliferative cancerous condition described herein, and exhibits one, two, three, four or more of: increased angiogenesis; increased inflammatory cell infiltration, e.g., in adipose tissues; shows enhanced tumor progression and/or metastatis; shows increased recruitment of tumor-associated macrophages (TAM); or shows increased activation of an angiogenic pathway, e.g., VEGFR-1 pathway.

In one embodiment, the subject is overweight or obese, and has breast cancer.

In other embodiments, the subject (e.g., an overweight or obese subject having a cancer or a fibrotic condition described herein (e.g., a breast or pancreatic cancer, desmoplastic tumor)) is treated with an AHCM (e.g., a composition comprising an AHCM as described herein) in combination with an anti-angiogenic agent, e.g., a VEGF/VEGFR inhibitor, an anti-diabetic drug, e.g., metformin, or a combination of the anti-angiogenic agent and the anti-diabetic drug. Accordingly, a method for treating an overweight or obese subject having a cancer or a fibrotic condition as described herein (e.g., a breast or pancreatic cancer, a desmoplastic tumor)). The method includes: administering to the subject an AHCM (e.g., a composition comprising an AHCM as described herein) in combination with an anti-angiogenic agent, e.g., a VEGF/VEGFR inhibitor, an anti-diabetic drug, e.g., metformin, or a combination of the anti-angiogenic agent and the anti-diabetic drug, in an amount sufficient to treat the cancer or the fibrotic conditions. In one embodiment, the administration reduces one, two, three, four or more of: fibrosis; angiogenesis; inflammatory cell infiltration, e.g., in adipose tissues; tumor progression and/or metastatis; recruitment of tumor-associated macrophages (TAM); or activation of an angiogenic pathway, e.g., VEGFR-1 pathway. The AHCM (e.g., a composition comprising an AHCM as described herein) can be administered prior to, concurrently with, or after the anti-angiogenic agent and/or anti-diabetic drug.

In such embodiments where the subject is, or is identified as being, overweight or obese, and has a hyperproliferative cancerous condition as described herein, e.g., a fibrotic or desmoplastic tumor, the AHCM is administered in combination with an anti-cancer therapy, e.g., a chemotherapeutic. In other embodiments, the AHCM is administered in combination with an anti-angiogenic agent, e.g., a VEGF/VEGFR inhibitor, an anti-diabetic drug, e.g., metformin, or a combination of both. In an embodiment, administration of the AHCM is initiated prior to the initiation of administration of the anti-cancer, anti-angiogenic, or anti-diabetic therapy (one or more of which are referred to herein as "the therapy"). In an embodiment, administration of the AHCM is concurrent with the administration of the therapy. In an embodiment, therapy with the AHCM continues during the entire therapy schedule. In yet other embodiments, administration of the AHCM is discontinued prior to cessation of the therapy. In other embodiments, administration of the AHCM is continued after cessation of the therapy. Administration of an AHCM with other therapies is further described herein in the section entitled "Combination Therapies."

In other embodiments where the subject is, or is identified as being, overweight or obese, and has a fibrotic condition, or a hyperproliferative cancerous condition as described herein, e.g., a fibrotic or desmoplastic tumor, any of the AHCM, alone or in combination with any of the anti-angiogenic therapy, the anti-diabetic therapy, the anti-cancer therapy, or a combination thereof, can be administered as a particle or conjugate as described herein. The particles or conjugates can include a single agent or combination of agents. In an embodiment, the particle or agent comprises an agent (e.g., an ARB, a chemotherapeutic, an anti-diabetic drug, and/or an inhibitor of the VEGF pathway). In an embodiment, administration of the ARB-containing particle is concurrent with the administration of an anti-diabetic drug, e.g., metformin, a chemotherapeutic, and/or an inhibitor of the VEGF pathway.

In any of the aforesaid embodiments, the AHCM can be administered as a free agent or as a composition (e.g., as a conjugate or a particle as described herein) comprising the AHCM). In certain embodiments, at least one, two or all of the AHCM, the anti-angiogenic agent, the anti-cancer agent, or the anti-diabetic therapy is administered as a particle (e.g., a pH-sensitive particle disclosed herein).

In one embodiment, the AHCM is provided in a particle, e.g., a targeted or non-targeted particle (e.g., any particle disclosed herein). In one embodiment, the particle is a pH-sensitive particle, e.g., comprises a polyacetal polymer and/or a linker as described herein. In such embodiments, the anti-angiogenic agent, the anti-cancer agent, and/or the anti-diabetic therapy can be administered as a free agent.

In one embodiment, the anti-angiogenic agent, the anti-cancer agent, and/or the anti-diabetic therapy is provided in a particle, e.g., a targeted or non-targeted particle (e.g., any particle disclosed herein). In one embodiment, the particle is a pH-sensitive particle, e.g., comprises a pH-sensitive polymer and/or linker as described herein. In such embodiments, the AHCM is provided as a free agent.

In other embodiments, the subject being selected for subjecting to the methods or pharmaceutical compositions herein does not have a renal disease or a disease associated with kidneys.

In one embodiment, the subject treated is a mammal, e.g., a primate, typically a human (e.g., a patient having, or at risk of, a cancer or tumor as described herein).

In certain embodiments, the subject treated has a disorder chosen from one or more of a hyperproliferative disorder, a cancer, a fibrotic disorder, an inflammatory disorder or an autoimmune disorder.

In one embodiment, the subject treated has a hyperproliferative disorder, e.g., a hyperproliferative connective tissue disorder (e.g., a hyperproliferative fibrotic disease). In one embodiment, the hyperproliferative fibrotic disease is multisystemic or organ-specific. Exemplary hyperproliferative fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the lung, liver, heart, kidney, pancreas, skin and other organs).

In other embodiment, the subject treated has a hyperproliferative genetic disorder, e.g., a hyperproliferative genetic disorder chosen from Marfan's syndrome or Loeys-Dietz syndrome.

In other embodiments, the hyperproliferative disorder (e.g., the hyperproliferative fibrotic disorder) is chosen from one or more of chronic obstructive pulmonary disease, asthma, aortic aneurysm, radiation-induced fibrosis, skeletal-muscle myopathy, diabetic nephropathy, and/or arthritis.

Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A, 1B, and 1C show the synthesis of an exemplary polyacetal polymer. FIG. 1A shows a scheme of the modular polymerization reaction comprising polyol and vinyl ether monomers into polyacetals. In some case, the polyacetal polymer may further comprise a PEG component, wherein the size of the PEG (shown as x in FIG. 1A) may range from 200 to 5000. FIG. 1B shows exemplary polyol monomers that may be incorporated into the polyacetal polymers, e.g., A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32. FIG. 1C shown exemplary vinyl ether monomers that may be incorporated into the polyacetal polymers, e.g., B1, B2, B3, B4, B5, and B6.

FIG. 2A shows the conjugation of a generic ARB to a free hydroxyl group in a polyacetal polymer to yield an ARB-linked polyacetal polymer. FIG. 2B shows the synthesis of an exemplary polyacetal polymer, namely a polyacetal polymer conjugated to the ARB valsartan. The carboxylic acid on the valsartan is activated by DIC in the presence of TEA and results in attachment of valsartan to the polyacetal polymer, yielding a valsartan-linked polymer.

FIGS. 3A, 3B, and 3C show the synthesis and characterization of conjugates containing drugs for treating pancreatic cancer and pH-sensitive polymers. FIG. 3A shows three drugs commonly used for treating pancreatic cancer. FIG. 3B shows different pH-sensitive linkers for screening for the most sensitive pH linker to link the drugs from FIG. 3A to the polymer. FIG. 3C shows reverse phase HPLC profiles (UV=350) of irinotecan and purified irinotecan-aconitic acid for the pH sensitive linker study.

FIG. 4A shows the different pH sensitive linkers. FIGS. 4B and 4C show the release profiles of irinotecan conjugates with the indicated pH-sensitive linkers as labeled in FIG. 4A when in buffers at pH 6.7 or 7.4.

FIG. 5A shows the activation of free hydroxyl groups on a polyacetal polymer with excess succinic anhydride to yield reactive carboxylic acid groups. FIG. 5B shows the conjugation of losartan to the succinylated polyacetal polymer. In this reaction, a sub-stoichiometric quantity of losartan is used in order to prevent full saturation of the free carboxylic acid groups. FIG. 5C shows the modification of the remaining free carboxylic acid groups on the polymer with ethylenediamine to yield a reactive amino group. FIG. 5D outlines the conjugation of M6P-isothiocyanate to the losartan-linked polyacetal polymer to produce a polyacetal polymer conjugated to both M6P and losartan.

FIG. 7A shows that high-fat (60%) versus low-fat (10%) diets generated a difference in body weight (BW) in C57BL/6, FVB and the spontaneous PDAC (KPC and iKRAS) models. Diet started at six weeks of age, continued for ten weeks (C57BL/6 and FVB), at which time tumors were implanted, and then continued until the end of experiments. In the spontaneous tumor models, diets were administered until tumor collection. Mice genetically deficient for leptin (ob/ob) on a standard chow for seven weeks gained weight compared to age matched WT mice (n=8-10/group for C57Bl/6, FVB and ob/ob, 4-10/group for KPC, 7-21/group for iKRAS). Left bars represent mice fed a low-fat diet, right bars represent mice fed a high fat diet for all groups except C57/B6 on the far right of the graph, in which the right bar represents the ob/ob mice. FIG. 7B shows the time to develop tumors of about 1 g in iKRAS mice fed low (left bars) or high-fat diet (right bars). FIG. 7C shows the effect of obesity on tumor growth. PAN02 and AK4.4 syngeneic tumors were orthotopically implanted in C57BL/6 and FVB mice respectively at ten weeks of diet (lean diet, left bars; and obese diet or ob/ob mice, right bars); ob/ob mice were implanted with PAN02 tumors at seven weeks of age. Tumors were collected 21 days later. Obese animals presented with higher tumor weights than lean counterparts in all models (n=8-10/group). FIG. 7D is representative images of mesenteric peritoneal dissemination in lean and obese mice implanted with PAN02 tumors. Mesenteries collected at the same time as tumors in FIG. 7C. FIG. 7E is a graph showing the quantification of mesenteric peritoneal metastasis in the PAN02 model. FIG. 7F is a graph showing the quantification of retro-peritoneal metastasis in the AK4.4 model. Data are shown as mean±standard error of the mean (SEM). P values were determined by the Student t-test. *, P<0.05; , P<0.01; *, P<0.001.

FIGS. 8A, 8B, 8C, 8D, 8E, 8F, 8G, 8H, 8J, 8I, 8J, and 8K show that obesity aggravates tumor desmoplasia. FIG. 8A is images showing adipocyte enlargement and fibrosis in visceral adipose tissue and tumors from obese mice. Masson's Trichrome staining denotes fibrosis in blue. Arrows: Adipocytes. Scale bars: 200 µm. Quantification of adipocyte count (FIG. 8B) and size (FIG. 8C) in PAN02 and AK4.4 tumors indicates an enrichment for enlarged adipocytes in the tumor microenvironment in lean (left bars) and obese mice (right bars) (n=3 tumors/group, 8 ROIs/tumor). FIG. 8D shows representative pictures of the adipose tissue-tumor interaction, revealing increased expression of fibrosis where tumors invade the adjacent adipose tissue. On the far right, tumor epithelium is observed in close proximity to fibrotic adipose tissue and normal pancreas. Tumor sections were stained for Masson's Trichrome. Scale bars: 100 µm (PAN02, left panel), 200 µm (AK4.4, middle panel), 500 µm (Ak4.4 right panel). FIG. 8E is representative pictures of collagen-I staining (immunofluorescence) in tumors. Scale bars: 1 mm. FIG. 8F is representative pictures of fibrillar collagen in tumors using second harmonic generation (SHG). Scale bars: 100 µm. FIG. 8G is a graph showing the quantification of collagen expression normalized to lean animals. Tumors from obese mice presented with increased collagen-I expression in three different tumor models. FIG. 8H is a graph showing the quantification of fibrillary collagen normalized to lean animals. Tumors from obese mice presented with increased expression of fibrillar collagen in PAN02 and AK4.4 orthotopic PDACs. (n=3-6/group). In FIGS. 8G and 8H, left bars represent lean mice, right bars represent obese mice. FIG. 8I is representative pictures of αSMA expression in AK4.4, PAN02 and KPC tumors by immunofluorescence. FIG. 8J is a graph showing the quantification of αSMA expression by immunofluorescence was performed as a % of αSMA expression in DAPI+ viable tumor area (FIG. 8J), as well as a % of double positive αSMA/Col-I expression in DAPI+ viable tumor area (FIG. 8K) (n=3-6/group). In FIGS. 8J and 8K, left bars represent lean mice, right bars represent obese mice. Representative pictures of αSMA/Col-I double staining in PAN02 and AK4.4 tumors are in FIGS. 16D and 16E. Data are shown as mean±SEM. P values were determined by the Student t-test. *, $P<0.05$; **, $P<0.01$.

FIGS. 9A, 9B, 9C, 9D, and 9E show that obesity-aggravated desmoplasia impairs drug delivery. FIG. 9A is representative pictures of CD31(+) vessels and lectin in PAN02 tumors. Scale bars: 200 μm. FIG. 9B is a graph showing the quantification of the total (CD31+) and lectin-positive (CD31/lectin+) vessel area in PAN02 tumors. Obese mice (right bars) presented with decreased perfusion (n=3-6 tumors/group) compared to lean mice (left bars). FIG. 9C shows the protein expression of hypoxia markers in PAN02 tumors. Obese mice presented with increased hypoxia in tumors. FIG. 9D shows the effect of obesity on the delivery of chemotherapy to tumors. 5-FU quantified via high performance liquid chromatography (HPLC). Obesity decreased delivery of the chemotherapeutic agent (n=4 tumors/group). FIG. 9E shows the effect of obesity on response to chemotherapy. PAN02 tumors were orthotopically implanted at ten weeks of diet, treatments were initiated at day seven post-implantation and tumors resected at day 19. 5-FU was less effective in preventing PAN02 tumor growth in obese animals than in lean (two-way ANOVA, n=8-10/group). Data are shown as mean±SEM. P values were determined by the Student t-test unless otherwise stated. *, $P<0.05$; **, $P<0.01$ FIGS. 10A, 10B, 10C, 10D, 10E, 10F, 10G, 10H, 10I, 10J, 10K, and 10L show that blockade of AT1 reverses the obesity-aggravated desmoplasia and improves response to chemotherapy. FIGS. 10A and 10B shows the effect of obesity on target genes of AT1 signaling. Expression of genes associated with AT-1 pathway activation and fibrosis/desmoplasia is increased in PAN02 (FIG. 10A) and AK4.4 (FIG. 10B) tumors from obese mice (right bars) in comparison to lean mice (left bars). Depicted genes where a 2-fold change in mRNA expression was observed in either tumor model. Data normalized to lean group. 3-4 samples per group pooled in one single PCR array fibrosis gene set plate. FIG. 10C shows that losartan reduced tumor αSMA protein expression more dramatically in the obese setting in AK4.4 tumors. FIG. 10D shows the quantification of protein expression was normalized to tubulin. FIG. 10E shows that losartan reduced tumor fibrillar collagen (top panels) as well as collagen-1 expression (bottom panels) in AK4.4 tumors from obese mice. Scale bars: 100 μm (SHG) and 1 mm (Col-1) FIGS. 10F-H shows the quantification of collagen was performed as a % of a region of interest (ROI) for SHG (n=4 tumors/group, 8 ROIs per tumor) (FIG. 10F) and as a % of viable tumor area in the whole tumor for collagen-1 immunofluorescence (n=4-6 tumors/group) (AK4.4 in FIG. 10G and PAN02 in FIG. 10H). FIG. 10I shows the protein expression by western blotting of AK4.4 tumors revealed that losartan normalized the obesity-augmented expression of several AT1 signaling and desmoplasia-related markers, i.e. AT1, TGFB, SMAD2, vimentin, snail, MMP9, and phospho-p38. Of note, similar to αSMA, the changes of AT1, as well as other desmoplasia related markers, were relatively mild in the lean setting. FIG. 10J shows the quantification of protein expression was normalized to tubulin (far left bars represent lean mice; middle left bars represent obese mice; middle right bars represent lean mice treated with losartan; and far right bars represent obese mice treated with losartan.) (Depicted are significant differences between control and losartan treatment). FIG. 10K shows that in the PAN02 model, losartan and AT1 genetic deficiency (Agtr1a−/− mice) improved response to chemotherapy in obese, but not in lean animals. FIG. 10L shows that in the AK4.4 model, losartan improved response to chemotherapy in both lean and obese settings but with higher magnitude in obese setting (FIGS. 10K and 10L: Two-way ANOVA with Bonferroni correction for multiple comparisons, n=4-8 tumors/group. Depicted are significant differences of treatment groups compared to control or 5-FU groups). Data are shown as mean±SEM with the exception of FIGS. 10A and 10B. P values were determined by the Student t-test unless otherwise stated. *, $P<0.05$; , $P<0.01$, *$p<0.001$.

FIG. 11A, 11B, 11C, 11D, 11E, 11F, 11G, 11H, 11I, AND 11J show that tumor-associated neutrophils mediate obesity-induced tumor progression and aggravated desmoplasia. FIG. 11A shows the effect of obesity on immune cell infiltration in PDACs. Obesity promoted infiltration of myeloid Gr-1(+)F4/80(−) cell population in PAN02 tumors in obese mice. FIG. 11B is a quantification normalized by total viable cells (i) or total CD45 leucocytes (ii) (n=4-6 tumors/group). FIG. 11C is representative FACS scatter plots of CD45(+)CD11b(+)Ly6G(+) tumor associated neutrophils (TANs), CD8(+) cytotoxic lymphocytes and CD4 (+)CD25(+) regulatory T cells in PAN02 tumors in lean and obese setting. FIGS. 11D and 11E shows quantification normalized by total viable cells (FIG. 11D) or total CD4 cells (FIG. 11E) (n=3-6 tumors/group). Obese promoted an increase in TANs and a decrease in CD8 cells in PAN02 tumors. A strong tendency for increased Tregs was also observed. FIG. 11F shows the effect of TAN depletion (TAN-D) on PDAC growth in obese mice. TAN depletion from day 1 using anti-Ly6G specific pharmacological inhibitory antibody in obese mice significantly reverted the obesity-increased tumor weight in PAN02 and AK4.4 models (n=4-6 tumors/group). FIG. 11G shows the preferential accumulation of TANs in areas with activated PSCs. Scale bars: 1 mm (whole tumors) and 100 μm (caption). FIG. 11I shows TAN depletion reduced AT1 expression, collagen production and MMP9 expression in PAN02 tumors in obese animals. FIG. 11J shows TAN depletion led to increasing in perfusion in PAN02 tumors in obese animals. % of CD31(+), lectin(+) or double positive vessel density in the viable area of whole tumors. (n=4-6 tumors/group). For bar graphs in FIGS. 11A, 11B, 11D, and 11E, left bars represent lean mice, and right bars represent obese mice. For the bar graph in FIG. 11J, left bars represent obese mice, and right bars represent obese mice with TAN depletion. Data are shown as mean±SEM. P values were determined by the Student t-test, or one-way ANOVA for panels C and E. *, $P<0.05$; , $P<0.01$, *$p<0.001$.

FIGS. 12A, 12B, 12C, 12D, 12E, 12F, 12G, 12H, 12I, 12J, and 12K show the adipose microenvironment promotes TAN infiltration and fibrosis via IL-1ß. FIG. 12A shows an effect of obesity on cytokine expression in PAN02 tumors. Multiplex protein revealed that PAN02 tumors from obese mice (right bars) had increased expression of IL-1ß (n=4-6 tumors/group) in comparison to lean mice (left bars). FIG. 12B shows that IL-1ß was abundantly expressed by adipocytes and PSCs in the adipocyte-rich areas where PSCs predominate in PAN02 tumors. Scale bars: 200 μm (upper panels), 30 μm (lower panels). FIG. 12C shows the effect of IL-1ß blockade on immune cell profile. An anti-IL1ß neutralizing antibody decreased CD45(+)CD11b(+)Ly6G(+) TAN infiltration while recovering CD4+ and CD8+Tcells (FIGS. 12C and 12D) and decreasing Tregs (FIG. 12E) (one-way ANOVA, n=3-6 tumors/group). In FIG. 12D, left bars represent lean mice, middle bars represent obese mice, and right bars represent obese mice with IL-1B inhibition. FIG. 12E shows that IL-1ß blockade normalized obesity-aggravated tumor growth. (one-way ANOVA, n=3-6 tumors/group). FIG. 12G is a western blot showing that IL-1ß inhibition decreased obesity-induced αSMA and AT1 expression (bands are part of a larger WB. Lean control group is depicted in FIG. 3E). FIG. 12H shows IL-1ß expression in TANs. Immunofluorescence for PAN02 tumor sections denoting co-localization. Scale bar: 30 µm. FIG. 12I shows TAN depletion using Ly6G specific antibody abolished obesity-induce IL1-ß expression in PAN02 tumors. (one-way ANOVA, n=4-6 tumors/group). FIGS. 12J and 12H shows the effect of AT1 blockade on immune cell profile. In tumors implanted in AT1-KO (PAN02), TANs were decreased. This was associated with increased CD8 cells and reduced Tregs (n=3-6 tumors/group). In FIGS. 12J and 12K, the far left bars represent lean mice; the middle left bars represent obese mice; the middle right bars represent lean AT1-KO mice; and the far right bars represent obese AT1-KO mice. Data in FIGS. 12C, 12D, 12E, 12J and 12K were parts of the same experiment. Data are shown as mean: SEM. P values were determined by the Student t-test unless otherwise stated. *, P<0.05; **, P<0.01.

FIGS. 13A, 13B, 13C, 13D, and 13E show that PDACs from obese patients recapitulate the findings in preclinical models. FIG. 13A is representative pictures of adipocytes in human PDAC from patients with normal weight [Body mass index (BMI)<25] and obesity (BMI>30). Scale bars: 100 µm. FIG. 13B shows the quantification of adipocyte size in human PDACs. Tumors from obese patients presented with hypertrophied adipocytes (n=8 tumors/group). FIG. 13C is representative pictures of Collagen-I and HA in human PDAC from patients with normal weight (BMI<25) and obesity (BMI>30). Scale bars: 1 mm. FIG. 13D shows the quantification of Collagen-I and HA in human PDACs (n=8 tumors/group); left bars represent patients with BMI<25 and right bars represent patients with BMI>30. Data are shown as mean±SEM. P values were determined by the Student t-test. *, P<0.05; **, P<0.01. FIG. 13E is a graphical summary of the key findings in this study. PDACs in obese hosts present with increased fatty stroma, inflammation, and desmoplasia. The amplified crosstalk between CAAs, TANs and PSCs that occurs in obesity leads to an aggravation of desmoplasia, increased tumor progression and reduced response to chemotherapy.

FIG. 14 shows the effect of obesity on KPC tumor initiation. Time to develop tumors of about 1 g in KPC mice fed low (lean mice, left bars) or high-fat diet (obese mice, right bars). Data are shown as mean±SEM. P value was determined by the Student t-test.

FIG. 15A is representative pictures of PAN02, AK4.4 and iKRAS tumors invading visceral adipose tissue in obese mice. FIG. 15B is additional pictures depicting an association of fibrosis with adipocytes in AK4.4 tumors from obese mice. Masson's trichrome staining in tumors revealed a predominance of fibrosis content in areas rich in adipocytes or adjacent to adipose tissue. Scale bars: 500 µm (upper panels, lower left panel), 250 µm (lower right panel).

FIG. 16A is representative pictures and FIG. 16B shows the quantification of hyaluronan (HA) binding protein (HABP, which detects HA) in AK4.4 tumors from lean and obese mice. Scale bars: 1 mm (n=3-6/group). FIG. 16C shows the quantification of HA (ELISA) in PAN02 tumors from lean and obese mice (n=3-6/group). FIG. 16D shows immunofluorescence demonstrating that αSMA-expressing PSCs associate with collagen-1 expression in PAN02 tumors. Whole tumor staining depicted on the left picture; caption of an area where the two markers overlap in the center picture; amplification of the center figure on the right. Scale bars: 1 mm (far left panel), 200 µm (center panel), 50 µm (caption). FIG. 16E is a representative picture of co-expression of αSMA with collagen-I and hyaluronan in AK4.4 tumors. Scale bar: 200 µm. FIG. 16F is a western blot denoting the effect of obesity on PSC marker αSMA expression in PAN02 tumors. Data in FIGS. 16B and 16C are shown as mean±SEM. P values were determined by the Student t-test.

FIGS. 17A, 17B, 17C, and 17D show that obesity-aggravated desmoplasia reduces perfusion and efficacy of chemotherapy in AK4.4 tumors. FIG. 17A shows the effect of obesity on AK4.4 tumor perfusion. Quantification of total and lectin-positive vessel area in AK4.4 tumors. Obese mice (right bars) presented with decreased perfusion (n=5-12 tumors/group) compared to lean mice (left bars). FIG. 17B shows the effect of obesity on protein expression of hypoxia markers in AK4.4 tumors. Obese mice presented with increased expression of the hypoxia marker Hif-1α in tumors. FIG. 17C shows the effect of obesity on the delivery of doxorubicin to PAN02 tumors. Doxorubicin quantified via immunofluorescence (n=4 tumors/group). FIG. 17D shows the effect of obesity on response to chemotherapy. AK4.4 syngeneic tumors were orthotopically implanted at ten weeks of diet; treatments were initiated at day 7 post-implantation and tumors resected at day 19. 5-FU was less effective in preventing tumor growth in obese animals (two-way ANOVA, n=6-8/group). Data in FIGS. 17A, 17C and 17D, are shown as mean±SEM. P values were determined by the Student t-test unless otherwise stated. *, P<0.05.

FIG. 18A shows the double immunofluorescence for αSMA and AT receptor in two orthotopic PDACs. ~70% of activated PSCs expressed AT1 receptor in PAN02 and ~35% in AK4.4. Scale bar: 30 µm (left panels), 500 µm (right panel). FIG. 18B shows the protein expression of the signaling molecules downstream of AT1 in PAN02 and AK4.4 tumors, revealing increased activity in obese mice. FIG. 18C shows the effect of losartan on the expression of fibrosis/desmoplasia-related markers in AK4.4 tumors. mRNA expression of markers of tumor fibrosis/desmoplasia was increased in tumors in obese mice and was reverted by losartan. Losartan did not alter these markers in lean mice (3-4 samples per group were pooled for the PCR array analysis). FIG. 18D shows the effect of losartan on αSMA expression in PAN02 tumors. Losartan induced a tendency for reduced tumor αSMA protein expression in obese but not lean setting (Two-way ANOVA, n=3-6/group). FIG. 18E is a western blot showing a decrease in αSMA expression in PAN02 tumors implanted in obese AT1 KO mice compared with obese WT mice (bands are part of a larger WB. Lean control group is depicted in FIG. 18F). FIGS. 18F and 18G shows that losartan tended to improve perfusion (FIG. 18F) and increase chemotherapy delivery (FIG. 18G) in PAN02 (left panels) and AK4.4 (right panels) tumors from obese but not lean mice (Two-way ANOVA with Bonferroni correction for multiple comparisons, n=4-8 tumors per group). Data in FIGS. 18D, 18F and 18G are shown as mean±SEM. In FIGS. 18C and 18F, far left bars represent lean mice, middle left bars represent lean mice treated with losartan, middle right bars represent obese mice, and far left bars represent obese mice treated with losartan.

FIG. 19A shows that obesity promoted infiltration of myeloid Gr-1(+)F4/80(−) cell population in AK4.4 tumors in obese mice. Quantification normalized by total CD45 leucocytes (n=4 tumors/group). FIG. 19B shows that obesity associated with increased levels of IL-1ß in AK4.4 tumors in obese mice (n=4 tumors/group). Data are shown as mean±SEM. P values were determined by the Student t-test. *, P<0.05. In FIGS. 19A and 19B, left bars represent lean mice, and right bars represent obese mice.

FIG. 20A is a representative FACS scatter plots of CD45(+)CD11b(+)Ly6G(+) tumor-associated neutrophils (TANs) in control and TAN-depleted obese mice. Ly6G specific inhibition led to a significant reduction (~90%) of the Ly6G(+) cell population in PAN02 tumors from obese mice. FIG. 20B shows the effect of TAN depletion on vessel perfusion in AK4.4 tumors in obese animals. % of CD31(+), lectin(+) or double positive vessel density in the viable area of whole AK4.4 tumors. FIG. 20C shows the % of CD31 expression that co-stains with lectin in PAN02 and AK4.4 tumors (n=4-6 tumors/group). FIG. 20D shows that TAN depletion reduced the expression of CXCL-1 (IL-8, KC), and tended to reduce the expression of TNFα and IL-12 in PAN02 tumors from obese mice. Data in FIGS. 20B, 20C, and 20D are shown as mean±SEM. P values were determined by the Student t-test. *, P<0.05. In FIGS. 20B, 20C, and 20D, left bars represent obese mice and right bars represent TAN-depleted obese mice.

FIG. 21A shows the effect of losartan on cytokine expression in PAN02 and AK4.4 tumors in obese mice. Multiplex protein revealed that losartan reduced the expression of multiple cytokines including IL-1 in PDACs (n=4-7 tumors/group). FIGS. 21B and 21C show that within the CD45 population, losartan treatment tended to decrease the enrichment for GR(+)F480 (−) cells (FIG. 21B), and within CD4 cells, the enrichment for T regulatory cells (FIG. 21C) (n=4 tumors/group). Error bars represent standard error of the mean. P values were determined by the Student t-test in A. *, P<0.05, , P<0.01, *, P<0.001.

DETAILED DESCRIPTION

Figure 1A:
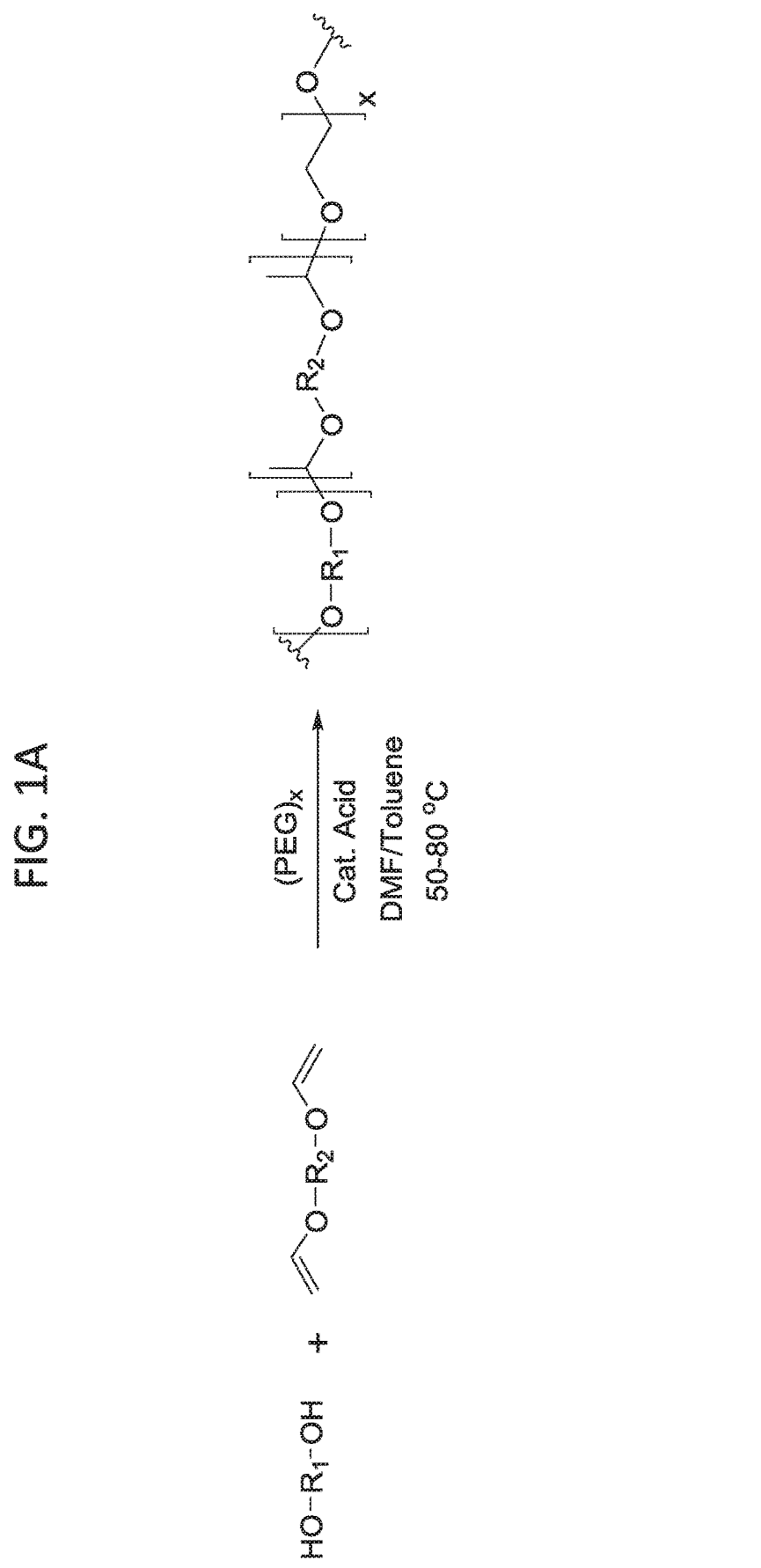

The mildly acidic pH in tumor tissues (pH~6.5-7.2), inflammatory tissues, as well as in the endosomal intracellular compartments (pH~4.5-6.5) may trigger drug release from pH sensitive delivery vehicles upon their arrival at the targeted disease sites. The release of contents of the delivery vehicles can be retarded or hindered if the vehicles are not sensitive enough to outer pH stimuli. Certain embodiments of the nanoparticles disclosed herein exhibit the sensitivity to the pH environment change. Further, the nanoparticles disclosed herein can keep integrity in the bloodstream pH, but release their contents when exposed to extracellular tumor microenvironment. In certain embodiments, the nanoparticles disclosed herein rapidly release the contents inside hypoxic cells (e.g., tumor cells or liver cells).

Accordingly, the present invention provides, at least in part, pH-sensitive and/or polyacetal polymers and/or linkers; conjugates comprising said polymers and/or linkers, optionally, coupled to one or more agents and/or targeting moieties; and particles (e.g., nanoparticles comprising the aforesaid polymers, linkers and/or conjugates), collectively referred to herein as "compositions," which can be used to enhance the delivery and/or efficacy of one or more agents in a subject. In one embodiment, the polymer is capable of forming micelles or self-assembling into nano-structures. In some embodiments, the pH-sensitive and/or polyacetal polymer disclosed herein is capable of forming micelles or self-assembling into nano-structures with diameters over about 12 nm.

Without being bound by theory, the compositions disclosed herein may improve the efficiency of an agent, e.g., a therapeutic and/or diagnostic agent, e.g., by one or more of: (i) increasing the localization and/or delivery of the agent to a target cell (e.g., a cancer or a liver cell); (ii) selectively penetrating into a fibrotic tissue (e.g., a desmoplastic tumor or fibrotic liver); (iii) selectively penetrating into a diseased blood vessel (e.g., a leaky tumor vessel); (iv) exhibiting increased pH-sensitivity and/or enhanced agent release in a hypoxic microenvironment, e.g., in a tumor or a fibrotic tissue (e.g., fibrotic or cirrhotic liver); (v) increasing the selective delivery and/or release of the agent to the tumor or fibrotic tissue; or (vi) increasing the half-life of the agent.

Certain embodiments disclosed herein provide compositions and methods for treating or preventing a disorder (e.g., a cancer (e.g., a desmoplastic tumor) or a liver disorder), by administering to a subject a particle, e.g., a pH-sensitive and/or polyacetal particle described herein, as a single agent or as a combination with one or more therapeutic agents. The pH-sensitive and/or polyacetal compositions disclosed herein can result in a significantly higher amount of released agent at a target site (e.g., a hypoxic tumor or liver).

Thus, provided herein are compositions and methods for improving the delivery and/or efficacy of a therapy (e.g., a cancer, a fibrotic or immunomodulary or liver therapy), ranging in size from a cell (e.g., an immune cell) or a large nanotherapeutic (e.g., lipid- or polymeric nanoparticles and viruses), protein and nucleic acid drugs, to low molecular weight chemotherapeutics and/or oxygen radicals.

Additional embodiments that can be combined with the compositions and methods of the invention are disclosed in WO 2012/068531 and WO 2013/169739, both of which are entitled "Novel Compositions and Uses of Anti-Hypertension Agents for Cancer Therapy," which are hereby expressly incorporated by reference in their entirety.

Certain terms are defined throughout the specification and in the section entitled "Selected Definitions" set forth below.

Polymers

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In one embodiment, the polymer has at least 2 repeat units. In other embodiments, the polymer has at least 4 repeat units, at least 7 repeat units, at least 12 repeat units, at least 17 repeat units, at least 44 repeat units, or at least 100 repeat units.

If more than one type of repeat unit is present within the polymer, then the polymer is said to be a "copolymer." It is to be understood that in any embodiment employing a polymer, the polymer being employed can be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block) and one or more regions each comprising a second repeat unit (e.g., a second block), etc. Block copolymers may have two (a diblock copolymer), three (a triblock copolymer) or more numbers of distinct blocks. The term "homopolymer" is a polymer incorporating a single species of monomer units. The polymer can be natural or synthetically derived. In some embodiments, the polymer is not biodegradable. In some other embodiments, the polymer is biodegradable. In some embodiments, the polymer is biocompatible.

Suitable polymers include polymers, copolymers, and block polymers based on monomers containing ionizable groups or polymerizable double bonds. Exemplary monomers include, but are not limited to, acrylic acid, methyl methacrylate, methyl acrylic acid, ethyl acrylate, vinyl sulfonic acid, styrene, styrene sulfonic acid (e.g., p-styrene sulfonic acid), maleic acid, butenoic acid, vinyl phosphate, vinyl phosphonate, ethylene, propylene, styrene, vinyl methyl ether, vinyl acetate, vinyl alcohol, acrylonitrile, acrylamide, N—($C_1$-$C_6$ alkyl) acrylamide (such as N-isopropylacrylamide, N-t-butylacrylamide), and the like. Polymer matrices are made by homopolymerizing or copolymerizing any of the foregoing monomers. Other suitable polymers can include alginate, chitosan, collagen, gelatin, hyaluronate, fibrin, agarose, and derivatives thereof. In some embodiments the polymer can be a polysaccharide, for example, but not limited to, dextran. In some embodiments the polymer can be a polypeptide. In some embodiments, the polymer can be an antibody.

In some embodiments, the polymer can be selected from the group consisting of polysaccharides, polypeptides, polyacetals, polyketals, polyanhydrides, polyhydroxybutyric acid, polyorthoesters, polysiloxanes, polycaprolactone, poly(lactic-co-glycolic acid), poly(lactic acid), poly(glycolic acid), and copolymers or block polymers prepared from the monomers of these polymers. Some exemplary polymers which can be used in the present invention include but are not limited to one or a mixture of polymers selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly glycolic acid (PGA), poly lactic-co-glycolic acid (PLGA), polylactic acid, poly e-caprolactone (PCL), polyethylene oxide, poly propylene fumarate (PPF), poly acrylic acid (PAA), hydrolysed polyacrylonitrile, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and any combinations thereof, as well as salts and esters thereof.

In some embodiments the polymer can be poly(lactic acid)-b-poly(ethylene glycol) (PLA-PEG), poly(lactic acid)-b-poly(ethylene glycol) (PLGA-PEG), or (cyclodextrin)-co-poly(ethylene glycol) (CDP). In some preferred embodiments, polymer is PLA-PEG, dextran, or a polyacetal polymer described herein.

In some embodiments of the various aspects disclosed herein, the polymer (e.g., the pH-sensitive or polyacetal polymer) comprises a compound according to Formula (I):

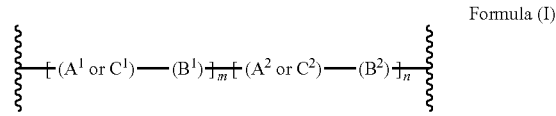

Formula (I)

wherein:

each of $A^1$ and $A^2$ is independently heteroalkylene, heteroalkenylene, heteroalkynylene, heterocyclyl, aryloxy, heteroaryloxy, wherein each heteroalkylene, heteroalkenylene, heteroalkynylene, heterocyclyl, aryloxy, or heteroaryloxy is optionally substituted with 1-5 $R^1$;

each of $B^1$ and $B^2$ is independently heteroalkyl, heterocyclyl, each of which is optionally substituted with 1-6 $R^2$;

each of $C^1$ and $C^2$ is independently heteroalkyl, cyclyl, or heterocyclyl, each of which is optionally substituted with 1-6 $R^3$, e.g., each of $C^1$ and $C^2$ is independently PEG400, PEG000, or PEG2050;

each of $R^1$, $R^2$, and $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, a protecting group, or a branching point, and each of m or n is independently an integer from 1 to 500.

In some embodiments of a polymer of Formula (I), each of $A^1$ and $A^2$ is independently heteroalkyl or aryloxy, each of which may be optionally substituted with 1-5 $R^1$. In some embodiments, each of $A^1$ and $A^2$ is independently heteroalkyl, each of which may be optionally substituted with 1-5 $R^1$. In some embodiments, each of $A^1$ and $A^2$ is independently $C_1$-$C_{20}$ heteroalkyl, each of which may be optionally substituted with 1-5 $R^1$. In some embodiments, each of $A^1$ and $A^2$ is the same $C_1$-$C_{20}$ heteroalkyl, each of which may be optionally substituted with 1-5 $R^1$. In some embodiments, each of $A^1$ and $A^2$ is a different $C_1$-$C_{20}$ heteroalkyl, each of which may be optionally substituted with 1-5 $R^1$.

In some embodiments, each of $A^1$ and $A^2$ is independently represented by a moiety of Formula (II):

Formula (II)

wherein:

$X^1$ is $C_1$-$C_{12}$ alkylene, $C_2$-$C_{12}$ alkenylene, $C_2$-$C_{12}$ alkynylene, $C_1$-$C_{12}$ heteroalkylene, $C_3$-$C_8$ cyclyl, or $C_3$-$C_8$ heterocyclyl, wherein each alkylene, alkenylene, alkynylene, heteroalkylene, cyclyl, or heterocyclyl is optionally substituted with 1-6 $R^4$;

each $R^4$ is independently $C_1$-$C_6$ alkyl, $C_2$-$C_6$ alkenyl, $C_2$-$C_6$ alkynyl, $C_1$-$C_6$ heteroalkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, ($C_1$-$C_6$ alkylene)-OC(O)O—($C_1$-$C_6$ alkylene)-$OR^5$, ($C_1$-$C_6$ alkylene)-$NR^6$—($C_1$-$C_6$ alkylene)-$OR^5$, ($C_1$-$C_6$ alkylene)-C(O)$NR^6$—($C_1$-$C_6$ alkylene)-$OR^5$, or ($C_1$-$C_6$ alkylene)-$NR^6$C(O)—($C_1$-$C_6$ alkylene)-$OR^5$, wherein each alkyl, alkenyl, alkynyl, heteroalkyl, or alkylene is optionally substituted with 1-6 $R^7$;

each $R^5$ is independently hydrogen, $C_1$-$C_6$ alkyl, cyclyl, heterocyclyl, aryl, heteroaryl, arylalkyl, heteroarylalkyl, a linker, an agent, a targeting moiety, a protecting group, or a branching point, wherein each alkyl, cyclyl, heterocyclyl, aryl, heteroaryl, arylalkyl, heteroarylalkyl is optionally substituted with 1-6 $R^8$;

$R^6$ is hydrogen or $C_1$-$C_6$ alkyl;

each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, ($C_1$-$C_6$ alkylene)-$OR^5$, ($C_1$-$C_6$ alkylene)-O—($C_1$-$C_6$ alkylene)-$OR^5$, cyano, cyclyl, heterocyclyl, aryl, or heteroaryl; and each $R^8$ is independently $C_1$-$C_6$ alkyl, $C_2$-$C_6$ alkenyl, $C_2$-$C_6$ alkynyl, $C_1$-$C_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 $R^9$; and each $R^9$ is independently $C_1$-$C_6$ alkyl, $C_1$-$C_6$ heteroalkyl, halo, cyano, cyclyl, or heterocyclyl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl, wherein each alkylene, heteroalkylene, cyclyl, or heterocyclyl is optionally substituted with 1-6 $R^4$. In some embodiments, $X^1$ is $C_1$-$C_{12}$ alkylene or $C_1$-$C_{12}$ heteroalkylene, optionally substituted with 1-6 $R^4$. In some embodiments, $X^1$ is $C_1$-$C_6$ alkylene, optionally substituted with 1-6 $R^4$. In some embodiments, $X^1$ is $C_1$-$C_{12}$ heteroalkylene, optionally substituted with 1-6 $R^4$.

In some embodiments, $X^1$ is $C_3$-$C_8$ cyclyl or $C_3$-$C_8$ heterocyclyl, wherein each cyclyl or heterocyclyl is optionally substituted with 1-6 $R^4$. In some embodiments, $X^1$ is $C_3$-$C_6$ cyclyl or $C_3$-$C_6$ heterocyclyl, wherein each cyclyl or heterocyclyl is optionally substituted with 1-6 $R^4$. In some embodiments, $X^1$ is $C_3$-$C_6$ cyclyl, optionally substituted with 1-6 $R^4$. In some embodiments, $X^1$ is cyclopropyl, cyclobutyl, cyclopentyl, or cyclohexyl, each of which is optionally substituted with 1-6 $R^4$. In some embodiments, $X^1$ is cyclopentyl or cyclohexyl, each of which is optionally substituted with 1-6 $R^4$. In some embodiments, $X^1$ is cyclopentyl or cyclohexyl, each of which is optionally substituted with 1-4 $R^4$. In some embodiments, $X^1$ is cyclopentyl or cyclohexyl, each of which is optionally substituted with 1-2 $R^4$, and each $R^4$ is independently $C_1$-$C_6$ alkyl or $OR^5$. In some embodiments, $X^1$ is cyclohexyl substituted with 1 $R^4$. In some embodiments, $X^1$ is cyclohexyl substituted with $OR^5$.

In some embodiments, $R^5$ is hydrogen, $C_1$-$C_6$ alkyl, cyclyl, heterocyclyl, aryl, heteroaryl, arylalkyl, or heteroarylalkyl. In some embodiments, $R^5$ is hydrogen. In some embodiments, $R^5$ is arylalkyl or heteroarylalkyl. In some embodiments, $R^5$ is a linker. In some embodiments, $R^5$ is an agent (e.g., an ARB). In some embodiments, $R^5$ is a targeting moiety. In some embodiments, $R^5$ is a protecting group. In some embodiments, $R^5$ is a branching point.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol) ethane and the polymer of Formula (I) is greater than about 10 kDa in size.

In some embodiments, each of $A^1$ and $A^2$ independently includes, or is independently derived from, tri(methylol) ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments of a polymer of Formula (I), each of $A^1$ and $A^2$ is independently hydrophobic. In some embodiments, each of $A^1$ and $A^2$ has a partition coefficient (c Log P) value greater than about −2.0. In some embodiments, each of $A^1$ and $A^2$ has a c Log P value greater than about −1.5, e.g., about −1.4, about −1.3, about −1.2, about −1.1, about −1.0, about −0.9, about −0.8, about −0.7, about −0.6, about −0.5, about −0.4, about −0.3, about −0.2, about −0.1, about 0, or higher. In some embodiments, each of $A^1$ and $A^2$ has a c Log P value between about −2.0 and 2.5. In some embodiments, each of $A^1$ and $A^2$ has a c Log P value greater than about −0.5, e.g., about −0.4, about −0.3, about −0.2, about −0.1, about 0, about 0.1, about 0.2, about 0.3, about 0.4, about 0.5, or higher. In some embodiments, each of $A^1$ and $A^2$ has a c Log P value greater than about 0, e.g., about 0.1, about 0.2, about 0.3, about 0.4, about 0.5, about 0.6, about 0.7, about 0.8, about 0.9, about 1.0, or higher. In some embodiments, each of $A^1$ and $A^2$ has a c Log P value between about −2.0 and 4.0.

In some embodiments, each of $A^1$ and $A^2$ has a linear structure. In some embodiments, each of $A^1$ and $A^2$ has a branched structure. In some embodiments, each of $A^1$ and $A^2$ comprises a protected reactive group, e.g., a protected hydroxyl, a protected carboxylic acid, or a protected amine. In some embodiments, each of $A^1$ and $A^2$ comprises 1, 2, 3, 4, 5, 6, 7, 8, or more protected reactive groups, e.g., a protected hydroxyl, a protected carboxylic acid, or a protected amine.

In some embodiments, each of $A^1$ and $A^2$ is represented by a compound of Formula (II-a):

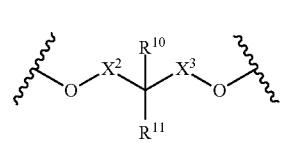

Formula (II-a)

wherein:

each of $X^2$ and $X^3$ is independently $C_1$-$C_6$ alkylene, $C_2$-$C_6$ alkenylene, $C_2$-$C_{12}$ alkynylene, $C_1$-$C_{12}$ heteroalkylene, $C_3$-$C_8$ cyclyl, $C_3$-$C_8$ heterocyclyl, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), ($C_1$-$C_6$ alkylene)-NR$^{13}$—($C_1$-$C_6$ alkylene), ($C_1$-$C_6$ alkylene)-C(O)NR$^{13}$—($C_1$-$C_6$ alkylene), or ($C_1$-$C_6$ alkylene)-NR$^{13}$C(O)—($C_1$-$C_6$ alkylene), wherein each alkylene, alkenylene, alkynylene, heteroalkylene, cyclyl, or heterocyclyl is optionally substituted with 1-6 $R^{12}$;

$R^{10}$ is $C_1$-$C_6$ alkyl, $C_2$-$C_6$ alkenyl, $C_2$-$C_6$ alkynyl, $C_1$-$C_6$ heteroalkyl, OR$^{14}$, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-C(O)—($C_1$-$C_6$ alkylene)-OR$^{14}$, ($C_1$-$C_6$ alkylene)-OC(O)—($C_1$-$C_6$ alkylene)-OR$^{14}$, ($C_1$-$C_6$ alkylene)-C(O)O—($C_1$-$C_6$ alkylene)-OR$^{14}$, ($C_1$-$C_6$ alkylene)-OC(O)O—($C_1$-$C_6$ alkylene)-OR$^{14}$, ($C_1$-$C_6$ alkylene)-NR$^{13}$—($C_1$-$C_6$ alkylene)-OR$^{14}$, ($C_1$-$C_6$ alkylene)-C(O)NR$^{13}$—($C_1$-$C_6$ alkylene)-OR$^{14}$, or ($C_1$-$C_6$ alkylene)-NR$^{13}$C(O)—($C_1$-$C_6$ alkylene)-OR$^{14}$, wherein each alkyl, alkenyl, alkynyl, heteroalkyl, or alkylene is optionally substituted with 1-6 $R^{15}$;

$R^{11}$ is hydrogen, $C_1$-$C_6$ alkyl, $C_2$-$C_6$ alkenyl, $C_2$-$C_6$ alkynyl, $C_1$-$C_6$ heteroalkyl, OR$^{14}$, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-C(O)—($C_1$-$C_6$ alkylene)-OR$^{14}$, ($C_1$-$C_6$ alkylene)-OC(O)—($C_1$-$C_6$ alkylene)-OR$^{14}$, ($C_1$-$C_6$ alkylene)-C(O)O—($C_1$-$C_6$ alkylene)-OR$^{14}$, ($C_1$-$C_6$ alkylene)-OC(O)O—($C_1$-$C_6$ alkylene)-OR$^{14}$, ($C_1$-$C_6$ alkylene)-NR$^{13}$—($C_1$-$C_6$ alkylene)-OR$^{14}$, ($C_1$-$C_6$ alkylene)-C(O)NR$^{13}$—($C_1$-$C_6$ alkylene)-OR$^{14}$, or ($C_1$-$C_6$ alkylene)-NR$^{13}$C(O)—($C_1$-$C_6$ alkylene)-OR$^{14}$, wherein each alkyl, alkenyl, alkynyl, heteroalkyl, or alkylene is optionally substituted with 1-6 $R^{15}$;

each $R^{12}$ and $R^{13}$ is independently $C_1$-$C_6$ alkyl, $C_2$-$C_6$ alkenyl, $C_2$-$C_6$ alkynyl, $C_1$-$C_6$ heteroalkyl, halo, OR$^{14}$, ($C_1$-$C_6$ alkylene)-OR$^{14}$, ($C_1$-$C_6$ alkylene)-O—($C_1$-$C_6$ alkylene)-OR$^{14}$, cyano, cyclyl, heterocyclyl, aryl, or heteroaryl;

$R^{13}$ is hydrogen or $C_1$-$C_6$ alkyl:

$R^{14}$ is hydrogen, $C_1$-$C_6$ alkyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^{16}$; and each $R^{16}$ is independently $C_1$-$C_6$ alkyl, $C_1$-$C_6$ heteroalkyl, halo, cyano, cyclyl, or heterocyclyl.

In some embodiments, each of $X^2$ and $X^3$ is independently $C_1$-$C_6$ alkylene, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), wherein each alkyl or alkylene is optionally substituted with 1-6 $R^8$. In some embodiments, each of $X^1$ and $X^2$ is independently $C_1$-$C_4$ alkyl, ($C_1$-$C_4$ alkylene)-O—($C_1$-$C_4$ alkylene), ($C_1$-$C_4$ alkylene)-C(O)—($C_1$-$C_4$ alkylene), ($C_1$-$C_4$ alkylene)-OC(O)—($C_1$-$C_4$ alkylene), ($C_1$-$C_4$ alkylene)-C(O)O—($C_1$-$C_4$ alkylene), ($C_1$-$C_4$ alkylene)-OC(O)O—($C_1$-$C_4$ alkylene), wherein each alkyl or alkylene is optionally substituted with 1-6 $R^{12}$.

In some embodiments, each of $X^2$ and $X^3$ is independently $C_1$-$C_2$ alkylene, e.g., $CH_2$, $CH_2CH_2$. In some embodiments, each of $X^2$ and $X^3$ is independently ($C_1$-$C_4$ alkylene)-O—($C_1$-$C_4$ alkylene), e.g., $CH_2$—O—$CH_2CH_2$, $CH_2CH_2$—O—$CH_2CH_2$. In some embodiments, each of $X^1$ and $X^2$ is independently ($C_1$-$C_4$ alkylene)-OC(O)—($C_1$-$C_4$ alkylene), e.g., $CH_2$—OC(O)—$CH_2$, $CH_2$—OC(O)—$CH_2CH_2$, $CH_2$—OC(O)—CH($CH_3$), $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—CH($CH_3$). In some embodiments, each of $X^2$ and $X^3$ is independently ($C_1$-$C_4$ alkylene)-OC(O)O—($C_1$-$C_4$ alkylene), e.g., $CH_2$—OC(O)O—$CH_2CH_2$). In some embodiments, each of $X^2$ and $X^3$ is the same.

In some embodiments, $R^{10}$ is $C_1$-$C_6$ alkyl, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-OC(O)—($C_1$-$C_6$ alkylene)-OR$^{14}$, ($C_1$-$C_6$ alkylene)-OC(O)O—($C_1$-$C_6$ alkylene)-OR$^{14}$, wherein each alkyl or alkylene is optionally substituted with 1-6 $R^{15}$. In some embodiments, $R^{10}$ is $C_1$-$C_6$ alkyl, e.g., $CH_3$, $CH_2CH_3$. In some embodiments, $R^{10}$ is ($C_1$-$C_6$ alkylene)-OR$^{14}$, e.g., $CH_2$OR$^{14}$, $CH_2CH_2$OR$^{14}$. In some embodiments, $R^{10}$ is ($C_1$-$C_6$ alkylene)-O—($C_1$-$C_6$ alkylene)-OR$^{14}$. In some embodiments, $R^{10}$ is ($C_1$-$C_6$ alkylene)-OC(O)—($C_1$-$C_6$ alkylene)-OR$^{14}$, e.g., $CH_2$—OC(O)—$CH_2$, $CH_2$—OC(O)—$CH_2CH_2$, $CH_2$—OC(O)—CH($CH_3$), $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—CH($CH_3$). In some embodiments, $R^{10}$ is ($C_1$-$C_4$ alkylene)-OC(O)O—($C_1$-$C_4$ alkylene), e.g., $CH_2$—OC(O)O—$CH_2CH_2$).

In some embodiments, $R^{11}$ is hydrogen or $C_1$-$C_6$ alkyl. In some embodiments, $R^{11}$ is hydrogen. In some embodiments, $R^{11}$ is $C_1$-$C_6$ alkyl. In some embodiments, $R^{11}$ is $C_1$-$C_4$ alkyl, e.g., $CH_3$, $CH_2CH_3$. In some embodiments, $R^{11}$ is ($C_1$-$C_6$ alkylene)-OR$^{14}$, e.g., $CH_2$OR$^{14}$, $CH_2CH_2$OR$^{14}$.

In some embodiments, $R^{14}$ is hydrogen, $C_1$-$C_6$ alkyl, cyclyl, heterocyclyl, aryl, heteroaryl, arylalkyl, or heteroarylalkyl. In some embodiments, $R^{14}$ is hydrogen. In some embodiments, $R^{14}$ is arylalkyl or heteroarylalkyl. In some embodiments, $R^{14}$ is a linker. In some embodiments, $R^{14}$ is an agent (e.g., an ARB). In some embodiments, $R^{14}$ is a targeting moiety. In some embodiments, $R^{14}$ is a protecting group. In some embodiments, $R^{14}$ is a branching point.

In some embodiments, each of $A^1$ and $A^2$ does not independently include, or is not independently derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol)ethane and the polymer of Formula (I) is greater than about 10 kDa in size.

In some embodiments, each of $A^1$ and $A^2$ independently includes, or is independently derived from, tri(methylol)ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments, each of $A^1$ and $A^2$ is represented by a compound of Formula (II-b):

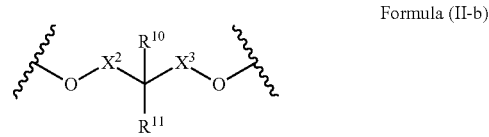

Formula (II-b)

wherein:
each of $X^2$ and $X^3$ is independently $C_1$-$C_6$ alkylene, ($C_1$-$C_6$ alkylene)-O—($C_1$-$C_6$ alkylene), ($C_1$-$C_6$ alkylene)-OC(O)—($C_1$-$C_6$ alkylene), or ($C_1$-$C_6$ alkylene)-OC(O)O—($C_1$-$C_6$ alkylene);

$R^{10}$ is $C_1$-$C_6$ alkyl, ($C_1$-$C_6$ alkylene)-OR$^{14}$, ($C_1$-$C_6$ alkylene)-O—($C_1$-$C_6$ alkylene)-OR$^{14}$, ($C_1$-$C_6$ alkylene)-OC(O)—($C_1$-$C_6$ alkylene)-OR$^{14}$, or ($C_1$-$C_6$ alkylene)-OC(O)

O—($C_1$-$C_6$ alkylene)-$OR^{14}$, wherein each alkylene is optionally substituted with 1-4 ($C_1$-$C_6$ alkylene)-$OR^{14}$;

$R^{11}$ is hydrogen, $C_1$-$C_6$ alkyl, or ($C_1$-$C_6$ alkylene)-$OR^{14}$; and $R^{14}$ is hydrogen, $C_1$-$C_6$ alkyl, cyclyl, heterocyclyl, aryl, heteroaryl, arylalkyl, heteroarylalkyl, a linker, an agent, a targeting moiety, a protecting group, or a branching point.

In some embodiments, each of $X^2$ and $X^3$ is independently $C_1$-$C_2$ alkylene, e.g., $CH_2$, $CH_2CH_2$. In some embodiments, each of $X^2$ and $X^3$ is independently ($C_1$-$C_4$ alkylene)-O—($C_1$-$C_4$ alkylene), e.g., $CH_2$—O—$CH_2CH_2$, $CH_2CH_2$—O—$CH_2CH_2$. In some embodiments, each of $X^1$ and $X^2$ is independently ($C_1$-$C_4$ alkylene)-OC(O)—($C_1$-$C_4$ alkylene), e.g., $CH_2$—OC(O)—$CH_2$, $CH_2$—OC(O)—$CH_2CH_2$, $CH_2$—OC(O)—$CH(CH_3)$, $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—$CH(CH_3)$. In some embodiments, each of $X^2$ and $X^3$ is independently ($C_1$-$C_4$ alkylene)-OC(O)O—($C_1$-$C_4$ alkylene), e.g., $CH_2$—OC(O)O—$CH_2CH_2$). In some embodiments, each of $X^2$ and $X^3$ is the same.

In some embodiments, $R^{10}$ is $C_1$-$C_6$ alkyl, e.g., $CH_3$, $CH_2CH_3$. In some embodiments, $R^{10}$ is ($C_1$-$C_6$ alkylene)-$OR^{14}$, e.g., $CH_2OR^{14}$, $CH_2CH_2OR^{14}$. In some embodiments, $R^{10}$ is ($C_1$-$C_6$ alkylene)-O—($C_1$-$C_6$ alkylene)-$OR^{14}$. In some embodiments, $R^{10}$ is ($C_1$-$C_6$ alkylene)-OC(O)—($C_1$-$C_6$ alkylene)-$OR^{14}$, e.g., $CH_2$—OC(O)—$CH_2$, $CH_2$—OC(O)—$CH_2CH_2$, $CH_2$—OC(O)—$CH(CH_3)$, $CH_2$—OC(O)—$CH_2CH_2CH_2$, $CH_2CH_2$—OC(O)—$CH_2$, $CH_2CH_2$—OC(O)—$CH_2CH_2$, $CH_2CH_2$—OC(O)—$CH(CH_3)$. In some embodiments, $R^{10}$ is ($C_1$-$C_4$ alkylene)-OC(O)O—($C_1$-$C_4$ alkylene), e.g., $CH_2$—OC(O)O—$CH_2CH_2$).

In some embodiments, $R^{11}$ is hydrogen or $C_1$-$C_6$ alkyl. In some embodiments, $R^{11}$ is hydrogen. In some embodiments, $R^{11}$ is $C_1$-$C_6$ alkyl. In some embodiments, $R^{11}$ is $C_1$-$C_4$ alkyl, e.g., $CH_3$, $CH_2CH_3$. In some embodiments, $R^{11}$ is ($C_1$-$C_6$ alkylene)-$OR^{14}$, e.g., $CH_2OR^{14}$, $CH_2CH_2OR^{14}$.

In some embodiments, $R^{14}$ is hydrogen, $C_1$-$C_6$ alkyl, cyclyl, heterocyclyl, aryl, heteroaryl, arylalkyl, or heteroarylalkyl. In some embodiments, $R^{14}$ is hydrogen. In some embodiments, $R^{14}$ is arylalkyl or heteroarylalkyl. In some embodiments, $R^{14}$ is a linker. In some embodiments, $R^{14}$ is an agent (e.g., an ARB). In some embodiments, $R^{14}$ is a targeting moiety. In some embodiments, $R^{14}$ is a protecting group. In some embodiments, $R^{14}$ is a branching point.

In some embodiments, each of $A^1$ and $A^2$ is the same. In some embodiments, each of $A^1$ and $A^2$ is the same, e.g., the same compound of Formula (II), Formula (II-a), or Formula (II-b). In some embodiments, each of $A^1$ and $A^2$ is different. In some embodiments, each of $A^1$ and $A^2$ is the different, e.g., a different compound of Formula (II), Formula (II-a), or Formula (II-b).

In some embodiments, the precursor of each of $A^1$ and $A^2$ is independently selected from the following polyols:

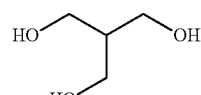

A1

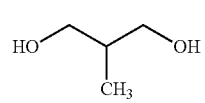

A2

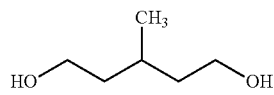

A3

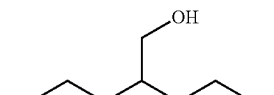

A4

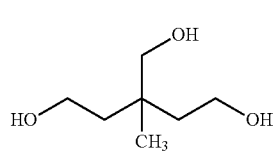

A5

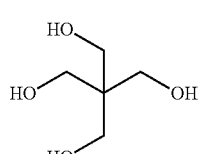

A6

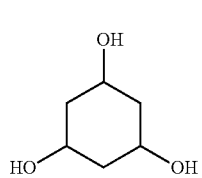

A7

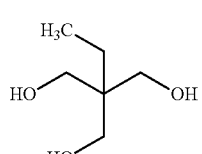

A8

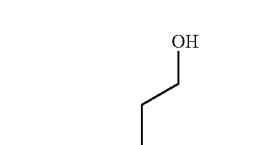

A9

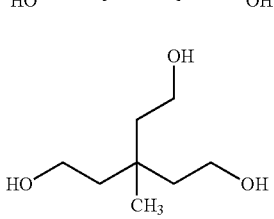

A10

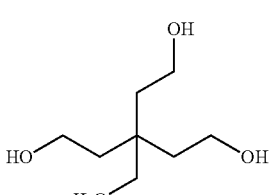

A11

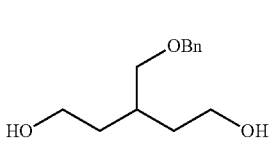

A12

-continued
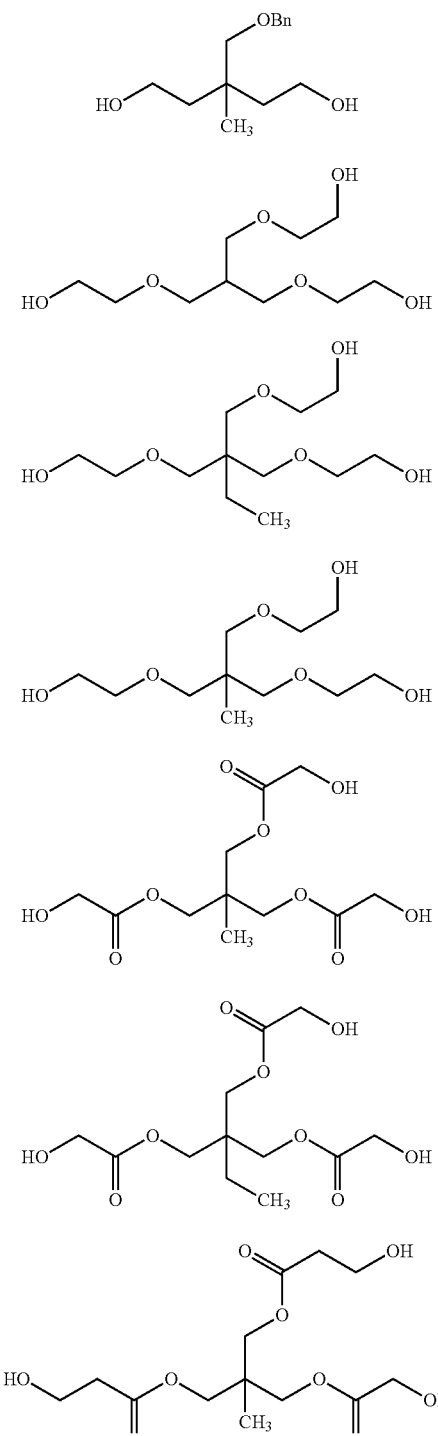
A13
A14
A15
A16
A17
A18
A19
A20
-continued
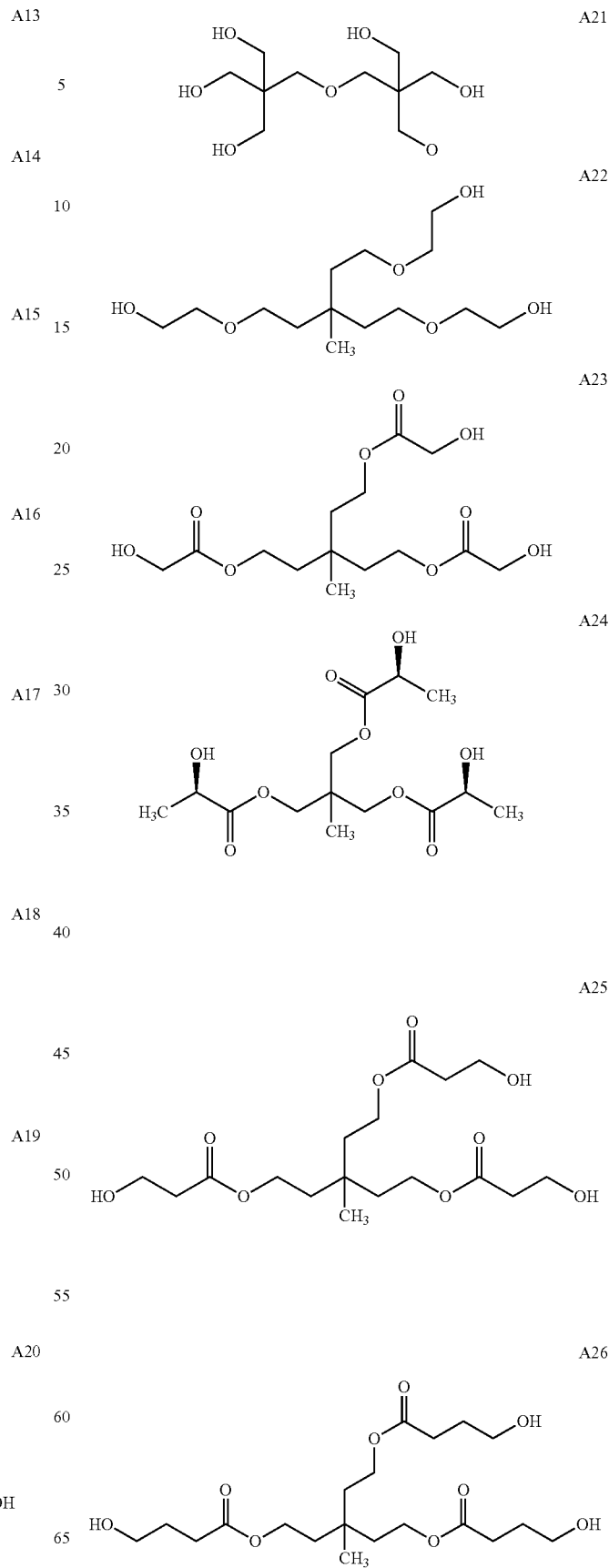
A21
A22
A23
A24
A25
A26

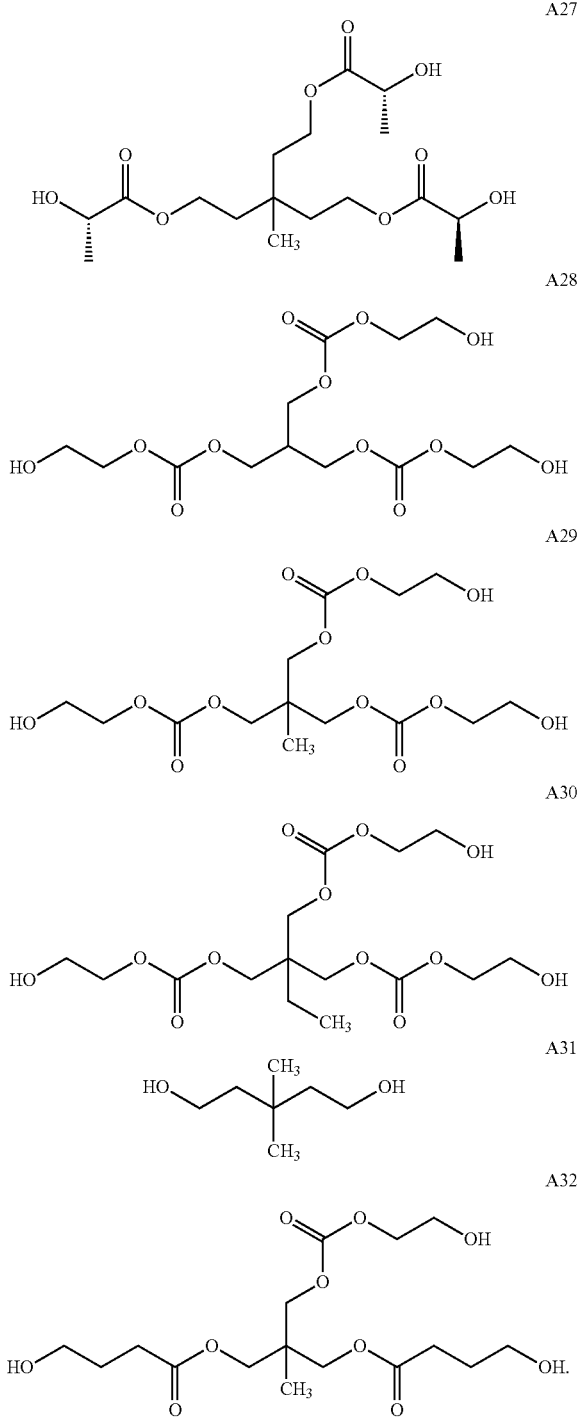

Figure 1B:
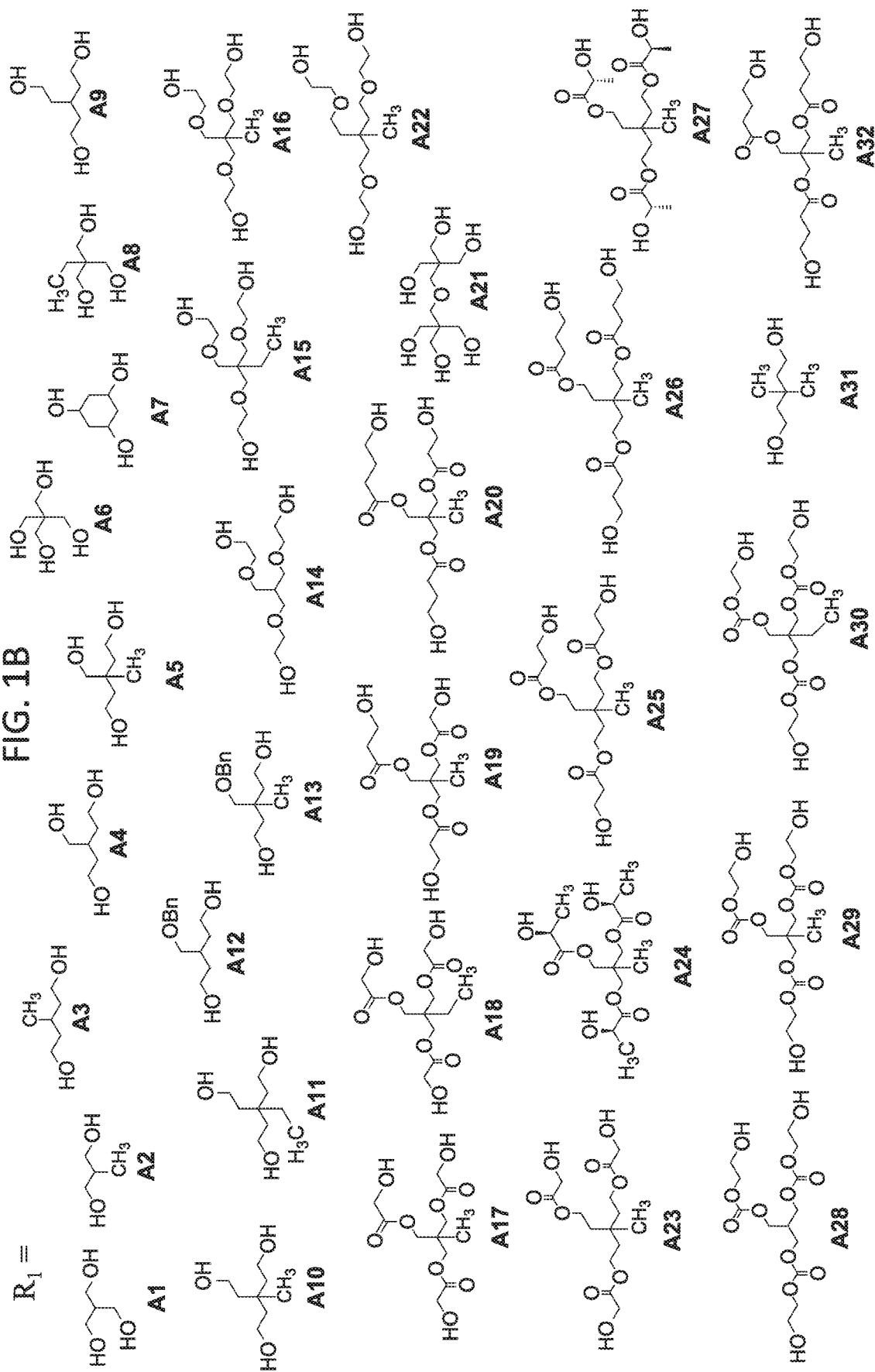
Figure 2A:
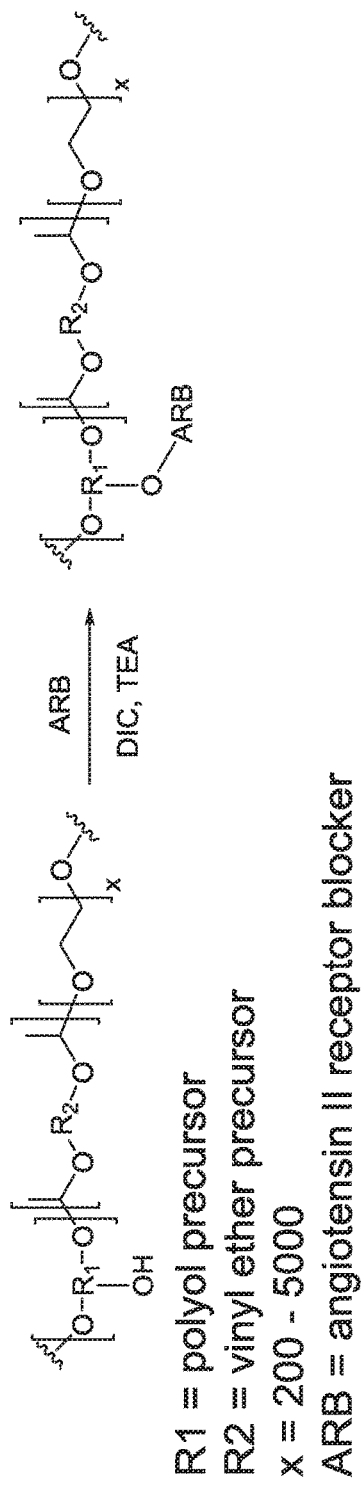
FIGS. 2A and 2B show the synthesis of exemplary polyacetal polymers conjugated to an ARB.
Figure 2B:
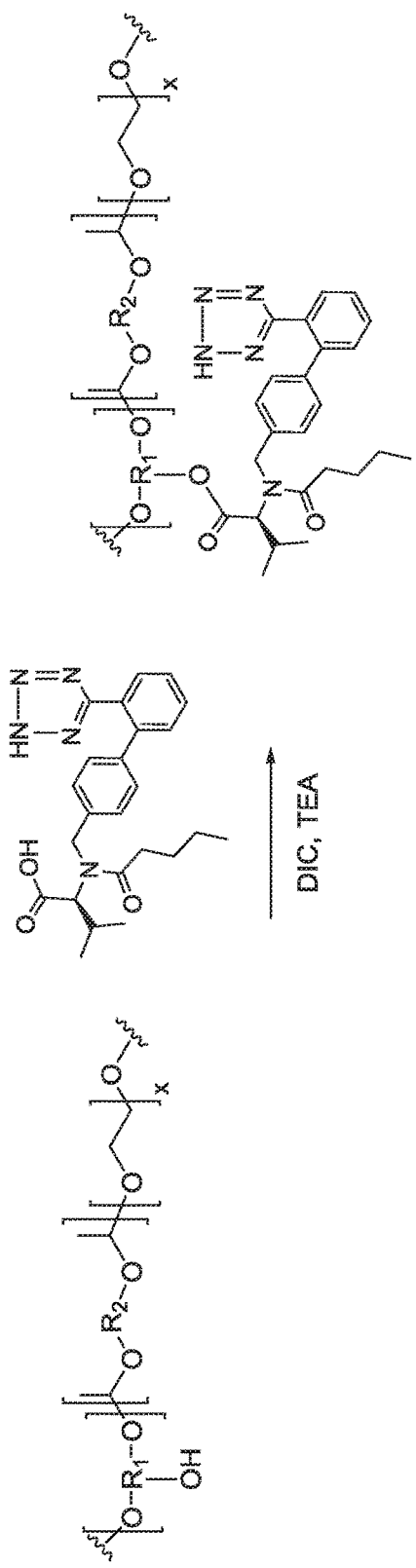

A13, A14, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, each of $A^1$ and $A^2$ is represented by a compound of Formula (II-c):

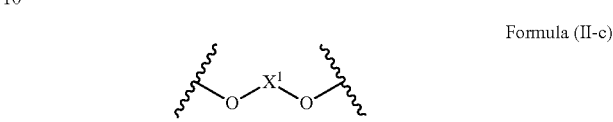

Formula (II-c)

wherein:

$X^1$ includes or is derived from any of the polyols shown in FIG. 1B, e.g., a polyol selected from one of A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, $X^1$ includes or is derived from any of the polyols shown in FIG. 1B, e.g., a polyol selected from one of A3, A4, A5, A9, A10, A11, A12, A13, A14, A15, A16, A17, A18, A19, A20, A21, A22, A23, A24, A25, A26, A27, A28, A29, A30, A31, and A32, and two of the hydroxyl groups of the polyol are replaced by the oxygen atoms in Formula (II-c).

In some embodiments, $X^1$ includes or is derived from A1. In some embodiments, $X^1$ includes or is derived from A2. In some embodiments, $X^1$ includes or is derived from A3. In some embodiments, $X^1$ includes or is derived from A4. In some embodiments, $X^1$ includes or is derived from A5. In some embodiments, $X^1$ includes or is derived from A6. In some embodiments, $X^1$ includes or is derived from A7. In some embodiments, $X^1$ includes or is derived from A8. In some embodiments, $X^1$ includes or is derived from A9. In some embodiments, $X^1$ includes or is derived from A10. In some embodiments, $X^1$ includes or is derived from A11. In some embodiments, $X^1$ includes or is derived from A12. In some embodiments, $X^1$ includes or is derived from A13. In some embodiments, $X^1$ includes or is derived from A14. In some embodiments, $X^1$ includes or is derived from A15. In some embodiments, $X^1$ includes or is derived from A16. In some embodiments, $X^1$ includes or is derived from A17. In some embodiments, $X^1$ includes or is derived from A18. In some embodiments, $X^1$ includes or is derived from A19. In some embodiments, $X^1$ includes or is derived from A20. In some embodiments, $X^1$ includes or is derived from A21. In some embodiments, $X^1$ includes or is derived from A22. In some embodiments, $X^1$ includes or is derived from A23. In some embodiments, $X^1$ includes or is derived from A24. In some embodiments, $X^1$ includes or is derived from A25. In some embodiments, $X^1$ includes or is derived from A26. In some embodiments, $X^1$ includes or is derived from A27. In some embodiments, $X^1$ includes or is derived from A28. In some embodiments, $X^1$ includes or is derived from A29. In some embodiments, $X^1$ includes or is derived from A30. In some embodiments, $X^1$ includes or is derived from A31. In some embodiments, $X^1$ includes or is derived from A32.

In some embodiments, each of $A^1$ and $A^2$ includes or is derived from the same polyol, e.g., a polyol selected from one of A1-A32. In some embodiments, each of $A^1$ and $A^2$ In some embodiments, the precursor to each of $A^1$ and $A^2$ is independently selected from one of A1, A2, A3, A4, A5, A6, A7, A8, A9, A10, A11, A12, A13, A4, A15, A16, A17, A18, A19, A20, A21, A22, A23, A24, A25, A26, A27, A28, A29, A30, A31, and A32, e.g., as depicted in FIG. 1B. It is to be understood that when the precursor to $A^1$ or $A^2$ is one of the polyols in the above-noted group selected from A1-A32, $B^1$ or $B^2$ is connected to one of the oxygen atoms of the hydroxyl groups in said polyols.

In some embodiments, $X^1$ includes or is derived from a polyol selected from one of A3, A4, A5, A9, A10, A11, A12, includes or is derived from a different polyol, e.g., a polyol selected from one of A1-A32.

In some embodiments, one or both of $A^1$ and $A^2$ is represented by a compound of Formula (II-d):

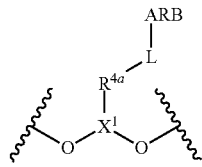

Formula (II-d)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl or ($C_1$-$C_6$ alkylene)-O-L-ARB;

L is a bond or a linker, e.g., a linker as described herein;

ARB is an angiotensin II receptor blocker, e.g., losartan, valsartan, telmisartan, candesartan, eprosartan, irbesartan, azilsartan, EXP-3174, olmesartan, or a prodrug or active metabolite thereof;

$R^6$ is hydrogen or $C_1$-$C_6$ alkyl; and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-ARB, ($C_1$-$C_6$ alkylene)-O-L-ARB, ($C_1$-$C_6$ alkylene)-O—($C_1$-$C_6$ alkylene)-O-L-ARB, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-ARB, e.g., ($CH_2$—O-L-ARB).

In some embodiments, L is a bond. In some embodiments, L is a linker. In some embodiments, L is a linker as described herein, e.g., a polyacetal polymer.

In some embodiments, ARB is losartan, valsartan, telmisartan, candesartan, eprosartan, irbesartan, azilsartan, EXP-3174, olmesartan, or a prodrug or active metabolite thereof. In some embodiments, ARB is losartan. In some embodiments, ARB is valsartan. In some embodiments, ARB is telmisartan. In some embodiments, ARB is candesartan. In some embodiments, ARB is eprosartan. In some embodiments, ARB is azilsartan. In some embodiments, ARB is EXP-3174. In some embodiments, ARB is olmesartan. In some embodiments, ARB is azilsartan medoxomil. In some embodiments, ARB is candesartan cilexetil. In some embodiments, ARB is olmesartan medoxomil. In some embodiments, ARB is a compound shown in FIG. 23.

In some embodiments, one or both of $A^1$ and $A^2$ is represented by a compound of Formula (II-e), Formula (II-f), Formula (II-g), Formula (II-h), or Formula (II-i):

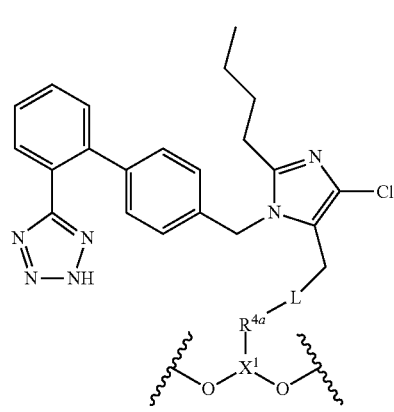

Formula (II-e)

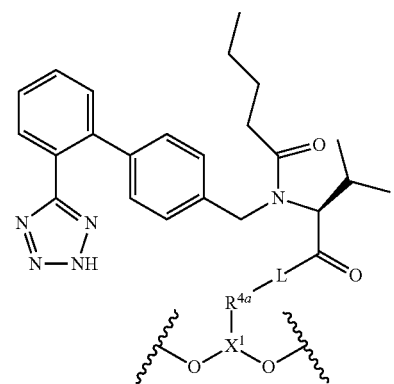

Formula (II-f)

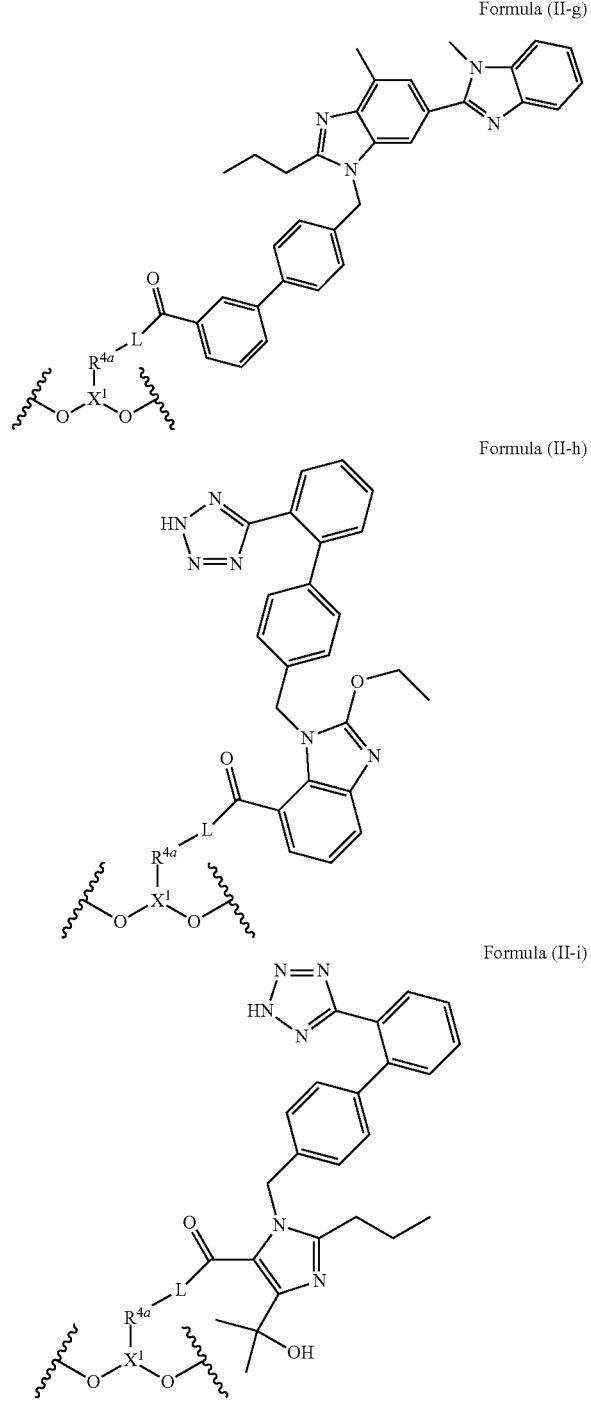

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl, ($C_1$-$C_6$ alkylene)-O-L-losartan, ($C_1$-$C_6$ alkylene)-O-L-valsartan, ($C_1$-$C_6$ alkylene)-O-L-telmisartan, ($C_1$-$C_6$ alkylene)-O-L-candesartan, or ($C_1$-$C_6$ alkylene)-O-L-olmesartan;

L is a linker, e.g., a linker as described herein;

$R^6$ is hydrogen or $C_1$-$C_6$ alkyl; and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-losartan, O-L-valsartan, O-L-telmisartan, O-L-candesartan, O-L-olmesartan, ($C_1$-$C_6$ alkylene)-O-L-losartan, ($C_1$-$C_6$ alkylene)-O-L-valsartan, ($C_1$-$C_6$ alkylene)-O-L-telmisartan, ($C_1$-$C_6$ alkylene)-O-L-candesartan, ($C_1$-$C_6$ alkylene)-O-L-olmesartan, ($C_1$-$C_6$ alkylene)-O—($C_1$-$C_6$ alkylene)-O-L-losartan, ($C_1$-$C_6$ alkylene)-O—($C_1$-$C_6$ alkylene)-O-L-valsartan, ($C_1$-$C_6$ alkylene)-O—($C_1$-$C_6$ alkylene)-O-L-telmisartan, ($C_1$-$C_6$ alkylene)-O—($C_1$-$C_6$ alkylene)-O-L-candesartan, ($C_1$-$C_6$ alkylene)-O—($C_1$-$C_6$ alkylene)-O-L-olmesartan, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-losartan, e.g., ($CH_2$—O-L-losartan). In some embodiments, $R^{4b}$ is ($C_1$-$C_6$ alkylene)-O-L-valsartan, e.g., ($CH_2$—O-L-valsartan). In some embodiments, $R^{4b}$ is ($C_1$-$C_6$ alkylene)-O-L-telmisartan, e.g., ($CH_2$—O-L-telmisartan). In some embodiments, $R^{4b}$ is ($C_1$-$C_6$ alkylene)-O-L-candesartan, e.g., ($CH_2$—O-L-candesartan). In some embodiments, $R^{4b}$ is ($C_1$-$C_6$ alkylene)-O-L-olmesartan, e.g., ($CH_2$—O-L-olmesartan).

In some embodiments, L is a bond. In some embodiments, L is a linker. In some embodiments, L is a linker as described herein, e.g., a polyacetal polymer.

In some embodiments, one or both of $A^1$ and $A^2$ is represented by a compound of Formula (II-j):

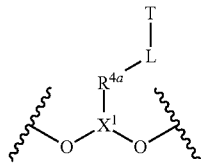

Formula (II-j)

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, and heterocyclyl is optionally substituted with 1-6 $R^{4b}$;

$R^{4a}$ is $C_1$-$C_6$ alkyl, $C_2$-$C_6$ alkenyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-C(O)—($C_1$-$C_6$ alkylene)-O, ($C_1$-$C_6$ alkylene)-OC(O)—($C_1$-$C_6$ alkylene)-O, ($C_1$-$C_6$ alkylene)-C(O)O—($C_1$-$C_6$ alkylene)-O, ($C_1$-$C_6$ alkylene)-OC(O)O—($C_1$-$C_6$ alkylene)-O, ($C_1$-$C_6$ alkylene)-NR$^6$—($C_1$-$C_6$ alkylene)-O—, ($C_1$-$C_6$ alkylene)-C(O)NR$^6$—($C_1$-$C_6$ alkylene)-O, or ($C_1$-$C_6$ alkylene)-NR$^6$C(O)—($C_1$-$C_6$ alkylene)-O, wherein each alkyl, alkenyl, alkynyl, heteroalkyl, or alkylene is optionally substituted with 1-6 $R^7$;

each $R^{4b}$ is independently $C_1$-$C_6$ alkyl, ($C_1$-$C_6$ alkylene)-O-L-T, or ($C_1$-$C_6$ alkylene)-O-L-ARB;

L is a bond or a linker, e.g., a linker as described herein;

T is a targeting moiety, e.g., mannose-6-phosphate;

ARB is an angiotensin II receptor blocker, e.g., losartan, valsartan, telmisartan, candesartan, eprosartan, irbesartan, azilsartan, EXP-3174, olmesartan, or a prodrug or active metabolite thereof;

$R^6$ is hydrogen or $C_1$-$C_6$ alkyl; and each $R^7$ is independently $C_1$-$C_6$ alkyl, $C_2$-$C_6$ alkenyl, $C_2$-$C_6$ alkynyl, $C_1$-$C_6$ heteroalkyl, halo, O-L-T, ($C_1$-$C_6$ alkylene)-O-L-T, ($C_1$-$C_6$ alkylene)-O—($C_1$-$C_6$ alkylene)-O-L-T, O-L-ARB, ($C_1$-$C_6$ alkylene)-O-L-ARB, ($C_1$-$C_6$ alkylene)-O—($C_1$-$C_6$ alkylene)-O-L-ARB, cyano, cyclyl, heterocyclyl, aryl, or heteroaryl.

In some embodiments, $X^1$ is $C_1$-$C_{12}$ alkylene, $C_1$-$C_{12}$ heteroalkylene, $C_1$-$C_8$ cyclyl, or $C_1$-$C_8$ heterocyclyl. In some embodiments, $X^1$ is $C_1$-$C_{12}$ alkylene or $C_1$-$C_{12}$ heteroalkylene. In some embodiments, $X^1$ is $C_1$-$C_6$ alkylene. In some embodiments, $X^1$ is $C_1$-$C_{12}$ heteroalkylene.

In some embodiments, $X^1$ is $C_3$-$C_8$ cyclyl or $C_3$-$C_8$ heterocyclyl. In some embodiments, $X^1$ is $C_3$-$C_6$ cyclyl or $C_3$-$C_6$ heterocyclyl. In some embodiments, $X^1$ is $C_3$-$C_6$ cyclyl. In some embodiments, $X^1$ is cyclopropyl, cyclobutyl, cyclopentyl, or cyclohexyl. In some embodiments, $X^1$ is cyclopentyl or cyclohexyl. In some embodiments, $X^1$ is cyclopentyl or cyclohexyl. In some embodiments, $X^1$ is cyclohexyl.

In some embodiments, $R^{4a}$ is $C_1$-$C_6$ alkyl, $C_1$-$C_6$ heteroalkyl, O, ($C_1$-$C_6$ alkylene)-O, ($C_1$-$C_6$ alkylene)-O—($C_1$-$C_6$ alkylene)-O, ($C_1$-$C_6$ alkylene)-OC(O)—($C_1$-$C_6$ alkylene)-O, or ($C_1$-$C_6$ alkylene)-OC(O)O—($C_1$-$C_6$ alkylene)-O, wherein each alkyl, heteroalkyl, or alkylene is optionally substituted with 1-6 $R^7$. In some embodiments, $R^{4a}$ is $C_1$-$C_6$ alkyl (e.g., $CH_3$ or $CH_2CH_3$). In some embodiments, $R^{4a}$ is O. In some embodiments, $R^{4a}$ is ($C_1$-$C_6$ alkylene)-O (e.g., $CH_2O$ or $CH_2CH_2O$). In some embodiments, $R^{4a}$ is ($C_1$-$C_6$ alkylene)-O—($C_1$-$C_6$ alkylene)-O (e.g., $CH_2OCH_2CH_2O$ or $CH_2CH_2OCH_2CH_2O$). In some embodiments, $R^{4a}$ is ($C_1$-$C_6$ alkylene)-OC(O)—($C_1$-$C_6$ alkylene)-O (e.g., $CH_2OC(O)CH_2O$, $CH_2CH_2OC(O)CH_2O$, $CH_2OC(O)CH_2CH_2O$, $CH_2OC(O)CH_2CH_2CH_2O$, $CH_2CH_2OC(O)CH_2CH_2O$, $CH_2CH_2OC(O)CH_2CH_2CH_2O$, $CH_2OC(O)CH(CH_3)O$, or $CH_2CH_2OC(O)CH(CH_3)O$). In some embodiments, $R^{4a}$ is ($C_1$-$C_6$ alkylene)-OC(O)O—($C_1$-$C_6$ alkylene)-O (e.g., $CH_2OC(O)OCH_2CH_2O$).

In some embodiments, $R^{4b}$ is $C_1$-$C_6$ alkyl (e.g., $CH_3$, $CH_2CH_3$). In some embodiments, $R^{4b}$ is ($C_1$-$C_6$ alkylene)-O-L-T, e.g., ($CH_2$—O-L-T). In some embodiments, $R^{4b}$ is ($C_1$-$C_6$ alkylene)-O-L-ARB, e.g., ($CH_2$—O-L-ARB).

In some embodiments, L is a bond. In some embodiments, L is a linker. In some embodiments, L is a linker as described herein, e.g., a polyacetal polymer.

In some embodiments, T is a targeting moiety described herein. In some embodiments, T is mannose-6-phosphate.

In some embodiments, ARB is losartan, valsartan, telmisartan, candesartan, eprosartan, irbesartan, azilsartan, EXP-3174, olmesartan, or an analogue or derivative thereof (e.g., a prodrug or active metabolite thereof). In some embodiments, ARB is losartan. In some embodiments, ARB is valsartan. In some embodiments, ARB is telmisartan. In some embodiments, ARB is candesartan. In some embodiments, ARB is eprosartan. In some embodiments, ARB is azilsartan. In some embodiments, ARB is EXP-3174. In some embodiments, ARB is olmesartan. In some embodiments, ARB is azilsartan medoxomil. In some embodiments, ARB is candesartan cilexetil. In some embodiments, ARB is olmesartan medoxomil. In some embodiments, ARB is a compound shown in FIG. 23.

In some embodiments, each of $A^1$ and $A^2$ does not independently include, or is independently not derived from, tri(methylol)ethane. In some embodiments, each of $A^1$ and $A^2$ does not independently include, or is not independently derived from, tri(methylol)ethane and the polymer of Formula (I) is greater than about 5 kDa in size. In some embodiments, each of $A^1$ and $A^2$ does not independently include, or is not independently derived from, tri(methylol) ethane and the polymer of Formula (I) is greater than about 10 kDa in size.

In some embodiments, each of $A^1$ and $A^2$ independently includes, or is independently derived from, tri(methylol) ethane. In some embodiments, each of $A^1$ and $A^2$ independently includes, or is independently derived from, tri(methylol)ethane and the polymer of Formula (I) is greater than about 5 kDa in size. In some embodiments, each of $A^1$ and $A^2$ independently includes, or is independently derived from, tri(methylol)ethane and the polymer of Formula (I) is greater than about 10 kDa in size.

In some embodiments of a polymer of Formula (I), each of $B^1$ and $B^2$ is independently heteroalkyl or aryloxy, each of which may be optionally substituted with 1-5 $R^1$. In some embodiments, each of $B^1$ and $B^2$ is independently heteroalkyl, each of which may be optionally substituted with 1-5 $R^1$. In some embodiments, each of $B^1$ and $B^2$ is independently $C_1$-$C_{20}$ heteroalkyl, each of which may be optionally substituted with 1-5 $R^1$. In some embodiments, each of $B^1$ and $B^2$ is the same. In some embodiments, each of $B^1$ and $B^2$ is the different.

In some embodiments, each of $B^1$ and $B^2$ is independently represented by a moiety of Formula (III):

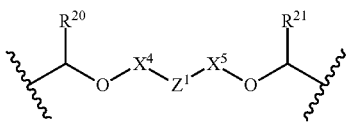

Formula (III)

wherein:

$Z^1$ is O, $C_3$-$C_8$ cyclyl, $C_3$-$C_8$ heterocyclyl, or $C(R^{22})(R^{23})$, wherein each of cyclyl and heterocyclyl is optionally substituted with 1-4 $R^{25}$;

each of $X^4$ and $X^5$ is independently $C_1$-$C_6$ alkylene, $C_2$-$C_6$ alkenylene, $C_2$-$C_6$ alkynylene, $C_1$-$C_6$ heteroalkylene, ($C_1$-$C_6$ alkylene)-O—($C_1$-$C_6$ alkylene), ($C_1$-$C_6$ alkylene)-C(O)—($C_1$-$C_6$ alkylene), ($C_1$-$C_6$ alkylene)-OC(O)—($C_1$-$C_6$ alkylene), ($C_1$-$C_6$ alkylene)-C(O)O—($C_1$-$C_6$ alkylene), ($C_1$-$C_6$ alkylene)-OC(O)O—($C_1$-$C_6$ alkylene), ($C_1$-$C_6$ alkylene)-NR$^{24}$—($C_1$-$C_6$ alkylene), ($C_1$-$C_6$ alkylene)-C(O)NR$^{24}$—($C_1$-$C_6$ alkylene), or ($C_1$-$C_6$ alkylene)-NR$^{24}$C(O)—($C_1$-$C_6$ alkylene), wherein each alkylene, alkenylene, alkynylene, or heteroalkylene is optionally substituted with 1-6 $R^{25}$;

each of $R^{20}$ and $R^{21}$ is independently $C_1$-$C_6$ alkyl, OR$^{26}$, cyclyl, heterocyclyl;

each of $R^{22}$ and $R^{23}$ is independently hydrogen, $C_1$-$C_6$ alkyl, OR$^{26}$, ($C_1$-$C_6$ alkylene)-OR$^{26}$, halo, cyclyl, heterocyclyl, aryl, heteroaryl, wherein each alkyl, alkylene, cyclyl, heterocyclyl, aryl, or heteroaryl is optionally substituted with 1-6 $R^{27}$;

each $R^{25}$ and $R^{27}$ is $C_1$-$C_6$ alkyl, $C_1$-$C_6$ heteroalkyl, halo, cyano, cyclyl, or heterocyclyl, and $R^{26}$ is hydrogen, $C_1$-$C_6$ alkyl, $C_1$-$C_6$ alkenyl, $C_1$-$C_6$ alkynyl, cyclyl, heterocyclyl, aryl, heteroaryl, arylalkyl, heteroarylalkyl, a linker, an agent, a targeting moiety, a protecting group, or a branching point, wherein each alkyl, cyclyl, heterocyclyl, aryl, heteroaryl, arylalkyl, heteroarylalkyl is optionally substituted with 1-6 $R^{28}$; and each $R^{28}$ is independently $C_1$-$C_6$ alkyl, $C_1$-$C_6$ heteroalkyl, halo, cyano, cyclyl, or heterocyclyl.

In some embodiments, $Z^1$ is O.

In some embodiments, $Z^1$ is $C_3$-$C_8$ cyclyl or $C_3$-$C_8$ heterocyclyl, each of which is optionally substituted with 1-4 $R^{25}$. In some embodiments, $Z^1$ is $C_3$-$C_6$ cyclyl or $C_3$-$C_6$ heterocyclyl, each of which is optionally substituted with 1-4 $R^{25}$. In some embodiments, $Z^1$ is $C_3$-$C_6$ cyclyl, optionally substituted with 1-4 $R^{25}$. In some embodiments, $Z^1$ is cyclopropyl, cyclobutyl, cyclopentyl, or cyclohexyl, each of which is optionally substituted with 1-4 $R^{25}$. In some embodiments, $Z^1$ is cyclopentyl, or cyclohexyl, each of which is optionally substituted with 1-4 $R^{25}$. In some embodiments, $Z^1$ is cyclohexyl, optionally substituted with 1-4 $R^{25}$. In some embodiments, $Z^1$ is cyclohexyl.

In some embodiments, $Z^1$ is $C(R^{22})(R^{23})$. In some embodiments, $Z^1$ is $C(R^{23})(R^{24})$ and each of $R^{22}$ and $R^{23}$ is independently hydrogen, $C_1$-$C_6$ alkyl, or ($C_1$-$C_6$ alkylene)-OR$^{26}$. In some embodiments, each of $R^{22}$ and $R^{23}$ is independently hydrogen. In some embodiments, each of $R^{22}$ and $R^{23}$ is independently hydrogen or $C_1$-$C_6$ alkyl, e.g., CH$_3$. In some embodiments, each of $R^{22}$ and $R^{23}$ is independently hydrogen. In some embodiments, each of $R^{22}$ and $R^{23}$ is independently $C_1$-$C_6$ alkyl, e.g., CH$_3$. In some embodiments, $R^{22}$ is hydrogen and $R^{23}$ is independently $C_1$-$C_6$ alkyl, e.g., CH$_3$. In some embodiments, each of $R^{22}$ and $R^{23}$ is independently ($C_1$-$C_6$ alkylene)-OR$^{26}$. In some embodiments, each of $R^{22}$ and $R^{23}$ is independently ($C_1$-$C_2$ alkylene)-OR$^{26}$. In some embodiments, each of $R^{22}$ and $R^{23}$ is independently ($C_1$-$C_2$ alkylene)-OR$^{26}$, and $R^{26}$ is $C_2$-$C_6$ alkenyl (e.g., CH=CH$_2$) or a branching point. In some embodiments, $R^{22}$ is hydrogen or $C_1$-$C_6$ alkyl (e.g., CH$_3$), $R^{23}$ is ($C_1$-$C_2$ alkylene)-OR$^{26}$, and $R^{26}$ is $C_2$-$C_6$ alkenyl (e.g., CH=CH$_2$) or a branching point. In some embodiments, $R^{22}$ is $C_1$-$C_6$ alkyl (e.g., CH$_3$), $R^{23}$ is ($C_1$-$C_2$ alkylene)-OR$^{26}$, and $R^{26}$ is $C_2$-$C_6$ alkenyl (e.g., CH=CH$_2$) or a branching point.

In some embodiments, each of $X^4$ and $X^5$ is independently $C_1$-$C_6$ alkylene, wherein alkylene is optionally substituted with 1-6 $R^{25}$. In some embodiments, each of $X^4$ and $X^5$ is independently $C_1$-$C_4$ alkylene, wherein alkylene is optionally substituted with 1-6 $R^{25}$. In some embodiments, each of $X^4$ and $X^5$ is independently $C_1$-$C_2$ alkylene, wherein alkylene is optionally substituted with 1-6 $R^{25}$. In some embodiments, each of $X^4$ and $X^5$ is independently $C_1$-$C_2$ alkylene (e.g., CH$_2$, CH$_2$CH$_2$).

In some embodiments, each of $R^{20}$ and $R^{21}$ is independently $C_1$-$C_6$ alkyl or OR$^{26}$. In some embodiments, each of $R^{20}$ and $R^{21}$ is independently $C_1$-$C_6$ alkyl. In some embodiments, each of $R^{20}$ and $R^{21}$ is independently $C_1$-$C_4$ alkyl. In some embodiments, each of $R^{20}$ and $R^{21}$ is independently $C_1$-$C_2$ alkyl, e.g., CH$_3$. In some embodiments, each of $R^{20}$ and $R^{21}$ is independently OR$^{26}$. In some embodiments, each of $R^{20}$ and $R^{21}$ is independently OR$^{26}$, and $R^{26}$ is $C_2$-$C_6$ alkenyl (e.g., CH=CH$_2$) or a branching point.

In some embodiments of a polymer of Formula (I), each of $B^1$ and $B^2$ is independently hydrophobic. In some embodiments, each of $B^1$ and $B^2$ has a partition coefficient (c Log P) value greater than about −2.0. In some embodiments, each of $B^1$ and $B^2$ has a c Log P value greater than about −1.5, e.g., about −1.4, about −1.3, about −1.2, about −1.1, about −1.0, about −0.9, about −0.8, about −0.7, about −0.6, about −0.5, about −0.4, about −0.3, about −0.2, about −0.1, about 0, or higher. In some embodiments, each of $B^1$ and $B^2$ has a c Log P value between about −1.5 and 2.5. In some embodiments, each of $B^1$ and $B^2$ has a c Log P value greater than about −0.5, e.g., about −0.4, about −0.3, about −0.2, about −0.1, about 0, about 0.1, about 0.2, about 0.3, about 0.4, about 0.5, or higher. In some embodiments, each of $B^1$ and $B^2$ has a c Log P value greater than about 0, e.g., about 0.1, about 0.2, about 0.3, about 0.4, about 0.5, about 0.6, about 0.7, about 0.8, about 0.9, about 1.0, or higher.

In some embodiments, each of $B^1$ and $B^2$ has a linear structure. In some embodiments, each of $B^1$ and $B^2$ has a branched structure. In some embodiments, each of $B^1$ and $B^2$ comprises a protected reactive group, e.g., a protected hydroxyl, a protected carboxylic acid, or a protected amine. In some embodiments, each of $B^1$ and $B^2$ comprises 1, 2, 3, 4, 5, 6, 7, 8, or more protected reactive groups, e.g., a protected hydroxyl, a protected carboxylic acid, or a protected amine.

In some embodiments, each of $B^1$ and $B^2$ is independently represented by a moiety of Formula (III-a):

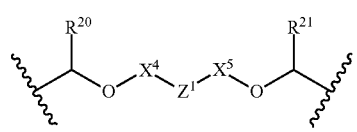

Formula (III-a)

wherein:

$Z^1$ is O, $C_3$-$C_8$ cyclyl, or $C(R^{22})(R^{23})$;

each of $X^4$ and $X^5$ is independently $C_1$-$C_6$ alkylene;

each of $R^{20}$ and $R^{21}$ is independently $C_1$-$C_6$ alkyl or $OR^{20}$;

each of $R^{22}$ and $R^{23}$ is independently hydrogen, $C_1$-$C_6$ alkyl, or ($C_1$-$C_6$ alkylene)-$OR^{26}$; and each $R^{26}$ is $C_1$-$C_6$ alkyl, $C_2$-$C_6$ alkenyl, a linker, an agent, a targeting moiety, a protecting group, or a branching point.

In some embodiments, $Z^1$ is O.

In some embodiments, $Z^1$ is $C_3$-$C_6$ cyclyl. In some embodiments, $Z^1$ is cyclopentyl, or cyclohexyl. In some embodiments, $Z^1$ is cyclohexyl.

In some embodiments, $Z^1$ is $C(R^{22})(R^{23})$. In some embodiments, $Z^1$ is $C(R^{23})(R^{24})$ and each of $R^{22}$ and $R^{23}$ is independently hydrogen. In some embodiments, each of $R^{22}$ and $R^{23}$ is independently hydrogen or $C_1$-$C_6$ alkyl, e.g., $CH_3$. In some embodiments, each of $R^{22}$ and $R^{23}$ is independently hydrogen. In some embodiments, each of $R^{22}$ and $R^{23}$ is independently $C_1$-$C_6$ alkyl, e.g., $CH_3$. In some embodiments, $R^{22}$ is hydrogen and $R^{23}$ is independently $C_1$-$C_6$ alkyl, e.g., $CH_3$. In some embodiments, each of $R^{22}$ and $R^{23}$ is independently ($C_1$-$C_6$ alkylene)-$OR^{26}$. In some embodiments, each of $R^2$ and $R^{23}$ is independently ($C_1$-$C_2$ alkylene)-$OR^{26}$. In some embodiments, each of $R^{22}$ and $R^{23}$ is independently ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is hydrogen or $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point. In some embodiments, $R^{22}$ is $C_1$-$C_6$ alkyl (e.g., $CH_3$), $R^{23}$ is ($C_1$-$C_2$ alkylene)-$OR^{26}$, and $R^{26}$ is $C_2$-$C_6$ alkenyl (e.g., $CH=CH_2$) or a branching point.

In some embodiments, each of $X^4$ and $X^5$ is independently $C_1$-$C_4$ alkylene. In some embodiments, each of $X^4$ and $X^5$ is independently $C_1$-$C_2$ alkylene. In some embodiments, each of $X^4$ and $X^5$ is independently $C_1$-$C_2$ alkylene (e.g., $CH_2$, $CH_2CH_2$).

In some embodiments, each of $R^{20}$ and $R^{21}$ is independently $C_1$-$C_6$ alkyl. In some embodiments, each of $R^2$ and $R^{21}$ is independently $C_1$-$C_4$ alkyl. In some embodiments, each of $R^{20}$ and $R^{21}$ is independently $C_1$-$C_2$ alkyl, e.g., $CH_3$. In some embodiments, each of $R^2$ and $R^{21}$ is independently $OR^{26}$. In some embodiments, each of $R^{20}$ and $R^{21}$ is independently $OR^{26}$, and $R^{26}$ is $C_2$-$C_6$ alkenyl (e.g., $CH=CH_2$) or a branching point.

In some embodiments, the precursor of each of $B^1$ to $B^2$ is independently selected from the following vinyl ethers:

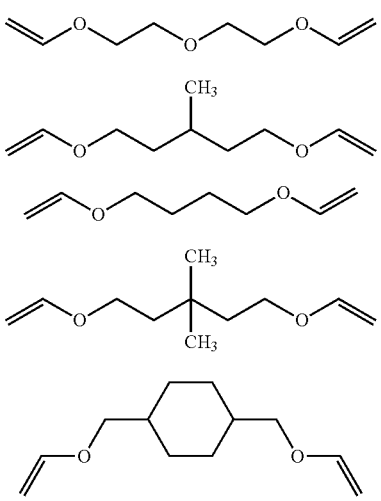

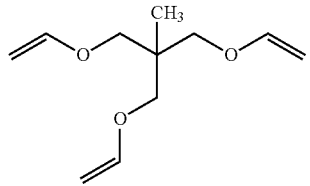

In some embodiments, the precursor to each of $B^1$ and $B^2$ is independently selected from one of B1, B2, B3, B4, B5, and B6, e.g., as depicted in FIG. 1C. It is to be understood that when the precursor to $B^1$ or $B^2$ is one of the vinyl ethers in the above-noted group selected from B1-B6, $A^1$ or $A^2$ and $C^1$ or $C^2$ is connected at the (CH) group of the vinyl moiety in each of said vinyl ethers.

In some embodiments, each of $B^1$ and $B^2$ is independently represented by a moiety of Formula (III-b):

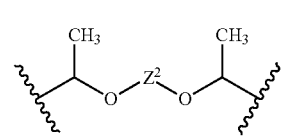

Formula (III-b)

wherein:

$Z^2$ includes or is derived from any of the vinyl ethers shown in FIG. 1C, e.g., a vinyl ether selected from one of B1, B2, B3, B4, B5, or B6, and two of the hydrogen atoms of the vinyl groups are replaced linkage indicated in Formula (III-b).

In some embodiments, $Z^2$ includes or is derived from B1. In some embodiments, $Z^2$ includes or is derived from B2. In some embodiments, $Z^2$ includes or is derived from B3. In some embodiments, $Z^2$ includes or is derived from B4. In some embodiments, $Z^2$ includes or is derived from B5. In some embodiments, $Z^2$ includes or is derived from B6.

In some embodiments, each of $B^1$ and $B^2$ includes or is derived from the same vinyl ether, e.g., a vinyl ether selected from one of B1-B6. In some embodiments, each of $B^1$ and $B^2$ includes or is derived from a different vinyl ether, e.g., a vinyl ether selected from one of B1-B6.

In some embodiments of a polymer of Formula (I), each of $C^1$ and $C^2$ is heteroalkyl, optionally substituted with 1-6 $R^3$. In some embodiments, each of $C^1$ and $C^2$ is $C_1$-$C_{20}$ heteroalkyl, optionally substituted with 1-6 $R^3$. In some embodiments, each of $C^1$ and $C^2$ is $C_1$-$C_{10}$ heteroalkyl. In some embodiments, each of C1 and $C^2$ is $C_1$-$C_{10}$ heteroalkyl. In some embodiments, each of $C^1$ and $C^2$ is $C_1$-$C_{10}$ heteroalkyl, e.g., an oxygen-containing $C_1$-$C_4$ heteroalkyl and/or an amine-containing heteroalkyl. In some embodiments, each of $C^1$ and $C^2$ comprises a polyethylene glycol (PEG), a polyethylene oxide (PEO), a polypropylene glycol (PPG), a polyglycerol (PG), a poloxamine (POX), a polybutylene oxide (PBO), polylactic acid (PLA), polyglycolic acid (PGA), poly(lactic-co-glycolic acid) (PLGA), polycaprolactone (PCL), polydioxanone (PDO), a polyanhydride, a polyacrylide, a polyvinyl, or a polyorthoester.

In some embodiments, each of $C^1$ and $C^2$ comprises a polyethylene glycol (PEG). In some embodiments, each of $C^1$ and $C^2$ comprises a polyethylene glycol (PEG) or a polyethylene oxide (PEO). In some embodiments, each of $C^1$ and $C^2$ comprises a polyethylene oxide (PEO) or a polypropylene glycol (PPG). In some embodiments, each of $C^1$ and $C^2$ comprises a polybutylene oxide (PBO).

In some embodiments, each of $C^1$ or $C^2$ has a linear structure, e.g., does not comprise a branching point or cyclic group. In some embodiments, each of $C^1$ or $C^2$ has a branched structure, e.g., comprising at least 1, at least 2, at least 3, at least 4, at least 5, or at least 6 branching points.

In some embodiments, each of $C^1$ or $C^2$ comprises a cyclic structure. In some embodiments, each of $C^1$ or $C^2$ comprises a cyclic structure, e.g., a cyclyl or heterocyclyl group. In some embodiments, each of $C^1$ or $C^2$ comprises a carbohydrate (e.g., a glucose derivative, galactose derivative, mannose derivative, fucose derivative, sialic acid derivative, or other carbohydrate derivative). In some embodiments, each of $C^1$ or $C^2$ comprises a dextran, a cyclodextran, chitosan, or other carbohydrate based moiety.

In some embodiments, each of $C^1$ or $C^2$ is independently about 200 Da to about 20,000 Da in size. In some embodiments, each of $C^1$ or $C^2$ is independently about 200 Da to about 17,500 Da, from about 200 Da to about 15,000 Da, from about 200 Da to about 12,500 Da, from about 200 Da to about 10,000 Da, from about 200 Da to about 9,000 Da, from about 200 Da to about 8,000 Da, from about 200 Da to about 7,000 Da, from about 200 Da to about 6,000 Da, from about 200 Da to about 5,000 Da, from about 200 Da to about 4,000 Da, from about 200 Da to about 3,000 Da, or from about 200 Da to about 2,000 Da in size. In some embodiments, each of $C^1$ or $C^2$ is independently from about 200 Da to about 5,000 Da in size. In some embodiments, each of $C^1$ or $C^2$ is independently from about 200 Da to about 2,000 Da in size.

In some embodiments, each of $C^1$ or $C^2$ is independently about 200 Da to about 2,000 Da in size. In some embodiments, each of $C^1$ or $C^2$ is independently about 200 Da to about 1,750 Da, from about 200 Da to about 1,500 Da, from about 200 to about 1,400 Da, from about 200 to about 1,300 Da, from about 200 to about 1,200, from about 200 to about 1,100, or from about 200 to about 1,000 in size. In some embodiments, each of $C^1$ or $C^2$ is independently about 200 Da to about 900 Da, from about 200 Da to about 800, from about 200 to about 700 Da, from about 200 to about 600 Da, from about 200 to about 500 Da, or from about 200 to about 400 Da. each of $C^1$ or $C^2$ is independently about 400 Da in size In some embodiments, each of $C^1$ or $C^2$ is independently about 200 Da to about 2,000 Da in size. In some embodiments, each of $C^1$ or $C^2$ is independently about 200 Da to about 2,000 Da in size, from about 250 Da to about 1,900 in size, from about 300 Da to about 1,800, from about 350 Da to about 1,700, or from about 400 Da to about 1,600 in size. In some embodiments, each of $C^1$ or $C^2$ is independently about 500 Da to about 1,500 in size, from about 600 Da to about 1,500 in size, from about 700 Da to about 1,400, from about 800 Da to about 1,300, or from about 900 Da to about 1,200 in size. In some embodiments, each of $C^1$ or $C^2$ is independently about 1,000 Da to about 1,200 Da in size. In some embodiments, each of $C^1$ or $C^2$ is independently about 1,000 Da in size.

In some embodiments, each of $C^1$ and $C^2$ is the same. In some embodiments, both of $C^1$ and $C^2$ is from about 200 Da to about 1200 Da, from about 300 Da to about 1100 Da, or from about 400 Da to about 1000 Da in size. In some embodiments, both of $C^1$ and $C^2$ are from about 100 Da to about 500 Da or from about 800 Da to about 1200 Da in size. In some embodiments, both of $C^1$ and $C^2$ are 400 Da or 1000 Da in size.

In some embodiments, each of $C^1$ and $C^2$ is different. In some embodiments, each of $C^1$ and $C^2$ is from about 200 Da to about 1200 Da, from about 300 Da to about 1100 Da, or from about 400 Da to about 1000 Da in size. In some embodiments, one of $C^1$ and $C^2$ is from about 100 Da to about 500 Da and the other of $C^1$ and $C^2$ is from bout 800 Da to about 1200 Da in size. In some embodiments, one of $C^1$ and $C^2$ is about 400 Da in size and the other of $C^1$ and $C^2$ is about 1000 Da in size.

In some embodiments of the polymer of Formula (I), the precursor to each of $C^1$ and $C^1$ is PEG (e.g., polyethylene glycol). In some embodiments, the PEG comprises PEG 100, PEG 200, PEG 300, PEG 400, PEG 500, PEG 600, PEG 800, PEG 1000, PEG 1500, PEG 2000, PEG 2050, PEG 4000, or PEG 6000, also referred to herein as P100, P200, P300, P400, P500, P600, P800, P1000, P1500, P2000, P2050, P4000, and P6000, or any combination thereof. In some embodiments, the PEG comprises P400, P1000, or a combination of P400 and P1000. In some embodiments, the PEG comprises P2050.

In some embodiments of a polymer (e.g., a polymer described herein, e.g., a polymer of Formula (I)), each of m and n independently an integer from 2 to 450, from 2 to 400, from 2 to 350, from 2 to 300, from 2 to 250, from 2 to 200, from 2 to 175, from 2 to 150, from 2 to 125, from 2 to 100, from 2 to 90, from 2 to 80, from 2 to 70, from 2 to 60, from 2 to 50, from 2 to 45, from 2 to 40, from 2 to 35, from 2 to 30, from 2 to 25, from 2 to 20, from 2 to 15, from 2 to 10, or from 2 to 5. In some embodiments, each of m and n independently is an integer from 2 to 250. In some embodiments, each of m and n independently is an integer from 2 to 100. In some embodiments, each of m and n independently is an integer from 2 to 50. In some embodiments, each of m and n independently is an integer from 2 to 25. In some embodiments, each of m and n independently is an integer from 2 to 10. In some embodiments, each of m and n independently is an integer from 10 to 500, from 10 to 250, from 10 to 200, from 10 to 150, from 10 to 100, from 10 to 75, from 10 to 50, or from 10 to 25. In some embodiments, each of m and n independently is an integer from 10 to 50.

In an embodiment, m and n taken together are between 10 and 100, 20 and 80, 20 and 60, or 30 and 60.

In one embodiment, the polymer, e.g., the polyacetal polymer, disclosed herein is pH sensitive. As used herein, the term "pH sensitive" in reference to the polyacetal polymers means that the polymer is sufficiently stable at a first pH but is cleaved or degraded at a second pH. In some embodiment, the polymer is cleaved at least 10 times or more, preferably at least 100 times faster at a second pH relative to the first pH. In some embodiments, the polymer degrades at an increased rate at a pH lower than 7.5 relative to degradation at pH 7.5 or higher. In some embodiments, the first pH can be pH about 7.5 or higher. In some embodiments, the second pH can be in the range of about between about 5.0 and about 7.4; pH between about 5.0 and about 7.0; pH between about 5.0 and 6.5; pH between about 5.0 and 6.0. In some embodiments, the second pH can be between about 5.9 and 6.2. In some embodiments, the second pH can be between about 5.5 and 6.5.

In the various aspects disclosed herein, the polyacetal polymers can be conjugated with a polyethylene glycol (PEG).

Linkers

As used herein, the term "pH sensitive linker" means a linker which is sufficiently stable at a first pH, but which is cleaved at a second pH to release the two parts the linker is holding together. In one embodiment, the pH sensitive linker is cleaved at least 10 times or more, preferably at least 100 times faster at a second pH relative to the first pH. In some embodiments, the first pH can be pH about 7.5 or higher. In some embodiments, the second pH is in the range of about between about 5.0 and about 7.4; pH between about 5.0 and about 7.0; pH between about 5.0 and 6.5; pH between about 5.0 and 6.0. In some embodiments, the second pH can be between about 5.9 and 6.2. In some embodiments, the second pH can be between about 5.5 and 6.5.

The pH sensitive linker can be selected via high-throughput strategy. The sensitivity can be tuned based on the variation of chemical structures. For example, in some embodiments, the linker is sensitive to pH between about 5.0 and about 7.4. In some embodiments, the linker is sensitive to pH between about 5.0 and about 7.0. In some embodiments, the linker is sensitive to pH between about 5.0 and 6.5. In some embodiments, the linker is sensitive to pH between about 5.0 and 5.5. In some embodiments, the linker is sensitive to pH between about 5.9 and 6.2. In some embodiments, the linker is sensitive to pH between about 5.5 and 6.5.

In some embodiments, the linker is sensitive to a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In some embodiments of the various aspects disclosed herein, the pH sensitive linker can be an acetal or ketal group, anhydride group, a silyl ether group, a combination of acetal or ketal with ester group, an oligo-acetal or oligo-ketal group, a combination of the oligo-ketal and silyl ether group, a combination of the oligo-ketal and vinyl ether group. The pH sensitive linker can be also a combination of acetal or ketal with cis-aconityl, hydrazine, oxime, imidazole or trityl groups in order to fine tune the pH sensitivity.

In some embodiments, the linker comprises a compound of Formula (VI):

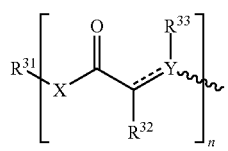

Formula (VI)

wherein:

$R^{31}$ is an agent, e.g., a therapeutic agent or diagnostic agent (e.g., an AHCM), or a targeting moiety (e.g., as described herein);

X is O or S;

$R^{32}$ is H or optionally substituted alkyl, $C_2$-$C_6$ alkenyl, cycloalkyl, or heterocyclyl;

Y is C, CH, N, O or S;

$R^{33}$ is —C(O)OR$^a$, or optionally substituted alkyl, $C_2$-$C_6$ alkenyl, cycloalkyl, heterocyclyl, aryl, or heteroaryl;

$R^a$ is H or optionally substituted alkyl;

n is an integer between 1 and 20;

wherein when Y is CH, N, O, or S, ==== represents a single bond;

when ==== represents a double bond, it may exist in either the E or Z configuration; and when Y is O or S, $R^{33}$ is absent.

In some embodiments, X is O. In some embodiments, X is S.

In some embodiments, $R^{32}$ is H. In some embodiments, $R^{32}$ is alkyl. In some embodiments, $R^{32}$ is methyl or ethyl.

In some embodiments, Y is C. In some embodiments, Y is CH. In some embodiments, Y is N, O, or S.

In some embodiments, $R^{33}$ is —C(O)OR$^a$, wherein $R^a$ is H or alkyl. In some embodiments, when Y is C or CH, $R^{33}$ is —C(O)OR$^a$. In some embodiments, when Y is C or CH, $R^{33}$ is —C(O)OR$^a$, wherein $R^a$ is H or alkyl. In some embodiments, when Y is N, O, or S, $R^{33}$ is alkyl, $C_2$-$C_6$ alkenyl, cycloalkyl, heterocyclyl, aryl, or heteroaryl. In some embodiments, when Y is N, O, or S, $R^{33}$ is alkyl. In some embodiments, when Y is N, O, or S, $R^{33}$ is methyl or ethyl. In some embodiments, when Y is CH, O, or S, $R^{33}$ is absent. In some embodiments, when Y is C, ==== represents a double bond. In some embodiments, when ==== represents a double bond, it may exist in either the E or Z configuration. In some embodiments, when Y is CH, N, O, or S, ==== represents a single bond.

In some embodiments, the linker is a compound of Formula (VII):

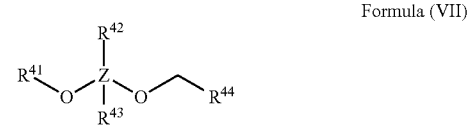

Formula (VII)

wherein:

$R^{41}$ is an agent, e.g., a therapeutic agent or diagnostic agent (e.g., an AHCM), or a targeting moiety (e.g., as described herein);

Z is C or Si;

each of $R^{42}$ or $R^{43}$ is independently alkyl, cycloalkyl, or heterocyclyl, or one of $R^{42}$ or $R^{43}$ is H; or $R^{42}$ and $R^{43}$ taken together with the Z atom they are attached to form a 4- to 8-membered cycloalkyl or heterocyclyl;

$R^{44}$ is alkyl, alkenyl, alkynyl, cycloalkyl, heterocyclyl, aryl, heteroaryl, or —C(O)NR$^c$R$^d$, —NR$^c$C(O)R$^e$—, —NR$^c$C(O)OR$^f$—, or $R^{44}$ taken together with the carbon atom it is attached to form a 5- to 8-membered ring with $R^{42}$ that encompasses O and Z; and each of R$^c$, R$^d$, R$^e$, or R$^f$ is independently H, or alkyl, cycloalkyl, heterocyclyl, aryl, or heteroaryl.

In some embodiments, Z is C. In some embodiments, Z is Si.

In some embodiments, each of $R^{42}$ or $R^{43}$ is independently alkyl. In some embodiments, each of $R^{42}$ or $R^{43}$ is independently methyl, ethyl, or isopropyl. In some embodiments, $R^{42}$ and $R^{43}$ are taken together with the Z atom to which they are attached to form a 4- to 8-membered cycloalkyl or heterocyclyl.

In some embodiments, $R^{44}$ is alkyl, alkenyl, alkynyl, cycloalkyl, heterocyclyl, aryl, or heteroaryl. In some embodiments, $R^{44}$ is alkyl, or cycloalkyl. In some embodiments, $R^{44}$ is alkyl, e.g., methyl or ethyl. In some embodiments, $R^{44}$ is cycloalkyl, e.g., cyclohexyl. In some embodiments, $R^{44}$ is —C(O)NR$^c$R$^d$, —NR$^c$C(O)R$^e$—, —NR$^c$C(O)OR$^f$—. In some embodiments, $R^{44}$ is —C(O)NR$^c$R$^d$, —NR$^c$C(O)R$^e$—, —NR$^c$C(O)OR$^f$—, wherein R$^c$, R$^d$, or R$^f$ is each independently H or alkyl and R$^e$ is alkyl. In some embodiments, $R^{44}$ is —NR$^c$C(O)R$^e$—, wherein R$^c$ is H or alkyl and R$^e$ is alkyl. In some embodiments, $R^{44}$ taken together with the carbon atom it is attached to forms a 5- to 8-membered ring with $R^{42}$ that encompasses O and Z (wherein e.g., Z is C).

Particles

As used herein, the term "nanoparticle" refers to particle having a particle size of about 0.1 nm to about 1000 nm. Generally, the nanoparticle can be of any shape or form, e.g., spherical, rod, elliptical, cylindrical, capsule, or disc; and these nanoparticles can be part of a network or an aggregate. Generally, the particles disclosed herein have an average size of from about 1 nm to about 500 nm. In some embodiments, the particles have an average size of from about 5 nm to about 100 nm. In some embodiments, the particles have an average size of from about 7.5 nm to about 50 nm. In one embodiment, the nanoparticles have an average size of about 7.5 nm to about 37.5 nm.

As used herein, the term "hydrodynamic diameter" refers to the diameter of the particles in the solution, which includes the actual size and the hydrodynamic water layer.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The particles can be, e.g., monodisperse or polydisperse and the variation in diameter of the particles of a given dispersion can vary. In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1. In some embodiments, the volume diameter of the 90th percentile of the small spherical particles to the volume diameter of the 10th percentile is about 2.1 to about 2.5.

A "narrow size distribution" can also mean that the hydrodynamic diameter distribution has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1. In some embodiments, the volume diameter of the 90th percentile of the small spherical particles to the volume diameter of the 10th percentile is about 2.1 to about 2.5.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In some embodiments, the particle is soluble in water (e.g., hydrophilic). In some embodiments, the particle is soluble in water, and between about 0.1 to about 5 parts water are required to dissolve 1 part particle, or between about 1 part to about 5 parts water are required to dissolve 1 part particle. In some embodiments, the particle is partially soluble in water. In some embodiments, the particle is partially soluble in water, and between about 5 to about 50 parts water are required to dissolve 1 part particle. In some embodiments, the particle is sparingly soluble in water. In some embodiments, the particle is sparingly soluble in water, and between about 25 to about 100 parts water is required to dissolve 1 part particle. In some embodiments, the particle is slightly soluble in water. In some embodiments, the particle is slightly soluble in water, and between 100 to about 1,000 parts water are required to dissolve 1 part particle. In some embodiments, the particle is very slightly soluble in water. In some embodiments, the particle is very slightly soluble in water, and between 1,000 to about 10,000 parts water are required to dissolve 1 part particle. In some embodiments, the particle is substantially insoluble in water (e.g., hydrophobic). In some embodiments, the particle is substantially insoluble in water and greater than about 10,000 parts water are required to dissolve 1 part particle.

The polymers for use in forming the nanoparticles can have a molecular weight of from about 20 kDa to about 1,000 kDa. In some embodiments, the average molecular weight of the polymer used in forming the nanoparticles (e.g., the nanoparticles as described herein) is from about 5 kDa to about 1,000 kDa, (e.g., from about 5 kDa to about 750 kDa, from about 6 kDa about 500 kDa, from about 7 kDa to about 400 kDa, from about 8 kDa to about 300 kDa, from about 9 kDa to about 200 kDa, from about 10 kDa to about 100 kDa, from about 12.5 kDa to about 75 kDa, from about 15 kDa to about 50 kDa). In some embodiments the average molecular weight of the polymer used in forming the nanoparticles (e.g., the nanoparticles as described herein) is from about 20 kDa to about 1,000 kDa, (e.g., from about 30 kDa to about 900 kDa, from about 40 kDa to about 800 kDa, from about 50 kDa to about 750 kDa, from about 80 kDa to about 600 kDa, from about 100 kDa to about 550 kDa, or about 100 kDa, about 200 kDa, about 300 kDa, about 400 kDa, about 500 kDa, about 550 kDa, or about 600 kDa. In some embodiments the average molecular weight of the polymer used in forming the nanoparticles (e.g., the nanoparticles as described herein) is from about 5 kDa to about 100 kDa, (e.g., from about 6 kDa to about 90 kDa, from about 7 kDa about 80 kDa, from about 8 kDa to about 70 kDa, from about 9 kDa to about 60 kDa, from about 10 kDa to about 65 kDa, from about 11 kDa to about 50 kDa, from about 12 kDa to about 45 kDa, from about 13 kDa to about 40 kDa, from about 14 kDa to about 35 kDa, from about 15 kDa to about 30 kDa, from about 15 kDa to about 25 kDa, from about 15 kDa to about 20 kDa). In some embodiments, the average molecular weight of the polymer used in forming the nanoparticles (e.g., the nanoparticles as described herein) is from about 5 kDa to about 50 kDa, (e.g., from about 6 kDa to about 45 kDa, from about 7 kDa about 40 kDa, from about 8 kDa to about 35 kDa, from about 9 kDa to about 30 kDa, from about 10 kDa to about 25 kDa, from about 10 kDa to about 20 kDa, from about 10 kDa to about 15 kDa). In some embodiments, the average molecular weight of the polymer used in forming the nanoparticles (e.g., the nanoparticles as described herein) is from about 5 kDa to about 25 kDa, (e.g., from about 5 kDa to about 20 kDa, from about 5 kDa to about 15 kDa, from about 5 kDa to about 10 kDa, or about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa). In one embodiment, the average molecular weight of the polymer used in a particle (e.g., a micelle or a nanoparticle as described herein) is from about 5 kDa to about 10 kDa. In another embodiment, the average molecular weight of the polymer used in a particle (e.g., a micelle or a nanoparticle as described herein) is from about 10 kDa to about 15 kDa. In another embodiment, the average molecular weight of the polymer used in a particle (e.g., a micelle or a nanoparticle as described herein) is from about 15 kDa to about 25 kDa. In another embodiment, the average molecular weight of the polymer used in a particle (e.g., a micelle or a nanoparticle as described herein) is from about 15 kDa to about 20 kDa.

In some embodiments, nanoparticles can have a molecular weight of about 100 kDa to about 550 kDa. Without limitations, the molecular weight can be the peak average molecular weight (Mp), the number average molecular weight (Mn), or the weight average molecular weight (Mw).

In some embodiments, the nanoparticle disclosed herein further comprises a therapeutic agent, which is not covalently linked to the polymer forming the nanoparticle. In other words, the nanoparticle further comprises a therapeutic agent encapsulated in therein. In some embodiments, the particle encapsulates the therapeutic agent at an efficiency of at least 1%, 5%, 10%, 20%, 30%, 40%, 50%, 60%, 70%, 80%, 90%, 95% or 99%. In some embodiments, the particle encapsulates the therapeutic agent at an efficiency of less than 10%, e.g., less than 9%, less than 8%, less than 7%, less than 6%, less than 5%, less than 4%, or less than 3%. In some embodiments, the particle encapsulates the therapeutic agent at an efficiency of between, or inclusive of 2% to 10%, 3% to 9%, or 4% to 6%.

In some embodiments, the net charge of the particle is neutral. In some embodiments, the net charge of the particle is more positive (or less negative) at an endosomal pH or at the pH at the site of a tumor than at physiological pH. In some embodiments, the net charge of the particle is more positive (or less negative) at a pH in the range of 4-6.5 than at a pH in the range of 7-8. In other embodiments, the net charge of the particle is more positive (or less negative) at a pH of 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5 than at a pH of 7, 7.1, 7.2, 7.3, 7.4, 7.5, 7.6, 7.7, 7.8, 7.9 or 8. In still some other embodiments, the particle is neutral or is negatively charged at physiological pH and is positively charged at an endosomal pH or at the pH at the site of a tumor. In some embodiments, the particle is more positively charged (or less negatively charged) at an endosomal pH or at the pH at the site of a tumor than at physiological pH.

The charge of the particle can be determined at pH in the range of pH 3-pH 9. In some embodiments, the pH is 4, 4.5, 5, 5.5, 6, 6.5, 7, 7.5, 8, 8.5 or 9. In some embodiments, the pH is an endosomal pH or the pH at the site of a tumor. In some embodiments, the pH is in the range of 4-6.5. In other embodiments, the pH is 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4 or 6.5. In other embodiments, the pH is physiological pH. In some embodiments, the pH is in the range of 7-8. In other embodiments, the pH is 7, 7.1, 7.2, 7.3, 7.4, 7.5, 7.6, 7.7, 7.8, 7.9 or 8.

In certain embodiments, the AHCM agents, the microenvironment modulators, the therapy, or any combination thereof, can be packaged in any nanoparticle delivery platform. Alternatively, or in combination, the AHCM agents and/or microenvironment modulators (or nanoparticles comprising the same) can be used (e.g., administered) in combination with any nanoparticle known in the art.

In one embodiment, a pH-sensitive particle disclosed herein can be used in combination with any nanoparticle delivery platform, e.g., any platform as disclosed herein.

Lipid- or oil-based nanoparticles, such as liposomes and solid lipid nanoparticles can be used to deliver agents described herein. DOXIL® is an example of a liposomic nanoparticle. Solid lipid nanoparticles for the delivery on anti-cancer agents are described in Serpe et al. (2004) *Eur. J. Pharm. Bioparm.* 58:673-680 and Lu et al. (20060 *Eur. J. Pharm. Sci.* 28: 86-95. Polymer-based nanoparticles, e.g., PLGA-based nanoparticles can be used to deliver agents described herein. These tend to rely on biodegradable backbone with the therapeutic agent intercalated (with or without covalent linkage to the polymer) in a matrix of polymer. PLGA is a widely used in polymeric nanoparticles, see Hu et al. (2009) J. Control. Release 134:55-61; Cheng et al. (2007) *Biomaterials* 28:869-876, and Chan et al. (2009) *Biomaterials* 30:1627-1634. PEGylated PLGA-based nanoparticles can also be used to deliver anti-cancer agents, see, e.g., Danhhier et al., (2009) *J. Control. Release* 133:11-17, Gryparis et al (2007) *Eur. J. Pharm. Biopharm.* 67:1-8. Metal-based, e.g., gold-based nanoparticles can also be used to deliver anti-cancer agents. Protein-based, e.g., albumin-based nanoparticles can be used to deliver agents described herein. E.g., an agent can be bound to nanoparticles of human albumin. An exemplary anti-cancer agent/protein nanoparticle is Abraxane®, in which paclitaxel is pund to nanoparticles of albumin.

Nanoparticles can employ active targeting, passive targeting or both. Active targeting can rely on inclusion of a ligand that binds with a target at or near a preselected site, e.g., a solid tumor. Passive targeting nanoparticles can diffuse and accumulate at sites of interest, e.g., sites characterized by excessively leaky microvasculature, e.g., as seen in tumors and sites of inflammation.

A broad range of nanoparticles are known in the art. Exemplary approaches include those described in WO2010/005726, WO2010/005723, WO2010/005721, WO2010/121949, WO2010/0075072, WO2010/068866, WO2010/005740, WO2006/014626, U.S. Pat. Nos. 7,820,788, 7,780,984, the contents of which are incorporated herein in reference by their entirety.

Exemplary nanoparticle delivery platforms that can be used to package the AHCM agent and/or microenvironment modulator, the therapy, or any combination thereof, include non-targeted and targeted nanoparticles. These platforms can be classified into the following categories: liposomes, nanoparticle albumin-bound technology, polymeric nanoparticles, dendrimers, metal nanoparticles, and molecular targeted nanoparticles (reviewed in e.g., Wang, A. Z. et al. (2012) Annu. Rev. Med. 63:185-98, incorporated herein by reference). Examples of these nanoparticle delivery platforms are discussed in more detail below.

Liposomes

Lipid- or oil-based nanoparticles, such as liposomes can be used to, deliver the agents described herein, or can be used in combination with the agents described herein. Coating liposomes with polymers such as PEG can improve their stability and half-life in the blood. Typically, liposomal drug formulations enhance the biodistribution and pharmacokinetic profile of a drug.

Liposomal formulations of anthracycline drugs have been approved for clinical use. Examples include, but are not limited to, liposomal daunorubicin (e.g., DaunoXome®: Gilead Sciences, approved for treatment of Kaposi's sarcoma); liposomal doxorubicin (e.g., Myocet (D-99)® Elan Pharmaceuticals, approved for treatment of breast cancer); PEGylated liposomal doxorubicin (e.g., Doxil®, Ortho Biotech Products (US), Caelyx: Schering-Plough (international), approved for treatment of breast cancer, ovarian cancer, or Kaposi's sarcoma).

Other liposomal formulations, include, but are not limited to, PEGylated liposomal topoisomerase inhibitor (e.g., Compound name S-CKD602, developed by Johnson & Johnson/Alza Corporation, which is in Phase II clinical trial for treatment of various malignancies); liposomal irinotecan metabolite (e.g., LE-SN38, developed by NeoPharm, which is in Phase I-II clinical trial for treatment of neoplasms and colorectal cancer; or a polymeric micelle of SN-38 (e.g., NK012 developed by Nippon Kayaku, Co.); lipid nanoparticle formulation of siRNA directed toward vascular endothelial growth factor and kinesin spindle protein (e.g., ALN-VSP), developed by Alnylam, which is in Phase I clinical trials for treatment of advanced solid tumors with liver involvement; liposomal thymidylate synthase inhibitor (e.g., OSI-7904L) and liposomal lurtotecan (e.g., OSI-211), both of which were developed by OSI Pharmaceuticals, which are in Phase II clinical trials. Additional examples of liposomal mixtures of drugs and nanoparticle delivery systems include, but are not limited to, liposomal irinotecan and floxuridine (e.g., CPX-1 in Phase II clinical trial for colorectal cancer); liposomal cytarabine and daunorubicin (e.g., CPX-351 in Phase III clinical trial for acute myeloid leukemia); and the CPX-8 nanoparticle delivery system, all of which are being developed by Celator Pharmaceuticals. Further examples include a glycoprotein micelle (e.g., SP1049C containing doxorubicin developed by Supratek Pharma Inc. to treat various cancers).

Additional examples of liposomal and lipid mixtures of drugs for intravenous delivery or injection, include, but are not limited to, liposomal cytarabine (e.g., DepoCyt which is commercially available for treating lymphomatous meningitis and leukemia); a lipid:drug suspension of two phospholipids (DMPC and DMPG) (e.g., Abelcet, which is a complex with amphotericin B to treat fungal infections), both of which are available from Sigma Tau Pharmaceuticals.

Other exemplary formulations include the lipid nanoparticle (LNP) technology developed by Tekmira described, e.g., in U.S. Pat. No. 7,244,448 entitled "Liposomal Antineoplastic Drugs and Uses Thereof;" U.S. Pat. No. 7,811,602 entitled "Liposomal Formulations comprising Dihydrosphingomyelin and Methods of Use Thereof;" U.S. Pat. No. 8,722,082 entitled "Lipids and Compositions for the Delivery of Therapeutics;" and Semple, S. C., et al. Rational design of cationic lipids for siRNA delivery (2010) Nature Biotechnology, 28:172-176, all of which are incorporated herein by reference. In some embodiments, lipid micelles/nanoparticle formulations (primarily cationic lipids) that encapsulate RNA molecules (e.g., RNAi, siRNA, or mRNA) can be used to allow for efficient transport through the bloodstream to target tissues. Exemplary nanoparticle formulations for RNA delivery include, e.g., LNP containing RNAi targeted toward polo-like kinase 1 (PLK1) (e.g., TKM-PLK1, which is in Phase I/II trials for gastrointestinal neuroendocrine tumors, adrenocortical carcinoma, and hepatocellular carcinoma).

Additional exemplary formulations include lipid nanoparticles comprising multiple lipid layers (multilamellar), in which the individual layers are chemically "stapled" together using dithiol crosslinkers, as described in, e.g., U.S. Pat. No. 8,747,869, entitled "Lipid Vesicle Compositions and Methods of Use;" and Moon, J J; Suh, H; et al. "Interbilayer-crosslinked multilamellar vesicles as synthetic vaccines for potent humoral and cellular immune responses" (2011) Nature Materials, 10:243-251, both of which are incorporated herein by reference. Such layered structure provides the particles with enhanced stability relative to liposomes. This technology, which is also termed "Interbilayer Crosslinked Multilamellar Vesicles (ICMVs)" is being developed by Vedranta Pharmaceuticals.

Liposomal formulations described herein can include a targeting agent, e.g., an antibody or antibody fragment (e.g., a human antibody fragment (GAH) targeting liposomal doxorubicin (e.g., MCC-465)), or a ligand, e.g., transferrin (e.g., transferring-targeted liposomal oxaliplatin (e.g., MBP-426 developed by Mebiopharm Co., Ltd to treat cancer); or transferrin targeted liposome with p53 gene (e.g., SGT53-01 developed by SynerGene Therapeutics to treat solid tumors).

Albumin-Bound (Nab) Nanoparticle

In other embodiments, albumin can be used as a carrier for the AHCM and/or microenvironment modulator, the therapy, or any combination thereof. For example, albumin can be complexed to the AHCM, microenvironment modulator, the agent (e.g., a chemotherapeutic drug) through noncovalent, reversible interactions. Alternatively, or in combination, the AHCM and/or microenvironment modulator (or a nanoparticle containing the same) can be used in combination with albumin-drug coated nanoparticles, e.g., a nanoparticle coated with albumin and paclitaxel (e.g., Abraxane® developed by Celgene, which is approved for treating breast cancer, non-small cell lung cancer, and pancreatic cancer).

Polymeric Nanoparticles

In yet other embodiments, the AHCM, the microenvironment modulator, the therapy, or any combination thereof can be packaged in a polymeric nanoparticle. Alternatively, or in combination, the AHCM (or a nanoparticle containing the AHCM) can be used in combination with one or more art-known polymeric nanoparticles. A common class of nanoparticles contains an inner core loaded with a drug and an outer shell for protection and/or immune shielding, with or without a targeting agent.

Examples of non-targeted polymeric nanoparticles include, but are not limited to, a polymeric-micelle composed of PEG and polylactic acid (PLA) (e.g., Cynviloq® which encapsulates paclitaxel (developed by Sorrento Therapeutics)); a polymeric PEG-polyamino acid (e.g., NC-6004, which encapsulates cisplatin (developed by Nano-Carrier Co.)); a polymeric PEG-polyaspartate (e.g., NK105, which encapsulates paclitaxel (developed by Nippon Kayaku Co.); a polymeric PEG-polyaspartate (e.g., NK911, which encapsulates doxorubicin (developed by Nippon Kayaku Co.); a cyclodextrin polymeric nanoparticle (CDP) as described in, e.g., U.S. Pat. Nos. 8,389,499, 8,314,230, 8,603,454, 8,404,799, all of which are incorporated herein by reference. Exemplary cyclodextin-PEG polymers comprising various chemotherapeutic drugs include CDPs bound to camptothecin (e.g., CRLX101 developed by Cerulean Pharma to treat relapsed renal cell carcinoma, ovarian cancer, rectal cancer), and CDPs bound to docetaxel (e.g., CRLX301 also developed by Cerulean Pharma).

Polymeric nanoparticles described herein can include a targeting agent, e.g., an antibody or antibody fragment, or a ligand, e.g., transferrin or other receptor ligand. Examples of targeted polymeric nanoparticles include, but are not limited to, polylactic co-glycolic acid (PLGA) nanoparticles encapsulating a reverse micelle, in which the interior is hydrophilic and the exterior is hydrophobic. Either part of the micelle may be loaded with therapeutics. The PLGA matrix is coated with PEG for immune shielding, and a targeting ligand (e.g., one or more of an antibody, an antibody fragment, or a ligand (e.g., a receptor ligand)); the ligand is linked to a PEG molecule to direct the particles within the body. These targeted nanoparticles are described in, e.g., U.S. Pat. Nos. 8,193,334, 7,534,449, and Hrkach, J. et al. Preclinical development and clinical translation of a PSMA-targeted docetaxel nanoparticle with a differentiated pharmacological profile. (2012) *Science Translational Medicine* 4:1-12, all of which are incorporated herein by reference. Exemplary PLGA nanoparticle containing a docetaxel payload interior and a prostate-specific membrane antigen (PSMA)-targeting ligand ACUPA (a PSMA substrate analog) on the surface is BIND-014, which is used to treat solid tumors (developed by BIND Bioscience).

Additional examples of targeted polymeric nanoparticles include, but are not limited to, transferring-targeted polymeric (e.g., cyclodextrin) nanoparticles (e.g., CALAA-01, which includes a siRNA and was developed by Calando Pharmaceuticals to treat solid tumors).

Metal/Carbon-Based Nanoparticles

In other embodiments, the AHCM, the microenvironment modulator, the therapy, or all can be packaged in a metal/carbon-based nanoparticle. Alternatively, or in combination, the AHCM and/or the microenvironment modulator (or a nanoparticle containing the same) can be used in combination with one or more art-known metal/carbon-based nanoparticles. These nanoparticles can contain a metal (gold, titanium) or carbon-based inner shell, surrounded by, e.g., an AHCM, a cytotoxic drug and/or a polymer, such as PEG, for immune shielding and/or targeted delivery.

Exemplary metal/carbon-based nanoparticle include a colloidal gold nanoparticle (e.g., 30-50 nm) coated with PEG-thiol as described in, e.g., U.S. Pat. Nos. 7,229,841, 7,387,900 and 6,274,552, incorporated herein by reference. Specific products of the Aurimune platform being developed by CytImmune include CYT-6091, which is a first generation Aurimune nanoparticle bearing tumor necrosis factor (TNF) on the surface; CYT-21000, which is a second generation Aurimune nanoparticle bearing TNF and Taxol on the surface, and CYT-61000 (particle bearing interferon) and CYT-71000 (particle bearing gemcitabine).

Synthetic Vaccine Particles (SVPs)

In other embodiments, the AHCM, the microenvironment modulator, the therapy, or any combination thereof, can be packaged in an SVP. Alternatively, or in combination, the AHCM and/or the microenvironment modulator (or a nanoparticle containing the same) can be used in combination with one or more SVPs. This platform involves a nanoparticle polymer embedded with B cell antigens; the nanoparticle encapsulates either T-cell antigens (e.g., disease-specific epitopes or protein antigens) or immunomodulators (e.g., TLR agonists or checkpoint inhibitors), as described in, e.g., US 20130028941, US 20140199340 and US 20120301498. Exemplary products developed by Selecta Biosciences include SEL-212 and SEL-068.

Light-Activated Drug Delivery

In other embodiments, the AHCM, the microenvironment modulator, the therapy, or any combination thereof, can be packaged in a light-activated drug delivery. Alternatively, or in combination, the AHCM and/or the microenvironment modulator (or a nanoparticle containing the same) can be used in combination with one or more light-activated nanoparticles. Fluorescent, porous silica nanoparticles filled with various chemotherapeutics (e.g. camptothecin) or nucleic acids. The pores in the particles are capped with "nanovalves" to prevent leakage. Upon exposure to exogenous two-photon radiation (laser light), the nanovalves open and release drug cargo. Typically, the nanoparticles treat tumors within 4 cm of skin surface due to ability of laser to penetrate skin, and fluorescent labels allow for tracking of nanoparticles through the body. The technology is described, e.g., in US 20120207795, US 20100310465, and Croissant, J., et al. Two-photon-triggered drug delivery via fluorescent nanovalves. (2014) Small. 10:1752-1755, all of which are incorporated herein by reference.

Nanodiamonds

In other embodiments, the AHCM, the microenvironment modulator, the therapy, or any combination thereof, can be packaged in one or more nanodiamonds. Alternatively, or in combination, the AHCM and/or the microenvironment modulator (or a nanoparticle containing the same) can be used in combination with one or more nanodiamonds. Nanodiamonds, carbon-based particles about, e.g., 4-5 nm in diameter, can be bound to a broad range of drug compounds. Binding seems to be through hydrophobic interactions between particle surface and drug molecules. Current uses include doxorubin linked nanodiamonds and daunorubicin-linked nanodiamonds for leukemia.

Other particles, e.g., encapsulated and/or carrier-targeted particles are within the scope of the invention.

Agents

As used herein, the term "agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof.

The term "agent" also includes an agent that is capable of providing a local or systemic biological, physiological, or therapeutic effect in the biological system to which it is applied. For example, a therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

An agent, e.g., a therapeutic agent, can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the agent, e.g., a therapeutic agent, is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents, e.g., a therapeutic agents, include, but are not limited to, those found in *Harrison's Principles of Internal Medicine*, 13th Edition, Eds. T. R. Harrison et al. McGraw-Hill N.Y., N.Y.; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure. Examples include an angiotensin receptor blocker, a CXCR4 inhibitor, a chemotherapeutic agent, a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an anti-arrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, an antibody or a nucleic acid.

Non-limiting examples of suitable agents, e.g., therapeutic agents, include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable medicaments may be selected from contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines, antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Some specific non-limiting examples of agents, e.g., therapeutic agents, include doxorubicin, mitomycin, cisplatin, daunorubicin, bleomycin, actinomycin D, neocarzinostatin, carboplatin, stratoplatin, Ara-C. Other examples include Capoten, Monopril, Pravachol, Avapro, Plavix, Cefzil, Duricef/Ultracef. Azactam, Videx, Zerit, Maxipime, VePesid, Paraplatin, Platinol, Taxol, UFT, Buspar, Serzone, Stadol NS, Estrace, Glucophage (Bristol-Myers Squibb); Ceclor, Lorabid. Dynabac, Prozac, Darvon, Permax, Zyprexa, Humalog, Axid, Gemzar, Evista (Eli Lily); VasotecNaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.); Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn); Lopid, Accrupil, Dilantin, Cognex, Neurontin, Loestrin, Dilzem, Fempatch, Estrostep, Rezulin, Lipitor, Omnicef, FemHRT, Suramin, or Clinafloxacin (Warner Lambert).

In some embodiments, the agent, e.g., therapeutic agent, can be an anti-cancer drug such as 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, siRNA, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

In some embodiments, the agent, e.g., therapeutic agent, can be an anti-infective such as Difloxacin Hydrochloride; Lauryl Isoquinolinium Bromide; Moxalactam Disodium; Ornidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); or Ciprofloxacin (Cipro).

In some embodiments, the agent, e.g., therapeutic agent, can be an anti-inflammatory agent such as Alclofenac; Alclometasone Dipropionate; Algestone Acetonide; Alpha Amylase; Amcinafal; Amcinafide; Amfenac Sodium; Amiprilose Hydrochloride; Anakinra; Anirolac, Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen, Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin or Zomepirac Sodium.

In some embodiments, the agent, e.g., therapeutic agent, can one for treating cardiovascular disease. Such drugs include anti-thrombotic and/or fibrinolytic agents, such as plasminogen; Streptokinase; Urokinase: Anisoylated Plasminogen-Streptokinase Activator Complex; Pro-Urokinase; (Pro-UK); rTPA (alteplase or activase; "r" denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Retaplase; Trifenagrel; Warfarin; and Dextrans. Such drugs also include anti-platelet agents such as Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; and Anagrelide. Such drugs also include lipid reducing agents such as gemfibrozil, cholystyramine, colestipol, nicotinic acid, probucol lovastatin, fluvastatin, simvastatin, atorvastatin, pravastatin, and cirivastatin. Such drugs include direct thrombin inhibitors such as hirudin, hirugen, hirulog, agatroban, PPACK, and thrombin aptamers. Such drugs also include calcium channel blockers such as dihydropyridines, such as nifedipine, the phenyl alkyl amines, such as verapamil, and the benzothiazepines, such as diltiazem. Other calcium channel blockers include amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin. Such drugs also include beta-adrenergic receptor blocking agents such as atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, sotalolnadolol, tiprenolol, tomalolol, timolol, bupranolol, penbutolol, trimepranol, 2-(3-(1,1-dimethyl-ethyl)-amino-2-hydroxypropoxy)-3-pyridenecarboni-trilHCI, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propyl-thio)-4-(5-carbamoyl-2-thienyl)thiazol, 7-(2-hydroxy-3-t-butylaminpropoxy)phthalide. Such drugs also include anticoagulant agents such as Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; and Warfarin Sodium.

In some embodiments, the therapeutic agent can for treating a neurological disease. Such drugs include, but are not limited to, Diazepam, Valium, Clonazepam, Methamphetamine, Adderall, Neurontin, K-Dur, Gabapentin, Klonopin, Methylphenidate, Provigil, Ritalin, Lamictal, Modafinil, Abilify, Aripiprazole, Azmacort, Concerta, Depakote, Dilantin, Divalproex sodium, Klor-Con, Lamotrigine, Lithium, Natalizumab, Phenergan, Phenytoin, Prednisone, Promethazine, Risperdal, Risperidone, Temazepam, Topamax, Topiramate, Triamcinolone, Tysabri and Verapamil.

Some specific non-limiting examples of agents, e.g., therapeutic agents, that can be included in a particle disclosed herein include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyidopa, methylergonovine, methylphenidate, methylprednisolone, methysergide, metoclopramide, matolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystafin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyrodoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B12, vitamin C, vitamin D, vitamin E, vitamin K, xanthine, and the like.

In some embodiments, the agent can be a diagnostic agent. For example, the diagnostic agent can be a fluorescent molecule; a gas; a metal; a commercially available imaging agents used in positron emissions tomography (PET), computer assisted tomography (CAT), single photon emission computerized tomography, x-ray, fluoroscopy, and magnetic resonance imaging (MRI); or a contrast agents. Non-limiting examples of suitable materials for use as contrast agents in MRI include gadolinium chelates, as well as iron, magnesium, manganese, copper, and chromium. Examples of materials useful for CAT and x-ray imaging include, but are not limited to, iodine-based materials.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present invention include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F.

In some embodiments, the agent, e.g., therapeutic agent, can be angiotensin receptor blocker (ARB), a CXCR-4 antagonist, or a chemotherapeutic drug.

In some embodiments, the agent, e.g., therapeutic agent, can be selected from the group consisting of losartan, valsartan, telmisartan, olmesartan, AMD3100, paclitaxel, docetaxel, doxorubicin, camptothecin, irinotecan, rapamycin, FK506, 5-FU, gemcitabine, oxaliplatin, cisplatin, leucovorin, and combinations thereof.

Many drugs have dose-limiting side effects that reduce the systemic administration in free drug formulation at high dose for patients; while the high dose is usually expected to achieve significant therapeutic efficacy. For example, the inventors recently demonstrated that the clinically approved angiotensin receptor blocker (ARB) losartan can reduce desmoplasia in PDAC. Losartan can enhance vascular perfusion by decompressing vessels, leading to improved drug delivery and chemotherapy effectiveness. Similarly, the CXCR4 inhibitor, AMD3100, can reduce fibrosis. Unfortunately, both drugs have dose-limiting side effects that limit their utility in patients: ARBs are primarily anti-hypertensive drugs and can at the higher doses induce severe hypotension; AMD3100 can potentially cause hematologic side effects as this pathway is critical in hematopoietic stem/progenitor cell trafficking. The particles described herein can limit the free drug release in blood circulation and promote rapid drug release intratumorally to enhance therapeutic efficacy, avoiding side effects caused by free drugs in circulation. In some embodiments, the therapeutic agent is an therapeutic agent that usually cannot be systemic administration at high dose due to the side effects, and thus requires formulations for selective release in a desired tissue or location. Accordingly, in some embodiments, the therapeutic agent(s) for use in the present disclosure include, but are not limited to, those having dose limiting side effects.

In some embodiments the drugs can be polypeptide. In some embodiments, the therapeutic agent can be an antibody. In some embodiments, the therapeutic agent can be an oligonucleotide.

For conjugation with the polymer, the agent can comprise a reactive group. The term "reactive group" refers to a functional group that is capable of reacting with another functional group. Exemplary reactive functional groups include, but are not limited to, hydroxyls, amines, thiols, thials, sulfinos, carboxylic acids, amides, and the like. The reactive functional group on the polymer and the agent can be the same or different. In some embodiments, the therapeutic agent comprises at least one the below groups for conjugation to pH sensitive linkers or polymers: hydroxyl group, amine group (primary or secondary amine group), carboxylic acid groups, aldehyde group, ketone group, hydrazine group, azide group, vinyl ether group, alkene group and acrylate group.

Anti-Hypertensive and or Collagen Modifying Agents (AHCM Agents)

The methods provided herein are directed to administration of an AHCM, in free or particle form, e.g., for treating or preventing a disease or disorder described herein, e.g., a cancer or a fibrotic disorder described herein. The method can include one, two, three or more AHCM agents, alone or in combination with one or more therapeutic agents described herein (e.g., a microenvironment modulator, and/or other stromal modulator, and/or an additional therapy, e.g., a anti-cancer, an immunomodulatory or anti-fibrotic therapy).

In certain embodiments, the AHCM agent used in the methods and compositions of the invention can be chosen from one or more of: an antagonist of renin angiotensin aldosterone system ("RAAS antagonist"), an renin antagonist, an angiotensin converting enzyme (ACE) inhibitor, an angiotensin II receptor blocker ($AT_1$ blocker), a thrombospondin 1 (TSP-1) inhibitor, a transforming growth factor beta 1 (TGF-β1) inhibitor, and a connective tissue growth factor (CTGF) inhibitor. The method can include one, two, three or more AHCM agents, alone or in combination with one or more cancer therapeutics.

In one embodiment, the AHCM is a RAAS antagonist. In an embodiment, the RAAS antagonist is chosen from one or more of: aliskiren (TEKTURNA®, RASILEZ®), remikiren (Ro 42-5892), enalkiren (A-64662), SPP635, or a derivative thereof.

Figure 23:
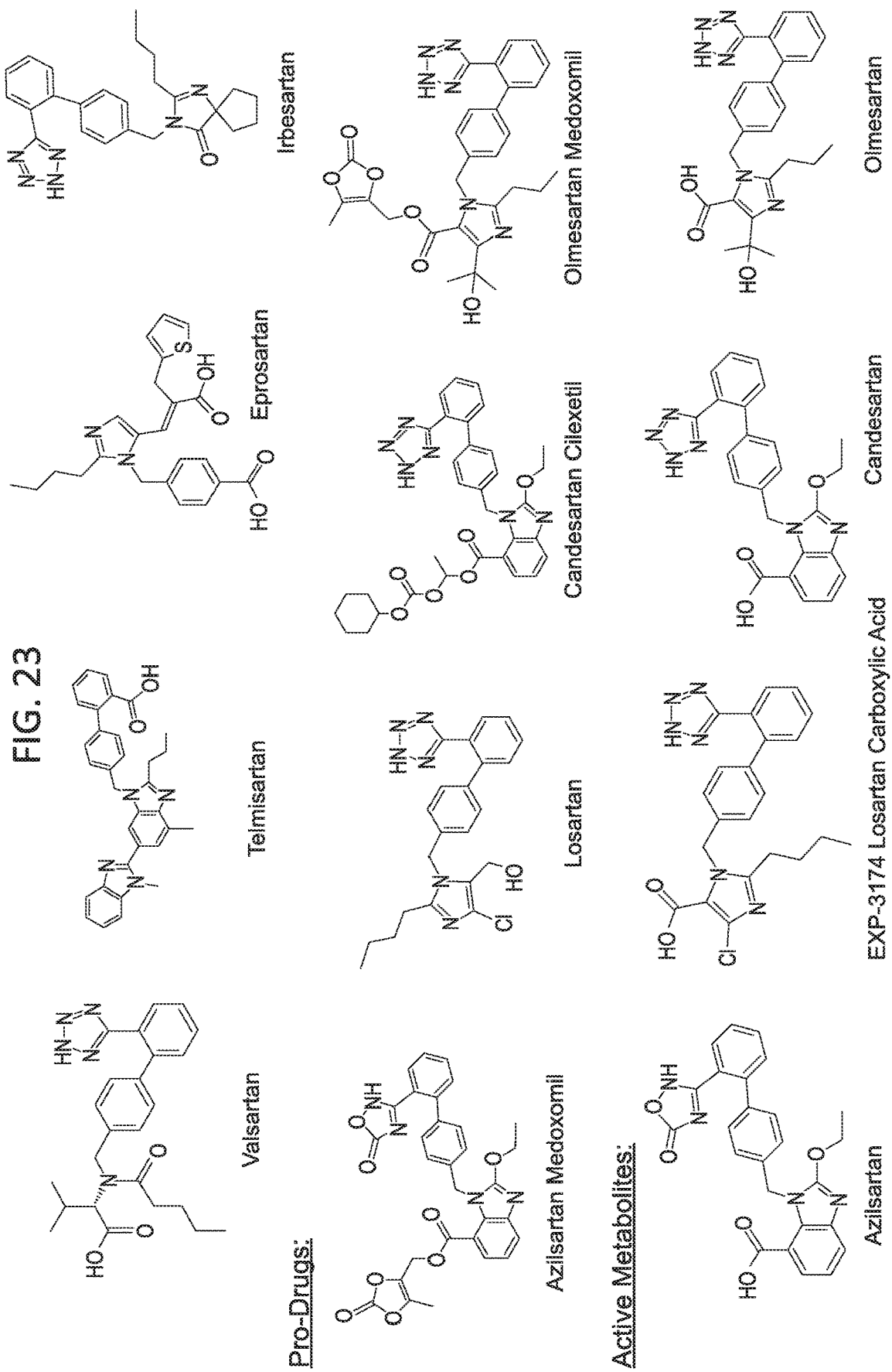
FIG. 23 shows representative ARBs, e.g., losartan, valsartan, telmisartan, candesartan, eprosartan, irbesartan, azilsartan, EXP-3174, olmesartan, or prodrugs or active metabolites thereof.

In yet another embodiment, the AHCM is an ACE inhibitor. In an embodiment, the ACE inhibitor is chosen from one or more of: benazepril (LOTENSIN®), captopril (CAPOTEN®), enalapril (VASOTEC®), fosinopril (MONOPRIL®), lisinopril (PRINIVIL®, ZESTRIL®), moexipril (UNIVASC®), perindopril (ACEON®), quinapril (ACCUPRIL®), ramipril (ALTACE®), trandolapril (MAVIK®), or a derivative thereof. Exemplary angiotensin II receptor blockers ($AT_1$ blockers) include, but are not limited to, losartan (COZAAR®), candesartan (ATACAND®), eprosartan mesylate (TEVETEN®), EXP 3174, irbesartan (AVAPRO®), L158,809, olmesartan (BENICAR®), saralasin, telmisartin (MICARDIS®), valsartan (DIOVAN®), and prodrugs, metabolites, and derivatives thereof, e.g., as shown in FIG. 23.

In one embodiment, the $AT_1$ blocker is losartan, or a derivative thereof. Losartan is an anti-hypertensive agent with minimal safety risks (Johnston C I (1995) *Lancet* 346:1403-1407). Furthermore, in addition to its antihypertensive properties, losartan is also an antifibrotic agent that has been shown to reduce the incidence of cardiac and renal fibrosis (Habashi J P, et al. (2006) *Science* 312:117-121; and. Cohn R D, et al. (2007) *Nat Med* 13:204-210). The antifibrotic effects of losartan are caused, in part, by the suppression of active transforming growth factor-β1 (TGF-β1) levels via an angiotensin II type I receptor (AGTR1) mediated down-regulation of TGF-β1 activators like thrombospondin-1 (TSP-1) (Habashi J P, et al. (2006) *Science* 312: 117-121; Cohn R D, et al. (2007) *Nat Med* 13:204-210; Lavoie P, et al. (2005) *J Hypertens* 23:1895-1903; Chamberlain J S (2007) *Nat Med* 13:125-126; and Dietz H C (2010) *J Clin Invest* 120:403-407).

In yet another embodiment, the AHCM is a thrombospondin 1 (TSP-1) inhibitor. In an embodiment, the TSP-1 inhibitor is chosen from one or more of: ABT-510, CVX-045, LSKL, or a derivative thereof.

In one embodiment, the AHCM is a transforming growth factor beta 1 (TGF-β1) inhibitor (e.g., an anti-TGF-β1 antibody, a TGF-β1 peptide inhibitor, or an inhibitor of a TGF-β1 receptor). In certain embodiment, the TGF-β1 inhibitor is chosen from one or more of: CAT-192, fresolimumab (GC1008), LY 2157299, Peptide 144 (P144), SB-431542, SD-208, compounds described in U.S. Pat. No. 7,846,908 and U.S. Patent Application Publication No. 2011/0008364, or a derivative thereof.

In yet another embodiment, the AHCM is a connective tissue growth factor (CTGF) inhibitor. In certain embodiment, the CTGF inhibitor is chosen from one or more of: DN-9693, FG-3019, and compounds described in European Patent Application Publication No. 1839655, U.S. Pat. No. 7,622,454, or a derivative thereof.

In yet another embodiment, the AHCM is an agonist of AT2 receptor. Exemplary AT2 agonists include, but are not limited to CGP 42112A, Compound 21 or C21 (e.g., as described by Steckelings, U M et al. (2012) *Curr Opin Nephrol Hypertens.* 21(2): 142-6; Steckelings, U M et al. (2011) *Curr Opin Pharmacol.* 11(2):187-192).

Exemplary beta-blockers include, but are not limited to, atenolol (TENORMIN®), betaxolol (KERLONE®), bisoprolol (ZEBETA®), metoprolol (LOPRESSOR®), metoprolol extended release (TOPROL XI®), nadolol (CORGARD®), propranolol (INDERAL®), propranolo long-acting (INDERAL LA®), timolol (BLOCADREN®), acebutolol (SECTRAL®), penbutolol (LEVATOL®), pindolol, carvedilol (COREG®), labetalol (NORMODYNE®, TRANDATE®), and derivatives thereof.

In one embodiment, the AHCM agent is a TGF-β1 inhibitor, e.g., an anti-TGF-β1 antibody, a TGF-β1 peptide inhibitor. In certain embodiment, the TGF-β1 inhibitor is chosen from one or more of: CAT-192, fresolimumab (GC1008), LY 2157299, Peptide 144 (P144), SB-431542, SD-208, compounds described in U.S. Pat. No. 7,846,908 and U.S. Patent Application Publication No. 2011/0008364, or a derivative thereof.

In yet another embodiment, the AHCM is an inhibitor of stromal cell-derived growth factor 1 alpha (SDF-1a/CXCL12a). In certain embodiments, the SDF-1a inhibitor is an anti-SDF1a antibody or fragment thereof. In other embodiments, the SDF-1a inhibitor is an inhibitor of an SDF-1a receptor (e.g., a CXCR4 inhibitor), for example the small molecule inhibitor Plerixafor (AMD-3100) or the peptide antagonist LY2510924.

In another embodiment, the AHCM is an endothelin receptor antagonist (ERA). Exemplary ERAs include, but are not limited to, selective ETA receptor antagonists (including, e.g., but not limited to, sitaxentan, ambrisentan, atrasentan, BQ-123, zibotentan), which affect endothelin A receptors; dual antagonists (including, e.g., but not limited to, bosentan, macitentan, tezosentan), which affect both endothelin A and B receptors; and selective ETB receptor antagonists (including, e.g., not limited to, BQ-788 and A192621) which affect endothelin B.

Suitable doses for administration of the AHCM agent can be evaluated based on the standard of care anti-hypertensive doses of the AHCM agents are available in the art.

Exemplary standard of care anti-hypertensive and anti-heart failure doses and dosage formulations for $AT_1$ inhibitors in humans are as follows: 25-100 mg $day^{-1}$ of losartan (available in a dosage form for oral administration containing 12.5 mg, 25 mg, 50 mg or 100 mg of losartan); 4 to 32 mg $day^{-1}$ of candesartan (ATACAND®) (e.g., available in a dosage form for oral administration containing 4 mg, 8 mg, 16 mg, or 32 mg of candesartan); 400 to 800 mg $day^{-1}$ of eprosartan mesylate (TEVETEN®) (e.g., available in a dosage form for oral administration containing 400 or 600 mg of eprosartan); 150 to 300 mg $day^{-1}$ of irbesartan (AVAPRO®) (e.g., available in a dosage form for oral administration containing 150 or 300 mg of irbesartan); 20 to 40 mg $day^{-1}$ of olmesartan (BENICAR®) (available in a dosage form for oral administration containing 5 mg, 20 mg, or 40 mg of olmesartan); 20 to 80 mg $day^{-1}$ of telmisartin (MICARDIS®) (e.g., available in a dosage form for oral administration containing of 20 mg, 40 mg or 80 mg of telmisartin); and 80 to 320 mg $day^{-1}$ of valsartan (DIOVAN®) (e.g., available in a dosage form for oral administration containing 40 mg, 80 mg, 160 mg or 320 mg of valsartan).

Exemplary standard of care anti-hypertensive and anti-heart failure doses and dosage formulations for ACE inhibitors in humans are as follows: 10 to 40 mg $day^{-1}$ of benazepril (LOTENSIN®) (Lotensin (benazepril) is supplied as tablets containing 5 mg, 10 mg, 20 mg, or 40 mg of benazepril hydrochloride for oral administration); 25 to 100 mg $day^{-1}$ of captopril (CAPOTEN®) (available in a dosage form for oral administration containing 12.5 mg, 25 mg, 50 mg or 100 mg of captopril); 5 to 40 mg $day^{-1}$ of enalapril (VASOTEC®) (available in a dosage form for oral administration containing 2.5 mg, 5 mg, 10 mg or 20 mg of enalapril; 10 to 40 mg $day^{-1}$ of fosinopril (MONOPRIL®) (available in a dosage form for oral administration containing 10 mg, 20 mg, or 40 mg of fosinopril); 10 to 40 mg $day^{-1}$ of lisinopril (PRINIVIL®, ZESTRIL®) (available in a dosage form for oral administration containing 2.5 mg, 5 mg, 10 mg, 20 mg, 30 mg or 40 mg of lisinopril); 7.5 to 30 mg $day^{-1}$ of moexipril (UNIVASC®) (available in a dosage form for oral administration containing 7.5 mg or 15 mg of Moexipril); 4 to 8 mg $day^{-1}$ of perindopril (ACEON®) (available in a dosage form for oral administration containing 2 mg, 4 mg or 8 mg of perindopril), 10 to 80 mg $day^{-1}$ of quinapril (ACCUPRIL®) (available in a dosage form for oral administration containing 5 mg, 10 mg, 20 mg, or 40 mg of quinapril); 2.5 to 20 mg $day^{-1}$ of ramipril (ALTACE®) (available in a dosage form for oral administration containing 1.25 mg, 2.5 mg, 5 mg, or 10 mg of ramipril); 1 to 4 mg day$^{-1}$ of trandolapril (MAVIK®) (available in a dosage form for oral administration containing 1 mg, 2 mg, or 4 mg of trandolapril).

In one embodiment, the AHCM agent is administered at a standard of care anti-hypertensive and anti-heart failure doses and dosage formulations, e.g., a dose or dosage formulation as described herein.

In certain embodiments, a sub-anti-hypertensive dose or dosage formulation of the AHCM agent is desirable, e.g., a dose of the AHCM agent that is less than the standard of care dose or dosage formulation. In one embodiment, the sub-anti-hypertensive dose or dosage formulation has a minimal effect in blood pressure in a hypertensive subject (e.g., decreases the mean arterial blood pressure in a hypertensive subject by less than 20%, 10%, or 5% or less). In certain embodiments, the AHCM agent is administered at a dose or dosage formulation that is less than 0.01, 0.05, 0.1, 0.2, 0.3, 0.4, 0.5, 0.6, 0.7, 0.8, 0.9, that of the standard of care anti-hypertensive dose (e.g., the lower standard of care dose). In one embodiment, the dose or dosage formulation is in the range of, for example, 0.01-0.9-fold, 0.02-0.8-fold, 0.05-0.7-fold, 0.1-0.5 fold, 0.1-0.2-fold, that of the standard of care dose or dosage formulation for anti-hypertensive or anti-heart failure use. Standard of care doses or dosage formulation of the AHCM are available in the art, some of which are exemplified herein.

In yet other embodiments, the AHCM agent is administered at a dose or dosage formulation that is greater than the standard of care dose or dosage formulation for anti-hypertensive or anti-heart failure use (e.g., a dose or dosage form that is greater than 1.1, 1.5, 1.7, 2, 3, 4, 5, 10-fold or higher, that of the standard of care dose for anti-hypertensive or anti-heart failure use). In one embodiment, the dose or dosage formulation is in the range of, for example, 1.1 to 10-fold, 1.5-5-fold, 1.7 to 4-fold, or 2-3-fold, that of the standard of care dose or dosage formulation for anti-hypertensive or anti-heart failure use. Standard of care doses or dosage formulation of the AHCM are available in the art, some of which are exemplified herein.

The standard of care dose and dosage forms are provided herein for a number of AHCMs, e.g., losartan. In an embodiment, the dose and/or dosage form is less than (or higher than) the standard of care dose and/or dosage form. In an exemplary embodiment, it is less than 0.01, 0.02, 0.05, 0.1, 0.2, 0.5, 0.7, 0.8, 0.9-fold, that of the standard of care dose or dosage form. In some embodiments, the dose or dosage form contains an amount of AHCM that is within a range of the reduced amounts of the standard of care dose and/or dosage form. E.g., an AHCM dosage form that is 0.01-0.9-fold, 0.02-0.8-fold, 0.05-0.7-fold, 0.1-0.5 fold, 0.1-0.2-fold, that of the standard of care dose or dosage form. In certain embodiments, the range of the dose or the dosage form is 0.5-2.0 times a reduced dose or dosage form recited herein, so long as the dose or dosage form value is less than the standard of care dose or dosage form. By way of example, a standard of care dosage form for losartan is 12.5 mg. Thus, in embodiments, the dosage form is 0.125 mg (0.01×12.5 mg); 0.625 mg (0.05×12.5 mg); 1.25 mg (0.1×12.5 mg); 2.5 mg (0.2×12.5 mg); or 6.25 mg (0.5×12.5 mg). In an embodiment, the AHCM dosage form is in the range 0.5-2.0 (0.125 mg)=0.0625-0.25 mg; 0.5-2.0 (0.625 mg)=0.312-1.25 mg; and so on, so long as the dose or dosage form value is less than the standard of care dose or dosage form. This calculation can be applied to any standard of care dose and/or dosage form for any AHCM described herein. In certain embodiment, the value is less than the standard of care values. In other embodiments, the value is greater than the standard of care values.

In one embodiment, the dose of the AHCM agent is calculated based on the severity of the fibrosis in the tumor sample.

In some embodiments, the dose of the AHCM agent can be a sub-anti-hypertensive dose, which does not have any anti-tumor effect, e.g., no significant effect on inhibiting or preventing tumor growth or progression when administered alone. In some embodiments, the dose of the AHCM agent alone can be comparable to or greater than the standard of care dose or dosage formulation for anti-hypertensive or anti-heart failure use, and does not have any anti-tumor effect, e.g., no significant effect on inhibiting or preventing tumor growth or progression when administered alone.

AHCM Dosage Forms

In another aspect, the invention features a pharmaceutically acceptable composition comprising, in a single dosage form, an AHCM and an anti-cancer agent, e.g., a small molecule or a protein, e.g., an antibody. In another embodiment, one or both of the AHCM and the anti-cancer agent are provided in a nanoparticle. The AHCM and anti-cancer agent can be in separate or the same entity. For example, if provided as separate entities the AHCM can be provided as a first nanoparticle and the anti-cancer agent provided as a second nanoparticle (e.g., where the second nanoparticle has a structural property (e.g., size or composition) or a functional property (e.g., release kinetics or a pharmacodynamic property) that differs from the first nanoparticle). Alternatively, an AHCM and an anti-cancer agent can be provided on the same entity, e.g., in the same nanoparticle.

In another aspect, the invention features a pharmaceutically acceptable composition (e.g., nanoparticle) comprising an AHCM, e.g., an AHCM described herein. In one embodiment, the AHCM is in a dosage described herein, e.g., a standard of care dosage form, a sub-anti-hypertensive dosage form, or a greater than a standard of care dosage form.

In one embodiment, the AHCM is formulated in a dosage form that is according to the standard of care anti-hypertensive or anti-heart failure dosage form, e.g., a standard of care dosage form as described herein.

In certain embodiments, the AHCM is formulated in a dosage form that is less than the standard of care anti-hypertensive or anti-heart failure dosage form (e.g., a dosage form that is less than 0.01, 0.02, 0.03, 0.04, 0.05, 0.06, 0.07, 0.08, 0.09, 0.1, 0.15, 0.16, 0.2, 0.3, 0.4, 0.5, 0.6, 0.7-fold, that of the standard of care dosage form, e.g., a standard of care dosage from as described herein).

In other embodiments, the AHCM is formulated in a dosage form that is greater than the standard of care anti-hypertensive or anti-heart failure dosage form (e.g., a dosage form that is greater than 1.1, 1.5, 1.7, 2, 3, 4, 5, 10-fold or higher, that of the standard of care dosage form, e.g., a standard of care dosage from as described herein).

In another aspect, the invention features a pharmaceutically acceptable composition comprising an anti-cancer agent, e.g., an anti-cancer agent described herein, as a nanoparticle, e.g., a nanoparticle configured for a method described herein.

In another aspect, the invention features a therapeutic kit that includes the AHCM, alone or in combination with a therapy, e.g., an anti-cancer agent, described herein, and optionally, instructions for use, e.g., for the treatment of cancer. In an embodiment, the kit comprises one or more dosage for or pharmaceutical preparation or nanoparticle described herein Exemplary AHCM Effects In an embodiment, the AHCM when administered to a subject as a particle described herein or in free form, as a single agent or in combination with a second agent or therapy described herein, is administered in an amount that can cause one, two, three, four, five, six, seven, eight, nine, ten, eleven, twelve, thirteen, fourteen, or fifteen, or more of:

(i) a decrease in the level or production of an extracellular matrix (ECM) component, such as a fiber (e.g., collagen, procollagen), and/or a polysaccharide (e.g., a glycosaminoglycan such as hyaluronan or hyaluronic acid);

(ii) a decrease in the level or production of collagen or procollagen;

(iii) a decrease in the level or production of hyaluronic acid;

(iv) a decrease in tumor or fibrosis (e.g., fibrillar collagen);

(v) an increase in interstitial tumor transport;

(vi) an improved tumor or perfusion of a fibrotic tissue, e.g., fibrotic liver;

(vii) an increase in tumor or fibrotic tissue (e.g., liver) oxygenation;

(viii) a decrease in tumor or fibrotic tissue (e.g., liver) hypoxia;

(ix) a decrease in tumor or fibrotic tissue (e.g., liver) acidosis;

(x) an increase in immune cell infiltration (e.g., in a tumor);

(xi) a decrease in immune cell infiltration (e.g., in a liver);

(xii) a decrease in immunosuppression (e.g., a decrease in the level of regulatory T cells (Tregs), or a decrease in PD-L1 expressing cells;

(xiii) an increase in antitumor immunity;

(xiv) an increase the number and/or activity of immune cells (e.g., immune effector cells or macrophages) at or within the tumor or fibrotic tissue (e.g., liver);

(xv) a decrease in the production of cancer stem cells (also referred to herein as tumor-initiating cells);

(xvi) an enhanced efficacy (e.g., penetration or diffusion), of the therapy, e.g., the cancer therapy (e.g., radiation, photodynamic therapy, chemotherapeutics and immunotherapies) in a tumor or tumor vasculature, a fibrotic tissue or organ, or a liver or liver vasculature, in the subject;

(xv) a decrease in tumor desmoplasia (e.g., a decrease in collagen-I in the tumor); or (xvi) a decrease in the level or activity of cancer associated fibroblasts (CAFs) (e.g., a decrease in the number of αSMA and/or collagen-I expressing cells, in the tumor).

In embodiments, a particle, e.g., a pH-sensitive and/or polyacetal particle as described herein, comprising the AHCM and/or microenvironment modulator when administered to a subject can have one, two, three, four, five, six, seven, eight, nine, ten, eleven, or more of properties:

(i) the particle selectively can release an active AHCM (e.g., losartan or valsartan) in a fibrotic tissue or tumor;

(ii) the AHCM-containing particle does not have a significant effect on a healthy subject's mean arterial pressure;

(iii) the AHCM-containing particle can selectively release the AHCM to a target site, e.g., a tumor or fibrotic tissue, (iv) the AHCM-containing particle can increase the AHCM concentration at a target site, e.g., a tumor or liver, at least 2-, 3-, 4-, 5-, 6-, 7-, 8-, 9-, 10-fold;

(v) the AHCM-containing particle can release the AHCM in a smaller amount in the plasma relative to a target site (e.g., tumor or fibrotic tissue);

(vi) the AHCM-containing particle can increase the AHCM half-life in a subject;

(vii) the AHCM-containing particle can decrease tumor desmoplasia in a subject to a greater level than free-AHCM;

(viii) the AHCM-containing particle decreases compressive solid stress in tumors to a greater level than free-AHCM;

(ix) the AHCM-containing particle as a single agent or in combination, e.g., with a low dose anti-angiogenic agent (e.g., sorafenib) can increase tumor or liver perfusion;

(x) the AHCM-containing particle as a single agent or in combination, e.g., with a low dose anti-angiogenic agent (e.g., sorafenib) can reduce hypoxia in a cirrhotic liver;

(xi) the AHCM-containing particle as a single agent or in combination, e.g., with a low dose anti-angiogenic agent (e.g., sorafenib) can reduce hepatic inflammation in a cirrhotic liver; or (xii) the AHCM-containing particle increases T-lymphocyte infiltration in a tumor.

In an embodiment, the AHCM and/or microenvironment modulator is administered (as a particle described herein or in free form) in a dosage sufficient to improve the delivery or effectiveness of the therapy.

In certain embodiments, the methods further comprise selecting or identifying the subject as being in need of receiving the AHCM or microenvironment modulator (or both) on the basis of the need for improved delivery and/or efficacy of the therapy (e.g., the cancer, fibrotic, or liver therapy).

Microenvironment Modulators

The compositions and methods provided herein can include a microenvironment modulator or other stromal modulator described herein, e.g., for treating or preventing a disease or disorder, e.g., a cancer, or a fibrotic or inflammatory disorder described herein. The method can include one, two, three or more microenvironment modulators or other stromal modulator, alone or in combination with one or more therapeutic agents described herein (e.g., an AHCM, or an additional therapy, e.g., a cancer, anti-inflammatory agent or anti-fibrotic therapy).

In certain embodiments, the combinations described herein can be further administered in combination with a microenvironment modulator. The combined administration of the microenvironment modulator can be used to further enhance the efficacy (e.g., penetration and/or diffusion), of the combination therapies described herein in a tumor or tumor vasculature in a subject. Such combination may cause one or more of: reduce solid stress (e.g., growth-induced solid stress in tumors); decrease tumor fibrosis; reduce interstitial hypertension or interstitial fluid pressure (IFP); increase interstitial tumor transport; increase tumor or vessel perfusion; increase vascular diameters and/or enlarge compressed or collapsed blood vessels; reduce or deplete one or more of: cancer cells, or stromal cells (e.g., tumor associated fibroblasts or immune cells); decrease the level or production of extracellular matrix components, such as fibers (e.g., collagen, procollagen), and/or polysaccharides (e.g., glycosaminoglycans such as hyaluronan or hyaluronic acid); decrease the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases cancer stem cells (also referred to herein as tumor initiating cells), thereby enhancing the penetration and/or distribution of the therapy, e.g., the cancer therapy.

Exemplary microenvironment modulators are disclosed herein, and include, but are not limited to, an anti-angiogenic therapy, for example, an inhibitor of vascular endothelial growth factor (VEGF) pathway; an agent that decreases the level or production of hyaluronic acid; an inhibitor of the hedgehog pathway; an agent that improves drug penetration in tumors. In one embodiment, the agent is a disulfide-based cyclic RGD peptide (iRGD) or an analogue thereof; a taxane therapy (e.g., taxane-induced apoptosis); an agent that decreases the level or production of collagen or procollagen; an anti-fibrotic agent and/or a profibrotic pathway inhibitor.

In one embodiment, the anti-angiogenic agent is chosen from a VEGF-inhibitor, an inhibitor of the angiopoietin-Tie-2 pathway (e.g., an Ang-1 or an Ang-2 inhibitor), or sorafenib. Examples of anti-angiopoietin/Tie-2 pathway agents (or inhibitors of the angiopoietin-Tie-2 pathway) include, but are not limited to, AMG 386, CVX-060. CVX-241, MEDI-3617, REGN910, AMG-780, CEP-1198, ARRY-614, MGCD265, Regorafenib, and combinations thereof. In one embodiment, the anti-angiogenic agent can be an inhibitor of tyrosine or Serine/Threonin kinases such as VEGFR, PDGFR, c-kit receptors, b-Raf, or combinations thereof. Additional examples of anti-angiogenic agents include, but are not limited to, agents that inhibit oncogene activation (e.g., anti-EGFR such as gefitinib; anti-HER2 such as Trastuzumab; anti-Pl3K-AKT-mTOR such as NVPBEZ235, Pl-103, Palomid-529, Nelfinavir; anti-Ras such as FTIs); agents that target androgens (e.g., Castration or endocrine therapy); agents that inhibits inflammatory cytokine-induced VEGF activation; anti-PlGF agents; anti-integrin agents (e.g., Cilengitide); agents that targets PHD2/HIF pathway; anti-Rgs5 agents; Ang-1 agonistic agents; SEMA3A/NRP-1 agonistic agents; PDGF-B agonistic agents; eNOS agonistic agents; PDGF-C agonistic agents; PDGF-D agonistic agents, IFN-β agonistic agents; TSP-1 agonistic agents; anti-TNFα/TNFR agents; anti-TGFβ/TGFR agents; anti-VE-PTP agents; anti-MMP agents (e.g., anti-MMP-2; anti-MMP-9; anti-MMP-14); WNT agonistic agents; extracellular matrix-inducing agents (e.g., fibronectin; laminin; netrin-1; thrombospondin 1, etc.); Notch1 agonistic agents; Frizzled agonistic agents; and a combination of two or more thereof.

In one embodiment, the microenvironment modulator includes an anti-angiogenic agent or therapy, for example, an inhibitor of vascular endothelial growth factor (VEGF) pathway. Exemplary VEGF pathway inhibitors include, but are not limited to, an antibody against VEGF (e.g., bevacizumab); a VEGF receptor inhibitor (e.g., an inhibitor of VEGFR-1 inhibitor, a VEGFR-2 inhibitor, or a VEGFR-3 inhibitor (e.g., VEGFR inhibitors such as Cediranib (AZD2171)); a VEGF trap (e.g., a fusion protein that includes a VEGFR domain (e.g., a VEGFR1 domain 2 and a VEGFR2 domain 3) fused to an Fc fragment of an IgG); and an anti-VEGF aptamer (or a pegylated derivative thereof (e.g., MACUGEN®).

In one embodiment, the microenvironment modulator is an inhibitor of the angiopoietin-Tie-2 pathway (e.g., an Ang-1 or an Ang-2 inhibitor). In one embodiment, the inhibitor is a dual inhibitor of VEGF and an angiopoietin (also known as a double anti-angiogenic protein or DAAP). In one embodiment, the inhibitor is an antibody against Ang-1 or Ang-2 or both. In other embodiments, the inhibitor is a peptibody that neutralizes Ang-1 or Ang-2.

Agents for anti-angiogenic/vascular normalization strategies as described in Goel et al. (2011) *Physiol Rev.* 91: 1071-1121, and Jain (2014) *Cancer Cell* 26(5): 605-622, the contents of which are incorporated herein by reference, can also be used as an anti-angiogenic agent for the compositions and methods described herein.

In one embodiment, the microenvironment modulator is sorafenib. In one embodiment, sorafenib is administered at anti-angiogenic dose. In other embodiments, sorafenib is administered at an angiogenic dose. In one embodiment, sorafenib is administered to a subject at a vascular/stromal normalizing dose (e.g., a sub-anti-angiogenic dose, also referred to herein as a "low dose") as a particle or a free agent, e.g., as described herein in the context of treatment of fibrotic conditions or disorders (e.g., liver diseases or disorders, kidney fibrosis, cardiovascular diseases, or idiopathic pulmonary fibrosis).

In one embodiment, the anti-angiogenic agent is administered at a vascular/stromal normalizing dose. A vascular/stromal normalizing dose can have an angiogenic effect. In one embodiment, the vascular/stromal normalizing dose of the second agent results in one or more of: (i) increase in hepatic vascular function; (ii) repair of hepatic blood vessels; (iii) increase in vascular normalization; (iv) reduction in pore size; (v) reduction in hypoxic tissue; (vi) increase in perfusion of the diseased liver tissue; (vii) restoration of agent delivery; (viii) improved stromal signaling; or (ix) improved or normalized angiocrine signaling. In one embodiment, the effect of the "vascular/stromal normalizing" is detected by one or more of: angiography imaging, immunostaining of level of hypoxia (e.g., using pimonidazol-FITC), increased sinusoidal perfusion, or increased stromal/angiocrine signaling.

In one embodiment, the anti-angiogenic agent is administered at a sub-anti-angiogenic dose, also referred to herein as a "low dose"). A "sub-anti-angiogenic dose," as used herein, refers to a dose of an anti-angiogenic agent that is typically less than the lowest dose that would be used to have a detectable anti-angiogenic effect in a subject. A sub-anti-angiogenic dose can have an angiogenic effect. In one embodiment, the sub-anti-angiogenic dose of the second agent results in one or more of: (i) increased hepatic vascular function; (ii) repaired hepatic blood vessels; (iii) increased vascular normalization: (iv) reduced pore size; (v) reduced hypoxic tissue; (vi) increased perfusion of the diseased liver tissue; or (vii) restored agent delivery. In one embodiment, the effect of the "sub-anti-angiogenic dose" is detected by one or more of: angiography imaging, immunostaining of level of hypoxia (e.g., using pimonidazol-FITC), or increased sinusoidal perfusion e.g., as shown in the appended Examples.

In some embodiments, the anti-angiogenic agent is sorafenib. In some embodiments, sorafenib is administered at a low dose, e.g., a dose of sorafenib that is less than the standard of care dose, e.g., less than an anti-angiogenic or anti-vascularization dose. In one embodiment, sorafenib is administered at a dose or dosage formulation that is less than 0.01, 0.05, 0.1, 0.2, 0.3, 0.4, 0.5, 0.6, 0.7, 0.8, 0.9, that of the standard of care dose. In one embodiment, the dose or dosage formulation is in the range of, for example, 0.01-0.9-fold, 0.02-0.8-fold, 0.05-0.7-fold, 0.1-0.5 fold, 0.1-0.2-fold, that of the standard care dose or dosage formulation. Standard of care doses or dosage formulations of sorafenib are available in the art, some of which are exemplified herein.

In an exemplary embodiment, the low dose or dosage formulation of sorafenib is provided in a dose ranging from 0.1 mg/kg to 4 mg/kg, 0.1 mg/kg to 1 mg/kg, 0.2 mg/kg to 4 mg/kg, 0.2 mg/kg to 1 mg/kg, 0.2 mg/kg to 0.5 mg/kg, 0.3 mg/kg to 4 mg/kg, or 0.3 mg/kg to 1 mg/kg. In an embodiment, the low dose or dosage formulation of sorafenib is provided in a dosage of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 3 mg/kg, or 4 mg/kg, but less than 4.2 mg/kg. Alternatively, the low dose or dosage formulation of sorafenib is administered at a dose ranging from 1 to 250 mg, 1 to 150 mg, 1 to 100 mg, 1 to 50 mg, 1 to 20 mg, 1 to 10 mg, or 1 to 5 mg. For example, the low dose or dosage formulation of sorafenib is administered at a dose of less than 250 mg, e.g., about 200 mg, 150 mg, 100 mg, 90 mg, 80 mg, 70 mg, 60 mg, 50 mg, 45 mg, 40 mg, 35 mg, 30 mg, 25 mg, 20 mg, 15 mg, 10 mg, or 5 mg. In an embodiment, the formulation of sorafenib is an oral composition. In another embodiment, the dosage formulation of sorafenib is administered once a day or more than once a day, e.g., twice a day.

In other embodiments, the anti-angiogenic agent is an inhibitor of vascular endothelial growth factor (VEGF) pathway. Exemplary VEGF pathway inhibitors include, but are not limited to, an antibody against VEGF (e.g., bevacizumab); a VEGF receptor inhibitor (e.g., an inhibitor of VEGFR-1 inhibitor, a VEGFR-2 inhibitor, or a VEGFR-3 inhibitor (e.g., VEGFR inhibitors such as Cediranib (AZD2171)); a VEGF trap (e.g., a fusion protein that includes a VEGFR domain (e.g., a VEGFR1 domain 2 and a VEGFR2 domain 3) fused to an Fc fragment of an IgG); and an anti-VEGF aptamer (or a pegylated derivative thereof (e.g., MACUGEN®). Any of these inhibitors can be administered at a sub-anti-angiogenic dose as described above for sorafenib. e.g., a dose of that is less than the standard of care dose, e.g., an anti-angiogenic or anti-vascularization dose. In one embodiment, the inhibitor is administered at a dose or dosage formulation that is less than 0.01, 0.05, 0.1, 0.2, 0.3, 0.4, 0.5, 0.6, 0.7, 0.8, 0.9, that of the standard of care dose. In one embodiment, the dose or dosage formulation is in the range of, for example, 0.01-0.9-fold, 0.02-0.8-fold, 0.05-0.7-fold, 0.1-0.5 fold, 0.1-0.2-fold, that of the standard care dose or dosage formulation. Standard of care doses or dosage formulations of the inhibitor are available in the art, some of which are exemplified herein.

In other embodiments, the anti-angiogenic agent is inhibitor of the angiopoietin-Tie-2 pathway (e.g., an Ang-1 or an Ang-2 inhibitor. In one embodiment, the inhibitor is a dual inhibitor of VEGF and an angiopoietin (also known as a double anti-angiogenic protein or DAAP). In one embodiment, the inhibitor is an antibody against Ang-1 or Ang-2 or both. In other embodiments, the inhibitor is a peptibody that neutralizes Ang-1 or Ang-2. In one embodiment, the inhibitor is administered at a dose or dosage formulation that is less than 0.01, 0.05, 0.1, 0.2, 0.3, 0.4, 0.5, 0.6, 0.7, 0.8, 0.9, that of the standard of care dose. In one embodiment, the dose or dosage formulation is in the range of, for example, 0.01-0.9-fold, 0.02-0.8-fold, 0.05-0.7-fold, 0.1-0.5 fold, 0.1-0.2-fold, that of the standard care dose or dosage formulation. Standard of care doses or dosage formulations of the inhibitor are available in the art, some of which are exemplified herein.

In another embodiment, the microenvironment modulator includes an agent that decreases the level or production of hyaluronic acid (HA). Enzymatic targeting of the stroma using systemic administration of a pegylated derivative of hyaluronidase (PEGPH20) has been shown to ablate stromal HA in a model for pancreatic ductal adenocarcinoma (PDA) and increase vessel diameter in pancreatic tumors; hyaluronidase derivatives, in combination with standard chemotherapeutic agents (e.g., gemcitabine), can remodel the tumor microenvironment and increase overall survival (see e.g., Provenzano, P. et al. (2012) Cancer Cell 21: 418-429). Thus, combined administration of the AHCM and the microenvironment modulator can be used to enhance penetration and/or diffusion of a cancer therapy in a tumor or tumor vasculature, by for example, decreasing certain matrix components, e.g., HA, in the stroma. Exemplary HA-depleting agents include, but are not limited to, an anti-hyaluronan enzymatic therapy such as hyaluronidase or a derivative thereof (e.g., pegylated recombinant human hyaluronidase) (e.g., PH20, PEGPH20); and an antibody against hyaluronic acid.

In another embodiment, the microenvironment modulator includes an agent that decreases the level or production of hyaluronic acid, including but not limited to, an antibody against hyaluronic acid, and an anti-hyaluronan enzymatic therapy, such as hyaluronidase or a derivative thereof (e.g., pegylated form thereof) (e.g., PH20, or pegylated, recombinant human hyaluronidase PEGPH20). In another embodiment, the microenvironment modulator includes an inhibitor of the hedgehog pathway. Hedgehog inhibitors have been shown to increase vessel density in pancreatic tumors (Olive, K. P. et al. (2009) Science 324:1457-61), presumably by reducing stromal cell density and solid stress. In one embodiment, the microenvironment modulator includes an inhibitor of the hedgehog pathway, e.g., IPI-926, GDC-0449, cylopamine or an analogue thereof, or GANT58. In another embodiment, the microenvironment modulator includes an agent that improves drug penetration in tumors. In one embodiment, the agent is a disulfide-based cyclic RGD peptide (iRGD) or an analogue thereof (e.g., described in Sugahara, K N et al. (2010) Science 328:1031-5; Ye, Y. et al. (2011) Bioorg Med Chem Lett. 21(4):1146-50).

In yet another embodiment, the microenvironment modulator includes a taxane therapy (e.g., taxane-induced apoptosis as described in Griffon-Etienne, G. et al. (1999) Cancer Res. 59(15):3776-82).

In another embodiment, the microenvironment modulator includes an agent that modulates (e.g, inhibits) a hypoxia inducible factor (HIF), for example, an agent that inhibits hypoxia-inducible factors 1α and 2α (HIF-1α and HIF-2α). HIF activity has been shown to be involved in inflammation (e.g., rheumatoid arthritis) and angiogenesis associated with cancer tumor growth. HIF inhibitors, such as phenethyl isothiocyanate (PEITC) are under investigation for anti-cancer effects (Syed Alwi S S, et al. (2010) Br. J. Nutr. 104 (9): 1288-96; Semenza G L (2007). Drug Discov. Today 12 (19-20): 853-9; Melillo G (2006). Mol. Cancer Res. 4 (9): 601-5. In one embodiment, the agent is an antibody against an HIF. In another embodiment, the agent is an HIF chemical inhibitor, such as phenethyl isothiocyanate (PEITC).

In another embodiment, the microenvironment modulator includes an agent that decreases the level or production of collagen or procollagen. For example, an agent that degrades collagen, e.g., collagenase.

In another embodiment, the microenvironment modulator includes an agent that modulates the crosslinking of matrix molecules. For example, the microenvironment modulator includes an agent that induces formation of crosslinks in collagens and/or elastin, e.g., LOX-L2.

In another embodiment, the microenvironment modulator includes an agent that depletes or changes the differentiation state of a fibroblast or a stellate cell, e.g., a PDGF-R inhibitor.

In yet another embodiment, the microenvironment modulator is an anti-fibrotic agent (e.g., a pirfenidone (PFD, 5-methyl-1-phenyl-2-(1H)-pyridone)) or inhibitor of a pro-fibrotic pathway (a "profibrotic pathway inhibitor") (e.g., a pathway dependent- or independent of TGF-beta and/or CTGF activation).

In one embodiment, the combinations described herein are administered in combination with one or more of: an inhibitor of endothelin-1, PDGF, Wnt/beta-catenin, IGF-1, TNF-alpha, and/or IL-4. In another embodiment, the combinations described herein are administered in combination with an inhibitor of endothelin-1 and/or PDGF. In other embodiments, the combinations described herein are administered in combination with an inhibitor of one or more of chemokine receptor type 4 (CXCR4) (e.g., AMD3100, MSX-122); stromal-derived-factor-1 (SDF-1) (e.g., tannic acid); hedgehog (e.g., IPI-926, GDC-0449, cylopamine or an analogue thereof, or GANT58).

In certain embodiments, an inhibitor of a CXCR4 receptor and/or its ligand, SDF-1, is administered in combination with a therapy (e.g., a cancer or hyperproliferative therapy as described herein). Certain embodiments may further include administration of a further AHCM and/or a microenvironment modulator as described herein. Without wishing to be bound by theory, inhibition of CXCR4 receptor and/or its ligand, SDF-1, alone or in combination with the combination therapies described herein, e.g., an angiotensin II receptor blocker, can be used to reduce the desmoplasia in certain fibrotic or desmoplastic cancers, e.g., a fibrotic or a desmoplastic solid tumor, such as pancreatic cancers (e.g., pancreatic ductal adenocarcinoma (PDAC)). For example, activation of SDF-1a/CXCR4 and angiotensin II (ATII) signaling pathways is known to promote carcinoma activated fibroblasts (CAF) recruitment, activation, and matrix production in PDAC. Hypoxia, which is associated with PDAC, can induce SDF-1a and CXCR4 expression in cancer cells and CAFs through HIF-1a activation (Schioppa, T., et al. (2003) *J Exp Med,* 198: 1391-1402) while promoting growth and metastasis (Chang, Q., et al. (2011) *Cancer Research,* 71: 3110-3120). These effects arise, at least in part, through SDF-1a/CXCR4-dependent activation of CAFs (Gao, Z. et al. (2010) *Pancreatology* 10: 186-193; Moriyama, T. et al. (2010) *Cancer* 116: 3357-3368) and a CD133+/CXCR4+ cancer stem cell population (Hermann, P. C. et al. (2007) *Cell Stem Cell* 1: 313-323), which also confers chemoresistance (Singh, S. et al. (2010) *Br J Cancer* 103: 1671-1679). High SDF-1a levels (Liang, J. J., et al. (2010) *Cancer Epidemiology Biomarkers & Prevention* 19: 2598-2604) and CXCR4 levels (Marechal, R. et al. (2009) *Br J Cancer,* 100: 1444-1451) can be predictive of poor prognosis in PDAC patients. On the other hand, ATII signaling can stimulate CAF proliferation (Hama, K. et al. (2006) *Biochemical and Biophysical Research Communications,* 340: 742-750; Hama, K. et al. (2004) *Biochem Biophys Res Commun.* 315: 905-911; Shimizu, K. et al. (2008) *J Gastroenterol Hepatol,* 23 Suppl 1: S119-121), and ATII signaling through ATII-receptor type 1 (AT1) can stimulate CAF matrix production via TGF-β1 and ERK-dependent mechanisms (Rodriguez-Vita, J. et al. (2005) *Circulation* 111: 2509-2517; Yang, F. et al. (2009) *Hypertension,* 54: 877-884). ATII also induces TGF-β1 (Elenbaas, B. and Weinberg, R. A. (2001) *Experimental Cell Research,* 264: 169-184) and SDF-1a (Chu, P. Y. et al. (2010) *Am J Pathol,* 176: 1735-1742) expression by both cancer cells and CAFs, which can promote CAF proliferation and matrix production. Thus, inhibition of a CXCR4 receptor and/or its ligand, SDF-1, can be used (alone or with an inhibitor of ATII signaling) to enhance the distribution of a therapy in fibrotic or desmoplastic cancers.

Exemplary SDF-1/CXCR4 inhibitors that can be used include, but are not limited to, 2,2'-bicyclam; 6,6'-bicyclam; AMD3100 (IUPAC name: 1,1'-[1,4-phenylene-bis(methylene)]-bis-1,4,8,11-tetraazacyclotetradecane), as described in e.g., U.S. Pat. Nos. 5,021,409, 6,001,826 and 5,583,131; Plerixafor (trade name: Mozobil; IUPAC name: 1,1'-[1,4-Phenylenebis-(methylene)]bis [1,4,8,11-tetraazacyclotetradecane); CXCR4 peptide inhibitors or analogs, e.g., T-140 analogs (e.g., 4F-benzoyl-TN14003, TC14012, TE14011, TC14003), CTCE-0214; CTCE-9908; the peptide antagonist LY2510924; and CP-1221, as well as other inhibitors such as antibodies against SDF-1 or CXCR4, RNA inhibitors (e.g., antisense, siRNAs), among others. Exemplary inhibitors are described in, for example, Tamamura, H. et al. *Org. Biomol. Chem.* 1:3656-3662, 2003; *FEBS Letter* 550; 1-3 (2003): 79-83; Wong, D. et al. (2008) Clin. Cancer Res. 14(24): 7975-7980; US Patent Publications 2010/0055088; 2009/0221683; 2004/0209921; 2005/0059702; 2005/0043367, 2005/0277670, 2010/0178271, and 2003/0220341; U.S. Pat. Nos. 5,021,409, 6,001,826, 5,583,131, and Patent Publications WO 03/011277, WO 01/85196; WO 99/50461; WO 01/94420; WO 03/090512, each of which is incorporated herein by reference in their entirety.

Other Stromal Modulators

In certain embodiments, the other stromal modulator is chosen from one or more of:

(i) an inhibitor of a receptor for a VEGF ligand (e.g., a Flt-1, -2, and/or -3 receptor), e.g., an inhibitor for a Flt-3 receptor (e.g., present in bone marrow stroma, blood vessels, and mesenchymal cells), exemplary inhibitors: Axitinib (AG-013736);

(ii) an inhibitor of an FGF receptor (FGFR, including FGFR2 or FGFR3), e.g., an FGFR that functions in angiogenesis and the bone marrow stroma, exemplary inhibitor, e.g., AZD1480, Crizotinib; and FGFR2 inhibitor (e.g., BG-J398 and Nintedanib);

(iii) a c-Met/HGF receptor inhibitor (e.g., a modulator of one or more of: EGFR signaling and in stromal cell motility and proliferation, hepatocyte proliferation);

(iv) a TNFR inhibitor (e.g., a modulator of one or more of: inflammatory stroma, cytokine signaling in the stroma, metabolic reprogramming of stroma);

(v) a cytokine/cytokine receptor inhibitor for, e.g., one or more of IL-1beta, IL-4, 6, 12, 13, and 17 (e.g., a modulator of stromal signals through STAT3);

(vi) a JAK/STAT3 inhibitor (e.g., a modulator of signaling mechanism for IL-6 and other cytokines), exemplary inhibitors include, e.g., AZD1480, and a JAK3 inhibitor such as Tofacitinib, CP-690550;

(vii) an Osteopontin (SPP1) modulator (e.g., a modulator of would healing, bone remodeling, immune functions);

(viii) Bone morphogenic protein (BMPs) inhibitor, e.g., a modulator of matrix and stromal modulation and signaling;

(ix) an inhibitor of FAK (integrin receptor signaling integrator/mediator of solid stress), e.g., exemplary inhibitor Tofacitinib, CP-690550 (a modulator of FAK signaling through CAS, and other substrates);

(xi) a CSF-1R inhibitor, e.g., exemplary inhibitor: Cabozantinib;

(xii) c-Kit inhibitor (both part of the sub-type 3 family of RPTKs, including PDGFRs), e.g., exemplary inhibitor of c-Kit: Masitinib (AB1010), Linifanib (ABT-869), Quizartinib (AC220); and/or (xiii) DDR1 inhibitor (modulates all forms of collagen), exemplary inhibitor: JNJ-28312141.

Exemplary other stromal modulators include, but are not limited to, AZD1480: inhibitor of JAK/STAT3 signaling and of FGFRs, including FGFR3; Tofacitinib, CP-690550. JAK3/FAK inhibitor; Masitinib (AB1010): c-Kit and PDGFR alpha receptor inhibitor; Linifanib (ABT-869): inhibits PDGFR-beta, VEGFR2, c-Kit, CSF-1R; Quizartinib (AC220): Flt-3, c-Kit, PDGFR-beta, and CSF-1 R inhibitor; Axitinib (AG-013736): PDGFRa and b, c-Kit, Flt1, and VEGFR2 inhibitor; Motesanib (AMG 706): c-Kit, CSF1-R, PDGFRa and b, and VEGFR2 inhibitor; AST-487: TIE1R, Flt3R inhibitor; Cediranib (AZD-2171): PFGFRa and b, c-Kit, Flt1, VEGFR2 inhibitor; Zykadia (LDK378): Alk, IGF1R, VEGFR1 and 3 inhibitor; Crizotinib: Alk, FGFR1 and 2 inhibitor; BIBF-1120: VEGFR2, Flt3 inhibitor; BMS-540215: VEGFR2, FLT1, PDGFRa and b, c-Kit inhibitor; CHIR-258/TKI-258: Flt3, PFGRb and a, c-Kit inhibitor CP-690550: JAK3/2/1, TYK2 inhibitor; Foretinib (Exel 2880, GSK1363089G, XL880): DDR1, VEGFRs, TIE1 and 2, PDGFRa and b, c-Kit inhibitor; Imatinib (Gleevec): Abl, c-Kit, PDGFRa and b, CSF1R inhibitor; INCB018424: JAK2/3/1 and TYK2 inhibitor; JNJ-28312141: CSF1R, c-Kit, AXL, DDR1 inhibitor; Ki-20227: PDGFRa and b, c-Kit, CSF1R, DDR1, VEGFR2 inhibitor; MLN-518: c-Kit, PDGFRa and b, CSF1R, Flt3/Flk2 inhibitor; Nilotinib: DDR1, c-Kit, Abl, PDGFR inhibitor; Pazopanib: c-Kit, PDGFRa and b, Flt1, DDR1, VEGFR2 inhibitor; PD-173955: Abl, CSF1R, PDGFRb, c-Kit inhibitor; PTK787: c-Kit, PDGFRa and b, CSF1R, VEGFR2, DDR1 inhibitor; SGX-523: c-Met inhibitor; Tivozanib: VEGFR inhibitor; Pazopanib: c-KIT, FGFR, PDGFR and VEGFR inhibitor; Cabozantinib: Ret, VEGFRs, c-Met, CSF1R, PDGFRa and b, c-Kit inhibitor; Dasatinib: Abl, CSF1R, PDGFRa and b, c-Kit inhibitor; Tocilizumab: IL-6R antagonist; TNF blockers: Enbrel, Remicade, and Humira; and inhibitors of BMPs:

In other embodiments, the other stromal modulator is a metabolic compound, e.g., a metabolic inhibitor. Without being bound by theory, metabolic reprogramming, or metabolic asymmetry, can be a consequence of hypoxia (reviewed in e.g., Martinez-Outschoorn, U. et al. (2014) *Cancer Cell* 5-7 and Valencia, T. et al. (2014) *Cancer Cell* 26, 121-135). Thus, metabolic compounds can be used to normalize the fibrosis and decompression of vessels as part of microenvironment modulation. In major cancers, the stromal cells render a catabolic state to sustain an anabolic tumor cell state. In hypoxic tumors the tumor microenvironment directly alters the metabolic dependencies of the cancer cells (also known as the 'Warburg' effect). As part of the anabolic tumor cell state, increased utilization of glucose via glycolysis is a common characteristic. In addition, there is altered tumor amino acid metabolism (glutamine) and the export of the glycolytic end product lactate and expression of carbonic anhydrases shift the pH ratio of the interior and exterior of the cancer cell resulting in decreased passive transport of basic drugs. These dependencies of the tumor cells for the microenvironment-induced altered metabolism can be exploited using the methods and compositions described herein.

Accordingly, metabolic compounds can be used in the methods and compositions described herein. Exemplary metabolic compounds, include but are not limited to, mitochondrial inhibitors, a metformin agent (e.g., metformin, phenformin), oxidative phosphorylation inhibitors (OX-Phos inhibitors) (e.g. MD Anderson), mTOR inhibitors (Rapamycin analogs and catalytic mTOR C1 inhibitors), LDHA, FK11, Glutaminase inhibitor (GLS1), CB-839 Calithera Biosciences, Gross et al. (2014) DOI: 10.1158/1535-7163.MCT-13-0870, PKM2 modulators, Shikonin, GLUT1/GLUT4 inhibitors, Phoretin, Ritonavir, MCT4 (Lactate excretion), TCA cycle/mitochondrial metabolism inhibitors, NAMPT (FK866), or other metabolic compounds as described in, e.g., Zhao et al. (2013) *Cell Death and Disease* 4, e532; doi:10.1038/cddis.2013.60, incorporated herein by reference.

In one embodiment, the other stromal modulator is a metformin agent. In certain embodiments, the metformin agent is a biguanide. In some embodiments, the metformin agent includes two linked guanidine moieties. Exemplary biguanides include, but are not limited to, metformin, phenformin, buformin, and biguanide, or any functional analog, derivative, or salt of any of the aforesaid compounds.

In an embodiment, the other stromal modulator can modulate the microenvironment. In one embodiment, the other stromal modulator (alone or in combination) enhances the efficacy, delivery and/or diffusion of a therapy.

Any of the other stromal modulators described herein can be used as a single agent (e.g., in free form, as a conjugate, or as a particle as described herein), or in combination, e.g., in combination with any of the agents described herein (e.g., an AHCM, a microenvironment modulator, and/or any of the therapies disclosed herein, each of which may be in free form, as a conjugate, or as a particle as described herein).

Metformin Agents

In certain embodiments, the metformin agent is a biguanide. In some embodiments, the metformin agent is characterized by two linked guanidine moieties. Exemplary biguanides include, but are not limited to, metformin, phenformin, buformin, and biguanide, or any functional analog, derivative, or a salt of any of the aforesaid compounds.

In some embodiments, the metformin agent is described by a compound of Formula (VIII):

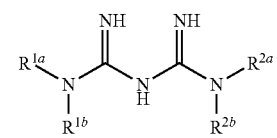

Formula (VIII)

or a pharmaceutically acceptable salt thereof, wherein each of $R^{1a}$, $R^{1b}$, $R^{2a}$, and $R^{2b}$ is independently hydrogen, $C_1$-$C_6$ alkyl, cycloalkylalkyl, or arylalkyl.

Figure 6:
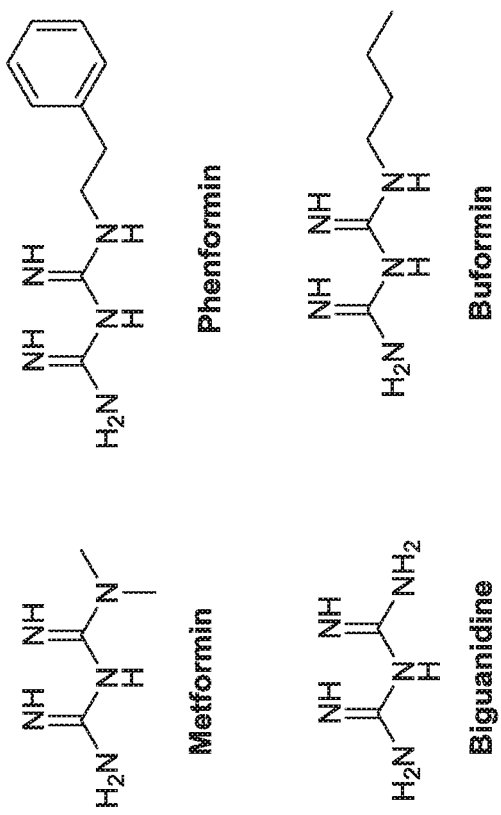
FIG. 6 shows the structure of the metformin agents metformin, phenformin, bisguanidine, and buformin.

In some embodiments, each of $R^{1a}$ and $R^{1b}$ is hydrogen. In some embodiments, each of $R^{2a}$ and $R^{2b}$ is independently hydrogen or $C_1$-$C_6$ alkyl. In some embodiments, each of $R^{2a}$ and $R^{2b}$ is independently $C_1$-$C_4$ alkyl. In some embodiments, each of $R^{2a}$ and $R^{2b}$ is independently $C_1$-$C_2$ alkyl. In some embodiments, each of $R^{2a}$ and $R^{2b}$ is independently methyl. In some embodiments, each of $R^{1a}$ and $R^{1b}$ is hydrogen, and each of $R^{2a}$ and $R^{2b}$ is methyl. In some embodiments, the compound of Formula (I) is metformin, e.g., 3-(diaminomethylidene)-1,1-dimethylguanidine. In some embodiments, the compound of Formula (VIII) is metformin, e.g., as depicted in FIG. 6.

In some embodiments, each of $R^{1a}$ and $R^{1b}$ is hydrogen. In some embodiments, $R^{2a}$ is hydrogen. In some embodiments, $R^{2b}$ is arylalkyl. In some embodiments, $R^{2b}$ is $C_1$-$C_4$ arylalkyl. In some embodiments, $R^{2b}$ is $C_1$-$C_2$ arylalkyl. In some embodiments, $R^{2b}$ is ethylphenyl. In some embodiments, each of $R^{1a}$ and $R^{1b}$ is hydrogen, $R^{2a}$ is hydrogen, and $R^{2b}$ is $C_1$-$C_2$ arylalkyl (e.g., ethylphenyl). In some embodiments, the compound of Formula (VIII) is phenformin, e.g., 1-(diaminomethylidene)-2-(2-phenylethyl)guanidine. In some embodiments, the compound of Formula (VIII) is phenformin, e.g., as depicted in FIG. 6.

In some embodiments, each of $R^{1a}$ and $R^{1b}$ is hydrogen. In some embodiments, $R^{2a}$ is hydrogen. In some embodiments, $R^{2b}$ is $C_1$-$C_6$ alkyl. In some embodiments, $R^{2b}$ is $C_1$-$C_4$ alkyl (e.g., butyl). In some embodiments, each of $R^{1a}$ and $R^{1b}$ is hydrogen, $R^{2a}$ is hydrogen, and $R^{2b}$ is $C_1$-$C_4$ alkyl (e.g., butyl). In some embodiments, the compound of Formula (VIII) is buformin, e.g., 2-butyl-1-(diaminomethylidene)guanidine. In some embodiments, the compound of Formula (VIII) is buformin, e.g., as depicted in FIG. 6.

In some embodiments, each of $R^{1a}$, $R^{1b}$, $R^{2a}$, and $R^{2b}$ is hydrogen. In some embodiments, a compound of Formula (VIII) is biguanide, as depicted in FIG. 6.

Metformin, also known as 3-(diaminomethylidene)-1,1-dimethylguanidine or N,N-Dimethylimidodicarbonimidic diamide, is a widely prescribed glucose-lowering drug for patients suffering from Type 2 diabetes.

In one embodiment, the amount of metformin administered may be a standard dose commonly used in therapeutic administration for treatment of type 2 diabetes, e.g., from about 1500 mg/day to about 2550 mg/day. For example, metformin is administered at 1500 mg/day, 1550 mg/day, 1600 mg/day, 1650 mg/day, 1700 mg/day, 1750 mg/day, 1800 mg/day, 1850 mg/day, 1900 mg/day, 1950 mg/day, 2000 mg/day, 2050 mg/day, 2100 mg/day, 2150 mg/day, 2200 mg/day, 2250 mg/day, 2300 mg/day, 2350 mg/day, 2400 mg/day, 2450 mg/day, 2500 mg/day or 2550 mg/day.

In certain embodiments, metformin is administered at a dose that is less than the standard of care dose or dosage formulation for lowering glucose levels or treatment of Type 2 diabetes. In certain embodiments, metformin is administered at a dose or dosage formulation that is less than 0.01, 0.05, 0.1, 0.2, 0.3, 0.4, 0.5, 0.6, 0.7, 0.8, 0.9, that of the standard of care (e.g., the lower standard of care dose). In one embodiment, the dose or dosage formulation is in the range of, for example, 0.01-0.9-fold, 0.02-0.8-fold, 0.05-0.7-fold, 0.1-0.5 fold, 0.1-0.2-fold, that of the standard of care dose or dosage formulation. Standard of care doses or dosage formulation of metformin is available in the art, some of which are exemplified herein.

In yet other embodiments, metformin is administered at a dose or dosage formulation that is greater than the standard of care dose or dosage formulation for lowering glucose levels or treatment of Type 2 diabetes (e.g., a dose or dosage form that is greater than 1.1, 1.5, 1.7, 2, 3, 4, 5, 10-fold or higher, that of the standard of care dose for treatment of Type 2 diabetes). In one embodiment, the dose or dosage formulation is in the range of, for example, 1.1 to 10-fold, 1.5-5-fold, 1.7 to 4-fold, or 2-3-fold, that of the standard of care dose or dosage formulation. Standard of care doses or dosage formulation of metformin is available in the art, some of which are exemplified herein.

In some embodiments, the metformin agent is administered to the subject as a particle (e.g., a nanoparticle) or as a free agent, as described herein. In some embodiments, the combinations, compositions, dosage formulations include the metformin agent as a particle (e.g., a nanoparticle) or as a free agent, as described herein.

Immunomodulators

The compositions and methods described herein can comprise an immunomodulator. In one embodiment, the immunomodulator is an anti-inflammatory agent described herein, e.g., for treating or preventing a disease or disorder, e.g., a cancer or a fibrotic disorder described herein. The composition and method can include one, two, three or more anti-inflammatory agents, alone or in combination with one or more therapeutic agents described herein (e.g., an AHCM agent, a microenvironment modulator, an immune-checkpoint inhibitor, or an additional therapy, e.g., a cancer or anti-fibrotic therapy).

In one embodiment, the anti-inflammatory agent is an agent that blocks, inhibits, or reduces inflammation or signaling from an inflammatory signaling pathway. In one embodiment, the anti-inflammatory agent inhibits or reduces the activity of one or more of any of the following: IL-1, IL-2, IL-3, IL-4, IL-5, IL-6, IL-7, IL-8, IL-9, IL-10, IL-12, IL-13, IL-15, IL-18, IL-23, interferons (IFNs), e.g., IFNα, IFNβ, IFNγ, IFN-γ inducing factor (IGIF), transforming growth factor-β (TGF-β), transforming growth factor-α (TGF-α), tumor necrosis factors TNF-α, TNF-β, TNF-RI, TNF-RII, CD23, CD30, CD40L, EGF, G-CSF, GDNF, PDGF-BB, RANTES/CCL5, IKK, NF-κB, TLR2, TLR3, TLR4, TL5, TLR6, TLR7, TLR8, TLR8, TLR9, and/or any cognate receptors thereof.

In one embodiment, the anti-inflammatory agent is an IL-1 or IL-1 receptor antagonist, such as anakinra (KINIRET®), rilonacept, or canakinumab.

In one embodiment, the anti-inflammatory agent is an IL-6 or IL-6 receptor antagonist, e.g., an anti-IL-6 antibody or an anti-IL-6 receptor antibody, such as tocilizumab (ACTEMRA®), olokizumab, clazakizumab, sarilumab, sirukumab, siltuximab, or ALX-0061.

In one embodiment, the anti-inflammatory agent is a TNF-α antagonist, e.g., an anti-TNFα antibody, such as infliximab (REMICADE®), golimumab (SIMPONI®), adalimumab (HUMIRA®), certolizumab pegol (CIMZIA®) or etanercept.

In one embodiment, the anti-inflammatory agent is a corticosteroid. Exemplary corticosteroids include, but are not limited to, cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®).

In another embodiment, the anti-inflammatory agent is a non-steroidal anti-inflammatory drug (NSAID). Exemplary anti-inflammatory agents (e.g., NSAIDs) include, but are not limited to, aspirin, ibuprofen, naproxen, celecoxib, diclofenac, diflunisal, etodolac, fenoprofen, flurbiprofen, ketoprofen, ketorolac, mefenamic acid, meloxicam, nabumetone, oxaprozin, piroxicam, sulindac, and tolmetin. In an embodiment, the anti-inflammatory agent is an immune selective anti-inflammatory derivative (ImSAID).

Immune-Checkpoint Inhibitors

The compositions and methods described herein can comprise an immune-checkpoint inhibitor described herein, e.g., for treating or preventing a disease or disorder, e.g., a cancer, inflammatory or a fibrotic disorder described herein. The compositions and methods can include one, two, three or more immune-checkpoint inhibitors, alone or in combination with one or more therapeutic agents described herein (e.g., an AHCM agent, a microenvironment modulator, an anti-inflammatory agent, or an additional therapy, e.g., a cancer or anti-fibrotic therapy).

Immune checkpoints refer to inhibitory pathways in the immune system that are important for maintaining selftolerance (i.e., prevention of autoimmunity) and for protection of tissues from damage during response to pathogenic infections. In cancer, tumors can often hijack immune-checkpoint pathways in order to promote immune resistance and evade attack by the immune system. Thus, blockade of these immune checkpoints, e.g., by immune-checkpoint inhibitors, is desirable to enhance anti-tumor immunity and improve cancer therapies.

Immune checkpoint inhibitors, as described herein, refer to molecules that block, inhibit, or reduce activity of one or more immune checkpoint proteins. The inhibitors may be an antibody, an antigen binding fragment thereof, an immunoadhesin, a fusion protein, or an oligopeptide. Examples of immune-checkpoint molecules include, but are not limited to, PD-1, PD-L1, PD-L2, CTLA4, B7-H3, B7-H4, HVEM, BTLA, a killer-cell immunoglobulin-like receptor (KIR), LAG3, TIM3, CEACAM-1, CEACAM-3, CEACAM-5, GAL9, VISTA, TIGIT, LAIR1, CD73, CD160, 2B4, TGFR-beta, and A2aR.

In some embodiments, the immune checkpoint inhibitor is a PD-1 inhibitor. Antibodies, antibody fragments, and other inhibitors of PD-1 and its ligands (e.g., PD-L1 or PD-L2) are available in the art and may be used combination with metformin as described herein. Exemplary anti-PD-1 antibodies include, but are not limited to, nivolumab (also known as MDX-1106 or BMS-936558), pembrolizumab (formerly known as lambrolizumab, also known as Merck 3475 or MK03475), and pidilizumab (also known as CT-011). Nivolumab (clone 5C4) and other human monoclonal antibodies that specifically bind to PD-1 are disclosed in U.S. Pat. No. 8,008,449 and WO2006/121168. Pidilizumab and other humanized anti-PD-1 monoclonal antibodies are disclosed in WO2009/101611. Pembrolizumab and other humanized anti-PD-1 antibodies are disclosed in U.S. Pat. No. 8,354,509 and WO2009/114335. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence), such as AMP-224.

In some embodiments, the immune checkpoint inhibitor is a PD-L1 inhibitor. Antibodies, antibody fragments, and other inhibitors of PD-L1 are available in the art and may be used combination with metformin as described herein. Exemplary anti-PD-L1 antibodies include, but are not limited to, YW243.55.S70 (as described in PCT Publication No. WO2010/077634), MPDL3280A (as described in U.S. Pat. No. 7,943,743 and U.S. Publication No. 20120039906), MEDI-4736, MSB-0010718C, or MDX-1105 (also referred to as BMS-936559, as described in WO2007/005874).

In some embodiments, the immune checkpoint inhibitor is a TIM3 inhibitor. Antibodies, antibody fragments, and other inhibitors of TIM3 and its ligands are available in the art and may be used combination with metformin as described herein. For example, antibodies, antibody fragments, small molecules, or peptide inhibitors that target TIM3 binds to the IgV domain of TIM3 to inhibit interaction with its ligands can be administered in combination with a metformin agent as described herein. Exemplary TIM3 inhibitors include, but are not limited to the antibodies and peptides disclosed in WO2013/006490 and US20100247521); anti-TIM3 inhibitors such as humanized versions of RMT3-23 (as disclosed in Ngiow et al., 2011, Cancer Res, 71:3540-3551) and clone 8B.2C12 (disclosed in Monney et al., 2002, Nature, 415: 536-541). Bi-specific antibodies that inhibit TIM3 and PD-1 are disclosed in US20130156774.

In some embodiments, the immune checkpoint inhibitor is a LAG3 inhibitor. Antibodies, antibody fragments, and other inhibitors of LAG3 and its ligands are available in the art and may be used combination with metformin as described herein. Exemplary anti-LAG3 antibodies include, but are not limited to monoclonal antibody BMS-986016 (Bristol-Myers Squib), IMP701 (Immutep), IMP731 (Immutep and GlaxoSmithKline), and antibodies disclosed in WO2010/019570. Other LAG3 inhibitors include IMP321 (Immutep), which is a recombinant fusion protein of a soluble portion of LAG3 and Ig that binds to MHC class II molecules and activates antigen presenting cells (APC).

In some embodiments, the immune checkpoint inhibitor is a CEACAM inhibitor, e.g., a CEACAM-1 inhibitor, a CEACAM-3 inhibitor, and/or a CEACAM-5 inhibitor. Antibodies, antibody fragments, and other inhibitors of CEACAM are available in the art and may be used combination with metformin as described herein. Exemplary anti-CEACAM-1 antibodies include, but are not limited to, antibodies described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Targeting Moieties

The composition can also include a targeting moiety, e.g., a targeting moiety that is specific to a cell type or tissue. The targeting moiety is also referred to as a targeting ligand or targeting agent herein. Targeting of particles with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the particle in such a manner that the targeting moiety is available for interaction with the target, for example, a cell surface receptor.

In one approach, a targeting moiety, such as receptor binding ligand, can be linked to a component of the nanoparticle. In some embodiments, the targeting ligand can be conjugated with the polymer used for forming the nanoparticle. A variety of different targeting ligands and methods are known and available in the art, including those described, e.g., in Sapra, P. and Allen, T M, *Prog. Lipid Res.* 42(5): 439-62 (2003); and Abra, R M et al., *J. Liposome Res.* 12:1-3, (2002).

Without limitation, a targeting ligand can be selected from the group consisting of peptides, polypeptides, proteins, enzymes, peptidomimetics, glycoproteins, antibodies (monoclonal or polyclonal) and portions and fragments thereof (e.g., antigen binding fragments), lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

Non-limiting examples of antibodies and other suitable targeting moieties include those that target tumor/cancer-associated antigens, antigens that are differentially expressed on inflamed tissue (e.g., EGFR, ICAM-1 VCAM-1), antigens that are differentially expressed during cell maturation or antigens that are expressed on diseased tissues, pathogens or bacteria (e.g., sugar moieties).

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, am11, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, and c-erbB-2.

As other examples, the targeting moieties include peptides that comprise Arg-Gly-Asp motifs (or RGD peptides) that target integrin present on angiogenic tumor vasculature.

In some embodiments, the targeting moiety includes a nucleic acid. The term "nucleic acids," or "oligonucleotides," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer may also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, MI-methyladenosine, pyrrolo-pyrimidine, 2-amino-6-chloropurine, 3-methyl adenosine, 5-propynylcytidine, 5-propynyluridine, 5-bromouridine, 5-fluorouridine, O-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide may include DNA, RNA, modified DNA, modified RNA, antisense oligonucleotides, expression plasmid systems, nucleotides, modified nucleotides, nucleosides, modified nucleosides, aptamers, intact genes, or combinations thereof. Other examples of polynucleotides include interfering RNA, natural or unnatural siRNAs, shRNAs, microRNAs, ribozymes, DNA plasmids, aptamers, antisense oligonucleotides, randomized oligonucleotides, or ribozymes. The targeting moiety can also be an Adnectin™ (a biologic derived from fibronectin).

Other nucleic acid targeting moieties include Spiegelmers® (mirror-image oligonucleotides that can bind to a target molecule), SMIP™ therapeutics (single chain polypeptides comprising one binding domain, one hinge domain and one effector domain) or SCORPION™ therapeutics (single chain polypeptides that is multi-specific and/or multivalent).

In some embodiments, the targeting moiety can include an aptamer, i.e., a nucleic acid able to specifically bind a specific target molecule, such as a biological moiety. Non-limiting examples of aptamers include RNA aptamers and DNA aptamers. For example, the size of the aptamer may be at least about 5 kDa, at least about 10 kDa, at least about 15 kDa, or at least about 20 kDa.

In some embodiments, the targeting ligand can be selected from the group consisting of polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacrylic acid), N-isopropylacrylamide polymers, polyphosphazine, polyethylenimine, spermine, spermidine, polyamine, pseudopeptide-polyamine, peptidomimetic polyamine, dendrimer polyamine, arginine, amidine, protamine, thyrotropin, melanotropin, lectin, surfactant protein A, mucin, transferrin, bisphosphonate, polyglutamate, polyaspartate, an aptamer, asialofetuin, hyaluronan, procollagen, insulin, transferrin, albumin, acridines, cross-psoralen, mitomycin C, TPPC4, texaphyrin, Sapphyrin, polycyclic aromatic hydrocarbons (e.g., phenazine, dihydrophenazine), bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), RGD peptide, radiolabeled markers, haptens, naproxen, aspirin, dinitrophenyl, HRP, AP, lectins, vitamin A, vitamin E, vitamin K, vitamin B, folic acid, B12, riboflavin, biotin, pyridoxal, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, GalNAc, galactose, mannose, mannose-6-phosphate, clusters of sugars such as GalNAc cluster, mannose cluster, galactose cluster, an aptamer, integrin receptor ligands, chemokine receptor ligands, serotonin receptor ligands, PSMA, endothelin, GCPII, somatostatin, cellular adhesion molecules (CAMS), and any combinations thereof.

In some embodiments, the targeting ligand is a tumor binding ligand.

In one embodiment, the targeting ligand is mannose-6-phosphate.

Liver Targeting Moieties

In some embodiments, any particle described herein can be targeted to the liver, e.g., targeted to a liver cell. Targeting to the liver or to a specific population of liver cells have the following advantages: reduction of off-target, and potentially toxic, side effects, increase amount of drug delivery to the desired site of action or to the desired cells, increase the specificity of the interaction between the drug delivery system and target cells or tissues, and increase the overall efficacy of the drug.

Examples of liver cells that can be targeted include hepatocytes, Kupffer cells, endothelial cells, hepatic stellate cells, bile duct epithelial cells, or hepatocellular carcinoma cells, or any combination thereof. To target a specific liver cell, a targeting moiety or ligand is present, e.g., covalently or non-covalently attached, to a component of the nanoparticle. The targeting moiety or ligand specifically binds to a receptor or surface molecule at the surface membrane of the targeted liver cell.

The following substances can be used as targeting moieties: antibodies or antigen-binding fragments thereof, lectins, proteins, lipoproteins, hormones, charged molecules, mono-, olio-, and polysaccharides, and low molecular weight ligands such as sugars, folic acids, and peptides.

For targeting hepatocytes, the targeting moiety can specifically bind or interact with one or more of the following: asialoglycoprotein receptor (ASGP-R), high density lipoprotein receptor (HDL-R), low density lipoprotein receptor (LDL-R), immunoglobulin A receptor (IgA-R), scavenger receptor (class BI), transferrin receptor, bile acid receptor, insulin receptor, glycyrrhizin receptor (GL receptor), and glycyrrhetinic acid receptor (GA receptor). Examples of targeting moieties for hepatocytes include ligands containing galactose, N-acetylgalactosamine, galatosamine, lactoferrin, lactobionic acid (LA), asialofetuin ligand (AF), soybean-derived SG ligand (e.g., sterylglucoside), glycyrrhizin (GL), glycyrrhetinic acid (GA), or derivatives thereof.

For targeting Kupffer cells, the targeting moiety can specifically bind or interact with one or more of the following: mannose/N-acetylglucosamine receptor, galactose particle receptor, galactose specific receptor, Fc receptor immune complexes and opsinized material, scavenger receptors (Class AI, BI, BII, MARCO, CD36, and macrosialin), low density lipoprotein receptor matrix compounds (fibronectin), complement receptor (C3b and C1q), LPS receptor $\alpha_2$, and macroglobulin receptor. Examples of targeting moieties for Kupffer cells include D-mannose, cetylmannoside, dexamethasone coupled to mannosylated albumin, and charged molecules with a net negative charge, e.g., albumin with modified lysines such that albumin has a net negative charge, or derivatives thereof.

For targeting endothelial cells, e.g., sinusoidal endothelial cells, the targeting moiety can specifically bind or interact with one or more of the following: mannose/N-acetyl glucosamine receptor, scavenger receptor (Class A1 and A11), Fc Receptor immune complexes, and matrix compounds (e.g., hyaluronan, fibronectin, denatured collagen, PIIINP).

For targeting hepatic stellate cells (HSCs), the targeting moiety can specifically bind or interact with one or more of the following: mannose-6-phosphate receptor, insuring growth factor II receptor (IGFII R), $\alpha_2$ macrogloblin receptor, ferritin receptor, uroplasminogen receptor, RBP receptor, and matrix compounds (e.g., integrin, collagen type VI, fibronectin, CD44). Examples of targeting moieties for HSCs include mannose-6-phosphate (M6P), and cyclic peptide moieties that serve as binding domains of cytokines and growth factors that bind to HSCs, or derivatives thereof.

For targeting bile duct epithelial cells, the targeting moiety can specifically bind or interact with secretin receptor.

For targeting hepatocellular carcinoma cells, e.g., liver cancer cells, the targeting moiety can specifically bind or interact with asialoglycoprotein receptor (ASGP-R). Examples of targeting moieties for HCC cells include lactosaminated ligands, galactosamine, galactosylated ligands, e.g., chitosan, N-lactosyl-dioleoylphosphatidylethanolamine (Lac-DOPE), or lactobionic acid, or derivatives thereof.

In some embodiments, the particles and/or conjugates comprising the AHCM, microenvironment modulator, other stromal modulators, and/or the liver disorder therapy (e.g., sorafenib, anti-angiogenic therapy) is not targeted to the liver.

In other embodiments, the particles and/or conjugates comprising the AHCM, microenvironment modulator, other stromal modulators, and/or the liver disorder therapy (e.g., sorafenib, anti-angiogenic therapy) is targeted to the liver, e.g., targeted to a liver cell. Examples of liver cells that can be targeted include hepatocytes, Kupffer cells, endothelial cells, hepatic stellate cells, bile duct epithelial cells, or hepatocellular carcinoma cells, or any combination thereof.

In some embodiments, the particles and/or conjugates comprising the AHCM, microenvironment modulator, other stromal modulators, and/or the liver disorder therapy (e.g., sorafenib, anti-angiogenic therapy) can be targeted to myofibroblasts present in the liver.

To target a specific liver cell, a targeting moiety or ligand can be coupled, e.g., covalently or non-covalently, to a component of a particle or a conjugate, e.g., a particle or conjugate as described herein. The targeting moiety or ligand specifically can bind to a receptor or surface molecule at the surface membrane of the targeted liver cell, and thus deliver the particle or conjugated to the targeted liver cell.

In some embodiments, the particles and/or conjugates target a hepatocyte. The liver targeting moiety can be chosen from an agent that specifically binds to, or interacts with, one or more of the following: asialoglycoprotein receptor (ASGP-R), high density lipoprotein receptor (HDL-R), low density lipoprotein receptor (LDL-R), immunoglobulin A receptor (IgA-R), scavenger receptor (class BI), transferrin receptor, bile acid receptor, insulin receptor, glycyrrhizin receptor (GL receptor), and glycyrrhetinic acid receptor (GA receptor). Examples of liver targeting moieties for hepatocytes include, but are not limited to, ligands containing galactose, N-acetylgalactosamine, galatosamine, lactoferrin, lactobionic acid (LA), asialofetuin ligand (AF), soybean-derived SG ligand (e.g., sterylglucoside), glycyrrhizin (GL), glycyrrhetinic acid (GA), or derivatives thereof.

In some embodiments, the particles and/or conjugates target a Kupffer cell. The liver targeting moiety can be chosen from an agent that specifically binds to, or interacts with, one or more of the following: mannose/N-acetylglucosamine receptor, galactose particle receptor, galactose specific receptor, Fc receptor immune complexes and opsinized material, scavenger receptors (Class AI, BI, BII, MARCO, CD36, and macrosialin), low density lipoprotein receptor matrix compounds (fibronectin), complement receptor (C3b and C1q), LPS receptor $\alpha_2$, and macroglobulin receptor. Examples of liver targeting moieties for Kupffer cells include, but are not limited to, D-mannose, cetylmannoside, dexamethasone coupled to mannosylated albumin, and charged molecules with a net negative charge, e.g., albumin with modified lysines such that albumin has a net negative charge, or derivatives thereof.

In some embodiments, the particles and/or conjugates target an endothelial cell, e.g., sinusoidal endothelial cells. The liver targeting moiety can be chosen from an agent that specifically binds to, or interacts with, one or more of the following: mannose/N-acetyl glucosamine receptor, scavenger receptor (Class A1 and A11), Fc Receptor immune complexes, and matrix compounds (e.g., hyaluronan, fibronectin, denatured collagen, PIIINP).

In some embodiments, the particles and/or conjugates target a hepatic stellate cell (HSC). The liver targeting moiety can be chosen from an agent that specifically binds to, or interacts with, one or more of the following: mannose-6-phosphate receptor, insulin growth factor II receptor (IG-FII R), $alpha_2$ macroglobulin receptor, ferritin receptor, uroplasminogen receptor, RBP receptor, and matrix compounds (e.g., integrin, collagen type VI, fibronectin, CD44). Examples of liver targeting moieties for HSCs include, but are not limited to, mannose-6-phosphate (M6P), and cyclic peptide moieties that serve as binding domains of cytokines and growth factors that bind to HSCs, or derivatives thereof. In one embodiment, the liver targeting moiety is M6P.

In some embodiments, the particles and/or conjugates target a bile duct epithelial cell. The liver targeting moiety can bind to, or interact with, a secretin receptor.

In some embodiments, the particles and/or conjugates target a liver cancer cell, e.g., a hepatocellular carcinoma cells. The liver targeting moiety can be chosen from an agent that specifically binds to, or interacts with, an asialoglycoprotein receptor (ASGP-R). Examples of targeting moieties for HCC cells include lactosaminated ligands, galactosamine, galactosylated ligands, e.g., chitosan, N-lactosyl-dioleoylphosphatidylethanolamine (Lac-DOPE), mannose-6-phosphate (M6P), lactobionic acid, or derivatives thereof.

Therapeutic Methods

In one aspect, the invention relates to a method of treating a disorder, e.g., a hyperproliferative disorder (e.g., a cancer) by administering to a patient an AHCM agent, alone or in combination with a therapy or a therapeutic agent, e.g., an anti-cancer agent as described herein.

As used herein, and unless otherwise specified, the terms "treat," "treating" and "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

For example, in the case of treating cancer, in some embodiments, therapeutic treatment can refer to inhibiting or reducing tumor growth or progression after administration in accordance with the methods or administration with the pharmaceutical compositions described herein. For example, tumor growth or progression is inhibited or reduced by at least about 10%, at least about 15%, at least about 20%, at least about 30%, at least about 40%, or at least about 50%, after treatment. In another embodiment, tumor growth or progression is inhibited or reduced by more than 50%, e.g., at least about 60%, or at least about 70%, after treatment. In one embodiment, tumor growth or progression is inhibited or reduced by at least about 80%, at least about 90% or greater, as compared to a control (e.g. in the absence of the pharmaceutical composition described herein).

In another embodiment, the therapeutic treatment refers to alleviation of at least one symptom associated with cancer. Measurable lessening includes any statistically significant decline in a measurable marker or symptom, such as measuring a cancer biomarker, such as serum/plasma cancer biomarker in a blood sample, after treatment. In one embodiment, at least one cancer biomarker or symptom is alleviated by at least about 10%, at least about 15%, at least about 20%, at least about 30%, at least about 40%, or at least about 50%. In another embodiment, at least one cancer biomarker or symptom is alleviated by more than 50%, e.g., at least about 60%, or at least about 70%. In one embodiment, at least one cancer biomarker or symptom is alleviated by at least about 80%, at least about 90% or greater, as compared to a control (e.g. in the absence of the pharmaceutical composition described herein).

As used herein, unless otherwise specified, the terms "prevent," "preventing" and "prevention" contemplate an action that occurs before a patient begins to suffer from the regrowth of the cancer and/or which inhibits or reduces the severity of the cancer.

As used herein, and unless otherwise specified, a "therapeutically effective amount" of a compound is an amount sufficient to provide a therapeutic benefit in the treatment of the disorder (e.g., cancer), or to delay or minimize one or more symptoms associated with the disorder (e.g., cancer). A therapeutically effective amount of a compound means an amount of therapeutic agent, alone or in combination with other therapeutic agents, which provides a therapeutic benefit in the treatment or management of the disorder. The term "therapeutically effective amount" can encompass an amount that improves overall therapy, reduces or avoids symptoms or causes of the disorder (e.g., cancer), or enhances the therapeutic efficacy of another therapeutic agent.

As used herein, and unless otherwise specified, a "prophylactically effective amount" of a compound is an amount sufficient to prevent a disorder (e.g., regrowth of the cancer, or one or more symptoms associated with the cancer, or prevent its recurrence). A prophylactically effective amount of a compound means an amount of the compound, alone or in combination with other therapeutic agents, which provides a prophylactic benefit in the prevention of the disorder. The term "prophylactically effective amount" can encompass an amount that improves overall prophylaxis or enhances the prophylactic efficacy of another prophylactic agent.

In some embodiments, the AHCM agent, alone or in combination, is a first line treatment for the cancer, i.e., it is used in a subject who has not been previously administered another drug intended to treat the cancer.

In other embodiments, the AHCM agent, alone or in combination, is a second line treatment for the cancer, i.e., it is used in a subject who has been previously administered another drug intended to treat the cancer.

In other embodiments, the AHCM agent, alone or in combination, is a third or fourth line treatment for the cancer, i.e., it is used in a subject who has been previously administered two or three other drugs intended to treat the cancer.

In some embodiments, the AHCM agent is administered to a subject before, during, and/or after radiation or surgical treatment of the cancer.

In some embodiments, the AHCM agent is administered, alone or in combination with a cancer therapy or an anti-cancer agent, to a subject who previously did not respond to at least one cancer therapy or anti-cancer agent, including at least two, at least three, or at least four cancer therapies or anti-cancer agents. In such embodiments, the AHCM agent can be administered to a subject in combination with the cancer therapy or anti-cancer agent to which he/she previously did not respond, or in combination with a cancer therapy or anti-cancer agent different from the one(s) he/she has been treated with.

In other embodiments, the AHCM agent is administered as adjunct therapy, i.e., a treatment in addition to primary therapy. In some embodiments, the adjuvant effect of the AHCM administered in combination with a primary therapy can be additive. In some embodiments, the adjuvant effect of the AHCM administered in combination with a primary therapy can be synergistic.

Disorders

The AHCM, alone or in combination with a microenvironment modulator and/or a therapy or a therapeutic agent, e.g., an anti-cancer agent as described herein can be used to treat or prevent a disorder, e.g., a hyperproliferative disorder (e.g., a cancer).

In certain embodiments, the disorder is chosen from one or more of a hyperproliferative disorder, a cancer, a fibrotic disorder, an inflammatory disorder or an autoimmune disorder.

In certain embodiments, the cancer is an epithelial, mesenchymal or hematologic malignancy. In certain embodiments, the cancer treated is a solid tumor (e.g., carcinoid, carcinoma or sarcoma), a soft tissue tumor (e.g., a heme malignancy), and a metastatic lesion, e.g., a metastatic lesion of any of the cancers disclosed herein. In one embodiment, the cancer treated is a fibrotic or desmoplastic solid tumor, e.g., a tumor having one or more of: limited tumor perfusion, compressed blood vessels, fibrotic tumor interstitium, or increased interstitial fluid pressure. In one embodiment, the solid tumor is chosen from one or more of pancreatic (e.g., pancreatic adenocarcinoma or pancreatic ductal adenocarcinoma), breast, colon, colorectal, lung (e.g., small cell lung cancer (SCLC) or non-small cell lung cancer (NSCLC)), skin, ovarian, liver cancer, esophageal cancer, endometrial cancer, gastric cancer, head and neck cancer, kidney, or prostate cancer.

By "hyperproliferative cancerous disease or disorder" is meant all neoplastic cell growth and proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and "cancer."

As used herein, "cancer" and "tumor" are synonymous terms.

As used herein, "cancer therapy" and "cancer treatment" are synonymous terms.

As used herein, "chemotherapy," "chemotherapeutic," "chemotherapeutic agent" and "anti-cancer agent" are synonymous terms.

As used herein, the terms "cancer," "tumor" or "tumor tissue" refer to an abnormal mass of tissue that results from excessive cell division, in certain cases tissue comprising cells which express, over-express, or abnormally express a hyperproliferative cell protein. A cancer, tumor or tumor tissue comprises "tumor cells" which are neoplastic cells with abnormal growth properties and no useful bodily function. Cancers, tumors, tumor tissue and tumor cells may be benign or malignant. A cancer, tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adeno-carcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma. Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In other embodiments, the AHCM agent, as described above and herein, is used to treat a hyperproliferative disorder, e.g., a hyperproliferative connective tissue disorder (e.g., a hyperproliferative fibrotic disease). In one embodiment, the hyperproliferative fibrotic disease is multisystemic or organ-specific. Exemplary hyperproliferative fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the eye, lung, liver, heart, kidney, pancreas, skin and other organs). In other embodiments, the disorder is chosen from liver cirrhosis or tuberculosis. In other embodiments, the disorder is leprosy.

In other embodiment, the subject treated has a hyperproliferative genetic disorder, e.g., a hyperproliferative genetic disorder chosen from Marfan's syndrome or Loeys-Dietz syndrome. Losartan has been shown to treat human Marfan syndrome, a connective tissue disorder caused by mutations in the gene that encodes the extracellular matrix protein, fibrillin-1 (Dietz, H. C. et al. (2010) *New Engl J Med* 363(9):852-863). Fibrillin-1 comprises the microfibrils of elastic tissue and a component of many other connective tissues. Affected patients with Marfan syndrome have blood vessel abnormalities such as aortic aneurysms. The vascular disease can result in blood vessel rupture and death in childhood and later in life. Dietz et al. first found in mouse models of Marfan syndrome that excessive activation of latent TGF-β has an important role in the pathophysiology. They used losartan in the affected mice and showed striking effects in improving blood vessel architecture and prevented the development of aortic aneurysms. They have also used losartan to treat children with Marfan syndrome and demonstrated that the drug can strikingly prevent progression of aortic and muscular lesions. Aortic diseases other than Marfan syndrome can also benefit from the use of losartan. Inhibition of activation of latent TGF-β locally and decreasing circulating levels of active TGF-β thus can have effects on components of connective tissues other than collagen in the extracellular matrix of cancer tissues that alter delivery and efficacy of nanotherapeutics.

In other embodiments, the hyperproliferative disorder (e.g., the hyperproliferative fibrotic disorder) is chosen from one or more of chronic obstructive pulmonary disease, asthma, aortic aneurysm, radiation-induced fibrosis, skeletal-muscle myopathy, diabetic nephropathy, and/or arthritis.

Additional exemplary hyperproliferative disorders that can be treated by the methods and compositions of the invention are disclosed in Sounni, N. E. et al. (2010) *Diseases Models & Mechanisms* 3:317-332.

In yet other embodiments, the disorder is chosen from an inflammatory or an autoimmune disorder chosen from multiple sclerosis, inflammatory bowel disease, scleroderma, lupus, rheumatoid arthritis or osteoarthritis.

In certain embodiments, the inflammatory disorder is an inflammatory disorder of: the gastrointestinal tract or a gastrointestinal organ, e.g., colitis, Crohn's disease, inflammatory bowel disease (IBD), Barrett's esophagus and chronic gastritis; the lung (e.g., asthma, chronic obstructive pulmonary disease (COPD); the skin (e.g., psoriasis), the cardiovascular system (e.g., atherosclerosis, cholesterol metabolic disorders, oxygen free radical injury, ischemia), the nervous system (e.g., Alzheimer's disease, multiple sclerosis), liver (e.g., hepatitis), kidney (e.g., nephritis), and the pancreas (e.g., pancreatitis).

In other embodiments, the inflammatory disorder is associated with an autoimmune disorder, e.g., arthritis (including rheumatoid arthritis, juvenile rheumatoid arthritis, osteoarthritis, psoriatic arthritis, lupus-associated arthritis, autoimmune thyroiditis or ankylosing spondylitis); scleroderma; lupus; systemic lupus erythematosis; HIV; Sjogren's syndrome; vasculitis; multiple sclerosis; dermatitis (including atopic dermatitis and eczematous dermatitis), myasthenia gravis, inflammatory bowel disease (IBD), Crohn's disease, colitis, diabetes mellitus (type 1); acute inflammatory conditions (e.g., endotoxemia, sepsis and septicemia, toxic shock syndrome and infectious disease); transplant rejection and allergy.

In one embodiment, the inflammatory disorder is a chronic inflammatory disorder.

In one embodiment, the inflammatory disorder is an osteomyelitis, e.g., chronic osteomyelitis.

Combination Therapies

It will be appreciated that the agents described herein, e.g., the AHCM, the microenvironment modulator and/or the other stromal modulator as described above and herein as a particle or as a free agent, can be administered in combination with one or more additional therapies, e.g., such as radiation therapy, PDT, surgery, immune therapy, and/or in combination with one or more therapeutic agents, to treat the cancers described herein.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

In general, it is expected that additional therapeutic agents utilized in combination be utilized at levels that do not exceed the levels at which they are utilized individually. In some embodiments, the levels utilized in combination will be lower than those utilized individually.

In certain embodiments, the AHCM and/or the therapy (e.g., the cancer or hyperproliferative therapy) is administered in combination with a microenvironment modulator. The combined administration of the AHCM and the microenvironment modulator can be used to enhance the efficacy (e.g., penetration and/or diffusion), of a therapy, e.g., a cancer therapy, in a tumor or tumor vasculature in a subject. Such combination may cause one or more of: reduce solid stress (e.g., growth-induced solid stress in tumors); decrease tumor fibrosis; reduce interstitial hypertension or interstitial fluid pressure (IFP); increase interstitial tumor transport; increase tumor or vessel perfusion; increase vascular diameters and/or enlarge compressed or collapsed blood vessels; reduce or deplete one or more of: cancer cells, or stromal cells (e.g., tumor associated fibroblasts or immune cells); decrease the level or production of extracellular matrix components, such as fibers (e.g., collagen, procollagen), and/or polysaccharides (e.g., glycosaminoglycans such as hyaluronan or hyaluronic acid); decrease the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases cancer stem cells (also referred to herein as tumor initiating cells), thereby enhancing the penetration and/or distribution of the therapy, e.g., the cancer therapy.

Exemplary microenvironment modulators are disclosed herein, and include, but are not limited to, an anti-angiogenic therapy, for example, an inhibitor of vascular endothelial growth factor (VEGF) pathway; an agent that decreases the level or production of hyaluronic acid; an inhibitor of the hedgehog pathway; an agent that improves drug penetration in tumors. In one embodiment, the agent is a disulfide-based cyclic RGD peptide (iRGD) or an analogue thereof; a taxane therapy (e.g., taxane-induced apoptosis); an agent that decreases the level or production of collagen or procollagen; an agent that modulates the crosslinking of matrix molecules; an agent that depletes or changes the differentiation state of fibroblasts or stellate cells; an anti-fibrotic agent and/or a profibrotic pathway inhibitor.

In one embodiment, the microenvironment modulator includes an anti-angiogenic therapy, for example, an inhibitor of vascular endothelial growth factor (VEGF) pathway.

Exemplary VEGF pathway inhibitors include, but are not limited to, an antibody against VEGF (e.g., bevacizumab); a VEGF receptor inhibitor (e.g., an inhibitor of VEGFR-1 inhibitor, a VEGFR-2 inhibitor, or a VEGFR-3 inhibitor (e.g., VEGFR inhibitors such as Cediranib (AZD2171)); a VEGF trap (e.g., a fusion protein that includes a VEGFR domain (e.g., a VEGFR1 domain 2 and a VEGFR2 domain 3) fused to an Fc fragment of an IgG); and an anti-VEGF aptamer (or a pegylated derivative thereof (e.g., MACU-GEN®).

In one embodiment, the microenvironment modulator includes an inhibitor of the angiopoietin-Tie-2 pathway (e.g., an Ang-1 or an Ang-2 inhibitor). Examples of anti-angiopoietin/Tie-2 pathway agents (or inhibitors of the angiopoietin-Tie-2 pathway) include, but are not limited to, AMG 386, CVX-060, CVX-241, MEDI-3617, REGN910, AMG-780, CEP-1198, ARRY-614, MGCD265, Regorafenib, and combinations thereof. In one embodiment, the inhibitor is a dual inhibitor of VEGF and an angiopoietin (also known as a double anti-angiogenic protein or DAAP). In one embodiment, the inhibitor is an antibody against Ang-1 or Ang-2 or both. In other embodiments, the inhibitor is a peptibody that neutralizes Ang-1 or Ang-2.

In another embodiment, the microenvironment modulator includes an agent that decreases the level or production of hyaluronic acid (HA). Enzymatic targeting of the stroma using systemic administration of a pegylated derivative of hyaluronidase (PEGPH20) has been shown to ablate stromal HA in a model for pancreatic ductal adenocarcinoma (PDA) and increase vessel diameter in pancreatic tumors; hyaluronidase derivatives, in combination with standard chemotherapeutic agents (e.g., gemcitabine), can remodel the tumor microenvironment and increase overall survival (see e.g., Provenzano, P. et al. (2012) *Cancer Cell* 21: 418-429). Thus, combined administration of the AHCM and the microenvironment modulator can be used to enhance penetration and/or diffusion of a cancer therapy in a tumor or tumor vasculature, by for example, decreasing certain matrix components, e.g., HA, in the stroma. Exemplary HA-depleting agents include, but are not limited to, an anti-hyaluronan enzymatic therapy such as hyaluronidase or a derivative thereof (e.g., pegylated recombinant human hyaluronidase) (e.g., PH20, PEGPH20); and an antibody against hyaluronic acid.

In another embodiment, the microenvironment modulator includes an inhibitor of the hedgehog pathway. Hedgehog inhibitors have been shown to increase vessel density in pancreatic tumors (Olive, K. P. et al. (2009) *Science* 324: 1457-61), presumably by reducing stromal cell density and solid stress. Exemplary hedgehog inhibitors include, but are not limited to, IPI-926, GDC-0449, cylopamine or an analogue thereof, and GANT58.

In another embodiment, the microenvironment modulator includes an agent that improves drug penetration in tumors. In one embodiment, the agent is a disulfide-based cyclic RGD peptide (iRGD) or an analogue thereof (e.g., described in Sugahara, K N et al. (2010) Science 328:1031-5; Ye, Y. et al. (2011) Bioorg Med Chem Lett. 21(4):1146-50).

In yet another embodiment, the microenvironment modulator includes a taxane therapy (e.g., taxane-induced apoptosis as described in Griffon-Etienne, G. et al. (1999) Cancer Res. 59(15):3776-82).

In another embodiment, the microenvironment modulator includes an agent that modulates (e.g, inhibits) a hypoxia inducible factor (HIF), for example, an agent that inhibits hypoxia-inducible factors 1α and 2α (HIF-1α and HIF-2α). HIF activity has been shown to be involved in inflammation (e.g., rheumatoid arthritis) and angiogenesis associated with cancer tumor growth. HIF inhibitors, such as phenethyl isothiocyanate (PEITC) are under investigation for anticancer effects (Syed Alwi S S, et al. (2010) Br. J. Nutr. 104 (9): 1288-96; Semenza G L (2007). Drug Discov. Today 12 (19-20): 853-9; Melillo G (2006). Mol. Cancer Res. 4 (9): 601-5. In one embodiment, the agent is an antibody against an HIF. In another embodiment, the agent is an HIF chemical inhibitor, such as phenethyl isothiocyanate (PEITC).

In another embodiment, the microenvironment modulator includes an agent that decreases the level or production of collagen or procollagen. For example, an agent that degrades collagen, e.g., collagenase.

In one embodiment, the AHCM and/or the therapy (e.g., the cancer or hyperproliferative therapy) is administered in combination with a microenvironment modulator chosen from an anti-fibrotic agent or an inhibitor of a profibrotic pathway (a "profibrotic pathway inhibitor") (e.g., a pathway dependent- or independent of TGF-beta and/or CTGF activation). In one embodiment, the AHCM and/or the cancer therapy is administered in combination with one or more of: an inhibitor of endothelin-1, PDGF, Wnt/beta-catenin, IGF-1, TNF-alpha, and/or IL-4. In another embodiment, the AHCM and/or the cancer therapy is administered in combination with an inhibitor of endothelin-1 and/or PDGF. In other embodiments, the AHCM and/or the cancer therapy is administered in combination with an inhibitor of one or more of chemokine receptor type 4 (CXCR4) (e.g., AMD3100, MSX-122); stromal-derived-factor-1 (SDF-1) (e.g., tannic acid); hedgehog (e.g., IPI-926, GDC-0449, cylopamine or an analogue thereof, or GANT58).

In certain embodiments, an inhibitor of a CXCR4 receptor and/or its ligand, SDF-1, is administered in combination with a therapy (e.g., a cancer or hyperproliferative therapy as described herein). Certain embodiments may further include administration of a further AHCM and/or a microenvironment modulator as described herein. Without wishing to be bound by theory, inhibition of CXCR4 receptor and/or its ligand, SDF-1, alone or in combination with an AHCM, e.g., an angiotensin II receptor blocker, can be used to reduce the desmoplasia in certain fibrotic or desmoplastic cancers, e.g., a fibrotic or a desmoplastic solid tumor, such as pancreatic cancers (e.g., pancreatic ductal adenocarcinoma (PDAC)). For example, activation of SDF-1a/CXCR4 and angiotensin II (ATII) signaling pathways is known to promote carcinoma activated fibroblasts (also known as cancer associated fibroblasts, or CAF) recruitment, activation, and matrix production in PDAC. Hypoxia, which is associated with PDAC, can induce SDF-1a and CXCR4 expression in cancer cells and CAFs through HIF-1a activation (Schioppa, T., et al. (2003) J Exp Med, 198: 1391-1402) while promoting growth and metastasis (Chang, Q., et al. (2011) Cancer Research, 71: 3110-3120). These effects arise, at least in part, through SDF-1a/CXCR4-dependent activation of CAFs (Gao, Z. et al. (2010) Pancreatology 10: 186-193; Moriyama, T. et al. (2010) Cancer 116: 3357-3368) and a CD133+/CXCR4+ cancer stem cell population (Hermann, P. C. et al. (2007) Cell Stem Cell 1: 313-323), which also confers chemoresistance (Singh, S. et al. (2010) Br J Cancer 103: 1671-1679). High SDF-1a levels (Liang, J. J., et al. (2010) Cancer Epidemiology Biomarkers & Prevention 19: 2598-2604) and CXCR4 levels (Marechal, R. et al. (2009) Br J Cancer, 100: 1444-1451) can be predictive of poor prognosis in PDAC patients. On the other hand, ATII signaling can stimulate CAF proliferation (Hama, K. et al. (2006) Biochemical and Biophysical Research Communications, 340: 742-750; Hama, K. et al. (2004) Biochem Biophys Res Commun. 315: 905-911; Shimizu, K. et al. (2008) J Gastroenterol Hepatol, 23 Suppl 1: Si 19-121), and ATII signaling through ATII-receptor type 1 (AT1) can stimulate CAF matrix production via TGF-β1 and ERK-dependent mechanisms (Rodriguez-Vita, J. et al. (2005) Circulation 111: 2509-2517; Yang, F. et al. (2009) Hypertension, 54: 877-884). ATII also induces TGF-β1 (Elenbaas, B. and Weinberg, R. A. (2001) Experimental Cell Research, 264: 169-184) and SDF-1a (Chu, P. Y. et al. (2010) Am J Pathol, 176: 1735-1742) expression by both cancer cells and CAFs, which can promote CAF proliferation and matrix production. Thus, inhibition of a CXCR4 receptor and/or its ligand, SDF-1, can be used (alone or with an inhibitor of ATII signaling) to enhance the distribution of a therapy in fibrotic or desmoplastic cancers.

Exemplary SDF-1/CXCR4 inhibitors that can be used include, but are not limited to, 2,2'-bicyclam; 6,6'-bicyclam; AMD3100 (IUPAC name: 1,1'-[1,4-phenylene-bis(methylene)]-bis-1,4,8,11-tetraazacyclotetradecane), as described in e.g., U.S. Pat. Nos. 5,021,409, 6,001,826 and 5,583,131; Plerixafor (trade name: Mozobil; IUPAC name: 1,1'-[1,4-Phenylenebis(methylene)]bis [1,4,8,11-tetraazacyclotetradecane); CXCR4 peptide inhibitors or analogs, e.g., T-140 analogs (e.g., 4F-benzoyl-TN14003, TC14012, TE14011, TC14003), CTCE-0214; CTCE-9908; and CP-1221, as well as other inhibitors such as antibodies against SDF-1 or CXCR4, RNA inhibitors (e.g., antisense, siRNAs), among others. Exemplary inhibitors are described in, for example, Tamamura, H. et al. Org. Biomol. Chem. 1:3656-3662, 2003; FEBS Letter 550:1-3 (2003): 79-83; Wong, D. et al. (2008) Clin. Cancer Res. 14(24): 7975-7980; US Patent Publications 2010/0055088; 2009/0221683; 2004/0209921, 2005/0059702, 2005/0043367, 2005/0277670, 2010/0178271, and 2003/0220341; U.S. Pat. Nos. 5,021,409, 6,001,826, 5,583,131, and Patent Publications WO 03/011277, WO 01/85196; WO 99/50461; WO 01/94420; WO 03/090512, each of which is incorporated herein by reference in their entirety.

In another embodiment, the AHCM, the microenvironment modulator and/or the other stromal modulator, and/or the cancer therapy is administered in combination with an anti-fibrotic agent, for example, a pirfenidone. Pirfenidone (PFD or 5-methyl-1-phenyl-2(1H)-pyridone, commercially available from Marnac, Inc.) is an agent that is being investigated for use in patients with pulmonary fibrosis. Pirfenidone has been shown to produce anti-fibrotic effects in several organs such as the heart, liver, lung and kidney. For example, PFD has been shown to have an inhibitory effect on fibroblast growth and collagen synthesis by reducing expression of profibrotic cytokines such as TGF-b (Iyer, S. N. et al. (2000) Inflammation 24:477-491). PFD has also been shown to reduce leiomyoma cell proliferation and collagen production in cultured cells, as well as reduce TGF-b expression in human malignant glioma cells (see e.g., Byung-Seok, L. et al. (1998) *J of Clinical Endocrinology and Metabolism* 83(1): 219-223; and Burghardt, I. et al. (2007) *Biochem and Biophys Res. Comm.* 354:542-547).

In other embodiments, the AHCM and/or the microenvironment modulator is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (Erwinia L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the AHCM agent and/or the microenvironment modulator is administered in conjunction with a biologic. Biologics useful in the treatment of cancers are known in the art and a binding molecule of the invention may be administered, for example, in conjunction with such known biologics.

For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL. OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In one embodiment, the antibody is an antibody drug conjugate (ADCs).

Any type of antibody can be used as an agent as described herein, e.g., a human, humanized, camelid, nanobody, single domain antibody, or a fragment thereof (e.g., Fab, VH region).

In other embodiments, the AHCM, the microenvironment modulator and/or the other stromal modulator is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA(6D)/TRICOM vaccine, recombinant vaccinia-CEA(6D)-TRICOM vaccine, recombinant modified vaccinia Ankara-5T4 vaccine, recombinant fowlpox-TRICOM vaccine, oncolytic herpes virus NV 1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC 1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multiantigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the AHCM, the microenvironment modulator and/or the other stromal modulator is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the AHCM, the microenvironment modulator and/or the other stromal modulator is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Exemplary a nucleic acid therapeutic include a CRISPR/Cas9 agent.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte-Colony Stimulating Factor, NEUPOGEN®), GM-CSF (Granulocyte Macrophage Colony Stimulating Factor, sargramostim, LEUKINE™), IL-11 (Interleukin-1, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®)).

In some embodiments, the AHCM, the microenvironment modulator and/or the other stromal modulator is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-ß inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, nSorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the AHCM, the microenvironment modulator and/or the other stromal modulator is administered in combination with one of one of: an anti-angiogenic agent, or a vascular targeting agent or a vascular disrupting agent. Exemplary anti-angiogenic agents include, but are not limited to, VEGF inhibitors (e.g., anti-VEGF antibodies or agents (e.g., bevacizumab, sunitinib, sorafenib, pazopanib, vandetanib, axitinib, regoranfenib, aflibercept, and combinations thereof); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) *Clin. Cancer Res. Vol.* 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

It will be appreciated that anti-tumor antibodies labeled with isotopes have been used successfully to destroy cells in solid tumors, as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

It will also be appreciated that, in accordance with the teachings herein, binding molecules can be conjugated to different radiolabels for diagnostic and therapeutic purposes. To this end the aforementioned U.S. Pat. Nos. 6,682,134, 6,399,061, and 5,843,439 disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

In other embodiments, the cancer therapy includes an immune therapy used in combination with the AHCM, other cancer therapies, the microenvironment modulator, and/or other stromal modulator, described herein. Without wishing to be bound by theory, hypoxia and/or limited perfusion are believed to cause immunosuppression and/or limit the efficacy of certain immune therapies. AHCM, alone or in combination with therapies described herein can be used to improve the efficacy of said immune therapies. Examples of immune therapies include, but are not limited to, CTLA-4 blockade (e.g., an anti-CTLA-4 antibody (e.g., ipilimumab)); inhibitors of PD-1, PD-L1 and/or PD-L2. The inhibitors may be an antibody, an antigen binding fragment thereof, an immunoadhesin, a fusion protein, or oligopeptide.

In some embodiments, the anti-PD-1 antibody is chosen from MDX-1106, Merck 3475 or CT-011. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence).

In some embodiments, the PD-1 inhibitor is AMP-224. In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 is an anti-PD-L1 described in WO 2010/077634.

In some embodiments, the anti-PD-1 antibody is Nivolumab. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

Additional examples of immune-based therapies (including, e.g., immune or dendritic cell-based vaccines and antagonists of immune inhibitory signals or checkpoints); cancer vaccines, e.g., Sipuleucel-T (APC8015, trade name Provenge, manufactured by Dendreon Corporation) is a therapeutic cancer vaccine for prostate cancer (CaP)); and adoptive T-cell-based therapies. Exemplary immune-based therapies include, but are not limited to, e.g., immune or dendritic cell-based vaccines (Seton-Rogers, S. (2012) *Nature Reviews Cancer* 12:230-231; Palucka, K. et al. (2012) *Nature Reviews Cancer* 12:265-277); effector memory CD8+ T cells (Bird, L. (2012) *Nature Reviews Immunology* 12:227); engineered tumor cells to activate Toll like Receptors (TLRs) and NOD-like Receptors (NLRs) (Leavy, O. (2012) *Nature Reviews Immunology* 12:227); antagonists of immune inhibitory signals or checkpoints (Pardoll, D. M. (2012) *Nature Reviews Cancer* 12:252-264).

In yet other embodiments, the cancer therapy includes PDT used in combination with the AHCM, other cancer therapies, the microenvironment modulator, and/or other stromal modulator, described herein. In certain embodiments, PDT includes administration of a photosensitizing agent (e.g., a porhyrin, a porpyrin precursor, a chorlin, or a phthalocyanine) followed by irradiation at a wavelength corresponding to an absorbance band of the sensitizer. In the presence of oxygen, a series of events lead to one or more of: cell death (e.g., tumor cell death), damage to the microvasculature, or induction of a local inflammatory reaction). PDT is reviewed in, e.g., Agostinis, P. et al. (2011) *CA Cancer J. Clin.* 61:250-281.

In other embodiments, the cancer therapy includes an inhibitor of a cancer stem cell (also referred to herein as a "cancer initiating cell"), used in combination with the AHCM, other cancer therapies, the microenvironment modulator and/or other stromal modulator, described herein. Without wishing to be bound by theory, hypoxia and cancer drugs (including anti-angiogenic drugs) and radiation therapy are believed to increase the number of cancer stem cells. AHCM, alone or in combination with, e.g., an inhibitor of a cancer stem cell, can be used to reduce the production of these stem cells. Exemplary inhibitors of cancer stem cells that can be used in combination include, but are not limited to, hedgehog (e.g., SMO) antagonists; and Wnt pathway antagonists (e.g., antibody, OMP-18R5).

Exemplary Combination Therapies

Any combination of particles and free forms of AHCM, microenvironment modulator and/or therapy can be used in the aforesaid methods.

In one exemplary embodiment, the AHCM is administered as a particle (e.g., any of the particles disclosed herein); and the microenvironment modulator, other stromal modulator and/or the therapy (e.g., the cancer, fibrotic, immunomodulatory, or liver therapy) is administered as a free agent (e.g., not conjugated or bound to a carrier or particle).

In another embodiment, the microenvironment modulator and/or other stromal modulator is administered as a particle (e.g., any of the particles disclosed herein); and the AHCM and/or the therapy (e.g., the cancer, fibrotic, immunomodulatory, or liver therapy) is administered as a free agent (e.g., not conjugated or bound to a carrier or particle).

In yet another embodiment, the therapy (e.g., the cancer or liver therapy) is administered as a particle (e.g., any of the particles disclosed herein); and the AHCM and/or microenvironment modulator or other stromal modulator is administered as a free agent (e.g., not conjugated or bound to a carrier or particle).

In other embodiments, the AHCM and the microenvironment modulator or other stromal modulator are administered as a particle (e.g., same or different particles disclosed herein); and the therapy (e.g., the cancer, fibrotic, immunomodulatory, or liver therapy) is administered as a free agent (e.g., not conjugated or bound to a carrier or particle).

In other embodiments, the therapy (e.g., the cancer, fibrotic, immunomodulatory, or liver therapy) and the AHCM are administered as a particle (e.g., same or different particles disclosed herein); and the microenvironment modulator is administered as a free agent (e.g., not conjugated or bound to a carrier or particle).

In other embodiments, the therapy (e.g., the cancer, fibrotic, immunomodulatory, or liver therapy) and microenvironment modulator are administered as a particle (e.g., same or different particles disclosed herein); and AHCM is administered as a free agent (e.g., not conjugated or bound to a carrier or particle).

In one embodiment, the AHCM and the therapy (e.g., a second therapeutic agent chosen from a cancer, fibrotic, immunomodulatory, or liver therapy) can be in separate or the same entity. For example, if provided as separate entities the AHCM can be provided as a first particle (e.g., a pH sensitive particle as disclosed herein; a particle (e.g., pH-sensitive and/or polyacetal particle comprising an AHCM and/or a microenvironment modulator)) and the second therapeutic agent (e.g., the anti-cancer agent and/or liver therapeutic agent) provided as a second particle (e.g., where the second particle has a structural property (e.g., size or composition) or a functional property (e.g., release kinetics or a pharmacodynamic property) that differs from the first particle. Alternatively, an AHCM and a second therapeutic agent (e.g., an anti-cancer agent, anti-fibrotic agent, immunomodulator, and/or liver therapeutic agent) can be provided on the same entity, e.g., in the same nanoparticle.

In one embodiment, the AHCM is administered as a first agent in combination with a second agent (e.g., one or more of: (i) a microenvironment modulator (including an anti-angiogenic agent, an inhibitor of the angiopoietin-Tie-2 pathway (e.g., an Ang-1 or an Ang-2 inhibitor), sorafenib (e.g., administered at a vascular/stromal normalizing dose the microenvironment modulator or other stromal modulator of (i), e.g., as described herein in the context of treatment of fibrotic and liver disorders)); (ii) an anti-cancer agent; (iii) a liver therapy, (iv) an immune modulator, (v) an anti-fibrotic therapy), wherein the first agent or the second agent, or both first and second agents, are administered as one or more particles, e.g., pH-sensitive particles as disclosed herein). Additional combination therapies are disclosed throughout, including the section entitled "Combination Therapies" below.

In some embodiments, the AHCM or the first agent contained in the particle can be administered at a dose or amount that is less than, equivalent to, or higher than, the dose or amount of the AHCM in free form to have a desired effect (e.g., a desired therapeutic effect).

In some embodiments, the therapy or the second agent contained in the particle or present in free form can be administered at a dose or amount that is less than, equivalent to, or higher than, the dose or amount of the therapy or second agent administered alone to have desired effect (e.g., a desired therapeutic effect). In some embodiments, the therapy or the second agent contained in the particle or present in free form can be administered at a dose or amount that is less than the dose or amount of the therapy or second agent administered alone to have desired effect (e.g., a desired therapeutic effect).

In an embodiment, the AHCM and/or microenvironment modulator: is a small molecule therapeutic; is a protein, e.g., an antibody, or is provided in a particle, e.g., a particle as described herein. In one embodiment, the AHCM is chosen from one or more of: an angiotensin II receptor blocker ($AT_1$ blocker or ARB), an antagonist of RAAS antagonist, an ACE inhibitor, a TSP-1 inhibitor, a TGF-β1 inhibitor, a CTGF inhibitor, an SDF-1a inhibitor, an agonist of $AT_2$ receptor: an ERA; an AT2 agonist; a VDR agonist; or a combination of two, three or more of the above.

In an embodiment, the anti-cancer agent, anti-cancer agent, the liver therapeutic agent, or second therapeutic agent: is a small molecule therapeutic with a hydrodynamic diameter of 1 nm or less; is a protein, e.g., an antibody; or is provided in a particle, e.g., a particle as described herein.

In certain embodiments, the AHCM, the microenvironment modulator, other stromal modulator and/or the additional anti-cancer agent are administered concurrently (e.g., administration of the two agents at the same time or day, or within the same treatment regimen) and/or sequentially (e.g., administration of one agent over a period of time followed by administration of the other agent for a second period of time, or within different treatment regimens).

In one embodiment, the AHCM, the microenvironment modulator and/or other stromal modulator is administered prior to the anti-cancer agent. In other embodiments, the AHCM, the microenvironment modulator and/or other stromal modulator is administered prior to the anti-cancer agent, and followed by concurrent administration of the AHCM, the microenvironment modulator, other stromal modulator and/or the anti-cancer agent.

In certain embodiments, the AHCM, the microenvironment modulator, other stromal modulator and/or and the additional anti-cancer agent are administered concurrently. For example, in certain embodiments, the AHCM, the microenvironment modulator, other stromal modulator and/or and the additional anti-cancer agent are administered at the same time, on the same day, or within the same treatment regimen. In certain embodiments, the AHCM, the microenvironment modulator and/or other stromal modulator is administered before the additional anti-cancer agent on the same day or within the same treatment regimen.

In certain embodiments, the AHCM, the microenvironment modulator and/or other stromal modulator is concurrently administered with additional anti-cancer agent for a period of time, after which point treatment with the additional anti-cancer agent is stopped and treatment with the AHCM agent continues.

In other embodiments, the AHCM, the microenvironment modulator and/or other stromal modulator is concurrently with the additional anti-cancer agent for a period of time, after which point treatment with the AHCM, the microenvironment modulator and/or other stromal modulator is stopped and treatment with the additional anti-cancer agent continues.

In certain embodiments, the AHCM, the microenvironment modulator, other stromal modulator and/or the additional anti-cancer agent are administered sequentially. For example, in certain embodiments, the AHCM agent is administered after the treatment regimen of the additional anti-cancer agent and/or microenvironment modulator has ceased.

In certain embodiments, the additional anti-cancer agent is administered after the treatment regimen of the AHCM agent and/or microenvironment modulator has ceased.

In some embodiments, the AHCM, the microenvironment modulator, other stromal modulator and/or the anti-cancer agent can be administered in a pulse administration. In other embodiments, they can be administered as a pulse-chase administration, e.g., where an AHCM agent is administered for a brief period of time (pulse), followed by administration of an anti-cancer agent for a longer period of time (e.g., chase), or vice versa.

Timing of Administration

Alternatively, or in combination with any of the embodiments of the methods and compositions disclosed herein, the method comprises one or more of:

a) treating the subject with a dosing regimen described herein, e.g., administration of the AHCM, the microenvironment modulator and/or other stromal modulator (each of the aforesaid is administered as a particle described herein or in free form) is initiated prior to the initiation of administration of the therapy (e.g., the fibrosis, cancer or liver therapy), e.g., it is initiated at least one, two, three, or five days, or one, two, three, four, five or more weeks prior to the therapy (e.g., the cancer or liver therapy) (e.g., the AHCM, the microenvironment modulator and/or other stromal modulator is administered at a minimum of two weeks prior to the therapy (e.g., the cancer or liver therapy));

b) administering the AHCM, the microenvironment modulator and/or other stromal modulator (as a particle described herein or in free form) sequentially and/or concurrently with the therapy, e.g., the cancer or liver therapy. The AHCM, the microenvironment modulator, other stromal modulator and/or the therapy can be administered (at the same or different dosages) in any order and/or overlap with the therapy. In one embodiment, the AHCM, the microenvironment modulator and/or other stromal modulator is administered (as a particle described herein or in free form) before the therapy (e.g., as described in step a)). In other embodiments, the AHCM, the microenvironment modulator and/or other stromal modulator is administered (as a particle described herein or in free form) sequentially and/or concurrently with the therapy (e.g., the AHCM, the microenvironment modulator and/or other stromal modulator is administered (as a particle described herein or in free form) prior to the therapy (e.g., as described in step a) and concurrently with the therapy). In yet other embodiments, the therapy is administered first (as a particle described herein or in free form), and the AHCM, the microenvironment modulator and/or other stromal modulator is administered (as a particle described herein or in free form) after initiation of the therapy, or is administered after cessation of the therapy. In other embodiments, the administration of the AHCM, the microenvironment modulator and/or other stromal modulator starts after cessation of the therapy. In other embodiments, the administration of the AHCM, the microenvironment modulator and/or other stromal modulator continues after cessation of the therapy. In some embodiments where administration of the AHCM, the microenvironment modulator and/or other stromal modulator and the therapy is concurrent, the administration of the AHCM, the microenvironment modulator and/or other stromal modulator and the therapy can be continued as clinically appropriate, for example, (i) as a combination therapy, (ii) with a period of therapy with either the AHCM or the therapy, or (iii) as a combination of (i) and (ii) in any order;

c) administering the AHCM, the microenvironment modulator and/or other stromal modulator (as a particle described herein or in free form) substantially continuously over a period of at least 1, 5, 10, or 24 hours; at least 2, 5, 10, or 14 days; at least 2, 3, 4, 5 or 6 weeks; at least 2, 3, 4, 5 or 6 months; or at least 1, 2, 3, 4 or 5 years, or longer. By way of example only, the AHCM, the microenvironment modulator and/or other stromal modulator can be administered daily or every other day over the period of treatment.

d) providing the AHCM, the microenvironment modulator and/or other stromal modulator (administered as a particle described herein or in free form), and the therapy according to a dosing regimen described herein, e.g., providing a first course of treatment with an AHCM at a sub-anti-hypertensive dose followed by a second, higher dose, course of treatment with an AHCM, e.g., at a dose that is at or above a standard anti-hypertensive dose (e.g., wherein the second course is administered in a time course that can counteract a hypertensive effect of an anti-cancer therapy);

In one embodiment, the AHCM, the microenvironment modulator and/or other stromal modulator alters (e.g., enhances), (e.g., is administered in an amount sufficient to alter (e.g., enhance)), the distribution or efficacy of the therapy, e.g., the cancer or liver therapy.

In some embodiments, the AHCM does not inhibit or prevent (e.g., is administered as an amount insufficient to inhibit or prevent) tumor growth by itself, but sufficient to alter (e.g., enhance) the distribution or efficacy of the therapy, e.g., the cancer or liver therapy.

In some embodiments, the AHCM is administered as an amount sufficient to slow down tumor growth by itself, and thus prolong survival of a recipient subject.

Additional Exemplary Combination Therapies

In one embodiment, the AHCM is administered in combination with a microenvironment modulator, and/or a therapy, e.g., a cancer therapy (e.g., one or more of anti-cancer agents, immunotherapy, photodynamic therapy (PDT), surgery and/or radiation) or a liver therapy.

In one embodiment, at least one, two or all of the AHCM, microenvironment modulator, cancer therapy, or a liver disorder therapy is administered as a particle (e.g., a pH-sensitive particle disclosed herein). In one embodiment, one, two, or more of the AHCM, microenvironment modulator, cancer therapy, or a liver disorder therapy is provided in a particle, e.g., a targeted or non-targeted particle (e.g., any particle disclosed herein).

In one embodiment, the AHCM is provided in a particle, e.g., a targeted or non-targeted particle (e.g., any particle disclosed herein). In one embodiment, the particle is a pH-sensitive particle, e.g., comprises a pH-sensitive polymer and/or a linker as described herein. In such embodiments, the microenvironment modulator, cancer therapy and/or a liver disorder therapy can be administered as a free agent.

In one embodiment, the microenvironment modulator, cancer therapy and/or a liver disorder therapy is provided in a particle, e.g., a targeted or non-targeted particle (e.g., any particle disclosed herein). In one embodiment, the particle is a pH-sensitive particle, e.g., comprises a pH-sensitive polymer and/or linker as described herein. In such embodiments, the AHCM is provided as a free agent.

The terms "chemotherapeutic," "chemotherapeutic agent," and "anti-cancer agent" are used interchangeably herein. The administration of the AHCM and the therapy, e.g., the cancer therapy, can be sequential (with or without overlap) or simultaneous. Administration of the AHCM and/or the microenvironment modulator can be continuous or intermittent during the course of therapy (e.g., cancer or liver therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

In an embodiment, administration of the AHCM and/or the microenvironment modulator is initiated prior to the initiation of administration of the therapy (e.g., the cancer or liver therapy), e.g., it is initiated at least one, two, three, or five days, or one, two, three, four, five or more weeks prior to cancer therapy (e.g., the AHCM and/or the microenvironment modulator is administered at a minimum of two weeks prior to cancer or liver therapy). In an embodiment, it is initiated no more than 5, 10, 20, 30, 60 or 120 days prior to initiation of the therapy, e.g., the cancer or liver therapy. In an embodiment, administration of the AHCM and/or the microenvironment modulator is initiated prior to the therapy, e.g., the cancer or liver therapy, and the therapy is not initiated until a criterion is met, e.g., a time-based criterion, e.g., administration of AHCM and/or the microenvironment modulator for a predetermined number of days or for a predetermined number of administrations. In an embodiment, the criterion is meeting a preselected level of AHCM and/or the microenvironment modulator, e.g., a preselected level in serum, plasma or tissue. In one embodiment, the criterion is meeting a preselected level of a biomarker in plasma, serum or tissue, including but not limited to, an angiotensin receptor (e.g., angiotension-II type-1 receptor; $AT_{1A}$ receptor ($AT_{1A}R$)), collagen I, collagen III, collagen IV, transforming growth factor beta 1 (TGF-β1), connective tissue growth factor (CTGF), or thrombospondin-1 (TSP-1). In another embodiment, the criterion is meeting a preselected level of alteration in tumor morphology.

In one embodiment, the administration of the AHCM and/or the microenvironment modulator is sequential and/or concurrent with the therapy, e.g., the cancer, anti-fibrotic, or liver therapy, as described herein.

In an embodiment, the AHCM and/or the microenvironment modulator is administered, or a preselected level, e.g., a plasma level, of AHCM and/or the microenvironment modulator is maintained for a preselected portion of the time the subject receives the therapy, e.g., the cancer or liver therapy. By way of example, the AHCM and/or the microenvironment modulator therapy is maintained for the entire period in which the therapy, e.g., the cancer or liver therapy, is administered, or for the entire period in which a preselected level of the therapy (e.g., an anti-cancer agent) persists in the subject.

Typically, therapy with the AHCM and/or the microenvironment modulator continues during the entire therapy, e.g., cancer, anti-fibrotic, or liver therapy, schedule. In yet other embodiments, administration of the AHCM and/or the microenvironment modulator is discontinued prior to cessation of the therapy, e.g., the cancer, anti-fibrotic, or liver therapy. In other embodiments, administration of the AHCM and/or the microenvironment modulator is continued after cessation of the therapy, e.g., the cancer, anti-fibrotic, or liver therapy, e.g., the administration continues hours, days, months or more, after cessation of the cancer, anti-fibrotic, or liver therapy.

In an embodiment, two or more doses of the AHCM and/or the microenvironment modulator are administered, alone or in combination with the therapy, e.g., the cancer therapy. In one embodiment, the AHCM is administered at a sub-anti-hypertensive dose and an anti-hypertensive dose during the course of therapy. For example, a sub-anti-hypertensive dose of the AHCM can be administered prior to, or at the time, of the therapy, e.g., the cancer therapy (e.g., treatment with an anti-cancer agent that increases mean arterial blood pressure, e.g, treatment with an anti-angiogenic drug (e.g., Avastin, sunitinib or sorafenib)); then followed by a subsequent hypertensive dose of the AHCM.

In one embodiment, the AHCM (alone or in combination) is administered substantially continuously over a period of, or at least 15, 30, 45 minutes; a period of, or at least, 1, 5, 10, 24 hours; a period of, or at least, 2, 5, 10, 14 days; a period of, or at least, 3, 4, 5, 6, 7, 8 weeks; a period of, or at least 2, 3, 4, 5, 6, 7, 8, 9, 10, 11 months; a period of, or at least, 1, 2, 3, 4, 5 years, or longer. In one embodiment, the AHCM is administered as a controlled- or sustained release formulation, dosage form, or device. In certain embodiments, the AHCM is formulated for continuous delivery, e.g., oral, subcutaneous or intravenous continuous delivery. In one embodiment, the AHCM (alone or in combination with the microenvironment modulator and/or cancer therapy) is in an oral controlled- or extended release dosage form or formulation. In one embodiment, the AHCM is administered via an implantable device, e.g., a pump (e.g., a subcutaneous pump), an implant or a depot. The delivery method can be optimized such that an AHCM dose as described herein (e.g., a standard, sub-hypertensive, or higher than standard dose) is administered and/or maintained in the subject for a pre-determined period (e.g., a period of, or at least: 15, 30, 45 minutes; 1, 5, 10, 24 hours 2, 5, 10, 14 days; 3, 4, 5, 6, 7, 8 weeks; 2, 3, 4, 5, 6, 7, 8, 9, 10, 11 months; 1, 2, 3, 4, 5 years, or longer). The substantially continuously or extended release delivery or formulation of the AHCM (with or without the combination of the microenvironment modulator and/or therapy) can be used for prevention or treatment of cancer for a period of hours, days, weeks, months or years. In one embodiment, the therapy is chosen from one or more of: nanotherapy (e.g., a viral cancer therapeutic agent (e.g., an oncolytic herpes simplex virus (HSV), a lipid nanoparticle (e.g., a liposomal formulation (e.g., pegylated liposomal doxorubicin (DOXIL®)), an encapsulated chemotherapeutic (e.g., encapsulated irinotecan (e.g., MM-398, Merrimack), or a polymeric nanoparticle); an antibody-targeted nanoparticle (e.g., HER2-targeted encapsulated doxorubicin); an antibody (e.g., mono- or bispecific antibody) that binds to a cancer target, e.g., EGFR, IGF-1R, HER2); an RNAi or antisense RNA agent; a nucleic acid therapeutic (e.g., CRISPR/Cas9 agent), a chemotherapeutic agent (e.g., a cytotoxic or a cytostatic agent); PDT, immunotherapy, radiation; or surgery; or any combination thereof. Additional examples of anti-cancer therapies that can be used in combination with the AHCM are provided below.

In other embodiments, the AHCM and the therapy (e.g., the cancer, liver or hyperproliferative therapy) are administered to a subject, e.g., a subject as described herein, in combination with the microenvironment modulator. In certain embodiments, the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics and immunotherapies) in a tumor or tumor vasculature, in the subject.

In one embodiment, the microenvironment modulator includes an anti-angiogenic therapy; an agent that decreases the level or production of hyaluronic acid, including but not limited to, an antibody against hyaluronic acid, and an anti-hyaluronan enzymatic therapy, such as hyaluronidase or a derivative thereof (e.g., pegylated form thereof) (e.g., PH20, or pegylated, recombinant human hyaluronidase PEGPH20); an inhibitor of the hedgehog pathway, e.g., IPI-926, GDC-0449, cylopamine or an analogue thereof, or GANT58; an agent that improves drug penetration in tumors; a taxane therapy (e.g., taxane-induced apoptosis as described in Griffon-Etienne, G. et al. (1999) *Cancer Res.* 59(15):3776-82); an agent that modulates (e.g, inhibits) a hypoxia inducible factor (HIF), for example, an agent that inhibits hypoxia-inducible factors 1α and 2α (HIF-1α and HIF-2α); an agent that decreases the level or production of collagen or procollagen; an agent that modulates the cross-linking of matrix molecules; an agent that depletes or changes the differentiation state of fibroblasts or stellate cells; an anti-fibrotic agent or inhibitor of a profibrotic pathway (a "profibrotic pathway inhibitor") (e.g., a pathway dependent- or independent of TGF-beta and/or CTGF activation).

In one embodiment, the AHCM and/or the cancer therapy is administered in combination with one or more of: an inhibitor of endothelin-1, PDGF, Wnt/beta-catenin, IGF-1, TNF-alpha, and/or IL-4. In another embodiment, the AHCM and/or the cancer therapy is administered in combination with an inhibitor of endothelin-1 and/or PDGF. In other embodiments, the AHCM and/or the cancer therapy is administered in combination with an inhibitor of one or more of: chemokine receptor type 4 (CXCR4) (e.g., AMD3100, MSX-122); stromal-derived-factor-1 (SDF-1) (e.g., tannic acid); hedgehog (e.g., IPI-926, GDC-0449, cylopamine or an analogue thereof, or GANT58).

In another embodiment, the AHCM and/or the cancer therapy is administered in combination with an anti-fibrotic agent, for example, a pirfenidone (PFD, 5-methyl-1-phenyl-2-(1H)-pyridone), as further described herein.

The administration of the AHCM, the cancer therapy, the microenvironment modulator and/or the profibrotic pathway inhibitor can be sequential (with or without overlap) or simultaneous (e.g., a described herein).

Cancer Therapies

In another embodiment, the AHCM, the microenvironment modulator and/or other stromal modulator (e.g., one of more as a free agent or in a particle or conjugate as described herein) is administered in combination with a cancer therapy (e.g., one or more of anti-cancer agents, photodynamic therapy (PDT), immunotherapy, surgery and/or radiation). In one embodiment, the cancer therapy includes one or more of: a cancer therapeutic, including, for example, a nanotherapy (e.g., one or more nanotherapeutic agents, including viral cancer therapeutic agents (e.g., an oncolytic herpes simplex virus (HSV)) a lipid nanoparticle (e.g., a liposomal formulation (e.g., pegylated liposomal doxorubicin (DOXIL®)), or a polymeric nanoparticle); one or more cancer therapeutic antibodies (e.g., anti-HER2, anti-EGFR, anti-CD20 antibodies); a nucleic acid therapeutic (e.g., CRISPR/Cas9 agent); RNAi and antisense RNA agents; one or more chemotherapeutic agents (e.g., low molecular weight chemotherapeutic agents, including a cytotoxic or a cytostatic agent)); photodynamic therapy; immunotherapy; radiation; or surgery, or any combination thereof. Any combination of one or more AHCMs and one or more therapeutic modalities (e.g., first, second, third) nanotherapeutic agent, antibody agent, low molecular weight chemotherapeutic agent, radiation can be used. Exemplary cancer therapeutics include, but are not limited to, nanotherapeutic agents (e.g., one or more lipid nanoparticles (e.g., a liposomal formulation (e.g., pegylated liposomal doxorubicin (DOXIL®) or liposomal paclitaxel (e.g., Abraxane®)), or a polymeric nanoparticle); one or more low molecular weight chemotherapeutics (e.g., gemcitabine, cisplatin, epirubicin, 5-fluorouracil, paclitaxel, oxaliplatin, or leucovorin); one or more antibodies against cancer targets (e.g., growth factor receptor such as HER-2/neu, HER3, VEGF)); one or more tyrosine kinase inhibitors, e.g., including low molecular weight and antibody agents, such as sunitinib, erlotinib, gefitinib, sorafenib, icotinib, lapatinib, neratinib, vandetanib, BIBW 2992 or XL-647, anti-EGFR antibody (e.g., cetuximab, panitumumab, zalutumumab, nimotuzumab necitumumab or matuzumab)). Additional examples of chemotherapeutic agents used in combination therapies are described hereinbelow.

In one embodiment, the chemotherapeutic agent used in combination with the AHCM, the microenvironment modulator and/or other stromal modulator is a cytotoxic or a cytostatic agent. Exemplary cytotoxic agents include anti-microtubule agents, topoisomerase inhibitors (e.g., irinotecan), or taxanes (e.g., docetaxel), antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

In other embodiments, the cancer therapy includes an immune or immunotherapy used in combination with the AHCM, other cancer therapies, the microenvironment modulator and/or other stromal modulator, described herein. Without wishing to be bound by theory, factor such as hypoxia and/or limited perfusion are believed to cause immunosuppression and/or limit the efficacy of certain immune therapies. AHCM, alone or in combination with therapies described herein, can be used to improve the efficacy of said immune therapies. Examples of immune therapies include, but are not limited to, CTLA-4 blockade (e.g., an anti-CTLA-4 antibody (e.g., ipilimumab)): immune-based therapies (including, e.g., immune or dendritic cell-based vaccines and antagonists of immune inhibitory signals or checkpoints); cancer vaccines, e.g., Sipuleucel-T (APC8015, trade name Provenge); and adoptive T-cell-based therapies. Exemplary immune-based therapies include, but are not limited to, e.g., immune or dendritic cell-based vaccines (Seton-Rogers, S. (2012) *Nature Reviews Cancer* 12:230-231; Palucka, K. et al. (2012) *Nature Reviews Cancer* 12:265-277); effector memory CD8+ T cells (Bird, L. (2012) *Nature Reviews Immunology* 12:227); engineered tumor cells to activate Toll like Receptors (TLRs) and NOD-like Receptors (NLRs) (Leavy, O. (2012) *Nature Reviews Immunology* 12:227); antagonists of immune inhibitory signals or checkpoints (Pardoll, D. M. (2012) *Nature Reviews Cancer* 12:252-264). In one embodiment, the therapy is a cell-based immunotherapy wherein immune cells are expanded ex vivo and injected into the subject.

In yet other embodiments, the cancer therapy includes PDT used in combination with the AHCM, other cancer therapies, the microenvironment modulator and/or other stromal modulator, described herein. In certain embodiments, PDT includes administration of a photosensitizing agent (e.g., a porhyrin, a porpyrin precursor, a chorlin, or a phthalocyanine) followed by irradiation at a wavelength corresponding to an absorbance band of the photosensitizing agent. In the presence of oxygen, a series of events lead to one or more of: cell death (e.g., tumor cell death), damage to the microvasculature, or induction of a local inflammatory reaction). PDT is reviewed in, e.g., Agostinis, P. et al. (2011) *CA Cancer J. Clin.* 61:250-281.

In other embodiments, the cancer therapy includes an inhibitor of a cancer stem cell (also referred to herein as a "cancer initiating cell"), used in combination with the AHCM, other cancer therapies, the microenvironment modulator and/or other stromal modulator, described herein. Without wishing to be bound by theory, hypoxia and cancer drugs (including anti-angiogenic drugs) and radiation therapy are believed to increase the number of cancer stem cells. AHCM, alone or in combination with, e.g., an inhibitor of a cancer stem cell, can be used to reduce the production of these stem cells. Exemplary inhibitors of cancer stem cells that can be used in combination include, but are not limited to, hedgehog (e.g., SMO) antagonists; and Wnt pathway antagonists (e.g., antibody, OMP-18R5). In one embodiment, the AHCM, the microenvironment modulator and/or other stromal modulator, alone or in combination with one or more cancer therapies described herein, are administered for cancer prevention (e.g., alone or in combination with cancer-prevention agents), during periods of active disorder, or during a period of remission or less active disorder. The AHCM, the microenvironment modulator and/or other stromal modulator, alone or in combination with one or more cancer therapies described herein, can be administered for cancer prevention, before treatment or prevention, concurrently with treatment or prevention, post-treatment or prevention, or during remission of the disorder. In one embodiment, the cancer therapy is administered simultaneously, sequentially, or a combination of both, with the AHCM, the microenvironment modulator and/or other stromal modulator.

In one embodiment, the AHCM, the microenvironment modulator and/or other stromal modulator is administered alone or in combination with cancer-prevention agents, e.g., to treat or prevent cancer in high risk subjects (e.g., a subject with pre-neoplasia or a genetic pre-disposition for cancer (e.g., a subject having a BRCA1 mutation); or a breast cancer patient treated with tamoxifen).

In some embodiments, the AHCM, the microenvironment modulator and/or other stromal modulator, alone or in combination with the cancer therapy, is a first line treatment for the cancer, e.g., it is used in a subject who has not been previously administered another drug intended to treat the cancer.

In other embodiments, the AHCM, the microenvironment modulator and/or other stromal modulator, alone or in combination with the cancer therapy, is a second line treatment for the cancer, e.g., it is used in a subject who has been previously administered another drug intended to treat the cancer.

In other embodiments, the AHCM, the microenvironment modulator and/or other stromal modulator, alone or in combination with the cancer therapy, is a third, fourth, or greater than fourth, line treatment for the cancer, e.g., it is used in a subject who has been previously administered two, three, or more than three, other drugs intended to treat the cancer.

In other embodiments, the AHCM, the microenvironment modulator and/or other stromal modulator is administered as adjunct therapy, e.g., a treatment in addition to a primary therapy.

In one embodiment, the AHCM, the microenvironment modulator and/or other stromal modulator is administered as adjuvant therapy.

In other embodiments, the AHCM, the microenvironment modulator and/or other stromal modulator is administered as neoadjuvant therapy.

In some embodiments, the AHCM, the microenvironment modulator and/or other stromal modulator is administered to a subject prior to, or following surgical excision/removal of the cancer.

In some embodiments, the AHCM, the microenvironment modulator and/or other stromal modulator is administered to a subject before, during, and/or after radiation treatment of the cancer.

In some embodiments, the AHCM, the microenvironment modulator and/or other stromal modulator is administered to a subject, e.g., a cancer patient who will undergo, is undergoing or has undergone cancer therapy (e.g., treatment with a chemotherapeutic agent, radiation therapy and/or surgery).

In other embodiments, the AHCM, the microenvironment modulator and/or other stromal modulator is administered prior to the cancer therapy. In other embodiments, the AHCM and/or the microenvironment modulator is administered concurrently with the cancer therapy. In yet other embodiments, the AHCM, the microenvironment modulator and/or other stromal modulator is administered prior to the cancer therapy and concurrently with the cancer therapy. In instances of concurrent administration, the AHCM, the microenvironment modulator and/or other stromal modulator can continue to be administered after the cancer therapy has ceased.

In other embodiments, the AHCM, the microenvironment modulator and/or other stromal modulator is administered sequentially with the cancer therapy. For example, the AHCM, the microenvironment modulator and/or other stromal modulator can be administered before initiating treatment with, or after ceasing treatment with, the cancer therapy. In one embodiment, the administration of the AHCM, the microenvironment modulator and/or other stromal modulator overlaps with the cancer therapy, and continues after the cancer therapy has ceased. In one embodiment, the AHCM, the microenvironment modulator and/or other stromal modulator is administered concurrently, sequentially, or as a combination of concurrent administration followed by monotherapy with either the cancer therapy, the AHCM, the microenvironment modulator and/or other stromal modulator.

In one embodiment, the method includes administering the AHCM, the microenvironment modulator and/or other stromal modulator as a first therapeutic agent, followed by administration of a cancer therapy (e.g., treatment with a second therapeutic agent, radiation therapy and/or surgery). In another embodiment, the method includes administering a cancer therapy first (e.g., treatment with a first therapeutic agent, radiation therapy and/or surgery), followed by administering the AHCM, the microenvironment modulator and/or other stromal modulator as a second therapeutic agent. In yet other embodiments, the method includes administering the AHCM, the microenvironment modulator and/or other stromal modulator in combination with a second, third or more additional therapeutic agents (e.g., anti-cancer agents as described herein).

The AHCM, the microenvironment modulator and/or other stromal modulator and/or the anticancer agent described herein can be administered to the subject systemically (e.g., orally, parenterally, subcutaneously, intravenously, rectally, intramuscularly, intraperitoneally, intranasally, transdermally, or by inhalation or intracavitary installation). Typically, the AHCMs are administered orally. In certain embodiments, the AHCM, the microenvironment modulator, other stromal modulator and/or the anticancer agent are administered locally or intratumorally (e.g., via an oncolytic virus).

In some embodiments, the AHCM is administered as a pharmaceutical composition comprising one or more AHCMs, and a pharmaceutically acceptable excipient.

In an embodiment, the AHCM is administered, or is present in the composition, e.g., the pharmaceutical composition (e.g., the same nanoparticle composition).

In some embodiments, the microenvironment modulator is administered as a pharmaceutical composition comprising one or more microenvironment modulators, and a pharmaceutically acceptable excipient.

In an embodiment, the microenvironment modulator is administered, or is present in the composition, e.g., the pharmaceutical composition (e.g., the same nanoparticle composition).

In some embodiments, the other stromal modulator is administered as a pharmaceutical composition comprising one or more other stromal modulators, and a pharmaceutically acceptable excipient.

In an embodiment, the other stromal modulator is administered, or is present in the composition, e.g., the pharmaceutical composition (e.g., the same nanoparticle composition).

In other embodiments, the AHCM, the microenvironment modulator, other stromal modulator and/or the cancer therapy are administered as separate compositions, e.g., pharmaceutical compositions (e.g., nanoparticle compositions). In other embodiments, the AHCM, the microenvironment modulator, other stromal modulator, and the cancer therapy are administered separately, but via the same route (e.g., orally or intravenously). In some embodiments, the AHCM, the microenvironment modulator, other stromal modulator, and the cancer therapy are administered by different routes (e.g., AHCM is administered orally; the microenvironment modulator is administered subcutaneously; and a cancer therapeutic is administered intravenously). In still other instances, the AHCM, the microenvironment modulator and/or other stromal modulator, and the cancer therapy are administered in the same composition, e.g., pharmaceutical composition (e.g., same nanoparticle composition).

Liver Conditions or Disorders

As used herein, "liver disorder therapy" refers to therapies or therapeutic agents used to treat or prevent a liver disorder described herein, and therefore encompasses liver cancer therapies and other liver disorder therapies, e.g., therapies for fibrotic liver disorders, fatty liver diseases, liver inflammation disorders, autoimmune liver diseases, and liver disorders induced by genetic diseases, alcoholism, drug toxicity, infection, or injury.

Examples of liver cancers include: hepatocellular carcinoma (HCC), primary liver cell carcinoma, hepatoma, fibrolamellar carcinoma, focal nodular hyperplasia, cholangiosarcoma, intrahepatic bile duct cancer, angiosarcoma or hemangiosarcoma, hepatic adenoma, hepatic hemangiomas, hepatic hamartoma, hepatoblastoma, infantile hemangioendothelialoma, mixed tumors of the liver, tumors of mesenchymal tissue, sarcoma of the liver. Examples of cancers that may metastasize to the liver include: breast cancer, colorectal cancer, esophageal cancer, kidney or renal cancer, lung cancer, ovarian cancer, pancreatic cancer, rectal cancer, skin cancer (e.g., melanoma), gastric or stomach cancer (including gastrointestinal cancer), and uterine cancer.

In an embodiment, the liver disorder is a fibrotic disorder or connective tissue disorder affecting the function or physiology of the liver. In one embodiment, the fibrotic disorder or connective tissue disorder can be systemic (affecting the whole body), multi-organ, or organ-specific (e.g., liver-specific). Examples of fibrotic liver disorders include liver fibrosis (hepatic fibrosis), liver cirrhosis, and any disorder associated with accumulation of extracellular matrix proteins, e.g., collagen, in the liver, liver scarring, and/or abnormal hepatic vasculature. Liver fibrosis is caused by liver inflammation or damage which triggers the accumulation of extracellular matrix proteins, including collagens, and scar tissue in the liver. Liver cirrhosis is the end stage of liver fibrosis, involves regenerative nodules (as a result of repair processes), and is accompanied with the distortion of the hepatic vasculature. Liver fibrotic disorders are most commonly caused by chronic viral infection (e.g., hepatitis B, hepatitis C), alcoholism, and fatty liver disease.

Examples of fatty liver diseases include fatty liver (or FLD), alcoholic liver disease, non-alcoholic fatty liver disease (NAFLD), non-alcoholic steatohepatitis (NASH), alcoholic steatohepatitis, simple steatosis, Reye's syndrome, and any disorder associated with abnormal retention of lipids in liver cells.

In one embodiment, the liver disease is NASH.

Metabolic disorders can also affect the liver and cause liver damage. Examples of metabolic disorders of the liver or affecting the liver include hemachromatosis, diabetes, obesity, hypertension, dyslipidemia, galactosemia, and glycogen storage disease.

Autoimmune disorders of the liver or affecting the liver can include systemic disorders or disorders that primarily affect an organ other than the liver, but with secondary effects to liver cells or liver function. Examples of such autoimmune disorders include autoimmune hepatitis (AIH), autoimmune liver disease, lupoid hepatitis, systemic lupus erythematosus, primary biliary cirrhosis (PBC), scleroderma, and systemic scerlosis.

Disorders associated with inflammation of the liver include steatohepatitis, primary sclerosing cholangitis (PSC), ulcerative colitis, Crohn's disease, inflammatory bowel disease, or any disorder associated with inflammation in the liver.

In an embodiment, the liver disorder is associated with an inherited or congenital disease, e.g., Wilson's disease, Gilbert's disease, Byler syndrome, Greenland-Eskimo familial cholestasis, Zellweger's syndrome, Alagilles syndrome (ALGS), progressive familial intrahepatic cholestasis (PFIC), or alpha 1-antitrypsin deficiency, cystic fibrosis, Indian childhood cirrhosis, and hereditary hemochromatosis.

In an embodiment, the liver disorder is associated with pancreatic or biliary tract damage or disorders, e.g., cerebrotendinous, xanthomatosis, gall stones, choledocholithiasis, obstruction of the biliary tree, biliary trauma, biliary atresia, pancreatitis, primary biliary cirrhosis, primary sclerosing cholangitis, cholestasis, cholestasis of pregnancy, or any disorder associated with the obstruction or damage to the biliary system or the pancreas.

In an embodiment, liver disorders can be induced by infection, for example, by viral infections such as hepatitis A virus, hepatitis B virus, hepatitis C virus, hepatitis D virus (hepatitis delta virus), hepatitis E virus, Epstein-Barr adenovirus, or cytomegalovirus; or parasitic infection, such as schistosomiasis.

In an embodiment, liver disorders can be induced by drugs, such as acetaminophen (e.g., paracetamol, TYLENOL®, or PANADOL®), nonsteroidal anti-inflammatory drugs (NSAIDS, e.g., aspirin and phenylbutazone, ibuprofen, piroxicam, diclofenac, sulindac, and indomethacin), glucocorticoids, anti-tuberculosis drugs (e.g., isoniazid), antibiotics, anesthetics, antihypertensives (e.g., statins), oral contraceptives, dietary aids, or herbal supplements (e.g., ackee fruit, bajiaolian, boragecamphor, copaltra, comfrey, cycasin, kava leaves, pyrrolizidine alkaloids, horse chestnut leaves, valerian); or toxins, such as arsenic, carbon tetrachloride, vinyl chloride, aflatoxins.

In an embodiment, liver disorders also include disorders or conditions induced by injury to the liver or affecting the liver, including drug toxicity, alcoholism, ischemia, malnutrition, or physical trauma.

Other liver disorders include hepatic vein thrombosis, Budd-Chiari syndrome, portal hypertension, hepatic encephalopathy, and hepatomegaly (or enlarged liver).

Combination Therapies for Treatment of Liver Disorders

Therapies for treating a liver cancer can include one or more of: surgery to remove the cancer (e.g., liver resection or partial hepatectomy), liver transplant, radiofrequency ablation (RFA), microwave ablation, cryotherapy (or cryosurgery), percutaneous ethanol injection (e.g., injecting alcohol directly into the liver tumor), trans arterial chemoembolisation (TACE, e.g., delivery of chemotherapeutic agents directly into the liver), radioembolisation or selective internal radiation therapy (SIRT) (e.g., delivery of microspheres containing radioactive materials, e.g., yttrium-90), or radiation therapy (e.g., external beam radiation therapy, three-dimensional conformal radiation therapy, stereotactic body radiation therapy), chemotherapy, treatment with other biologics, or any combination thereof.

Therapeutics that can be used for treating liver cancer include: sorafenib (sorafenib tosylate, NEXAVAR®), sunitinib (SUTENT®), erlotinib (TARCEVA®), bevacizumab (AVASTIN®), brivanib (BMS-582664), tefinostat, and viral therapy with JX-594.

Chemotherapeutic agents for treating liver cancer include: doxorubicin (adriamycin), cisplatin (platinol), 5-fluorouracil (5-FU), mitomycin C, gemcitabine, and combinations thereof, or in combination with anti-cancer agents listed above. Other chemotherapeutic agents are known in the art, and may be suitable for treating a liver cancer described herein, e.g., 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID)), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (*Erwinia* L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

A primary therapy option for treating liver fibrosis or liver cirrhosis is liver transplant. Other therapeutic agents that may have therapeutic efficacy in treating liver fibrosis and/or liver cirrhosis include silymarin, silibinin (silybin), colchicines, trimethylcolchicinic acid (TMCA), introduction of metalloproteinases, and gene therapy with neuronal nitric oxide synthase (NOS) or dominant negative type II transforming growth factor-b receptor gene.

Therapeutic agents for treating fatty liver disease include metformin (FORTAMET®, GLUCOPHAGE®, GLUCOPHAGE® XR, GLUMETZA®, RIOMET®), orlistat (XENICAL®), rosiglitazone (AVANDIA®), vildagliptin (LAF237, GALVUS®, ZOMELIS®), pioglitzaone (ACTOS®), gemfibrozil (Lopid®), atorvastatin (LIPITOR®), and pravastatin (PRAVACHOL®).

In one embodiment, the liver disorder is NASH or NASH-related fibrosis. The compositions (e.g., AHCM in free or particle form) can be used in combination with a therapy for NASH. Exemplary therapies for treating NASH include Intercept, Orlistat, an enteric lipase inhibitor, insulin sensitizing agents, thiazolidinediones and metformin.

In an embodiment, the liver disorder therapy includes anti-inflammatory agents such as angiotensin converting enzyme antagonists; angiotensin II type I receptor antagonists, glucocorticoids, e.g., aldosterone, betamethasone, cortisol, cortisone, deoxycorticosterone, dexamethasone, methylprednisolone, prednisone, prednisolone, or triamcinolone; pentoxiphylline (PTX); TNF alpha inhibitors, e.g., pentoxyphylline, adalimumab (HUMIRA®), entanercept (ENBREL®), infliximab (REMICADE®); salicylates, e.g., aspirin, diflunisal (DOLOBID™), salsalate (DISALCID™), choline magnesium trisalicylate (TRILISATE™); propionic acid derivatives, e.g., ibuprofen, naproxen, fenoprofen, ketoprofen, oxaprozin, loxoprofen; acetic acid derivatives, e.g., indomethacin, tolmetin, slindac, etodolac; selective Cox-2 inhibitors, e.g., celecoxib, rofecoxib, valdecoxib, parecoxib, lumiracoxib, etoricoxib; oxicam derivatives, e.g., piroxicam, meloxicam, tenoxicam, droxicam, lornoxicam, isoxicam; anthranilic acid derivates (fenamates), e.g., mefenamic acid, meclofenamic acid, flufenamic acid, tolfenamic acid; sulfonanilides, e.g., nimesulide; H-harpagide; and ursodeoxycholic acid, and derivatives thereof.

In an embodiment, the liver disorder therapy includes immunosuppressive agents such as glucocorticoids, e.g., aldosterone, betamethasone, cortisol, cortisone, deoxycorticosterone, dexamethasone, methylprednisolone, prednisone, prednisolone, or triamcinolone; Mycophenolate mofetil (MMF); rapamycin (sirolimus); fingolimod; calcineurin inhibitors, e.g., ciclosporin (SANDIMMUNE®), tacrolimus (PROGRAF®); and cytostatics, e.g., cyclophosphamide, methotrexate, azathioprine, mitomycin C, bleomycin, and anthracyclines.

In an embodiment, the liver disorder therapy includes agents for treating metabolic disorders, e.g., metformin (FORTAMET®, GLUCOPHAGE®, GLUCOPHAGE® XR, GLUMETZA®, RIOMET®), orlistat (XENICAL®), rosiglitazone (AVANDIA®), vildagliptin, pioglitzaone (ACTOS®), gemfibrozil (Lopid®), thiazolidinediones.

In an embodiment, the liver disorder therapy includes anti-viral agents such as interferons, e.g., interferon α2b, pegylated interferon α2a; nucleoside reverse transcriptase inhibitors (NRTIs), e.g., adefovir, entecavir, lamivudine, ribavirin, telbivudine, and tenofovir; and nucleoside analogs, e.g., 5-iodo 2'-deoxyuridine 5' monophosphate.

In an embodiment, the liver disorder therapy includes antioxidants 3-carotene, biotin, vitamin A, vitamin C, vitamin E, selenium, methionine, allopurinol, desferrioxamine, N-acetylcysteine, manganese, copper, magnesium, folic acid and coenzyme Q.

In an embodiment, the liver disorder therapy includes hepatoprotectants, such as hepatocyte growth factor (HGF) and HGF variants, e.g., HGF deletion variants, HGF synthetic mimetics (Kim et al., 2005, Am J Pathol; Ueki et al., 1999, Nat Med; and Masunaga et al., 1998, Eur J Pharmacol); insulin-like growth factor I; caspase inhibitors, e.g., IDN-6556; farnesoid X receptor (FXR) ligands, e.g., chenodoxycholic acid (CDCA).

In an embodiment, the liver disorder therapy includes agents for palliative care, e.g., medications and procedures that are noncurative but alleviate symptoms, pain, or stress of the liver disorder. Other lifestyle changes may be used concurrently with liver disorder therapies to improve treatment of the disease, such as weight loss, adjustment of diet, nutritional therapy or supplementation, abstinence from alcohol or reduction in alcohol consumption, and abstinence from smoking.

Fibrotic Conditions or Disorders

In another aspect, the invention features a method of treating or preventing a fibrotic condition or disorder in a subject. The method includes administering a composition described herein (e.g., one or more of: a particle or conjugate as described herein; an AHCM, microenvironment modulator or other stromal modulator in free form or as a conjugate or particle), as a single agent or in combination with another agent or therapeutic modality, to a subject in need thereof, in an amount sufficient to decrease or inhibit the fibrotic condition in the subject.

In certain embodiments, reducing fibrosis, or treatment of a fibrotic condition, includes reducing or inhibiting one or more of: formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In certain embodiments, the fibrotic condition is a fibrotic condition of the lung, a fibrotic condition of the liver (e.g., as described herein), a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods of the invention is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

Pulmonary fibrosis can occur as a secondary effect in disease processes such as asbestosis and silicosis, and is known to be more prevalent in certain occupations such as coal miner, ship workers and sand blasters where exposure to environmental pollutants is an occupational hazard (Green, F H et al. (2007) *Toxicol Pathol.* 35:136-47). Other factors that contribute to pulmonary fibrosis include cigarette smoking, and autoimmune connective tissue disorders, like rheumatoid arthritis, scleroderma and systemic lupus erythematosus (SLE) (Leslie, K O et al. (2007) *Semin Respir Crit Care Med.* 28:369-78; Swigris, J J et al. (2008) *Chest.* 133:271-80; and Antoniou, K M et al. (2008) *Curr Opin Rheumatol.* 20:686-91). Other connective tissue disorders such as sarcoidosis can include pulmonary fibrosis as part of the disease (Paramothayan, S et al. (2008) *Respir Med.* 102:1-9), and infectious diseases of the lung can cause fibrosis as a long term consequence of infection, particularly chronic infections.

Pulmonary fibrosis can also be a side effect of certain medical treatments, particularly radiation therapy to the chest and certain medicines like bleomycin, methotrexate, amiodarone, busulfan, and nitrofurantoin (Catane, R et al. (1979) *Int J Radiat Oncol Biol Phys.* 5:1513-8; Zisman, D A et al. (2001) *Sarcoidosis Vasc Diffuse Lung Dis.* 18:243-52; Rakita, L et al. (1983) Am Heart J. 106:906-16; Twohig, K J et al. (1990) *Clin Chest Med.* 11:31-54; and Witten C M. (1989) *Arch Phys Med Rehabil.* 70:55-7). In other embodiments, idiopathic pulmonary fibrosis can occur where no clear causal agent or disease can be identified. Genetic factors can play a significant role in these cases of pulmonary fibrosis (Steele, M P et al. (2007) *Respiration* 74:601-8; Brass, D M et al. (2007) *Proc Am Thorac Soc.* 4:92-100 and du Bois R M. (2006) *Semin Respir Crit Care Med.* 27:581-8).

In other embodiments, pulmonary fibrosis includes, but is not limited to, pulmonary fibrosis associated with chronic obstructive pulmonary disease (COPD), acute respiratory distress syndrome, scleroderma, pleural fibrosis, chronic asthma, acute lung syndrome, amyloidosis, bronchopulmonary dysplasia, Caplan's disease, Dressler's syndrome, histiocytosis X, idiopathic pulmonary haemosiderosis, lymphangiomyomatosis, mitral valve stenosis, polymyositis, pulmonary edema, pulmonary hypertension (e.g., idiopathic pulmonary hypertension (IPH)), pneumoconiosis, radiotherapy (e.g., radiation induced fibrosis), rheumatoid disease, Shaver's disease, systemic lupus erythematosus, systemic sclerosis, tropical pulmonary eosinophilia, tuberous sclerosis, Weber-Christian disease, Wegener's granulomatosis, Whipple's disease, or exposure to toxins or irritants (e.g., pharmaceutical drugs such as amiodarone, bleomycin, busulphan, carmustine, chloramphenicol, hexamethonium, methotrexate, methysergide, mitomycin C, nitrofurantoin, penicillamine, peplomycin, and practolol; inhalation of talc or dust, e.g., coal dust, silica). In certain embodiments, the pulmonary fibrosis is associated with an inflammatory disorder of the lung, e.g., asthma, and/or COPD.

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins). Additional examples of liver conditions and disorders are provided in the Sections entitled "Liver Conditions or Disorders," provided herein.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, focal segmental glomerulosclerosis (FSGS), endothelial/thrombotic microangiopathy injury, scleroderma of the kidney, HIV-associated nephropathy (HIVVAN), or exposure to toxins, irritants, chemotherapeutic agents.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogenous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis or leprosy), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In other embodiments, the fibrotic condition is associated with leprosy or tuberculosis.

In certain embodiments, the fibrotic condition is a fibrotic condition of the bone marrow. In certain embodiments, the fibrotic condition of the bone marrow is myelofibrosis (e.g., primary myelofibrosis (PMF)), myeloid metaplasia, chronic idiopathic myelofibrosis, or primary myelofibrosis. In other embodiments, bone marrow fibrosis is associated with a hematologic disorder chosen from one or more of hairy cell leukemia, lymphoma, or multiple myeloma.

In other embodiments, the bone marrow fibrosis is associated with one or more myeloproliferative neoplasms (MPN) chosen from: essential thrombocythemia (ET), polycythemia vera (PV), mastocytosis, chronic eosinophilic leukemia, chronic neutrophilic leukemia, or other MPN.

In one embodiment, the fibrotic condition is primary myelofibrosis. Primary myelofibrosis (PMF) (also referred to in the literature as idiopathic myeloid metaplasia, and Agnogenic myeloid metaplasia) is a clonal disorder of multipotent hematopoietic progenitor cells (reviewed in Abdel-Wahab, O. et al. (2009) *Annu. Rev. Med.* 60:233-45; Varicchio, L. et al. (2009) *Expert Rev. Hematol.* 2(3):315-334; Agrawal, M. et al. (2010) *Cancer* 1-15).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g. endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In some embodiments, the fibrotic condition is associated with an autoimmune disease selected from scleroderma or lupus, e.g., systemic lupus erythematosus.

In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In some embodiments, the fibrotic condition is scleroderma. In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In one embodiment, the fibrotic condition is a chronic fibrotic condition or disorder. In certain embodiments, the fibrotic condition is associated with an inflammatory condition or disorder.

In some embodiments, the fibrotic and/or inflammatory condition is osteomyelitis, e.g., chronic osteomyelitis.

In some embodiments, the fibrotic condition is an amyloidosis. In certain embodiments, the amyloidosis is associated with chronic osteomyelitis.

In some embodiments, the one or more compositions described herein is administered in combination with one or more other therapeutic agents. Exemplary therapeutic agents include, but are not limited to, anti-fibrotics, corticosteroids, antiinflammatories, immunosuppressants, chemotherapeutic agents, anti-metabolites, and immunomodulators.

An example of suitable therapeutics for use in combination with the composition(s) for treatment of liver fibrosis includes, but is not limited to, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI1262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, and combinations thereof.

An example of suitable therapeutics for use in combination with the composition(s) for treatment of lung fibrosis includes, but is not limited to, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, anti-pseudomonas IgY gargle, ARIKACE™, AUREXIS® (tefibazumab), AZAPRED, azathioprine, azithromycin, azithromycin, AZLI, aztreonam lysine, BIBF1120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Molil901, MP-376 (levofloxacin solution for inhalation), mucoid exopolysaccharide P. aeruginosa immune globulin IV, mycophenolate mofetil, nacetylcysteine, N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhD-NAse, SB656933, SB-656933-AAA, sildenafil, tamoxifen, technetium [Tc-99m] sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, and combinations thereof.

An example of suitable therapeutics for use in combination with the composition(s) for treatment of kidney fibrosis includes, but is not limited to, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, and combinations thereof.

Diagnostic Methods and Assays

AHCM agents can be used to improve diagnosis, treatment, prevention and/or prognosis of cancers in mammals, preferably humans. These diagnostic assays can be performed in vivo or in vitro, such as, for example, on blood samples, biopsy tissue or autopsy tissue.

Thus, the invention provides a diagnostic method useful during diagnosis of a cancer, which involves measuring the expression level of target protein or transcript in tissue or other cells or body fluid from an individual and comparing the measured expression level with a standard target expression levels in normal tissue or body fluid, whereby an increase in the expression level compared to the standard is indicative of a disorder.

One embodiment provides a method of detecting the presence of abnormal hyperproliferative cells, e.g., precancerous or cancerous cells, in a fluid or tissue sample, comprising assaying for the expression of the target in tissue or body fluid samples of an individual and comparing the presence or level of target expression in the sample with the presence or level of target expression in a panel of standard tissue or body fluid samples, where detection of target expression or an increase in target expression over the standards is indicative of aberrant hyperproliferative cell growth.

One aspect of the invention is a method for the in vivo detection or diagnosis of a cancer in a subject, preferably a mammal and most preferably a human. In one embodiment, diagnosis comprises: a) administering (for example, parenterally, subcutaneously, or intraperitoneally) to a subject an effective amount of a labeled antibody or fragment thereof against a cancer antigen, to a subject that has been treated with an AHCM or is being treated with the AHCM; b) waiting for a time interval following the administering for permitting the labeled antibody to preferentially concentrate at sites in the subject where target is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of target. Background level can be determined by various methods including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of, e.g., $^{99}$Tc. The labeled binding molecule, e.g., antibody or antibody fragment, will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: *The Radiochemical Detection of Cancer*, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 7 to 10 days.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography, X-radiography, nuclear magnetic resonance imaging (NMR), CAT-scans or electron spin resonance imaging (ESR).

Pharmaceutical Compositions

The particles can be combined with pharmaceutically acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc. In some embodiments, the administration is oral, parenteral, nasal, intravenous, transdermal, intraarterial, intraarticular, subcutaneous, intramuscular, rectal or vaginal administration.

As used herein, the term "pharmaceutically acceptable carrier" means a non-toxic, inert solid, semi-solid or liquid filler, diluent, encapsulating material or formulation auxiliary of any type. Remington's Pharmaceutical Sciences Ed. by Gennaro, Mack Publishing, Easton, Pa., 1995 discloses various carriers used in formulating pharmaceutical compositions and known techniques for the preparation thereof. The compositions provided herein can be formulated for in vivo administration to a subject. In some embodiments, the compositions are sterile.

The pharmaceutical compositions of this invention can be administered to a subject, e.g., a patient, by any means known in the art. In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables Compositions for rectal or vaginal administration may be suppositories which can be prepared by mixing the inventive composition with suitable non-irritating excipients or carriers such as cocoa butter, polyethylene glycol, or a suppository wax which are solid at ambient temperature but liquid at body temperature and therefore melt in the rectum or vaginal cavity and release the inventive composition.

Dosage forms for topical or transdermal administration of an inventive pharmaceutical composition include ointments, pastes, creams, lotions, gels, powders, solutions, sprays, inhalants, or patches. The inventive composition can be admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive compositions of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body.

Powders and sprays can contain, in addition to the inventive compositions of this invention, excipients such as lactose, talc, silicic acid, aluminum hydroxide, calcium silicates, and polyamide powder, or mixtures thereof.

When administered orally, the inventive compositions can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Acc. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive compositions may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid.

Solid dosage forms for oral administration include capsules, tablets, pills, powders, and granules. In such solid dosage forms, the encapsulated or unencapsulated composition is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of the composition is chosen by the individual physician in view of the patient to be treated. In general, dosage and administration are adjusted to provide an effective amount of the composition to the patient being treated. As used herein, the "effective amount" of a composition refers to the amount necessary to elicit the desired biological response. As will be appreciated by those of ordinary skill in this art, the effective amount of a composition may vary depending on such factors as the desired biological endpoint, the drug to be delivered, the target tissue, the route of administration, etc. For example, the effective amount of the composition containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The compositions of the invention may be formulated in dosage unit form for ease of administration and uniformity of dosage. The expression "dosage unit form" as used herein refers to a physically discrete unit of composition appropriate for the patient to be treated. It will be understood, however, that the total daily usage of the compositions of the present invention will be decided by the attending physician within the scope of sound medical judgment. For any composition, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of composition can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

Delivery Methods

In another aspect, the invention features a method optimizing access to a target tissue, e.g., a cancer, or optimizing delivery to a target tissue, e.g., a cancer, of an agent, e.g., a systemically administered agent, e.g., a diagnostic or imaging agent. The method comprises:

administering an AHCM to the subject (e.g., wherein the AHCM is administered as a particle (e.g., a pH-sensitive particle as disclosed herein)); and optionally, administering an agent, e.g., a diagnostic or imaging agent to said subject.

In an embodiment, the method includes one or more of the following:

a) the AHCM is an anti-hypertensive agent and is administered at a standard of care dose, a sub-anti-hypertensive dose, or a greater than a standard of care-anti-dose;

b) the agent, e.g., diagnostic or imaging agent, has a hydrodynamic diameter of greater than 1, 5, or 20 nm, e.g., is nanoparticle;

c) the agent is an imaging agent, e.g., radiologic agent, an NMRA agent, a contrast agent; or d) the subject is treated with a dosing regimen described herein, e.g., AHCM administration is initiated prior to administration of the agent, e.g., for at least one, two, three, or five days, or one, two, three, four, five or more weeks prior to administration of the agent.

In an embodiment, the AHCM is administered in an amount sufficient to alter (e.g., enhance) the distribution or efficacy of the agent. In one embodiment, the AHCM is administered in an amount sufficient to alter (e.g., enhance) the distribution or efficacy of the agent, but in an amount insufficient to inhibit or prevent tumor growth or progression by itself.

In an embodiment, the AHCM is administered at a dose that causes one or more of the following: a decrease in the level or production of collagen, a decrease in tumor fibrosis, an increase in interstitial tumor transport, improvement of tumor perfusion, or enhanced penetration or diffusion, of the cancer therapeutic in a tumor or tumor vasculature, in the subject.

In an embodiment, the subject is further treated with a cancer therapy, e.g., as therapy as described herein.

In an embodiment, the subject is a human, or a non-human animal, e.g., a mouse, a rat, a non-human primate, horse, or cow.

Evaluation of AHCM, Microenvironment Modulator and Other Stromal Modulators

In an embodiment the particles and method results in, or comprises (e.g., the AHCM, microenvironment modulator or other stromal modulator is administered in a dosage sufficient to result in) improvement of a disorder-related parameter in said subject, as compared to a subject treated with said therapy but without administration of the AHCM, microenvironment modulator or other stromal modulator. "Disorder-related parameter," as used herein, refers to a parameter that varies with the alleviation of the disorder or a symptom of the disorder.

In an embodiment, an AHCM (and, in embodiments not a microenvironment modulator or other stromal modulator) is administered and the improvement is as compared to a subject treated with said therapy but without administration of the AHCM.

In an embodiment, a microenvironment modulator or other stromal modulator (and, in embodiments not an AHCM) is administered and the improvement is as compared to a subject treated with said therapy but without administration of the microenvironment modulator or other stromal modulator.

In an embodiment, an AHCM and a microenvironment modulator or other stromal modulator are administered and the improvement is as compared to a subject treated with said therapy but without administration of the AHCM and the microenvironment modulator or other stromal modulator.

In an embodiment, the parameter comprises relief of a symptom of said disorder.

In an embodiment, the parameter comprises outcome of a patient scored evaluation of symptoms or quality of life, e.g., a quality of life questionnaire, e.g., outcome on an evaluation of number of meals consumed on the day prior to the evaluation, pain, weight loss or gain.

In an embodiment, the parameter comprises one or more or all of: objective response rate (ORR); progression free survival (PFS); overall survival (OS), or reduction in toxicity (whether or not accompanied by an increase on OS. ORR evaluations will differ between disorders, but such evaluations are within the skill of the art. For an example, see Willett et al. (2009) *Journal of Clinical Oncology* 27: 3020-6, which discusses the use of pathological response estimated from evaluation of tissue after surgical resection. Evaluation of PFS is within the skill of the art. For an example, for brain tumors, APF6 (alive and progression-free at 6 months) has been used, see Batchelor et al. (2010) *J. Clinical Oncology* 28: 2817-23. For radiation therapy, criteria such as "Disease-free survival" and "Freedom from metastasis" have been used, see, e.g., Willett et al, 2010, *The Oncologist,* 15:845-851. Some evaluations of ORR and PFS rely on imaging methods, e.g., PET, PET-MRI, or PET-CT. Evaluation of toxicity will vary by disorder and treatment modality. One example can be seen in Willett et al. (2010) *The Oncologist* 15:845-851.

In an embodiment, the parameter comprises one or more or all of: a) drug concentration, e.g., at a disorder or disease site, e.g., in a solid tumor; b) tumor response; c) blood perfusion, e.g., at a disorder or disease site, e.g., in a solid tumor; d) oxygenation, e.g., at a disorder or disease site, e.g., in a solid tumor; e) interstitial fluid pressure at a disorder or disease site, e.g., in a solid tumor; or f) extracellular matrix content or composition, e.g., level of collagen, hyaluronic acid.

In an embodiment, the parameter is evaluated by a non-invasive method, e.g., a magnetic resonance method, e.g., MRI or MRS, PET, or SPECT.

In an embodiment, the disorder is, e.g., cancer, said parameter is drug concentration, e.g., at a disorder or disease site, e.g., in a solid tumor. In some embodiments the parameter can be evaluated by a method described herein, e.g., with any of PET-CT, e.g., generally as described in Saleem et al. (2000) *The Lancet* 355: 2125-2131, MRS, e.g., generally as described in Meisamy et al. (2004) *Radiology* 233: 424-431, or SPECT, e.g., generally as described in Perik et al. (2006) *Journal of Clinical Oncology* 24: 2276-2282.

In an embodiment, the disorder is, e.g., cancer, said parameter is blood perfusion, e.g., at a disorder or disease site, e.g., in a solid tumor. In some embodiments, the parameter can be evaluated by a method described herein, e.g. MRI, e.g., generally as described in Sorensen et al. (2012) *Cancer Research* 72: 402-407, or perfusion CT e.g., generally as described in Park et al. (2009) *Radiology* 250: 110-117, or Doppler ultrasound generally as described in Singh et al. (2010) *European J. of Radiology* 75: e158-162.

In an embodiment, the disorder is, e.g., cancer, said parameter is oxygenation, e.g., at a disorder or disease site, e.g., in a solid tumor. In some embodiments, the parameter can be evaluated by a method described herein, e.g., PET, PET-CT, e.g. generally as described in Rajendran et al. (2006) *Clinical Cancer Research* 12: 5435-5441, or Eppendorf electrode, e.g. generally described in Le et al. (2007) *International J. of Radiation Oncology Biology Physics* 69: 167-175, or immunohistochemistry, e.g. generally described in Rademakers et al. (2011) *BMC Cancer* 11: 167.

In an embodiment, the disorder is, e.g., cancer, said parameter is metabolic activity, e.g., at a disorder or disease site, e.g., in a solid tumor In some embodiments the parameter can be evaluated by a method described herein, e.g., functional MRI, or PET, PET-MRI, PET-CT, e.g. generally as described in Shankar et al. (2006) *The Journal of Nuclear Medicine* 47:1059-1066.

In an embodiment the disorder is, e.g., cancer, said parameter is interstitial fluid pressure, e.g., at a disorder or disease site, e.g., in a solid tumor. In some embodiments, the parameter can be evaluated by a method described herein, e.g., the wick-in-needle technique, e.g., generally as described in Boucher et al. (1991) *Cancer Research* 51: 6691-6694.

In an embodiment, the disorder is a hyperproliferative fibrotic disease and said parameter is amount of connective tissue matrix or blood perfusion.

In an embodiment, the disorder is an inflammatory disorder, said parameter is amount of connective tissue matrix. In some embodiments, the parameter can be evaluated immunohistochemically.

In an embodiment, the disorder is an autoimmune disorder, said parameter is amount of connective tissue matrix. In some embodiments, the parameter can be evaluated immunohistochemically.

In some embodiments, the parameter is evaluated in a sample from said subject, e.g., a tumor sample, e.g., a biopsy, or a blood or serum sample.

In an embodiment, the parameter comprises one or more or all of:

a) drug concentration, e.g., as evaluated by HPLC, or NMR, e.g., evaluated generally as described in Olive et al. (2009) *Science* 324: 1475, HPLC with tandem MS, generally as described in Hu et al. (2011) *JNCI* 103: 893-905, or by histological measures, e.g., fluorescence imaging of fluorescent drugs, generally as described in Primeau et al. (2005) *Clinical Cancer Research* 11: 8782-8788;

b) collagen content, e.g., as evaluated by total collagen content measured by hydroxyproline content, e.g., generally as described in Netti et al. (2000) *Cancer Research* 60: 2497-2503, or immunohistochemistry by antibody staining, e.g., generally as described in Pluen et al. (2001) *PNAS* 98:4628-4633;

c) hyaluronan content, e.g., as evaluated by hyaluronan-binding protein labeling of tissue sections, as generally described in Pluen et al. (2001) *PNAS* 98:4628-4633, or glycosaminoglycan analysis in tissue extracts, e.g., generally as described in Netti et al. (2000) *Cancer Research* 60: 2497-2503;

d) pathological response, e.g., the prevalence of tumor cells in a sample, e.g., evaluated generally as described in Minckwitz et al. (2012) *Journal of Clinical Oncology published as* 10.1200/JCO.2011.38.8595;

e) vessel morphology, e.g., size, can be evaluated generally as described in Provenzano et al. (2012) *Cancer Cell* 21:418-429, patency (fraction of perfused vessels), e.g., evaluated generally as described in Jacobetz et al. (2012) *Gut* published on line Mar. 30, 2012, network structure, e.g., evaluated as generally described in Baish et al. (2011) *PNAS* 108: 1799-1803, luminal opening (measure of perfusion), e.g., evaluated generally as described in Padera et al. (2004) *Nature* 427: 695, or vessel structure (normalization), e.g., evaluated generally as described in Mazzone et al. (2009) *Cell* 136:839-851; or f) hypoxia, e.g., generally as described in Rademakers et al. (2011) *BMC Cancer* 11: 167 or Le et al. (2007) *International J. of Radiation Oncology Biology Physics* 69: 167-175. Hypoxia can be evaluated in a number of ways, e.g.: by a pimonizadole method, see, e.g., Kaanders, J. H. et al. (2002) *Cancer Res.* 62, 7066-7074; an EF5 method, see, e.g., Evans, S. M. et al. (2007) *Int. J. Radiat. Oncol. Biol. Phys.* 69, 1024-1031; a CA9 method, see, e.g., Koukourakis, M. I. et al., (2006) *J. Clin. Oncol.* 24, 727-735; a LOX method, see, e.g., Erler, J. T. et al., (2006) *Nature* 440, 1222-1226; a HIF method, see, e.g., Bos, R. et al. (2003) *Cancer* 97, 1573-1581, Yan, et al. (2009) *Br. J. Cancer* 101, 1168-1174, or Koukourakis, M. I. et al., (2006) *J. Clin. Oncol.* 24, 727-735; or an electrode method, see, e.g., Nordsmark, M. et al. (2005) *Radiother. Oncol.* 77, 18-24, Brizel, D. M. et al. (1996) *Cancer Res.* 56, 941-943, Movsas, B. et al. (2002) *Urology* 60, 634-639, or Fyles, A. et al. (2002) *J. Clin. Oncol.* 20, 680-687. See generally Table 2 of Wilson and Hays (2011) *Nature Rev Cancer*, 11: 393-410

In an embodiment, the parameter is evaluated by immunostaining.

In an embodiment, the parameter comprises one or more or all of:

serum degraded collagen (ICTP), or collagen synthesis (PIP), e.g., evaluated generally as described in Lopez et al. (2001) *Circulation* 104:286-291;

serum hyaluronan, e.g., evaluated generally as described in Miele et al. (2009) *Translational Research* 154:194-201; or serum or plasma pro-fibrotic factors (connective tissue growth factor (CTGF), transforming growth factor-beta (TGF-beta), interleukin-1, -4, -6, -8, -10 and -13, platelet-derived growth factor (PDGF), stromal cell-derived factor 1 (SDF1), e.g., evaluated generally as described in Harti et al. (2006) *American J. of Respiratory Medicine* 173: 1371-1376.

In an embodiment, the parameter is drug concentration and said parameter is evaluated by a chromatographic method, e.g., HPLC.

In an embodiment, the disorder is a hyperproliferative fibrotic disease and the parameter is fibrosis.

In an embodiment, the disorder is an inflammatory disorder and the parameter is fibrosis.

In an embodiment, the disorder is an autoimmune disorder and the parameter is fibrosis.

In an embodiment the parameter is a morphological parameter, e.g., evaluated at a disorder or disease site, e.g., in a solid tumor and comprises one or more or all of:

collagen morphology, e.g., evaluated generally as described in Diop-Frimpong et al. (2011) *PNAS* 108:2909-2914;

collagen or hyaluronan content, e.g., evaluated generally as described in Pluen et al. (2001) *PNAS* 98:4628-4633;

vessel patency (fraction of perfused vessels), e.g., evaluated generally as described in Jacobetz et al. (2012) *Gut* published on line Mar. 30, 2012; or vessel diameter or size evaluated, e.g., evaluated generally as described in Provenzano et al. (2012) *Cancer Cell* 21:418-429.

Kits

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition. In some embodiments, the kits can contain one or more of the polymers provided herein with instructions for mixing (e.g., to produce a particle as provided herein). In other embodiments, the kits can contain one or more of the components provided herein with other reagents and instructions for producing a particle or polymer as provided herein. In some embodiments, the kits further contain an agent.

The kits described herein may also contain one or more containers, which may contain an inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In some embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

The invention also involves, in another aspect, promotion of the administration of any of the compositions described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

In another aspect, the invention features a diagnostic kit that includes the AHCM, alone or in combination with the agent, e.g., a diagnostic or imaging agent, described herein, and optionally, instructions for use, e.g., for the diagnosis of a disorder disclosed herein, e.g., a cancer or liver disorder.

Other features and embodiments of the present invention include one or more of the following numbered paragraphs.

1. A polyacetal polymer according to Formula (IV):

Formula (IV)

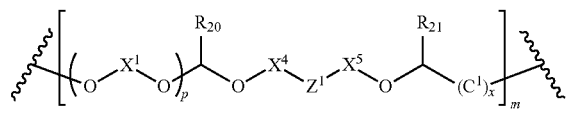

wherein:

$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, or heterocyclyl is optionally substituted with 1-6 $R^4$;

each of $X^4$ and $X^5$ is independently $C_1$-$C_6$ alkylene, optionally substituted with 1-6 $R^4$;

$Z^1$ is O, $C_3$-$C_8$ cyclyl, or $C(R^{22})(R^{23})$;

$C^1$ is heteroalkyl, cyclyl, or heterocyclyl, each of which is optionally substituted with 1-6 $R^3$;

each of $R^3$ is independently alkyl, hydroxyl, halo, heteroalkyl, keto, alkoxy, ester, cyclyl, heterocyclyl, arylalkyl, heteroarylalkyl, a linker, an agent, a targeting moiety, or a branching point;

each $R^4$ is independently $C_1$-$C_6$ alkyl, $C_2$-$C_6$ alkenyl, $C_2$-$C_6$ alkynyl, $C_1$-$C_6$ heteroalkyl, $OR^5$, ($C_1$-$C_6$ alkylene)-$OR^5$, ($C_1$-$C_6$ alkylene)-O—($C_1$-$C_6$ alkylene)-$OR^5$, ($C_1$-$C_6$ alkylene)-C(O)—($C_1$-$C_6$ alkylene)-$OR^5$, ($C_1$-$C_6$ alkylene)-OC(O)—($C_1$-$C_6$ alkylene)-$OR^5$, ($C_1$-$C_6$ alkylene)-C(O)O—($C_1$-$C_6$ alkylene)-$OR^5$, or ($C_1$-$C_6$ alkylene)-OC(O)O—($C_1$-$C_6$ alkylene)-$OR^5$, wherein each alkyl, alkenyl, alkynyl, heteroalkyl, or alkylene is optionally substituted with 1-6 $R^7$;

each $R^5$ is independently hydrogen, $C_1$-$C_6$ alkyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^8$;

each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, ($C_1$-$C_6$ alkylene)-$OR^5$, ($C_1$-$C_6$ alkylene)-O—($C_1$-$C_6$ alkylene)-$OR^5$, cyano, cyclyl, heterocyclyl, aryl, or heteroaryl; and each $R^8$ is independently $C_1$-$C_6$ alkyl, $C_2$-$C_6$ alkenyl, $C_2$-$C_6$ alkynyl, $C_1$-$C_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 $R^9$;

each $R^9$ is independently $C_1$-$C_6$ alkyl, $C_1$-$C_6$ heteroalkyl, halo, cyano, cyclyl, or heterocyclyl;

each of $R^{20}$ and $R^{21}$ is independently $C_1$-$C_6$ alkyl or $OR^{26}$;

each of $R^{22}$ and $R^{23}$ is independently hydrogen, $C_1$-$C_6$ alkyl, or ($C_1$-$C_6$ alkylene)-$OR^{26}$; and each $R^{26}$ is $C_1$-$C_6$ alkyl, $C_2$-$C_6$ alkenyl, a linker, a branching point, an agent, or a targeting moiety;

each of p and x is independently 0 or 1;

wherein at least one of p or x is 1; and m is an integer from 2 to 500.

2. The polymer of paragraph 1, wherein at least one of $R^{21}$, $R^{22}$, $R^{25}$, and $R^{26}$ is methyl.

3. The polymer of any of paragraphs 1 or 2, wherein $R^{21}$ and $R^{22}$ are same.

4. The polymer of any of paragraphs 1-3, wherein the polymer is conjugated with a therapeutic agent.

5. The polymer of paragraph 4, wherein the therapeutic agent is selected from the group consisting of angiotensin receptor blockers, CXCR-4 antagonists, chemotherapeutic drugs, and any combinations thereof.

6. The polymer of paragraph 4 or 5, wherein the therapeutic agent is an angiotensin receptor blocker (ARB).

7. The polymer of any of paragraphs 4-6, wherein the therapeutic agent is selected from the group consisting of losartan, valsartan, telmisartan, candesartan, eprosartan, irbesartan, azilsartan, EXP-3174, olmesartan, or a prodrug or active metabolite thereof, e.g., a compound shown in FIG. 23, AMD3100, paclitaxel, docetaxel, doxorubicin, camptothecin, irinotecan, rapamycin, FK506, 5-FU, gemcitabine, oxaliplatin, cisplatin, leucovorin, and combinations thereof.

8. The polymer of any of paragraphs 1-7, wherein the polymer is conjugated with a targeting ligand.

9. The polymer of paragraph 8, wherein the targeting ligand is selected from the group consisting of peptides, polypeptides, proteins, enzymes, peptidomimetics, glycoproteins, antibodies (monoclonal or polyclonal) and portions and fragments thereof (e.g., antigen binding fragments), lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

10. The polymer of paragraph 8 or 9, wherein the targeting ligand is mannose-6-phosphate.

11. The polymer of any of paragraphs 1-10, wherein the polymer degrades between pH about 5.0 to about 7.4.

12. The polymer of any of paragraphs 1-11, wherein the polymer further comprises a PEG conjugated thereto.

13. A polymer comprising a therapeutic agent conjugated thereto via a linker, wherein the linker comprises:
(i) a polymer of any one of paragraphs 190-192;
(ii) a compound selected from

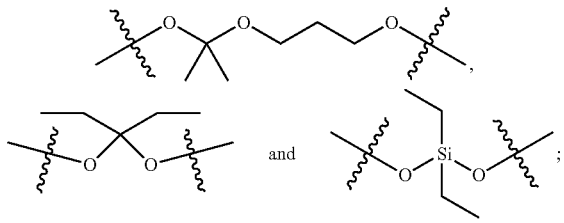

or
(iii) any combination of (i) and (ii).

14. The polymer of paragraph 13, wherein the therapeutic agent is selected from the group consisting of angiotensin receptor blockers, CXCR-4 antagonists, chemotherapeutic drugs, and any combinations thereof.

15. The polymer of paragraph 13 or 15, wherein the therapeutic agent is an angiotensin receptor blocker (ARB).

16. The polymer of any of paragraphs 13-15, wherein the therapeutic agent is selected from the group consisting of losartan, valsartan, telmisartan, candesartan, eprosartan, irbesartan, azilsartan, EXP-3174, olmesartan, or a prodrug or active metabolite thereof, e.g., a compound shown in FIG. 23, AMD3100, paclitaxel, docetaxel, doxorubicin, camptothecin, irinotecan, rapamycin, FK506, 5-FU, gemcitabine, oxaliplatin, cisplatin, leucovorin, and combinations thereof.

17. The polymer of any of paragraphs 13-16, wherein the polymer is conjugated with a targeting ligand.

18. The polymer of paragraph 17, wherein the targeting ligand is selected from the group consisting of peptides, polypeptides, proteins, enzymes, peptidomimetics, glycoproteins, antibodies (monoclonal or polyclonal) and portions and fragments thereof (e.g., antigen binding fragments), lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

19. The polymer of paragraph 17 or 18, wherein the targeting ligand is mannose-6-phosphate.

20. The polymer of any of paragraphs 13-19, wherein the linker degrades between pH about 5.0 to about 7.4.

21. The polymer of any of paragraphs 13-20, wherein the polymer is selected from the group consisting of: (i) polysaccharides, polypeptides, polyacetals, polyketals, polyanhydrides, polyhydroxybutyric acid, polyorthoesters, polysiloxanes, polycaprolactone, poly(lactic-co-glycolic acid), poly(lactic acid), poly(glycolic acid), and copolymers or block polymers prepared from the monomers of these polymers; (ii) a polyacetal polymer of any of paragraphs 190-192; and (iii) any combinations of (i) and (ii).

22. The polymer of paragraph 21, wherein the polymer is poly(lactic acid)-b-poly(ethylene glycol) (PLA-PEG), poly(lactic acid)-b-poly(ethylene glycol) (PLGA-PEG), dextran, (cyclodextrin)-co-poly(ethylene glycol) (CDP), or a polyacetal polymer of any one of the preceding paragraphs.

23. The polymer of paragraph 22, wherein the polymer is selected from the group consisting of PLGA, dextran, or a polyacetal polymer of any one of the preceding paragraphs.

24. A particle comprising the polymer of any of paragraphs 190-210.

25. The particle of paragraph 24, wherein the nanoparticle has an average size of from about 1 nm to about 100 nm, e.g., from about 5 nm to about 50 nm.

26. The particle of any of paragraphs 1-25, wherein the particle has a neutral charge.

27. A conjugate comprising the polymer of any of paragraphs 1-23.

28. The conjugate of paragraph 27, wherein the ARB is chosen from losartan, valsartan, telmisartan, candesartan, eprosartan, irbesartan, azilsartan, EXP-3174, olmesartan, or a prodrug or active metabolite thereof, e.g., a compound shown in FIG. 23.

29. The conjugate of paragraph 27 or 28, wherein the targeting moiety is a liver targeting moiety, e.g., M6P.

30. A linker comprising the polymer of paragraph 1-13.

31. A method of making a polymer (e.g., a polyacetal polymer described herein), comprising: polymerizing a polyol and a vinyl ether to produce a polymer of Formula (IV):

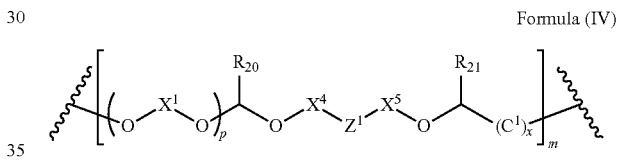

Formula (IV)

wherein:
$X^1$ is $C_1$-$C_{12}$ alkylene, $C_1$-$C_{12}$ heteroalkylene, $C_3$-$C_8$ cyclyl, or $C_3$-$C_8$ heterocyclyl, wherein each alkylene, heteroalkylene, cyclyl, or heterocyclyl is optionally substituted with 1-6 $R^4$;

each of $X^4$ and $X^5$ is independently $C_1$-$C_6$ alkylene, optionally substituted with 1-6 $R^4$;

$Z^1$ is O, $C_3$-$C_8$ cyclyl, or $C(R^{22})(R^{23})$;

$C^1$ is heteroalkyl, cyclyl, or heterocyclyl, each of which is optionally substituted with 1-6 $R^3$;

each of $R^3$ is independently alkyl, hydroxyl, halo, heteroalkyl, keto, alkoxy, ester, cyclyl, heterocyclyl, arylalkyl, heteroarylalkyl, a linker, an agent, a targeting moiety, or a branching point;

each $R^4$ is independently $C_1$-$C_6$ alkyl, $C_2$-$C_6$ alkenyl, $C_2$-$C_6$ alkynyl, $C_1$-$C_6$ heteroalkyl, $OR^5$, $(C_1$-$C_6$ alkylene)-$OR^5$, $(C_1$-$C_6$ alkylene)-O—$(C_1$-$C_6$ alkylene)-$OR^5$, $(C_1$-$C_6$ alkylene)-C(O)—$(C_1$-$C_6$ alkylene)-$OR^5$, $(C_1$-$C_6$ alkylene)-OC(O)—$(C_1$-$C_6$ alkylene)-$OR^5$, $(C_1$-$C_6$ alkylene)-C(O)O—$(C_1$-$C_6$ alkylene)-$OR^5$, or $(C_1$-$C_6$ alkylene)-OC(O)O—$(C_1$-$C_6$ alkylene)-$OR^5$, wherein each alkyl, alkenyl, alkynyl, heteroalkyl, or alkylene is optionally substituted with 1-6 $R^7$;

each $R^5$ is independently hydrogen, $C_1$-$C_6$ alkyl, cyclyl, heterocyclyl, aryl, heteroaryl, arylalkyl, heteroarylalkyl, a linker, a branching point, a protecting group, an agent, or a targeting moiety, wherein each alkyl, cyclyl, heterocyclyl, aryl, heteroaryl, arylalkyl, heteroarylalkyl is optionally substituted with 1-6 $R^8$;

each $R^7$ is independently $C_1$-$C_6$ alkyl, $C_2$-$C_6$ alkenyl, $C_2$-$C_6$ alkynyl, $C_1$-$C_6$ heteroalkyl, halo, $OR^5$, $(C_1$-$C_6$ alkylene)-OR$^5$, (C$_1$-C$_6$ alkylene)-O—(C$_1$-C$_6$ alkylene)-OR$^5$, cyano, cyclyl, heterocyclyl, aryl, or heteroaryl; and each R$^8$ is independently C$_1$-C$_6$ alkyl, C$_2$-C$_6$ alkenyl, C$_2$-C$_6$ alkynyl, C$_1$-C$_6$ heteroalkyl, halo, cyano, cyclyl, heterocyclyl, aryl, or heteroaryl, wherein each alkyl, alkenyl, alkynyl, heteroalkyl, cyclyl, heterocyclyl, aryl, or heteroaryl is optionally substituted with 1-6 R$^9$;

each R$^9$ is independently C$_1$-C$_6$ alkyl, C$_1$-C$_6$ heteroalkyl, halo, cyano, cyclyl, or heterocyclyl;

each of R$^{20}$ and R$^{21}$ is independently C$_1$-C$_6$ alkyl or OR$^{26}$;

each of R$^{22}$ and R$^{23}$ is independently hydrogen, C$_1$-C$_6$ alkyl, or (C$_1$-C$_6$ alkylene)-OR$^{26}$; and each R$^{26}$ is C$_1$-C$_6$ alkyl, C$_2$-C$_6$ alkenyl, a linker, a branching point, an agent, or a targeting moiety;

each of p and x is independently 0 or 1;

wherein at least one of p or x is 1; and m is an integer from 2 to 500.

32. The method of paragraph 31, wherein the method further comprises a Lewis acid catalyst (e.g., p-toluene sulfonic acid, pTSA).

33. The method of any one of paragraphs 31-33, wherein method is carried out in a solvent comprising toluene, chloroform, tetrahydrofuran (THF), dichloromethane (DCM), dimethylformamide (DMF), or dimethylsulfoxide (DMSO).

34. The method of any one of paragraphs 31-33, wherein the method further comprises a base (e.g., trimethylamine (TEA) or 4-dimethylaminopyridine (DMAP)).

35. The method of any one of paragraphs 31-34, wherein the temperature of the polymerization is maintained between or 40-60° C.

36. The method of any one of paragraphs 31-35, wherein the individual monomer units of the polymerization comprise a polyol (e.g., a compound represented by Formula (II), Formula (II-a), Formula (II-b), Formula (II-c), Formula (II-d), Formula (II-e), Formula (II-f), Formula (II-g), Formula (II-h), Formula (II-i), Formula (II-j), or as depicted in FIG. 1B), and a vinyl ether (e.g., a compound represented by Formula (III), Formula (III-a), Formula (III-b), or as depicted in FIG. 1C).

37. The method of paragraph 36, wherein the ratio of the polyol to the vinyl ether is about 1.5:1 to about 1:1.

38. The method of any one of paragraphs 31-37, wherein the method further comprises a PEG (e.g., as described by C$^1$ or C$^2$ in Formula (I), Formula (I-a), Formula (I-b), Formula (I-c), Formula (I-d), Formula (I-e), or Formula (IV)).

39. The method of paragraph 38, wherein only one PEG is used in the polymerization (e.g., PEG 400, PEG 1000, or PEG 2050).

40. The method of paragraph 38, wherein more than one PEG is used in the polymerization (e.g., PEG 400, PEG 1000, or PEG 2050).

41. The method of any one of paragraphs 31-40, wherein the method further comprises conjugation of the polymer to an agent (e.g., an agent described herein, e.g., an ARB), a targeting moiety (e.g., M6P), or a linker (e.g., a linker described herein).

42. The method of paragraph 41, wherein the conjugation takes place through a free hydroxyl group on the polyacetal polymer.

43. The method of any one of paragraphs 31-42, wherein the conjugation comprising a coupling agent (e.g., DIC, DCC, HOAt, HOBt, or PyBOP) and a base (e.g., TEA or pyridine).

44. The method of paragraph 42, wherein a free hydroxyl group on a polymer (e.g., a polyacetal polymer described herein) must be exposed through removal of a hydroxyl protecting group (e.g., a benzyl ether, a t-butyl ether, a benzoic acid ester, an acetic acid ester, or an allyl ether).

Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, and more typically, within 5%, 4%, 3%, 2% or 1% of a given value or range of values.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease," "reduced," "reduction," "decrease," or "inhibit" are all used herein generally to mean a decrease by a statistically significant amount. However, for avoidance of doubt, "reduced," "reduction," "decrease," or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased," "increase," "enhance," or "activate" are all used herein to generally mean an increase by a statically significant amount, for the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

"Delivery," as used herein in the context of delivery of an agent(s) to a tumor, refers to the placement of the agent(s) in sufficient proximity to one or more (or all) of: the tumor vasculature, the tumor interstitial matrix, or tumor cells or tumor-associated cells (e.g., fibroblasts), to have a desired effect. The agent(s) can be, e.g., a cancer therapy (e.g., a cancer therapeutic agent(s) as described herein), or a diagnostic or imaging agent(s). Unless noted otherwise, the term "agent" or "agent(s)" as used generically herein can include one, two or more agents.

In one embodiment, the therapeutic agent includes, e.g., one or more of a small molecule, a protein or a nucleic acid drug, an oncolytic virus, a vaccine, an antibody or a fragment thereof, or a combination thereof. The therapeutic agent can be "free" or packaged or formulated into a delivery vehicle, e.g., a particle, e.g., a nanoparticle (e.g., a lipid nanoparticle, a polymeric nanoparticle, or a viral particle). Delivery of a therapeutic agent is characterized by placement of the therapeutic agent in sufficient proximity to the cell to alter an activity of the cell, e.g., to kill the cell and/or reduce its ability to divide.

In other embodiments, the agent is a diagnostic or an imaging agent (e.g., one or more of a radiologic agent, an NMRA agent, a contrast agent, or the like). The diagnostic or imaging agent can be "free" or packaged or formulated into a delivery vehicle. Delivery of a diagnostic or imaging agent is characterized by placement of the agent in sufficient proximity to a target cell or tissue to allow detection of the target cell or tissue.

In some embodiments, increased (or improved) delivery (as compared with a delivery which is the same or similar except that it is carried out in the absence of an AHCM) can include one or more of:

increased delivery to, or amount or concentration in, the tumor vasculature, of the agent;

increased delivery to, or amount or concentration in, the tumor, e.g., the tumor vasculature interstitial matrix, of the agent;

increased delivery to, or amount or concentration in, in the tumor cells or tumor-associated cells (e.g., fibroblasts), of the agent;

increased flow rate, e.g., of the agent, in the tumor vasculature;

improved (or normalized) vasculature morphology (e.g., less tumor-like);

decompression of tumor vasculature;

increased pore size, or rate of diffusion of the agent, in the tumor, e.g., in the interstitial matrix;

increased perfusion of the agent, in the tumor, e.g., in the interstitial matrix;

broader and/or more homogeneous distribution of the agent throughout the tumor;

broader and/or more homogeneous distribution of the agent throughout the tumor interstitial matrix;

increased proportion of the agent in the tumor, e.g., the tumor interstitial matrix, as opposed to non-tumor tissue, e.g., peripheral blood;

inhibition of the TGF-beta pathway in the tumor, e.g., in the tumor vasculature interstitial matrix;

inhibition of the CTGF pathway in the tumor, e.g., in the tumor vasculature interstitial matrix;

inhibition of activity of the angiotension-II type-1 receptor;

decrease in fibrosis, in the tumor, e.g., the tumor vasculature interstitial matrix;

decrease in the level or production of an extracellular matrix component, such as a fiber (e.g., collagen, procollagen), and/or a polysaccharide (e.g., a glycosaminoglycan such as hyaluronan or hyaluronic acid);

decrease in collagen or collagen deposition, in the tumor, e.g., the tumor vasculature interstitial matrix; or decrease hyaluronan levels in the tumor, e.g., the tumor vasculature interstitial or stromal matrix.

In some embodiments, increased (or improved) delivery (as compared with a delivery which is the same or similar except that it is carried out in the absence of an AHCM) can also include increased amount of the agent distributed to at least a portion of the tumor. In some embodiments, the increased amount of the agent delivered to the tumor in the presence of the AHCM can be distributed homogenously or heterogeneously throughout the tumor.

"Efficacy" as used herein in the context of therapy, e.g., cancer therapy, can be characterizes as the extent to which a therapy has a desired effect, including but not limited to, alleviation of a symptom, diminishment of extent of disease, stabilized state of disease, delay or slowing of disease progression, amelioration or palliation of the disease state, and remission (whether partial or total), whether detectable or undetectable.

Improved efficacy, in the context of efficacy of cancer therapy, can be characterized by one or more of the following: an increase in an anti-tumor effect, of the cancer therapy, and/or a lessening of unwanted side effects (e.g., toxicity), of the cancer therapy, as compared with a treatment which is the same or similar except that it is carried out in the absence of treatment with an AHCM. In one embodiment, the increase in the anti-tumor effect of the cancer therapy includes one or more of: inhibiting primary or metastatic tumor growth; reducing primary or metastatic tumor mass or volume; reducing size or number of metastatic lesions; inhibiting the development of new metastatic lesions; reducing one or more of non-invasive tumor volume or metabolism; providing prolonged survival; providing prolonged progression-free survival; providing prolonged time to progression; and/or enhanced quality of life.

In some embodiments, the term "improved efficacy" as used herein, with respect to a cancer therapy in combination with an AHCM, can refer to an increase in reduction of primary or metastatic tumor growth by at least about 5%, at least about 10%, at least about 20%, at least about 30%, at least about 40%, at least about 50%, at least about 60%, at least about 70%, at least about 80%, at least about 90%, at least about 95%, up to and including 100%, as compared to the reduction of primary or metastatic tumor growth during a cancer therapy alone (i.e., in the absence of an AHCM). In some embodiments, the administration of an AHCM in combination with a cancer therapy can increase the reduction of primary or metastatic tumor growth by at least about 1-fold, at least about 2-fold, at least about 3-fold, at least about 5-fold, at least about 6-fold, at least about 7-fold, or higher, as compared to the reduction of primary or metastatic tumor growth during a cancer therapy alone (i.e., in the absence of an AHCM). Methods for monitoring tumor growth in vivo are well known in the art, e.g., but not limited to, X-ray, CT scan, MRI and other art-recognized medical imaging methods.

In some embodiments, the term "improved efficacy" as used herein, with respect to a therapy (e.g., cancer or liver therapy) in combination with an AHCM, microenvironment modulator and/or other stromal modulator (administered as a particle or a free agent), can refer to an increase in perfusion of a therapeutic agent (e.g., low molecular weight therapeutics or nanotherapeutics such as DOXIL® or immune cells) into a target site, e.g., a tumor, e.g., by at least about 5%, at least about 10%, at least about 20%, at least about 30%, at least about 40%, at least about 50%, at least about 60%, at least about 70%, at least about 80%, at least about 90%, at least about 95%, up to and including 100%, as compared to perfusion of the agent alone (i.e., in the absence of an AHCM, microenvironment modulator and/or other stromal modulator). In some embodiments, the administration of an AHCM, microenvironment modulator and/or other stromal modulator in combination with a therapy (e.g., cancer or liver therapy) can increase perfusion of the agent (e.g., low molecular weight therapeutics or nanotherapeutics such as DOXIL®) into a tumor, by at least about 1-fold, at least about 2-fold, at least about 3-fold, at least about 5-fold, at least about 6-fold, at least about 7-fold, or higher, as compared to the perfusion efficiency of the agent alone (i.e., in the absence of an AHCM, microenvironment modulator and/or other stromal modulator). Methods to measure tumor perfusion in vivo are well established in the art, including, but not limited to, positron emission tomography (PET), and ultrasound or contrast-enhanced ultrasound.

In some embodiments, the term "improved efficacy" as used herein, with respect to a therapy (e.g., cancer or liver therapy) in combination with an AHCM, microenvironment modulator and/or other stromal modulator (administered as a particle or a free agent), can refer to an increase in reduction in expression level of at least one biomarker, e.g., at least one cancer biomarker (e.g., in a biological sample such as a blood sample, a serum sample, a plasma sample or a tissue biopsy), e.g., by at least about 5%, at least about 10%, at least about 20%, at least about 30%, at least about 40%, at least about 50%, at least about 60%, at least about 70%, at least about 80%, at least about 90%, at least about 95%, up to and including 100%, as compared to the reduction in expression level of the at least one biomarker, e.g., cancer or liver biomarker, when administered with a therapy, alone (i.e., in the absence of an AHCM, microenvironment modulator and/or other stromal modulator). In some embodiments, the administration of an AHCM in combination with a therapy can increase the reduction in expression level of at least one biomarker (e.g., in a biological sample such as a blood sample, a serum sample, a plasma sample or a tissue biopsy) by at least about 1-fold, at least about 2-fold, at least about 3-fold, at least about 5-fold, at least about 6-fold, at least about 7-fold, or higher, as compared to the reduction in expression level of the at least one cancer biomarker when administered with a therapy alone (i.e., in the absence of an AHCM, microenvironment modulator and/or other stromal modulator). Examples of a biomarker in the serum, plasma or tissue can include, but are not limited to, TGF-beta 1, TGF-beta 2, CTGF, TSP-1, collagen I, collagen II, collagen III, or collagen IV. Expression levels of biomarkers can be measured on a transcript level and/or a protein level, using any art-recognized analytical methods, e.g., PCR, western blot, ELISA, and/or immunostaining.

"Blood pressure" is usually classified based on the systolic and diastolic blood pressures. "Systolic blood pressure" or Psys refers to the blood pressure in vessels during a heart beat. "Diastolic blood pressure" or Pdias refers to the pressure between heartbeats. A systolic or the diastolic blood pressure measurement higher than the accepted normal values for the age of the individual is classified as prehypertension or hypertension. A systolic or the diastolic blood pressure measurement lower than the accepted normal values for the age of the individual is classified as hypotension. A "normal" systolic pressure for an adult is typically in the range of 90-120 mmHg; a "normal" diastolic pressure is usually in the range of 60-80 mmHg. In the population, the average blood pressure (Psys/Pdias ratio) can range from 110/65 to 140/90 mmHg for an adult; 95/65 mmHg for a 1 year infant, and 100/65 mmHg for a 6-9 year old.

As used herein, the term "mean arterial pressure" (MAP) is art recognized and refers to the average over a cardiac cycle and is determined by the cardiac output (CO), systemic vascular resistance (SVR), and central venous pressure (CVP), MAP=(CO×SVR)+CVP. MAP can be approximately determined from measurements of the systolic pressure (Psys) and the diastolic pressure (Pdias), while there is a normal resting heart rate, MAP is approximately Pdias+ ⅓(Psys−Pdias).

Selected Chemical Definitions

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alkyl" means a straight or branched, saturated aliphatic radical having a chain of carbon atoms. C, alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In some embodiments, a straight chain or branched chain alkyl has 30 or fewer carbon atoms in its backbone (e.g., C1-C30 for straight chains, C3-C30 for branched chains), and more preferably 20 or fewer. The term "alkyl" as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like.

As used herein, the term "alkenyl" refers to unsaturated straight-chain, branched-chain or cyclic hydrocarbon radicals having at least one carbon-carbon double bond. C$_x$ alkenyl and C$_x$-C$_y$alkenyl are typically used where X and Y indicate the number of carbon atoms in the chain. For example, C$_2$-C$_6$ alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S. The term "alkenyl" as used throughout the specification, examples, and claims is intended to include both "unsubstituted alkenyls" and "substituted alkenyls", the latter of which refers to alkenyl moieties having one or more substituents replacing a hydrogen on one or more carbons of the hydrocarbon backbone As used herein, the term "alkynyl" refers to unsaturated hydrocarbon radicals having at least one carbon-carbon triple bond. C$_x$ alkynyl and C$_x$-C$_y$alkynyl are typically used where X and Y indicate the number of carbon atoms in the chain. For example, C$_2$-C$_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S. The term "alkynyl" as used throughout the specification, examples, and claims is intended to include both "unsubstituted alkynyls" and "substituted alkynyls", the latter of which refers to alkynyl moieties having one or more substituents replacing a hydrogen on one or more carbons of the hydrocarbon backbone The terms "alkylene," "alkenylene," and "alkynylene" refer to divalent alkyl, alkelyne, and alkynylene" radicals. Prefixes C$_x$ and C$_x$-C$_y$ are typically used where X and Y indicate the number of carbon atoms in the chain. For example, C$_1$-C$_6$alkylene includes methylene, (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). Each of the terms "alkylene," "alkenylene," and "alkynylene" is intended to include encompass unsubstituted and substituted variants, the latter of which refers to moieties having one or more substituents replacing a hydrogen on one or more carbons of the hydrocarbon backbone The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups. The term "heteroalkyl" as used throughout the specification, examples, and claims is intended to include both "unsubstituted heteroalkyls" and "substituted heteroalkyls", the latter of which refers to heteroalkyl moieties having one or more substituents replacing a hydrogen on one or more carbons of the hydrocarbon backbone The terms "vinyl ether", "divinyl ether", or "trivinyl ether," as used herein, refers to one, two, or three C$_2$-C$_8$ alkenyl groups bound to one or more oxygen atoms. Exemplary vinyl ethers of the present invention include B1, B2, B3, B4, B5, and B6. The terms "DVE" and "EVE" as used herein are interchangeable and refer to the same compound, diethylene glycol divinyl ether.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

As used herein, the term "aromatic" refers to a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

The term "aromatic ring system" is art-recognized and refers to a monocyclic, bicyclic or polycyclic hydrocarbon ring system, wherein at least one ring is aromatic.

The term "aryl" refers to an aromatic ring system, and includes monocyclic, bicyclic, or tricyclic fused aryl rings. C$_x$ aryl and C$_x$-C$_y$aryl are typically used where X and Y indicate the number of carbon atoms in the ring system. Exemplary aryl groups include, but are not limited to, benzyl, phenyl, naphthyl, anthracenyl, as well as ring systems where an aromatic carbon ring is fused to one or more non-aromatic carbon rings, such as indanyl, phthalimidyl, naphthimidyl, and tetrahydronaphthyl, and the like. In some embodiments, 1, 2, 3, or 4 hydrogen atoms of each ring can be substituted by a substituent.

The term "heteroaromatic ring system" is art-recognized and refers to monocyclic, bicyclic or polycyclic ring system wherein at least one ring is both aromatic and comprises a heteroatom. In certain instances, a ring which is aromatic and comprises a heteroatom contains 1, 2, 3, or 4 independently selected ring heteroatoms in such ring.

The term "heteroaryl" refers to a heteroaromatic ring system, and includes monocyclic, bicyclic, and tricyclic fused heteroaryl rings. Exemplary heteroaryls encompass 5-8 membered monocyclic, 8-12 membered fused bicyclic, or 11-14 membered fused tricyclic ring systems having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. C heteroaryl and C$_x$-C$_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "cyclic" means a moiety comprising a nonaromatic ring structure. Cyclic moieties can be saturated or partially unsaturated with one or more double or triple bonds. Cyclic moieties can also optionally comprise heteroatoms such as nitrogen, oxygen and sulfur. The nitrogen atoms can be optionally quaternerized or oxidized and the sulfur atoms can be optionally oxidized. Examples of cyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. Preferred cyclyls have from 3-10 carbon atoms in their ring structure, and more preferably have 5, 6 or 7 carbons in the ring structure. $_x$cyclyl and $C_x$-$C_y$cyclyl are typically used where X and Y indicate the number of carbon atoms in the ring system. The cyclyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

The terms "cyclylalkyl" or "cycloalkylalkyl" as used herein refer to an alkyl group substituted with a cyclyl group.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The term "heterocyclylalkyl" as used herein refers to an alkyl group substituted with a heterocyclyl group.

The terms "bicyclic" and "tricyclic" refers to fused, bridged, or joined by a single bond polycyclic ring assemblies.

As used herein, the terms "carbonyl", "oxo", or "keteo" refer to the radical —C(O)—. It is noted that the carbonyl radical can be further substituted with a variety of substituents to form different carbonyl groups including aldehyde (e.g., formyl), acids, acid halides, amides, esters, ketones, and the like. In some embodiments, the carbonyl group is substituted with a cyclyl or heterocyclyl. For example, the carbonyl group can be in the form of an ester or amide when connected to an oxygen or nitrogen atom of heterocyclyl.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —$NR^N$—, —$N^+(O^-)$=, —O—, —S— or —$S(O)_2$—, —$OS(O)_2$—, and —SS—, wherein $R^N$ is H or a further substituent.

The term "hydroxy" means the radical —OH.

The term "nitro" means the radical —$NO_2$.

Unless otherwise specified, each of the terms used herein may be "substituted" or "unsubstituted." As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, heterocyclylalkyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

As used herein, the term "amino" means —$NR^9R^{10}$, wherein each of $R^9$ and $R^{10}$ independently represent hydrogen, alkyl, alkenyl, —$(CH_2)_m$—$R^8$, or $R^9$ and $R^{10}$ taken together with the nitrogen atom to which they are attached complete a heterocyclyl having between 3 and 8 atoms in the ring structure. $R^8$ represents aryl, cycloalkyl, cycloalkenyl, heterocyclyl, and m is zero or an integer between 1 to 8. For example, representative amino groups include —$NH_2$, —$NHCH_3$, —$N(CH_3)_2$, —$NH(C_1$-$C_{10}$alkyl), —$N(C_1$-$C_{10}$alkyl)$_2$, and the like.

The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —$NH(C_1$-$C_{10}$alkyl), —$N(C_1$-$C_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The term "aryloxy" means —O-(aryl), such as —O-phenyl, —O-pyridinyl, and the like.

The term "arylalkyl" means -(alkyl)-(aryl), such as benzyl (i.e., —$CH_2$phenyl), —$CH_2$-pyrindinyl, and the like.

The term "cycloalkylalkylamino"-NH-(alkyl)-(cycloalkyl), such as —$NHCH_2$-cyclohexyl, and the like.

The term "silyl ether" as used herein refers to a silicon atom bound to one or more carbon-containing groups through an oxygen atom, such as $(CH_3)_3Si$—O—$R^4$, wherein $R^4$ is an alkyl, cycloalkyl, heterocyclyl, aryl, or heteroaryl group.

As used herein, the term "acetal" or "ketal" refers to the radical —$C(OR')_2$—$R^1$, wherein $R^1$ and R' may include alkyl, alkenyl, alkynyl, cycloalkyl, heterocyclyl, and the like. The term "polyacetal" refers to a compound or moiety containing one or more acetal or ketal groups or monomers.

As used herein, the term "polyethylene glycol" or "PEG" means an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG2050, PEG3350, PEG4000, PEG4600, PEG5000, PEG6000, PEG8000, PEG11000, PEG12000, PEG2000000 and any mixtures thereof. Polyethylene glycols used in the present invention are also referred to herein as e.g., P20, P30, P40, P60, P80, P100, P115, P200, and the like.

As used herein, the term "protecting group" refers to a chemical moiety that is used to mask a reactive chemical group, e.g., a hydroxyl, an amine, a carboxylic acid, a thiol, a ketone, or an aldehyde. In some embodiments, a protecting group may be selectively removed to reveal the reactive group using methods known in the art. Exemplary protecting groups include, but are not limited to, 9-fluorenylmethyl carbamate, t-butyl carbamate, benzyl carbamate, phthalimide, p-toluenesulfonamide, dimethyl acetal, 1,3-dioxane, 1,3,-dithiane, methyl ester, t-butyl ester, benzyl ester, 2-alkyl-1,3-oxazoline, acetonide, benzylidene acetal, t-butyl ether, methoxymethyl ether, tetrahydropyranyl ether, allyl ether, benzyl ether, t-butyldimethylsilyl ether, t-butyldiphenylsilyl ether, acetic acid ester, benzoic acid ester, or pivalic acid ester.

As used herein, the term "branching point" refers to a point in an individual monomer or repeating unit of a polymer (e.g., a polyacetal polymer described herein) in which another segment, region, or section of the polymer is attached. In some embodiments, an individual monomer or repeating unit of the polymer (e.g., the polyacetal polymer described herein) may comprise 0 (e.g., it is a linear polymer), 1 (e.g., it is a mono-branched monomer or subunit), 2 (e.g., it is a bi-branched monomer or subunit), 3, 4, 5, 6, 7, 8, or more branching points.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Synthesis of Vinyl Ether Monomers

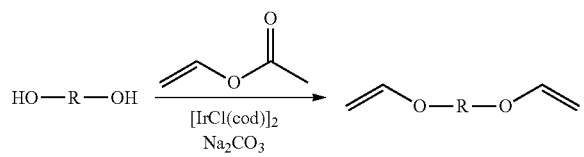

General Procedure:

Divinyl and trivinyl monomers were generated according to the protocol outlined in Okimoto, Y. et al (*J Am Chem Soc* (2002) 124:1590-1591) and shown in the scheme above. Briefly, a target alcohol (1 mmol) and vinyl acetate (2 mmol) were added to a solution of [IrCl(cod)]$_2$ (0.01 mmol) and Na$_2$CO$_3$ (0.6 mmol) in toluene under argon. The reaction mixture was stirred at 100° C. for 2 hours. After quenching with wet ether, the product was isolated by column chromatography (230-400 mesh silica gel, n-hexane). In the case of trivinyl ether synthesis, a triol was used in the place of a diol as the starting material. Exemplary vinyl ethers are shown in FIG. 1.

Example 2: Synthesis of Polyol Monomers

Synthesis of 3-Benzyloxymethyl-1,5-pentanediol (A12)

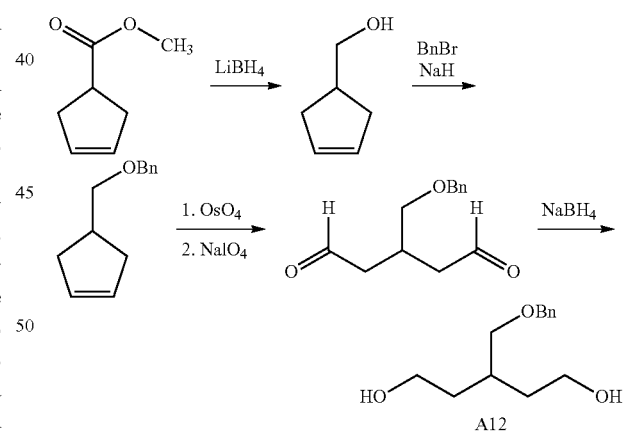

Step 1: Cyclopent-3-en-1-ylmethanol

To a solution of methyl cyclopent-3-ene-1-carboxylate (6 mmol) in anhydrous methanol (12 mmol) and toluene (35 mL) was added LiBH$_4$ (4.0 M solution in THF, 12.0 mmol). The resulting mixture was refluxed under N$_2$ for 6 hours, then cooled to ambient temperature and quenched with water, acidified with 3 M HCl, and diluted with DCM. The organic layer was washed with H$_2$O and brine, dried over Na$_2$SO$_4$, filtered, and concentrated under vacuum to provide the title compound.

Step 2: 4-[(Phenylmethoxy)methyl]-3-cyclopentene

To a solution of NaH (23 mmol) in anhydrous THF (15 mL) was added cyclopent-3-en-1-ylmethanol (20 mmol). After stirring at room temperature for 30 minutes, benzyl bromide (20 mmol) was added to the solution followed by the addition of a catalytic amount of tetrabutyl iodide. The reaction was stirred for 8 hours, after which the mixture was quenched with $H_2O$ and the organic layer was separated. The aqueous layer was extracted with ethyl ether, and the combined extracts were dried $Na_2SO_4$, filtered, concentrated, and purified on silica gel to afford the title compound as a colorless liquid.

Step 3: 3-((Benzyloxy)methyl)pentanedial

To a solution of 4-methylmorpholine N-oxide (2.89 mmol) and $OSO_4$ (0.013 mmol) in acetone and $H_2O$ at 0° C. was added 4-[(phenylmethoxy)methyl]-3-cyclopentene (2.22 mol). The reaction mixture was stirred for 18 h at room temperature, and then cooled to 0° C. and quenched with sat. aqueous $Na_2SO_3$. The reaction mixture was then stirred for an additional 3 hours while warming to room temperature. The acetone was removed by vacuum, and the mixture was cooled again to 0° C. and acidified to pH 2 through the addition of concentrated $H_2SO_4$. The reaction mixture was washed with EtOAc (3×), and the combined organic layers were dried with $MgSO_4$, filtered, and concentrated. The resulting residue was purified by flash chromatography, and then added to a solution of sodium periodate (1.91 mmol) in THF and $H_2O$. The reaction was stirred at room temperature for 3 hours, then filtered to provide the title compound ad an aqueous solution, which was used directly in the next step without further purification.

Step 4: 3-Benzyloxymethyl-1,5-pentanediol (A12)

An aqueous solution of 3-((benzyloxy)methyl)pentanedial (1.68 mmol) was slowly added to a suspension of $NaBH_4$ (3.70 mmol) in dry EtOH at 15° C. After stirring for 2 hours, the reaction was quenched with $H_2O$, then diluted with EtOAc. The aqueous layer was extracted with EtOAc, and the combined organic layers were washed with $H_2O$, and brine, dried over $MgSO_4$, filtered, and concentrated under vacuum to afford the title product as a colorless oil.

Synthesis of 3-((benzyloxy)methyl)-3-methylpentane-1,5-diol (A13)

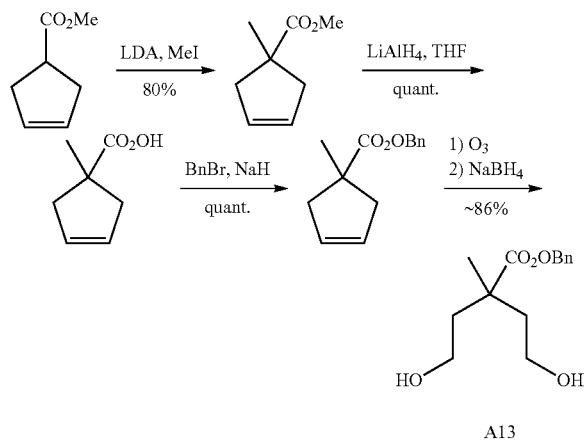

A13

Step 1: 1-Methylcyclopent-3-ene Carboxylate

To a solution of diisopropylamine (70 mL, 0.505 mol, 1.5 eq.) in THF (350 mL) at −78° C., n-BuLi (2.5M in hexanes, 205 mL, 0.505 mol, 1.5 eq.) was added slowly in about 20 minutes. The mixture was allowed to warm to 0° C. and stirred for 1 hour. The reaction mixture was cooled again to −78° C. and a solution of cyclopent-3-ene carboxylate (42.36 g, 0.336 mol, 1.0 eq.) in THF (350 mL) was added slowly. After stirring for 1 hour at −78° C., MeI (31.5 mL, 0.505 mol, 1.5 eq.) was added slowly over about 20 minutes. The reaction mixture was allowed to warm up to room temperature and stirred for 2 hours. The reaction was quenched with sat. aq. $NH_4Cl$, the aqueous layer was separated, and the aqueous layer was extracted with $Et_2O$ (3×700 mL). The combined organic layers were washed with 1N aq. HCl (800 mL) and brine (800 mL), dried over $Na_2SO_4$ and concentrated, yielding 37.40 g (80%) of the desired product.

Step 2: 1-Methylcyclopent-3-en-1-yl)methanol

To a suspension of $LiAlH_4$ (10.13 g, 0.267 mol, 1.0 eq.) in THF (500 mL) at 0° C., a solution of 1-methylcyclopent-3-ene carboxylate (37.40 g, 0.267 mol, 1.0 eq.) was added slowly. The reaction mixture was allowed to warm to room temperature and stirred for 4 hours. The reaction mixture was cooled to 0° C., diluted with TBME and water (11 mL) was slowly added. After 15 minutes, 150% aq. NaOH (11 mL) was added dropwise. After another 15 minutes, water (33 mL) was added and the reaction mixture was stirred for 15 minutes. The slurry was dried by addition of $MgSO_4$ and stirred for 15 minutes. The solids were filtered off and the filter cake was washed with TBME and EtOAc. The combined filtrates were evaporated to dryness, yielding 29.88 g (99.8%) of the desired product.

Step 3: (((1-Methylcyclopent-3-en-1-yl)methoxy)methyl)benzene

To a slurry of NaH (60% in mineral oil, 12.25 g, 0.306 mol, 1.15 eq.) in THF (150 mL), a solution of (1-methyl-cyclopent-3-en-1-yl)methanol (29.88 g, 0.266 mol, 1.0 eq.) in THF (25 mL) was added slowly. The reaction mixture was stirred for 30 minutes at room temperature and $Bu_4NI$ (4.92 g, 0.013 mol, 0.05 eq.) was added, followed by slow addition of BnBr (32 mL, 0.266 mol, 1.0 eq.). The resulting mixture was stirred overnight. The reaction mixture was cooled to 0° C. and water (120 mL) was added slowly. After 30 minutes, the layers were separated. The aqueous layer was extracted with $Et_2O$ (2×250 mL). The combined organic layers were dried over $Na_2SO_4$ and evaporated to dryness, yielding 60.25 g of crude product. This material was short plugged over silica (300 g), eluting with $CH_2Cl_2$.

Step 4: 3-((Benzyloxy)methyl)-3-methylpentane-1,5-diol

A solution of (((1-methylcyclopent-3-en-1-yl)methoxy)-methyl)benzene (54.98 g, 0.272 mol, 1.0 eq.) in $CH_2Cl_2$ (400 mL) and MeOH (100 mL) was cooled to −78° C. Some Sudan Red 7B was added as an indicator. Ozone was bubbled through the reaction mixture, while keeping the temperature below −40° C. When the indicator turned yellow the reaction was finished (also checked with TLC in $CH_2Cl_2$). $NaBH_4$ (22.62 g, 0.598 mol, 2.2 eq.) was added portion wise at −20° C. The resulting mixture was stirred for 2 hours. The reaction mixture was cooled again to 0° C. and water (750 mL) was added slowly. The layers were separated. The aqueous layer was extracted with $CH_2Cl_2$ (3×400 mL). The combined organic layers were washed with water (500 mL) and brine (500 mL), dried over $Na_2SO_4$ and concentrated to dryness, yielding 61.77 g of crude product. The crude product was portioned between acetonitrile (350 mL) and heptanes (250 mL). The acetonitrile layer was evaporated to dryness, yielding 55.83 g (86%) of the desired material.

Synthesis of 2,2'-((2-((2-Hydroxyethoxy)methyl)propane-1,3-diyl)bis(oxy))bis(ethan-1-ol) (A14)

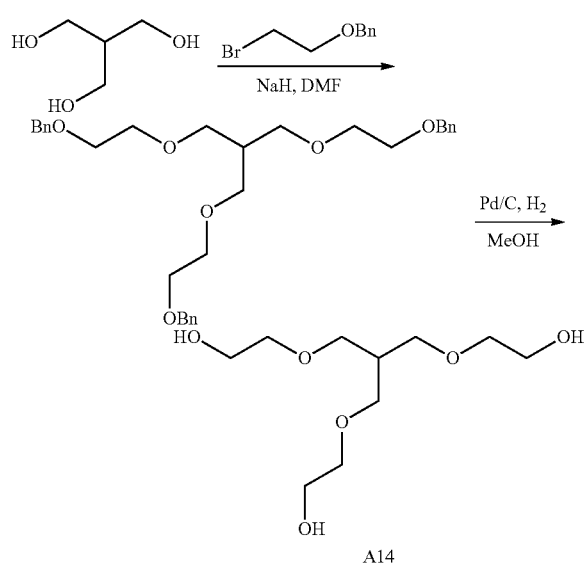

A14

Step 1: 7-((2-(Benzyloxy)ethoxy)methyl)-1,13-diphenyl-2,5,9,12-tetraoxatridecane To a 2000 mL round bottom flask was added 2-(hydroxymethyl)propane-1,3-diol (20.00 g, 188.47 mmol) and DMF (1.20 mL) DMF (1.20 mL). The mixture was cooled to 0° C. in an ice/brine bath, and then NaH (60.31 g, 1.51 mol) was added to the mixture in portions. After the addition, the mixture was allowed to warm to room temperature (~24° C.) and stirred for 1 hour, followed by the addition of 2-bromoethoxymethylbenzene (243.22 g, 1.13 mol) at 0° C. The resulting mixture was stirred at room temperature (~24° C.) for 16 hours, after which LCMS indicated that the desired product was produced. The mixture was quenched with saturated aqueous $NH_4Cl$ (2000 mL) and acidified to pH~6 with critic acid. The mixture was extracted with EtOAc (800 mL×3), and the combined EtOAc layers were dried over $Na_2SO_4$, filtered, concentrated under reduced pressure, and purified by column chromatography (PE/EtOAc from 100/0 to 90/10) to afford the title compound (45.00 g, 46.94% yield) as a colorless oil. $^1$H-NMR: 400 MHz $CDCl_3$: δ 7.24-7.39 (m, 15H) 4.56 (s, 6H) 3.60 (s, 12H) 3.54 (s, 3H) 3.55 (s, 3H);
LC-MS $(M+H)^+=531.0$ Step 2: 2,2'-((2-((2-Hydroxyethoxy)methyl)propane-1,3-diyl)bis(oxy))bis(ethan-1-ol) (A14)

To a 2000 mL round bottom flask was added 7-((2-(Benzyloxy)ethoxy)methyl)-1,13-diphenyl-2,5,9,12-tetraoxatridecane (90.00 g, 176.94 mmol) and MeOH (1.00 L), followed by dry 10% wt Pd/C (25.00 g), and the resulting mixture was degassed and purged with $H_2$ 3 times. The mixture was then stirred under $H_2$ at 50 psi at room temperature (~25° C.) for 48 hours, at which point LCMS showed that the starting material was completely consumed. The mixture was filtered through a celite pad and concentrated under reduced pressure to afford the title compound A14 (26.5 g, 63% yield) as a yellow oil. $^1$H NMR: 400 MHz $CDCl_3$ δ 3.70-3.84 (m, 6H) 3.55-3.68 (m, 12H) 2.66 (brs, 3H) 2.20-2.42 (m, 1H); LC-MS $(M+H)^+=239.1$ Synthesis of 7-((2-(benzyloxy)ethoxy)methyl)-7-methyl-1,13-diphenyl-2,5,9,12-tetraoxatridecane (A16)

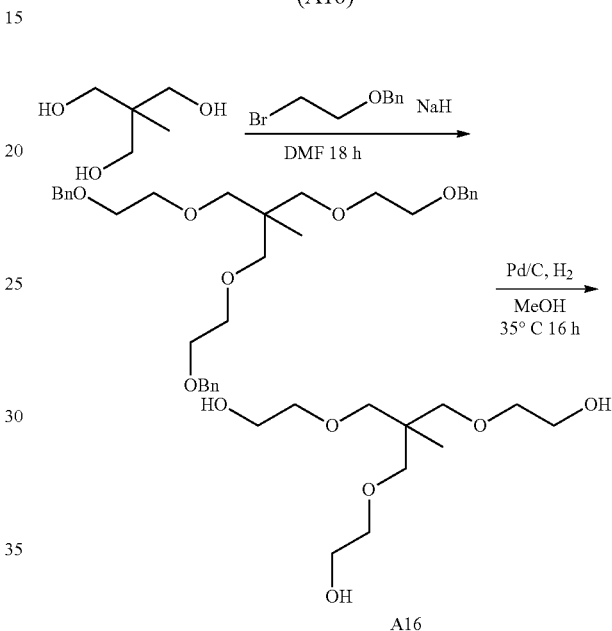

A16

Step 1: 7-((2-(benzyloxy)ethoxy)methyl)-7-methyl-1,13-diphenyl-2,5,9,12-tetraoxatridecane To a mixture of 2-(hydroxymethyl)-2-methylpropane-1,3-diol (25.00 g, 208.07 mmol) in DMF (750.00 mL) was added NaH (74.91 g, 1.87 mol) at 0° C., and the resulting mixture was stirred at 25° C. for 1 h under $N_2$ atmosphere. 2-Bromoethoxymethylbenzene (223.77 g, 1.04 mol, 164.54 mL) in DMF (250.00 mL) was then added dropwise at 25° C., and the mixture was stirred at 25° C. for an additional 17 hr until LC-MS analysis indicated the formation of the desired product. The reaction mixture was quenched by the addition of saturated $NH_4Cl$ aqueous solution to pH=7 then extracted with ethyl acetate (800 mL×5). The combined organic layers were washed with $H_2O$ (300 mL×3), dried over $Na_2SO_4$, filtered, concentrated under reduced pressure, and purified by column chromatography ($SiO_2$, petroleum ether/ethyl acetate=50/1 to 5:1) followed by flash C18 chromatography (eluent of 0~100% acetonitrile/water, 100 mL/min) to give the title compound (35 g, 99% purity, 31.9% yield) as a colorless oil. LCMS $(M+H)^+=545.0$.

Step 2: 2,2'-((2-((2-hydroxyethoxy)methyl)-2-methylpropane-1,3-diyl)bis(oxy))bis(ethan-1-ol) (A16)

A mixture of 7-((2-(benzyloxy)ethoxy)methyl)-7-methyl-1,13-diphenyl-2,5,9,12-tetraoxatridecane (35.00 g, 66.96 mmol) and Pd/C (8.00 g, 10% w/t) in MeOH (900.00 mL) was degassed and purged with Ar 3 times, and then the mixture was degassed and purged with $H_2$ (50 psi) 3 times and stirred at 35° C. for 16 hours, at which point LC-MS showed the reaction was complete. The reaction mixture was filtered through a celite pad and concentrated under reduced pressure to give the title compound (14.50 g, 57.47 mmol, 85.83% yield) as a colorless oil. $^1$H-NMR 400 MHz $CDCl_3$ δ 3.67 (d, J=3.76 Hz, 6H), 3.50-3.53 (m, 6H), 3.37 (s, 6H), 3.24 (br. s., 3H), 0.90 (s, 3H). LCMS (M+H)$^+$=253.1.

Synthesis of 2,2'-((2-ethyl-2-((2-hydroxyethoxy)methy)propane-1,3-diyl)bis(oxy))bis(ethan-1-ol) (A15)

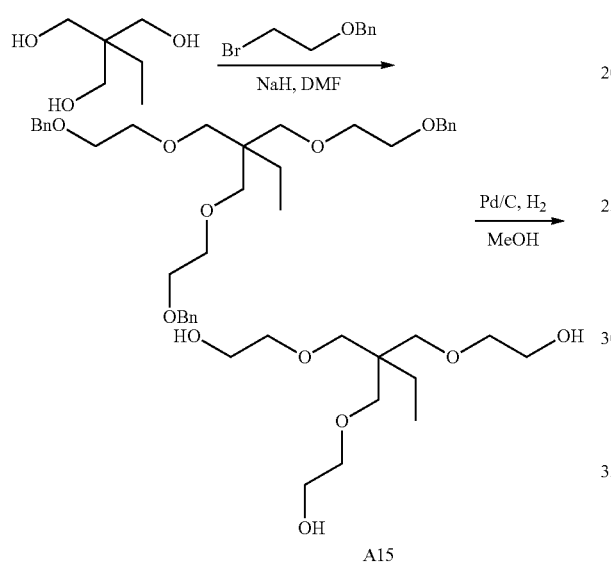

A15

Step 1: 7-((2-(benzyloxy)ethoxy)methyl)-7-ethyl-1,13-diphenyl-2,5,9,12-tetraoxatridecane To a 1000 mL round bottom flask was added 2-ethyl-2-(hydroxymethyl)propane-1,3-diol (50.00 g, 372.66 mmol) and DMF (3.00 L), and the mixture was cooled to 0° C. in an ice/brine bath. NaH (119.25 g, 2.98 mol) was added to the mixture in portions, and after addition, the mixture was allowed to warm to room temperature (~20° C.) and stirred for 1 hour. 2-bromoethoxymethylbenzene (480.93 g, 2.24 mol) was added to the mixture at 0° C., and the resulting mixture was stirred at room temperature (~20° C.) for an additional 16 hours until LCMS analysis indicated formation of the desired product. The mixture was quenched with saturated aqueous $NH_4Cl$ (4000 mL) and acidified to pH-6 with critic acid. The mixture was then extracted with EtOAc (1500 mL×3), and the combined EtOAc layers were dried over $Na_2SO_4$, filtered, concentrated under reduced pressure, purified by column chromatography (PE/EtOAc from 100/0 to 90/10), then purified by flash silica gel chromatography (ISCO®; 200 g SepaFlash® C16 Flash Column, Eluent of 0~80% MeCN/H2O @ 100 mL/min) to afford the title compound (72.00 g, 36.00% yield) as a colorless oil. $^1$H NMR: 400 MHz $CDCl_3$ δ 7.21-7.46 (m, 8H), 4.59 (s, 3H), 3.63 (s, 6H), 3.42 (s, 3H), 1.39-1.58 (m, 1H), 0.91 (t, J=7.53 Hz, 2H). LCMS (M+H)$^+$=537.0.

Step 2: 2,2'-((2-ethyl-2-((2-hydroxyethoxy)methyl)propane-1,3-diyl)bis(ox))bis(ethan-1-ol) (A15)

To a 2 L bottle was added 7-((2-(benzyloxy)ethoxy)methyl)-7-ethyl-1,13-diphenyl-2,5,9,12-tetraoxatridecane (75.00 g, 139.74 mmol) and MeOH (1.00 L), followed by dry 10% wt Pd/C (15.00 g), and the resulting mixture was degassed and purged with $H_2$ 3 times. The mixture was then stirred under 50 Psi $H_2$ at room temperature (~25° C.) for and additional 36 hours, at which point TLC showed starting material was consumed completely. The mixture was filtered through a celite pad and concentrated under reduced pressure to afford the title compound (26.5 g, 71% yield) as a yellow oil. $^1$H NMR: 400 MHz $CDCl_3$ δ 3.63-3.74 (m, 6H), 3.48-3.59 (m, 6H), 3.36-3.43 (m, 6H), 3.07 (brs, 2H), 1.39 (q, J=7.36 Hz, 2H), 0.74-0.89 (m, 3H). LCMS (M+H)$^+$=267.2

Synthesis of 2-ethyl-2-((2-hydroxyacetoxy)methyl)propane-1,3-diyl-bis(2-hydroxyacetate) (A18)

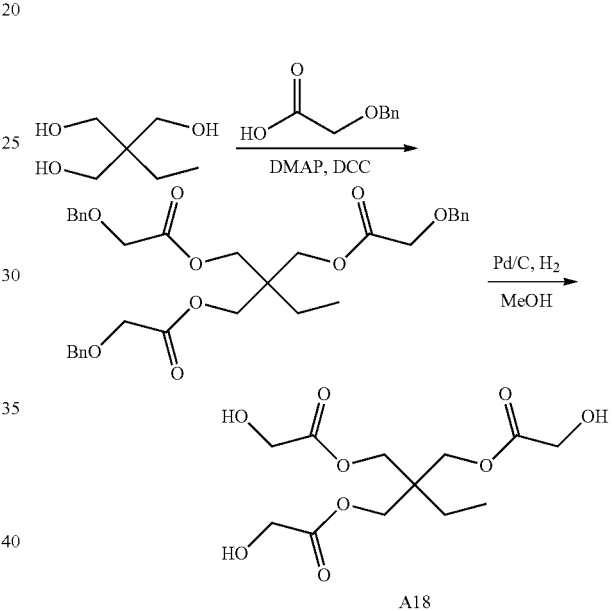

A18

Step 1: 2-((2-(benzyloxy)acetoxy)methyl)-2-ethyl-propane-1,3-diyl-bis(2-(benzyloxy)acetate)

A mixture of 2-ethyl-2-(hydroxymethyl)propane-1,3-diol (10.0 g, 74 mmol), 2-(benzyloxy)acetic acid (61.9 g, 373 mmol), and DMAP (5.5 g, 45 mmol) was dissolved in DCM (100 mL). DCC (76.9 g, 373 mmol) was then added in one portion and the reaction mixture was allowed to stir at 20-25° C. for 16 h until TLC (petroleum ether/ethyl acetate=5/1, $R_f$=0.3) showed the reaction was complete. The reaction mixture was filtered and the resulting filtrate was concentrated and purified by column chromatography on silica gel (100-200 mesh size) using petroleum ether/EtOAc (20:1-10:1) as eluent to give the title compound (43.0 g, 99% yield) as a colourless oil. $^1$H NMR: 400 MHz $CDCl_3$ δ 7.36-7.31 (m, 15H), 4.62 (s, 6H), 4.11-4.10 (m, 12H), 1.46 (q, J=7.2 Hz, 2H), 0.89 (t, J=7.2 Hz, 3H). LCMS (M+H)$^+$=601.0.

Step 2: 2-ethyl-2-((2-hydroxyacetoxy)methyl)propane-1,3-diyl-bis(2-hydroxyacetate) (A18)

To a solution of 2-((2-(benzyloxy)acetoxy)methyl)-2-ethylpropane-1,3-diyl-bis(2-(benzyloxy)acetate) (43 g, 74.3 mmol) in MeOH (500 mL) was added Pd/C (5.0 g, 41.7 mmol) under $N_2$, and the suspension was degassed under vacuum and purged with $H_2$ several times. The mixture was stirred under $H_2$ (48 psi) at 20-25° C. for 24 hours, at which point TLC (petroleum ether/ethyl acetate=5/1, $R_f$=0.1) showed the reaction was complete. The reaction mixture was filtered through a celite pad and the resulting filtrate was concentrated by evaporating under vacuum to give the title compound (23.5 g, 99% yield) as a white solid. $^1$H NMR: 400 MHz DMSO-$d_6$ δ 5.36 (s, 3H), 403 (s, 12H), 1.41 (q, J=7.6 Hz, 2H), 0.83 (t, J=7.6 Hz, 3H). LCMS (M+H)$^+$ =326.1.

Synthesis of 2-((((2-hydroxyethoxy)carbonyl)oxy) methyl)propane-1,3-diyl bis(2-hydroxyethyl) bis (carbonate) (A28)

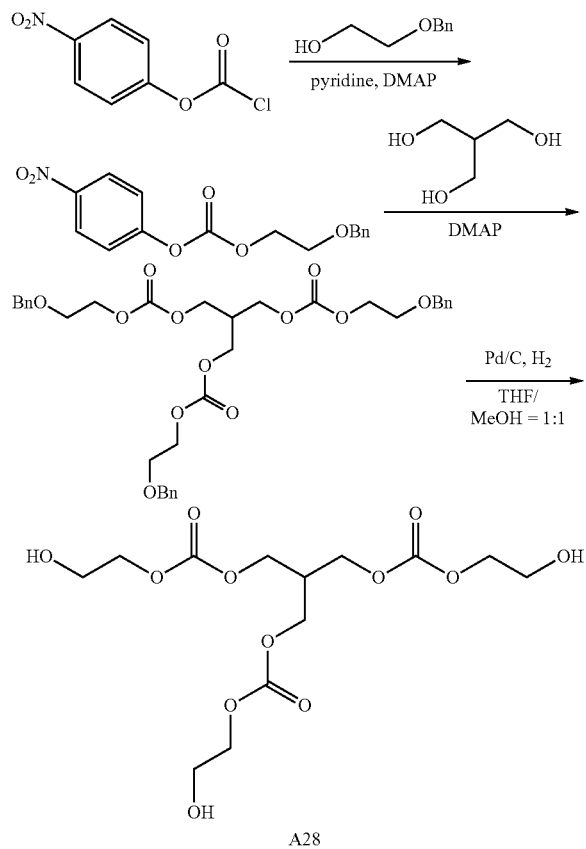

A28

Step 1: 2-(benzyloxy)ethyl (4-nitrophenyl) carbonate

To a solution of 4-nitrophenyl carbonochloridate (133 g, 659.8 mmol) in DCM (2.5 L) was added pyridine (104 g, 1.3 mol, 106 mL) and DMAP (24.2 g, 198 mmol) at 20° C. The mixture was then added to a solution of 2-benzyloxyethanol (100 g, 659 mmol, 94 mL) in DCM (500 mL) dropwise over the course of 30 min at 0° C., and then stirred at 20° C. for 6 hr, after which the mixture was concentrated under reduced pressure to give the title compound (300 g, crude) as a brown oil. LCMS (M+H)$^+$=352.9.

Step 2: 2-((((2-(benzyloxy)ethoxy)carbonyl)oxy) methyl)propane-1,3-diyl bis(2-(benzyloxy)ethyl) bis(carbonate)

A solution of 2-(benzyloxy)ethyl (4-nitrophenyl) carbonate (300 g, crude), 2-(hydroxymethyl)propane-1,3-diol (14 g, 132.3 mmol), and DMAP (138 g, 1.1 mol) in DMF (2 L) was stirred at 20° C. for 16 hr. DMF was removed under reduced pressure and the residue was diluted with EtOAc (2 L); washed with successive quantities of 0.5M HCl (500 mL), saturated aqueous $Na_2CO_3$ (500 mL×5), $H_2O$ (500 mL), and brine (500 mL); dried over anhydrous $Na_2SO_4$; concentrated under reduced pressure; and purified by silica gel column (PE:EtOAc=1:1) to give the crude product, which was further purified by flash C18 chromatography (ISCO®; 360 g SepaFlash® C18 Flash Column, Eluent of 0~100% H2O/MeCN ethergradient) to afford the title compound (80.00 g, crude) as a colorless oil. $^1$H NMR: 400 MHz CDCl$_3$ δ 7.20-7.57 (m, 15H), 4.53-4.64 (m, 6H), 4.28-4.36 (m, 6H), 4.25 (d, J=5.77 Hz, 6H), 3.64-3.75 (m, 6H), 2.50 (m, 1H). LCMS (M+H)$^+$=663.0

Step 3: 2-((((2-hydroxyethoxy)carbonyl)oxy) methyl)propane-1,3-diyl bis(2-hydroxyethyl) bis (carbonate) (A28)

A mixture of 2-((((2-(benzyloxy)ethoxy)carbonyl)oxy) methyl)propane-1,3-diyl bis(2-(benzyloxy)ethyl) bis(carbonate) (40 g, 62.4 mmol) and Pd/C (10 g, 62.4 mmol, 10% w/t) in MeOH (200 mL) and THF (200 mL) was stirred at 20° C. under $H_2$ (50 psi) for 24 hr. The mixture was then filtered and the filtrate was added to another batch of Pd/C (10 g, 62.4 mmol, 10% w/t) at 20° C. and stirred under $H_2$ (50 psi) for an additional 24 hr. The mixture was filtered through a celite pad, and the filtrate was concentrated under reduced pressure to give the title compound (20 g, 54 mmol, 86% yield) as a white solid. $^1$H NMR: (CDCl$_3$, 400 MHz) δ 4.27 (d, J=5.77 Hz, 6H), 4.19-4.25 (m, 6H), 3.73-3.80 (m, 6H), 2.52 (m, 1H). LCMS (M+H)$^+$=388.1

Synthesis of 3,3-dimethylpentane-1,5-diol (A31)

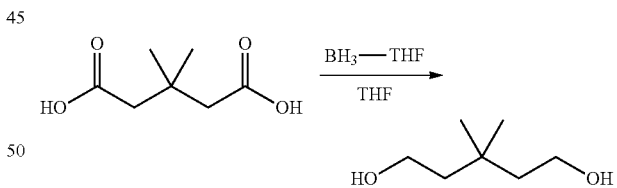

Synthesis of A31 was carried according to the scheme described above. $^1$H NMR: 400 MHz CDCl$_3$ δ 3.60-3.70 (m, 4H), 1.55 (m, 4H), 0.9 (s, 6H). LCMS (M+H)$^+$=133.

Example 3: Synthesis of Polyacetal Polymers

General Scheme 1

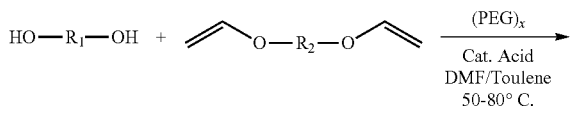

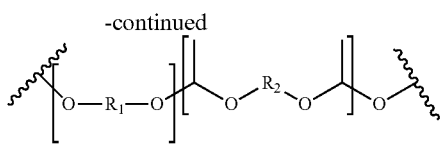

A round bottom flask was charged with PEG1000 and/or PEG400, pTSA hydrate, and anhydrous toluene (120 mL) and stirred at 140° C. for 4 h, during which 100 mL of the toluene was azeotropically distilled. The mixture was then cooled to 50° C., and a solution of an exemplary polyol, $R_1(OH)_2$, in anhydrous DMF followed by an exemplary vinyl ether, $R_2(OCHCH_2)_2$, was added. After the reaction was complete, the mixture was quenched with trimethylamine (1 mL) and concentrated, and the residue was triturated with hexanes (1 L), diethyl ether (500 mL), petroleum ether (300 mL), and MBTE (300 mL). The mixture was cooled to 0° C. for several hours between each step. The residue was the dried under vacuum and characterized by gel permeation chromatography (GPC) to determine the average molecular weight of the resulting polymer (Mn). Prior to reaction, all reagents were dried under vacuum (<0.2 torr) or freshly distilled. The synthesis of exemplary polymers produced using this protocol is summarized in Table 1A, and $^1$H-NMR data from selected polymers is summarized in Table 1B. Unless otherwise noted, all chemical shifts are reported as δ ppm from TMS in $CDCl_3$.

TABLE 1A

Exemplary polyacetal polymers produced via Scheme 1

| Example No. | VE Amount (g) | Conditions | OH:Vinyl Ratio | Catalyst | Yield (%) | $M_n$ of Polymer (Da) |
|---|---|---|---|---|---|---|
| 3A | 5.0 B1 | 0.58 equiv A2<br>0.28 equiv PEG 400<br>0.14 equiv PEG 1000<br>75° C. | 1:1 | pTSA (0.003 equiv) | 45 | 7,278 |
| 3B | 5.0 B1 | 0.6 equiv A3<br>0.28 equiv PEG 400<br>0.14 equiv PEG 1000<br>75° C. | 1:1 | pTSA (0.003 equiv) | 28 | 7,955 |
| 3C | 5.0 B1 | 0.6 equiv A3<br>0.28 equiv PEG 400<br>0.14 equiv PEG 1000<br>75° C., 22 h | 1:1 | pTSA (0.003 equiv) | 45 | 10,574 |
| 3D | 5.0 B1 | 0.6 equiv A3<br>0.28 equiv PEG 400<br>0.14 equiv PEG 1000<br>75° C., 2 h | 1:1 | pTSA (0.003 equiv) | 58 | 16,853 |
| 3E | 2.0 B1 | 0.5 equiv A7<br>0.5 equiv PEG 1000<br>50° C., 2 h | 1.25:1 | pTSA (0.008 equiv) | 71 | 6,609 |
| 3F | 1.15 B1 | 0.27 equiv A16<br>0.5 equiv PEG 1000<br>50° C., 2 h | 1:1 | pTSA (0.01 equiv) | 75 | 9,356 |
| 3G | 2.78 B1 | 0.22 equiv A16<br>0.33 equiv PEG 400<br>0.33 equiv PEG 1000<br>50° C., 4 h | 1:1 | pTSA (0.009 equiv) | 55 | 22,619 |
| 3H | 2.3 B1 | 0.28 equiv A16<br>0.59 equiv PEG 1000<br>50° C., 20 h | 1:1 | pTSA (0.01 equiv) | 71 | 8,422 |
| 3I | 2.17 B1 | 0.27 equiv A15<br>0.59 equiv PEG 1000<br>50° C., 17 h | 1:1 | pTSA (0.01 equiv) | 71 | 8,179 |
| 3J | 3.76 B1 | 0.27 equiv A16<br>0.5 equiv PEG 400<br>50° C., 18 h | 1:1 | pTSA (0.006 equiv) | 70 | 10,508 |
| 3K | 2.44 B1 | 0.27 equiv A14<br>0.59 equiv PEG 1000<br>50° C., 4 h | 1:1 | pTSA (0.009 equiv) | 75 | 7,795 |
| 3L | 3.71 B1 | 0.07 equiv A30<br>0.89 equiv PEG 1000<br>50° C., 4 h | 1:1 | pTSA (0.006 equiv) | 83 | 18,814 |
| 3M | 2.77 B1 | 0.22 equiv A16<br>0.33 equiv PEG 400<br>0.33 equiv PEG 1000<br>50° C., 4 h | 1:1 | pTSA (0.006 equiv) | 63 | 13,617 |
| 3N | 4.41 B1 | 0.07 equiv A16<br>0.89 equiv PEG 1000<br>50° C., 4 h | 1:1 | pTSA (0.006 equiv) | 88 | 31,478 |
| 3O | 2.97 B1 | 0.07 equiv A28<br>0.89 equiv PEG 1000<br>50° C., 4 h | 1:1 | pTSA (0.006 equiv) | 83 | 12,461 |
| 3P | 1.42 B1 | 0.19 equiv A30<br>0.89 equiv PEG 1000<br>50° C., 4 h | 1:1 | pTSA (0.015 equiv) | 76 | 8,093 |

TABLE 1A-continued

Exemplary polyacetal polymers produced via Scheme 1

| Example No. | VE Amount (g) | Conditions | OH:Vinyl Ratio | Catalyst | Yield (%) | $M_n$ of Polymer (Da) |
|---|---|---|---|---|---|---|
| 3Q | 4.69 B1 | 0.07 equiv A14<br>0.89 equiv PEG 1000<br>50° C., 4 h | 1:1 | pTSA (0.006 equiv) | 83 | 14,927 |
| 3R | 5.0 B1 | 1.1 equiv PEG 1000<br>50° C., 2 h | 1.1:1 | pTSA (0.006 equiv) | 84 | 12,670 |
| 3S | 3.7 B1 | 0.07 equiv A30<br>0.89 equiv PEG 1000<br>50° C., 20 h | 1:1 | pTSA (0.007 equiv) | 86 | 11,264 |
| 3T | 1.7 B1 | 0.18 equiv A16<br>0.72 equiv PEG 1000<br>50° C., 4 h | 1:1 | pTSA (0.013 equiv) | 69 | 6,878 |
| 3U | 4.2 B1 | 0.07 equiv A15<br>0.89 equiv PEG 1000<br>50° C., 4 h | 1:1 | pTSA (0.005 equiv) | 86 | 8,001 |
| 3V | 2.0 B1 | 0.86 equiv A15<br>0.28 equiv PEG 400<br>0.24 equiv PEG 1000<br>50° C., 2 h | 1.8:1 | pTSA (0.006 equiv) | 3 | 2,838 |
| 3W | 2.0 B1 | 0.86 equiv A16<br>0.28 equiv PEG 400<br>0.24 equiv PEG 1000<br>50° C., 3 h | 1.8:1 | pTSA (0.007 equiv) | 15 | 3,219 |
| 3X | 2.0 B1 | 0.86 equiv A16<br>0.52 equiv PEG 1000<br>50° C., 3 h | 1.8:1 | pTSA (0.0088 equiv) | 66 | 3,511 |
| 3Y | 0.6 B1 | 0.5 equiv A16<br>0.25 equiv PEG 1000<br>50° C., 4 h | 1:1 | pTSA (0.018 equiv) | 34 | 3,685 |
| 3Z | 4.0 B3 | 0.07 equiv A16<br>0.89 equiv PEG 1000<br>50° C., 4 h | 1:1 | pTSA (0.005 equiv) | 79 | 11,904 |
| 3AA | 1.6 B3 | 0.18 equiv A16<br>0.72 equiv PEG 1000<br>50° C., 4 h | 1:1 | pTSA (0.0088 equiv) | 66 | 12,557 |
| 3AB | 5.55 B5 | 0.07 equiv A16<br>0.89 equiv PEG 1000<br>50° C., 4 h | 1:1 | pTSA (0.0088 equiv) | 55 | 25,363 |
| 3AC | 2.2 B5 | 0.18 equiv A16<br>0.72 equiv PEG 1000<br>50° C., 4 h | 1:1 | pTSA (0.009 equiv) | 78 | 15,965 |
| 3AD | 2.0 B1 | 1.09 equiv PEG 1000 | 1.09:1 | pTSA (0.005 equiv) | 87 | 10,917 |

TABLE 1B

1H NMR data for selected exemplary polyacetal polymers produced via Scheme 1

| Example No. | 1H NMR (δ ppm) |
|---|---|
| 3A | 4.8 (q, 1.0), 3.5-3.8 (m, 34.6), 1.3 (d, 3) |
| 3B | 4.6-4.9 (m, 2.0), 3.5-3.8 (m, 52.4), 3.4-3.5 (m), 1.5-1.7 (m, 1.6), 1.4-1.5 (m, 1.0), 1.3-1.4 (m, 6.2), 0.9-1.0 (m, 1.7) |
| 3E | 4.7-4.9 (m, 3.7), 3.9 (m, 1.3), 3.5-3.9 (m, 131.6), 3.4 (m, 1.3), 2.1-2.4 (br m, 2.2), 1.3-1.4 (m, 12.8), 1.2 (m, 1.0) |
| 3F | 4.8 (m, 2.1), 3.5-3.8 (m, 99.0), 3.3-3.4 (m, 2.0), 1.3-1.4 (m, 6.5), 0.9-1.0 (m, 1.0) |
| 3G | 4.8-4.9 (m, 2.7), 3.5-3.8 (m, 88.5), 3.3-3.4 (m, 1.9), 2.2 (s, 1.7), 1.3-1.4 (m, 8.2), 0.9-1.0 (m, 1) |
| 3H | 4.8-4.9 (m, 2.0), 3.5-3.8 (m, 94.3), 3.3-3.4 (m, 2.0), 2.0 (s, 3.4), 1.3-1.4 (m, 6.3), 0.9-1.0 (m, 1.0) |
| 3I | 4.8-4.9 (m, 2.8), 3.5-3.8 (m, 129.9), 3.2-3.4 (m, 2.8), 1.7 (s, 5.5), 1.4 (m, 1.0), 1.3-1.4 (m, 8.5), 0.8-0.9 (m, 1.4) |
| 3J | 4.8-4.9 (m, 3.3), 3.6-3.8 (m, 67.6), 3.3-3.4 (m, 1.8), 1.3 (m, 10.0), 0.9-1.0 (m, 1) |
| 3K | 4.8-4.9 (m, 10.5), 3.4-3.9 (m, 526.3), 2.7 (m, |

TABLE 1B-continued

1H NMR data for selected exemplary polyacetal polymers produced via Scheme 1

| Example No. | 1H NMR (δ ppm) |
|---|---|
| 3L | 1.8), 2.5 (m, 1.0), 2.2 (m, 1.7), 1.7 (s, 22.8), 1.3-1.4 (m, 31.9) 4.8-4.9 (m, 9.8), 4.1-4.2 (m, 4.3), 3.6-3.8 (m, 500.0), 3.5 (m, 2.5), 1.9 (br s, 20.1), 1.4-1.5 (m, 29.5), 0.9 (m, 1.0) |
| 3M | 4.8-4.9 (m, 2.7), 3.3-3.8 (2m, 84.0), 2.0 (s, 2.4), 1.3 (m, 9.2), 0.9-1.0 (m, 1.0) |
| 3N | 4.8-4.9 (m, 9.4), 3.6-3.8 (m, 454.5), 3.5 (m, 4.2), 3.3 (m, 2.0), 2.0 (s, 6.8), 1.3 (m, 28.3), 0.9-1.0 (m, 1.0) |
| 3Q | 4.8-4.9 (q, 1.7), 3.5-3.8 (m, 84.0), 3.5 (m, 1.0), 2.3 (s, 2.7), 1.3 (d, 5.1) |
| 3Z | 4.6-4.9 (m, 8.8), 4.9 (m, 3.1), 3.5-3.8 (m, 416.7), 3.3-3.5 (m, 12.9), 1.8 (s, 11.3), 1.6-1.7 (br m, 16.5), 1.3-1.4 (m, 25.9), 0.9-1.0 (m, 1.0) |
| 3AA | 4.6-4.9 (m, 3.6), 3.9 (m, 1), 3.5-3.8 (m, 156.3), 3.3-3.5 (2m, 6.5), 2.1 (s, 3.0), 1.6-1.7 (br s, 5.8), 1.3 (m, 10.8), 0.9-1.0 (m, 1.2) |
| 3AB | 4.6-4.9 (m, 3.9), 4.9 (m, 1.0), 3.5-3.8 (m, 161.3), 3.1-3.5 (m, 10.4), 1.8-1.9 (m, 13.0), 1.3-1.6 (m, 6.8), 1.2-1.3 (m, 6.5), 0.8-1.1 (m, 6.5) |

General Scheme 2

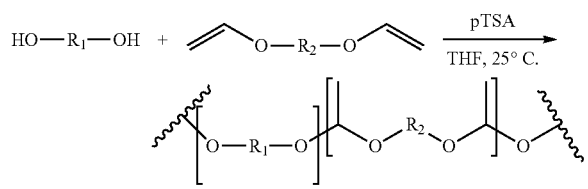

A round bottom flask was charged with p-TSA and dried under high vacuum (8-11 torr) at 80° C. for 3-5 hours. Nitrogen gas was then applied to purge the system, and anhydrous THF was then added via syringe. A solution of an exemplary polyol, R₁(OH)₂, in anhydrous THF was prepared in anaerobic conditions and added to the flask, followed by an exemplary vinyl ether, R₂(OCHCH₂)₂, in THF. The reaction was stirred at room temperature for 5-30 hours, quenched with TEA, and then diluted with THF prior to transfer to a hexane solution (20 mL). The hexane solution was carefully decanted, and the remaining viscous liquid was dissolved in THF (2 mL) and precipitated in hexanes again. A separate layer formed at the bottom of the hexane solution after several hours. The hexane solution was again carefully decanted and the bottom layer was dried under high vacuum overnight and characterized by ¹H-NMR and GPC. The synthesis of exemplary polymers produced through this method is summarized in Table 1C.

TABLE 1C

Exemplary polyacetal polymers produced via Scheme 2

| Example No. | VE Amount (g) | Conditions | OH:Vinyl Ratio | Catalyst | $M_n$ of Polymer (Da) |
|---|---|---|---|---|---|
| 3AE | 2.0 B1 | 1.0 equiv A3 25° C., 24 h | 1:1 | pTSA (1.0 equiv) | 11,100 |
| 3AF | 2.0 B1 | 1.0 equiv A3 25° C., 24 h | 1:1 | pTSA (0.005 equiv) | 16,400 |
| 3AG | 1.79 B3 | 1.0 equiv A3 25° C., 24 h | 1:1 | pTSA (0.005 equiv) | 15,400 |
| 3AH | 1.79 B3 | 1.0 equiv A31 25° C., 19 h | 1:1 | pTSA (0.005 equiv) | 9,400 |

Example 4: Conjugation of ARBs to Polyacetal Polymers

General Scheme

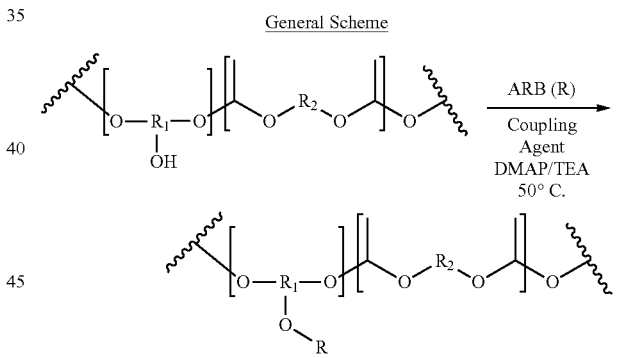

A polyacetal polymer (5.0 g) was added to a to a round bottom flask, followed by the addition of an ARB, a coupling agent, and DMAP (0.4 equiv). TEA was then added, and the reaction was allowed to stir at 50° C. under a nitrogen atmosphere. The reaction was monitored by HPLC, and upon completion (roughly at 16.5 hours), the mixture was concentrated and the residue was dissolved in MeOH (20 mL). The solution was then added slowly to a solution of MTBE (100 mL) to form a turbid mixture, which turned clear upon warming to 40° C. The solution was cooled in a freezer for two hours to precipitate the product, which was filtered, rinsed with MTBE (50 mL), and dried under vacuum to afford the polyacetal polymer conjugate in good yield. The resulting conjugate was characterized by GPC and ¹H-NMR. Table 2 summarizes the conjugation reactions carried out for several exemplary polyacetal polymers with valsartan.

TABLE 2

Exemplary conjugates

| Example No. | Valsartan Amount (g) | Conditions | Yield (%) | Conjugate MW (Da) |
|---|---|---|---|---|
| 4A | 0.54 | 9.4 wt Polymer 3D<br>4.1 equiv DIC<br>4.3 equiv TEA<br>50° C., 18 h | 74 | 15,836 |
| 4B | 0.41 | 4.9 wt Polymer 3F<br>3.9 equiv DIC<br>3.8 equiv TEA<br>50° C., 18.5 h | 76 | 9,583 |
| 4C | 0.44 | 4.9 wt Polymer 3H<br>4 equiv DIC<br>4 equiv TEA<br>50° C., 17 h | 59 | 11,940 |
| 4D | 0.75 | 6.7 wt Polymer 3L<br>4 equiv DIC<br>4 equiv TEA<br>50° C., 18 h | 73 | 13,212 |
| 4E | 1.93 | 5.2 wt Polymer 3R<br>4 equiv DIC<br>4 equiv TEA<br>50° C., 8 h | 46 | 12,995 |
| 4F | 0.5 | 5 wt Polymer 3R<br>2 equiv CDI<br>50° C., 10 h | 78 | 10,536 |
| 4G | 0.5 | 5 wt Polymer 3R<br>2 equiv DIC<br>2 equiv TEA<br>50° C., 10 h | 67 | 9,664 |
| 4H | 1.0 | 5 wt Polymer 3N<br>4 equiv DIC<br>4 equiv TEA<br>50° C., 10.5 h | 75 | 32,649 |
| 4I | 0.4 | 5 wt Polymer 3AA<br>4 equiv DIC<br>4 equiv TEA<br>50° C., 17 h | 60 | 22,920 |
| 4J | 0.4 | 5 wt Polymer 3Z<br>4 equiv DIC<br>4 equiv TEA<br>50° C., 18 h | 70 | 19,852 |
| 4K | 0.75 | 6.7 wt Polymer 3AB<br>4 equiv DIC<br>4 equiv TEA<br>50° C., 18 h | 45 | 34,828 |
| 4L | 0.75 | 6.7 wt Polymer 3AB<br>4 equiv DIC<br>4 equiv TEA<br>50° C., 18 h | 72 | 22,331 |
| 4M | 0.75 | 6.5 wt Polymer 3AD<br>4 equiv DIC<br>4 equiv TEA<br>50° C., 18 h | 82 | 13,715 |

Example 5: Characterization of Polyacetal Polymers and Conjugates

Determination of Aqueous Solubility

In order to investigate the water solubility of exemplary polyacetal polymers of the present invention, each polyacetal polymer produced was dissolved in three volumes of water. The resulting solutions were mixed and examined visually to assess solubility. The polymers produced in Examples 3Z and 3AB were partially soluble in water. All other polymers tested were soluble in water.

Determination of Melting Point

The melting points of exemplary polymers and conjugates of the present invention were determined through differential scanning calorimetry (DSC) analysis using a Mettler Toledo DSC instrument. Table 3 summarizes the resulting melting points ($T_m$).

TABLE 3

Melting point determination of exemplary polymers and conjugates

| Example No. | Tm (° C.) |
|---|---|
| 3L | 37.0 |
| 3N | 37.6 |
| 3O | 37.6 |
| 3R | 37.9 |
| 3Z | 40.3 |
| 3AA | 39.6 |
| 4H | 35.4 |
| 4M | 35.3 |

Example 6: Synthesis of ARB-Linked Monoester

Valsartan-TME

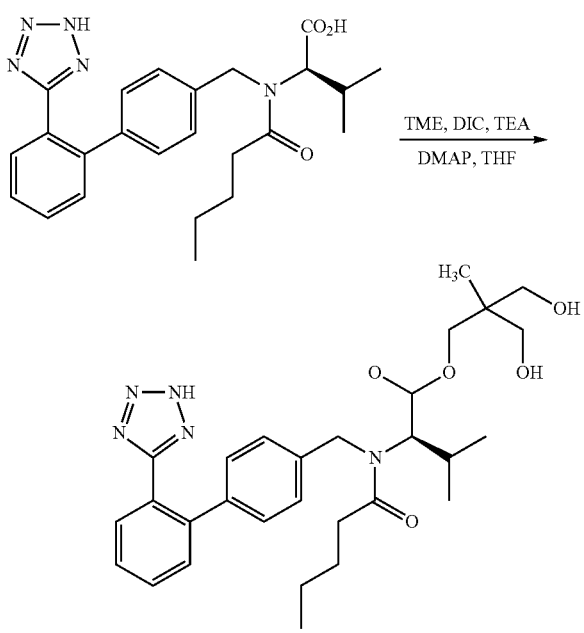

In order to produce an ARB-linked monoester for polymer synthesis, an ARB (valsartan, shown above, 5 g) was incubated with a polyol, TME (8.30 g) and N,N'-diisopropylcarbodiimide (DIC, 2.16 g) in the presence DMAP (0.56 g) in THF (250 mL). Triethylamine (TEA, 2.21 g) was added and the mixture was stirred for 21 hours at 23° C., after which HPLC analysis indicated that the reaction was complete. The solvents were removed by evaporation, and the residue was partitioned between DCM and water. The DCM layer was washed with 2 N HCl, dried over Na2SO4, filtered, and concentrated, and purified by silica gel chromatography to provide the valsartan-TME monoester. LC-MS: [M+]=537.65.

3-Candesartan-oxymethyl-3-methyl-1,5-pentanediol (Can-OMP)

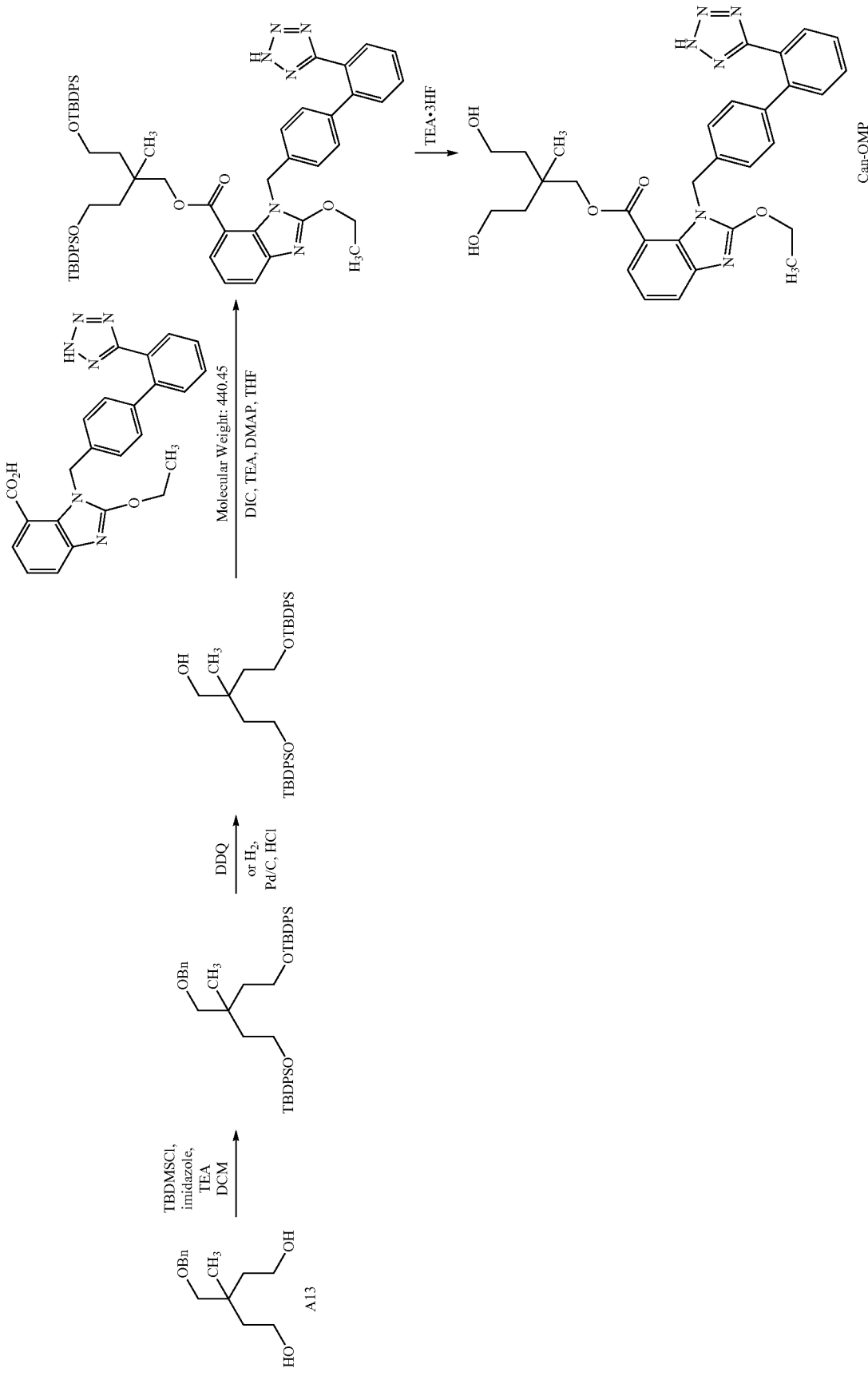

The TBDPS protection of A13 was performed using TBDP-SCl (2.2 eq), imidazole (2.5 eq) in DCM (experiment SKG-T-185). The reaction was complete in 4 hours. The mixture was washed with saturated sodium carbonate and was purified on a silica column to afford 15 g of product in 98% yield. The product (78) was reacted with DDQ (3 equivalents) in refluxing DCM (20 vol) and water (2 vol) for several hours. The IPC by proton NMR showed the reaction progressed to about 90% conversion. The batch was filtered, washed with water (2×10 vol), and then with half saturated sodium thiosulfate solution (3 vol). It was purified by column chromatography to afford 6 g of the protected product. The coupling of the protected product (1 eq) with candesartan (1.1 eq) was conducted on a 7 g scale. The reaction was performed with 3 equivalents of EDC.HCl, 1 eq of DMAP, and 3 eq of DIPEA in DCM (10 vol) at room temperature. It was then washed with 0.5N HCl and extracted with ethyl acetate (3×200 mL). The organic phase was washed with saturated sodium carbonate and was purified by silica column to afford 5.7 g of the protected Can-OMP. Deprotection was performed with TEA.3HF (4 eq) in THF (10 vol) to afford 2.4 g of Can-OMP. Can-OMP was initially isolated as a TEA salt. It was re-dissolved in DCM (50 mL) and was washed with 0.1 N HCl solution to isolate the free acid.

Example 7: Synthesis of Polyacetal Polymers from Agent-Linked Monomers

A polyacetal polymer was prepared using Can-OMP and 1,4-butanediol divinyl ether (BDDVE, B3). The polymerization was performed using BDDVE (1 eq), Can-OMP (0.6 eq), and PEG2050 (0.4 eq). Can-OMP and PEG were dried together with THF distillation down to ~120 ppm of water. The catalyst, pTSA, was azeotropically dried separately with THF (KF=80 ppm). BDDVE was added to the reaction containing Can-OMP monomer and PEG followed by pTSA (5 mol %). The reaction was quenched with TEA and precipitated with MeOH/MTBE to afford 1.8 g of product (Can-DPC) in 79% yield. The polymer had Mn=14772.

The Can-DPC stock in NMP at 30 mg/mL was made by weighing 150.6 mg of Can-DPC and adding 5.02 mL of NMP. 150 mL of a solution of 300 mOsm isotonic aqueous mannitol was prepared using distilled water. The solution was sterile filtered using a 0.22 μm vacuum filter bottle. 60 mL of this aqueous mannitol solution was added to each of two 150 mL beakers with a stir bar. The beakers were placed on a stir plate and set to the maximum speed possible without forming bubbles in the mannitol solution. 2 mL of the Can-DPC stock solution was added dropwise to each beaker into the mannitol solution using a 1 mL pipet at a rate of 1 mL/min (2 min total addition time) to produce a nanoparticle suspension. The 150 mL beakers with the particle suspension were cured by continuing to mix at the same speed on the stir plate for 20 min. The particle suspension was concentrated by spin filtration at 4° C. and 1800 rcf in a centrifuge for 60 min. The retentate suspension that did not pass through the filter unit was combined, and the nanoparticle suspension was sterile filtered using a 0.22 μm syringe filter. This filtered solution is the final Can-nanoparticle (Can-DPC) drug product. Nanoparticle size measured by dynamic light scattering to resulted in a z-average of 19 nm with a PDI=0.13. The final drug product was stored at 4° C. protected from light and dosed within 18-30 hrs after nanoparticle production.

Example 8: Determination of Conjugate-Agent Loading Level

In order to determine the kinetics of the release of the agents from exemplary conjugates, the conjugate prepared in Example 4M was dissolved in THF (6 vol) and 6 N HCl was added to provide a solution with a pH<1. After acidification, LiOH was added and the mixture was stirred and monitored at various time points by HPLC for the presence of free valsartan. As summarized in Table 4, nearly all of the coupled valsartan was released from the conjugate within the experimental time period.

TABLE 4

ARB release from an exemplary conjugate

| Example No. | Conditions | Time (h) | Valsartan HPLC Area (%) |
|---|---|---|---|
| 8A | 6 vol THF | 1.0 | 0.9 |
| | 6 vol 6N HCl for 2 h | 2.5 | 3.7 |
| | 1 equiv NaOH after 2 h | 21 | 40.4 |
| | 1 equiv LiOH after 28 h | 27 | 50.5 |
| | 20° C. for 26 h | 41.5 | 98.1 |
| | 40° C. for 15.5 h | | |
| 8B | 6 vol THF | 2.33 | 0.9 |
| | 6 vol 6N HCl for 1 h | 4.5 | 3.7 |
| | 2 equiv LiOH for 19.5 h | 20.5 | 40.4 |
| | 20° C. | | |
| 8C | 6 vol THF | 1 | 36.4 |
| | 6 vol 6N HCl for 1 h | 4 | 80.5 |
| | 2 equiv LiOH for 19.5 h | | |
| | 10 vol H$_2$O, 40° C. | | |

The conjugate prepared in Example 7 (Can-DPC) was also analyzed for overall drug-loading level. 5 mg of Can-DPC was incubated for 1 hr in 1 mL of 1N HCl at room temperature, followed by 20 hrs in 1N LiOH at room temperature. The total candesartan concentration was measure by LC/MS/MS and the candesartan drug loading was determined to be 7.1% wt/wt.

Example 9: Conjugation of Agents to pH-Sensitive Linkers

In this example, conjugation of agents to pH-sensitive linkers is demonstrated. The chemotherapeutic irinotecan was used as the model drug for conjugation. Irinotecan was conjugated to cis-aconitic anhydride in the presence of DMAP and TEA and purified by HPLC as demonstrated in FIG. 3. The activated irinotecan was then incubated in acidic buffer and analyzed by HPLC to indicate release of intact irinotecan (FIG. 3).

Figure 4A:
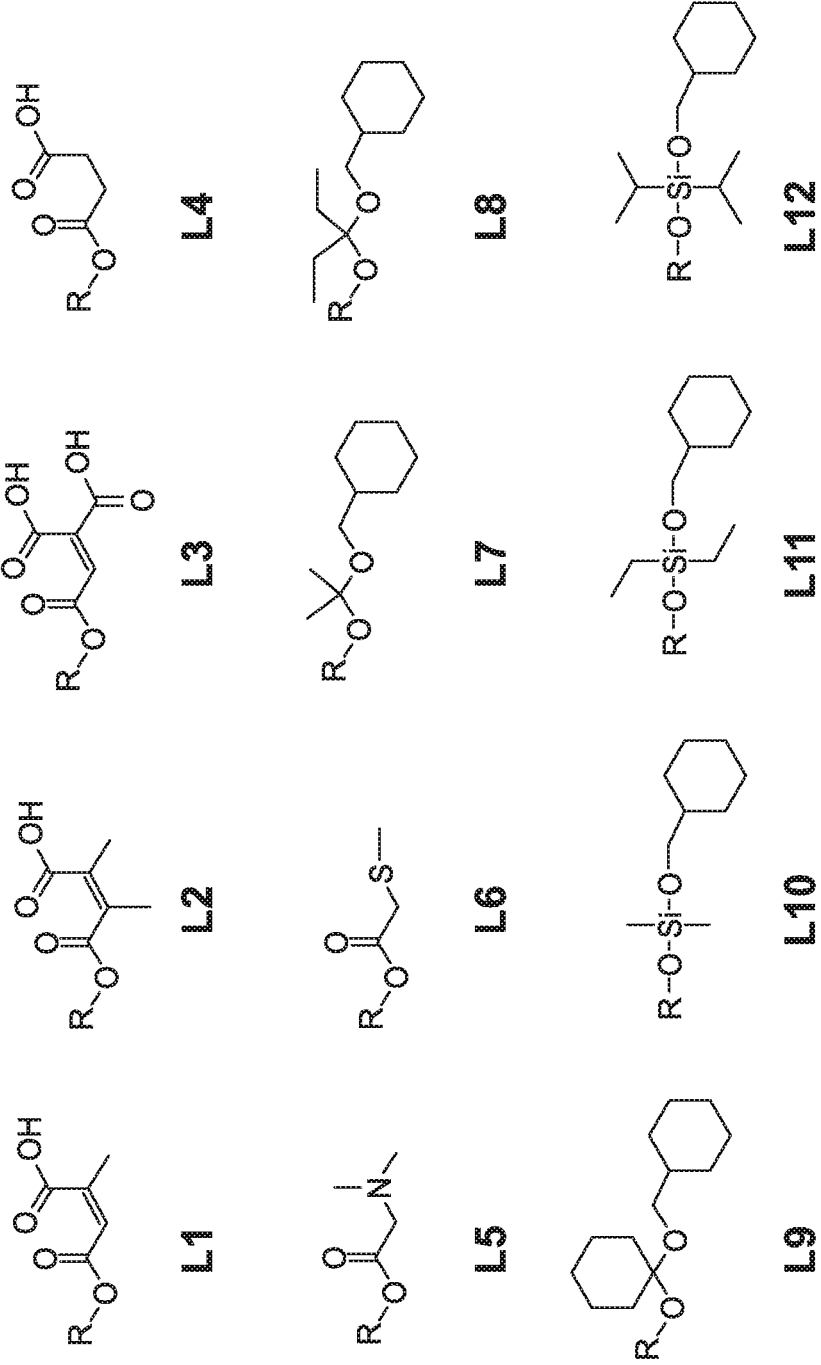
FIGS. 4A, 4B, and 4C show the selection of pH-sensitive linkers for conjugates for irinotecan and gemcitabine.
Figure 4C:
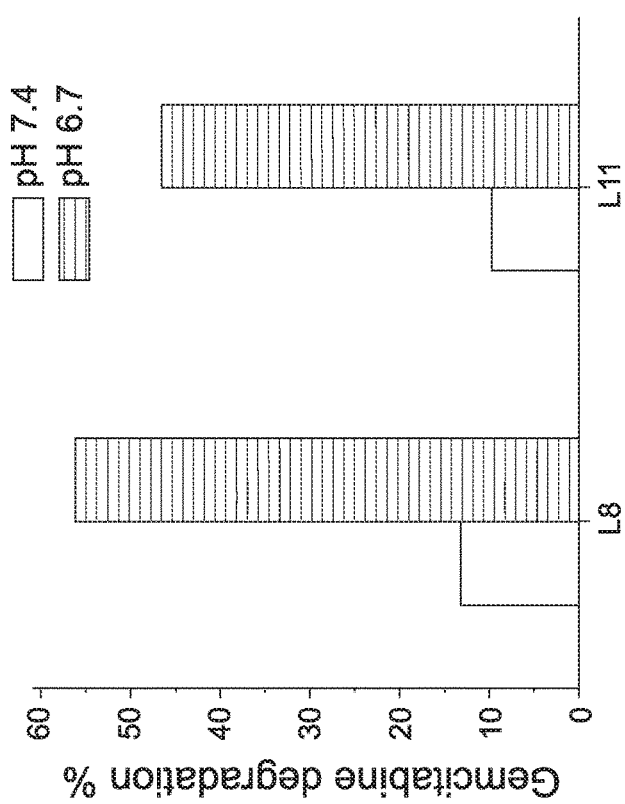
Figure 4B:
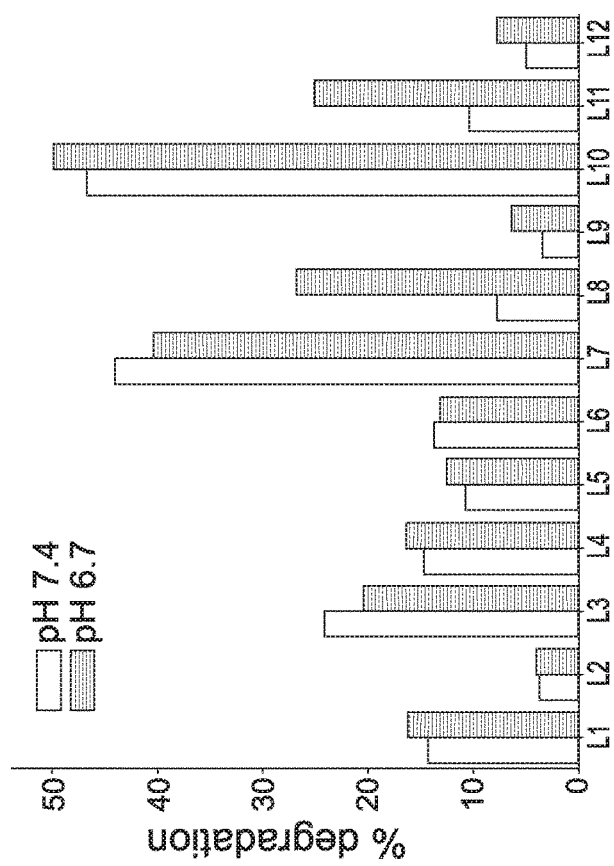

A panel of pH-sensitive linkers L1 through L12 was then conjugated to either gemcitabine or irinotecan using the conjugation protocol outlined above on a 1-5 mg scale (FIG. 4). During the conjugation reaction, excess cyclohexane methanol was added to block the active chloride or methoxyl group and deactivate unreacted coupling agents. Solvents were then removed by evaporation after filtration, and the resulting activated agents were purified by HPLC. The activated agents were then dissolved in buffers (pH 7.4 and 6.7) and subjected to degradation analysis by HPLC. The results of this analysis are summarized in FIG. 4. For activated gemcitabine prodrugs, linker L8 and L11 exhibited the largest degradation ratio (degradation % at pH=6.7 versus % at pH=7.4) within 12 hours (FIG. 12C; degradation ratio at different pH was 3.44 for L8 and 2.39 for L11).

Example 10: Formation of Nanoparticles

To prepare polymeric nanoparticles, the conjugates are dissolved in THF at 20 mg/mL and dried overnight. PBS solution is then added into the dried film, and the solution is ultra-sonicated in cold water bath for 5 minutes. Alternately, the conjugate dissolved in dimethylformamide (DMF, 500 µL, 10 mg/mL) is carefully pipetted into water (15 mL) under rapid stirring conditions. The resulting nanoparticles are then collected following ultrafiltration (7 min, 3000 rpm, Ultracel membrane with 40,000 NMWL, Millipore, Billerica, Mass.) and washed with water to remove organic solvent.

Nanoparticles may be nanoprecipitated from DMF solution to PBS buffer to assemble to obtain particles. The sizes of nanoparticles can be characterized by HPLC or dynamic light scattering, and will be expected to range in size from 10 nm-100 nm. To determine release kinetics of ARB from nano-ARB, 1 mL of nano-ARB solution (1 mg/mL) can be added into Spectrum Float-A-Lyzer dialysis device (Fisher Scientific Inc., MWCO 8-10 k) and dialyzed against different 500 mL of phosphate buffers at different pHs (pH 7.4, 6.9, 6.7, 6.3, 6.0) at 37° C. with gentle stirring. At designated time points, the remaining nano-ARB solution in dialysis device can be sampled by analytical HPLC (n=5) to assess the rate of release of the ARB.

Example 11: Synthesis of Nanoparticles Comprising a Targeting Moiety and an Agent Tissue targeting moieties can also be conjugated to the polymer-drug conjugate for the assembly of a nanoparticle that delivers the drug to a specific tissue or disease site. Mannose-6-phosphate is an example of a tissue-specific moiety for targeting to the liver, specifically, to hepatic stellate cells.

Figure 5A:
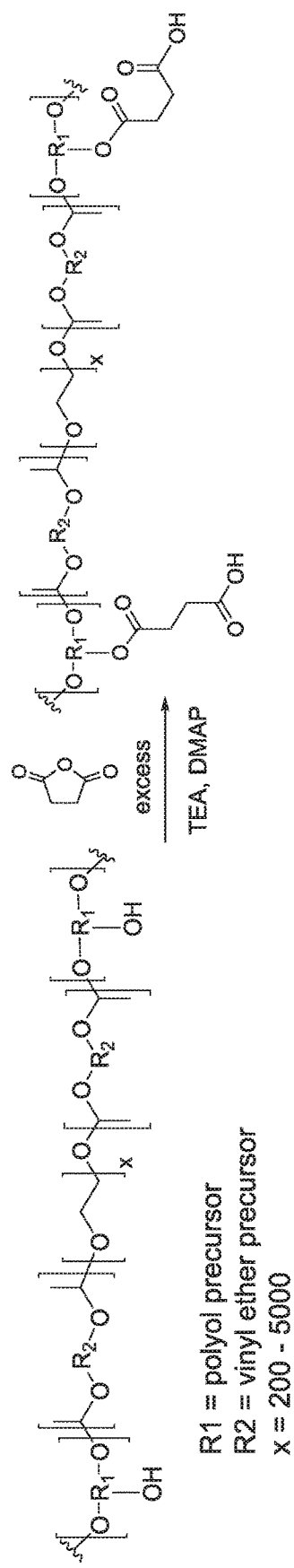
FIGS. 5A, 5B, 5C, and 5D show a schematic representation of the synthesis of an exemplary conjugate comprising a polyacetal polymer linked to the ARB losartan and a targeting moiety, mannose-6-phosphate.
Figure 5B:
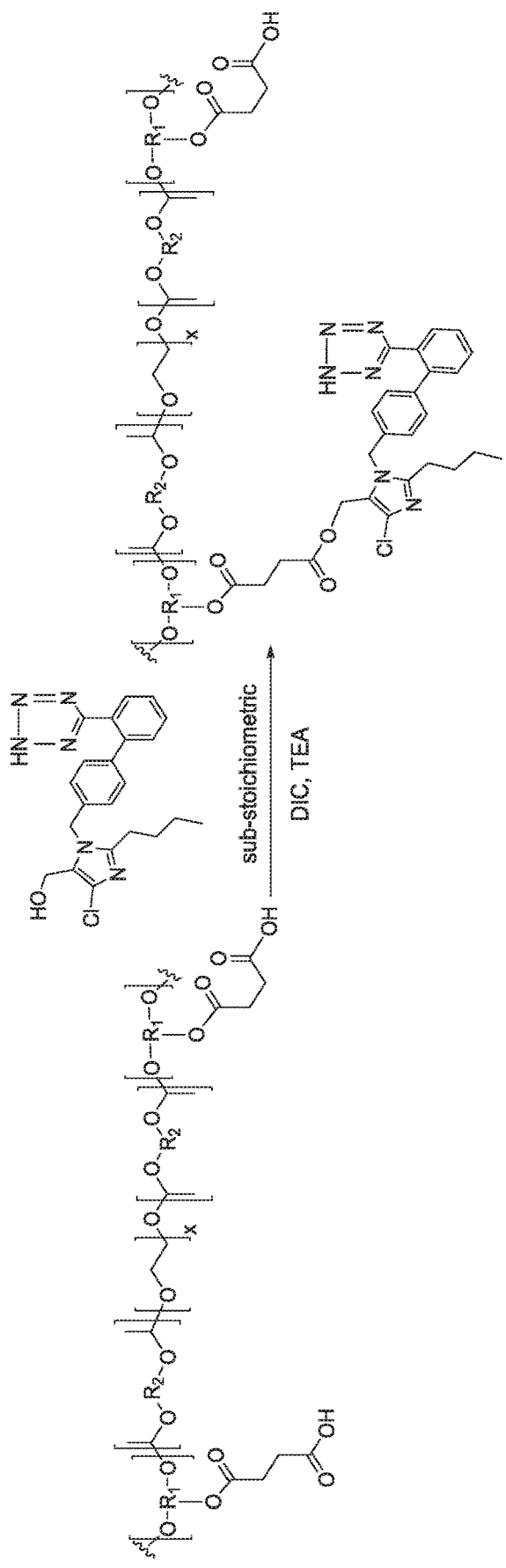
Figure 5C:
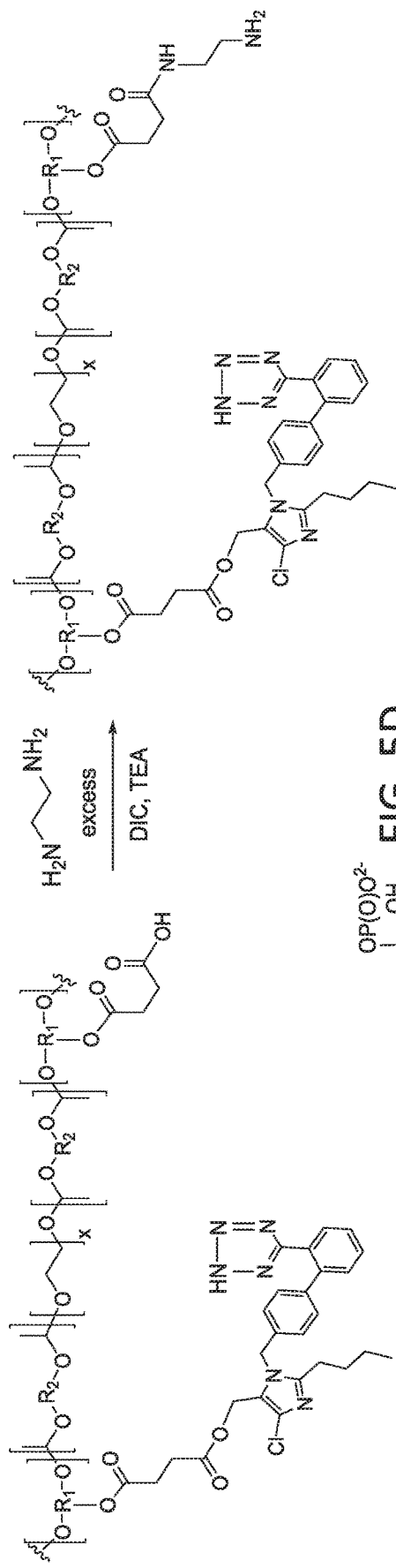
Figure 5D:
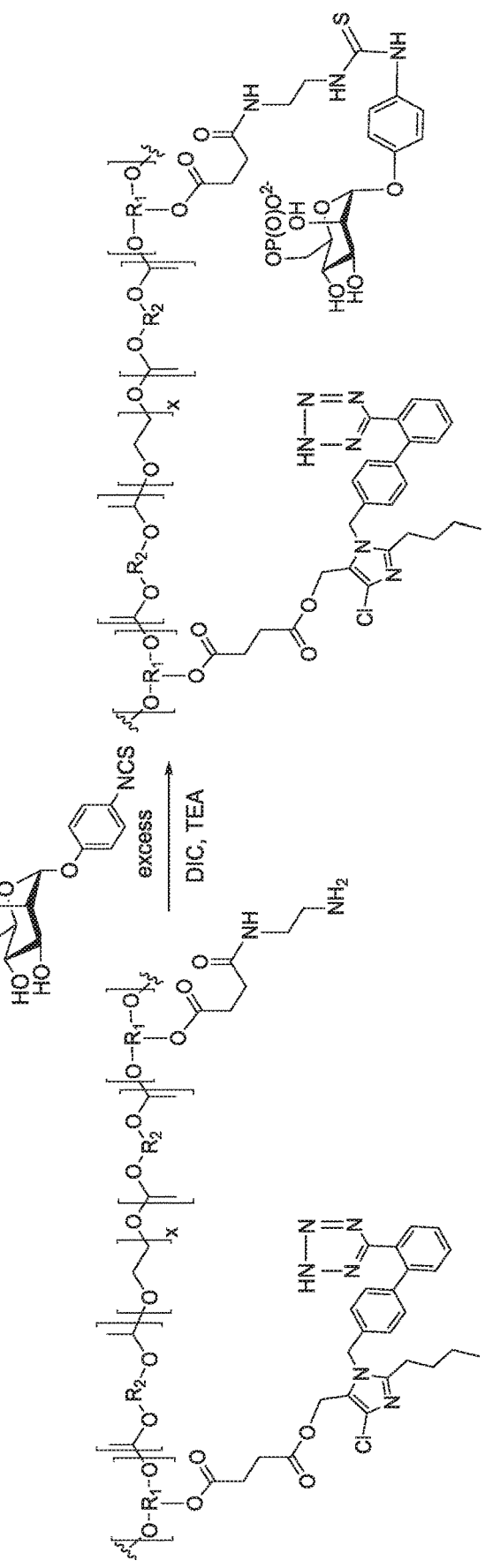

Nanoparticles containing an ARB (e.g., losartan) and a targeting moiety (e.g., M6P) can be prepared by the method outlined in FIGS. 5A-5D. In this example, polyacetal polymers are first prepared according to the protocol presented in Example 4. After synthesis, the polyacetal polymers can be treated with an activating agent such as succinic anhydride in the presence of TEA and DMAP in THF to provide activated polymers, in which the free hydroxyl groups on the polymer backbone are modified with a carboxylic acid (FIG. 5A). In order to attach an ARB, a sub-stoichiometric quantity of an ARB such as losartan is conjugated to polymer using DIC, TEA and DMAP in THF to afford a polymer-ARB conjugate (e.g., as shown in FIG. 5B). The remaining carboxylate groups on the polymer can then be further modified with a linker, such as ethylenediamine (e.g., as shown in FIG. 5C), followed by incubation with M6P-isothiocyanate to provide the M6P-ARB-polymer (FIG. 5D).

After synthesis, a nanoparticle may be prepared from the resulting conjugate by adding the conjugate dropwise into water, causing the conjugate to self-assemble into nanoparticles. The extra, or free, M6P-isothiocynate, losartan, and other reagents will be removed by extensive centrifugal wash.

Example 12: Obesity-Induced Inflammation and Desmoplasia Promote Pancreatic Cancer Progression and Resistance to Chemotherapy Pancreatic cancer is the fourth-leading cause of cancer-associated death worldwide (1), with an overall five-year rate survival of 7% (2). The risk for pancreatic cancer is about 50% greater for individuals with obesity (body mass index>30), those with increased abdominal adiposity (3). Excess body weight also worsens the already dismal outcome of pancreatic ductal adenocarcinoma (PDAC) patients by increasing the relative risk of cancer mortality by more than 2-fold (McWilliams, R. R., et al. *Cancer* 116, 5054-5062 (2010); Li, D., et al. *JAMA: the journal of the American Medical Association* 301, 2553-2562 (2009); Bracci, P. M. *Mol Carcinog* 51, 53-63 (2012); and Smits, M. M. & van Geenen, E. J. *Nature reviews. Gastroenterology & hepatology* 8, 169-177 (2011)). As a consequence of the obesity pandemic, with nearly 70% of the United States adult population being either overweight or obese (Ogden, C. L., et al. *JAMA: the journal of the American Medical Association* 311, 806-814 (2014)), the majority of PDAC patients have excess weight at diagnosis. Understanding why obesity confers worse prognosis might lead to novel treatments and enhance the outcome of current therapies.

PDAC is a highly desmoplastic cancer characterized by an excessive extracellular matrix and activated PSCs (12, 13). Extracellular matrix components and PSCs promote direct prosurvival and pro-migratory signals to cancer cells (14-16). In addition, desmoplasia increases solid stress and stiffness (17, 18), and these mechanical changes create a formidable barrier to drug delivery. Solid stress compresses blood vessels and causes heterogeneous tumor perfusion, which results in poorer treatment outcomes (14, 19-22). Importantly, obesity itself is a pro-desmoplastic condition. In fact, the hypoxia that results from abnormal blood vessels and decreased blood flow due to the rapidly expanding adipose tissue in obesity causes adipocyte dysfunction and immune cell recruitment (23-25). The latter leads to cytokine production, inflammation, and ultimately fibrosis (23-25). In particular, obesity significantly enhances angiotensin II type-1 receptor (AT1) signaling in adipose tissues, a major pro-fibrotic pathway that becomes activated in a pro-inflammatory environment (26, 27). The condition leading to hypoxia also results in acidosis in general even if they may not colocalize in microscale (Ref #1). Hence, pH-sensitive and/or polyacetal polymer and/or linker conjugates should be able to deliver drugs selectively to adipose tissues in obesity. Such agents can effectively block chemokines, cytokines and growth factors derived from dysfunctional adipocytes and accumulated immune cells. For example, targeting angiogenic factor signaling (e.g., vascular endothelial growth factor) can inhibit body weight gain without altering food intake (Refs #2, 3). Obesity also leads to accumulation of fat in the normal pancreas (steatosis), which generates a similar inflammatory process with increased expression of cytokines, extracellular matrix remodeling, and fibrosis (9, 28-30). Importantly, PDACs in obese mice and patients also have an increased adipocyte content (31, 32). Of clinical relevance, the interaction of cancer cells with adipocytes—both in the form of accumulation of fat in pancreas and when cancer cells at the expanding edge of the tumor invade the local adipose tissue—is associated with worse outcomes in PDAC patients (9, 33). However, the role of adipocytes during obesity-induced PDAC progression remains unclear. Ref #1: G. Helmlinger, F. Yuan, M. Dellian and R. K. Jain, "Interstitial pH and pO2 Gradients in Solid Tumors In Vivo: High-Resolution Measurements Reveal a Lack of Correlation," *Nature Medicine*, 3:177-182 (1997). Ref #2: Fukumura D, Ushiyama A, Duda D G, Xu L, Tam J, Chattejee V K K, Garkavtsev I, Jain R K. Paracrine regulation of angiogenesis and adipocyte differentiation during in vivo adipogenesis. Circulation Res, 2003; 93:e88-

97. Ref #3: Tam J, Duda D G, Perentes J Y, Quadri R S, Fukumura D, Jain R K. Antiangiogenic treatment by blockade of VEGFR2 in local-tissue derived endothelial cells can reduce diet-induced fat tissue expansion. PLoS One, 2009; 4:e4974. PMCID: PMC2659427.

The experiments in this example test whether obesity-associated fatty infiltration in PDACs generates a proinflammatory and pro-fibrotic microenvironment in tumors, which promotes growth and progression, and hinders the delivery and efficacy of chemotherapy in human samples as well as in clinically relevant orthotopic and genetically engineered mouse models (GEMMs) of PDAC. To reduce the obesity-instigated desmoplastic reaction in PDAC, AT1 knockout (Agtr1a−/−) mice and a clinically-approved AT1 inhibitor (AT1 blocker, ARB) were used, which was previously found to reduce PSC activation, matrix expression, and solid stress in PDAC (21). In addition, it was determined whether the obesity exacerbated desmoplasia in PDAC results from increased inflammation, and we uncovered the cellular and molecular mechanisms involved.

Materials and Methods

Animal Experiments

Wild-type (WT) C57BL/6 and FVB male mice were originally obtained from Jackson Laboratory (The Jackson Laboratory, Bar Harbor, Me.) and bred and maintained in our defined-flora colony. KPC (Ptf1-Cre/LSL-KRAS$^{G12D}$/p53-R172H) and iKRAS (p48-Cre;R26-rtTa-IRES-EGFP; TetO-Kras$^{G12D}$ mice) mice were obtained. To generate an obese model, mice (6-week old) were given either 10% or a 60% fat diet (D12450J and D12492, Research Diets, New Brunswick, N.J.) for 10 weeks (or until tumor collection in spontaneous models), as previously described (Surwit, R. S., et al. *Metabolism: clinical and experimental* 44, 645-651 (1995)). For implanted tumor experiments, AK4.4 cells (KrasG12D and p53 Þ/) were isolated from mice generating spontaneous pancreatic tumors (Ptf1-Cre/LSL-Kras$^{G12D}$/p53Lox/Þ) (Bardeesy, N., et al. *Proc Natl Acad Sci USA* 103, 5947-5952 (2006)). Orthotopic pancreatic tumors were generated by implanting a small piece (1 mm$^3$) of viable tumor tissue (from a source tumor in a separate animal) into the pancreas of a 6-8 week-old male lean or obese FVB (AK4.4 model) or C57BL/6 (PAN02 model) mouse. PAN02 tumor chunks and AK4.4 cells were authenticated by IDEXX laboratories. (PAN02: IDEXX RADIL Case #22366-2013. AK4.4: IDEXX RADIL Case #27818-2014). For AT1- and AT2-knockout studies, tumors were implanted into the pancreas of a 6-8-week-old male lean or obese C57BL/6, agtr1a−/− or agtr2−/− mice. With exception of PAN02, these orthotopically grown pancreatic cancers are characterized by a dense collagenous stroma, a hallmark of pancreatic cancer desmoplasia (Diop-Frimpong, B., et al. *Proc Natl Acad Sci USA* 108, 2909-2914 (2011)).

Human Samples

Human samples of pancreatic cancer were obtained from the MGH tissue repository under an active IRB protocol (Partners Healthcare IRB approval number: 2013P001969). Written informed consent from the donor or the next of kin was obtained for the use of these samples in research. Tumors selected received no prior chemotherapy or radiation therapy before the surgical specimen was collected at the time of tumor resection. Body mass index (BMI) was obtained for the respective sample. A total of 16 samples were randomly selected from this subset of samples (8 with BMI<25 and 8 with BMI>30). Paraffin sections were stained for collagen-I and HA as described below. Images are acquired using confocal microscopy and quantified using Matlab. Data were analyzed anonymously.

Pancreatic Tumor Growth Studies

For all experiments unless specified below, mice bearing orthotopic PAN02 or AK4.4 pancreatic tumors were randomized into treatment groups (or no treatment) and tumors were collected at day 21 after implantation. For tumor growth study with chemotherapy, mice were divided into treatment groups 7 days after implantation, and treated with either 5-FU (30 mg/Kg i.v. every 4 days) or an equal volume of saline by intravenous injection on days 7, 11 and 15 after implantation, with tumors collected at day 19. For tumor growth study with losartan, mice were treated with losartan (90 mg/Kg i.p. every day) or an equal volume of PBS intraperitoneally starting on day 5 after implantation and for the duration of the study. In the combined experiment of losartan and 5-FU, the same protocol was used for each drug as described above. TAN depletion by a Ly6G specific inhibitor (BioExcell, 4 mg/Kg i.p. every 2 days) was administered to PAN02 bearing animals starting at day 1 or day 7, and to AK4.4 bearing animals at day 7. IL-1β inhibition (MM425B, Endogen/Pierce Biotechnology, 2 mg/Kg i.p. every 2 days) was administered to PAN02 bearing animals starting at day 7. At the completion of the study, adipose tissue and tumor samples were collected, weighed, and processed for further analysis. When spontaneous models were used, tumors were collected when palpable.

Drug Preparation

Angiotensin inhibitor losartan was obtained as pills, crushed and dissolved in PBS over 24 h. The solution was then sterile filtered for injection. Doxorubicin and 5-FU were obtained as solutions for injection. All drugs were purchased from the pharmacy at Massachusetts General Hospital.

Analysis of Desmoplasia

To assess obesity-induced ECM remodeling and fibrosis fibrillar collagen accumulation was quantified using second harmonic generation imaging, and collagen-I content, hyaluronan, MMPs levels and fibrosis related signaling pathways (e.g. AT-I, CTGF, TSP 1, TGFβ1, and P38/ERK signaling) were measured by rtPCR array, immunohistochemistry and immunoblotting. The topographical distribution and density of cancer-associated fibroblasts (CAFs) in tumor sections was detected by staining for αSMA activated fibroblast marker. Vessel morphology and perfusion was assessed using standard histological analyses.

Drug Delivery

Mice bearing orthotopic PAN02 were injected with 30 mg/kg of 5-FU 3 weeks after tumor implantation, administered retro-orbitally 30 min prior to tumor removal. The tissue was dabbed of excess blood and then snap-frozen in liquid nitrogen for analysis. 5-FU was isolated from the tissues and measured using liquid-liquid extraction followed by reverse-phase HPLC with tandem mass-spectrometry.

Gene Expression

Immediately following excision, tumor tissue was snap frozen and stored in liquid nitrogen. Total RNA was extracted and relative gene expression was determined using RT2 Profiler PCR Arrays system (Qiagen) on a Stratagene Mx3000P QPCR System. The pre-made pathway-focused array used (mouse genes) was "Fibrosis" (Cat. Number: PAMM011Z).

Protein Expression

Western Blot Analysis

Each tumor sample was homogenized directly in lysis buffer for protein extraction 30 ug of denatured protein per sample was loaded on 7%, 10% and 12% SDS-polyacrylamide gels. Antibodies used: phospho-AKT$^{Ser473}$ and AKT; phospho-p38 MAPKT$^{180/Y182}$ and p38; phosphopS6$^{Ser235/236}$ and S6, phospho-ERK(p44/42 MAPK)$^{T202/Y204}$ and ERK; MMP-9; phospho-4EBP1$^{Thr37/46}$ and 4EBP1; phospho-JNK (SAPK/JNK)$^{Thr183/Tyr185}$ and JNK; Phospho-NF-κB p65$^{Ser536}$; TGF-ß; ATR1; Smad2; E-Cadherin; vimentin; snail, αSMA, col-1; GAPDH and ß-actin. All Antibodies listed above were obtained from Cell Signaling Technology (Beverly, Mass.), and diluted 1:1000 with exception of phospho-JNK (SAPK/JNK)$^{Thr183/Tyr185}$ (1:500) and Phospho-NF-κB p65$^{Ser536}$ (1:500). Other antibodies used were: for αSMA (1:1000, abcam, MA); col-1 (1:1000); MMP-9 (1:500, EMD Millipore-Billerica, MA), GAPDH (1:2000, Ambion, NY), ß-actin (1:5000, Sigma, MO), α-tubulin (1:5000, Sigma, MO).

Multiplex Array

Each tumor sample was homogenized directly in lysis buffer for protein extraction. 2 ug/ul of sample was used. The pre-made inflammatory multiple cytokines protein array was used (V-PLEX Proinflammatory Panel1 mouse kit, Cat. Number K15048D).

Immunohistochemistry/Immunofluorescence

Vessel Perfusion and Hypoxia Histology

On the day of the last treatment, mice were slowly (B2 min) injected with 100 µl of 1 mg/ml biotinylated lectin (Vector Labs), administered via the retro-orbital sinus 5 min before tumour removal. For hypoxia studies, the mice were also injected with 60 mg/kg i.p. of pimonidazole at 10 mg/ml 45' before tumour removal. The tumours were then excised and frozen in optimal cutting temperature compound (Tissue-Tek). Transverse tumour sections, 40 mm thick, were immuno-stained with antibodies to endothelial marker CD31 (MEC13.3 antibody, Bio-sciences (BD), 1:100 dilution) and counterstained with 40,6-diamidino-2-pheny-lindole (Vector Labs). Collagen-I and hyaluronan were detected using the LF-68 antibody (1:50 dilution) provided by Dr Larry Fisher (NIDCR) and a biotinylated hyaluronan proteoglycan fragment (385911, Calbiochem), respectively. Staining for αSMA (C6198 antibody, Sigma, 1:100 dilution), active TGF-b1 (G122A antibody, Promega, 1:15 dilution), CCN2 (TP-243 antibody, Torrey Pines, 1:100 dilution), AT1 (ab18801 antibody, Abcam, 1:100 dilution) and AT2 (AAR-012 antibody, Alomone, 1:200 dilution) were carried out in 10 mm sections. For the detection of collagen I in AK4.4, KPC and human pancreatic ductal adenocarcinoma, the paraffin-embedded sections were treated with a pH-9.0 antigen retrieval solution and counterstained with haematoxylin.

Histological Image Analysis

Whole tumor mosaics from each slide were analyzed using a confocal microscope (Olympus, 10× air objective). For vascular analysis, vessels were skeletonized and segmented using a custom, semi-automated tracing program developed in MATLAB (The MathWorks), allowing the removal of structures under 30 pixels and regions of autofluorescence. For perfusion fraction, the number of vessels counted by this program with colocalization of lectin and CD31 staining was divided by the number of vessels counted with CD31 staining. For vessel metrics, including diameter and density, the program determined the average size of all counted vessels and their length, as well as the count per area. Identical analysis settings and thresholds were used for all tumours.

Flow Cytometry

Tumor-bearing mice were perfused through intracardiac injection of PBS and sacrificed. Pancreatic tumor tissues were harvested, minced, and digested at 37° C. for 1 h with DMEM containing collagenase type 1A (1.5 mg/mL), hyaluronidase (1.5 mg/mL), and DNase (2 mg/mL). The digestion mixtures were filtered through 70-µm cell strainers. Single-cell suspensions were incubated with rat anti-mouse CD16/CD32 mAb for blocking and then stained with fluorochrome-conjugated antibodies in cold buffer cold buffer (1% BSA, 0.1% NaN3 in PBS). 7-amino-actinomycin D (7AAD) reagent (eBioscience) was added to the stained tubes per manufacturer's instruction just before running the flow analysis. Flow cytometry data were acquired on an LSRII flow cytometer (Becton Dickinson) and were analyzed with FACSDiva software. FSC-A vs. FSC-W and SSC-A vs. SSC-W was applied to discriminate the doublet/aggregated events. The following monoclonal anti-mouse antibodies were used: CD4-FITC, CD4-PE-Cy7, CD8a-FITC, CD8a-PE, CD45-PE, CD45-PE-Cy7, CD25-APC-Cy7, CD86, CD206, LY6C, and CD11b-APC-Cy7 (BD Biosciences) and F4/80-FITC and F4/80-PE (eBioscience).

Statistical Analysis

Statistical analyses were performed using GraphPad Prism Version 6.0f. Error bars indicate the standard error of the mean of data from replicate experiments. Significance of difference between samples within figures was confirmed using unpaired t-tests, one-way anova, or two-way anova with Bonferroni correction for multiple comparisons, depending on the experimental setting. A p<0.05 value indicates significance.

Results

Diet- or Genetically-Induced Obesity Promotes Pancreatic Tumor Progression

Figure 7B:
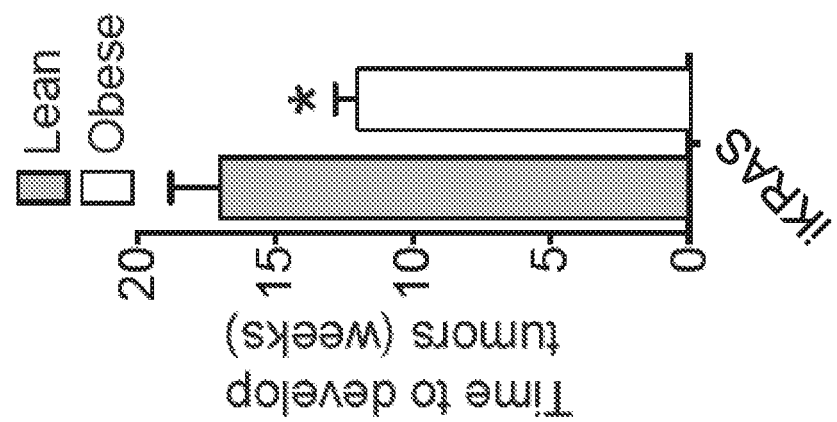
FIGS. 7A, 7B, 7C, 7D, 7E, and 7F show that obesity promotes tumor initiation and progression.
Figure 7A:
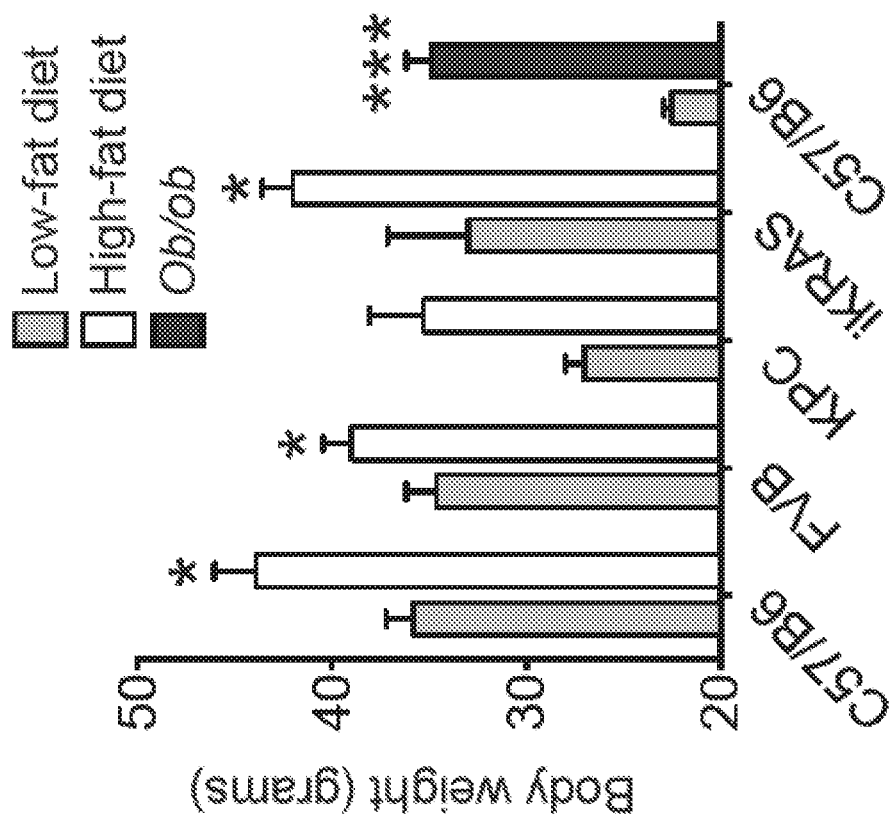
Figure 7F:
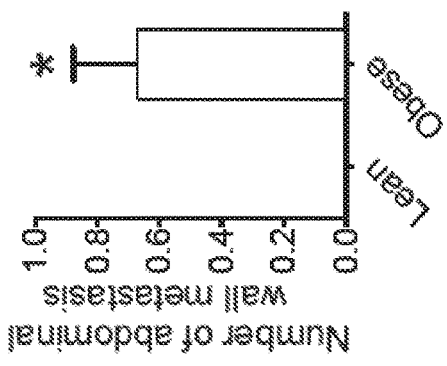
Figure 7E:
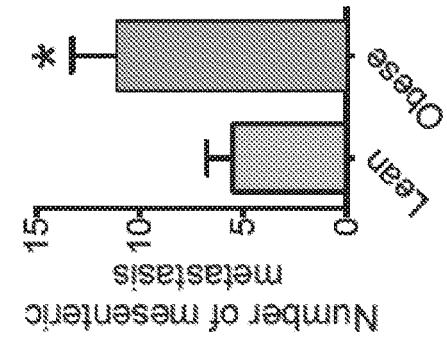
Figure 7D:
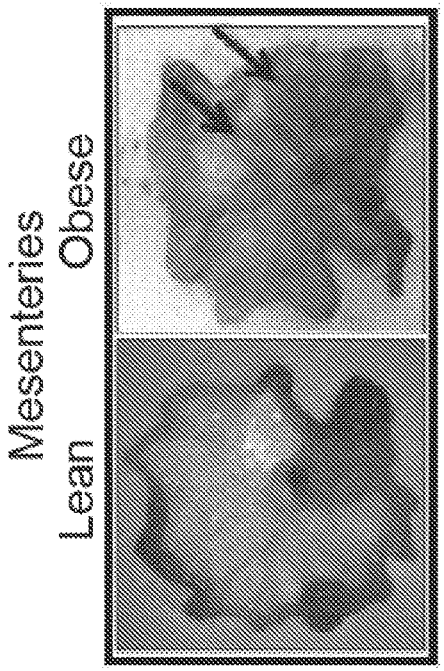
Figure 7C:
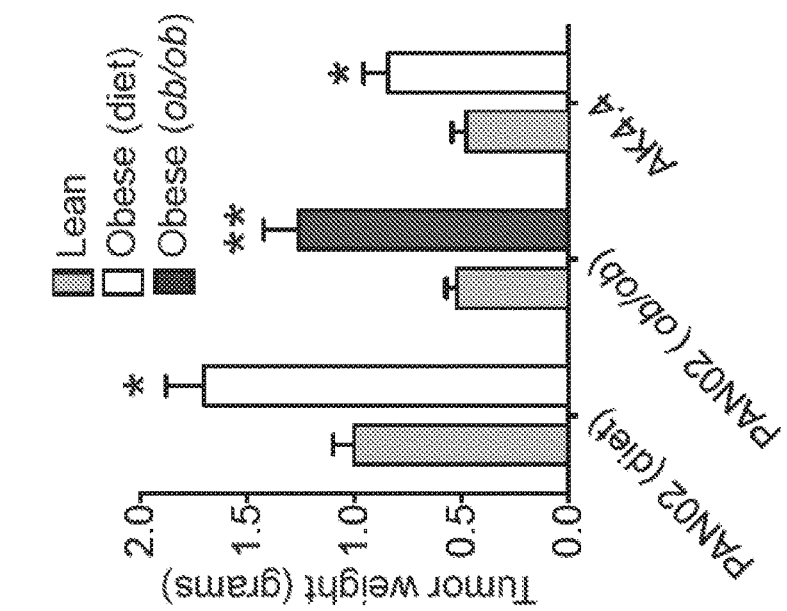
Figure 24:
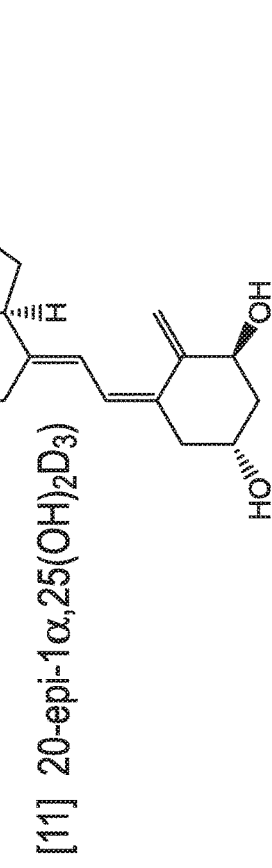
FIG. 24 shows representative vitamin D analogs, e.g., paricalcitol, doxercalciferol, falecalcitriol, maxacalcitol, tacalcitol, alfacalcidol, eldecalcidol, seocalcitol, lexicalcitol, CD578, inecalcitol, calcipotriol, TX527, 2MD, WY1112, PRI-2205, ILX23-7553, and analogs and derivatives thereof.
Figure 25A:
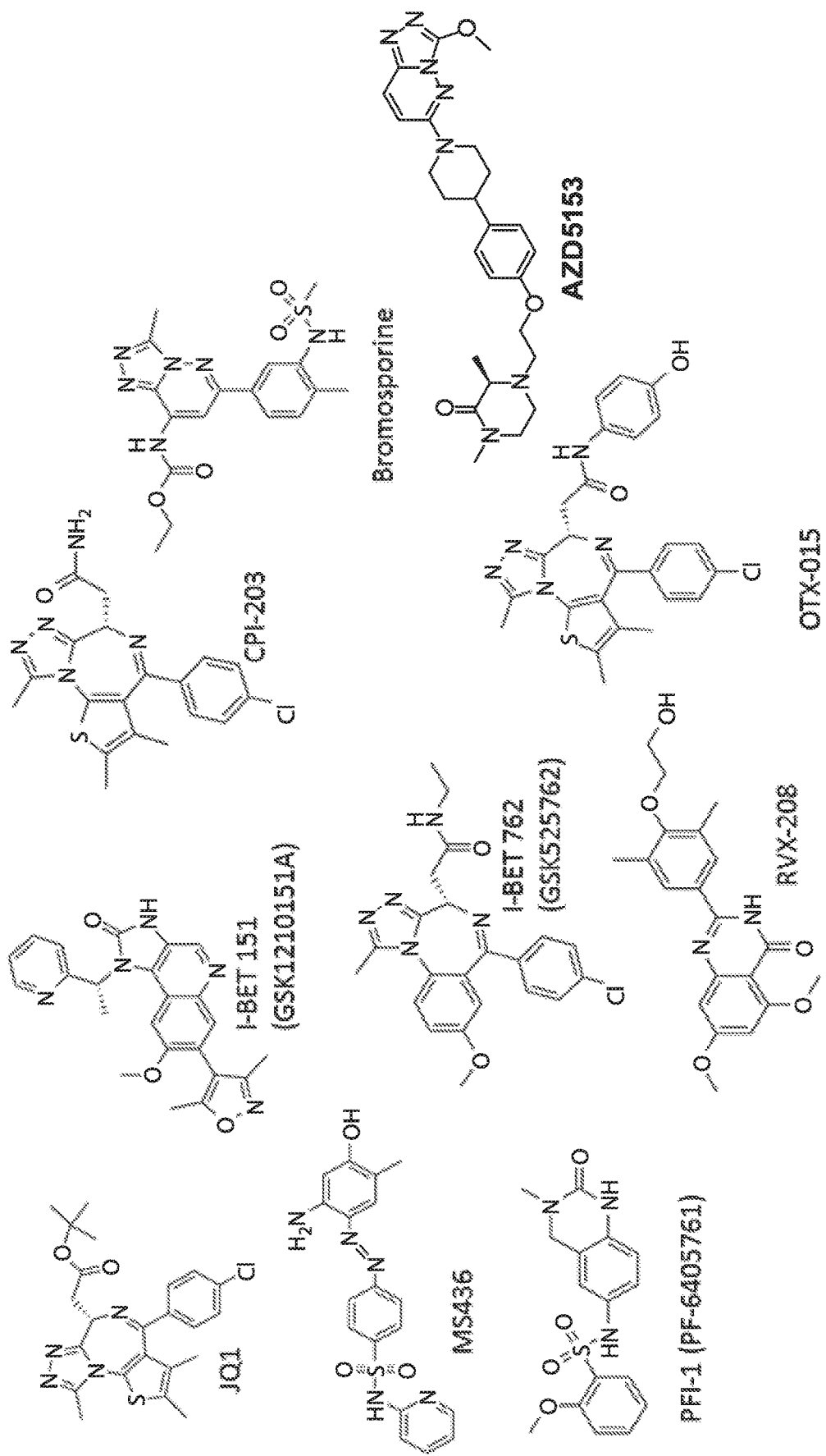
FIGS. 25A and 25B show representative bromodomain and extra-terminal protein inhibitors (i-BET), e.g., MS436, PFI-1, I-BET 151, OTX-015, JQ1, CPI-203, bromosporine, RVX-208, I-BET 762, I-BET 151, OFXBD02, OFXBD03, XD14, AZD5153, and analogs and derivatives thereof.
Figure 25B:
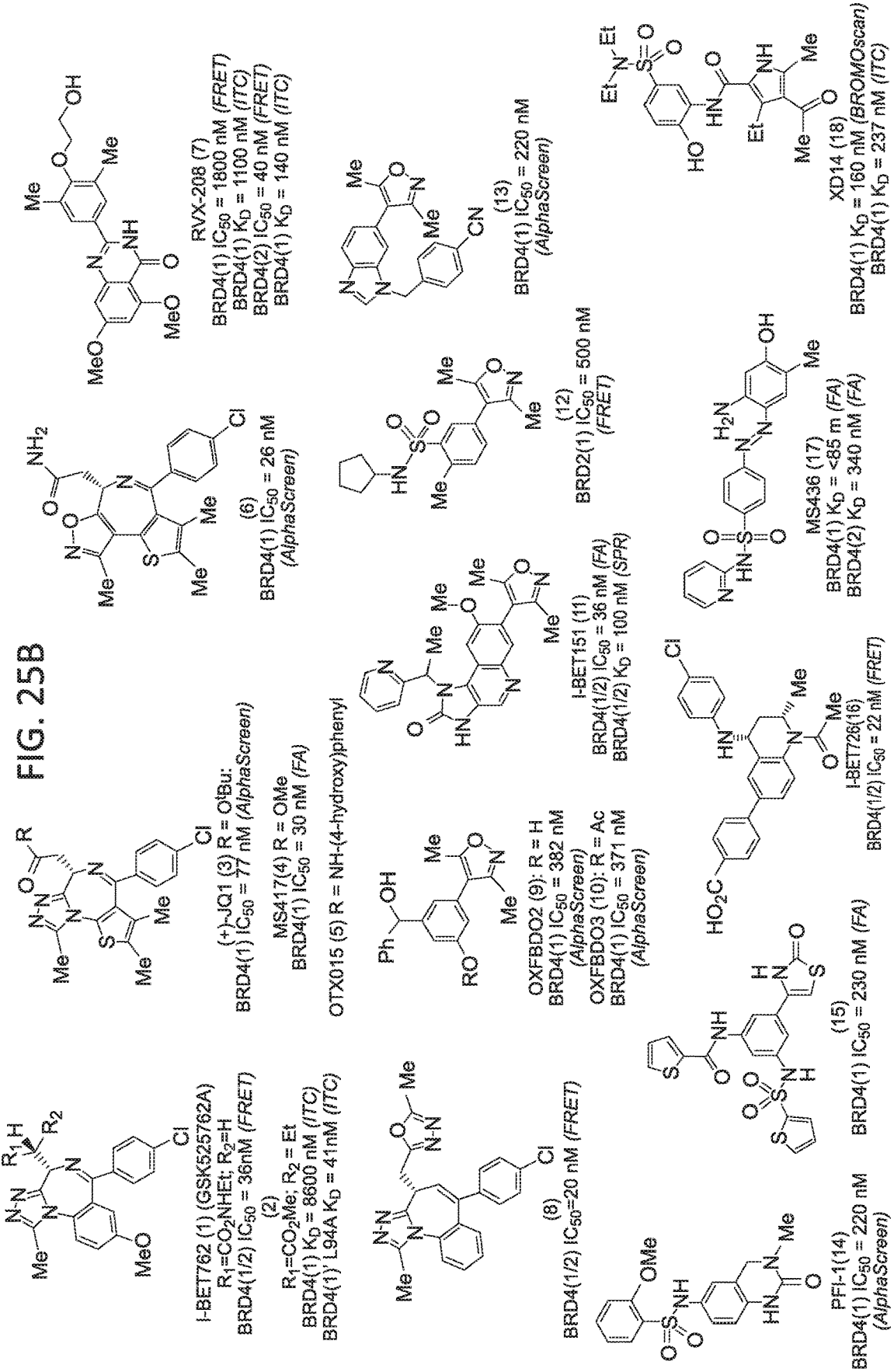

A high-fat diet was fed to four different strains of mice to generate diet-induced obesity (DIO) (FIG. 7A). In addition, a genetic model of leptin deficiency (ob/ob) was used (FIG. 7A). Consistent with previous studies (8, 31), obesity promoted tumor initiation and progression consistently across tumor models. Using spontaneous PDAC models—KPC (Ptf1-Cre/Kras$^{LSL-G12D/+}$/p53$^{LSL-R172H/+}$) and iKRAS (Ptf1-Cre/ROSA26-LSL-rtTa-IRES-eGFP/TetO-Kras$^{TetO-LSL-G12D}$/p53$^{L/+}$) mice (36-42), it was found that obese animals tended to develop tumors earlier than lean mice (FIG. 7B and FIG. 24). Furthermore, DIO and genetically-induced obesity accelerated the growth of implanted tumors in two orthotopic syngeneic PDAC models—PAN02 and AK4.4. Obese mice presented with increased tumor weight (FIG. 7C) as well as increased metastatic dissemination to the mesenteric peritoneum (PAN02) (FIG. 7D and FIG. 7E) or local infiltration of the retroperitoneum (AK4.4; mesenteric/peritoneal metastases are not detected in this model) (FIG. 7F) as compared to their lean counterparts. Taken together, these mouse models confirm the tumor-promoting effect of obesity on pancreatic cancer.

Obesity Induces a Steatotic and Fibrotic Microenvironment in PDACs

Figure 8C:
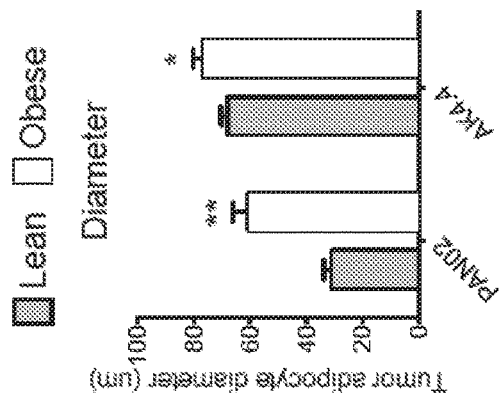
Figure 8B:
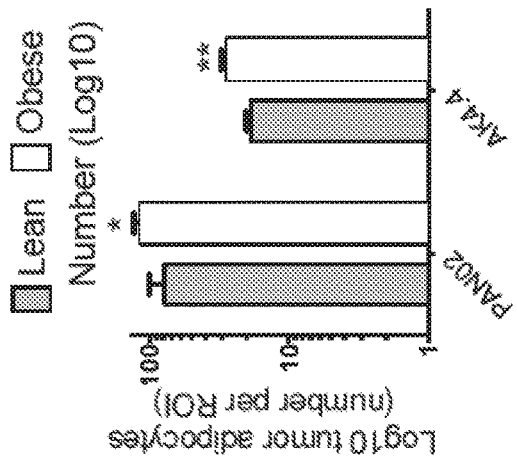
Figure 8A:
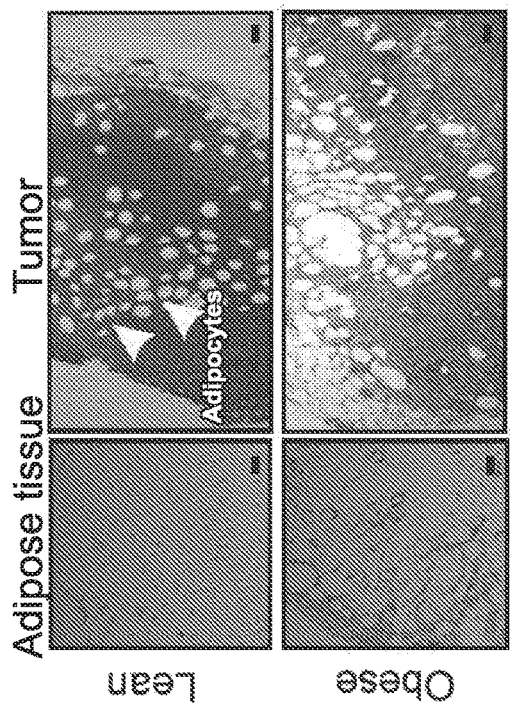
Figure 8D:
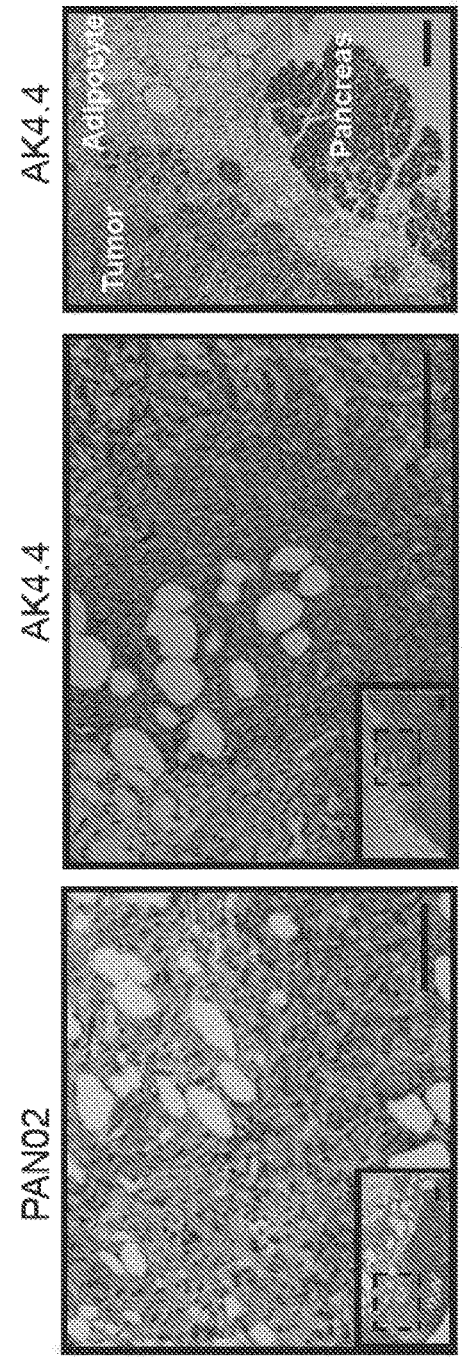
Figure 15A:
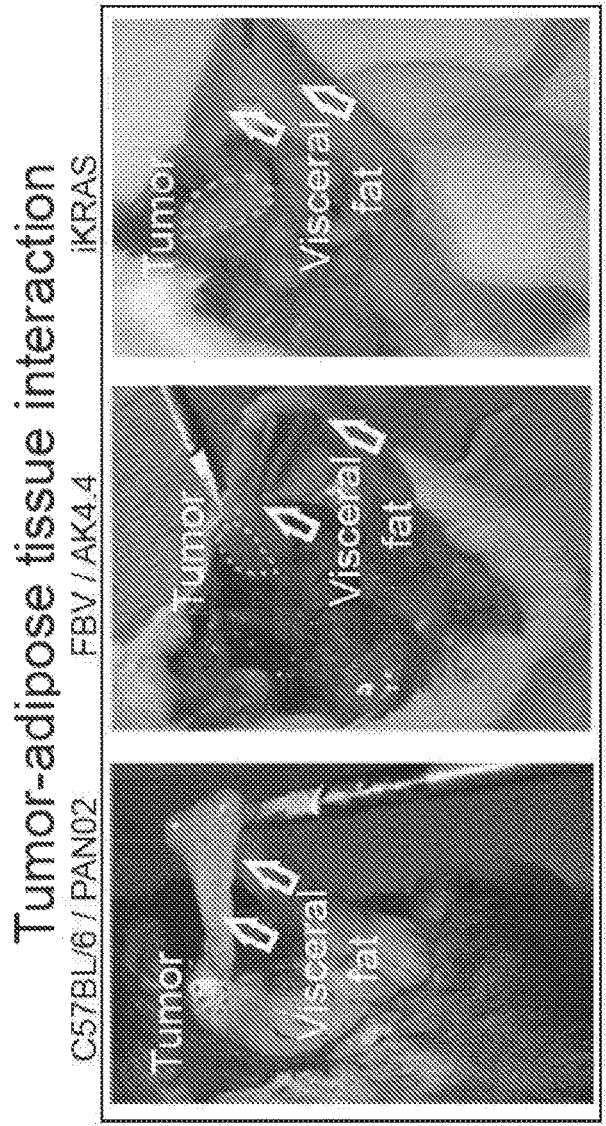
FIGS. 15A and 15B show the adipose tissue-tumor interaction.
Figure 15B:
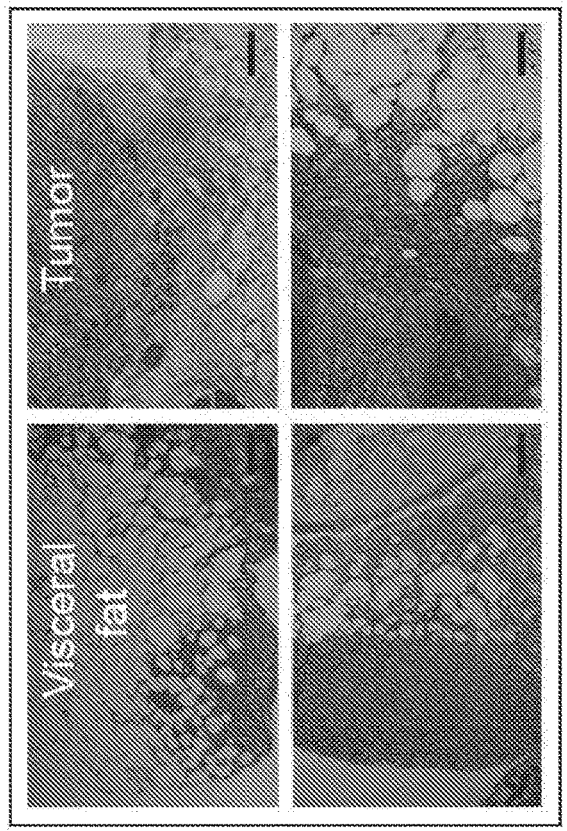

The dysfunctional hypertrophic adipocytes that accumulate in adipose and pancreatic tissues in obesity lead to the development of a local desmoplastic reaction characterized by fibrosis and inflammation (23-25). In tumors, desmoplasia stimulates growth and impairs response to chemotherapy via reduced vessel perfusion (21). The following experiments test whether obesity augments the desmoplasia in the pancreatic tumor microenvironment, ultimately fostering tumor progression. As expected (27), hypertrophic adipocytes and associated fibrosis were observed in the visceral adipose tissue of obese mice (FIG. 8A). Importantly, the tumor microenvironment also contained more and larger adipocytes (FIGS. 8A, 8B, and 8C). In part, this was due to tumors invading the neighboring visceral adipose tissue (FIG. 15A), as reported in pancreatic cancer patients (9, 33). Furthermore, Masson's trichrome staining revealed an abundance of fibrosis in the tumor areas enriched with adipocytes or alongside adjacent visceral adipose tissues (FIGS. 8A and 8D, FIG. 15B). These data suggest that, in obesity, PDACs adopt a fibrotic adipose microenvironment as they invade the adjacent adipose tissues.

Figure 16B:
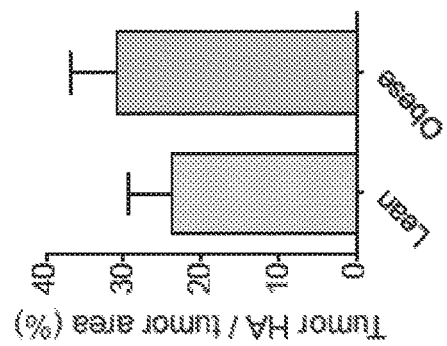
FIGS. 16A, 16B, 16C, 16D, 16E, and 16F show the co-expression of collagen-I and hyaluronan in PSCs, and impact of obesity on tumor hyaluronan levels.
Figure 16C:
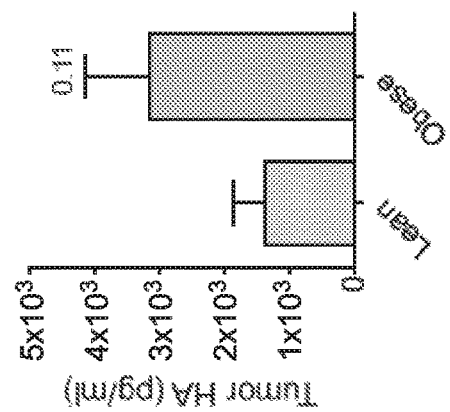
Figure 16A:
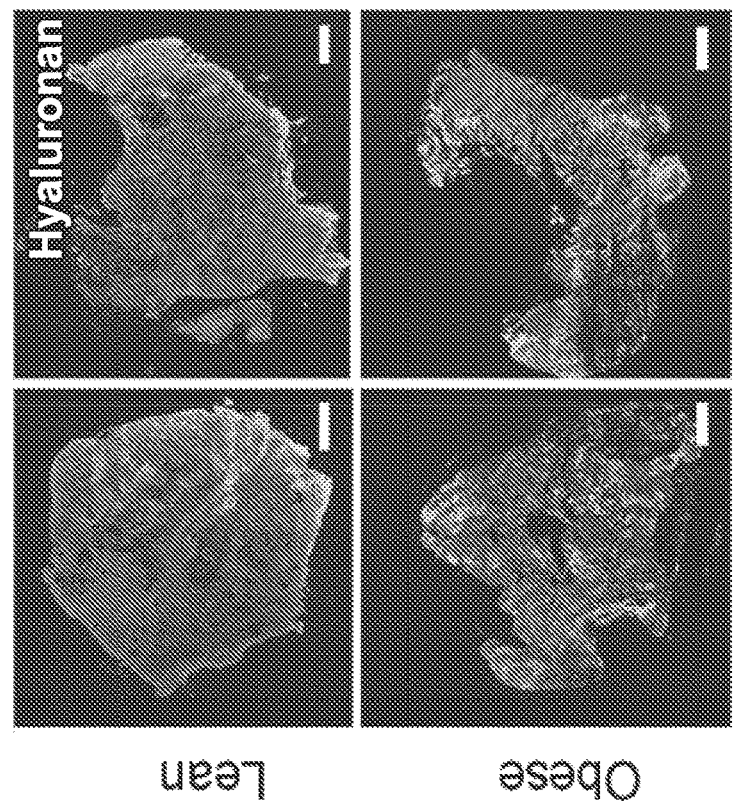
Figure 16D:
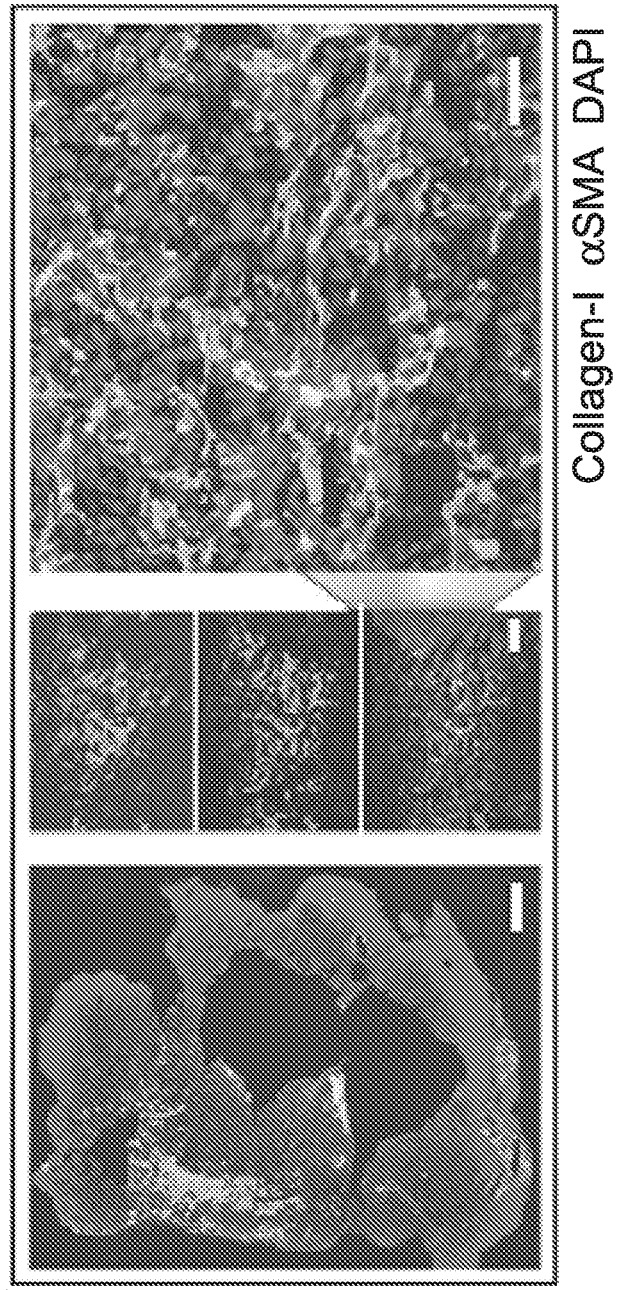
Figure 16F:
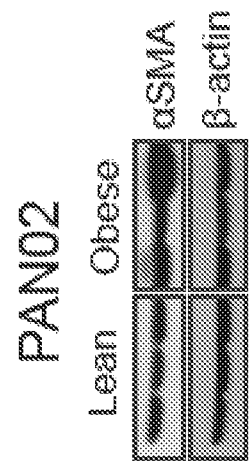
Figure 16E:
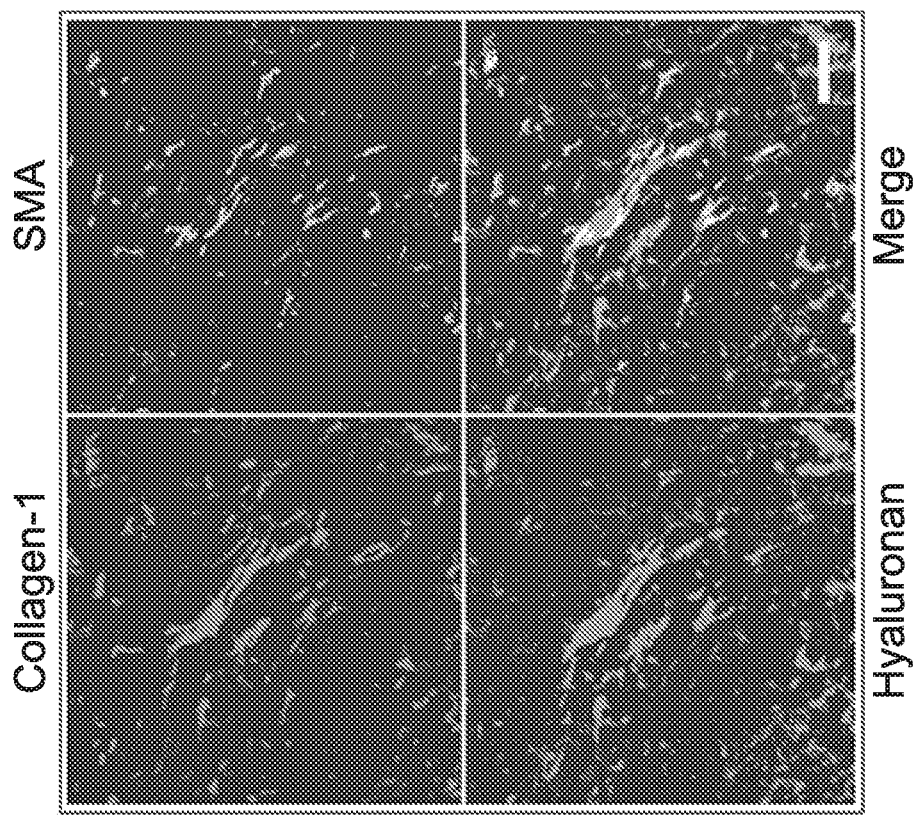

Next, it was determined whether this abundance of fibrotic adipocyte-rich areas in tumors from obese mice led to an overall increase in tumor fibrosis. Using second harmonic generation multiphoton microscopy (SHG) and immunofluorescence, obesity increased the expression of fibrillar collagen, including collagen-I, in both PAN02 and AK4.4 orthotopic PDACs as well as in the KPC PDAC model (FIGS. 8E, 8F, 8G, and 8H). A significant increase in hyaluronan (HA) levels in tumors from obese mice was not observed, although there was a similar trend (FIGS. 16A, 16B, and 16C). Similar to increased activation of stellate cells in adipose tissues and the steatotic pancreas in the obese setting, it was next determined whether the abundance of activated PSCs was also increased in tumors in obese mice. First, it was confirmed that αSMA-expressing activated PSCs indeed associate with collagen-I and HA expression in our PDAC models (FIGS. 16D and 16E). Western blotting and immunofluorescence staining revealed an increased density of activated PSCs in obese animals by almost two-fold in the AK4.4 and KPC models and three-fold in PAN02 (FIG. 8I, 8J, 8K, and FIG. 10C). As expected, the percentage of αSMA and collagen-I double positive PSCs (collagen-producing PSCs) also increased in obesity (FIGS. 8I, 8J, and 8K). Taken together, the tumors in the obese setting were enriched in enlarged adipocytes, activated PSCs, and collagen.

Figure 9C:
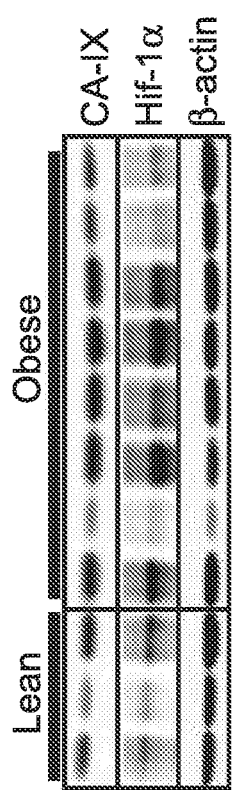
Figure 9E:
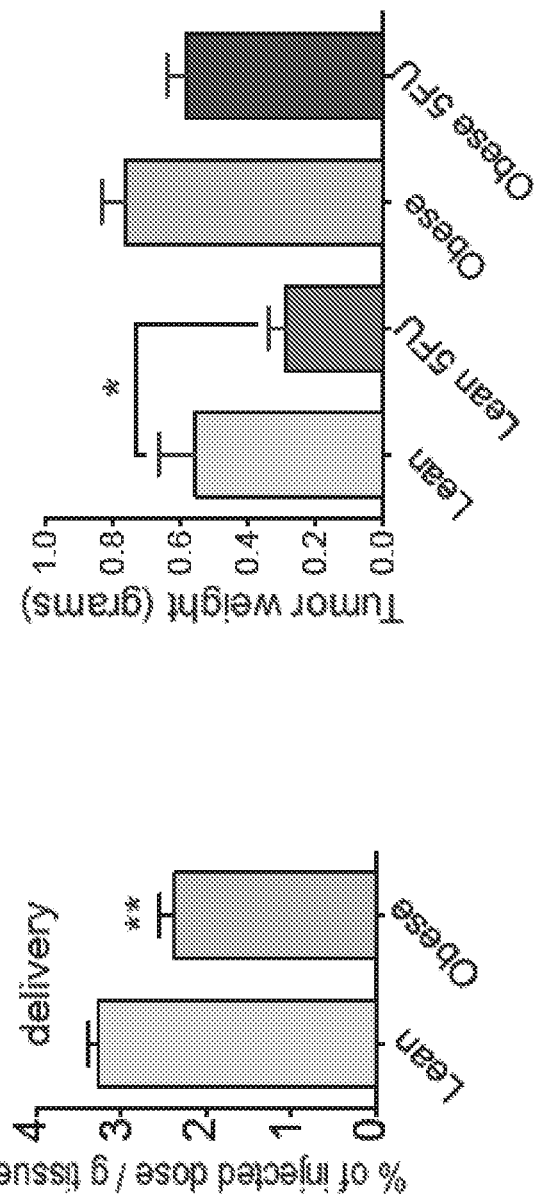
Figure 9D:
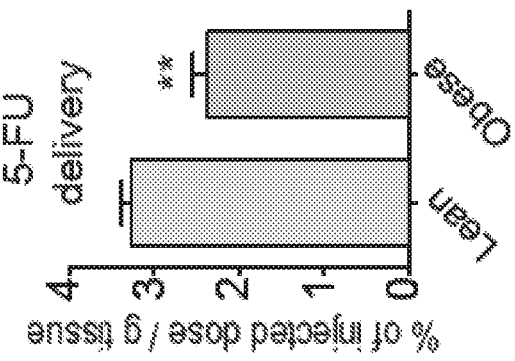

Obesity-Augmented Desmoplasia in PDACs Associates with Reduced Chemotherapy Efficacy Desmoplasia reduces the delivery and efficacy of chemotherapy in PDAC by decreasing vessel perfusion (21). It was next tested whether obesity-augmented desmoplasia also affected the efficacy of chemotherapy. Indeed, tumors in obese animals had reduced perfusion and a concomitant increase in hypoxia (FIG. 9A, 9B, 9C and FIGS. 17A and 17B) were observed. This was associated with increased stiffness and solid stress (not shown). To determine if reduced perfusion impairs delivery of chemotherapeutic agents, tumor-bearing mice were treated with 5-Fluorouracil (5-FU), an approved chemotherapeutic agent for PDAC (43). Delivery of 5-FU was decreased in tumors in obese mice (FIG. 9D). A similar trend was observed with doxorubicin (FIG. 17C). Furthermore, lean mice treated with 3 doses of 5-FU (30 mg/kg BW q4d) had a significant 50% reduction in tumor weight as compared to untreated controls in both PAN02 and AK4.4 models (FIG. 9E and FIG. 17D). In contrast, 5-FU did not significantly reduce tumor weight significantly under obese conditions (FIG. 9E and FIG. 17D). Collectively, these data shows that, in addition to directly promoting PDAC growth and metastasis, obesity reduces the response to chemotherapy.

Blockade of AT1 Signaling Reduces Obesity-Induced Desmoplasia and Accelerated Tumor Progression, and Increases Response to Chemotherapy.

Figure 10J:
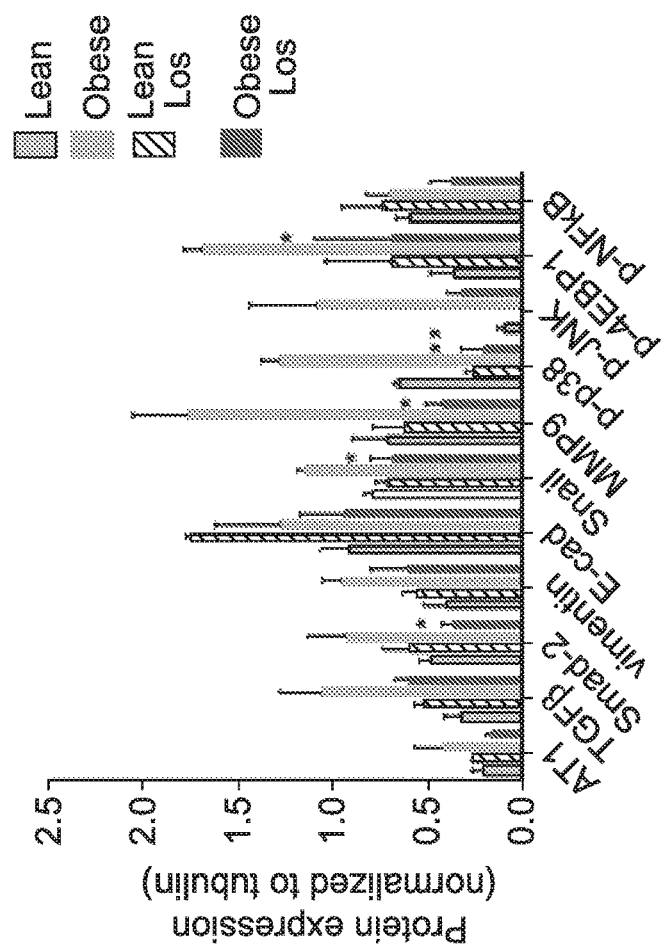
Figure 10I:
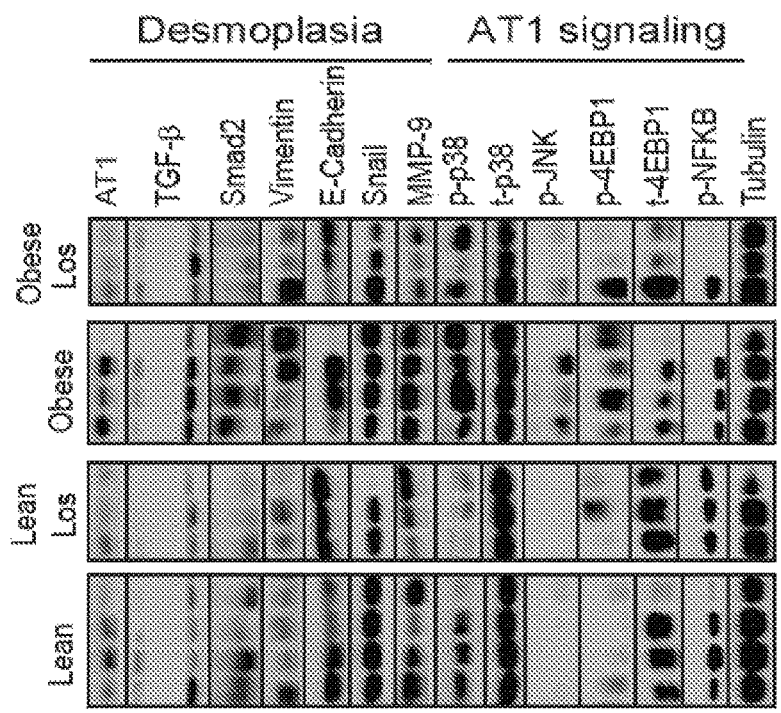
Figure 10L:
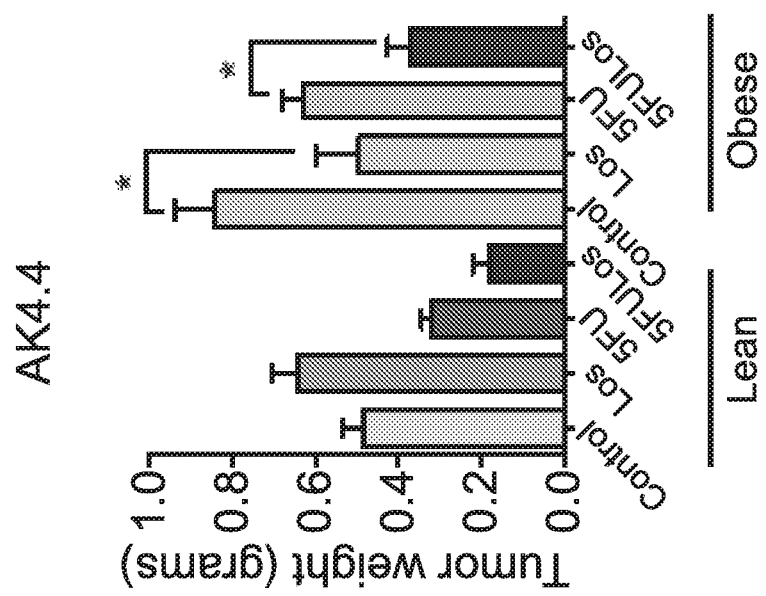
Figure 10K:
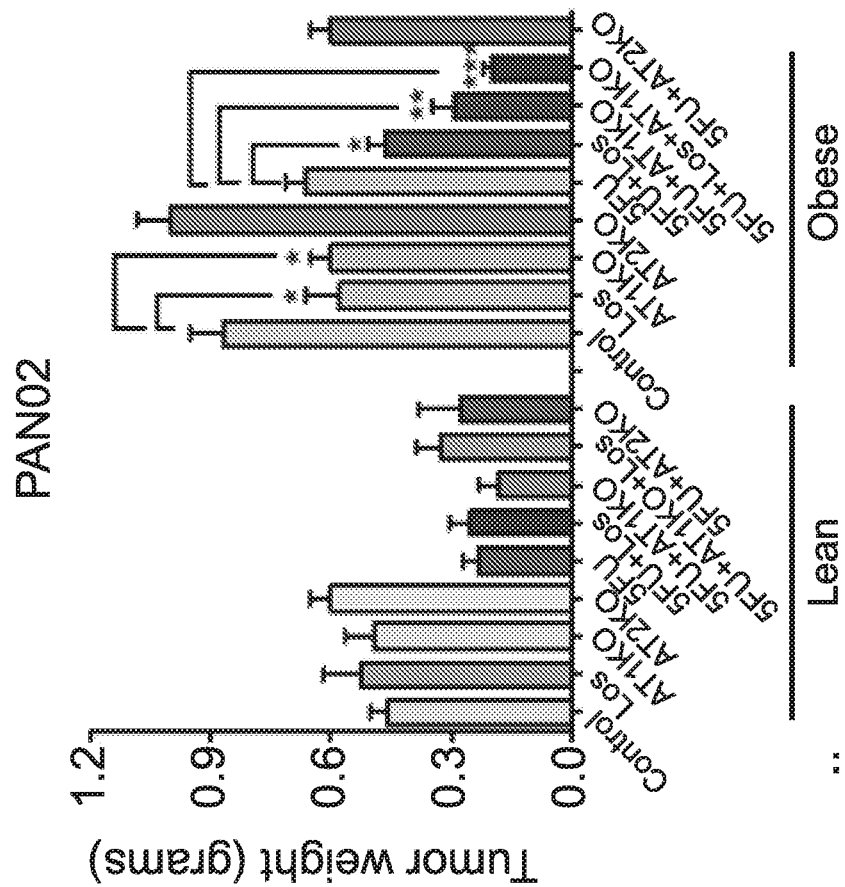
Figure 18B:
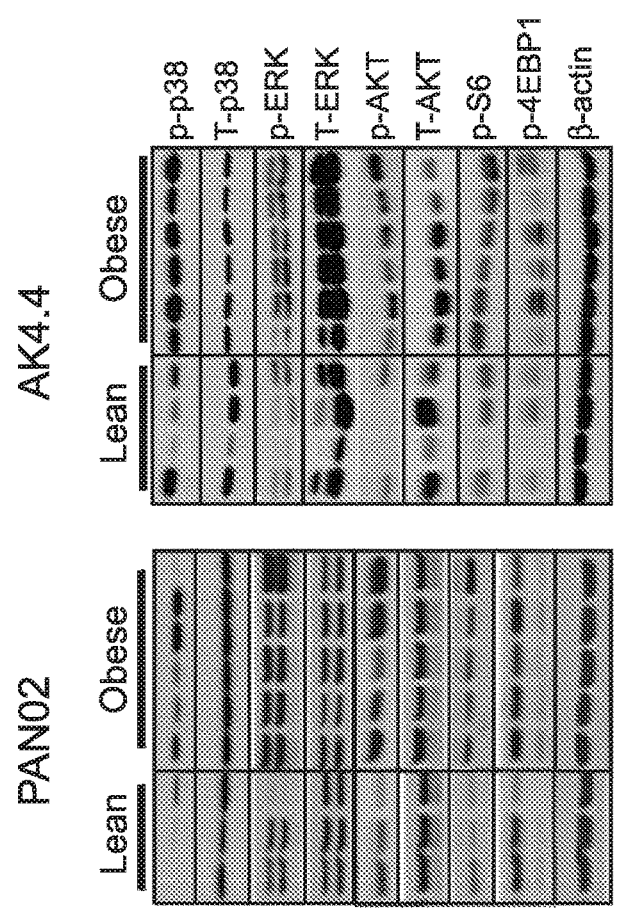
FIGS. 18A, 18B, 18C, 18D, 18E, 18F, and 18G show the additional effects of AT-1 inhibition on obesity-aggravated desmoplasia, perfusion and drug delivery.
Figure 18A:
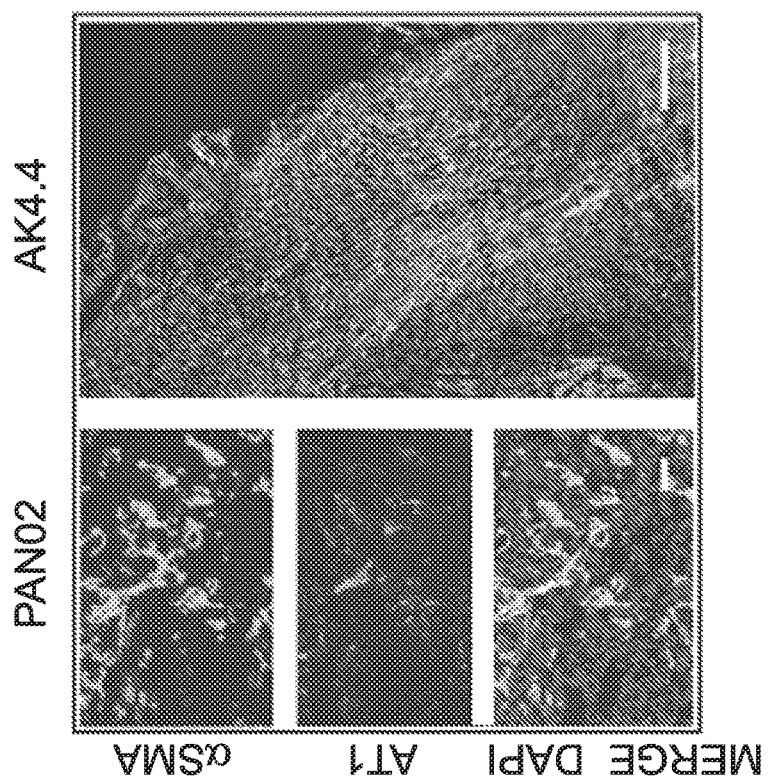
Figure 18D:
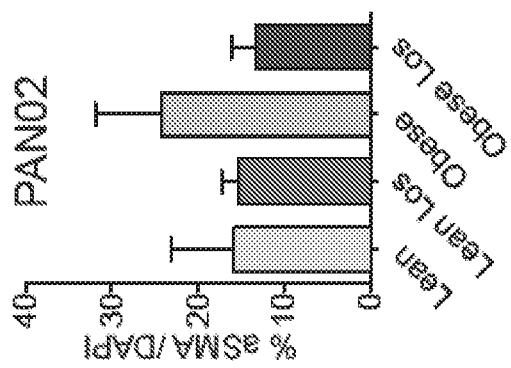
Figure 18E:
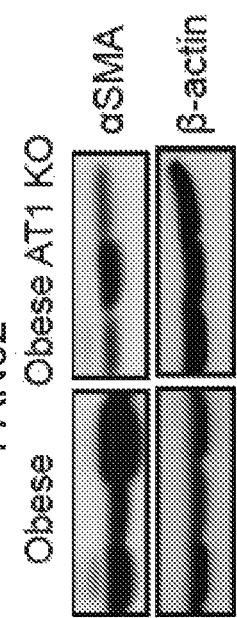
Figure 18C:
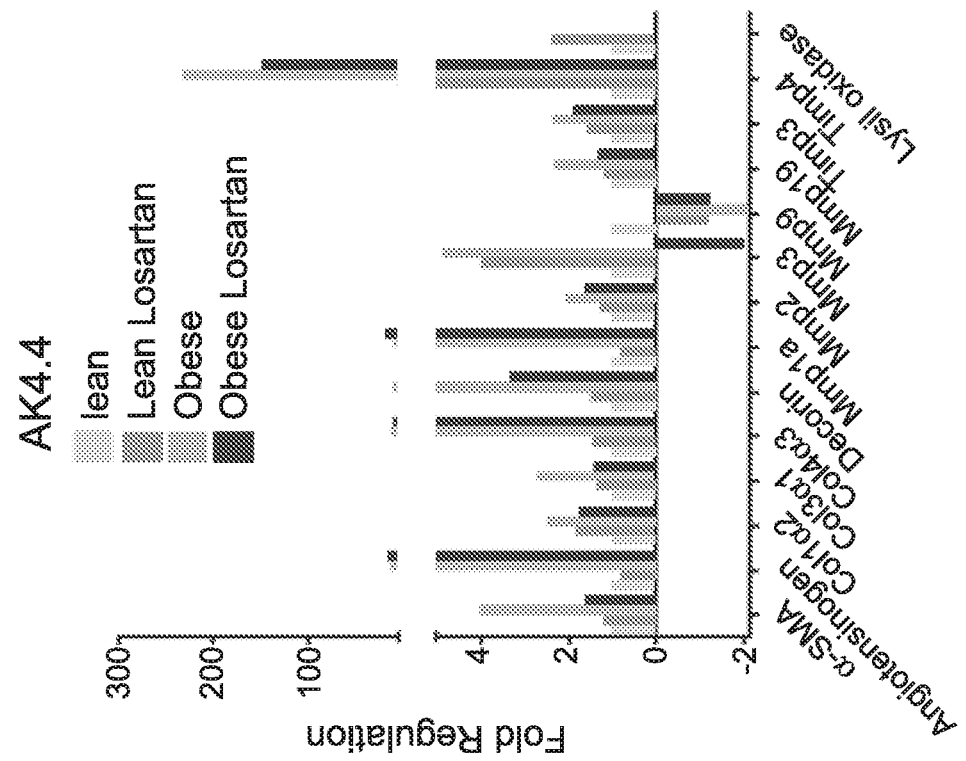
Figure 18F:
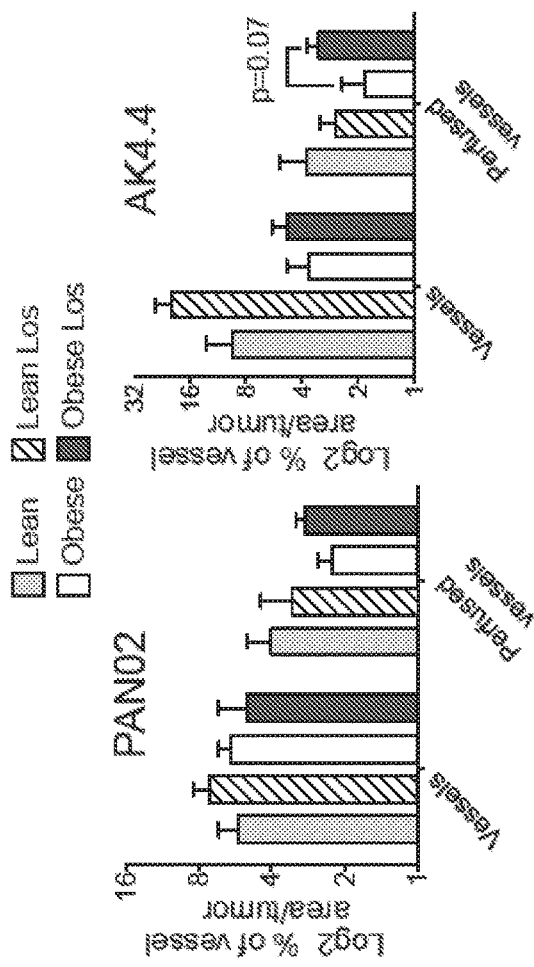
Figure 18G:
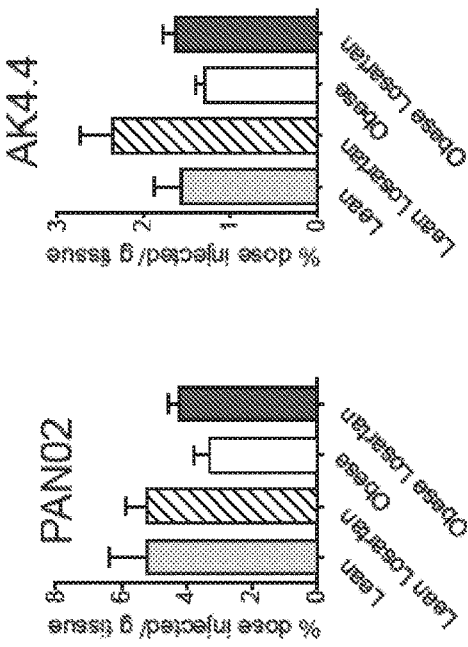
Figure 20A:
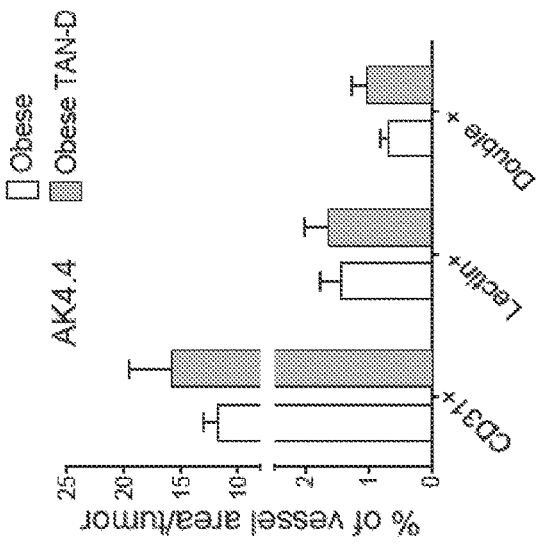
FIGS. 20A, 20B, 20C, and 20D show the effects of TAN depletion on vessel perfusion and cytokine expression in obese mice.

Tumor desmoplasia results in part from the activation of PSCs through AT1 signaling (21, 44). Expression of AT1 in PSCs was confirmed, which ranged from 70.3% (SEM=5.7) in PSCs in PAN02 tumors to 35.3% (SEM=12.8) in AK4.4 tumors (FIG. 18A). Consistent with the observed increase in activated PSC numbers in tumors from obese mice, the activation of AT1 downstream pathways such as p38, ERK, AKT and their targets pS6 and 4EBP1 (21, 45-47) were increased in tumors in obese mice in both models (FIG. 18B). In addition, many target genes of the AT1 pathway, including Col1a1, Mmp genes, and Tgfβ1 were upregulated in PAN02 and AK4.4 tumors from obese mice (FIGS. 10A and 10B). Next, it was tested whether blockade of AT1 signaling could reverse obesity-promoted desmoplasia using the ARB losartan and mice deficient in AT1 (Agtr1a$^{-/-}$). In both tumor models, losartan was able to reduce gene and protein expression of the activated PSC marker αSMA in tumors from obese animals but did so only mildly in lean animals (FIGS. 10C and 10D, FIGS. 18C and 18D). The reduction of activated PSCs was associated with a decrease in gene and protein expression of collagen-I as well as fibrillar collagen in tumors from obese, but not lean mice (FIGS. 10E, 10F, 10G, and 10H, and FIG. 18C). Moreover, losartan normalized the obesity-induced abnormal expression of several desmoplasia-related markers in tumors including AT1, TGF-ß, SMAD2, vimentin, E-cadherin, snail, MMP9, and decorin as well as AT1 downstream signaling pathways (FIG. 10I, 10J and FIG. 18C). These effects were only modest in lean animals, consistent with the small reduction in αSMA expression in this setting. Similarly, reduced αSMA expression was observed in the PAN02 tumors of obese Agtr1a$^{-/-}$ mice as compared to these tumors in obese wild-type mice (FIG. 18E). Next, it was determined whether AT1 blockade could improve the response to chemotherapy particularly in highly desmoplastic tumors in the obese setting. Pharmacological and genetic AT1 blockade enhanced the response of the PAN02 model to chemotherapy in obese but not in lean animals (FIG. 10K). In the AK4.4 model, AT1 blockade was somewhat effective in the lean setting, but it improved therapeutic response in tumors to a greater extent in obese mice (FIG. 10L). In both AK4.4 and PAN02 models a trend for increased tumor perfusion as well as for increased delivery of chemotherapeutics by AT1 blockade was observed, particularly in obese mice (FIGS. 18F and 18G). In addition to AT1, PSCs also express the angiotensin II type-2 receptor (AT2), which has anti-fibrotic effects as opposed to the pro-fibrotic effects of AT signaling (21). However, here, PAN02 tumor response to chemotherapy in AT2-/- mice was similar to that in WT, regardless of diet group (FIG. 20K). Importantly, losartan monotherapy or genetic deletion of AT1 led to reduced tumor weight in obese mice, indicating that obesity-augmented desmoplasia also promotes tumor growth (FIGS. 10K and 10L). In summary, obesity associates with an increase in pro-fibrotic enlarged adipocytes, AT1- and αSMA-expressing (activated) PSCs, upregulation of signaling pathways involved in desmoplasia, collagen-I production, and ultimately an increase in tumor fibrosis and tumor growth. AT1 signaling inhibition is particularly effective in preventing these effects in the obese setting, leading to reduced tumor progression and re-sensitization of tumors to cytotoxic therapies in obese mice.

Tumor-Associated Neutrophils Mediate Obesity-Induced Desmoplasia and Tumor Progression.

Figure 11B:
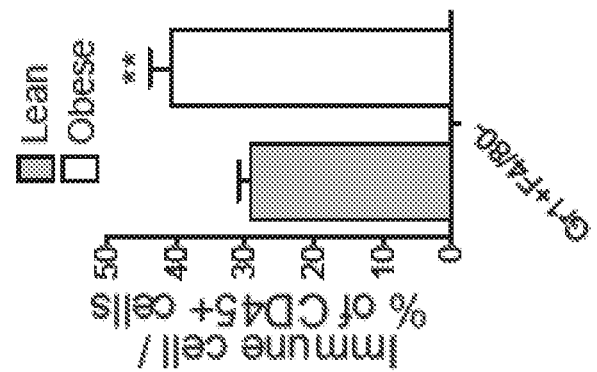
Figure 11A:
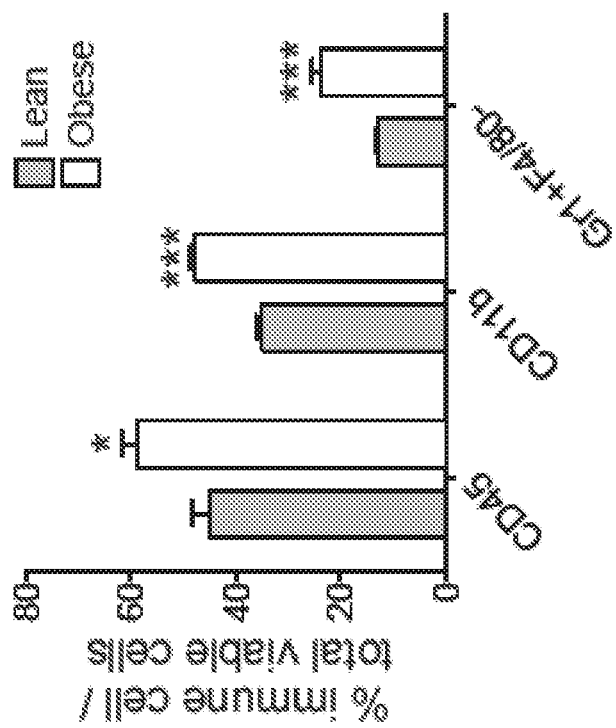
Figure 19B:
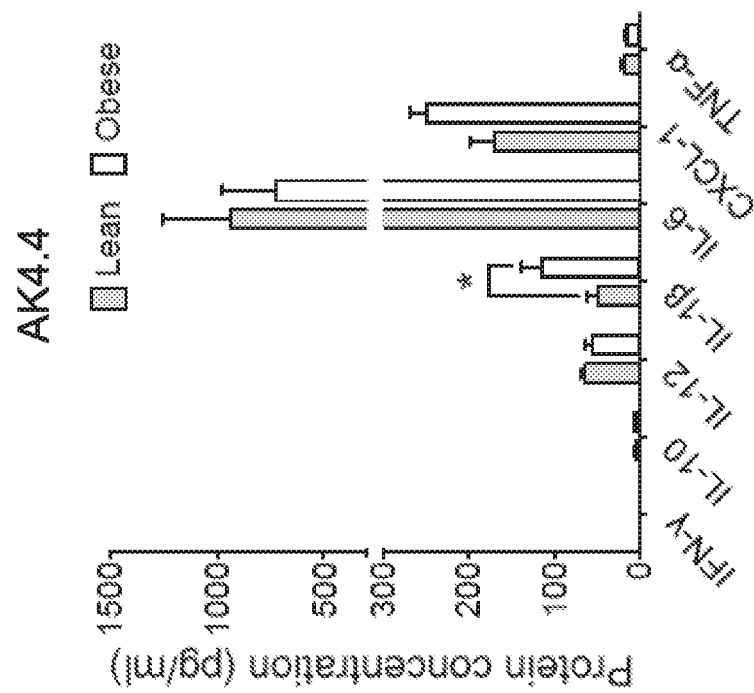
FIGS. 19A and 19B show the effect of obesity on immune cell infiltration and cytokine profile in AK4.4 tumors.
Figure 19A:
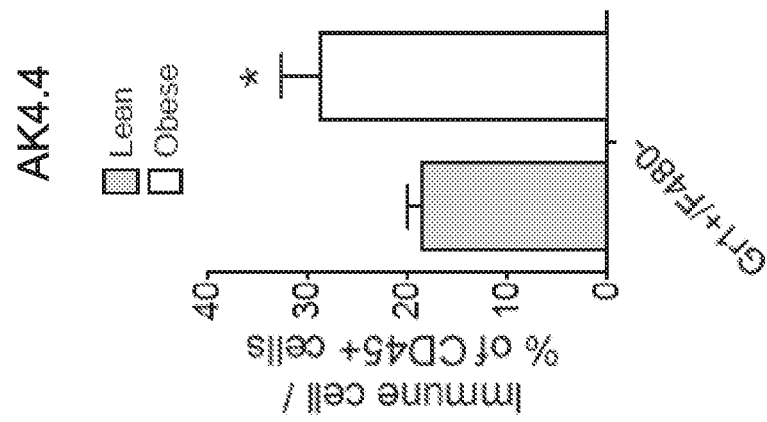

The fibrotic phenotype in adipose tissues and normal pancreas in obesity is largely the consequence of a persistent pro-inflammatory state, which is characterized by the production of cytokines by the hypoxic and dysfunctional hypertrophic adipocytes and recruitment of immune cells (24, 25, 40). Hence, it was next determined whether adipocyte-associated inflammation was responsible for the augmented tumor desmoplasia and accelerated tumor growth observed in obese animals. Flow cytometric analysis revealed that obesity promotes the infiltration of CD11b(+) Gr-1(+)F4/80(-) myeloid cells in two syngeneic PDAC models in obese mice (FIG. 11A, 11B, and FIG. 19A). The majority of this increased cell population were Ly6G(+) tumor-associated neutrophils (TANs) was confirmed (FIGS. 11C and 11D). In addition, TAN recruitment was accompanied by a reduction in the CD8(+) cytotoxic T cell population in PAN02 tumors (FIGS. 1C and 1D), as well as by a trend toward an increased number of regulatory T cells (Tregs) (FIGS. 11C and 11E). This was associated with an increased expression of IL-4, IL-5, and IL-10 in tumors in both models, suggesting an immunosuppressive tumor microenvironment in obese animals. TAN depletion (TAN-D) in both PDAC models—using an anti-Ly6G antibody that resulted in a ~90% decrease in TANs (FIG. 20A)—reverted the increased tumor weight in obese mice to levels almost similar to lean mice in both models, confirming the relevance of these cells for tumor progression in the context of obesity (FIGS. 11C and 11E). This effect only occurred when TAN depletion was initiated at day 1 but not at day 7 of the experiment, indicating a relative importance of TANs in tumor progression at an early stage (FIGS. 11C and 11D).

In addition to a direct effect on tumor growth, it was determined whether TANs could affect desmoplasia. Preferential accumulation of TANs in areas with activated PSCs was observed (FIG. 11F), suggesting a paracrine crosstalk of TANs and PSCs.

Figure 11H:
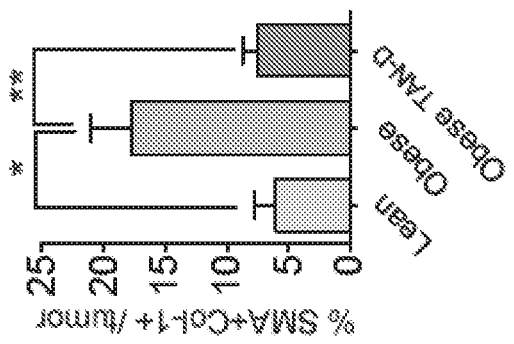
Figure 11F:
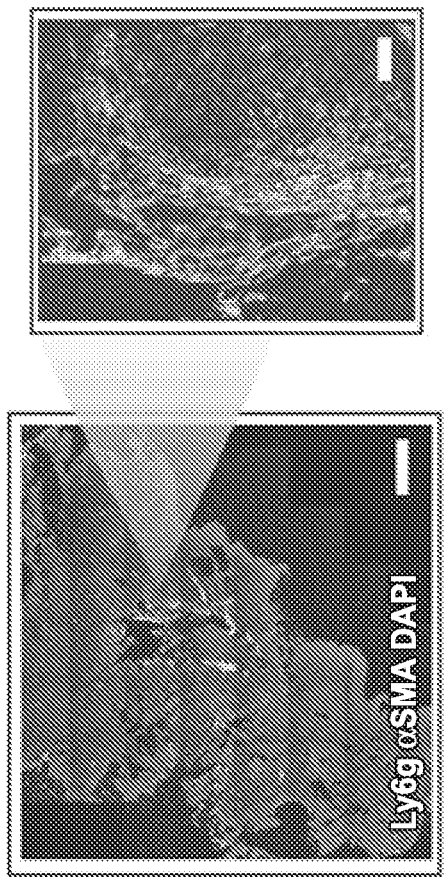
Figure 11G:
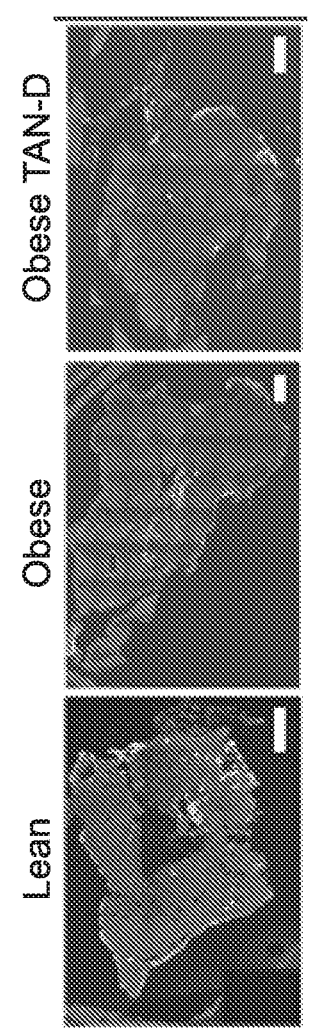
Figure 11J:
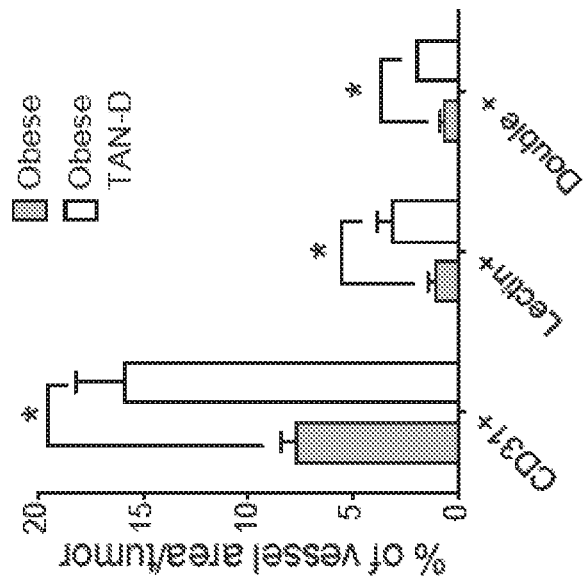
Figure 11I:
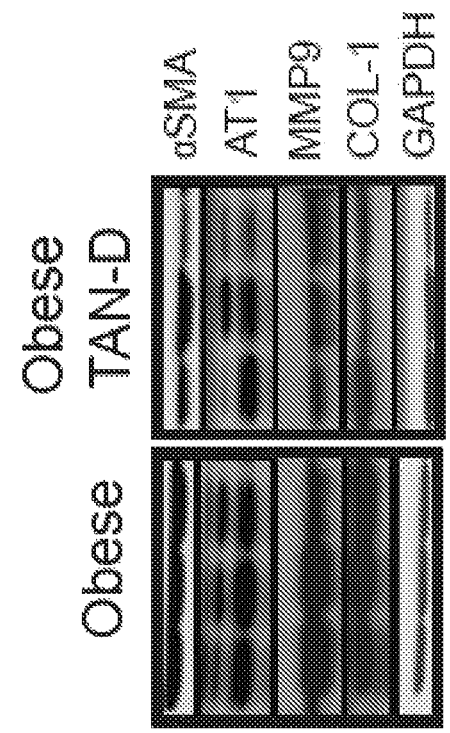
Figure 20B:
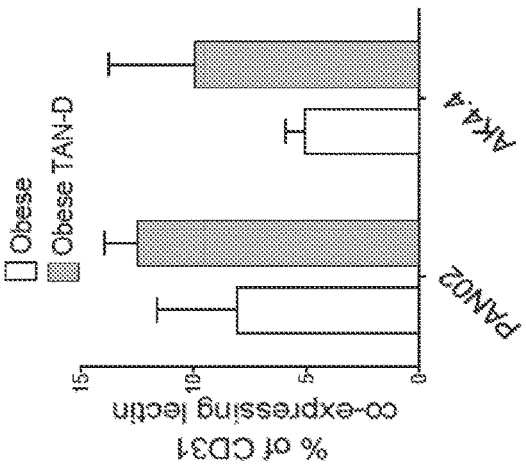
Figure 20C:
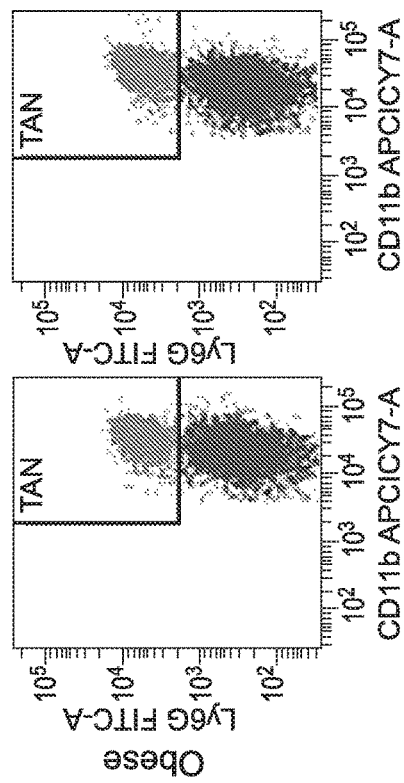

Consistently, TAN depletion decreased the number of activated PSCs in tumors from obese mice to the level observed in lean counterparts (FIGS. 11G, 11H, and 11I). Notably, the percentage of αSMA-positive PSCs that express collagen-1 (within the total αSMA positive PSC population) also dropped by 33% after TAN depletion (data not shown). Consistent with the reduction of activated PSCs, we observed reduction of AT1 expression, collagen production, and MMP9 expression in tumors from obese mice after TAN depletion (FIG. 11I). This corresponded to an increase in perfused vessels, although to a lesser extent in AK4.4 tumors (FIG. 11J, FIGS. 20B and 20C). These data indicate that obesity increases PSC activation, collagen production, and tumor progression at least in part due to increased recruitment of TANs.

IL-1ß Mediates Obesity-Induced TAN Infiltration and Fibrosis in PDACs

Figure 12B:
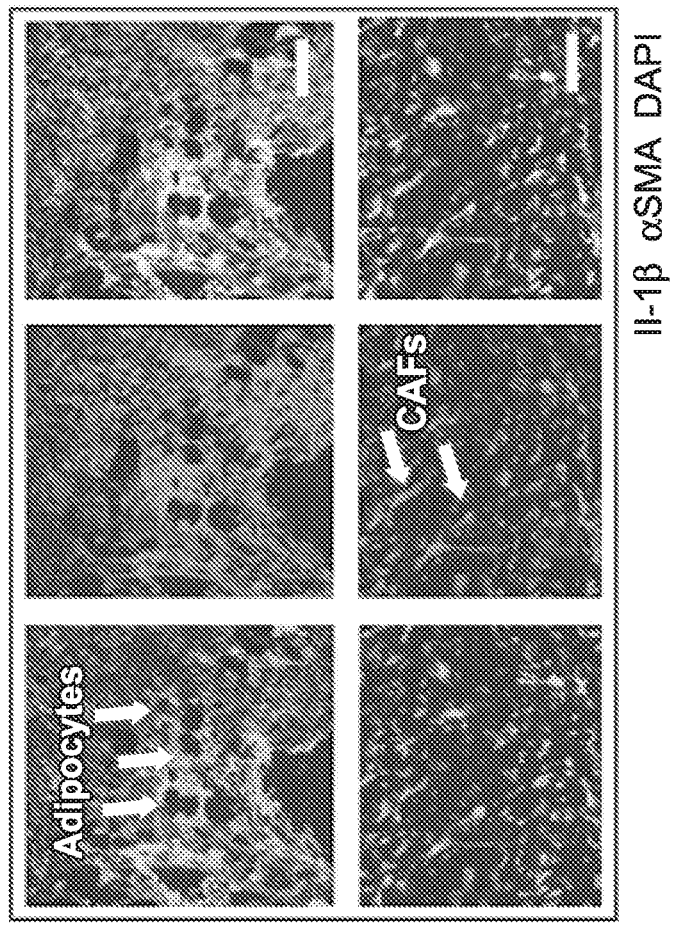
Figure 12A:
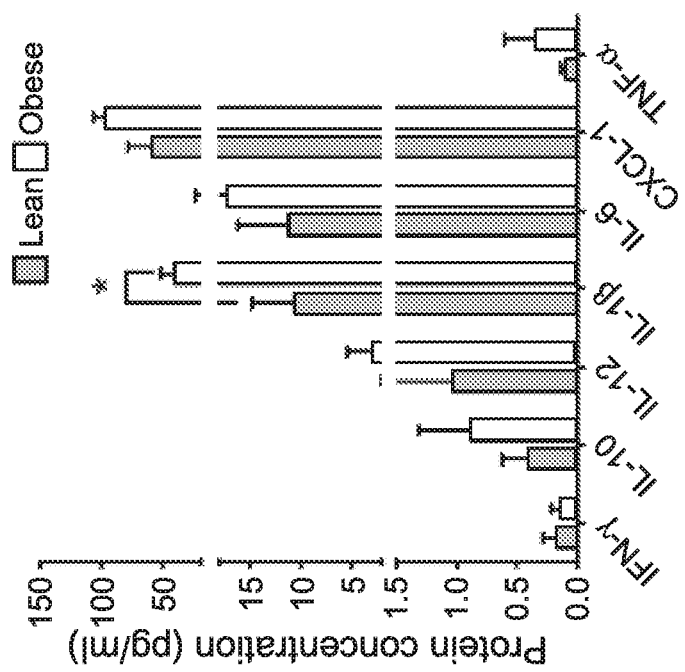
Figure 12G:
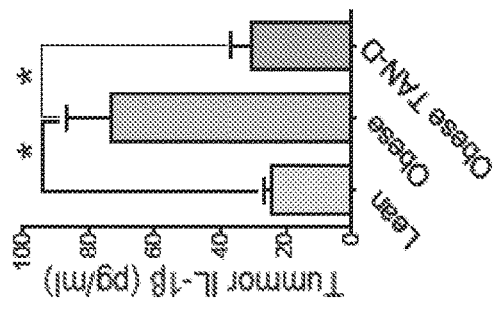
Figure 12F:
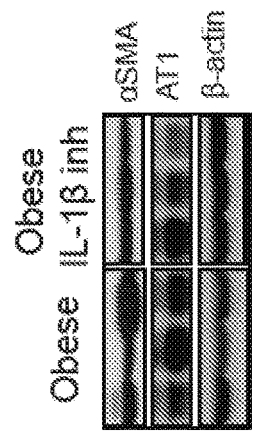
Figure 12H:
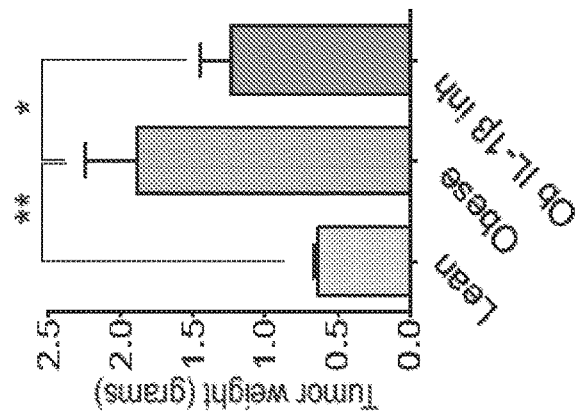
Figure 12I:
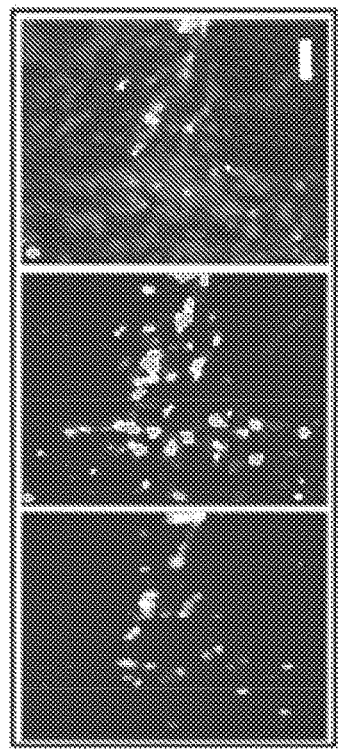
Figure 20D:
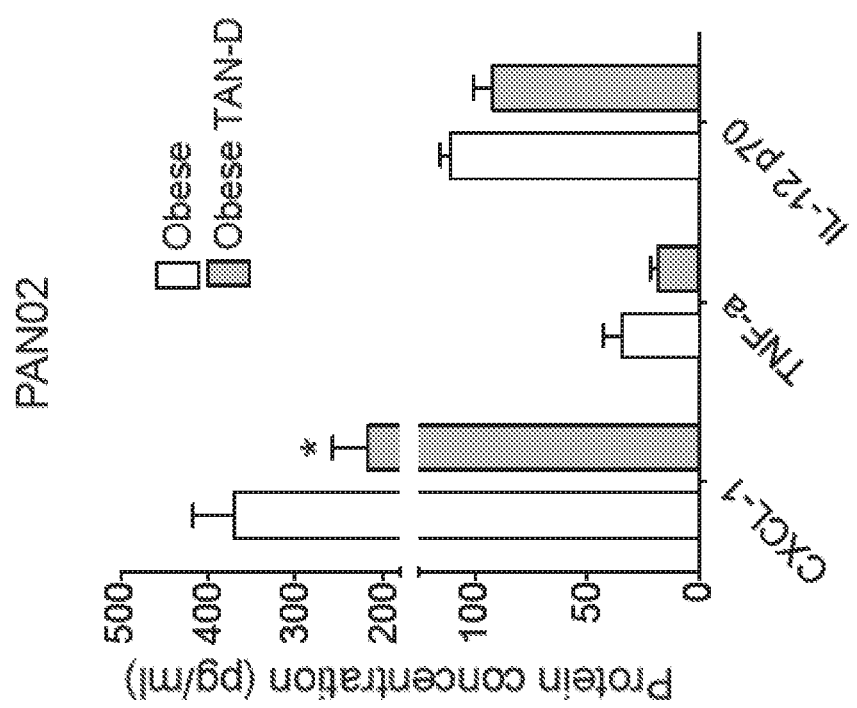

The pro-inflammatory/pro-fibrotic response and immune cell recruitment that occur in adipose tissue under obese condition is mediated by cytokine production from dysfunctional adipocytes, such as IL-1ß and IL-6 (24, 25, 48). Hence, it was determined whether these inflammatory cytokines mediated obesity-induced fibrotic processes and TAN infiltration in the tumor microenvironment. Indeed PAN02 tumors from obese mice had a 5-fold increased expression of IL1-ß, as well as a trend towards increased expression of IL-6, TNF-α, IL-12 and CXCL1 (FIG. 12A). Consistently, IL-1ß was abundantly expressed by adipocytes in the adipocyte-rich areas where PSCs predominate (FIG. 12B, upper row). Using an IL-1ß neutralizing antibody (MM425B, Endogen/Pierce Biotechnology, 2 mg/Kg i.p. q4d) in obese mice implanted with PAN02 tumors, a decrease in TAN infiltration (FIGS. 12C and 12D), as well as an increase in CD8(+) T cells and a decrease in Tregs was observed (FIG. 12E), suggesting reversal of the obesity-induced immunosuppressive microenvironment. Similar to the effects of TAN depletion, tumor growth in obese animals was reduced after IL-1ß inhibition, and the expression levels of αSMA and AT1 also decreased (FIGS. 12F and 12G). In addition to adipocytes, IL-1ß was also expressed in about 70% of TANs themselves (FIG. 12H), and TAN depletion reduced tumor IL-1ß levels (FIG. 12I). This suggests the presence of an autocrine mechanism that enables further TAN recruitment and potentiates inflammation and fibrosis. Association of obesity with increased levels of IL-1ß in tumors was confirmed in a second model, AK4.4 tumors (FIG. 19B). Other cytokines were also reduced with TAN depletion (CXCL1, and a trend for TNF-α and IL-12), indicating that these cytokines may also contribute to obesity-associated inflammation (FIG. 20D). Finally, αSMA-positive PSCs also abundantly expressed IL-1ß (FIG. 12B, lower row).

Figure 21A:
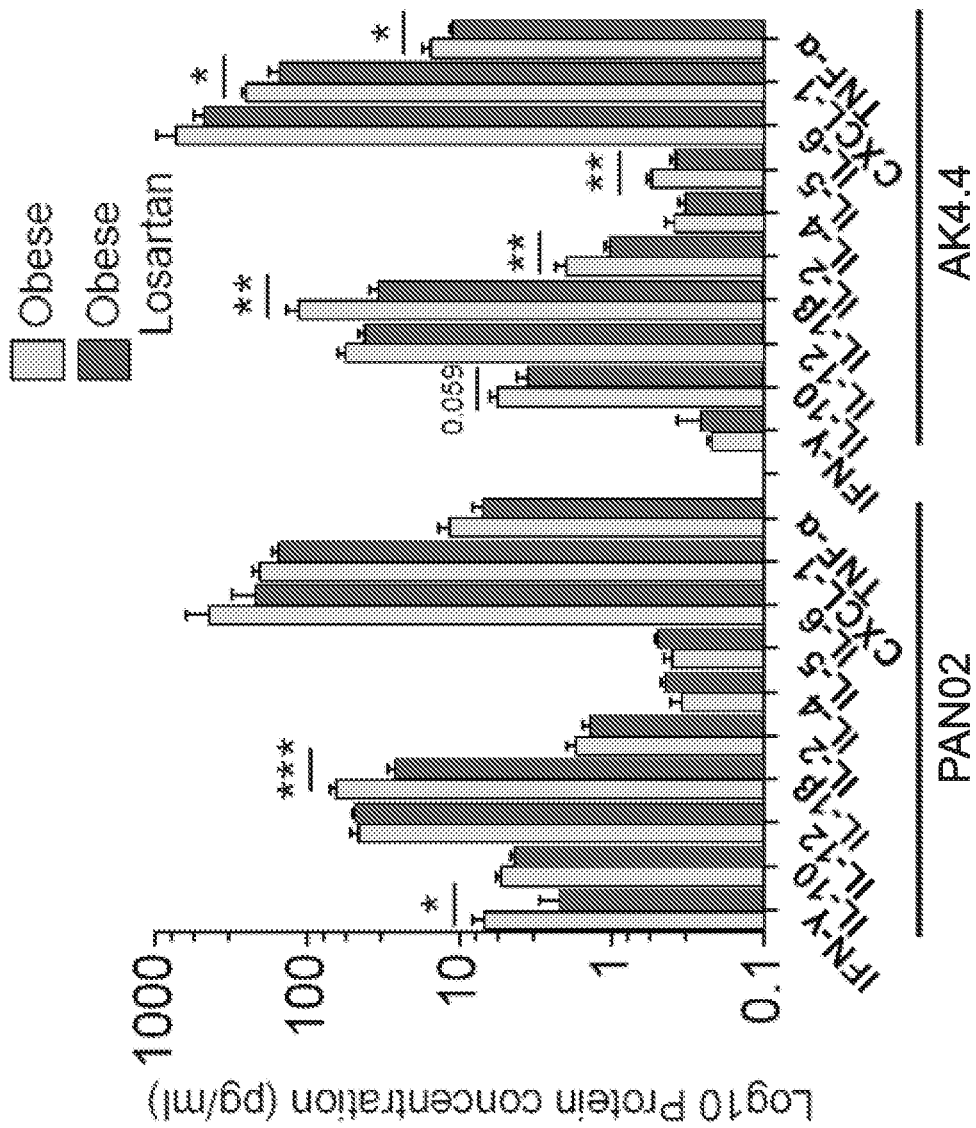
FIGS. 21A, 21B, and 21C show the effect of losartan on the immune tumor microenvironment.
Figure 21B:
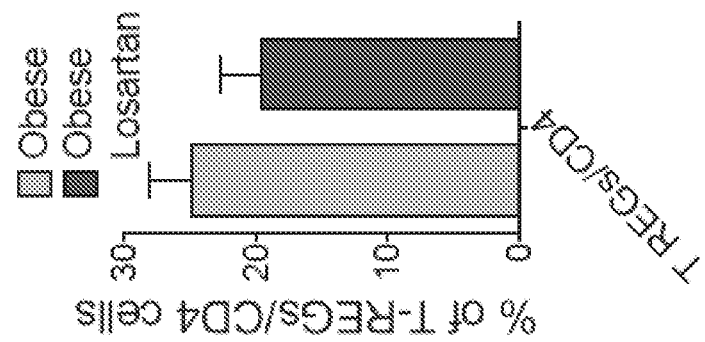
Figure 21C:
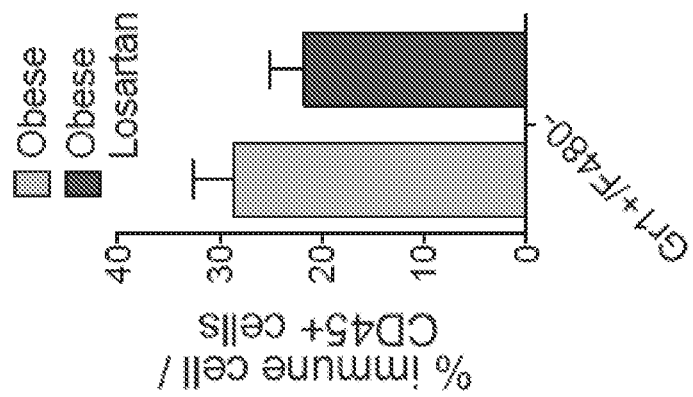

Since IL-1ß recruits TANs, which localize in close proximity to PSCs, the ability of targeting PSCs to interfere with IL-1ß production and TAN recruitment was examined in PAN02 tumors. Indeed, inhibition of PSC activation by genetic AT1 inhibition decreased IL-1ß and TAN levels in obese but not lean mice (FIG. 12J, 12K, and FIG. 21A). Consequently, recapitulating IL-1ß inhibition or TAN depletion, AT1 blockade increased CD8(+) T cells and reduced Tregs in tumors from obese but not lean mice (FIGS. 12J and 12K. Similar trends were observed for losartan in the AK4.4 tumor model (FIGS. 21B and 21C). These effects on tumor-promoting IL-1ß and immune cells are consistent with the prevention of obesity-induced tumor growth observed earlier (FIG. 10K). Taken together, these findings indicate that a crosstalk between fibrosis and inflammation induces the fibro-inflammatory microenvironment, promotes tumor progression, and causes chemotherapy resistance in obesity.

PDAC in Obese Patients Presents with Increased Adipocyte Area and Fibrosis

Figure 13D:
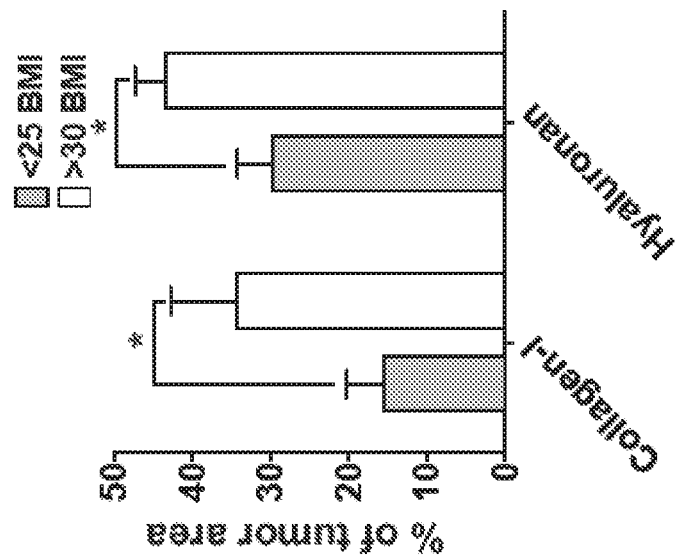
Figure 13C:
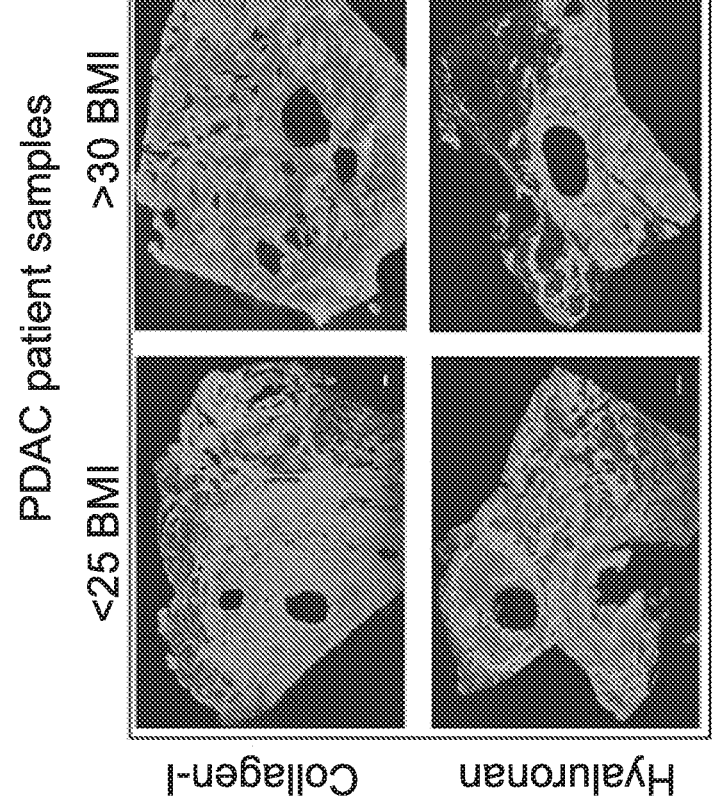

To validate the findings from mouse models of PDAC, human PDAC samples were analyzed from treatment-naïve patients that presented with a body mass index (BMI) either below 25 or above 30. As in the mouse models, tumors from obese (BMI>30) patients presented with hypertrophic adipocytes (FIGS. 13A and 13B) and more pronounced ECM deposition—as shown by increased collagen-I and hyaluronan expression (FIGS. 13C and 13D).

Discussion

Obesity Promotes AT-1-Dependent PSC Activation, Tumor Desmoplasia and Hinders Efficacy of Chemotherapy Although preclinical models have shown that obesity promotes pancreatic tumor initiation, growth, and metastasis (31, 49-52), the underlying mechanisms remain largely elusive. Furthermore, no study has evaluated whether obesity interferes with the response to chemotherapy in pancreatic cancer. Here it is demonstrated for the first time that obesity worsens the fibro-inflammatory microenvironment in PDACs, which leads to increased tumor growth and metastasis and reduced delivery and efficacy of chemotherapy. PSCs and their activation via AT1 signaling are known to play a fundamental role in the production of ECM in pancreatic cancer (21). However, an alteration of PSC behavior in obesity had not been demonstrated. Here it is demonstrated that AT1 signaling mediates obesity-induced PSC activation, which results in the accumulation of ECM components such as collagen-I and HA. AT1 inhibition could normalize collagen-I levels by using a widely prescribed ARB (losartan) or genetic deficiency in mice. This occurred particularly in the more fibrotic tumors in obese mice, leading to a significantly improved response to chemotherapy in the obese but not lean setting. These data are consistent with fibrotic changes observed in early pancreatic lesions (PanIN) in mice fed a high-fat diet (51, 52), and with a recent publication showing the effect of obesity-altered ECM on breast tumorigenesis (53). However, the impact of obesity on desmoplasia and treatment outcome of PDACs was not homogeneous among different PDAC models. Indeed, differences between the lean and obese settings were more pronounced in PDACs with low baseline desmoplasia (e.g., PAN02) than in PDACs with high baseline desmoplasia (e.g., AK4.4).

IL-1ß-Mediated TAN Recruitment in Adipocyte-Rich Regions Augments PSC Activation and Desmoplasia in Obesity Fibrosis is a natural consequence of chronic inflammation. Indeed, obesity promotes secretion of inflammatory cytokines from hypertrophic adipocytes in adipose tissues and the pancreas, and this ultimately leads to local tissue fibrosis (24, 25, 28, 30, 54). In addition, fibrosis is also accompanied by inflammation in early-stage neoplastic lesions in the pancreas in mice fed with a high-fat diet (51, 52). However, how hypertrophic adipocytes facilitate the interaction between inflammation and desmoplasia to ultimately promote progression of PDACs in the obese setting was not known. Similar to previous reports (31, 32, 34), we demonstrated that hypertrophic, and hence dysfunctional, adipocytes accumulate in both mouse tumors and patient samples. These intratumoral adipocytes, which have been referred to as cancer-associated adipocytes (CAAs) in breast cancer (34), localize to tumor extremities and can promote tumor invasion (35). Furthermore, it was shown that CAAs abundantly expressed IL-1ß in PDACs, leading to increased total levels of this cytokine in tumors in obese mice. Not surprising given the ability of adipocytes to produce this cytokine, non-cancer obese patients have increased plasma levels of IL-1ß (55). In this example, an accumulation of activated PSCs was observed around adipocyte-rich areas where adipocytes produce IL-1ß abundantly. In line with IL-1ß being a major activator of PSCs (56), blockade of IL-1ß inhibits PSC activation in the obese PDACs. Given the increased adipocyte burden in tumors in obese animals, the overall PSC activation and fibrotic content in tumors was consequently increased. In addition to PSC activation, IL-1ß could recruit/activate TANs. This is consistent with increased levels of myeloperoxidase—a marker for intrapancreatic neutrophil sequestration/activation—in association with IL-1ß in the steatotic pancreas of obese mice (28, 57). Furthermore, it was observed that TANs can also secrete further IL-1ß, which then activates PSCs and TANs themselves. Consequently, TAN specific depletion reduced PSC activation, AT1 signaling, MMP-9 expression and collagen-I production. It is important to note that the accumulation of PSCs in tumors in obese mice may have been caused in part by a dedifferentiation of adipocytes. During tumor invasion in breast cancer, the direct interaction between adipocytes and epithelial cancer cells promote phenotypic changes of CAAs, which lead to adipocyte dedifferentiation and ultimately to an accumulation of fibroblast-like cells (35, 58).

TANs and IL-1ß Play a Major Role on Immunosuppression and Tumor Progression in Obesity Inflammation in obesity may also promote tumor progression via immunosuppression. The obesity-induced increase in TANs occurs concomitant with decreased CD8(+) cells and increased Tregs, typical of an immunosuppressive microenvironment that promotes tumor progression (59). Importantly, we found that depleting TAN in obese mice increased CD8(+) cells in tumors, as previously reported (60), and this associated with reduced tumor growth acceleration. This is consistent with the correlation between TAN infiltration and more aggressive types of pancreatic tumors (61). Importantly, and as expected due to TAN-recruiting effect of IL-1ß, IL-1ß inhibition recapitulates the effect of TAN depletion on the immune phenotype and tumor growth. Considering that the immune environment in obesity appears to be suppressed, and the unprecedented success of therapies that block immune checkpoint pathways (59), it would be interesting to evaluate whether these therapies will be particularly effective in obese hosts.

A Reciprocal Crosstalk Between CAAs, TANs and PSCs is Enhanced in Obesity to Worsen Desmoplasia and Promote Tumor Growth It was also found that PSC inactivation after AT1 blockade, in addition to decreasing obesity-associated desmoplasia, also reduces levels of IL-1ß, decreases the infiltration of TANs and Tregs, increases the number of CD8(+) cells, and reduces obesity-associated tumor growth.

Figure 13E:
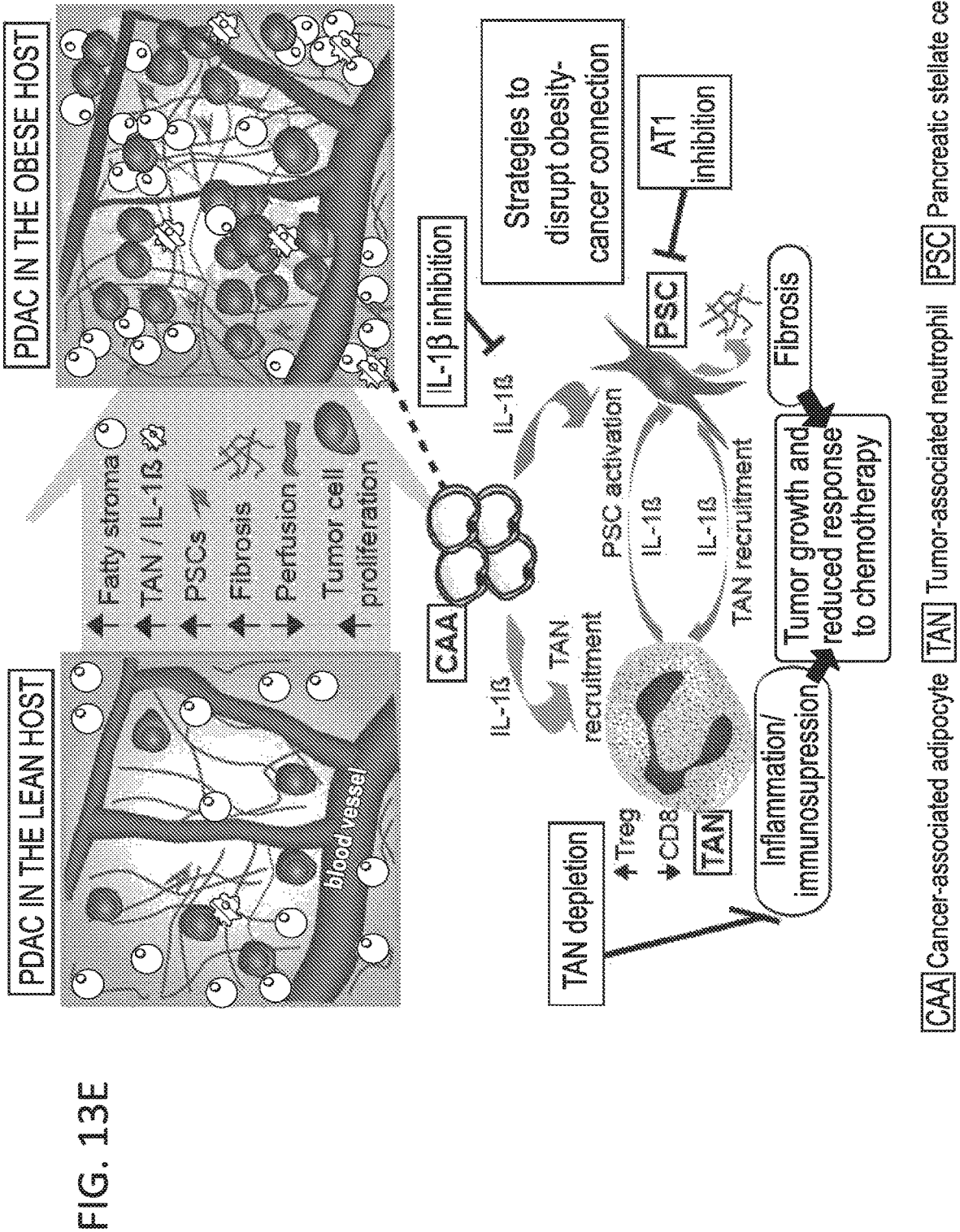

Thus, these results reveal that the interaction of inflammation and fibrosis is bidirectional—targeting inflammation reduces desmoplasia, and in turn targeting desmoplasia reduces inflammation, with both approaches reducing tumor growth. This is consistent with previous in vitro work demonstrating that neutrophils interact reciprocally with myofibroblasts and PSCs (62, 63). As discussed, these results reveal a crosstalk between CAAs, TANs, and PSCs that promotes tumor progression and desmoplasia in obese hosts, with IL-1ß (secreted by all these cells) playing a major role in this cooperation (FIG. 13E). This explains that fat reserves can drive tumor growth (64). Importantly, in more than half of PDAC patients, adipocytes infiltrate >20% of pancreatic tissue (32), underlining the importance of the interactions of these cells in the tumor microenvironment. Indeed, increased intra-pancreatic fat correlates with increased incidence of PDAC and lymphatic spread of tumor cells and resulting decreased survival in pancreatic cancer patients (32, 65).

Figure 22:
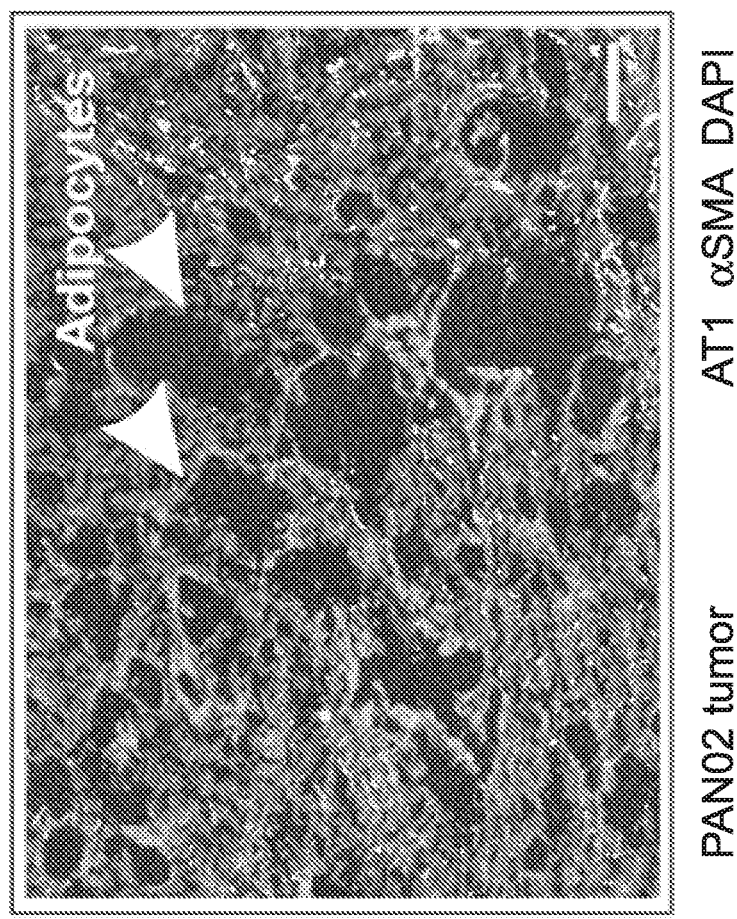
FIG. 22 is a representative picture of AT1 expression in cancer-associated adipocytes in PAN02 tumors. Cancer-associated adipocytes (arrows), similar to normal adipocytes, express AT1. Scale bar: 100 µm.

Interestingly, the effect of AT1 inhibition on improving response to chemotherapy in obese mice may occur not only via reduced desmoplasia, but also by directly affecting tumor growth. Since TANs and adipocytes also abundantly expressed AT1 (FIG. S9), AT1 blockade may be acting not just on PSCs, but also directly on those cells. Hence, AT-1 blockade would also directly reduce IL-1ß production, TAN infiltration, tumor growth and the enhanced desmoplasia that occurs with obesity. In fact, AT1 is highly expressed in adipocytes (FIG. 22) (26) and increases its activity in adipose tissues in obesity (26, 27). Furthermore, as mentioned above adipocytes can dedifferentiate to become fibroblast-like cells capable of producing collagen in both tumor and non-tumor settings (66-68). Hence AT1 blockade could be affecting the central culprit of the fibro-inflammatory cycle generated in the obese setting—the CAA.

Of note, consistent with previous work in PAN02 tumors (69), by using both genetic and diet-induced obese mouse models, it was determined that obesity promotes tumor growth independently of diet. This was also confirmed by the finding that FVB mice which do not gain weight despite a high-fat diet (~25% of mice), observed tumor growth similar to that in lean animals (not shown).

Conclusions

Obesity is considered to be responsible for 14-20% of all cancer-related deaths in the United States (5). Consequently, the epidemic of obesity—which also affects the majority of PDAC patients—highlights the importance of understanding the pathophysiology underlying the obesity-cancer connection. Here, it is shown that obesity induces a pro-inflammatory and desmoplastic tumor microenvironment, which directly promotes tumor growth, as well as impairs the response to systemic treatment. Both of these two factors may explain the poor outcomes in obese patients. The finding that obesity-induced desmoplasia better responds to clinically available anti-fibrotic therapies (e.g., ARBs) as well as anti-inflammatory agents (e.g., IL-1ß inhibitor), is extremely encouraging and calls for an investigation and clinical trials on the efficacy of these therapies in obese PDAC patients in combination with the current standard-of-care. Since epidemiological and molecular evidence suggests a link between obesity and other desmoplastic cancer types, the strategies established in this study may also apply to a broader patient population.

REFERENCES FOR EXAMPLE 12

1. ACS CFF. Cancer Facts & Figures 2014. ACS, 2014; Available from: http://www.cancer.org/research/cancer-factsstatistics/cancerfactsfigures2014
2. American Cancer Society: Cancer Facts and Figures 2015. http://wwwcancerorg/acs/groups/content/@editorial/documents/document/acspc-044552pdf.
3. Genkinger J M, Spiegelman D, Anderson K E, Bernstein L, van den Brandt P A, Calle E E, et al. A pooled analysis of 14 cohort studies of anthropometric factors and pancreatic cancer risk. International journal of cancer Journal international du cancer. 2011; 129:1708-17.
4. Yuan C, Bao Y, Wu C, Kraft P, Ogino S, Ng K, et al. Prediagnostic body mass index and pancreatic cancer survival. Journal of clinical oncology: official journal of the American Society of Clinical Oncology. 2013; 31:4229-34.
5. Calle E E, Rodriguez C, Walker-Thurmond K, Thun M J. Overweight, obesity, and mortality from cancer in a prospectively studied cohort of U.S. adults. N Engl J Med. 2003; 348:1625-38.
6. McWilliams R R, Matsumoto M E, Burch P A, Kim G P, Halfdanarson T R, de Andrade M, et al. Obesity adversely affects survival in pancreatic cancer patients. Cancer. 2010; 116:5054-62.
7. Li D, Morris J S, Liu J, Hassan M M, Day R S, Bondy M L, et al. Body mass index and risk, age of onset, and survival in patients with pancreatic cancer. JAMA: the journal of the American Medical Association. 2009; 301: 2553-62.
8. Bracci P M. Obesity and pancreatic cancer: overview of epidemiologic evidence and biologic mechanisms. Molecular carcinogenesis. 2012; 51:53-63.
9. Smits M M, van Geenen E J. The clinical significance of pancreatic steatosis. Nature reviews Gastroenterology & hepatology. 2011; 8:169-77.
10. Goodwin P J, Stambolic V. Impact of the obesity epidemic on cancer. Annual review of medicine. 2015; 66:281-96.
11. Ogden C L, Carroll M D, Kit B K, Flegal K M. Prevalence of childhood and adult obesity in the United States, 2011-2012. JAMA: the journal of the American Medical Association. 2014; 311:806-14.
12. Dvorak H F. Tumors: wounds that do not heal. Similarities between tumor stroma generation and wound healing. N Engl J Med. 1986; 315:1650-9.
13. Whatcott C J, Diep C H, Jiang P, Watanabe A, LoBello J, Sima C, et al. Desmoplasia in primary tumors and metastatic lesions of pancreatic cancer. Clin Cancer Res. 2015.
14. Olive K P, Jacobetz M A, Davidson C J, Gopinathan A, McIntyre D, Honess D, et al. Inhibition of Hedgehog signaling enhances delivery of chemotherapy in a mouse model of pancreatic cancer. Science. 2009; 324:1457-61.
15. Hwang R F, Moore T, Arumugam T, Ramachandran V, Amos K D, Rivera A, et al. Cancer-associated stromal fibroblasts promote pancreatic tumor progression. Cancer Res. 2008; 68:918-26.
16. Neesse A, Frese K K, Bapiro T E, Nakagawa T, Sternlicht M D, Seeley T W, et al. CTGF antagonism with mAb FG-3019 enhances chemotherapy response without increasing drug delivery in murine ductal pancreas cancer. Proceedings of the National Academy of Sciences of the United States of America. 2013; 110:12325-30.
17. Stylianopoulos T, Martin J D, Chauhan V P, Jain S R, Diop-Frimpong B, Bardeesy N, et al. Causes, consequences, and remedies for growth-induced solid stress in murine and humantumors. Proceedings of the National Academy of Sciences of the United States of America. 2012; 109:15101-8.
18. Chauhan V P, Boucher Y, Ferrone C R, Roberge S, Martin J D, Stylianopoulos T, et al. Compression of pancreatic tumor blood vessels by hyaluronan is caused by solid stress and not interstitial fluid pressure. Cancer Cell. 2014; 26:14-5.
19. Alvarez R, Musteanu M, Garcia-Garcia E, Lopez-Casas P P, Megias D, Guerra C, et al. Stromal disrupting effects of nab-paclitaxel in pancreatic cancer. British Journal of Cancer. 2013; 109:926-33.
20. Hidalgo M, Von Hoff D D. Translational Therapeutic Opportunities in Ductal Adenocarcinoma of the Pancreas. Clinical Cancer Research. 2012; 18:4249-56.
21. Chauhan V P, Martin J D, Liu H, Lacorre D A, Jain S R, Kozin S V, et al. Angiotensin inhibition enhances drug delivery and potentiates chemotherapy by decompressing tumor blood vessels. Nature Communications. 2013; 4:2516.
22. Endrich B, Reinhold H S, Gross J F, Intaglietta M. Tissue perfusion inhomogeneity during early tumor growth in rats. J Natl Cancer Inst. 1979; 62:387-95.
23. Costa C, Incio J, Soares R. Angiogenesis and chronic inflammation: cause or consequence? Angiogenesis. 2007; 10:149-66.
24. Hosogai N, Fukuhara A, Oshima K, Miyata Y, Tanaka S, Segawa K, et al. Adipose tissue hypoxia in obesity and its impact on adipocytokine dysregulation. Diabetes. 2007; 56:901-11.
25. Incio J, Soares R. Obesity, Diabetes and Metabolic Syndrome Impact on TUMOR ANGIOGENESIS. In: Ruben R. Gonzalez-Perez B R R, editor. Tumor Angiogenesis Regulators: CRC Press; 2013.
26. http://biogps.org. AGTR1 (angiotensin II receptor, type 1) gene expression, activity chart. 2015.
27. Sun K, Tordjman J, Clement K, Scherer P E. Fibrosis and adipose tissue dysfunction. Cell metabolism. 2013; 18:470-7.
28. Mathur A, Marine M, Lu D, Swartz-Basile D A, Saxena R, Zyromski N J, et al. Nonalcoholic fatty pancreas disease. HPB: the official journal of the International Hepato Pancreato Biliary Association. 2007; 9:312-8.
29. Matsuda A, Makino N, Tozawa T, Shirahata N, Honda T, Ikeda Y, et al. Pancreatic fat accumulation, fibrosis, and acinar cell injury in the Zucker diabetic fatty rat fed a chronic high-fat diet. Pancreas. 2014; 43:735-43.
30. Hursting S D. Minireview: the year in obesity and cancer. Molecular endocrinology. 2012; 26:1961-6.
31. Zyromski N J, Mathur A, Pitt H A, Wade T E, Wang S, Nakshatri P, et al. Obesity potentiates the growth and dissemination of pancreatic cancer. Surgery. 2009; 146: 258-63.

32. Hori M, Takahashi M, Hiraoka N, Yamaji T, Mutoh M, Ishigamori R, et al. Association of pancreatic Fatty infiltration with pancreatic ductal adenocarcinoma. Clinical and translational gastroenterology. 2014; 5:e53.
33. Hefetz-Sela S, Scherer P E. Adipocytes: impact on tumor growth and potential sites for therapeutic intervention. Pharmacology & therapeutics. 2013; 138:197-210.
34. Dirat B, Bochet L, Dabek M, Daviaud D, Dauvillier S, Majed B, et al. Cancer-associated adipocytes exhibit an activated phenotype and contribute to breast cancer invasion. Cancer Res. 2011; 71:2455-65.
35. Wang Y Y, Lehuede C, Laurent V, Dirat B, Dauvillier S, Bochet L, et al. Adipose tissue and breast epithelial cells: a dangerous dynamic duo in breast cancer. Cancer letters. 2012; 324:142-51.
36. Hingorani S R, Wang L, Multani A S, Combs C, Deramaudt T B, Hruban R H, et al. Trp53R172H and KrasG12D cooperate to promote chromosomal instability and widely metastatic pancreatic ductal adenocarcinoma in mice. Cancer cell. 2005; 7:469-83.
37. Kawaguchi Y, Cooper B, Gannon M, Ray M, MacDonald RJ, Wright C V. The role of the transcriptional regulator Ptf1a in converting intestinal to pancreatic progenitors. Nature genetics. 2002; 32:128-34.
38. Tam J, Duda D G, Perentes J Y, Quadri R S, Fukumura D, Jain R K. Blockade of VEGFR2 and not VEGFR1 can limit diet-induced fat tissue expansion: role of local versus bone marrow-derived endothelial cells. PloS one. 2009; 4:e4974.
39. Fukumura D, Ushiyama A, Duda D G, Xu L, Tam J, Krishna V, et al. Paracrine regulation of angiogenesis and adipocyte differentiation during in vivo adipogenesis. Circulation research. 2003; 93:e88-97.
40. Kanasaki K, Koya D. Biology of obesity: lessons from animal models of obesity. Journal of biomedicine & biotechnology. 2011; 2011:197636.
41. Koshiba T, Hosotani R, Wada M, Miyamoto Y, Fujimoto K, Lee J U, et al. Involvement of matrix metalloproteinase-2 activity in invasion and metastasis of pancreatic carcinoma. Cancer. 1998:82:642-50.
42. Collins M A, Bednar F, Zhang Y, Brisset J C, Galban S, Galban C J, et al. Oncogenic Kras is required for both the initiation and maintenance of pancreatic cancer in mice. J Clin Invest. 2012; 122:639-53.
43. Neoptolemos J P, Moore M J, Cox T F, Valle J W, Palmer D H, McDonald A C, et al. Effect of adjuvant chemotherapy with fluorouracil plus folinic acid or gemcitabine vs observation on survival in patients with resected periampullary adenocarcinoma: the ESPAC-3 periampullary cancer randomized trial. JAMA: the journal of the American Medical Association. 2012; 308:147-56.
44. Apte M V, Park S. Phillips P A, Santucci N, Goldstein D, Kumar R K, et al. Desmoplastic reaction in pancreatic cancer—Role of pancreatic stellate cells. Pancreas. 2004; 29:179-87.
45. Yang F, Chung A C, Huang X R, Lan H Y. Angiotensin II induces connective tissue growth factor and collagen I expression via transforming growth factor-beta-dependent and -independent Smad pathways: the role of Smad3. Hypertension. 2009; 54:877-84.
46. Hama K, Ohnishi H, Yasuda H, Ueda N, Mashima H, Satoh Y, et al. Angiotensin II stimulates DNA synthesis of rat pancreatic stellate cells by activating ERK through EGF receptor transactivation. Biochemical and Biophysical Research Communications. 2004; 315:905-11.
47. Hama K, Ohnishi H, Aoki H, Kita H, Yamamoto H, Osawa H, et al. Angiotensin II promotes the proliferation of activated pancreatic stellate cells by Smad7 induction through a protein kinase C pathway. Biochemical and Biophysical Research Communications. 2006; 340:742-50.
48. Weisberg S P, McCann D, Desai M, Rosenbaum M, Leibel R L, Ferrante A W, Jr. Obesity is associated with macrophage accumulation in adipose tissue. J Clin Invest. 2003, 12:1796-808.
49. Murtaugh L C. Pathogenesis of pancreatic cancer: lessons from animal models. Toxicologic pathology. 2014; 42:217-28.
50. White P B, True E M, Ziegler K M, Wang S S, Swartz-Basile D A, Pitt H A, et al. Insulin, leptin, and tumoral adipocytes promote murine pancreatic cancer growth. Journal of gastrointestinal surgery: official journal of the Society for Surgery of the Alimentary Tract. 2010; 14:1888-93; discussion 93-4.
51. Philip B, Roland C L, Daniluk J, Liu Y, Chatterjee D, Gomez S B, et al. A high-fat diet activates oncogenic Kras and COX2 to induce development of pancreatic ductal adenocarcinoma in mice. Gastroenterology. 2013; 145: 1449-58.
52. Khasawneh J, Schulz M D, Walch A, Rozman J, Hrabe de Angelis M, Klingenspor M, et al. Inflammation and mitochondrial fatty acid beta-oxidation link obesity to early tumor promotion. Proc Natl Acad Sci USA. 2009; 106:3354-9.
53. Seo B R, Bhardwaj P, Choi S, Gonzalez J, Andresen Eguiluz R C, Wang K, et al. Obesity-dependent changes in interstitial ECM mechanics promote breast tumorigenesis. Science translational medicine. 2015; 7:301ra130.
54. Hursting S D, Dunlap S M. Obesity, metabolic dysregulation, and cancer: a growing concern and an inflammatory (and microenvironmental) issue. Annals of the New York Academy of Sciences. 2012; 1271:82-7.
55. Um J Y, Chung H S, Song M Y, Shin H D, Kim H M. Association of interleukin-1beta gene polymorphism with body mass index in women. Clinical chemistry. 2004; 50:647-50.
56. Masamune A, Satoh M, Kikuta K, Sakai Y, Satoh A, Shimosegawa T. Inhibition of p38 mitogen-activated protein kinase blocks activation of rat pancreatic stellate cells. The Journal of pharmacology and experimental therapeutics. 2003; 304:8-14.
57. Zyromski N J, Mathur A, Pitt H A, Lu D, Gripe J T, Walker J J, et al. A murine model of obesity implicates the adipokine milieu in the pathogenesis of severe acute pancreatitis. American journal of physiology Gastrointestinal and liver physiology. 2008; 295:G552-8.
58. Tan J, Buache E, Chenard M P, Dali-Youcef N, Rio M C. Adipocyte is a non-trivial, dynamic partner of breast cancer cells. The International journal of developmental biology. 2011; 55:851-9.
59. Coussens L M, Zitvogel L, Palucka A K. Neutralizing tumor-promoting chronic inflammation: a magic bullet? Science. 013; 339:286-91.
60. Fridlender Z G, Sun J, Kim S, Kapoor V, Cheng G, Ling L, et al. Polarization of tumor-associated neutrophil phenotype by TGF-beta: "N1" versus "N2" TAN. Cancer Cell. 2009; 16:183-94.
61. Reid M D, Basturk O, Thirabanjasak D, Hruban R H, Klimstra D S, Bagci P, et al. Tumor-infiltrating neutrophils in pancreatic neoplasia. Modern pathology: an official journal of the United States and Canadian Academy of Pathology, Inc. 2011; 24:1612-9.
62. Chrysanthopoulou A, Mitroulis I, Apostolidou E, Arelaki S, Mikroulis D, Konstantinidis T, et al. Neutrophil extracellular traps promote differentiation and function of fibroblasts. The Journal of pathology. 2014; 233:294-307.
63. Zhu Q, Zhang X, Zhang L, Li W, Wu H, Yuan X, et al. The IL-6-STAT3 axis mediates a reciprocal crosstalk between cancer-derived mesenchymal stem cells and neutrophils to synergistically prompt gastric cancer progression. Cell death & disease. 2014; 5:e1295.
64. Williams S C. Link between obesity and cancer. Proc Natl Acad Sci USA. 2013; 110:8753-4.
65. Mathur A, Zyromski N J, Pitt H A, Al-Azzawi H, Walker J J, Saxena R, et al. Pancreatic steatosis promotes dissemination and lethality of pancreatic cancer. J Am Coll Surg. 2009; 208:989-94-6;
66. Jotzu C, Alt E, Welte G, Li J, Hennessy B T, Devarajan E, et al. Adipose tissue derived stem cells differentiate into carcinoma-associated fibroblast-like cells under the influence of tumor derived factors. Cellular oncology. 2011; 34:55-67.
67. Park J, Euhus D M, Scherer P E. Paracrine and endocrine effects of adipose tissue on cancer development and progression. Endocr Rev. 2011; 32:550-70.
68. Matsumoto T, Kano K, Kondo D, Fukuda N, Iribe Y, Tanaka N, et al. Mature adipocyte-derived dedifferentiated fat cells exhibit multilineage potential. J Cell Physiol. 2008; 215:210-22.
69. White P B, Ziegler K M, Swartz-Basile D A, Wang S S, Lillemoe K D, Pitt H A, et al. Obesity, but not high-fat diet, promotes murine pancreatic cancer growth. Journal of gastrointestinal surgery: official journal of the Society for Surgery of the Alimentary Tract. 2012; 16:1680-5.
70. Surwit R S, Feinglos M N, Rodin J, Sutherland A, Petro A E, Opara E C, et al. Differential effects of fat and sucrose on the development of obesity and diabetes in C57BL/6J and A/J mice. Metabolism: clinical and experimental. 1995; 44:645-51.
71. Bardeesy N, Aguirre A J, Chu G C, Cheng K H, Lopez L V, Hezel A F, et al. Both p16(Ink4a) and the p19(Arf)-p53 pathway constrain progression of pancreatic adenocarcinoma in the mouse. Proc Natl Acad Sci USA. 2006; 103:5947-52.
72. Diop-Frimpong B, Chauhan V P, Krane S, Boucher Y, Jain R K. Losartan inhibits collagen I synthesis and improves the distribution and efficacy of nanotherapeutics in tumors. Proceedings of the National Academy of Sciences of the United States of America. 2011; 108:2909-14.

Example 13: Biodistribution and Pharmacokinetic Profile of Can-DPC

The purpose of this single-dose PK study was to evaluate the in vivo drug release of Can-DPC in 4T1 tumor bearing animals by collecting whole blood, tumor, and liver tissue for bioanalytical quantification of polymer-conjugated and released drug (i.e., candesartan). In this example, the Can-DPC formulation (10 mg/kg) was administrated intravenously as a single bolus and compared directly with the PK profile of candesartan cilexetil administered by oral gavage (10 mg/kg) using 0.5% HPMC as a vehicle (Table 5).

The mammary fat pads of Balb/C female mice (6-8 weeks old; Taconic) were implanted with syngeneic 4T1 mouse tumor cells (150,000 cells/per animal) obtained from ATCC. Tumors were allowed to develop for 10 days, reaching an average size of 150-450 mm³ (caliper measurements), before the mice were randomized into three dose groups (Table 5). Following a single administration of the test agents (10 mg/kg) or vehicle alone, whole blood, tumor, and liver tissues were collected at 2, 24, 48 and 144 hrs post dose. In addition, intermediate submandibular bleeds (~100 µL whole blood) were collected at 5 min, 30 min, 4 hrs, and 6 hrs (n=3 animals per timepoint) following the i.v. and p.o. dosing. At the time of sacrifice, each tumor and liver sample was split into two equal parts for PK analysis (flash frozen) and immunohistochemistry (fixed in 10% neutral buffered formalin), respectively. Whole blood was collected directly into EDTA tubes and frozen at −30 C.

TABLE 5

(In vivo dose is listed by amount of Candesartan)

| Study Groups | 2 hr | 24 hr | 48 hr | 144 hr | Total Mice per group |
|---|---|---|---|---|---|
| #1 Vehicle (0.5% HPMC) p.o. once | | | n = 3 | | 3 |
| #2 Candesartan (10 mg/kg) p.o. once | n = 3 | n = 3 | n = 3 | | 9 |
| #3 Drug Can-DPC (10 mg/kg) i.v. once | n = 3 | n = 3 | n = 3 | n = 3 | 12 |
| Total mice per time point | 6 | 6 | 9 | 3 | Total n = 24 |

Figure 26A:
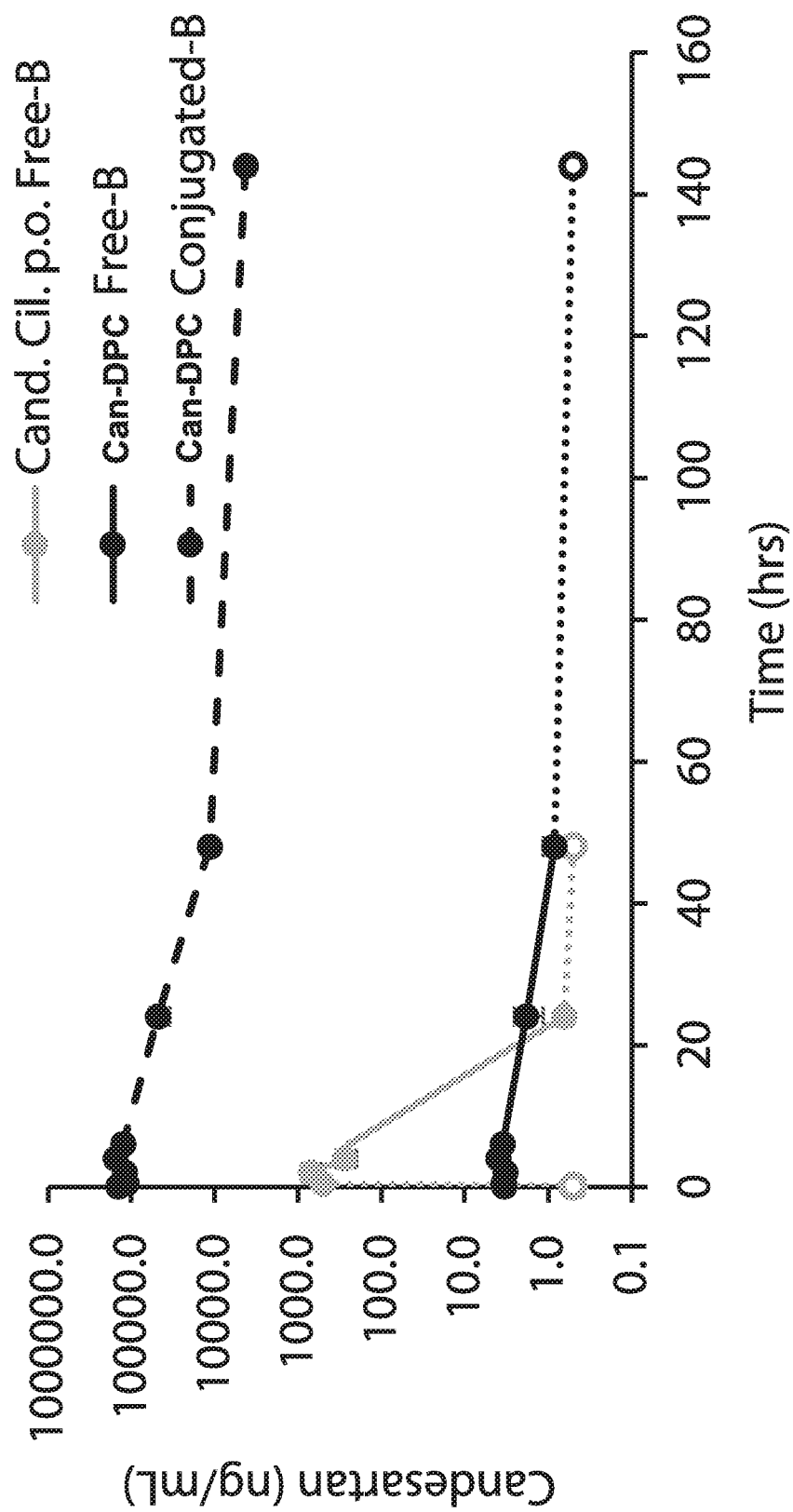
FIGS. 26A, 26B, and 26C show the results of a single dose pharmacokinetic study of Can-DPC in whole blood (FIG. 26A), tumor (FIG. 26B), and liver (FIG. 26C) as measured by LC/MS/MS as described in Example 13.
Figure 26B:
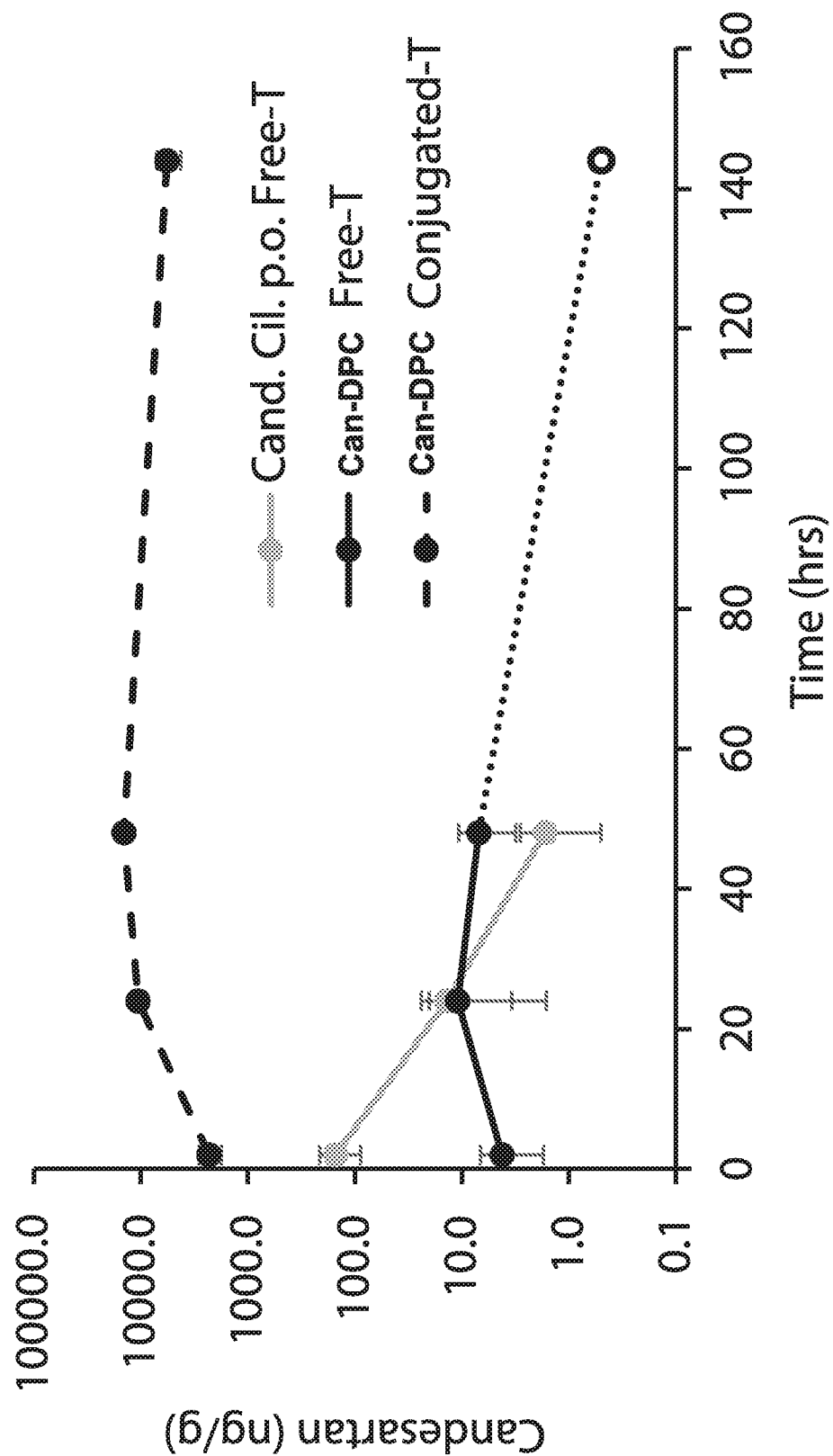
Figure 26C:
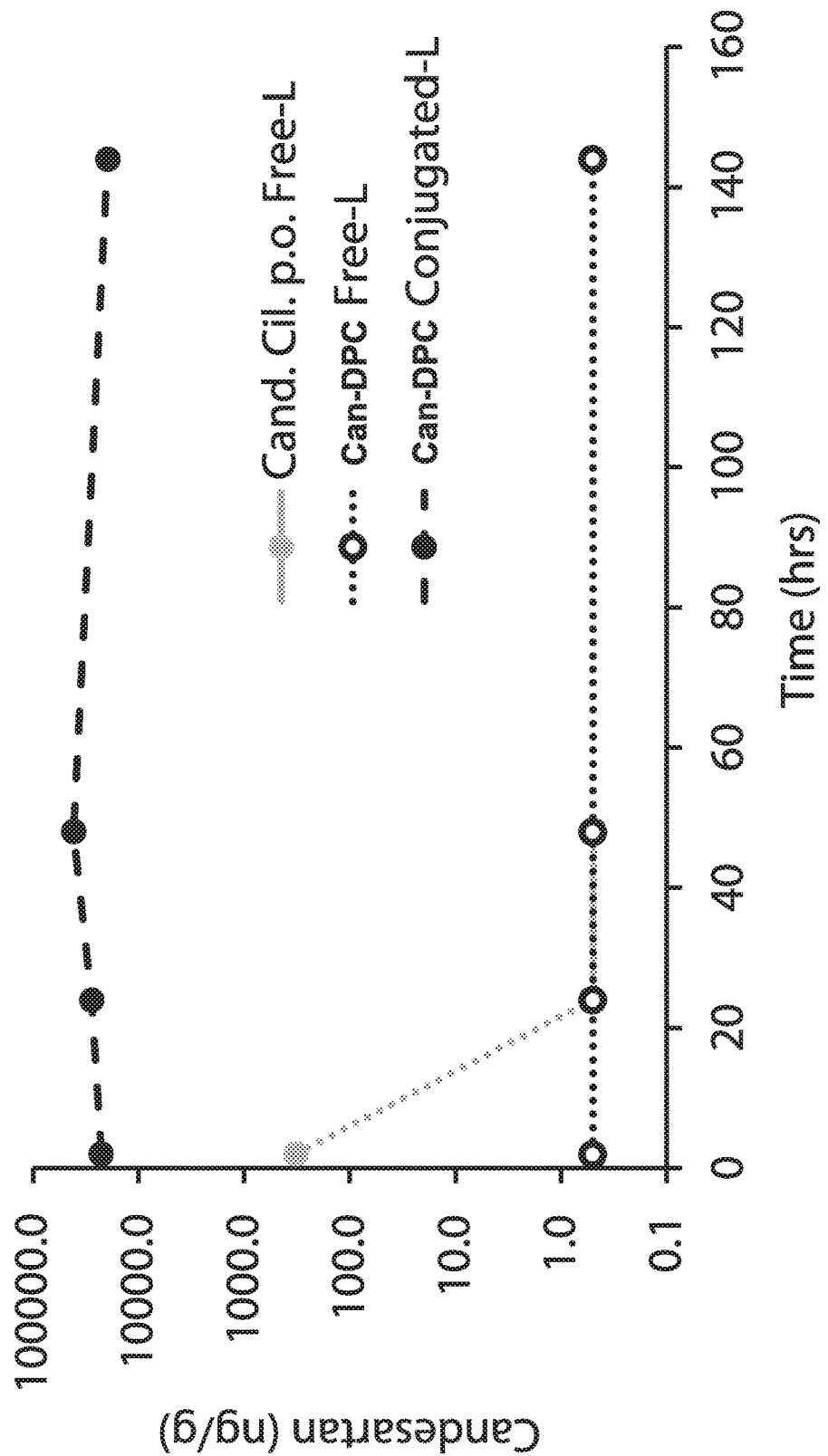

The results of the single-dose PK study are shown in FIGS. 26A-26C for whole blood (FIG. 26A), Tumor (FIG. 26B), and Liver (FIG. 26C) as measured using LC/MS/MS. For comparison, the PK data from generic candesartan cilexetil is graphed together with the PK data for Can-DPC. First, the blood PK profile (FIG. 26A) revealed a significantly prolonged half-life of candesartan enabling the continuous 'feeding' of tissues with polymer-conjugated drug, while the systemic, free concentration of released drug remained low in the blood compartment (FIG. 26A). Consistent with this blood PK profile, tissue analysis confirmed a time-dependent, accumulation and retention of the conjugated drug in the tumor tissue reaching 7.5% of the injected dose/g in tumor at 48 hrs. This is compared to 0.001% of the injected dose/g in tumor at 48 hrs for the generic candesartan cilexeltil group (FIG. 26B). Likewise, in liver, 21.7% of the injected dose/g tissue accumulated in the liver at 48 hrs, whereas the candesartan was non-detectable in the candesartan cilexetil group at 24 and 48 hrs (FIG. 26C). Hence, the Can-DPC formulation results in prolonged exposure of active released candesartan compared to the equivalent dose of generic candesartan.

Importantly, the observed exposure of candesartan in tumor and liver tissue was achieved concomitant with steady-state blood levels of released (i.e., active) candesartan being below drug-induced blood pressure lowering levels reported in the literature (i.e., ~200-400 ng/ml). Altogether, the Can-DPC formulation produced sustained high levels of total candesartan (i.e., conjugated+released) in target tissues that cannot be achieved with a single dose of non-conjugated candesartan.

INCORPORATION BY REFERENCE

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EQUIVALENTS

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A conjugate, comprising:
   a polyacetal polymer;
   an agent, and
   (optionally) a targeting moiety;
   wherein the polyacetal polymer, and the agent and/or a targeting moiety are coupled; and
   the conjugate has a hydrodynamic diameter of about 10 nm to 50 nm, and has at least one of the following properties:
   (i) the conjugate shows a ratio of release or degradation rate at pH=6.7 relative to pH=7.4 that is greater than 1.5;
   (ii) the conjugate shows increased pH-sensitivity in a hypoxic microenvironment;
   (iii) the conjugate is sparingly soluble or slightly soluble in water; or
   (iv) the polyacetal polymer has a melting temperature ($T_m$) of about 35° C. or greater,
   wherein the polyacetal polymer comprises a structure according to Formula (I-c):

Formula (I-c)

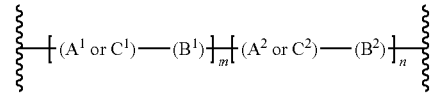

wherein:
each of $A^1$ and $A^2$ is independently represented by a structure of Formula (II-d), Formula (II-e), Formula (II-f), Formula (II-g), Formula (II-h), Formula (II-i), or Formula (II-j);
each of $B^1$ and $B^2$ is independently represented by a structure of Formula (III-a);
each of $C^1$ and $C^2$ is heteroalkyl, cyclyl, or heterocyclyl, each of which is optionally substituted with 1-6 $R^3$;
each of $R^3$ is independently alkyl, alkenyl, alkynyl, hydroxyl, halo, heteroalkyl, keto, alkoxy, ester, cyclyl, heterocyclyl, cycloalkyl, heterocyclylalkyl, arylalkyl, heteroarylalkyl, a linker, an agent, a targeting moiety, or a branching point;

each of m or n is independently an integer from 1 to 200; and wherein the structures of Formula (II-d), Formula (II-e), Formula (II-f), Formula (II-g), Formula (II-h), Formula (II-i), and Formula (II j) are represented by:

Formula (II-d)

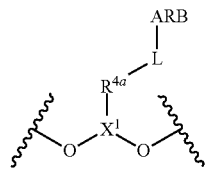

Formula (II-e)

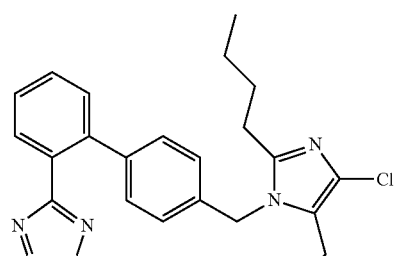

Formula (II-f)

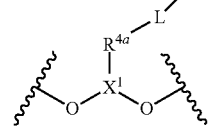

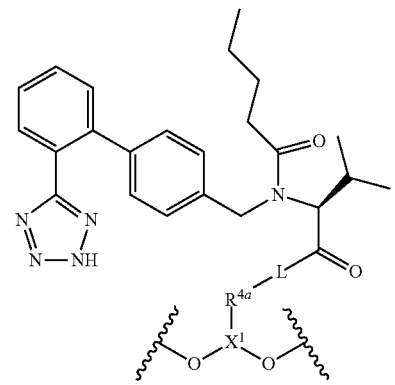

Formula (II-g)

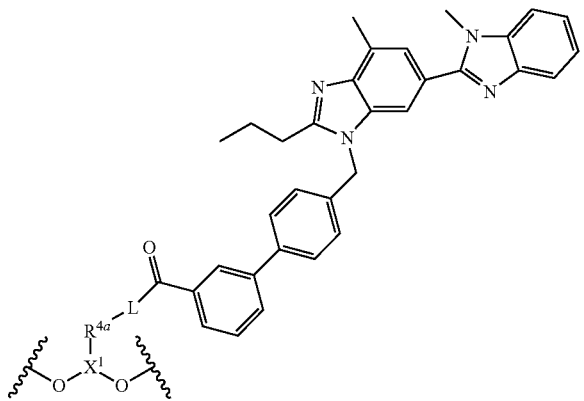

293

-continued

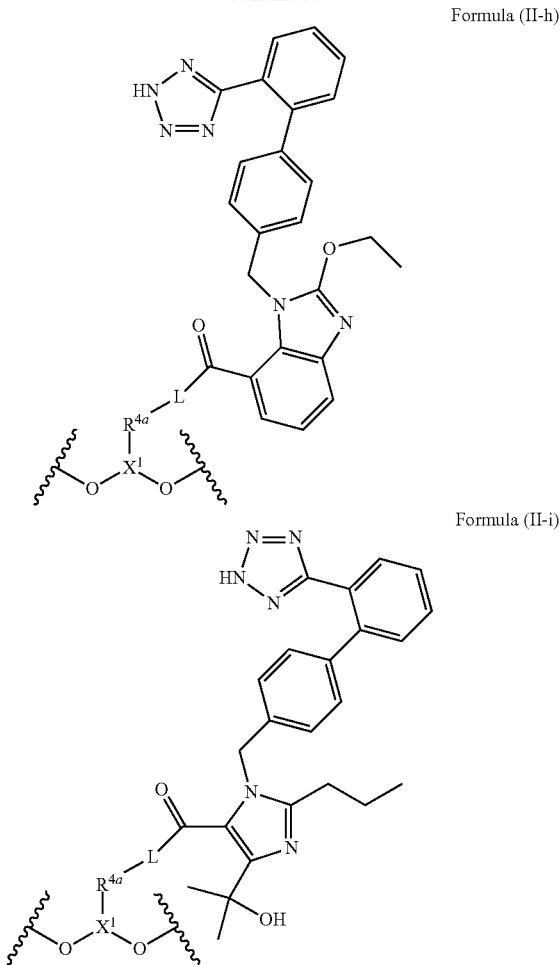

Formula (II-h)

Formula (II-i)

wherein:
X$^1$ is C$_1$-C$_{12}$ alkylene, C$_1$-C$_{12}$ heteroalkylene, C$_3$-C$_8$ cyclyl, or C$_3$-C$_8$ heterocyclyl, wherein each alkylene, heteroalkylene, cyclyl, and heterocyclyl is optionally substituted with 1-6 R$^{4b}$;

R$^{4a}$ is C$_2$-C$_6$ alkenyl, C$_1$-C$_6$ heteroalkyl, O, (C$_1$-C$_6$ alkylene)-O, (C$_1$-C$_6$ alkylene)-O—(C$_1$-C$_6$ alkylene)-O, (C$_1$-C$_6$ alkylene)-C(O)—(C$_1$-C$_6$ alkylene)-O, (C$_1$-C$_6$ alkylene)-OC(O)—(C$_1$-C$_6$ alkylene)-O, (C$_1$-C$_6$ alkylene)-C(O)O—(C$_1$-C$_6$ alkylene)-O, (C$_1$-C$_6$ alkylene)-OC(O)O—(C$_1$-C$_6$ alkylene)-O, (C$_1$-C$_6$ alkylene)-NR$^6$—(C$_1$-C$_6$ alkylene)-O—, (C$_1$-C$_6$ alkylene)-C(O)NR$^6$—(C$_1$-C$_6$ alkylene)-O, or (C$_1$-C$_6$ alkylene)-NR$^6$C(O)—(C$_1$-C$_6$ alkylene)-O, wherein each alkyl, alkenyl, alkynyl, heteroalkyl, or alkylene is optionally substituted with 1-6 R$^7$;

each R$^{4b}$ is independently C$_1$-C$_6$ alkyl, (C$_1$-C$_6$ alkylene)-O-L-losartan, (C$_1$-C$_6$ alkylene)-O-L-valsartan, (C$_1$-C$_6$ alkylene)-O-L-telmisartan, (C$_1$-C$_6$ alkylene)-O-L-candesartan, or (C$_1$-C$_6$ alkylene)-O-L-olmesartan;

L is absent or comprises an acetal, ketal, anhydride, ester, hydrazone, or silyl ether;

R$^6$ is hydrogen or C$_1$-C$_6$ alkyl; and each R$^7$ is independently C$_1$-C$_6$ alkyl, C$_2$-C$_6$ alkenyl, C$_2$-C$_6$ alkynyl, C$_1$-C$_6$ heteroalkyl, halo, O-L-losartan, O-L-valsartan, O-L-telmisartan, O-L-candesartan, O-L-olmesartan, (C$_1$-C$_6$ alkylene)-O-L-losartan, (C$_1$-C$_6$ alkylene)-O-L-valsartan, (C$_1$-C$_6$ alkylene)-O-L-

294 telmisartan, (C$_1$-C$_6$ alkylene)-O-L-candesartan, (C$_1$-C$_6$ alkylene)-O-L-olmesartan, (C$_1$-C$_6$ alkylene)-O—(C$_1$-C$_6$ alkylene)-O-L-losartan, (C$_1$-C$_6$ alkylene)-O—(C$_1$-C$_6$ alkylene)-O-L-valsartan, (C$_1$-C$_6$ alkylene)-O—(C$_1$-C$_6$ alkylene)-O-L-telmisartan, (C$_1$-C$_6$ alkylene)-O—(C$_1$-C$_6$ alkylene)-O-L-candesartan, (C$_1$-C$_6$ alkylene)-O—(C$_1$-C$_6$ alkylene)-O-L-olmesartan, cyano, cyclyl, heterocyclyl, aryl, or heteroaryl;

and the structure of Formula (III-a) is represented by:

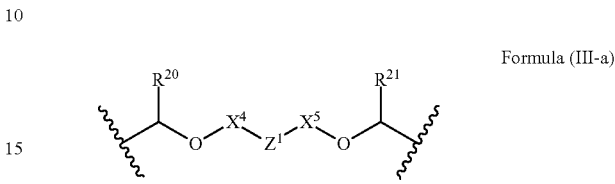

Formula (III-a)

wherein:
Z$^1$ is O, C$_3$-C$_8$ cyclyl, or C(R$^{22}$)(R$^{23}$);
each of X$^4$ and X$^5$ is independently C$_1$-C$_6$ alkylene;
each of R$^{20}$ and R$^{21}$ is independently C$_1$-C$_6$ alkyl or OR$^{20}$;
each of R$^{22}$ and R$^{23}$ is independently hydrogen, C$_1$-C$_6$ alkyl, or (C$_1$-C$_6$ alkylene)-OR$^{26}$;
and each R$^{26}$ is C$_1$-C$_6$ alkyl, C$_2$-C$_6$ alkenyl, a linker, an agent, a targeting moiety, a protecting group, or a branching point, and wherein: (i) for Formula (II-e), Formula (II-f), Formula (II-g), Formula (II-h), or Formula (II-i), X$^1$ is C$_3$-C$_6$ cyclyl, optionally substituted with 1-6 R$^4$; or (ii) for Formula (II-e), Formula (II-f), Formula (II-g), Formula (II-h), or Formula (II-i), each R$^{4a}$ is independently C$_1$-C$_6$ alkyl, O, (C$_1$-C$_6$ alkylene)-O, (C$_1$-C$_6$ alkylene)-O—(C$_1$-C$_6$ alkylene)-O, (C$_1$-C$_6$ alkylene)-C(O)—(C$_1$-C$_6$ alkylene)-O, (C$_1$-C$_6$ alkylene)-OC(O)—(C$_1$-C$_6$ alkylene)-O, (C$_1$-C$_6$ alkylene)-C(O)O—(C$_1$-C$_6$ alkylene)-O, or (C$_1$-C$_6$ alkylene)-OC(O)O—(C$_1$-C$_6$ alkylene)-O.

2. The conjugate of claim 1 comprised in a particle, wherein the particle has a hydrodynamic diameter of less than about 100 nm and has at least one of the following properties:
   (i) the particle shows a ratio of release or degradation rate at pH=6.7 relative to pH=7.4 that is greater than 1.5;
   (ii) the particle shows increased pH-sensitivity in a hypoxic microenvironment;
   (iii) the particle is slightly soluble or very slightly soluble in water; or
   (iv) the polyacetal polymer has a melting temperature (T$_m$) of about 35° C. or greater.

3. The conjugate of claim 1, wherein for Formula (II-e), Formula (II-f), Formula (II-g), Formula (II-h), or Formula (II-i), X$^1$ is C$_3$-C$_6$ cyclyl, optionally substituted with 1-6 R$^4$.

4. The conjugate of claim 1, wherein for Formula (II-e), Formula (II-f), Formula (II-g), Formula (II-h), or Formula (II-i), each R$^{4a}$ is independently C$_1$-C$_6$ alkyl, O, (C$_1$-C$_6$ alkylene)-O, (C$_1$-C$_6$ alkylene)-O—(C$_1$-C$_6$ alkylene)-O, (C$_1$-C$_6$ alkylene)-C(O)—(C$_1$-C$_6$ alkylene)-O, (C$_1$-C$_6$ alkylene)-OC(O)—(C$_1$-C$_6$ alkylene)-O, (C$_1$-C$_6$ alkylene)-C(O)O—(C$_1$-C$_6$ alkylene)-O, or (C$_1$-C$_6$ alkylene)-OC(O)O—(C$_1$-C$_6$ alkylene)-O.

5. The conjugate of claim 1, wherein for Formula Z$^1$ is C(R$^{23}$)(R$^{24}$) and each of R$^{22}$ and R$^{23}$ is independently hydrogen, C$_1$-C$_6$ alkyl, or (C$_1$-C$_6$ alkylene)-OR$^{26}$.

6. The conjugate of claim 1, wherein for Formula (III-a), R$^{22}$ is hydrogen or C$_1$-C$_6$ alkyl, R$^{23}$ is independently C$_1$-C$_6$ alkyl or C$_1$-C$_2$ alkylene)-OR$^{26}$ and R$^{26}$ is C$_2$-C$_6$ alkenyl or a branching point.

7. The conjugate of claim 1, wherein a precursor to each of $B^1$ and $B^2$ is independently selected from the following vinyl ethers:

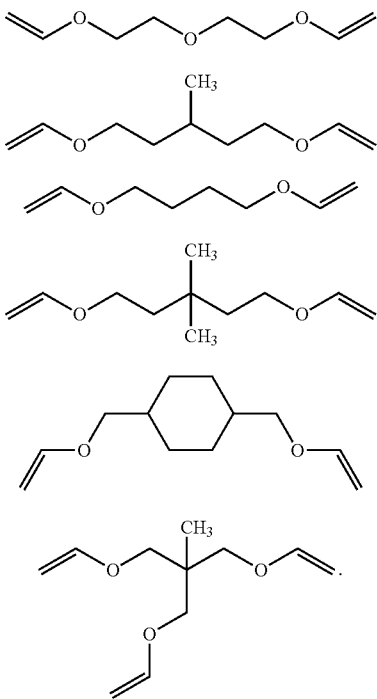

8. The conjugate of claim 1 wherein each of $C^1$ and $C^2$ is independently a polyethylene glycol (PEG) and is between about 200 and 4000 Da in size.

9. The conjugate of claim 1, wherein the polymer, the linker, the agent and/or targeting moiety in the conjugate are covalently coupled via a linker.

10. The conjugate of claim 9, wherein the linker is a polyacetal polymer.

11. The conjugate of claim 1, wherein the agent is a therapeutic agent and/or a diagnostic agent.

12. The conjugate of claim 1, wherein the conjugate has at least two of the following properties:
 (i) the conjugate shows a ratio of release or degradation rate at pH=6.7 relative to pH=7.4 that is greater than 1.5;
 (ii) the conjugate shows increased pH-sensitivity in a hypoxic microenvironment;
 (iii) the conjugate is sparingly soluble or slightly soluble in water; or
 (iv) the polyacetal polymer has a melting temperature ($T_m$) of about 35° C. or greater.

13. A composition comprising one or more of the conjugates of claim 1 and a pharmaceutically acceptable carrier.

14. A method of treating a hyperproliferative and/or fibrotic disorder in a subject, or of improving the delivery and/or efficacy of a therapy-in a subject, the method comprising:
 administering a particle according to claim 2, as a single agent or in combination, to the subject;
 administering the therapy,
 under conditions sufficient to treat or prevent the disorder or condition in the subject, or to improve the delivery and/or efficacy of the therapy provided to the subject.

* * * * *